(12) United States Patent
Georgopoulos et al.

(10) Patent No.: US 7,196,170 B2
(45) Date of Patent: Mar. 27, 2007

(54) AIOLOS, HELIOS, DAEDALOS AND IKAROS: GENES, POLYPEPTIDES, REGULATORY ELEMENTS AND USES THEREOF

(75) Inventors: Katia Georgopoulos, Lexington, MA (US); Bruce A. Morgan, Lexington, MA (US); Clair Kelley, Memphis, TN (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/885,227

(22) Filed: Jul. 6, 2004

(65) Prior Publication Data

US 2005/0130265 A1 Jun. 16, 2005

Related U.S. Application Data

(63) Continuation-in-part of application No. 10/037,667, filed on Oct. 25, 2001, now Pat. No. 6,759,201, and a continuation-in-part of application No. 09/259,389, filed on Feb. 26, 1999, now abandoned.

(60) Provisional application No. 60/243,110, filed on Oct. 25, 2000, provisional application No. 60/076,325, filed on Feb. 27, 1998.

(51) Int. Cl.
    *A61K 14/00* (2006.01)
(52) U.S. Cl. .................................... 530/350
(58) Field of Classification Search .............. 530/350
    See application file for complete search history.

(56) References Cited

OTHER PUBLICATIONS

Multi-zinc finger helios protein from *Mus musculus*: Accession code: AAC00513, deposit date, Feb. 4, 1998. Sequence alignments of SEQ ID Nos. 24, 26 and 28 vs. AAC00513.*
Wells, "Additivity of Mutational Effects in Proteins", 1990, Biochemistry, 29(37), 8509-8517.*
Bowie et al., "Deciphering the message in protein sequences: Tolerance to amino acid substitutions", 1990, Science, 247, 1306-1310.*
Christiansen et al. "The role of the MoFe protein alpha-125-Phe and beta-235-Phe residues in Azotobacter vinelandii MoFe protein Fe protein interaction". Journal of Inorganic Biochemistry. 2000. vol. 80, pp. 195-204.*
Sorlie et al. "Mechanistic features and structure of the nitrogenase alpha-Gln-195 MoFe protein". Biochemistry. 2001. vol. 40, pp. 1540-1549.*
Anderson, W. F., Nature 293:25-30 (Apr. 1998).
Brown et al. (1997) *Cell*, 91:845-854.
GenBank Accession No. 042244, Jan. 1, 1998.
GenBank Accession No. AF024439, Oct. 29, 1997.
Georgopoulos et al. (1992) *Science*, 258:808-812.
Georgopoulos et al. (1994) *Cell*, 79:143-156.
Georgopoulos et al. (1997) *Ann. Rev. Immunol.* 15:155-176.
Hahm K. et al., Genbank entry: Accession No. AF044257 (Feb. 1998).
Hansen et al. (1997) *Eur. J. Immunol.*, 11:3049-3058.
Kelly, C.M. et al., Current Biology 8:508-515 (Apr. 1998).
Liippo et al., (1997) *Eur. J. Immunol.*, 8:1853-1857.
Lo et al. (1991) *Mol. Cell Biol.*, 11:5229-5243.
Molnar et al. (1994) *Mol. Cell Biol.*, 14(12):8292-8303.
Molnar et al., "The Ikaros Gene Encodes a Family of Lymphocyte-Restricted . . . ", 1996, J. Immun., vol. 156, No. 2;585-592.
Molnar, A. et al., Molecular and Cellular Biology 14(2):8292-8303 (Dec. 1994).
Morgan et al., (1997) *EMBO J.*, 16:2004-2013.
Nietfeld et al., "Cloning and sequencing of hIk-1, a cDNA . . . ", 1996, Immun. Letters, vol. 49, No. 1-2;139-141.
Ogawa et al. (1991) *J. Exp. Med.*, 174:63-71.
Ogawa et al. (1993) *Blood*, 81:2844-2853.
Sun et al. (1996) *EMBO J.*, 15:5358-5369.
Turpen et al. (1997) *Immunity*, 7:325-334.
Verma, I.M. et al., Nature 389:239-242 (Sep. 1997).
Wang et al. (1996) *Immunity*, 5:237-549.
Winandy et al. (1995) *Cell*, 83:289-299.
Wu et al. (1997) *Immunity*, 7:483-492.

* cited by examiner

*Primary Examiner*—Karen Cochrane Carlson
*Assistant Examiner*—Suzanne M. Noakes
(74) *Attorney, Agent, or Firm*—Fish & Richardson P.C.

(57) ABSTRACT

Provided herein are (a) Aiolos gene, Aiolos polypeptides, Aiolos homodimers, Aiolos/Ikaros heterodimers and methods of using Aiolos nucleic acids and polypeptides; (b) Helios gene, Helios polypeptides, Helios homodimers, Helios/Ikaros heterodimers, Helios/Aiolos heterodimers, and methods of using Helios nucleic acids and polypeptides; (c) Daedalos nucleic acids, Daedalos polypeptides, and other related molecules and methods of making and using the same; and (d) Ikaros regulatory elements and uses thereof.

4 Claims, 46 Drawing Sheets

1A. MOUSE AIOLOS cDNA SEQUENCE

CACGAGCGCACACCGCTCGGCTCTCCTTGCGACACGCCCTCATCCCCGGTGTT
TCTCAAGTAGACGTCCCGAGACGGTCGCTGAGGCACTGTTTCCACGCGATCA
GGGTTCCTCAGGCTTGACATTCAAAAGTGGGTGCGGAACCCGCGGCACTCGG
AGCGTGCTTTAAAGCGGCCGCCAGCCAGCGCCGCTCTAACCTCGCGCCCCGG
CTGCCGGCGGCTCCCGCCCTGCATCTGCGCCGACGCGACCGAGCGATCCCGG
GGCCTCCCTGCGCCCGGAATCTCCCGCCAGCCGCGCGGGTCCCCACGGCAGC
AGCACGTGGAGCGGCCGCGGAGCCTGAGCGACAGCTGCAGCCCGCGCGGCC
CGCGGCGACATGGAAGATATACAACCGACTGTGGAGCTGAAAAGCACGGAG
GAGCAGCCTCTGCCCACAGAGAGCCCAGACGCTCTGAATGACTACAGCTTGC
CCAAACCTCATGAGATAGAAACGTGGACAGTAGAGAAGCCCCAGCCAATG
AAGACGAAGATGCAGGAGAAGATTCGATGAAAGTGAAAGATGAATACAGCG
ACAGAGATGAGAACATTATGAAGCCGGAGCCCATGGGAGATGCAGAAGAGA
GTGAAATGCCTTACAGCTATGCAAGAGAATACAGCGACTATGAAAGCATTAA
GCTGGAGAGACACGTGCCCTATGACAACAGCAGACCAACCAGTGGGAAGAT
GAACTGCGACGTGTGCGGGTTATCCTGCATTAGCTTCAACGTCTTGATGGTTC
ATAAGCGAAGCCATACCGGCGAACGCCCGTTCCAGTGTAATCAGTGCGGGGC
ATCTTTTACTCAGAAAGGTAACCTCCTCCGTCATATTAAACTGCACACGGGGG
AAAAACCTTTTAAGTGTCACCTCTGCAACTACGCATGCCAAAGGAGAGATGC
GCTCACGGGACACCTTAGGACACATTCTGTGGAGAAGCCGTACAAGTGTGAG
TTCTGCGGAAGAAGCTACAAGCAGAGAAGCTCCCTGGAGGAGCACAAGGAA
CGCTGCCGAGCTTTTCTTCAGAACCCTGACCTGGGGGACGCTGCAAGTGTGG
AGGCAAGACACATCAAAGCCGAGATGGGAAGTGAGAGAGCTCTCGTCCTGG
ACAGATTAGCAAGCAATGTGGCTAAGCGAAAAAGCTCGATGCCTCAGAAATT
CATCGGTGAGAAGCGGCACTGCTTCGATGCCAACTACAATCCCGGCTACATG
TACGAGAAGGAGAACGAGATGATGCAGACCCGGATGATGGACCAAGCCATC
AATAACGCCATCAGCTATCTAGGGGCTGAAGCCTTCCGCCCCTTAGTCCAGA
CTCCGCCTGCTCCCACCTCTGAGATGGTCCCAGTCATCAGCAGTGTGTACCCC
ATAGCACTTACTCGGGCCGATATGCCAATGGGGGCCCCGCAgGAGATGGAAA
AGAAACGGATCCTCCTGCCAGAGAAGATCTTGCCTTCTGAACGAGGTCTGTC
CCCCAATAACAGTGCCCAGGACTCCACAGACACCGACAGCAACCACGAGGAT
CGCCAACATCTCTACCAGCAAAGCCACGTGGTCCTCCCCCAGGCCCGCAATG
GGATGCCTCTTCTGAAGGAGGTCCCTCGCTCTTTTGAACTCCTCAAGCCCCCT
CCCATCTGCCTGAGGGACTCCATCAAAGTGATCAACAAAGAAGGGGAGGTGA
TGGATGTGTTTCGATGTGACCACTGCCACGTCCTCTTCCTAGATTATGTGATG
TTCACCATCCACATGGGGTGCCATGGTTTCCGTGATCCCTTTGAGTGTAACAT
GTGTGGCTATCGAAGCCACGATCGCTATGAGTTCTCCTCTCACATCGCCAGAG
GAGAGCACAGAGCCATGTTGAAGTGAGCATCTGTCCTCAATGCGAGGGTCAA
CATTGTTTTTTAAAGCTGATGGTAGCCTTATCCAGTAGACTGAACTCAAACCC
ACCTCGAG

FIG. 1A

1B. MOUSE AIOLOS PEPTIDE SEQUENCE

MEDIQPTVELKSTEEQPLPTESPDALNDYSLPKPHEIENVDSREAPANEDEDAGED
SMKVKDEYSDRDENIMKPEPMGDAEESEMPYSYAREYSDYESIKLERHVPYDNS
RPTSGKMNCDVCGLSCISFNVLMVHKRSHTGERPFQCNQCGASFTQKGNLLRHI
KLHTGEKPFKCHLCNYACQRRDALTGHLRTHSVEKPYKCEFCGRSYKQRSSLEE
HKERCRAFLQNPDLGDAASVEARHIKAEMGSERALVLDRLASNVAKRKSSMPQ
KFIGEKRHCFDANYNPGYMYEKENEMMQTRMMDQAINNAISYLGAEAFRPLVQ
TPPAPTSEMVPVISSVYPIALTRADMPMGAPQEMEKKRILLPEKILPSERGLSPNN
SAQDSTDTDSNHEDRQHLYQQSHVVLPQARNGMPLLKEVPRSFELLKPPPICLRD
SIKVINKEGEVMDVFRCDHCHVLFLDYVMFTIHMGCHGFRDPFECNMCGYRSH
DRYEFSSHIARGEHRAMLK

FIG. 1B

```
                  Ex7       ACTIVATION DOMAIN
          1        ▼                                                    50
cAio    PPLLLVPGEK RHCFDANYNP GYMYEKENEM MQTRMMDQAI NNAISYLGAE
mAio    .......GEK RHCFDANYNP GYMYEKENEM MQTRMMDQAI NNAISYLGAE
mIka    ........GD KCLSDMPYDS .ANYEKE.DM MTSHVMDQAI NNAINYLGAE
cIka    .......... .DRLDLPYDA TTNYEKENEI MQTHVIDQAI NNAISYLGAE
                                                         ◀——— YAS 5
          51                                                          100
cAio    AVRPLVQTPP APTSEMVPVI SSVYPIALTR AD....MPNGA PQEMEKKRIL
mAio    AC..LVQTPP APTSEMVPVI SSVYPIALTR AD...MPMGA PQEMEKKRIL
Chu1    SLRPLVQTPP G.SSEVVPVI SSMYQLHKPP SDGPPRSNHS AQD.AVDNLL
cIka    SLRPLVQTPP V.GSEVVPVI SPMYQLHKPH GDNQTRSNHT AQDSAVENLL
                                               YAS 3 ◀——▶
         101                                                          150
cAio    L..PEKILPS ERGLSPNNSA QDSTDTDSNH ED.RQHLYQQ SHVVLPQARN
mAio    L..PEKILPS ERGLSPNNSA QDSTDTDSNH ED.RQHLYQQ SHVVLPQARN
mIka    LLSKAKSVSS EREASPSNSC QDSTDTESNA EEQRSGLIYL TNHINPHARN
cIka    LLSKAKSVSS ERDASPSNSC QDSTDTESNN EE.RSGLIYL TNHIGPHARN
                                       ◀——— YIZ
         151                                                          200
cAio    GMPLLKEVPR SFELLKPPPI CLRDSIKVIN KEGEVMDVFR CDHCHVLFLD
mAio    GMPLLKEVPR SFELLKPPPI CLRDSIKVIN KEGEVMDVFR CDHCHVLFLD
mIka    GLA.LKEEQR AYEVLRAASE NSQDAFRVVS TSGEQLKVYK CEHCRVLFLD
cIka    GIS.VKEESR QFDVLRAGTD NSQDAFKVIS SNGEQVRVYK CEHCRVLFLD 201                                                       249
cAio    YVMFTIHM.GCHGFRDPF ECNMCGYRSH DRYEFSSHIA RGEHRAMLK
mAio    YVMFTIHM.GCHGFRDPF ECNMCGYRSH DRYEFSSHIA RGEHRAMLK
mIka    HVMYTIHM GCHGFRDPF ECNMCGYHSQ DRYEFSSHIT RGEHRYHLS
cIka    HVMYTIHM.GCHGFRDPF ECNMCGYHSQ DRYEFSSHIT RGEHRFHMS
```

YAS 5 = interaction domain
YAS 3 = interaction domain
YIZ = Ikaros dimerization domain

FIG. 2

```
        1                                                          50
aio     ..........  ..........  ..........  ..........  ..........
Ik1     MDVDEGQDMS  QVSGKESPPV  SDTPDEGDEP  MPVPEDLSTT  SGAQQNSKSD 51                                                         100
aio     ..........  ..........  ..........  ..........  ..........
Ik1     RGMASNVKVE  TQSDEENGRA  CEMNGEECAE  DLRMLDASGE  KMNGSHRDQG
                                                          Ex4
        101                                                ▼       150
Ik      ..........  NSARGKMNCD  VCGLSCISFN  VLMVHKRTHT  GERPFQCNQC
Ik1     SSALSGVGGI  RLPNGKLKCD  ICGIVCIGPN  VLMVHKRSHT  GERPFQCNQC
                                                          Ex5
        151                                                ▼200
aio     GASFTQKGNL  LRHIKLHTGE  KPFKCHLCNY  ACQRRDALTG  HLRTHSVEKP
Ik1     GASFTQKGNL  LRHIKLHSGE  KPFKCHLCNY  ACRRRDALTG  HLRTHSVGKP
                                              Ex6
        201                                    ▼                   250
Aio     YKCEFCGRSY  KQRSSLEEHK  ERCRAFLQNP  DLGDAASV..  ......EARH
Ik1     HKCGYCGRSY  KQRSSLEEHK  ERCHNYLESM  GLPGMYPVIK  EETNHNEMAE
                                              Ex7
        251                                    ▼                   300
Aio     IKAEMGSERA  LVLDRLASNV  AKRKSSMPQK  FIGEKRHCFD  ANYNPGYMYE
Ik1     DLCKIGAERS  LVLDRLASNV  AKRKSSMPQK  FLGDK..CLS  DMPYDSANYE 301                                                        350
Aio     KENEMMQTRM  MDQ.......  ..........  ..........  ..........
Ik1     KE.DMMTSHV  MDQ
```

FIG. 3

Exon 3
IRHEEAPANEDEDAGAGEDSMKVKDEYSDRDENIMKPEPMGDAEESEMPYSYA
REYSDYESIKLERHVPYDNSRPTSGKMNCDVCGLSCISFNVLMVHKRSHT Exon 4
GERPFQCNQCGASFTQKGNLLRHIKLHTGEKPFKCHLCNYACQRRDALTGH
LRTHS Exon 5
VEKPYKCEFCGRSYKQRSSLEEHKERCRAFLQNPDLGDA Exon 6
ASVEARHIKAEMGSERALVLDRLASNVAKRKSSMPQKFI Exon 7
GEKRHCFDANYNPGYMYEKENEMMQTRMMDQAINNAISYLGAEAFRPLVQ
TPPAPTSEMVPVISSVYPIALTRADMPMGAPQEMEKKRILLPEKILPSERG
LSPNNSAQDSTDTDSNHEDRQHLYQQSHVVLPQARNGMPLLKEVPRSFEL
LKPPPICLRDSIKVINKEGEVMDVFRCDHCHVLFLDYVMFTIHMGCHGFRD
PFECNMCGYRSHDRYEFSSHIARGEHRAMLK

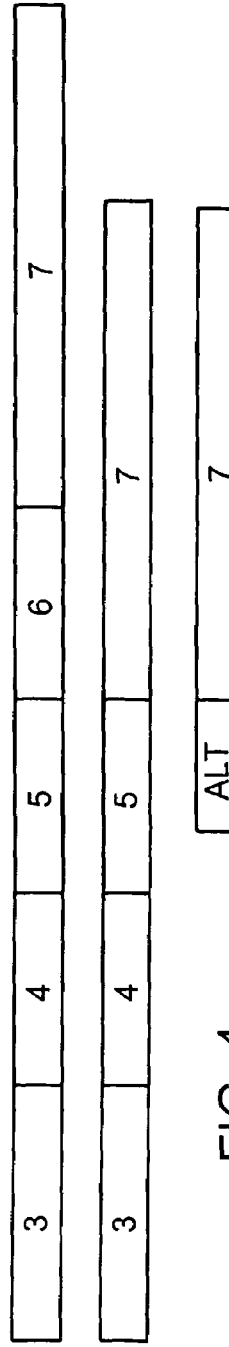

FIG. 4

GAAGAGATGAGAATGTTTAAGCTCAGAGAACCATGGAAATGCAGAAGAGTATTCAAGAGAGTATaaTGAA 90
TATGAAACATTAAGTTGGAGAGACATGTCTCATTCGATAGTTAGCCAGCCAACCAGTCGAAAGATGAATGTGTGGATTA 180
TCCTGCATCAGCTTCAATGTCTTATAGTTCATAGAGGAGCCATACTgGtgaacgccattccagtgtaatcagtgggcatctttt 270
actcagaaggtaactcctccGccacattaaActgcacacaggggaaaaacctctgcaactatgtcaactctgcaaga 360
agagatgcgctcacgggcatcttaggacacattctggtggagaaacctacaaatgtgagttttgtgaaggagtt acaagcagaagt 450
tccttgagagagcacaagagcgctgccgtacattctt cagagactgaccaggggacactgcAAGTGCGGAGGCAAGACATCAAA 540
GCaGAGATGGAAGTGAAGAGCCTCTCCTACTGGACAGATTACCAGCAATGTGGCAAAAACGAAAAAGCTCAAATGCCCTCAGAAATTCA 628

```
Lipman-Pearson Protein Alignment
kTuple: 2; Gap Penalty: 4; Gap Length Penalty: 12
Seq1(1>209)                                            Similarity  Gap     Gap      Concensus
Seq2(1>508)                                            Index       Length  Number   Length
human Aiolos protein AioC/hAio2     mouseaiolos.protein
 (1>209)                             (66>273)           89.5         1       1        209 human Aiolos protein AioC/hAio2   ERDENYLKSEPMGNAEEPEIPYSYSREYNEYENIKLERHVVSFDSSRPTSGKMNCDVCGL  80
                                  :RDEN:.K:EPMG:·AEE:·E:·PYSY:·REY::·YE:·IKLERHV·::·D:·SRPTSGKMNCDVCGL
mouseaiolos.protein               DRDENIMKPEPMGDAEESEMPYSYAREYSDYESIKLERHV-PYDNSRPTSGKMNCDVCGL 124 human Aiolos protein AioC/hAio2   SCISFNYLMVHKRSHTGERPFQCNQCGASFTQKGNLLRHIKLHTGEKPFKCHLCNYACQR 120
                                  SCISFNYLMVHKRSHTGERPFQCNQCGASFTQKGNLLRHIKLHTGEKPFKCHLCNYACQR
mouseaiolos.protein               SCISFNVLMVHKRSHTGERPFQCNQCGASFTQKGNLLRHIKLHTGEKPFKCHLCNYACQR 184 human Aiolos protein AioC/hAio2   RDALTGHLRTHSVEKPYKCEFCGRSYKQRSSLEEHKERCRTFLQSTDPGDTASAEARHIK 180
                                  RDALTGHLRTHSVEKPYKCEFCGRSYKQRSSLEEHKERCR:·FLQ:.·D··GD:·AS.·EARHIK
mouseaiolos.protein               RDALTGHLRTHSVEKPYKCEFCGRSYKQRSSLEEHKERCRAFLQNPDLGDAASVEARHIK 244 human Aiolos protein AioC/hAio2   AEMGSERALVLDRLASNVAKRKSSMPQKF 209
                                  AEMGSERALVLDRLASNVAKRKSSMPQKF
mouseaiolos.protein               AEMGSERALVLDRLASNVAKRKSSMPQKF 273
```

FIG. 5B

```
  1 MEDIQPTVELKSTEEQPLPTESPDALNDYSLPKPHEIENVDSREAPAMED  50
    ::: |.  ::.:.|..|:.......::   | .:| |.::.....:   |..|..
    MDVDEGQDMSQVSGKESPPVSDTPDEG..DEPMPVPEDLSTTSG..AQQMSK  48

51 EDAGEDSAKVKDEYSDRDENIAKPEPAGDAEESEMPYSVAREYSDYESIK  100
    .| | .|. .|| |   . :|| . .|    |:.  ..::.    |.:  .  :| :
 49 SDRGMAS.NVKVETQSDEENGRACEMNGEECAEDLRMLDASGEKMNGSHA   97

101 LERHVPY...DNSRPTSGKMNCDVCGLSCISFNVLMVHKRSHTGERPFQC  147
    :   :.      :. | ..||:.|||:|||: ||: ||||||||||||||||||
 98 DQGSSALSGVGGIRLPNGKLKCDICGIVCIGPNVLMVHKRSHTGERPFQC  147

148 NQCGASFTQKGNLLRHIKLHTGEKPFKCHLCNYACQRRDALTGHLRTHSV  197
    ||||||||||||||||||||.|||||||||||||.|||||||||||||||
148 NQCGASFTQKGNLLRHIKLHSGEKPFKCHLCNYACRRRDALTGHLRTHSV  197

198 EKPYKCEFCGRSYKQRSSLEEHKERCRAFLQNPDLGDAASV........E  239
    :||.|||::|||||||||||||||||||:..:|:.  :|.:....|       |
198 GKPHKCGYCGRSYKQRSSLEEHKERCHNYLESMGLPGVCPVIKEETNHHE  247

240 ARHIKAEMGSERALVLDRLASNVAKRKSSMPQKFIGEKRHCFDANYHPGY  289
    .  ..:|.||.|||||||||||||||||||||||:|:|  |:..   .:
248 MREDLCKIGRERSLVLDRLASNVAKRKSSMPQKFLGDK..CLSDMPYDSA  295

290 MYEKEMEMMQTRMMDQAINHAISYLGAEAFAPLVQTPPAPTSEMVPVISS  339
    ||||  :||  .::|||||||||.|||||.:|||||||||:.  ||:||||||
296 NYEKE.DMMTSKVMDQAINHAINYLGAESLAPLVQTPPGS.SEVVPVISS  343

340 VYPIALTRADMPM....GAPQEMEKKRILLPEKILPSERGLSPNHSAQDS  385
    :|..:   ...| |     :|.:.::.   :|  ..| :.|||: ||.||.|||
344 MYQLHKPPSDGPPRSNHSAQDAVDNLLLLSKAKSVSSEREASPSNSCQDS  393

386 TDTDSN.HEDRQHLYQQSHVVLPQARNGMPLLKEVPRSFELLKPPPICLA  434
    |||:||  .|:|  |.  .: : |:||||:: |||  .|.:|:|:::.
394 TDTESNAEEQRSGLIYLTNHINPHARNGLA.LKEEQRAYEVLRAASEHSQ  442

435 DSIKVINKEGEVMDVFRCDHCHVLFLDYVMFTIHMGCHGFRDPFECNMCG  481
    |.::|:...|| :.|:::|||:|||||||.||:||||||||||||||||||
443 DAFRVVSTSGEQLKVYKCEHCRVLFLDHVMYTIHMGCHGFRDPFECNMCG  492

482 YRSHDRYEFSSHIARGEHRAMLK  507
    |:|:|||||||||.|||||  |.
493 YHSQDRYEFSSHITAGEHRYHLS  518
```

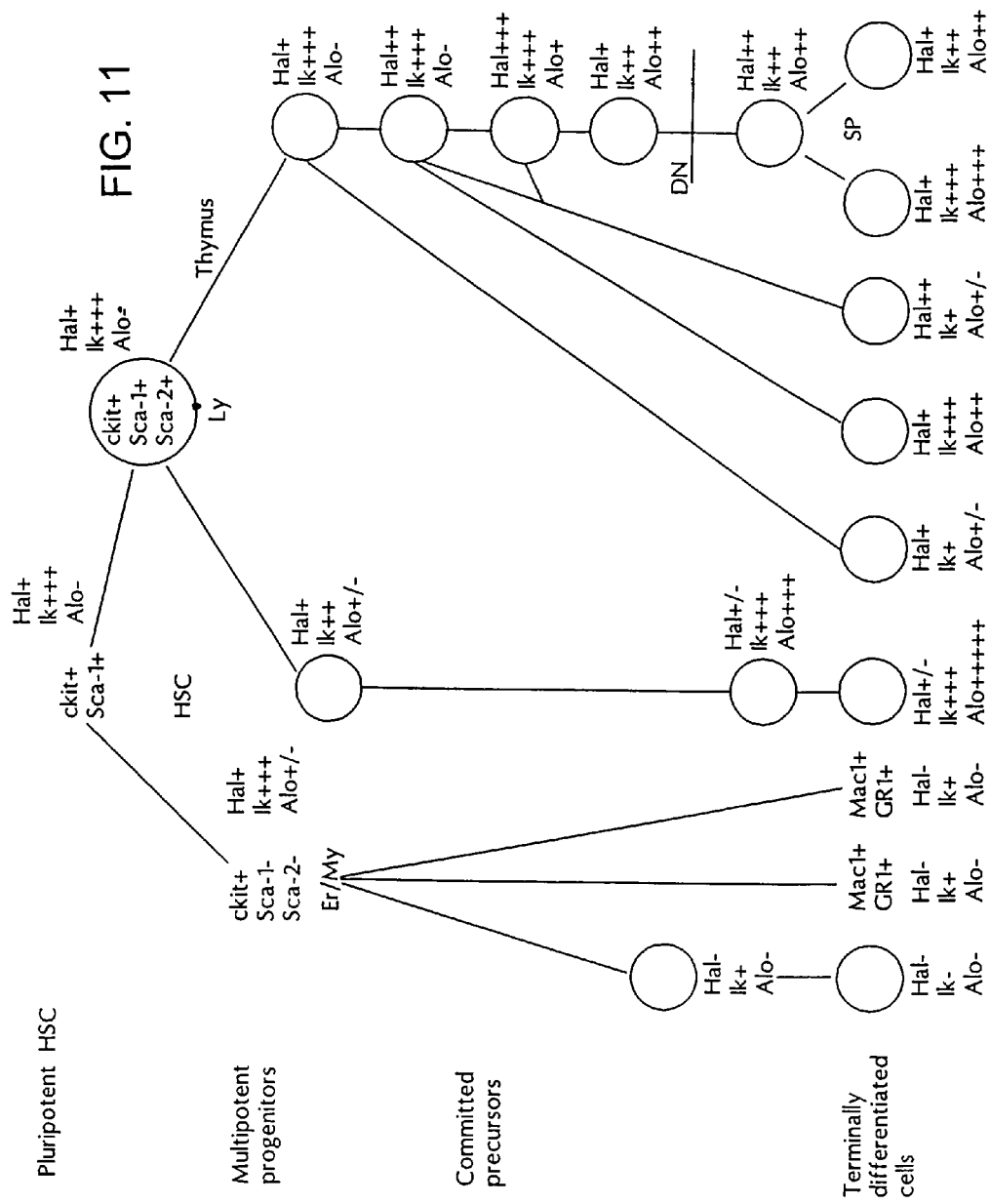

```
ATGGAAACAGACGCTATTGATGGCTATATAACATGTGACAATGAGCTTTCACCCGAAGGGGAACACGCCA
|----|----|----|----|----|----|----|----|----|----|----|----|----|----| 70
TACCTTTGTCTGCGATAACTACCGATATATTGTACACTGTTACTCGAAAGTGGGCTTCCCCTTGTGCGGT
  M  E  T  D  A  I  D  G  Y  I  T  C  D  N  E  L  S  P  E  G  E  H  A

ATATGGCCATTGACCTCACCTCAAGCACGCCCAATGGACAGCACGCCTCGCCAAGTCACATGACAAGCAC
|----|----|----|----|----|----|----|----|----|----|----|----|----|----| 140
TATACCGGTAACTGGAGTGGAGTTCGTGCGGGTTACCTGTCGTGCGGAGCGGTTCAGTGTACTGTTCGTG
  N  M  A  I  D  L  T  S  S  T  P  N  G  Q  H  A  S  P  S  H  H  T  S  T

AAATTCTGTAAAGCTGGAAATGCAGAGTGATGAAGAGTGTGACAGGCAGCCCCTGAGCCGTGAGGATGAG
|----|----|----|----|----|----|----|----|----|----|----|----|----|----| 210
TTTAAGACATTTCGACCTTTACGTCTCACTACTTCTCACACTGTCCGTCGGGGACTCGGCACTCCTACTC
  N  S  V  K  L  E  M  Q  S  D  E  E  C  D  R  Q  P  L  S  R  E  D  E

ATCAGGGGCCACGATGAGGGGAGCAGCCTAGAAGAACCCCTAATTGAGAGCAGCGAGGTGGCCGACAACA
|----|----|----|----|----|----|----|----|----|----|----|----|----|----| 280
TAGTCCCCGGTGCTACTCCCCTCGTCGGATCTTCTTGGGGATTAACTCTCGTCGCTCCACCGGCTGTTGT
  I  R  G  H  D  E  G  S  S  L  E  E  P  L  I  E  S  S  E  V  A  D  N

GGAAAGTCCAGGACCTTCAAGGCGAGGGAGGAATCCGGCTTCCGAATGGTAAACTGAAATGTGACGTCTG
|----|----|----|----|----|----|----|----|----|----|----|----|----|----| 350
CCTTTCAGGTCCTGGAAGTTCCGCTCCCTCCTTAGGCCGAAGGCTTACCATTTGACTTTACACTGCAGAC
  R  K  V  Q  D  L  Q  G  E  G  G  I  R  L  P  N  G  K  L  K  C  D  V  C

TGGCATGGTTTGCATTGGGCCCAATGTGCTTATGGTACATAAAAGGAGTCACACTGGTGAGCGGCCCTTC
|----|----|----|----|----|----|----|----|----|----|----|----|----|----| 420
ACCGTACCAAACGTAACCCGGGTTACACGAATACCATGTATTTTCCTCAGTGTGACCACTCGCCGGGAAG
   G  M  V  C  I  G  P  N  V  L  M  V  H  K  R  S  H  T  G  E  R  P  F

CACTGTAACCAGTGCGGAGCTTCTTTTACCCAGAAGGGCAACCTTCTGAGACAGATAAAGTTACACTCTG
|----|----|----|----|----|----|----|----|----|----|----|----|----|----| 490
GTGACATTGGTCACGCCTCGAAGAAAATGGGTCTTCCCGTTGGAAGACTCTGTGTATTTCAATGTGAGAC
   H  C  N  Q  C  G  A  S  F  T  Q  K  G  N  L  L  R  H  I  K  L  H  S

GAGAGAAGCCCTTCAAATGTCCTTTCTGTAGCTATGCTTGTAGAAGAAGGGACGCTCTCACAGGACACCT
|----|----|----|----|----|----|----|----|----|----|----|----|----|----| 560
CTCTCTTCGGGAAGTTTACAGGAAAGACATCGATACGAACATCTTCTTCCCTGCGAGAGTGTCCTGTGGA
   G  E  K  P  F  K  C  P  F  C  S  Y  A  C  R  R  R  D  A  L  T  G  H  L

CAGGACCCATTCTGTGGGTAAACCTCACAAGTGTAACTACTGTGGCCGAAGCTACAAGCAGCGCACGTCA
|----|----|----|----|----|----|----|----|----|----|----|----|----|----| 630
GTCCTGGGTAAGACACCCATTTGGAGTGTTCACATTGATGACACCGGCTTCGATGTTCGTCGCGTGCAGT
   R  T  H  S  V  G  K  P  H  K  C  N  Y  C  G  R  S  Y  K  Q  R  T  S
```

FIG. 12A

```
CTGGAGGAACACAAGGAACGCTGTCACAACTATCTCCAGAATGTCAGCATGGAGGCTGCCGGGCAGGTCA
                                                                      700
GACCTCCTTGTGTTCCTTGCGACAGTGTTGATAGAGGTCTTACAGTCGTACCTCCGACGGCCCGTCCAGT
  L  E  E  H  K  E  R  C  H  N  Y  L  Q  N  V  S  M  E  A  A  G  Q  V

TGAGTCACCATGTACCGCCTATGGAAGATTGTAAGGAACAAGAGCCTATCATGGACAACAATATTTCTCT
                                                                      770
ACTCAGTGGTACATGGCGGATACCTTCTAACATTCCTTGTTCTCGGATAGTACCTGTTGTTATAAAGAGA
  M  S  H  H  V  P  P  M  E  D  C  K  E  Q  E  P  I  M  D  N  N  I  S  L

GGTGCCTTTTGAGAGACCTGCTGTCATAGAGAAGCTCACGGCAAATATGGGAAAGCGCAAAAGCTCCACT
                                                                      840
CCACGGAAAACTCTCTGGACGACAGTATCTCTTCGAGTGCCGTTTATACCCTTTCGCGTTTTCGAGGTGA
   V  P  F  E  R  P  A  V  I  E  K  L  T  A  N  M  G  K  R  K  S  S  T

CCTCAGAAGTTTGTGGGGGAAAAGCTTATGCGATTCAGCTACCCAGATATTCATTTTGATATGAACTTAA
                                                                      910
GGAGTCTTCAAACACCCCCTTTTCGAATACGCTAAGTCGATGGGTCTATAAGTAAAACTATACTTGAATT
    P  Q  K  F  V  G  E  K  L  M  R  F  S  Y  P  D  I  H  F  D  M  N  L

CATATGAGAAGGAGGCTGAGCTGATGCAGTCTCATATGATGGACCAAGCCATCAACAATGCAATCACCTA
                                                                      980
GTATACTCTTCCTCCGACTCGACTACGTCAGAGTATACTACCTGGTTCGGTAGTTGTTACGTTAGTGGAT
   T  Y  E  K  E  A  E  L  M  Q  S  H  M  M  D  Q  A  I  N  N  A  I  T  Y

CCTTGGAGCTGAGGCCCTTCACCCTCTGATGCAGCATGCACCAAGCACAATCGCTGAGGTGGCCCCAGTT
                                                                      1050
GGAACCTCGACTCCGGGAAGTGGGAGACTACGTCGTACGTGGTTCGTGTTAGCGACTCCACCGGGGTCAA
    L  G  A  E  A  L  H  P  L  M  Q  H  A  P  S  T  I  A  E  V  A  P  V

ATAAGCTCAGCTTATTCTCAGGTCTATCATCCAAACAGGATAGAAAGACCCATTAGCAGGGAAACATCTG
                                                                      1120
TATTCGAGTCGAATAAGAGTCCAGATAGTAGGTTTGTCCTATCTTTCTGGGTAATCGTCCCTTTGTAGAC
   I  S  S  A  Y  S  Q  V  Y  H  P  N  R  I  E  R  P  I  S  R  E  T  S

ATAGTCACGAAAACAACATGGATGGCCCCATCTCTCTCATCAGACCAAAGAGTCGACCCCAGGAAAGAGA
                                                                      1190
TATCAGTGCTTTTGTTGTACCTACCGGGGTAGAGAGAGTAGTCTGGTTTCTCAGCTGGGGTCCTTTCTCT
  D  S  H  E  N  N  M  D  G  P  I  S  L  I  R  P  K  S  R  P  Q  E  R  E

GGCCTCGCCCAGCAATAGCTGCCTCGATTCTACTGACTCAGAAAGTAGCCATGATGACCGCCAGTCCTAC
                                                                      1260
CCGGAGCGGGTCGTTATCGACGGAGCTAAGATGACTGAGTCTTTCATCGGTACTACTGGCGGTCAGGATG
     A  S  P  S  N  S  C  L  D  S  T  D  S  E  S  S  H  D  D  R  Q  S  Y
```

FIG. 12B

```
CAAGGAAACCCTGCCTTAAATCCCAAGAGGAAACAAAGCCCAGCTTACATGAAGGAGGATGTCAAGGCTT
                                                                        1330
GTTCCTTTGGGACGGAATTTAGGGTTCTCCTTTGTTTCGGGTCGAATGTACTTCCTCCTACAGTTCCGAA
  Q  G  N  P  A  L  N  P  K  R  K  Q  S  P  A  Y  M  K  E  D  V  K  A

TGGATGCTACCAAGGCCCCCAAGGGCTCTCTGAAGGACATCTATAAGGTTTTCAATGGAGAAGGAGAACA
                                                                        1400
ACCTACGATGGTTCCGGGGGTTCCCGAGAGACTTCCTGTAGATATTCCAAAAGTTACCTCTTCCTCTTGT
  L  D  A  T  K  A  P  K  G  S  L  K  D  I  Y  K  V  F  N  G  E  G  E  Q

GATAAGGGCCTTCAAGTGTGAGCACTGCCGAGTCCTTTTTCTAGACCATGTCATGTACACCATTCACATG
                                                                        1470
CTATTCCCGGAAGTTCACACTCGTGACGGCTCAGGAAAAAGATCTGGTACAGTACATGTGGTAAGTGTAC
   I  R  A  F  K  C  E  H  C  R  V  L  F  L  D  H  V  M  Y  T  I  H  M

GGTTGCCATGGCTACCGGGACCCACTGGAATGCAACATCTGTGGCTACAGAAGCCAGGACCGCTACGAAT
                                                                        1540
CCAACGGTACCGATGGCCCTGGGTGACCTTACGTTGTAGACACCGATGTCTTCGGTCCTGGCGATGCTTA
   G  C  H  G  Y  R  D  P  L  E  C  N  I  C  G  Y  R  S  Q  D  R  Y  E

TTTCATCACACATTGTTGGGGGGCAGCACACATTCCACTAGGCGTTTGCATTCCAAGG
                                                           1598
AAAGTAGTGTGTAACAACCCCCCGTCGTGTGTAAGGTGATCCGCAAACGTAAGGTTCC
  F  S  S  H  I  V  G  G  Q  H  T  F  H     A  F  A  F  Q  G
```

FIG. 12C

```
ATGGAAACAGACGCTATTGATGGCTATATAACATGTGACAATGAGCTTTCACCCGAAGGGGAACACGCCA
                                                                       70
TACCTTTGTCTGCGATAACTACCGATATATTGTACACTGTTACTCGAAAGTGGGCTTCCCCTTGTGCGGT
  M  E  T  D  A  I  D  G  Y  I  T  C  D  N  E  L  S  P  E  G  E  H  A

ATATGGCCATTGACCTCACCTCAAGCACGCCCAATGGACAGCACGCCTCGCCAAGTCACATGACAAGCAC
                                                                       140
TATACCGGTAACTGGAGTGGAGTTCGTGCGGGTTACCTGTCGTGCGGAGCGGTTCAGTGTACTGTTCGTG
  N  M  A  I  D  L  T  S  S  T  P  N  G  Q  H  A  S  P  S  H  M  T  S  T

AAATTCTGTAAAGCTGGAAATGCAGAGTGATGAAGAGTGTGACAGGCAGCCCCTGAGCCGTGAGGATGAG
                                                                       210
TTTAAGACATTTCGACCTTTACGTCTCACTACTTCTCACACTGTCCGTCGGGGACTCGGCACTCCTACTC
   N  S  V  K  L  E  M  Q  S  D  E  E  C  D  R  Q  P  L  S  R  E  D  E

ATCAGGGGCCACGATGAGGGGAGCAGCCTAGAAGAACCCCTAATTGAGAGCAGCGAGGTGGCCGACAACA
                                                                       280
TAGTCCCCGGTGCTACTCCCCTCGTCGGATCTTCTTGGGGATTAACTCTCGTCGCTCCACCGGCTGTTGT
  I  R  G  H  D  E  G  S  S  L  E  E  P  L  I  E  S  S  E  V  A  D  N

GGAAAGTCCAGGACCTTCAAGGCGAGGGAGGAATCCGGCTTCCGAATGGTGAGCGGCCCTTCCACTGTAA
                                                                       350
CCTTTCAGGTCCTGGAAGTTCCGCTCCCTCCTTAGGCCGAAGGCTTACCACTCGCCGGGAAGGTGACATT
  R  K  V  Q  D  L  Q  G  E  G  G  I  R  L  P  N  G  E  R  P  F  H  C  N

CCAGTGCGGAGCTTCTTTTACCCAGAAGGGCAACCTTCTGAGACACATAAAGTTACACTCTGGAGAGAAG
                                                                       420
GGTCACGCCTCGAAGAAAATGGGTCTTCCCGTTGGAAGACTCTGTGTATTTCAATGTGAGACCTCTCTTC
   Q  C  G  A  S  F  T  Q  K  G  N  L  L  R  H  I  K  L  H  S  G  E  K

CCCTTCAAATGTCCTTTCTGTAGCTATGCTTGTAGAAGAAGGGACGCTCTCACAGGACACCTCAGGACCC
                                                                       480
GGGAAGTTTACAGGAAAGACATCGATACGAACATCTTCTTCCCTGCGAGAGTGTCCTGTGGAGTCCTGGG
   P  F  K  C  P  F  C  S  Y  A  C  R  R  R  D  A  L  T  G  H  L  R  T

ATTCTGTGGGTAAACCTCACAAGTGTAACTACTGTGGCCGAAGCTACAAGCAGCGCACGTCACTGGAGGA
                                                                       560
TAAGACACCCATTTGGAGTGTTCACATTGATGACACCGGCTTCGATGTTCGTCGCGTGCAGTGACCTCCT
  H  S  V  G  K  P  H  K  C  N  Y  C  G  R  S  Y  K  Q  R  T  S  L  E  E

ACACAAGGAACGCTGTCACAACTATCTCCAGAATGTCAGCATGGAGGCTGCCGGGCAGGTCATGAGTCAC
                                                                       630
TGTGTTCCTTGCGACAGTGTTGATAGAGGTCTTACAGTCGTACCTCCGACGGCCCGTCCAGTACTCAGTG
   H  K  E  R  C  H  N  Y  L  Q  N  V  S  M  E  A  A  G  Q  V  M  S  H
```

FIG. 13A

```
CATGTACCGCCTATGGAAGATTGTAAGGAACAAGAGCCTATCATGGACAACAATATTTCTCTGGTGCCTT
                                                                       700
GTACATGGCGGATACCTTCTAACATTCCTTGTTCTCGGATAGTACCTGTTGTTATAAAGAGACCACGGAA
  H  V  P  P  M  E  D  C  K  E  Q  E  P  I  M  D  N  N  I  S  L  V  P

TTGAGAGACCTGCTGTCATAGAGAAGCTCACGGCAAATATGGGAAAGCGCAAAAGCTCCACTCCTCAGAA
                                                                       770
AACTCTCTGGACGACAGTATCTCTTCGAGTGCCGTTTATACCCTTTCGCGTTTTCGAGGTGAGGAGTCTT
  F  E  R  P  A  V  I  E  K  L  T  A  N  M  G  K  R  K  S  S  T  P  Q  K

GTTTGTGGGGGAAAAGCTTATGCGATTCAGCTACCCAGATATTCATTTTGATATGAACTTAACATATGAG
                                                                       840
CAAACACCCCCTTTTCGAATACGCTAAGTCGATGGGTCTATAAGTAAAACTATACTTGAATTGTATACTC
   F  V  G  E  K  L  M  R  F  S  Y  P  D  I  H  F  D  M  N  L  T  Y  E

AAGGAGGCTGAGCTGATGCAGTCTCATATGATGGACCAAGCCATCAACAATGCAATCACCTACCTTGGAG
                                                                       910
TTCCTCCGACTCGACTACGTCAGAGTATACTACCTGGTTCGGTAGTTGTTACGTTAGTGGATGGAACCTC
  K  E  A  E  L  M  Q  S  H  M  M  D  Q  A  I  N  N  A  I  T  Y  L  G

CTGAGGCCCTTCACCCTCTGATGCAGCATGCACCAAGCACAATCGCTGAGGTGGCCCCAGTTATAAGCTC
                                                                       980
GACTCCGGGAAGTGGGAGACTACGTCGTACGTGGTTCGTGTTAGCGACTCCACCGGGGTCAATATTCGAG
  A  E  A  L  H  P  L  M  Q  H  A  P  S  T  I  A  E  V  A  P  V  I  S  S

AGCTTATTCTCAGGTCTATCATCCAAACAGGATAGAAAGACCCATTAGCAGGGAAACATCTGATAGTCAC
                                                                       1050
TCGAATAAGAGTCCAGATAGTAGGTTTGTCCTATCTTTCTGGGTAATCGTCCCTTTGTAGACTATCAGTG
   A  Y  S  Q  V  Y  H  P  N  R  I  E  R  P  I  S  R  E  T  S  D  S  H

GAAAACAACATGGATGGCCCCATCTCTCTCATCAGACCAAAGAGTCGACCCCAGGAAAGAGAGGCCTCGC
                                                                       1120
CTTTTGTTGTACCTACCGGGGTAGAGAGAGTAGTCTGGTTTCTCAGCTGGGGTCCTTTCTCTCCGGAGCG
   E  N  N  M  D  G  P  I  S  L  I  R  P  K  S  R  P  Q  E  R  E  A  S

CCAGCAATAGCTGCCTCGATTCTACTGACTCAGAAAGTAGCCATGATGACCGCCAGTCCTACCAAGGAAA
                                                                       1190
GGTCGTTATCGACGGAGCTAAGATGACTGAGTCTTTCATCGGTACTACTGGCGGTCAGGATGGTTCCTTT
  P  S  N  S  C  L  D  S  T  D  S  E  S  S  H  D  D  R  Q  S  Y  Q  G  N

CCCTGCCTTAAATCCCAAGAGGAAACAAAGCCCAGCTTACATGAAGGAGGATGTCAAGGCTTTGGATGCT
                                                                       1260
GGGACGGAATTTAGGGTTCTCCTTTGTTTCGGGTCGAATGTACTTCCTCCTACAGTTCCGAAACCTACGA
   P  A  L  N  P  K  R  K  Q  S  P  A  Y  M  K  E  D  V  K  A  L  D  A
```

FIG. 13B

```
ACCAAGGCCCCCAAGGGCTCTCTGAAGGACATCTATAAGGTTTTCAATGGAGAAGGAGAACAGATAAGGG
                                                                      1330
TGGTTCCGGGGGTTCCCGAGAGACTTCCTGTAGATATTCCAAAAGTTACCTCTTCCTCTTGTCTATTCCC
  T  K  A  P  K  G  S  L  K  D  I  Y  K  V  F  N  G  E  G  E  D  I  R

CCTTCAAGTGTGAGCACTGCCGAGTCCTTTTTCTAGACCATGTCATGTACACCATTCACATGGGTTGCCA
                                                                      1400
GGAAGTTCACACTCGTGACGGCTCAGGAAAAAGATCTGGTACAGTACATGTGGTAAGTGTACCCAACGGT
  A  F  K  C  E  H  C  R  V  L  F  L  D  H  V  M  Y  T  I  H  M  G  C  H

TGGCTACCGGGACCCACTGGAATGCAACATCTGTGGCTACAGAAGCCAGGACCGCTACGAATTTTCATCA
                                                                      1470
ACCGATGGCCCTGGGTGACCTTACGTTGTAGACACCGATGTCTTCGGTCCTGGCGATGCTTAAAAGTAGT
   G  Y  R  D  P  L  E  C  N  I  C  G  Y  R  S  Q  D  R  Y  E  F  S  S

CACATTGTTGGGGGGCAGCACACATTCCACTAGGCGTTTGCATTCCAAGG
                                                    1520
GTGTAACAACCCCCGTCGTGTGTAAGGTGATCCGCAAACGTAAGGTTCC
  H  I  V  G  G  Q  H  T  F  H     A  F  A  F  Q  G
```

FIG. 13C

```
1/1                                                31/11
GCC CGG GCA GGT CGC ATT GCT ATA GCA CTG ACT GAC CTC TCT CTC TCT CTT TTT TTT CCT
 A   R   A   G   R   I   A   I   A   L   T   D   L   S   L   S   L   F   F   P
61/21                                              91/31
CTT TCC TGA AAC CCG ACA TTG TCA CCT CCT CTT TGA GGG TTA GAA GAA GCT GAG ATC TCC
 L   S   *   N   P   T   L   S   P   P   L   *   G   L   E   E   A   E   I   S
121/41                                             151/51
CGA CAG AGC TGG AAA TGG TGA TGA ATC TTT TTT AAT CAA AGG ACA ATT TCT TTT CAT TGC
 R   Q   S   W   K   W   *   *   I   F   F   N   Q   R   T   I   S   F   H   C
181/61                                             211/71
ACT TTG ACT ATG GAA ACA GAG GCT ATT GAT GGC TAT ATA ACG TGT GAC AAT GAG CTT TCA
 T   L   T   M   E   T   E   A   I   D   G   Y   I   T   C   D   N   E   L   S
241/81                                             271/91
CCC GAA AGG GAG CAC TCC AAT ATG GCA ATT GAC CTC ACC TCA AGC ACA CCC AAT GGA CAG
 P   E   R   E   H   S   N   M   A   I   D   L   T   S   S   T   P   N   G   Q
301/101                                            331/111
CAT GCC TCA CCA AGT CAC ATG ACA AGC ACA GAT TCA GTA AAG CTA GAA ATG CAG AGT GAT
 H   A   S   P   S   H   M   T   S   T   D   S   V   K   L   E   M   Q   S   D
361/121                                            391/131
GAA GAG TGT GAC AGG AAA CCC CTG AGC CGT GAA GAT GAG ATC AGG GGC CAT GAT GAG GGT
 E   E   C   D   R   K   P   L   S   R   E   D   E   I   R   G   H   D   E   G
421/141                                            451/151
AGC AGC CTA GAA GAA CCC CTA ATT GAG AGC AGC GAG GTG GCT GAC AAC AGG GAA GTC CAG
 S   S   L   E   E   P   L   I   E   S   S   E   V   A   D   N   R   E   V   Q
481/161                                            511/171
GAG CTT CAA GGC GAG GGA GGA ATC CGG CTT CCG AAT GGT AAA CTG AAA TGT GAC GTC TGT
 E   L   Q   G   E   G   G   I   R   L   P   N   G   K   L   K   C   D   V   C
541/181                                            571/191
GGC ATG GTT TGC ATT GGG CCC AAT GTG CTT ATG GTA CAT AAA AGG AGT CAC ACT GGT GAA
 G   M   V   C   I   G   P   N   V   L   M   V   H   K   R   S   H   T   G   E
601/201                                            631/211
CGC CCC TTC CAC TGT AAC CAG TGT GGA GCT TCT TTT ACT CAG AAG GGC AAC CTT CTG AGA
 R   P   F   H   C   N   Q   C   G   A   S   F   T   Q   K   G   N   L   L   R
661/221                                            691/231
CAC ATA AAG TTA CAC TCT GGA GAG AAG CCG TTC AAA TGT CCT TTC TGT AGT CAC GCC TGT
 H   I   K   L   H   S   G   E   K   P   F   K   C   P   F   C   S   H   A   C
721/241                                            751/251
AGA AGA AGG GAC GCC CTC ACA GGA TAC CTC AGG ACC CAT TCT GTG GGT AAA CCT CAC AAG
 R   R   R   D   A   L   T   G   Y   L   R   T   H   S   V   G   K   P   H   K
781/261                                            811/271
TGC AAC TAC TGT GGA CGA AGC TAC AAG CAG CGC AGT TCA CTG GAG GAG CAC AAG GAA CGC
 C   N   Y   C   G   R   S   Y   K   Q   R   S   S   L   E   E   H   K   E   R
841/281                                            871/291
TGC CAC AAC TAT CTC CAG AAT GTC AGC ATG GAG GCT GCT GGG CAG GTC ATG AGT CAC CAT
 C   H   N   Y   L   Q   N   V   S   M   E   A   A   G   Q   V   M   S   H   H
901/301                                            931/311
GTA CCT CCT ATG GAA GAT TGT AAG GAA CAA GAG CCT ATT ATG GAC AAC AAT ATT TCT CTG
 V   P   P   M   E   D   C   K   E   Q   E   P   I   M   D   N   N   I   S   L
961/321                                            991/331
GTG CCT TTT GAG AGA CCT GCT GTC ATA GAG AAG CTC ACG GGG AAT ATG GGA AAA CGT AAA
 V   P   F   E   R   P   A   V   I   E   K   L   T   G   N   M   G   K   R   K
1021/341                                           1051/351
AGC TCC ACT CCA CAA AAG TTT GTG GGG GAA AAG CTC ATG CGA TTC AGC TAC CCA GAT ATT
 S   S   T   P   Q   K   F   V   G   E   K   L   M   R   F   S   Y   P   D   I
1081/361                                           1111/371
CAC TTT GAT ATG AAC TTA ACA TAT GAG AAG GAG GCT GAG CTG ATG CAG TCT CAT ATG ATG
 H   F   D   M   N   L   T   Y   E   K   E   A   E   L   M   Q   S   H   M   M
1141/381                                           1171/391
GAC CAA GCC ATC AAC AAT GCA ATC ACC TAC CTT GGA GCT GAG GCC CTT CAC CCT CTG ATG
 D   Q   A   I   N   N   A   I   T   Y   L   G   A   E   A   L   H   P   L   M
1201/401                                           1231/411
CAG CAC CCG CCA AGC ACA ATC GCT GAA GTG GCC CCA GTT ATA AGC TCA GCT TAT TCT CAG
 Q   H   P   P   S   T   I   A   E   V   A   P   V   I   S   S   A   Y   S   Q
```

FIG. 14A

```
1261/421                                    1291/431
GTC TAT CAT CCA AAT AGG ATA GAA AGA CCC ATT AGC AGG GAA ACT GCT GAT AGT CAT GAA
 V   Y   H   P   N   R   I   E   R   P   I   S   R   E   T   A   D   S   H   E
1321/441                                    1351/451
AAC AAC ATG GAT GGC CCC ATC TCT CTC ATC AGA CCA AAG AGT CGA CCC CAG GAA AGA GAG
 N   N   M   D   G   P   I   S   L   I   R   P   K   S   R   P   Q   E   R   E
1381/461                                    1411/471
GCC TCT CCC AGC AAT AGC TGC CTG GAT TCC ACT GAC TCA GAA AGC AGC CAT GAT GAC CAC
 A   S   P   S   N   S   C   L   D   S   T   D   S   E   S   S   H   D   D   H
1441/481                                    1471/491
CAG TCC TAC CAA GGA CAC CCT GCC TTA AAT CCC AAG AGG AAA CAA AGC CCA GCT TAC ATG
 Q   S   Y   Q   G   H   P   A   L   N   P   K   R   K   Q   S   P   A   Y   M
1501/501                                    1531/511
AAG GAG GAT GTC AAA GCT TTG GAT ACT ACC AAG GCT CCT AAG GGC TCT CTG AAG GAC ATC
 K   E   D   V   K   A   L   D   T   T   K   A   P   K   G   S   L   K   D   I
1561/521                                    1591/531
TAC AAG GTC TTC AAT GGG GAA GGA GAA CAG ATT AGG GCC TTC AAG TGT GAG CAC TGC CGA
 Y   K   V   F   N   G   E   G   E   Q   I   R   A   F   K   C   E   H   C   R
1621/541                                    1651/551
GTC CTT TTC CTA GAC CAT GTC ATG TAC ACC ATT CAC ATG GGT GCC ATG GCC TAC CGG GAC
 V   L   F   L   D   H   V   M   Y   T   I   H   M   G   C   H   G   Y   R   D
1681/561                                    1711/571
CCA CTG GAA TGT AAC ATC TGT GGC TAC AGA AGC CAG GAC CGT TAT GAG TTT TCA TCA CAC
 P   L   E   C   N   I   C   G   Y   R   S   Q   D   R   Y   E   F   S   S   H
1741/581                                    1771/591
ATT GTT CGA GGG GAG CAC ACA TTC CAC TAG GCC TTT TCA TTC CAA AGG GGA CCC TAT GAA
 I   V   R   G   E   H   T   F   H   *   A   F   S   F   Q   R   G   P   Y   E
1801/601                                    1831/611
GTA AAG ACT GCA CAT GAA GAA ATA CTG CAC TTA CAA TCC CAC CTT TCC TCA AAT GTT GTA
 V   K   T   A   H   E   E   I   L   H   L   Q   S   H   L   S   S   N   V   V
1861/621                                    1891/631
CCT TTT ATT TTT TTA ATA TAA TAC TGG TGA TAA TCT TAT TTT GTG GAG CAG TGT CAT TTG
 P   F   I   F   L   I   *   Y   W   *   *   S   Y   F   V   E   Q   C   H   L
1921/641
CTC TGC T
 L   C
```

FIG. 14B

```
  1 ATGGAAACAGACGCTATTGATGGCTATATAACATGTGACAATGAGCTTTC  50
    ||||||||||| ||||||||||||||||||||| ||||||||||||||||
190 ATGGAAACAGAGGCTATTGATGGCTATATAACGTGTGACAATGAGCTTTC 239

51 ACCCGAAGGGGAACACGCCAATATGGCCATTGACCTCACCTCAAGCACGC 100
    ||||||| |||| ||| ||||||||||| |||||||||||||||||||| |
240 ACCCGAAAGGGAGCACTCCAATATGGCAATTGACCTCACCTCAAGCACAC 289

101 CCAATGGACAGCAcGCCTCGCCAAGTCACATGACAAGCACAAATTCTGTA 150
    ||||||||||||| ||||| ||||||||||||||||||||| |||| |||
290 CCAATGGACAGCATGCCTCACCAAGTCACATGACAAGCACAGATTCAGTA 339

151 AAGCTGGAAATGCAGAGTGATGAAGAGTGTGACAGGCAGCCCCTGAGCCG 200
    ||||| ||||||||||||||||||||||||||||||| | ||||||||||
340 AAGCTAGAAATGCAGAGTGATGAAGAGTGTGACAGGAAACCCCTGAGCCG 389

201 TGAGGATGAGATCAGGGGCCACGATGAGGGGAGCAGCCTAGAAGAacCCC 250
    ||| |||||||||||||||| |||||||| ||||||||||||||||||||
390 TGAAGATGAGATCAGGGGCCATGATGAGGGTAGCAGCCTAGAAGAACCCC 439

251 TAATTGAGAGCAGCGAGGTGGCCGACAACAGGAAAGTCCAGGACCTTCAA 300
    |||||||||||||||||||||||| |||||||| ||||||||| ||||||
440 TAATTGAGAGCAGCGAGGTGGCTGACAACAGGGAAGTCCAGGAGCTTCAA 489

301 GGCGAGGGAGGAATCCGGCTTCCGAATGGTAAACTGAAATGTGACGTCTG 350
    ||||||||||||||||||||||||||||||||||||||||||||||||||
490 GGCGAGGGAGGAATCCGGCTTCCGAATGGTAAACTGAAATGTGACGTCTG 539

351 TGGCATGGTTTGCATTGGGCCCAATGTGCTTATGGTACATAAAAGGAGTC 400
    ||||||||||||||||||||||||||||||||||||||||||||||||||
540 TGGCATGGTTTGCATTGGGCCCAATGTGCTTATGGTACATAAAAGGAGTC 589

401 ACACTGGTGAGCGGCCCTTCCACTGTAACCAGTGCGGAGCTTCTTTTACC 450
    ||||||||| || |||||||||||||||||||| ||||||||||||||||
590 ACACTGGTGAACGCCCCTTCCACTGTAACCAGTGTGGAGCTTCTTTTACT 639

451 CAGAAGGGCAACCTTCTGAGACACATAAAGTTACACTCTGGAGAGAAGCC 500
    ||||||||||||||||||||||||||||||||||||||||||||||||||
640 CAGAAGGGCAACCTTCTGAGACACATAAAGTTACACTCTGGAGAGAAGCC 689

501 CTTCAAATGTCCTTTCTGTAGCTATGCTTGTAGAAGAAGGGACGCTCTCA 550
    |||||||||||||||||||||| | || ||||||||||||||||| ||||
690 GTTCAAATGTCCTTTCTGTAGTCACGCCTGTAGAAGAAGGGACGCCCTCA 739

551 CAGGACACCTCAGGACCCATTCTGTGGGTAAACCTCACAAGTGTAACTAC 600
    ||||| |||||||||||||||||||||||||||||||||||||| |||||
740 CAGGATACCTCAGGACCCATTCTGTGGGTAAACCTCACAAGTGCAACTAC 789

601 TGTGGCCGAAGCTACAAGCAGCGCACGTCACTGGAGGAACACAAGGAACG 650
    ||||| |||||||||||||||||||| ||||||||||| |||||||||||
790 TGTGGACGAAGCTACAAGCAGCGCAGTTCACTGGAGGAGCACAAGGAACG 839

651 CTGTCACAACTATCTCCAGAATGTCAGCATGGAGGCTGCCGGGCAGGTCA 700
    ||| ||||||||||||||||||||||||||||||||||| |||||||||| 
840 CTGCCACAACTATCTCCAGAATGTCAGCATGGAGGCTGCTGGGCAGGTCA 889

701 TGAGTCACCATGTACCGCCTATGGAAGATTGTAAGGAACAAGAGCCTATC 750
    ||||||||||||||| | |||||||||||||||||||||||||||||||
890 TGAGTCACCATGTACCTCCTATGGAAGATTGTAAGGAACAAGAGCCTATT 939

751 ATGGACAACAATATTTCTCTGGTGCCTTTTGAGAGACCTGCTGTCATAGA 800
    ||||||||||||||||||||||||||||||||||||||||||||||||||
```

FIG. 15A

```
 940 ATGGACAACAATATTTCTCTGGTGCCTTTTGAGAGACCTGCTGTCATAGA  989
 801 GAAGCTCACGGCAAATATGGGAAAGCGCAAAAGCTCCACTCCTCAGAAGT  850
     |||||||||||  ||||||||||| || |||||||||||||| || ||||
 990 GAAGCTCACGGGGAATATGGGAAAACGTAAAAGCTCCACTCCACAAAAGT 1039

851 TTGTGGGGAAAAGCTTATGCGATTCAGCTACCCAGATATTCATTTTGAT   900
     ||||||||||||||| ||||||||||||||||||||||||||| ||||||
1040 TTGTGGGGAAAAGCTCATGCGATTCAGCTACCCAGATATTCACTTTGAT  1089

901 ATGAACTTAACATATGAGAAGGAGGCTGAGCTGATGCAGTCTCATATGAT  950
     ||||||||||||||||||||||||||||||||||||||||||||||||||
1090 ATGAACTTAACATATGAGAAGGAGGCTGAGCTGATGCAGTCTCATATGAT 1139

951 GGACCAAGCCATCAACAATGCAATCACCTACCTTGGAGCTGAGGCCCTTC 1000
     ||||||||||||||||||||||||||||||||||||||||||||||||||
1140 GGACCAAGCCATCAACAATGCAATCACCTACCTTGGAGCTGAGGCCCTTC 1189

1001 ACCCTCTGATGCAGCATGCACCAAGCACAATCGCTGAGGTGGCCCCAGTT 1050
     |||||||||||||| | |||||||||||||||||||| ||||||||||||
1190 ACCCTCTGATGCAGCACCCGCCAAGCACAATCGCTGAAGTGGCCCCAGTT 1239

1051 ATAAGCTCAGCTTATTCTCAGGTCTATCATCCAAACAGGATAGAAAGACC 1100
     |||||||||||||||||||||||||||||||||||| |||||||||||||
1240 ATAAGCTCAGCTTATTCTCAGGTCTATCATCCAAATAGGATAGAAAGACC 1289

1101 CATTAGCAGGGAAACATCTGATAGTCACGAAAACAACATGGATGGCCCCA 1150
     ||||||||||||||||| ||||||||| ||||||||||||||||||||||
1290 CATTAGCAGGGAAACTGCTGATAGTCATGAAAACAACATGGATGGCCCCA 1339

1151 TCTCTCTCATCAGACCAAAGAGTCGACCCCAGGAAAGAGAGGCCTCGCCC 1200
     |||||||||||||||||||||||||||||||||||||||||||||| |||
1340 TCTCTCTCATCAGACCAAAGAGTCGACCCCAGGAAAGAGAGGCCTCTCCC 1389

1201 AGCAATAGCTGCCTCGATTCTACTGACTCAGAAAGTAGCCATGATGACCG 1250
     ||||||||||||| ||||| |||||||||||||||| |||||||||||
1390 AGCAATAGCTGCCTGGATTCCACTGACTCAGAAAGCAGCCATGATGACCA 1439

1251 CCAGTCCTACCAAGGAAACCCTGCCTTAAATCCCAAGAGGAAACAAAGCC 1300
     |||||||||||||| ||||||||||||||||||||||||||||||||||
1440 CCAGTCCTACCAAGGACACCCTGCCTTAAATCCCAAGAGGAAACAAAGCC 1489

1301 CAGCTTACATGAAGGAGGATGTCAAGGCTTTGGATGCTACCAAGGCCCCC 1350
     |||||||||||||||||||||||| ||||||||| ||||||||||| ||
1490 CAGCTTACATGAAGGAGGATGTCAAAGCTTTGGATACTACCAAGGCTCCT 1539

1351 AAGGGCTCTCTGAAGGACATCTATAAGGTTTTCAATGGAGAAGGAGAACA 1400
     ||| |||||||||||||||||| ||||| |||||||| |||||||||||
1540 AAGGGCTCTCTGAAGGACATCTACAAGGTCTTCAATGGGGAAGGAGAACA 1589

1401 GATAAGGGCCTTCAAGTGTGAGCACTGCCGAGTCCTTTTTCTAGACCATG 1450
     ||| ||||||||||||||||||||||||||||||||||| ||||||||||
1590 GATTAGGGCCTTCAAGTGTGAGCACTGCCGAGTCCTTTTCCTAGACCATG 1639

1451 TCATGTACACCATTCACATGGGTTGCCATGGCTACCGGGACCCACTGGAA 1500
     ||||||||||||||||||||||||||||||||||||||||||||||||||
1640 TCATGTACACCATTCACATGGGTTGCCATGGCTACCGGGACCCACTGGAA 1689

1501 TGCAACATCTGTGGCTACAGAAGCCAGGACCGCTACGAATTTTCATCACA 1550
     || ||||||||||||||||||||||||||||| || ||||||||||||||
1690 TGTAACATCTGTGGCTACAGAAGCCAGGACCGTTATGAGTTTTCATCACA 1739

1551 CATTGTTGGGGGGCAGCACACATTCCACTAGGCGTTTGCATTCCAAGG   1598
     ||||||| | ||| ||||||||||||||||||| |||| |||||||| |
1740 CATTGTTCGAGGGGAGCACACATTCCACTAGGCCTTTTCATTCCAAAG  1787
```

FIG. 15B

```
  1 METEAIDGYITCDNELSPEREHSNMAIDLTSSTPNGQHASPSHMTSTDSV  50
    |||||||||||||||||||||||||||||||||||||||||||||||||
  1 METEAIDGYITCDNELSPEREHSNMAIDLTSSTPNGQHASPSHMTSTDSV  50

51 KLEMQSDEECDRKPLSREDEIRGHDEGSSLEEPLIESSEVADNREVQELQ 100
    |||||||||||||||||||||||||||||||||||||||||||||||||
 51 KLEMQSDEECDRKPLSREDEIRGHDEGSSLEEPLIESSEVADNREVQELQ 100

101 GEGGIRLPNGKLKCDVCGMVCIGPNVLMVHKRSHTGERPFHCNQCGASFT 150
    |||||||||||||||||||||||||||||||||||||||||||||||||
101 GEGGIRLPNGKLKCDVCGMVCIGPNVLMVHKRSHTGERPFHCNQCGASFT 150

151 QKGNLLRHIKLHSGEKPFKCPFCSHACRRRDALTGYLRTHSVGKPHKCNY 200
    |||||||||||||||||||||||||||||||||||||||||||||||||
151 QKGNLLRHIKLHSGEKPFKCPFCSHACRRRDALTGYLRTHSVGKPHKCNY 200

201 CGRSYKQRSSLEEHKERCHNYLQNVSMEAAGQVMSHHVPPMEDCKEQEPI 250
    |||||||||||||||||||||||||||||||||||||||||||||||||
201 CGRSYKQRSSLEEHKERCHNYLQNVSMEAAGQVMSHHVPPMEDCKEQEPI 250

251 MDNNISLVPFERPAVIEKLTGNMGKRKSSTPQKFVGEKLMRFSYPDIHFD 300
    |||||||||||||||||||||||||||||||||||||||||||||||||
251 MDNNISLVPFERPAVIEKLTGNMGKRKSSTPQKFVGEKLMRFSYPDIHFD 300

301 MNLTYEKEAELMQSHMMDQAINNAITYLGAEALHPLMQHPPSTIAEVAPV 350
    |||||||||||||||||||||||||||||||||||||||||||||||||
301 MNLTYEKEAELMQSHMMDQAINNAITYLGAEALHPLMQHPPSTIAEVAPV 350

351 ISSAYSQVYHPNRIERPISRETADSHENNMDGPISLIRPKSRPQEREASP 400
    |||||||||||||||||||||||||||||||||||||||||||||||||
351 ISSAYSQVYHPNRIERPISRETADSHENNMDGPISLIRPKSRPQEREASP 400

401 SNSCLDSTDSESSHDDHQSYQGHPALNPKRKQSPAYMKEDVKALDTTKAP 450
    |||||||||||||||||||||||||||||||||||||||||||||||||
401 SNSCLDSTDSESSHDDHQSYQGHPALNPKRKQSPAYMKEDVKALDTTKAP 450

451 KGSLKDIYKVFNGEGEQIRAFKCEHCRVLFLDHVMYTIHMGCHGYRDPLE 500
    |||||||||||||||||||||||||||||||||||||||||||||||||
451 KGSLKDIYKVFNGEGEQIRAFKCEHCRVLFLDHVMYTIHMGCHGYRDPLE 500

501 CNICGYRSQDRYEFSSHIVRGEHTFH 526
    ||||||||||||||||||||||||||
501 CNICGYRSQDRYEFSSHIVRGEHTFH 526
```

FIG. 16

```
         1                                                             50                                                       100
DAED     ----------  ---MESLFCE  SSGDSSLEKE  FLGAPVGPSV  STPNSQHSSP    SRSLSANSIK  VEMYSDEESS  RL.LGPDERL  LDKDDSVIVE  DSLSEPLGYC
HEL      ---MHCTLTM  ETDAIDGYIT  CQNELSPEGE  HANMAIDLTS  STPNGQQASP    SHMTSTNSVK  LEMQSDEECQ  RQPLSREDEI  RGHDEGSSLE  EALIESSEVA
AIO      -MEDIQPTVE  LKSTEEQPLP  TESPDALNDY  SLPKPHELEN  VDSREAPANE    DEDAGEDSMK  VKDEYSDRDE  N..IMKPEPM  GDAEESEM.P  YSYAREYSDY
IK       MDVDEGQDMS  QVSGKESPPV  SDTPDE.GDE  PMPVPEDLST  TSGAQQNSKS    DRGMA.SNVK  VETQSDEENG  R..ACEMNGE  ECAEDLRMLD  ASGEKMNGSH 101                                                           150                                                      200
DAED     DGSGPEP.HS  PGGIRLPNGK  LKCDVCGMVC  IGPNVLMVHK  RSHTGERPFH    CNQCGASFTQ  KGNLLRHIKL  HSGEKPFKCP  FCNYACRRRD  ALTGHLRTHS
HEL      DNRKVQDLQG  ERGIRLPNGK  LKCDVCGMVC  IGPNVLMVHK  RSHTGERPFH    CNQCGRSFTQ  KGNLLRHIKL  HSGEKPFKCP  FCSYACRRRD  ALTGHLRTHS
AIO      ESIKLERHVP  YDNSRPTSGK  MNCDVCGLSC  ISFNVLMVHK  RSHTGERPFQ    CNQCGASFTQ  KGNLLRHIKL  HTGEKPFKCH  LCNYACQRRD  ALTGHLRTHS
IK       RDQGSSALSG  VGGIRLPNGK  LKCDICGIVC  IGPNVLMVHK  RSHTGERPFQ    CNQCGASFTQ  KGNLLRHIKL  HSGEKPFKCH  LCNYACRRRD  ALTGHLRTHS 201                                                           250                                                      300
DAED     VSSPTVGKPY  KCNYCGRSYK  QQSTLEEHKE  RCHNYLQSLS  TDA..QALTG    Q..PGDEIRD  LEMVPDSMLH  .PSTERPTFI  DRLANSLTKR  KRSTPQKFVG
HEL      .....VGKPH  KCNYCGRSYK  QRTSLEEHKE  RCHNYLQNVS  MEAAGQVMSH    HVPPMEDCKE  QEPIMDNNIS  LVAFERPAVI  EKLTANMGKR  KSSTPQKFVG
AIO      .....VEKPY  KCEFCGRSYK  QRSSLEEHKE  RCRAFLQNPD  LGDAASV...    EARHIK....  .AEM......  ..GSERALVL  DRLASNVAKR  KSSMPQKFIG
IK       .....VGKPH  KCGYCGRSYK  QRSSLEEHKE  RCHNYLESMG  LPGVCPVIKE    ETNHNEMAED  LCKI......  ..GAERSLVL  DRLASNVAKR  KSSMPQKFLG 301                                                           350                                                      400
DAED     EKQMRFSLSD  LPYDVNASGG  YEKDVELVAH  HGLEPGFGGS  LAFVGTEHLR    PLRLPPTNCI  SELTPVISSV  YTQMPIPSR  LELPGSREAG  EGPEDLGDGG
HEL      EKLMRFSYPD  IHFHMNLT..  ..YEKEAELMQS  HMMDQAINNA  ITYLGAEALH  PLMQHAPSTI  AEVAPVISSA  YSQVYH.PNR  IERPISRETS  DSHENNMDGP
AIO      EKRHCFD...  .ANYNPGYM  YEKENEMMQT  RMMDQAINNA  ISYLGAEAFR    PLVQTPPAPT  SEMVPVISSV  YPIALTRAD.  ....MP....  MGAPQEMEKK
IK       DK..CLS...  ..DMPYDSAN  YEKE.DMMTS  HVMDQAINNA  INYLGAESLR    PLVQTPPG.S  SEVVPVISSM  YQLHKPPSD.  ....GPPRSN  HSAQDAVDNL 401                                                           450                                                      500
DAED     PLLYRARGSL  TDPGASPSNG  CQDSTDTESN  HEDRIGGVVS  LPQGPPPQPP    PTIVGRHSP  AYAKEDPKPQ  EGLLRGTPGP  SKEVLRVWGE  SGEPVKAFKC
HEL      ISLIRPKSRP  QEREASPSNS  CLOSTDSESS  HDDR.....Q  SYQGNPALNP    KR....KQSP  AYMKEDVKAL  DA.TKAPKGS  LKDIYKVFNG  EGEQIRAFKC
AIO      RILLPEKILP  SERGLSPNNS  AQDSTDTDSN  HEDR.QHLYQ  QSHVVLPQ..    .....ARNGM  PLLKEVPRSF  E.LLKPPPIC  LRDSIKVINK  EGEVMDVFRC
IK       LLLSKAKSVS  SEREASPSNS  CQDSTDTESN  AEEQRSGLIY  LTNHJNPH..    ......ARNGL  ALKEEQRAY  E.VLRAASEN  SQDAFRVVST  SGEQLKYYKC 501                                                           550
DAED     EHCRILFLDH  VMFTIHMGCH  GFRDPFECNI  CGYHSQDRYE  FSSHIVRGEH    KVGSCRI
HEL      EHCRVLFLDH  VMYTIHMGCH  GYRDPLECNI  CGYRSQDRYE  FSSHIVGGQH    TFH--
AIO      DHCHVLFLDY  VMFTIHMGCH  GFRDPFECNM  CGYRSHDRYE  FSSHIARGEH    RAMLK--
IK       EHCRVLFLDH  VMYTIHMGCH  GFRDPFECNM  CGYHSQDRYE  FSSHITRGEH    RYHLS--
```

FIG. 17B

```
          1                                        50                                        100
MDAED     ----- ---------- ---------- -MESLFCES SGDSSLEKEF LGAPVGPSVS TPNSQHSSPS RSLSANSIKV EMYSDEESSR LLGPDERLLD KDDSVIVEDS
XDAED     MSGSTFPTVV GHKLESIFYS STVAALDRPK AGDSSLEKDF SDALIGPTVS TPNSRHSSPS RSRSANSIKV EMYGDDESGR LLSHEDRLSE KEDEIMGDDS 101                                      150                                       200
MDAED     LSEPLGYCDG SGPEPHSPGG IRLPNGKLKC DVCGMVCIGP NVLMVHKRSH TGERPFHCNQ CGASFTQKGN LLRHIKLHSG EKPFKCPFCN YACRRRDALT
XDAED     LVEPLGYCDG PGDDPHSP.G ILLPNGKLKC DICGMVCIGP NVLMVHKRSH TGERPFHCNQ CGAPFTQKGN LLRHIKLHSG EKPFKCPFCN YACRRRDALS 201                                      250                                       300
MDAED     GHLRTHSVSS PTVGKPYKCN YCGRSYKQQS TLEEHKERCH NYLQSLSTDA QALTGQPGDE IRDLEMVPDS MLHPSTERPT FIDRLANSLT KRKRSTPQKF
XDAED     GHLRTHA... ..VGKPYKCN YCGRSYKQQN TLEEHKERCH NYLQSLSNEA QHLPAHPG.. ....EWGPQG ......... ......GNCIC TR....

301                                      350                                       400
MDAED     VGEKQMRFSL SDLPYDVNAS GGYEKDVELV AHHGLEPGFG GSLAFVGTEH LPL.RLPPTN CISELTPVIS SVYTQMQPIP SRLELPGSRE AGEGPEDLGD
XDAED     ..EKQMRLSL ADLPYEMNSS ..FEKDVEIV SHHPLDTAYG NSLAFVG... .GPMRLPPTN CISEITPVIS SVYTQLPMQ GRPDMPGNRE AAEGHEDIPD 401                                      450                                       500
MDAED     GGPLLYRARG SLTDPGASPS NGCQDS.TDT ESNHEDRIGG VVSLPQGPPP QPPPTIVVGR HSPAYAKEDP KPQEGLL... .RGTPGPSKE VLRVVGESGE
XDAED     GTQIHYRGR. ..SEHGASPT NGCQDSNTDT ESNHEERGSQ ATS....... .......... ......SR QSSAYAKEDQ RPSDGGLLLP SRSMPGTAKE SLRVLGEDGV 501                                      550
MDAED     PVKAFKCEHC RILFLDHVMF TIHMGCHGFR DPFECNICGY HSQDRYEFSS MDAED HIVRGEHKVG SCRI
XDAED     QVKVFKCEHC RVLFLDHVMF TIHMGCHGFR DPFECNICGY HCQDRYEFSS XDAED HIVRGEHKV- ----
```

FIG. 17C

```
AATTCGTTCT ACCTTCTCTG AACCCCAGTG GTGTGTCAAG GCCGGACTGG GAGCTTGGGG    60

GAAGAGGAAG AGGAAGAGGA ATCTGCGGCT CATCCAGGGA TCAGGGTCCT TCCCAAGTGG   120

CCACTCAGAG GGGACTCAGA GCAAGTCTAG ATTTGTGTGG CAGAGAGAGA CAGCTCTCGT   180

TTGGCCTTGG GGAGGCACAA GTCTGTTGAT AACCTGAAGA CA                     222
```

| | | | | | | | | | | | | | | | |
|---|---|---|---|---|---|---|---|---|---|---|---|---|---|---|---|
| ATG | GAT | GTC | GAT | GAG | GGT | CAA | GAC | ATG | TCC | CAA | GTT | TCA | GGA | AAG | GAG |
| Met | Asp | Val | Asp | Glu | Gly | Gln | Asp | Met | Ser | Gln | Val | Ser | Gly | Lys | Glu |
| 1 | | | | 5 | | | | | 10 | | | | | 15 | |

```
ATG GAT GTC GAT GAG GGT CAA GAC ATG TCC CAA GTT TCA GGA AAG GAG     270
Met Asp Val Asp Glu Gly Gln Asp Met Ser Gln Val Ser Gly Lys Glu
1               5                   10                  15

AGC CCC CCA GTC AGT GAC ACT CCA GAT GAA GGG GAT GAG CCC ATG CCT     318
Ser Pro Pro Val Ser Asp Thr Pro Asp Glu Gly Asp Glu Pro Met Pro
            20                  25                  30

GTC CCT GAG GAC CTG TCC ACT ACC TCT GGA GCA CAG CAG AAC TCC AAG     366
Val Pro Glu Asp Leu Ser Thr Thr Ser Gly Ala Gln Gln Asn Ser Lys
        35                  40                  45

AGT GAT CGA GGC ATG GGT GAA CGG CCT TTC CAG TGC AAC CAG TCT GGG     414
Ser Asp Arg Gly Met Gly Glu Arg Pro Phe Gln Cys Asn Gln Ser Gly
    50                  55                  60

GCC TCC TTT ACC CAG AAA GGC AAC CTC CTG CGG CAC ATC AAG CTG CAC     462
Ala Ser Phe Thr Gln Lys Gly Asn Leu Leu Arg His Ile Lys Leu His
65              70                  75                  80

TCG GGT GAG AAG CCC TTC AAA TGC CAT CTT TGC AAC TAT GCC TGC CGC     510
Ser Gly Glu Lys Pro Phe Lys Cys His Leu Cys Asn Tyr Ala Cys Arg
            85                  90                  95

CGG AGG GAC GCC CTC ACC GGC CAC CTG AGG ACG CAC TCC GTT GGT AAG     558
Arg Arg Asp Ala Leu Thr Gly His Leu Arg Thr His Ser Val Gly Lys
            100                 105                 110

CCT CAC AAA TGT GGA TAT TGT GGC CGG AGC TAT AAA CAG CGA AGC TCT     606
Pro His Lys Cys Gly Tyr Cys Gly Arg Ser Tyr Lys Gln Arg Ser Ser
            115                 120                 125

TTA GAG GAG CAT AAA GAG CGA TGC CAC AAC TAC TTG GAA AGC ATG GGC     654
Leu Glu Glu His Lys Glu Arg Cys His Asn Tyr Leu Glu Ser Met Gly
    130                 135                 140

CTT CCG GGC GTG TGC CCA GTC ATT AAG GAA GAA ACT AAC CAC AAC GAG     702
Leu Pro Gly Val Cys Pro Val Ile Lys Glu Glu Thr Asn His Asn Glu
145                 150                 155                 160

ATG GCA GAA GAC CTG TGC AAG ATA GGA GCA GAG AGG TCC CTT GTC CTG     750
Met Ala Glu Asp Leu Cys Lys Ile Gly Ala Glu Arg Ser Leu Val Leu
            165                 170                 175

GAC AGG CTG GCA AGC AAT GTC GCC AAA CGT AAG AGC TCT ATG CCT CAG     798
Asp Arg Leu Ala Ser Asn Val Ala Lys Arg Lys Ser Ser Met Pro Gln
            180                 185                 190
```

FIG. 19A

```
AAA TTT CTT GGA GAC AAG TGC CTG TCA GAC ATG CCC TAT GAC AGT GCC       846
Lys Phe Leu Gly Asp Lys Cys Leu Ser Asp Met Pro Tyr Asp Ser Ala
        195                 200                 205

AAC TAT GAG AAG GAG GAT ATG ATG ACA TCC CAC GTG ATG GAC CAG GCC       894
Asn Tyr Glu Lys Glu Asp Met Met Thr Ser His Val Met Asp Gln Ala
        210                 215                 220

ATC AAC AAT GCC ATC AAC TAC CTG GGG GCT GAG TCC CTG CGC CCA TTG       942
Ile Asn Asn Ala Ile Asn Tyr Leu Gly Ala Glu Ser Leu Arg Pro Leu
225                 230                 235                 240

GTG CAG ACA CCC CCC GGT AGC TCC GAG GTG GTG CCA GTC ATC AGC TCC       990
Val Gln Thr Pro Pro Gly Ser Ser Glu Val Val Pro Val Ile Ser Ser
                    245                 250                 255

ATG TAC CAG CTG CAC AAG CCC CCC TCA GAT GGC CCC CCA CGG TCC AAC      1038
Met Tyr Gln Leu His Lys Pro Pro Ser Asp Gly Pro Pro Arg Ser Asn
        260                 265                 270

CAT TCA GCA CAG GAC GCC GTG GAT AAC TTG CTG CTG CTG TCC AAG GCC      1086
His Ser Ala Gln Asp Ala Val Asp Asn Leu Leu Leu Leu Ser Lys Ala
        275                 280                 285

AAG TCT GTG TCA TCG GAG CGA GAG GCC TCC CCG AGC AAC AGC TGC CAA      1134
Lys Ser Val Ser Ser Glu Arg Glu Ala Ser Pro Ser Asn Ser Cys Gln
        290                 295                 300

GAC TCC ACA GAT ACA GAG AGC AAC GCG GAG GAA CAG CGC AGC GGC CTT      1182
Asp Ser Thr Asp Thr Glu Ser Asn Ala Glu Glu Gln Arg Ser Gly Leu
305                 310                 315                 320

ATC TAC CTA ACC AAC CAC ATC AAC CCG CAT GCA CGC AAT GGG CTG GCT      1230
Ile Tyr Leu Thr Asn His Ile Asn Pro His Ala Arg Asn Gly Leu Ala
                325                 330                 335

CTC AAG GAG GAG CAG CGC GCC TAC GAG GTG CTG AGG GCG GCC TCA GAG      1278
Leu Lys Glu Glu Gln Arg Ala Tyr Glu Val Leu Arg Ala Ala Ser Glu
        340                 345                 350

AAC TCG CAG GAT GCC TTC CGT GTG GTC AGC ACG AGT GGC GAG CAG CTG      1326
Asn Ser Gln Asp Ala Phe Arg Val Val Ser Thr Ser Gly Glu Gln Leu
        355                 360                 365

AAG GTG TAC AAG TGC GAA CAC TGC CGC GTG CTC TTC CTG GAT CAC GTC      1374
Lys Val Tyr Lys Cys Glu His Cys Arg Val Leu Phe Leu Asp His Val
        370                 375                 380

ATG TAT ACC ATT CAC ATG GGC TGC CAT GGC TGC CAT GGC TTT CGG GAT      1422
Met Tyr Thr Ile His Met Gly Cys His Gly Cys His Gly Phe Arg Asp
385                 390                 395                 400

CCC TTT GAG TGT AAC ATG TGT GGT TAT CAC AGC CAG GAC AGG TAC GAG      1470
Pro Phe Glu Cys Asn Met Cys Gly Tyr His Ser Gln Asp Arg Tyr Glu
                405                 410                 415
```

FIG. 19B

```
TTC TCA TCC CAT ATC ACG CGG GGG GAG CAT CGT TAC CAC CTG AGC            1515
Phe Ser Ser His Ile Thr Arg Gly Glu His Arg Tyr His Leu Ser
            420                 425                 430

TAAACCCAGC CAGGCCCCAC TGAAGCACAA AGATAGCTGG TTATGCCTCC TTCCCGGCAG      1575

CTGGACCCAC AGCGGACAAT GTGGGAGTGG ATTTGCAGGC AGCATTTGTT CTTTTATGTT      1635

GGTTGTTTGG CGTTTCATTT GCGTTGGAAG ATAAGTTTTT AATGTTAGTG ACAGGATTGC      1695

ATTGCATCAG CAACATTCAC AACATCCATC CTTCTAGCCA GTTTTGTTCA CTGGTAGCTG      1755

AGGTTTCCCG GATATGTGGC TTCCTAACAC TCT                                   1788
```

(SEQ.ID.NO:1)

FIG. 19C

```
AAT GTT AAA GTA GAG ACT CAG AGT GAT GAA GAG AAT GGG CGT GCC TGT         48
Asn Val Lys Val Glu Thr Gln Ser Asp Glu Glu Asn Gly Arg Ala Cys
 1           5                   10                  15

GAA ATG AAT GGG GAA GAA TGT GCG GAG GAT TTA CGA ATG CTT GAT GCC         96
Glu Met Asn Gly Glu Glu Cys Ala Glu Asp Leu Arg Met Leu Asp Ala
            20                  25                  30

TCG GGA GAG AAA ATG AAT GGC TCC CAC AGG GAC CAA GGC AGC TCG GCT        144
Ser Gly Glu Lys Met Asn Gly Ser His Arg Asp Gln Gly Ser Ser Ala
        35                  40                  45

TTG TCG GGA GTT GGA GGC ATT CGA CTT CCT AAC GGA AAA CTA AAG TGT        192
Leu Ser Gly Val Gly Gly Ile Arg Leu Pro Asn Gly Lys Leu Lys Cys
    50                  55                  60

GAT ATC TGT GGG ATC ATT TGC ATC GGG CCC AAT GTG CTC ATG GTT CAC        240
Asp Ile Cys Gly Ile Ile Cys Ile Gly Pro Asn Val Leu Met Val His
65                  70                  75                  80

AAA AGA AGC CAC ACT GGA GAA CGG CCC TTC CAG TGC AAT CAG TGC GGG        288
Lys Arg Ser His Thr Gly Glu Arg Pro Phe Gln Cys Asn Gln Cys Gly
                85                  90                  95

GCC TCA TTC ACC CAG AAG GGC AAC CTG CTC CGG CAC ATC AAG CTG CAT        336
Ala Ser Phe Thr Gln Lys Gly Asn Leu Leu Arg His Ile Lys Leu His
            100                 105                 110

TCC GGG GAG AAG CCC TTC AAA TGC CAC CTC TGC AAC TAC GCC TGC CGC        384
Ser Gly Glu Lys Pro Phe Lys Cys His Leu Cys Asn Tyr Ala Cys Arg
        115                 120                 125

CGG AGG GAC GCC CTC ACT GGC CAC CTG AGG ACG CAC TCC GTT GGT AAA        432
Arg Arg Asp Ala Leu Thr Gly His Leu Arg Thr His Ser Val Gly Lys
    130                 135                 140

CCT CAC AAA TGT GGA TAT TGT GGC CGA AGC TAT AAA CAG CGA ACG TCT        480
Pro His Lys Cys Gly Tyr Cys Gly Arg Ser Tyr Lys Gln Arg Thr Ser
145                 150                 155                 160

TTA GAG GAA CAT AAA GAG CGC TGC CAC AAC TAC TTG GAA AGC ATG GGC        528
Leu Glu Glu His Lys Glu Arg Cys His Asn Tyr Leu Glu Ser Met Gly
                165                 170                 175

CTT CCG GGC ACA CTG TAC CCA GTC ATT AAA GAA GAA ACT AAG CAC AGT        576
Leu Pro Gly Thr Leu Tyr Pro Val Ile Lys Glu Glu Thr Lys His Ser
            180                 185                 190

GAA ATG GCA GAA GAC CTG TGC AAG ATA GGA TCA GAG AGA TCT CTC GTG        624
Glu Met Ala Glu Asp Leu Cys Lys Ile Gly Ser Glu Arg Ser Leu Val
        195                 200                 205

CTG GAC AGA CTA GCA AGT AAT GTC GCC AAA CGT AAG AGC TCT ATG CCT        672
Leu Asp Arg Leu Ala Ser Asn Val Ala Lys Arg Lys Ser Ser Met Pro
    210                 215                 220

CAG AAA TTT CTT GGG GAC AAG GGC CTG TCC GAC ACG CCC TAC GAC AGT        720
Gln Lys Phe Leu Gly Asp Lys Gly Leu Ser Asp Thr Pro Tyr Asp Ser
225                 230                 235                 240
```

FIG. 20A

```
GCC ACG TAC GAG AAG GAG AAC GAA ATG ATG AAG TCC CAC GTG ATG GAC      768
Ala Thr Tyr Glu Lys Glu Asn Glu Met Met Lys Ser His Val Met Asp
            245             250             255

CAA GCC ATC AAC AAC GCC ATC AAC TAC CTG GGG GCC GAG TCC CTG CGC      816
Gln Ala Ile Asn Asn Ala Ile Asn Tyr Leu Gly Ala Glu Ser Leu Arg
            260             265             270

CCG CTG GTG CAG ACG CCC CCG GGC GGT TCC GAG GTG GTC CCG GTC ATC      864
Pro Leu Val Gln Thr Pro Pro Gly Gly Ser Glu Val Val Pro Val Ile
            275             280             285

AGC CCG ATG TAC CAG CTG CAC AGG CGC TCG GAG GGC ACC CCG CGC TCC      912
Ser Pro Met Tyr Gln Leu His Arg Arg Ser Glu Gly Thr Pro Arg Ser
            290             295             300

AAC CAC TCG GCC CAG GAC AGC GCC GTG GAG TAC CTG CTG CTG CTC TCC      960
Asn His Ser Ala Gln Asp Ser Ala Val Glu Tyr Leu Leu Leu Leu Ser
305             310             315             320

AAG GCC AAG TTG GTG CCC TCG GAG CGC GAG GCG TCC CCG AGC AAC AGC     1008
Lys Ala Lys Leu Val Pro Ser Glu Arg Glu Ala Ser Pro Ser Asn Ser
            325             330             335

TGC CAA GAC TCC ACG GAC ACC GAG AGC AAC AAC GAG GAG CAG CGC AGC     1056
Cys Gln Asp Ser Thr Asp Thr Glu Ser Asn Asn Glu Glu Gln Arg Ser
            340             345             350

GGT CTT ATC TAC CTG ACC AAC CAC ATC GCC CGA CGC GCG CAA CGC GTG     1104
Gly Leu Ile Tyr Leu Thr Asn His Ile Ala Arg Arg Ala Gln Arg Val
            355             360             365

TCG CTC AAG GAG GAG CAC CGC GCC TAC GAC CTG CTG CGC GCC GCC TCC     1152
Ser Leu Lys Glu Glu His Arg Ala Tyr Asp Leu Leu Arg Ala Ala Ser
            370             375             380

GAG AAC TCG CAG GAC GCG CTC CGC GTG GTC AGC ACC AGC GGG GAG CAG     1200
Glu Asn Ser Gln Asp Ala Leu Arg Val Val Ser Thr Ser Gly Glu Gln
385             390             395             400

ATG AAG GTG TAC AAG TGC GAA CAC TGC CGG GTG CTC TTC CTG GAT CAC     1248
Met Lys Val Tyr Lys Cys Glu His Cys Arg Val Leu Phe Leu Asp His
            405             410             415

GTC ATG TAC ACC ATC CAC ATG GGC TGC CAC GGC TTC CGT GAT CCT TTT     1296
Val Met Tyr Thr Ile His Met Gly Cys His Gly Phe Arg Asp Pro Phe
            420             425             430

GAG TGC AAC ATG TGC GGC TAC CAC AGC CAG GAC CGG TAC GAG TTC TCG     1344
Glu Cys Asn Met Cys Gly Tyr His Ser Gln Asp Arg Tyr Glu Phe Ser
            435             440             445

TCG CAC ATA ACG CGA GGG GAG CAC CGC TTC CAC ATG AGC TAA             1386
Ser His Ile Thr Arg Gly Glu His Arg Phe His Met Ser
450             455             460
```

FIG. 20B

↓Ex1/2
MDVDEGQDMS QVSGKESPPV SDTPDEGDEP MPVPEDLSTT SGAQQNSKSD RGMASNVKVE

TQSDEENGRA CEMNGEECAE DLRMLDASGE KMNGSHRDQG SSALSGVGGI RLPNGKLK|CD|
                                                      ↓Ex3
|ICGIVCIGPN VLMVHKRSHT| GERPF|CNQC GASFTOKGNL LRHIKLH|SGE KPF|KCHLCNY|
 F1                    ↓Ex4  F2                                    ↓Ex6
|ACRRRDALTG HLRTH|SVGKP HK|CGYCGRSY KORSSLEEHK ERC|HNYLESM GLPGMYPVIK
 F3                       F4                   ↓Ex7

EETNHNEMAE DLCKIGAERS LVLDRLASNV AKRKSSMPQK FLGDKCLSDM PYDSANYEKE

DMMTSHVMDQ AINNAINYLG AESLRPLVQT PPGSSEVVPV ISSMYQLHKP PSDGPPRSNH

SAQDAVDNLL LLSKAKSVSS EREASPSNSC QDSTDTESNA EEQRSGLIYL TNHINPHARN

GLALKEEQRA YEVLRAASEN SQDAFRVVST SGEQLKVYK|C EHCRVLFLDH VMYTIHMGCH|
                                            F5

GCHGFRDPFE |CNMCGYHSOD RYEFSSHITR GEHRYHLS|
            F6

FIG. 21

Oligo1/2 IK-1/IK-2/IK-4
Oligo3/4 IK-1/IK-3/IK-5

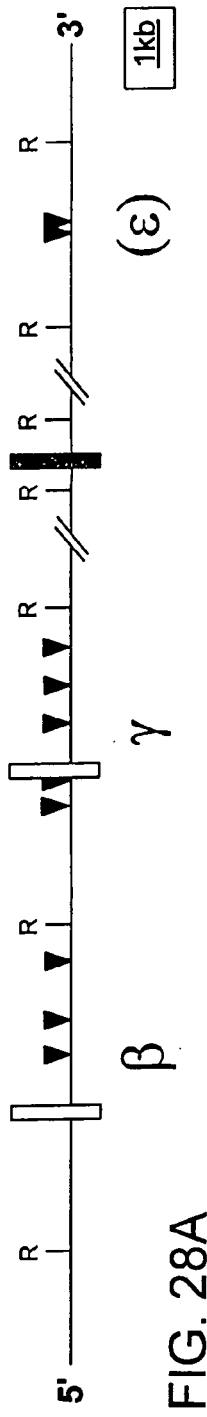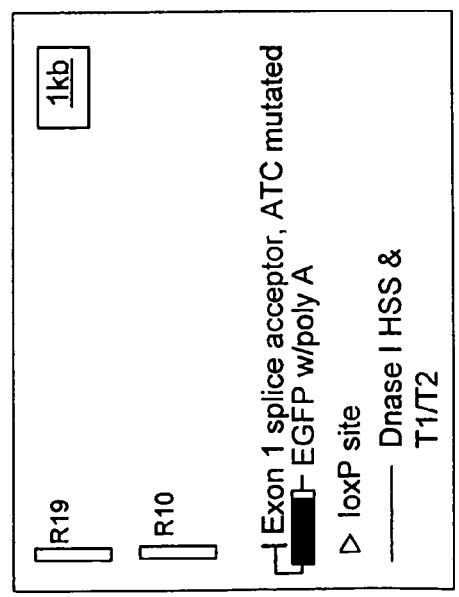
FIG. 28A
FIG. 28B

AIOLOS, HELIOS, DAEDALOS AND IKAROS: GENES, POLYPEPTIDES, REGULATORY ELEMENTS AND USES THEREOF

CROSS-REFERENCE TO RELATED APPLICATIONS

This application is a continuation in part of (a) U.S. Ser. No. 09/259,389 filed on Feb. 26, 1999, now abandoned which claims benefit of U.S. Provisional Application 60/076,325 filed on Feb. 27, 1998, the contents of both of which are hereby incorporated by reference in their entirety; and (b) U.S. Ser. No. 10/037,667 filed on Oct. 25, 2001, now U.S. Pat. No. 6,759,201, which claims the benefit of U.S. Provisional Application Ser. No. 60/243,110, filed on Oct. 25, 2000, the contents of which are incorporated herein by reference in their entirety.

TECHNICAL FIELD

In one aspect, the invention relates to the Aiolos gene, Aiolos polypeptide, Aiolos homodimers, Aiolos/Ikaros heterodimers and methods of using Aiolos nucleic acids and polypeptides.

In another aspect, the invention relates to the Helios gene, Helios polypeptide, Helios homodimers, Helios/Ikaros heterodimers, Helios/Aiolos heterodimers and methods of using Helios nucleic acids and polypeptides.

In yet another aspect, the invention relates to the Daedalos nucleic acids, Daedalos polypeptides, and other related molecules and methods of making and using the same.

In another aspect, the invention relates to Ikaros regulatory elements and uses thereof.

BACKGROUND

Aiolos

The invention relates to the Aiolos gene, Aiolos polypeptide, Aiolos homodimers, Aiolos/Ikaros heterodimers and methods of using Aiolos nucleic acids and polypeptides.

Helios

The invention relates to the Helios gene, Helios polypeptide, Helios homodimers, Helios/Ikaros heterodimers, Helios/Aiolos heterodimers and methods of using Helios nucleic acids and polypeptides.

Dedalos

The maintenance of tissues that require regeneration during the life of an organism is often achieved by the asymmetric division of a less differentiated stem cell to regenerate itself as well as give rise to a daughter cell that can then differentiate to repopulate the organ. The best characterized stem cells in the adult animal are those that regenerate the hematopoietic system. The production or proliferation of the hematopoietic stem cells (HSCs), and the subsequent expansion of progenitors with progressively restricted developmental potential derived from them, is regulated in part by members of the Ikaros gene family (Georgopoulos et al. (1997) Annu. Rev. Immunol. 15:155). Ikaros, Aiolos and Helios comprise the previously identified members of the Ikaros gene family. They encode conserved zinc finger DNA binding proteins which are expressed at varying levels in cells progressing through the hematopoietic lineages (Kelley et al. (1998) Curr. Biol, 8:508). Mutations in Ikaros cause defects in the hematopoietic stem cell as well as in later stages of lymphoid differentiation (Georgopoulos et al. (1994) Cell 79:143), while Aiolos mutations cause defects which are restricted to the lymphoid lineages, particularly in the sub-lineage that gives rise to B cells (Wang et al. (1998) Immunity 9:543).

Co-localization studies on the Ikaros family proteins suggest that these proteins bind to lineage specific genes in lymphoid cells and may serve to mediate rapid transitions between subsequently heritable repressed and active states in response to extrinsic signals. In support of this model, both Ikaros and Aiolos assemble into at least two distinct chromatin remodeling complexes (Kim et al. (1999) Immunity 10:345). One of these includes Mi-2 and histone deacetylase (HDAC) and can assemble chromatin in a closed conformation while the other includes members of a SWI/SNF complex associated with chromatin opening. Ikaros family proteins also regulate proliferative responses in maturing T cells, possibly by regulating access of the replication machinery to DNA (Avitahl et al. (1999) Immunity 10:333). These observations led to the general model that changes in the combinatorial expression of Ikaros family members during progression through the lymphoid lineage regulate the gene expression changes associated with successive steps in lymphoid development (Kelley et al. (1998) Curr. Biol. 8:508–515).

Ikaros

The generation of the T cell repertoire from a progenitor stem cell proceeds through a differentiation pathway. All blood cells originate from a hematopoietic stem cell. This population of stem cells can self renew or become pluripotent stem cells. Such pluripotent stem cells can become committed to differentiate along particular lineages. For example, pluripotent stem cells can give rise to either lymphoid progenitor cells or myeloid progenitor cells. Such lymphoid progenitor can in turn give rise to either B-lymphocytes or T-lymphocytes. Myeloid progenitor cells can become committed to differentiate into, for example, erthyroid, megakaryocyte, granulocytic or monocytic lineages.

In the differentiation pathway, the later intrathymic steps are well documented while the early extrathymic events are only poorly characterized. One of the earliest definitive T cell differentiation markers is the CD3δ gene of the CD3/TCR complex.

SUMMARY

Summary of Aiolos

In general, the invention features an Aiolos polypeptide, e.g., a polypeptide which includes all or part of the sequence shown in SEQ ID NO:2 or SEQ ID NO:8. The invention also features fragments and analogs of Aiolos polypeptides, preferably having at least one biological activity of an Aiolos polypeptide.

In preferred embodiments, the polypeptide is a recombinant or a substantially pure preparation of an Aiolos polypeptide.

In preferred embodiments, the polypeptide is a vertebrate, e.g., a mammalian, e.g., a human polypeptide.

In preferred embodiments, the Aiolos polypeptide includes additional Aiolos coding sequences 5' to that of SEQ ID NO:8. In preferred embodiments: the additional sequence includes at least 1, 10, 20, 40, 60, 70, 80 or 100 amino acid residues; the additional sequence is equal to or less than 1, 10, 20, 40, 60, 70, 80 or 100 amino acid residues.

In preferred embodiments: the polypeptide has at least one biological activity, e.g., it reacts with an antibody, or antibody fragment, specific for an Aiolos polypeptide; the polypeptide includes an amino acid sequence at least 60%, 80%, 90%, 95%, 98%, or 99% homologous to an amino acid sequence from SEQ ID NO:2 or SEQ ID NO:8; the polypeptide includes an amino acid sequence essentially the same as an amino acid sequence in SEQ ID NO:2 or SEQ ID NO:8; the polypeptide is at least 5, 10, 20, 50, 100, 150, 200, or 250 amino acids in length; the polypeptide includes at least 5, preferably at least 10, more preferably at least 20, most preferably at least 50, 100, 150, 200, or 250 contiguous amino acids from SEQ ID NO:2 or SEQ ID NO:8; the polypeptide is preferably at least 10, but no more than 100, amino acids in length; the Aiolos polypeptide is either, an agonist or an antagonist, of a biological activity of a naturally occurring Aiolos polypeptide.

In preferred embodiments: the Aiolos polypeptide is encoded by the nucleic acid sequence of SEQ ID NO:1 or SEQ ID NO:7, or by a nucleic acid having at least 60%, 70%, 80%, 90%, 95%, 98%, or 99% homology with the nucleic acid of SEQ ID NO:1 or SEQ ID NO:7. For example, the Aiolos polypeptide can be encoded by a nucleic acid sequence which differs from a nucleic acid sequence of SEQ ID NO:1 or SEQ ID NO:7 due to degeneracy in the genetic code.

In a preferred embodiment, the Aiolos polypeptide encodes amino acid residues 1–507 of SEQ ID NO:2 or a functionally equivalent residue in the Aiolos sequence of another vertebrate or mammal, e.g., a human.

In a preferred embodiment, the Aiolos polypeptide encodes amino acid residues 58–507 of SEQ ID NO:2 or a functionally equivalent residue in the Aiolos sequence of another vertebrate or mammal, e.g., a human.

In a preferred embodiment, the Aiolos polypeptide encodes amino acid residues 72–507 of SEQ ID NO:2 or a functionally equivalent residue in the Aiolos sequence of another vertebrate or mammal, e.g., a human.

In a preferred embodiment, the Aiolos polypeptide encodes amino acid residues 76–507 of SEQ ID NO:2 or a functionally equivalent residue in the Aiolos sequence of another vertebrate or mammal, e.g., a human.

In a preferred embodiment, the Aiolos polypeptide encodes amino acid residues 1–206 of SEQ ID NO:8.

In a preferred embodiment the Aiolos polypeptide is an agonist of a naturally-occurring mutant or wild type Aiolos polypeptide (e.g., a polypeptide having an amino acid sequence shown in SEQ ID NO:2 or SEQ ID NO:8). In another preferred embodiment, the polypeptide is an antagonist which, for example, inhibits an undesired activity of a naturally-occurring Aiolos polypeptide (e.g., a mutant polypeptide).

In a preferred embodiment, the Aiolos polypeptide differs in amino acid sequence at 1, 2, 3, 5, 10 or more residues, from a sequence in SEQ ID NO:2 or SEQ ID NO:8. The differences, however, are such that the Aiolos polypeptide exhibits at least one biological activity of an Aiolos polypeptide, e.g., the Aiolos polypeptide retains a biological activity of a naturally occurring Aiolos polypeptide.

In preferred embodiments the Aiolos polypeptide includes an Aiolos polypeptide sequence, as described herein, as well as other N-terminal and/or C-terminal amino acid sequences.

In preferred embodiments, the polypeptide includes all or a fragment of an amino acid sequence from SEQ ID NO:2 or SEQ ID NO:8, fused, in reading frame, to additional amino acid residues, preferably to residues encoded by genomic DNA 5' to the genomic DNA which encodes a sequence from SEQ ID NO:2 or SEQ ID NO:8.

In yet other preferred embodiments, the Aiolos polypeptide is a recombinant fusion protein having a first Aiolos polypeptide portion and a second polypeptide portion having an amino acid sequence unrelated to an Aiolos polypeptide. The second polypeptide portion can be, e.g., any of glutathione-S-transferase, a DNA binding domain, or a polymerase activating domain. In preferred embodiment the fusion protein can be used in a two-hybrid assay.

In a preferred embodiment, the Aiolos polypeptide is a fragment or analog of a naturally occurring Aiolos polypeptide which inhibits reactivity with antibodies, or F(ab')$_2$ fragments, specific for a naturally occurring Aiolos polypeptide.

In a preferred embodiment, the Aiolos polypeptide includes a sequence which is not present in the mature protein.

Polypeptides of the invention include those which arise as a result of the existence of multiple genes, alternative transcription events, alternative RNA splicing events, and alternative translational and postranslational events.

In preferred embodiments, the Aiolos polypeptide: is expressed in spleen and thymus; is expressed in mature T and/or B cells; is highly homologous, preferably at least 90% or 95% homologous, with the 50 most C-terminal amino acids of the Ikaros gene (e.g., the dimerization domain of exon 7 of the Ikaros gene); is highly homologous, preferably at least 90% or 95% homologous with the activation domain of exon 7 of the Ikaros gene; is capable of forming Aiolos dimers and/or Aiolos/Ikaros dimers; is involved in lymphocyte differentiation, e.g., T cell maturation.

In preferred embodiments, the Aiolos polypeptide includes: the YAS5 interaction domain; the YAS3 interaction domain; the YIZ Ikaros dimerization domain.

In preferred embodiments, an Aiolos polypeptide encodes: one, two, three, four, five exons, or more exons; exons 3, 4, 5 and 7; exons 3–7; exon 7 (the exons are shown in FIG. 4).

In preferred embodiments, the Aiolos polypeptide has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has at least one zinc finger domain;
(f) it is not expressed in stem cells;
(g) it is a transcriptional activator of a lymphoid gene.

In other preferred embodiments, the Aiolos polypeptide has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has an N-terminal zinc finger domain;
(f) it is not expressed in stem cells; or
(g) it is a transcriptional activator of a lymphoid gene.

In yet other preferred embodiments, the Aiolos polypeptide has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has at least one or preferably two C-terminal zinc finger domains;
(f) it is not expressed in stem cells; or
(g) it is a transcriptional activator of a lymphoid gene.

The invention includes an immunogen which includes an active or inactive Aiolos polypeptide, or an analog or a fragment thereof, in an immunogenic preparation, the immunogen being capable of eliciting an immune response specific for the Aiolos polypeptide, e.g., a humoral response, an antibody response, or a cellular response. In preferred embodiments, the immunogen comprising an antigenic determinant, e.g., a unique determinant, from a protein represented by SEQ ID NO:2 or SEQ ID NO:8. For example, the immunogen comprises amino acids 1–124 of SEQ ID NO:2 or amino acids 275–448 of SEQ ID NO:2.

The invention also includes an antibody preparation, preferably a monoclonal antibody preparation, specifically reactive with an epitope of the Aiolos immunogen or generally of an Aiolos polypeptide.

In another aspect, the invention provides a substantially pure nucleic acid having, or comprising, a nucleotide sequence which encodes a polypeptide, the amino acid sequence of which includes, or is, the sequence of an Aiolos polypeptide, or analog or fragment thereof.

In preferred embodiments, the nucleic acid encodes a vertebrate, e.g., a mammalian, e.g., a human polypeptide.

In preferred embodiments, the nucleic acid encodes an Aiolos polypeptide which includes additional Aiolos coding sequences 5' to that SEQ ID NO:8. In preferred embodiments: the additional sequence includes at least 1, 10, 20, 40, 60, 70, 80 or 100 amino acid residues; the additional sequence is equal to or less than 1, 10, 20, 40, 60, 70, 80 or 100 amino acid residues.

In preferred embodiments, the nucleic acid encodes a polypeptide having one or more of the following characteristics: at least one biological activity of an Aiolos, e.g., a polypeptide specifically reactive with an antibody, or antibody fragment, directed against an Aiolos polypeptide; an amino acid sequence at least 60%, 80%, 90%, 95%, 98%, or 99% homologous to an amino acid sequence from SEQ ID NO:2 or SEQ ID NO:8; an amino acid sequence essentially the same as an amino acid sequence in SEQ ID NO:2 or SEQ ID NO:8, the polypeptide is at least 5, 10, 20, 50, 100, 150, 200, or 250 amino acids in length; at least 5, preferably at least 10, more preferably at least 20, most preferably at least 50, 100, 150, 200, or 250 contiguous amino acids from SEQ ID NO:2 or SEQ ID NO:8; an amino acid sequence which is preferably at least 10, but no more than 100, amino acids in length; the ability to act as an agonist or an antagonist of a biological activity of a naturally occurring Aiolos polypeptide.

In preferred embodiments: the nucleic acid is or includes the nucleotide sequence of SEQ ID NO:1 or SEQ ID NO:7; the nucleic acid is at least 60%, 70%, 80%, 90%, 95%, 98%, or 99% homologous with a nucleic acid sequence of SEQ ID NO:1 or SEQ ID NO:7; the nucleic acid includes a fragment of SEQ ID NO:1 or SEQ ID NO:7 which is at least 25, 50, 100, 200, 300, 400, 500, or 1,000 bases in length; the nucleic acid differs from the nucleotide sequence of SEQ ID NO:1 due to degeneracy in the genetic code.

In a preferred embodiment, the Aiolos encoding nucleic acid sequence encodes amino acid residues 1–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 58–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 72–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 76–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 1–206 of SEQ ID NO:8.

In a preferred embodiment the polypeptide encoded by the nucleic acid is an agonist which, for example, is capable of enhancing an activity of a naturally-occurring mutant or wild type Aiolos polypeptide. In another preferred embodiment, the encoded polypeptide is an antagonist which, for example, inhibits an undesired activity of a naturally-occurring Aiolos polypeptide (e.g., a polypeptide having an amino acid sequence shown in SEQ ID NO:2 or SEQ ID NO:8).

In a preferred embodiment, the encoded Aiolos polypeptide differs in amino acid sequence at 1, 2, 3, 5, 10 or more residues, from a sequence in SEQ ID NO:2 or SEQ ID NO:8. The differences, however, are such that the encoded Aiolos polypeptide exhibits at least one biological activity of a naturally occurring Aiolos polypeptide (e.g., the Aiolos polypeptide of SEQ ID NO:2 or SEQ ID NO:8).

In preferred embodiments, the nucleic acid encodes an Aiolos polypeptide which includes an Aiolos polypeptide sequence, as described herein, as well as other N-terminal and/or C-terminal amino acid sequences.

In preferred embodiments, the nucleic acid encodes a polypeptide which includes all or a portion of an amino acid sequence shown in SEQ ID NO:2 or SEQ ID NO:8, fused, in reading frame, to additional amino acid residues, preferably to residues encoded by genomic DNA 5' to the genomic DNA which encodes a sequence from SEQ ID NO:2 or SEQ ID NO:8.

In preferred embodiments, the encoded polypeptide is a recombinant fusion protein having a first Aiolos polypeptide portion and a second polypeptide portion having an amino acid sequence unrelated to an Aiolos polypeptide. The second polypeptide portion can be, e.g., any of glutathione-S-transferase; a DNA binding domain; or a polymerase activating domain. In preferred embodiments the fusion protein can be used in a two-hybrid assay.

In preferred embodiments, the encoded polypeptide is a fragment or analog of a naturally occurring Aiolos polypeptide which inhibits reactivity with antibodies, or $F(ab')_2$ fragments, specific for a naturally occurring Aiolos polypeptide.

In preferred embodiments, the nucleic acid will include a transcriptional regulatory sequence, e.g., at least one of a transcriptional promoter or transcriptional enhancer sequence, operably linked to the Aiolos gene sequence, e.g., to render the Aiolos gene sequence suitable for use as an expression vector.

In yet another preferred embodiment, the nucleic acid of the invention hybridizes under stringent conditions to a nucleic acid probe corresponding to at least 12 consecutive nucleotides from SEQ ID NO:1 or SEQ ID NO:7, or more preferably to at least 20 consecutive nucleotides from SEQ ID NO:1 or SEQ ID NO:7, or more preferably to at least 40 consecutive nucleotides from SEQ ID NO:1 or SEQ ID NO:7.

In a preferred embodiment, the nucleic acid encodes an Aiolos polypeptide which includes a sequence which is not present in the mature protein.

In preferred embodiments, the nucleic acid encodes an Aiolos polypeptide which: is expressed in spleen and thymus; is expressed in mature T and/or B cells; is highly homologous, preferably at least 90% or 95% homologous, with the 50 most C-terminal amino acids of the Ikaros gene (e.g., the dimerization domain of exon 7 of the Ikaros gene); is highly homologous, preferably at least 90% or 95% homologous, with the activation domain of exon 7 of the Ikaros gene; is capable of forming Aiolos dimers and/or Aiolos/Ikaros dimers; is involved in lymphocyte differentiation, e.g., T cell maturation.

In preferred embodiments, the nucleic acid encodes an Aiolos polypeptide which includes: the YAS5 interaction domain; the YAS3 interaction domain; the YIZ Ikaros dimerization domain.

In preferred embodiments, the nucleic acid encodes an Aiolos polypeptide which encodes: one, two, three, four, five exons, or more exons; exons 3, 4, 5 and 7; exons 3–7; exon 7 (the exons are shown in FIG. 4).

In preferred embodiments, the nucleic acid encodes an Aiolos polypeptide which has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has at least one zinc finger domain;
(f) it is not expressed in stem cells; or
(g) it is a transcriptional activator of a lymphoid gene.

In other preferred embodiments, the nucleic acid encodes an Aiolos polypeptide which has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has an N-terminal zinc finger domain;
(f) it is not expressed in stem cells; or
(g) it is a transcriptional activator of a lymphoid gene.

In yet other preferred embodiments, the nucleic acid encodes an Aiolos polypeptide which has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has at least one or preferably two C-terminal zinc finger domains;
(f) it is not expressed in stem cells; or
(g) it is a transcriptional activator of a lymphoid gene.

In another aspect, the invention includes: a vector including a nucleic acid which encodes an Aiolos polypeptide; a host cell transfected with the vector; and a method of producing a recombinant Aiolos polypeptide, including culturing the cell, e.g., in a cell culture medium, and isolating the Aiolos polypeptide, e.g., an Aiolos polypeptide from the cell or from the cell culture medium.

In another aspect, the invention features, a purified recombinant nucleic acid having at least 50%, 60%, 70%, 80%, 90%, 95%, 98%, or 99% homology with a nucleotide sequence shown in SEQ ID NO:1 or SEQ ID NO:7.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:1 or SEQ ID NO:8, or naturally occurring mutants thereof. In preferred embodiments, the probe or primer further includes a label group attached thereto. The label group can be, e.g., a radioisotope, a fluorescent compound, an enzyme, and/or an enzyme cofactor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

The invention includes vertebrate, e.g., mammalian, e.g., rodent, e.g., mouse or rat, or human Aiolos polypeptides.

In another aspect, the invention features a method of evaluating a compound for the ability to interact with, e.g., bind, or modulate, e.g., inhibit or promote, the activity of an Aiolos polypeptide, e.g., an Aiolos monomer, or an Aiolos-Aiolos dimer or an Aiolos-Ikaros dimer. The method includes contacting the compound with the Aiolos polypeptide, and evaluating the ability of the compound to interact with or form a complex with the Aiolos polypeptide. This method can be performed in vitro, e.g., in a cell free system, or in vivo, e.g., in a two-hybrid interaction trap assay. This method can be used to identify naturally occurring molecules which interact with the Aiolos polypeptide. It can also be used to find natural or synthetic inhibitors of mutant or wild type Aiolos polypeptide. The compound can be a peptide or a non peptide molecule, e.g., a small molecule preferably 500 to 5,000 molecular weight, more preferably 500 to 1,000 molecular weight, having an aromatic scaffold, e.g., a bis-amide phenol, decorated with various functional groups.

In brief, a two hybrid assay system (see e.g., Bartel et al. (1993) *Cellular Interaction in Development: A practical Approach*, D. A. Hartley, ed., Oxford University Press, Oxford, pp. 153–179) allows for detection of protein-protein interactions in yeast cells. The known protein, e.g., an Aiolos polypeptide, is often referred to as the "bait" protein. The proteins tested for binding to the bait protein are often referred to as "fish" proteins. The "bait" protein, e.g., an Aiolos polypeptide, is fused to the GAL4 DNA binding domain. Potential "fish" proteins are fused to the GAL4 activating domain. If the "bait" protein and a "fish" protein interact, the two GAL4 domains are brought into close proximity, thus rendering the host yeast cell capable of surviving a specific growth selection.

In another aspect, the invention features a method of identifying active fragments or analogs of an Aiolos polypeptide. The method includes first identifying a compound, e.g., an Ikaros peptide, which interacts with an Aiolos polypeptide and determining the ability of the compound to bind the candidate fragment or analog. The two hybrid assay described above can be used to obtain fragment-binding compounds. These compounds can then be used as "bait" to fish for and identify fragments of the Aiolos polypeptide which interact, bind, or form a complex with these compounds.

In another aspect, the invention features a method of making an Aiolos polypeptide, having a non-wild type activity, e.g., an antagonist, agonist, or super agonist of a naturally occurring Aiolos polypeptide. The method includes altering the sequence of an Aiolos polypeptide (e.g., SEQ ID NO:2 or SEQ ID NO:8) by, for example, substitution or deletion of one or more residues of a non-conserved region, and testing the altered polypeptide for the desired activity.

In another aspect, the invention features a method of making a fragment or analog of an Aiolos polypeptide, e.g., an Aiolos polypeptide having at least one biological activity of a naturally occurring Aiolos polypeptide. The method includes altering the sequence, e.g., by substitution or deletion of one or more residues, preferably which are non-conserved residues, of an Aiolos polypeptide, and testing the altered polypeptide for the desired activity.

In another aspect, the invention features, a method of evaluating a compound for the ability to bind a nucleic acid encoding an Aiolos gene regulatory sequence. The method includes: contacting the compound with the nucleic acid; and evaluating ability of the compound to form a complex with the nucleic acid. In preferred embodiments the Aiolos gene regulatory sequence is functionally linked to a heterologous gene, e.g., a reporter gene.

In another aspect, the invention features a human cell, e.g., a hematopoietic stem cell or a lymphocyte e.g., a T or a B cell, transformed with a nucleic acid which encodes an Aiolos polypeptide.

In another aspect, the invention features a method for treating an animal, e.g., a human, a mouse, a transgenic animal, or an animal model for a disorder, e.g., an immune system disorder, e.g., a T or B cell related disorder, e.g., a nude mouse or a SCID mouse, including administering a therapeutically-effective amount of an Aiolos polypeptide to the animal. The Aiolos polypeptide can be monomeric or an Aiolos-Aiolos or Aiolos-Ikaros dimer.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a cell selected, e.g., selected in vitro, for the expression of a product of the Aiolos gene, e.g., hematopoietic stem cells, e.g., cells transformed with Aiolos-peptide-encoding DNA, e.g., hematopoietic stem cells transformed with Aiolos-peptide-encoding DNA.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a nucleic acid encoding an Aiolos peptide and expressing the nucleic acid.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method of evaluating the effect of a treatment, e.g., a treatment designed to promote or inhibit hematopoiesis, including carrying out the treatment and evaluating the effect of the treatment on the expression of the Aiolos gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Aiolos gene, e.g., a proliferative disorder, e.g., a leukemic disorder, Hodgkin's lymphoma, a cutaneuous cell lymphoma, e.g., a cutaneous T cell lymphoma; or a disorder of the immune system, e.g., an immunodeficiency, or a T or B cell related disorder, e.g., a disorder characterized by a shortage of T or B cells. The method includes examining the subject for the expression of the Aiolos gene, non-wild type expression or mis-expression being indicative of risk.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is In one general aspect, the invention features an Aiolos polypeptide, e.g., a polypeptide which includes all or part of the sequence shown in SEQ ID NO:2 or SEQ ID NO:8. The invention also features fragments and analogs of Aiolos polypeptides, preferably having at least one biological activity of an Aiolos polypeptide.

In preferred embodiments, the polypeptide is a recombinant or a substantially pure preparation of an Aiolos polypeptide.

In preferred embodiments, the polypeptide is a vertebrate, e.g., a mammalian, e.g., a human polypeptide.

In preferred embodiments, the Aiolos polypeptide includes additional Aiolos coding sequences 5' to that of SEQ ID NO:8. In preferred embodiments: the additional sequence includes at least 1, 10, 20, 40, 60, 70, 80 or 100 amino acid residues; the additional sequence is equal to or less than 1, 10, 20, 40, 60, 70, 80 or 100 amino acid residues.

In preferred embodiments: the polypeptide has at least one biological activity, e.g., it reacts with an antibody, or antibody fragment, specific for an Aiolos polypeptide; the polypeptide includes an amino acid sequence at least 60%, 80%, 90%, 95%, 98%, or 99% homologous to an amino acid sequence from SEQ ID NO:2 or SEQ ID NO:8; the polypeptide includes an amino acid sequence essentially the same as an amino acid sequence in SEQ ID NO:2 or SEQ ID NO:8; the polypeptide is at least 5, 10, 20, 50, 100, 150, 200, or 250 amino acids in length; the polypeptide includes at least 5, preferably at least 10, more preferably at least 20, most preferably at least 50, 100, 150, 200, or 250 contiguous amino acids from SEQ ID NO:2 or SEQ ID NO:8; the polypeptide is preferably at least 10, but no more than 100, amino acids in length; the Aiolos polypeptide is either, an agonist or an antagonist, of a biological activity of a naturally occurring Aiolos polypeptide.

In preferred embodiments: the Aiolos polypeptide is encoded by the nucleic acid sequence of SEQ ID NO:1 or SEQ ID NO:7, or by a nucleic acid having at least 60%, 70%, 80%, 90%, 95%, 98%, or 99% homology with the nucleic acid of SEQ ID NO:1 or SEQ ID NO:7. For example, the Aiolos polypeptide can be encoded by a nucleic acid sequence which differs from a nucleic acid sequence of SEQ ID NO:1 or SEQ ID NO:7 due to degeneracy in the genetic code.

In a preferred embodiment, the Aiolos polypeptide encodes amino acid residues 1–507 of SEQ ID NO:2 or a functionally equivalent residue in the Aiolos sequence of another vertebrate or mammal, e.g., a human.

In a preferred embodiment, the Aiolos polypeptide encodes amino acid residues 58–507 of SEQ ID NO:2 or a functionally equivalent residue in the Aiolos sequence of another vertebrate or mammal, e.g., a human.

In a preferred embodiment, the Aiolos polypeptide encodes amino acid residues 72–507 of SEQ ID NO:2 or a functionally equivalent residue in the Aiolos sequence of another vertebrate or mammal, e.g., a human.

In a preferred embodiment, the Aiolos polypeptide encodes amino acid residues 76–507 of SEQ ID NO:2 or a functionally equivalent residue in the Aiolos sequence of another vertebrate or mammal, e.g., a human.

In a preferred embodiment, the Aiolos polypeptide encodes amino acid residues 1–206 of SEQ ID NO:8.

In a preferred embodiment the Aiolos polypeptide is an agonist of a naturally-occurring mutant or wild type Aiolos polypeptide (e.g., a polypeptide having an amino acid sequence shown in SEQ ID NO:2 or SEQ ID NO:8). In another preferred embodiment, the polypeptide is an antagonist which, for example, inhibits an undesired activity of a naturally-occurring Aiolos polypeptide (e.g., a mutant polypeptide).

In a preferred embodiment, the Aiolos polypeptide differs in amino acid sequence at 1, 2, 3, 5, 10 or more residues, from a sequence in SEQ ID NO:2 or SEQ ID NO:8. The differences, however, are such that the Aiolos polypeptide exhibits at least one biological activity of an Aiolos polypeptide, e.g., the Aiolos polypeptide retains a biological activity of a naturally occurring Aiolos polypeptide.

In preferred embodiments the Aiolos polypeptide includes an Aiolos polypeptide sequence, as described herein, as well as other N-terminal and/or C-terminal amino acid sequences.

In preferred embodiments, the polypeptide includes all or a fragment of an amino acid sequence from SEQ ID NO:2 or SEQ ID NO:8, fused, in reading frame, to additional amino acid residues, preferably to residues encoded by genomic DNA 5' to the genomic DNA which encodes a sequence from SEQ ID NO:2 or SEQ ID NO:8.

In yet other preferred embodiments, the Aiolos polypeptide is a recombinant fusion protein having a first Aiolos polypeptide portion and a second polypeptide portion having an amino acid sequence unrelated to an Aiolos polypeptide. The second polypeptide portion can be, e.g., any of glutathione-S-transferase, a DNA binding domain, or a polymerase activating domain. In preferred embodiment the fusion protein can be used in a two-hybrid assay.

In a preferred embodiment, the Aiolos polypeptide is a fragment or analog of a naturally occurring Aiolos polypeptide which inhibits reactivity with antibodies, or $F(ab')_2$ fragments, specific for a naturally occurring Aiolos polypeptide.

In a preferred embodiment, the Aiolos polypeptide includes a sequence which is not present in the mature protein.

Polypeptides of the invention include those which arise as a result of the existence of multiple genes, alternative transcription events, alternative RNA splicing events, and alternative translational and postranslational events.

In preferred embodiments, the Aiolos polypeptide: is expressed in spleen and thymus; is expressed in mature T and/or B cells; is highly homologous, preferably at least 90% or 95% homologous, with the 50 most C-terminal amino acids of the Ikaros gene (e.g., the dimerization domain of exon 7 of the Ikaros gene); is highly homologous, preferably at least 90% or 95% homologous with the activation domain of exon 7 of the Ikaros gene; is capable of forming Aiolos dimers and/or Aiolos/Ikaros dimers; is involved in lymphocyte differentiation, e.g., T cell maturation.

In preferred embodiments, the Aiolos polypeptide includes: the YAS5 interaction domain; the YAS3 interaction domain; the YIZ Ikaros dimerization domain.

In preferred embodiments, an Aiolos polypeptide encodes: one, two, three, four, five exons, or more exons; exons 3, 4, 5 and 7; exons 3–7; exon 7 (the exons are shown in FIG. 4).

In preferred embodiments, the Aiolos polypeptide has one or more of the following properties:

(a) it can form a dimer with an Aiolos or Ikaros polypeptide;
(b) it is expressed in committed lymphoid progenitors;
(c) it is expressed in committed T and B cells;
(d) it has a molecular weight of approximately 58 kD;
(e) it has at least one zinc finger domain;
(f) it is not expressed in stem cells; or
(g) it is a transcriptional activator of a lymphoid gene.

In other preferred embodiments, the Aiolos polypeptide has one or more of the following properties:

(a) it can form a dimer with an Aiolos or Ikaros polypeptide;
(b) it is expressed in committed lymphoid progenitors;
(c) it is expressed in committed T and B cells;

(d) it has a molecular weight of approximately 58 kD;

(e) it has an N-terminal zinc finger domain;

(f) it is not expressed in stem cells; or (g) it is a transcriptional activator of a lymphoid gene.

In yet other preferred embodiments, the Aiolos polypeptide has one or more of the following properties:

(a) it can form a dimer with an Aiolos or Ikaros polypeptide;

(b) it is expressed in committed lymphoid progenitors;

(c) it is expressed in committed T and B cells;

(d) it has a molecular weight of approximately 58 kD;

(e) it has at least one or preferably two C-terminal zinc finger domains;

(f) it is not expressed in stem cells; or (g) it is a transcriptional activator of a lymphoid gene.

The invention includes an immunogen which includes an active or inactive Aiolos polypeptide, or an analog or a fragment thereof, in an immunogenic preparation, the immunogen being capable of eliciting an immune response specific for the Aiolos polypeptide, e.g., a humoral response, an antibody response, or a cellular response. In preferred embodiments, the immunogen comprising an antigenic determinant, e.g., a unique determinant, from a protein represented by SEQ ID NO:2 or SEQ ID NO:8. For example, the immunogen comprises amino acids 1–124 of SEQ ID NO:2 or amino acids 275–448 of SEQ ID NO:2.

The invention also includes an antibody preparation, preferably a monoclonal antibody preparation, specifically reactive with an epitope of the Aiolos immunogen or generally of an Aiolos polypeptide.

In another aspect, the invention provides a substantially pure nucleic acid having, or comprising, a nucleotide sequence which encodes a polypeptide, the amino acid sequence of which includes, or is, the sequence of an Aiolos polypeptide, or analog or fragment thereof.

In preferred embodiments, the nucleic acid encodes a vertebrate, e.g., a mammalian, e.g., a human polypeptide.

In preferred embodiments, the nucleic acid encodes an Aiolos polypeptide which includes additional Aiolos coding sequences 5' to that SEQ ID NO:8. In preferred embodiments: the additional sequence includes at least 1, 10, 20, 40, 60, 70, 80 or 100 amino acid residues; the additional sequence is equal to or less than 1, 10, 20, 40, 60, 70, 80 or 100 amino acid residues.

In preferred embodiments, the nucleic acid encodes a polypeptide having one or more of the following characteristics: at least one biological activity of an Aiolos, e.g., a polypeptide specifically reactive with an antibody, or antibody fragment, directed against an Aiolos polypeptide; an amino acid sequence at least 60%, 80%, 90%, 95%, 98%, or 99% homologous to an amino acid sequence from SEQ ID NO:2 or SEQ ID NO:8; an amino acid sequence essentially the same as an amino acid sequence in SEQ ID NO:2 or SEQ ID NO:8, the polypeptide is at least 5, 10, 20, 50, 100, 150, 200, or 250 amino acids in length; at least 5, preferably at least 10, more preferably at least 20, most preferably at least 50, 100, 150, 200, or 250 contiguous amino acids from SEQ ID NO:2 or SEQ ID NO:8; an amino acid sequence which is preferably at least 10, but no more than 100, amino acids in length; the ability to act as an agonist or an antagonist of a biological activity of a naturally occurring Aiolos polypeptide.

In preferred embodiments: the nucleic acid is or includes the nucleotide sequence of SEQ ID NO:1 or SEQ ID NO:7; the nucleic acid is at least 60%, 70%, 80%, 90%, 95%, 98%, or 99% homologous with a nucleic acid sequence of SEQ ID NO:1 or SEQ ID NO:7; the nucleic acid includes a fragment of SEQ ID NO:1 or SEQ ID NO:7 which is at least 25, 50, 100, 200, 300, 400, 500, or 1,000 bases in length; the nucleic acid differs from the nucleotide sequence of SEQ ID NO:1 due to degeneracy in the genetic code.

In a preferred embodiment, the Aiolos encoding nucleic acid sequence encodes amino acid residues 1–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 58–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 72–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 76–507 of SEQ ID NO:2 or a functionally equivalent residue in the Aiolos sequence of another vertebrate or mammal, e.g., a human.

In a preferred embodiment, the Aiolos encoding nucleic acid sequence encodes amino acid residues 1–206 of SEQ ID NO:8.

In a preferred embodiment the polypeptide encoded by the nucleic acid is an agonist which, for example, is capable of enhancing an activity of a naturally-occurring mutant or wild type Aiolos polypeptide. In another preferred embodiment, the encoded polypeptide is an antagonist which, for example, inhibits an undesired activity of a naturally-occurring Aiolos polypeptide (e.g., a polypeptide having an amino acid sequence shown in SEQ ID NO:2 or SEQ ID NO:8).

In a preferred embodiment, the encoded Aiolos polypeptide differs in amino acid sequence at 1, 2, 3, 5, 10 or more residues, from a sequence in SEQ ID NO:2 or SEQ. ID NO:8. The differences, however, are such that the encoded Aiolos polypeptide exhibits at least one biological activity of a naturally occurring Aiolos polypeptide (e.g., the Aiolos polypeptide of SEQ ID NO:2 or SEQ ID NO:8).

In preferred embodiments, the nucleic acid encodes an Aiolos polypeptide which includes an Aiolos polypeptide sequence, as described herein, as well as other N-terminal and/or C-terminal amino acid sequences.

In preferred embodiments, the nucleic acid encodes a polypeptide which includes all or a portion of an amino acid sequence shown in SEQ ID NO:2 or SEQ ID NO:8, fused, in reading frame, to additional amino acid residues, preferably to residues encoded by genomic DNA 5' to the genomic DNA which encodes a sequence from SEQ ID NO:2 or SEQ ID NO:8.

In preferred embodiments, the encoded polypeptide is a recombinant fusion protein having a first Aiolos polypeptide portion and a second polypeptide portion having an amino acid sequence unrelated to an Aiolos polypeptide. The second polypeptide portion can be, e.g., any of glutathione-S-transferase; a DNA binding domain; or a polymerase activating domain. In preferred embodiments the fusion protein can be used in a two-hybrid assay.

In preferred embodiments, the encoded polypeptide is a fragment or analog of a naturally occurring Aiolos polypeptide which inhibits reactivity with antibodies, or F(ab')$_2$ fragments, specific for a naturally occurring Aiolos polypeptide.

In preferred embodiments, the nucleic acid will include a transcriptional regulatory sequence, e.g., at least one of a transcriptional promoter or transcriptional enhancer sequence, operably linked to the Aiolos gene sequence, e.g., to render the Aiolos gene sequence suitable for use as an expression vector.

In yet another preferred embodiment, the nucleic acid of the invention hybridizes under stringent conditions to a nucleic acid probe corresponding to at least 12 consecutive nucleotides from SEQ ID NO:1 or SEQ ID NO:7, or more preferably to at least 20 consecutive nucleotides from SEQ ID NO:1 or SEQ ID NO:7, or more preferably to at least 40 consecutive nucleotides from SEQ ID NO:1 or SEQ ID NO:7.

In a preferred embodiment, the nucleic acid encodes an Aiolos polypeptide which includes a sequence which is not present in the mature protein.

In preferred embodiments, the nucleic acid encodes an Aiolos polypeptide which: is expressed in spleen and thymus; is expressed in mature T and/or B cells; is highly homologous, preferably at least 90% or 95% homologous, with the 50 most C-terminal amino acids of the Ikaros gene (e.g., the dimerization domain of exon 7 of the Ikaros gene); is highly homologous, preferably at least 90% or 95% homologous, with the activation domain of exon 7 of the Ikaros gene; is capable of forming Aiolos dimers and/or Aiolos/Ikaros dimers; is involved in lymphocyte differentiation, e.g., T cell maturation.

In preferred embodiments, the nucleic acid encodes an Aiolos polypeptide which includes: the YAS5 interaction domain; the YAS3 interaction domain; the YIZ Ikaros dimerization domain.

In preferred embodiments, the nucleic acid encodes an Aiolos polypeptide which encodes: one, two, three, four, five exons, or more exons; exons 3, 4, 5 and 7; exons 3–7; exon 7 (the exons are shown in FIG. 4).

In preferred embodiments, the nucleic acid encodes an Aiolos polypeptide which has one or more of the following properties:
 (a) it can form a dimer with an Aiolos or Ikaros polypeptide;
 (b) it is expressed in committed lymphoid progenitors;
 (c) it is expressed in committed T and B cells;
 (d) it has a molecular weight of approximately 58 kD;
 (e) it has at least one zinc finger domain;
 (f) it is not expressed in stem cells; or
 (g) it is a transcriptional activator of a lymphoid gene.

In other preferred embodiments, the nucleic acid encodes an Aiolos polypeptide which has one or more of the following properties:
 (a) it can form a dimer with an Aiolos or Ikaros polypeptide;
 (b) it is expressed in committed lymphoid progenitors;
 (c) it is expressed in committed T and B cells;
 (d) it has a molecular weight of approximately 58 kD;
 (e) it has an N-terminal zinc finger domain;
 (f) it is not expressed in stem cells; or
 (g) it is a transcriptional activator of a lymphoid gene.

In yet other preferred embodiments, the nucleic acid encodes an Aiolos polypeptide which has one or more of the following properties:
 (a) it can form a dimer with an Aiolos or Ikaros polypeptide;
 (b) it is expressed in committed lymphoid progenitors;
 (c) it is expressed in committed T and B cells;
 (d) it has a molecular weight of approximately 58 kD;
 (e) it has at least one or preferably two C-terminal zinc finger domains;
 (f) it is not expressed in stem cells; or
 (g) it is a transcriptional activator of a lymphoid gene.

In another aspect, the invention includes: a vector including a nucleic acid which encodes an Aiolos polypeptide; a host cell transfected with the vector; and a method of producing a recombinant Aiolos polypeptide, including culturing the cell, e.g., in a cell culture medium, and isolating the Aiolos polypeptide, e.g., an Aiolos polypeptide from the cell or from the cell culture medium.

In another aspect, the invention features, a purified recombinant nucleic acid having at least 50%, 60%, 70%, 80%, 90%, 95%, 98%, or 99% homology with a nucleotide sequence shown in SEQ ID NO:1 or SEQ ID NO:7.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:1 or SEQ ID NO:8, or naturally occurring mutants thereof. In preferred embodiments, the probe or primer further includes a label group attached thereto. The label group can be, e.g., a radioisotope, a fluorescent compound, an enzyme, and/or an enzyme cofactor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

The invention includes vertebrate, e.g., mammalian, e.g., rodent, e.g., mouse or rat, or human Aiolos polypeptides.

In another aspect, the invention features a method of evaluating a compound for the ability to interact with, e.g., bind, or modulate, e.g., inhibit or promote, the activity of an Aiolos polypeptide, e.g., an Aiolos monomer, or an Aiolos-Aiolos dimer or an Aiolos-Ikaros dimer. The method includes contacting the compound with the Aiolos polypeptide, and evaluating the ability of the compound to interact with or form a complex with the Aiolos polypeptide. This method can be performed in vitro, e.g., in a cell free system, or in vivo, e.g., in a two-hybrid interaction trap assay. This method can be used to identify naturally occurring molecules which interact with the Aiolos polypeptide. It can also be used to find natural or synthetic inhibitors of mutant or wild type Aiolos polypeptide. The compound can be a peptide or a non peptide molecule, e.g., a small molecule preferably 500 to 5,000 molecular weight, more preferably 500 to 1,000 molecular weight, having an aromatic scaffold, e.g., a bis-amide phenol, decorated with various functional groups.

In brief, a two hybrid assay system (see e.g., Bartel et al. (1993) *Cellular Interaction in Development: A practical Approach*, D. A. Hartley, ed., Oxford University Press, Oxford, pp. 153–179) allows for detection of protein-protein interactions in yeast cells. The known protein, e.g., an Aiolos polypeptide, is often referred to as the "bait" protein. The proteins tested for binding to the bait protein are often referred to as "fish" proteins. The "bait" protein, e.g., an Aiolos polypeptide, is fused to the GAL4 DNA binding domain. Potential "fish" proteins are fused to the GAL4 activating domain. If the "bait" protein and a "fish" protein interact, the two GAL4 domains are brought into close proximity, thus rendering the host yeast cell capable of surviving a specific growth selection.

In another aspect, the invention features a method of identifying active fragments or analogs of an Aiolos polypeptide. The method includes first identifying a compound, e.g., an Ikaros peptide, which interacts with an Aiolos polypeptide and determining the ability of the compound to bind the candidate fragment or analog. The two hybrid assay described above can be used to obtain fragment-binding compounds. These compounds can then be used as "bait" to fish for and identify fragments of the Aiolos polypeptide which interact, bind, or form a complex with these compounds.

In another aspect, the invention features a method of making an Aiolos polypeptide, having a non-wild type activity, e.g., an antagonist, agonist, or super agonist of a naturally occurring Aiolos polypeptide. The method includes altering the sequence of an Aiolos polypeptide (e.g., SEQ ID NO:2 or SEQ ID NO:8) by, for example, substitution or deletion of one or more residues of a non-conserved region, and testing the altered polypeptide for the desired activity.

In another aspect, the invention features a method of making a fragment or analog of an Aiolos polypeptide, e.g., an Aiolos polypeptide having at least one biological activity of a naturally occurring Aiolos polypeptide. The method includes altering the sequence, e.g., by substitution or deletion of one or more residues, preferably which are non-conserved residues, of an Aiolos polypeptide, and testing the altered polypeptide for the desired activity.

In another aspect, the invention features, a method of evaluating a compound for the ability to bind a nucleic acid encoding an Aiolos gene regulatory sequence. The method includes: contacting the compound with the nucleic acid; and evaluating ability of the compound to form a complex with the nucleic acid. In preferred embodiments the Aiolos gene regulatory sequence is functionally linked to a heterologous gene, e.g., a reporter gene.

In another aspect, the invention features a human cell, e.g., a hematopoietic stem cell or a lymphocyte e.g., a T or a B cell, transformed with a nucleic acid which encodes an Aiolos polypeptide.

In another aspect, the invention features a method for treating an animal, e.g., a human, a mouse, a transgenic animal, or an animal model for a disorder, e.g., an immune system disorder, e.g., a T or B cell related disorder, e.g., a nude mouse or a SCID mouse, including administering a therapeutically-effective amount of an Aiolos polypeptide to the animal. The Aiolos polypeptide can be monomeric or an Aiolos-Aiolos or Aiolos-Ikaros dimer.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a cell selected, e.g., selected in vitro, for the expression of a product of the Aiolos gene, e.g., hematopoietic stem cells, e.g., cells transformed with Aiolos-peptide-encoding DNA, e.g., hematopoietic stem cells transformed with Aiolos-peptide-encoding DNA.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a nucleic acid encoding an Aiolos peptide and expressing the nucleic acid.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema; an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method of evaluating the effect of a treatment, e.g., a treatment designed to promote or inhibit hematopoiesis, including carrying out the treatment and evaluating the effect of the treatment on the expression of the Aiolos gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Aiolos gene, e.g., a proliferative disorder, e.g., a leukemic disorder, Hodgkin's lymphoma, a cutaneuous cell lymphoma, e.g., a cutaneous T cell lymphoma, or a disorder of the immune system, e.g., an immunodeficiency, or a T or B cell related disorder, e.g., a disorder characterized by a shortage of T or B cells. The method includes examining the subject for the expression of the Aiolos gene, non-wild type expression or mis-expression being indicative of risk.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features a method for determining if a subject, e.g., a human, is at risk for a disorder related to mis-expression of the Aiolos gene, e.g., a proliferative disorder, e.g., a leukemic disorder, Hodgkin's lymphoma, a cutaneuous cell lymphoma, e.g., a cutaneous T cell lymphoma, or a disorder of the immune system, e.g., an immunodeficiency, or a T or B cell related disorder, e.g., a disorder characterized by a shortage of T or B cells. The method includes providing a nucleic acid sample from the subject and determining if the structure of an Aiolos gene allele of the subject differs from wild type.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In preferred embodiments: the determination includes determining if an Aiolos gene allele of the subject has a gross chromosomal rearrangement; the determination includes sequencing the subject's Aiolos gene.

In another aspect, the invention features, a method of evaluating an animal or cell model for a proliferative disorder, e.g., a leukemic disorder, Hodgkin's lymphoma, a cutaneuous cell lymphoma, e.g., a cutaneous T cell lymphoma, or an immune disorder, e.g., a T cell related disorder, e.g., a disorder characterized by a shortage of T or B cells. The method includes determining if the Aiolos gene in the animal or cell model is expressed at a predetermined level or if the Aiolos gene is mis-expressed. In preferred embodiments: the predetermined level is lower than the level in a wild type or normal animal; the predetermined level is higher than the level in a wild type or normal animal; or the pattern of isoform expression is altered from wildtype.

In preferred embodiments: the disorder is characterized by unwanted, e.g., higher than normal, antibody, e.g., IgE, production or levels; the disorder is characterized by an antibody mediated response, e.g., an IgE mediated response; the disorder is characterized by an aberrant or unwanted B cell response; the disorder is asthma, an immune mediated skin disorder, e.g., excema, an allergic reaction, hay fever, hives, a food allergy; the disorder is characterized by a hypersensitive response, e.g., an IgE mediated hypersensitive response; the disorder is characterized by an anaphylactic response; the disorder is characterized by a local B cell mediated response; the disorder is characterized by a systemic B cell mediated response; the disorder is characterized by unwanted mast cell degranulation.

In another aspect, the invention features, a transgenic animal, e.g., a mammal, e.g., a mouse or a nonhuman primate having an Aiolos transgene.

In preferred embodiments the animal is a transgenic mouse having a mutated Aiolos transgene, the mutation occurring in, or altering, e.g., a domain of the Aiolos gene described herein.

In other preferred embodiments the transgenic animal or cell: is heterozygous for an Aiolos transgene; homozygous for an Aiolos transgene; includes a first Aiolos transgene and a second Aiolos transgene; includes an Aiolos transgene and a second transgene which is other than an Aiolos transgene, e.g., an Ikaros transgene.

In another aspect, the invention features a method for evaluating the effect of a treatment on a transgenic cell or animal having an Aiolos transgene, e.g., the effect of the treatment on the development of the immune system. The method includes administering the treatment to a cell or animal having an Aiolos transgene, and evaluating the effect of the treatment on the cell or animal. The effect can be, e.g., the effect of the treatment on: Aiolos or Ikaros expression or misexpression; the immune system or a component thereof; the nervous system or a component thereof; or the cell cycle. Immune system effects include e.g., T cell activation, T cell development, the ability to mount an immune response, the ability to give rise to a component of the immune system, B cell development, NK cell development, or the ratios $CD4^+/CD8^+$, $CD4^+/CD8^-$ and $CD4^-/CD8^+$.

In preferred embodiments the treatment can include: the administration of a drug, chemical, or other substance; the administration of ionizing radiation; the administration of an antibody, e.g., an antibody directed against a molecule or cell of the immune system; administration of a substance or other treatment which suppresses the immune system; or administration of a substance or other treatment which activates or boosts the function of the immune system; introduction of a nucleic acid, e.g., a nucleic acid which encodes or expresses a gene product, e.g., a component of the immune system; the introduction of a protein, e.g., a protein which is a component of the immune system.

In another aspect, the invention features a method for evaluating the effect of a treatment on an immune system component. The method includes: (1) supplying a transgenic cell or animal having an Aiolos transgene; (2) supplying the immune system component; (3) administering the treatment; and (4) evaluating the effect of the treatment on the immune system component.

In yet another aspect, the invention features a method for evaluating the interaction of a first immune system component with a second immune system component. The method includes: (1) supplying a transgenic cell or animal, e.g., a mammal, having an Aiolos transgene; (2) introducing the first and second immune system component into the transgenic cell or mammal; and (3) evaluating an interaction between the first and second immune system components.

Mice with mutant Aiolos transgenes which eliminate many of the normal components of the immune system, e.g., mice homozygous for a transgene having a deletion for some or all of exon 7 (corresponding to amino acids 275–507 of SEQ ID NO:2), are particularly useful for "reconstitution experiments."

In another aspect, the invention features a method for evaluating the effect of a treatment on an immune system disorder, e.g., a neoplastic disorder, a leukemia or a lymphoma, a T cell related lymphoma, including: administering the treatment to a cell or animal having an Aiolos transgene, and evaluating the effect of the treatment on the cell or animal. The effect can be, e.g., the effect of the treatment on: Aiolos or Ikaros expression or misexpression; the immune system or a component thereof; or the cell cycle. Immune system effects include e.g., T cell activation, T cell development, the ability to mount an immune response, the ability to give rise to a component of the immune system, B cell development, NK cell development, or the ratios $CD4^+/CD8^+$, $CD4^+/CD8^-$ and $CD4^-/CD8^+$.

The inventors have also discovered that Ikaros and Aiolos can form dimers (heterodimers) with other polypeptides. E.g., an Ikaros polypeptide can form dimers not only with Ikaros polypeptides, but with other polypeptides which bind to its C terminal region, e.g, other polypeptides having Zinc-finger regions, e.g., Aiolos polypeptides. Similarly, an Aiolos polypeptide can form dimers not only with Aiolos polypeptides, but with other polypeptides which bind to its C terminal region, e.g, other polypeptides having Zinc-finger regions, e.g., Ikaros polypeptides.

The invention also includes Ikaros-Aiolos dimers. The Ikaros member of the dimer can be any Ikaros polypeptide, e.g., any naturally occuring Ikaros or any Ikaros referred to in U.S. Ser. No. 08/238,212, filed May 2, 1994, hereby incorporated by reference. The proteins of the Ikaros family are isoforms which arise from differential splicing of Ikaros gene transcripts. The isoforms of the Ikaros family generally include a common 3' exon (Ikaros exon E7, which includes amino acid residues 283–518 of the mouse Ikaros protein represented by SEQ ID NO:18, and amino acid residues 229–461 of the human Ikaros protein represented by SEQ ID NO:16) but differ in the 5' region. The Ikaros family includes all naturally occurring splicing variants which arise from transcription and processing of the Ikaros gene. Five such isoforms are described herein and in U.S. Ser. No. 08/238, 212, filed May 2, 1994, hereby incorporated by reference. The Ikaros family also includes other isoforms, including those generated by mutagenesis and/or by in vitro exon shuffling. The naturally occurring Ikaros proteins can bind and activate (to differing extents) the enhancer of the CD3δ gene, and are expressed primarily in early hematopoietic and lymphoid cells in the adult. The expression pattern of this transcription factor during embryonic development suggests that Ikaros proteins play a role as a genetic switch regulating entry into the lymphoid and T cell lineages. The Ikaros gene is also expressed in the proximal corpus striatum during early embryogenesis in mice. As is discussed herein, Ikaros and Aiolos polypeptide can form Ikaros-Aiolos dimers.

Accordingly, the invention includes a substantially pure dimer which includes (or consiststs essentially of) an Aiolos polypeptide and an Ikaros polypeptide.

The Ikaros polypeptide of the Ikaros-Aiolos dimer includes one or more Ikaros exons. In preferred embodiments: the Ikaros exon is E1/2, E3, E4, E5, E6, or E7; the peptide does not include exon E7.

In other preferred embodiments: the Ikaros peptide of the Ikaros-Aiolos dimer further includes a second Ikaros exon; the second exon is any of E1/2, E3, E4, E5, E6, or E7; the first exon is E7 and the second exon is any of E1/2, E3, E4, E5, E6.

In other preferred embodiments: the Ikaros peptide of the Ikaros-Aiolos dimer further includes a third Ikaros exon; the third exon is any of E1/2, E3, E4, E5, E6, or E7; the first exon is E7, the second exon is E3, and the third exon is E1/2; the peptide is Ikaros isoform 5.

In other preferred embodiments: the Ikaros peptide of the Ikaros-Aiolos dimer further includes a fourth Ikaros exon; the fourth exon is any of E1/2, E3, E4, E5, E6, or E7; the first exon is E7, the second exon is E4, the third exon is E3, and the fourth exon is E1/2; the first exon is E7, the second exon is E4, the third exon is E3, and the fourth exon is E1/2; the peptide is Ikaros isoform 3 or 4.

In other preferred embodiments: the Ikaros peptide of the Ikaros-Aiolos dimer further includes a fifth Ikaros exon; the fifth exon is any of E1/2, E3, E4, E5, E6, or E7; the first exon is E7, the second exon is E6, the third exon is E5, the fourth exon is E4, and the fifth exon is E1/2; the peptide is Ikaros Isoform 2.

In other preferred embodiments: the Ikaros peptide of the Ikaros-Aiolos dimer further includes a sixth Ikaros exon; the sixth exon is any of E1/2, E3, E4, E5, E6, or E7; the first exon is E7, the second exon is E6, the third exon is E5, the fourth exon is E4, the fifth exon is E3, and the sixth exon is E1/2; the peptide is Ikaros isoform 1. In preferred embodiments: the sequence of the Ikaros exon is essentially the same as that of a naturally occurring Ikaros exon, or a fragment thereof having Ikaros activity; the amino acid sequence of the Ikaros exon is such that a nucleic acid sequence which encodes it is at least 85%, more preferably at least 90%, yet more preferably at least 95%, and most preferably at least 98 or 99% homologous with a naturally occurring Ikaros exon, or a fragment thereof having Ikaros activity, e.g., Ikaros having an amino acid sequence represented in any of SEQ ID NOS:15–21 or SEQ ID NO:22; the amino acid sequence of the Ikaros exon is such that a nucleic acid sequence which encodes it hybridizes under high or low stringency to a nucleic acid which encodes a naturally occurring Ikaros exon, or a fragment thereof having Ikaros activity, e.g., an Ikaros exon with the same, or essentially the same, amino acid sequence as an Ikaros exon represented in any of SEQ ID NOS:15–21 the amino acid sequence of the Ikaros exon is at least 30, more preferably at least 40, more preferably at least 50, and most preferably at least 60, 80, 100, or 200 amino acid residues in length; the encoded Ikaros amino acid sequence is at least 50% more preferably 60%, more preferably 70%, more preferably 80%, more preferably 90%, and most preferably 95% as long as a naturally occurring Ikaros exon, or a fragment thereof having Ikaros activity; the Ikaros exon is essentially equal in length to a naturally occurring Ikaros exon; the amino acid sequence of the Ikaros exon is at least 80%, more preferably at least 85%, yet more preferably at least 90%, yet more preferably at least 95%, and a most preferably at least 98 or 99% homologous with a naturally occurring Ikaros exon sequence, or a fragment thereof having Ikaros activity, e.g., an Ikaros exon sequence of SEQ ID NO:15, SEQ ID NO:16, SEQ ID NO:17, SEQ ID NO:18, SEQ ID NO:19, SEQ ID NO:20, or SEQ ID NO:21; the Ikaros exon amino acid sequence is the same, or essentially the same, as that of a naturally occurring Ikaros exon, or a fragment of the sequence thereof, e.g., an Ikaros exon described in any of SEQ ID NOS:15–21; and the peptide has Ikaros peptide activity; the peptide has Ikaros antagonist activity.

In preferred embodiments: the Ikaros protein of the Ikaros-Aiolos dimer comprises a polypeptide represented by the general formula A-B-C-D-E, wherein A represents Exon 3 or is absent, B represents Exon 4 or is absent, C represents Exon 5 or is absent, D represents Exon 6 or is absent, and E represents Exon 7 or is absent; the polypeptide includes at least two of said exons; the polypeptide includes at least one exon containing a zinc finger domain; the polypeptide includes at least one exon selected from E3, E4 or E5.

In preferred embodiments: the exons in the Ikaros peptide of the Ikaros-Aiolos dimer are arranged in the same relative linear order as found in a naturally occurring isoform, e.g., in Ikaros isoform 1, e.g., in a peptide having the exons E3 and E7, E3 is located N-terminal to E7; the linear order of the exons is different from that found in a naturally occurring isoform, e.g., in Ikaros isoform 1, e.g., in a peptide having exons E3, E5, and E7, the direction N-terminal to C-terminal end, is E5, E3, E7; the exons in the peptide differ in one or more of composition (i.e., which exons are present), linear order, or number (i.e., how many exons are present or how many times a given exon is present) from a naturally occurring Ikaros isoform, e.g., from Ikaros isoform 1, 2, 3, 4, or 5; e.g., the Ikaros protein is an isoform generated by in vitro exon shuffling.

The invention also includes: a cell, e.g., a cultured cell or a stem cell, containing purified Ikaros-protein-encoding-DNA and purified Aiolos-protein-encoding-DNA; a cell capable of expressing an Ikaros and an Aiolos protein; a cell capable of giving rise to a transgenic animal or to a homogeneous population of hemopoietic cells, e.g., lymphoid cells, e.g., T cells; an essentially homogeneous population of cells, each of which includes purified Ikaros-protein-encoding-DNA and purified Aiolos-protein-encoding-DNA; and a method for manufacture of a dimer of the invention including culturing a cell which includes a DNA, preferably a purified DNA, of the invention in a medium to express the peptides.

The invention also includes: a preparation of cells, e.g., cultured cells or a stem cells, including a cell a containing purified Ikaros-protein-encoding-DNA and a cell encoding purified Aiolos-protein-encoding-DNA.

The invention also includes substantially pure preparation of an antibody, preferably a monoclonal antibody directed against an Ikaros-Aiolos dimer (which preferably does not bind to an Ikaros-Ikaros or Aiolos-Aiolos dimer); a therapeutic composition including an Ikaros-Aiolos dimer and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering a therapeutically-effective amount of an Ikaros-Aiolos dimer to the animal.

In another aspect, the invention features a method for treating an animal, e.g., a human, a mouse, a transgenic animal, or an animal model for an immune system disorder, e.g., a T or B cell related disorder, e.g., a nude mouse or a SCID mouse including administering to the animal cells selected, e.g., selected in vitro, for the expression of a product of the Ikaros gene and of the Aiolos gene, e.g., hematopoietic stem cells, e.g., cells transformed with Ikaros-peptide-encoding DNA and or Aiolos-peptide-encoding DNA, e.g., hematopoietic stem cells transformed with Ikaros and or Aiolos-peptide-encoding DNA. The Ikaros and Aiolos DNA can be present in the same or in different cells.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering to the animal a nucleic acid encoding an Ikaros peptide and a nucleic acid encoding an Aiolos peptide and expressing the nucleic acids.

In another aspect, the invention features a method of evaluating the effect of a treatment, e.g., a treatment designed to promote or inhibit-hematopoiesis, including carrying out the treatment and evaluating the effect of the treatment on the expression of the Ikaros and the Aiolos gene.

In preferred embodiments the treatment is administered: to an animal, e.g., a human, a mouse, a transgenic animal, or an animal model for an immune system disorder, e.g., a T or B cell related disorder, e.g.; a nude mouse or a SCID mouse, or a cell, e.g., a cultured stem cell.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including examining the subject for the expression of the Ikaros-Aiolos dimers, non-wild type expression or mis-expression being indicative of risk.

In another aspect, the invention features, a method of evaluating an animal or cell model for an immune disorder, e.g., a T cell related disorder, e.g., a disorder characterized by a shortage of T or B cells, including determining if Ikaros-Aiolos dimers in the animal or cell model are expressed at a predetermined level. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an Ikaros gene or Ikaros protein encoding DNA and an Aiolos gene or Aiolos protein encoding DNA. In preferred embodiments: the Ikaros and or Aiolos gene or DNA includes a deletion, e.g., a deletion of all or part of one or more exons.

In another aspect, the invention features a method for treating an animal, e.g., a human, a mouse, a transgenic animal, or an animal model for a disorder of the nervous system, e.g., a disorder of the corpus striatum, e.g., Alzheimer's disease, immune system disorder, including administering a therapeutically effective amount of an Ikaros-Aiolos dimer to the animal.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal cells selected, e.g., selected in vitro, for the production of an Ikaros-Aiolos dimer, e.g., hematopoietic stem cells, e.g., cells transformed with Ikaros and or Aiolos protein-encoding DNA, e.g., hematopoietic stem cells transformed with Ikaros and or Aiolos-protein-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered: the cells are taken from an animal which is of the same species as is the animal to which they are administered.

In another aspect, the invention features a method for treating an animal, e.g., a human, a mouse, a transgenic animal, or an animal model for a disorder of the nervous system, e.g., a disorder of the corpus striatum, e.g., Alzheimer's disease, including administering to the animal a nucleic acid encoding an Ikaros peptide and a nucleic acid encoding an Aiolos peptide and expressing the nucleic acids.

In another aspect, the invention features a method for determining if a subject, e.g., a human, is at risk for a disorder related to mis-expression of an Ikaros-Aiolos dimer, e.g., a disorder of the nervous system, e.g., a disorder of the corpus striatum, e.g., Alzheimer's disease, including examining the subject for the expression of an Ikaros-Aiolos dimer, non-wild type expression or mis-expression being indicative of risk.

In another aspect, the invention features, a method of inhibiting an interaction, e.g., binding, between a protein, e.g., an Ikaros isoform, Aiolos, an Ikaros-Ikaros dimer, an Aiolos-Aiolos dimer, or a first Ikaros-Aiolos dimer, and a DNA sequence, e.g., a DNA sequence under the control of a δA sequence, an NKFB sequence, a sequence which corresponds to an Ikaros or Aiolos binding site, or a site present in the control region of a lymphocyte restricted gene, e.g., TCR-α, -β, or -δ, CD3-δ, -ε, -γ genes, the SL3 gene, or the HIV LTR gene. The methods includes contacting the DNA sequence with an effective amount of a second Ikaros-Aiolos dimer, e.g., an Ikaros-aiolos dimer described herein.

In another aspect, the invention features, a method of inhibiting an interaction, e.g., binding, between a protein, e.g., an Ikaros isoform, Aiolos, an Ikaros-Ikaros dimer, an Aiolos-Aiolos dimer, or an Ikaros-Aiolos dimer, and a DNA sequence, e.g., a δA sequence, an NKFB sequence, a sequence which corresponds to an Ikaros binding oligonucleotide described herein, or a site present in the control region of a lymphocyte restricted gene, e.g., TCR-α, -β, or -δ, CD3-δ, -ε, -γ genes, the SL3 gene, or the HIV LTR gene. The methods includes contacting the protein with an effective amount of an Ikaros, Aiolos, or Ikaros-Aiolos dimer-binding oligonucleotide.

In another aspect, the invention features, a method of modulating hematopoietic development, e.g., a progression of a cell through a lymphoid lineage, e.g., a lymphocyte maturation and/or function, the method including altering, in a cell or animal, a wild type expression of Ikaros-Aiolos and/or Aiolos-Aiolos dimers.

In preferred embodiments, the expression can be altered by providing Aiolos and/or Ikaros polypeptides.

In other preferred embodiments, the method includes supplying to a cell or animal a mutant Aiolos and/or Ikaros polypeptide, e.g., a polypeptide having a dominant negative mutation, e.g., a DNA binding mutation.

In another aspect, the invention features, a method of modulating hematopoietic development, e.g., a progression of a cell through a lymphoid lineage, e.g., a lymphocyte maturation and/or function, the method including altering, in a cell or animal, the ratio of Ikaros-Ikaros dimers to any of Aiolos-Aiolos or Aiolos-Ikaros dimers.

In preferred embodiments, the ratio can be altered by providing Aiolos or Ikaros polypeptides.

In other preferred embodiments, the method includes supplying to a cell or animal a mutant Aiolos and/or Ikaros polypeptide, e.g., a polypeptide having a dominant negative mutation, e.g., a DNA binding mutation.

In another aspect, the invention features, a method of modulating hematopoietic development, e.g., a progression of a cell through a lymphoid lineage, e.g., a lymphocyte maturation and/or function, the method including altering, in a cell or animal, the ratio of Aiolos-Aiolos dimers to any of Ikaros-Ikaros or Aiolos-Ikaros dimers.

In preferred embodiments, the ratio can be altered by providing Aiolos or Ikaros polypeptides.

In other preferred embodiments, the method includes supplying to a cell or animal a mutant Aiolos and/or Ikaros polypeptide, e.g., a polypeptide having a dominant negative mutation, e.g., a DNA binding mutation.

In general, the invention also features, a method of providing a proliferation-deregulated cell, or a cell which has non-wild type, e.g., increased, antibody production. The method includes: providing a mammal having a cell which misexpresses Aiolos, e.g., a hematopoietic cell; and isolating a proliferation-deregulated or antibody overexpressing cell from the mammal. The proliferation-deregulated or antibody overexpressing cell can be, e.g., a hematopoietic cell, e.g., a B lymphocyte.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell to divide and give rise to a proliferation-deregulated or antibody producing cell, e.g., a lymphocyte; providing a plurality of the proliferation-deregulated cells e.g., lymphocytes or transformed lymphocytes from the mammal.

In preferred embodiments: the proliferation-deregulated or antibody producing cell e.g., a lymphocyte, e.g., a transformed lymphocyte, is isolated from a lymphoma of the mammal.

In preferred embodiments: the mammal is heterozygous at the Aiolos locus; the mammal carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal is heterozygous or homozygous for an Aiolos transgene; the mammal carries a mutation in the control region of the Aiolos gene.

In preferred embodiments: the mammal carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries deletion for all or part of exon 7.

In preferred embodiments: the proliferation-deregulated or antibody producing cell is a homozygous mutant Aiolos cell e.g., a lymphocyte; the proliferation-deregulated or antibody producing lymphocyte is a B lymphocyte; the proliferation-deregulated or antibody producing cell is heterozygous or homozygous for an Aiolos transgene.

In preferred embodiments, the cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In a preferred embodiment: the Aiolos-misexpressing cell, e.g., a lymphocyte, is supplied exogenously to the mammal, e.g., to a homozygous wild-type Aiolos mammal or a mammal carrying a mutation at the Aiolos gene, e.g., a point mutation or a deletion for all or part of the Aiolos gene. If exogenously supplied, the cell can be a human or a nonhuman, e.g., a swine, nonhuman primate, e.g., a monkey, a goat, or a rodent, e.g., a rat or a mouse, lymphocyte.

In a preferred embodiment the method further comprises isolating one or more cells, e.g., lymphocytes, from the mammal, and allowing the cell or cells to proliferate into a clonal population of cells, e.g., lymphocytes.

In preferred embodiments: the mammal is immunized with an antigen; the cell is exogenously supplied and one or both of the mammal or the mammal which donates the cell are immunized with an antigen. The antigen can be: an alloantigen; a xenoantigen; an autoantigen; a protein; or an antigen which gives rise to an anti-idiotypic lymphocyte.

In preferred embodiments the method further includes providing a lymphocyte e.g., a B lymphocyte, or a substantially homogenous population of lymphocytes, e.g., B lymphocytes, which produce an antibody molecule, e.g., an IgG, IgA, or IgE molecule, which recognizes a selected antigen.

In another aspect, the invention features, a method of providing a proliferation-deregulated cell, or a cell which has non-wild type, e.g., increased, antibody production. The method includes: causing a subject cell to misexpress the Aiolos gene, e.g., by inducing an Aiolos mutation, thereby providing a proliferation-deregulated or antibody overexpressing cell. The proliferation-deregulated or antibody overexpressing cell can be, e.g., a hematopoietic cell, e.g., a B lymphocyte.

In preferred embodiments: the subject cell is from a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell to divide and give rise to a proliferation-deregulated or antibody producing cell, e.g., a lymphocyte; providing a plurality of the proliferation-deregulated cells e.g., lymphocytes or transformed lymphocytes from the mammal.

In preferred embodiments: the proliferation-deregulated or antibody producing cell e.g., a lymphocyte, e.g., a transformed lymphocyte, is isolated from cell or tissue culture.

In preferred embodiments: the cell is heterozygous at the Aiolos locus; the cell carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal is heterozygous or homozygous for an Aiolos transgene; the cell carries a mutation in the control region of the Aiolos gene.

In preferred embodiments: the cell carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries deletion for all or part of exon 7.

In preferred embodiments: the proliferation-deregulated or antibody producing cell is a homozygous mutant Aiolos cell e.g., a lymphocyte; the proliferation-deregulated or antibody producing lymphocyte is a B lymphocyte; the proliferation-deregulated or antibody producing cell is heterozygous or homozygous for an Aiolos transgene.

In preferred embodiments, the cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In a preferred embodiment the method further comprises allowing the subject cell, to proliferate into a clonal population of cells, e.g., lymphocytes.

In preferred embodiments: the mammal which supplies the subject cell is immunized with an antigen. The antigen can be: an alloantigen; a xenoantigen; an autoantigen; a protein; or an antigen which gives rise to an anti-idiotypic lymphocyte.

In preferred embodiments the method further includes providing a lymphocyte e.g., a B lymphocyte, or a substantially homogenous population of lymphocytes, e.g., B lymphocytes, which produce an antibody molecule, e.g., an IgG, IgA, or IgE molecule, which recognizes a selected antigen.

In another aspect, the invention features, a cell, e.g., a hematopoietic cell, e.g., a B lymphocyte, or, a clonal population or substantially purified preparation of such cells, preferably produced by a method of the invention described herein. Preferably, the cells misexpress Aiolos.

In another aspect, the invention features, a cell which produces or over produces an antibody, e.g., an IgA, IgG, or IgE antibody. The cell can be, e.g., a hematopoietic cell, e.g., a B lymphocyte, or a population, or substantially purified preparation, of such cells, preferably produced by a method of the invention described herein. Preferably the cells misexpress Aiolos.

In another aspect, the invention features, a proliferation-deregulated cell. The cell can be, e.g., a hematopoietic cell, e.g., a B lymphocyte, or a population, or substantially purified preparation, of such cells, preferably produced by a method of the invention described herein. Preferably the cells misexpress Aiolos.

In another aspect, the invention features, a lymphocyte, e.g., a B lymphoctye, or, a substantially homogenous population or substantially purified preparation of lymphocytes, preferably produced by a method of the invention described herein, which lymphocytes or population recognize a selected antigen. Preferably, the lymphocytes misexpress Aiolos.

In another aspect, the invention features, a method of culturing an Aiolos-misexpressing cell having at least one mutant allele at the Aiolos locus. The cell can be, e.g., a hematopoietic cell, e.g., a B lymphocyte. The method includes: introducing the cell into a mammal, wherein, preferably, the mammal is other than the one from which the cell has been isolated originally; and culturing the cell.

In a preferred embodiment, the method further includes: allowing the cell to proliferate in the mammal.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Aiolos-misexpressing cell to divide and give rise to a proliferation-deregulated cell, e.g., a transformed lymphocyte; providing a plurality of the proliferation-deregulated cells, e.g., lymphocytes or transformed lymphocytes from the mammal.

In preferred embodiments: the mammal, the cell or both, are heterozygous at the Aiolos locus; the mammal, the cell or both, carry a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the mammal is heterozygous or homozygous for an Aiolos transgene; the mammal, the cell or both, carry a mutation in the control region of the Aiolos gene.

In preferred embodiments: the mammal, the cell or both, carry a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal, the cell or both, carry a deletion for all or part of exon 7.

In preferred embodiments: the Aiolos-misexpressing cell is a homozygous mutant Aiolos cell e.g., a lymphocyte; the Aiolos-misexpressing cell is a B lymphocyte; the Aiolos-misexpressing cell is heterozygous or homozygous for an Aiolos transgene.

In preferred embodiments, the Aiolos-misexpressing cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In preferred embodiments: the mammal is immunized with an antigen; the cell is exogenously supplied and one or both of the mammal or the mammal which donates the cell are immunized with an antigen. The antigen can be: an alloantigen; a xenoantigen; an autoantigen; a protein; or an antigen which gives rise to an anti-idiotypic lymphocyte.

In a preferred embodiment: the Aiolos-misexpressing cell, e.g., a lymphocyte, is supplied exogenously to the mammal, e.g., to a homozygous wild-type Aiolos mammal or a mammal carrying a mutation at the Aiolos gene, e.g., a point mutation or a deletion for all or part of the Aiolos gene. If exogenously supplied, the cell can be a human or a nonhuman, e.g., a swine, nonhuman primate, e.g., a monkey, a goat, or a rodent, e.g., a rat or a mouse, lymphocyte.

Aiolos wild type cells can be cultured in Aiolos misexpressing mammals.

In another aspect, the invention features, a method of modulating the activity of, or promoting the interaction of an Aiolos misexpressing cell with, a target tissue or cell. The method includes: supplying the target; and exposing the target to a Aiolos misexpressing cell, e.g., a hematopoietic cell, e.g., a B lymphocyte, preferably having at least one mutant allele at the Aiolos locus, preferably provided that: the target is not Aiolos-misexpressing; the target and the cell differ in genotype at a locus other than the Aiolos locus; the target and the cell are from different animals; the target and the cell are from different species; the target activity is modulated in a recipient mammal and either the target or the cell is from a donor mammal other than the recipient mammal; or the target is exposed to the cell in an in vitro system.

In a preferred embodiment: the donor of the Aiolos-misexpressing cell is heterozygous or homozygous for an Aiolos transgene; the donor of the Aiolos-misexpressing cell is heterozygous at the Aiolos locus; the donor of the Aiolos-misexpressing cell carries a point mutation in or a deletion for all or part of the Aiolos gene, e.g., mutation in the DNA binding region, e.g., a point mutation in, or a deletion for all or part of one or more of the four N-terminal zinc finger regions which mediate Aiolos binding to DNA or in one or both of the C-terminal zinc finger regions which mediates Aiolos dimerization; the donor of the Aiolos-misexpressing cell is human or a non-human mammal, e.g., a swine, a monkey, a goat, or a rodent, e.g., a rat or a mouse. In preferred embodiments, e.g., in the case of the human donor, the manipulation that gives rise to Aiolos deregulation, e.g., an Aiolos lesion, can be made in vitro.

In preferred embodiments: the mammal which provides the Aiolos misexpressing cell carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the mammal carries deletion for all or part of exon 7.

In another preferred embodiment: the cell is heterozygous or homozygous for an Aiolos transgene; the cell is a heterozygous Aiolos cell; the cell is a homozygous mutant Aiolos cell; the lymphocyte is a B lymphocyte.

In preferred embodiments, the cell is a lymphocyte and is: a B cell; a cell which secretes one or more anti-inflammatory cytokines; a T cell which is antigen or idiotype specific.

In a preferred embodiment: the method is performed in an in vitro system; the method is performed in vivo, e.g., in a mammal, e.g., a rodent, e.g., a mouse or a rat, or a primate, e.g., a non-human primate or a human. If the method is performed in vitro, the donor of the target cell or tissue and the lymphocyte can be same or different. If the method is performed in vivo, there is a recipient animal and one or more donors.

In preferred embodiments: the method is performed in vivo and one or more of the recipient, the donor of the target cell or tissue, the donor of the cell, is immunized with an antigen; the method is performed in vitro and one or more of the donor of the target cell or tissue, the donor of the cell is immunized with an antigen. The antigen can be: an alloantigen; a xenoantigen or an autoantigen; a protein; or an antigen which gives rise to an anti-idiotypic lymphocyte.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, bone marrow tissue, lymph node tissue or thymic tissue, or the target is a syngeneic, allogeneic, or xenogeneic tissue.

In another preferred embodiment, the target is from a mammal, e.g., a human; the mammal is a non-human mammal, e.g., a swine, a monkey, a goat, or a rodent, e.g., a rat or a mouse.

In preferred embodiments, the activity of the target which is modulated is: the production of a cytokine; the proliferation or activation of a cell of the immune system; the production of an antibody; the lysis of an antigen presenting cell or the activation of a cytolytic T lymphocyte; the effect of target on resistance to infection; the effect of target on life span; the effect of target on body weight; the effect of target on the presence, function, or morphology of tissues or organs of the immune system; the effect of target on the ability of a component of the immune system to respond to a stimulus (e.g., a diffusable substance, e.g., cytokines, other cells of the immune system, or antigens); the effect of target on the ability to exhibit immunological tolerance to an alloantigen or a xenoantigen.

In preferred embodiments the interaction is the binding of an antibody produced by the Aiolos misexpressing cell with the target.

In preferred embodiments: the target and the cell differ in genotype at a locus other than the Aiolos locus; the target and the cell are from different animals; the target is not Aiolos-misexpressing.

In another aspect, the invention features, a method of reconstituting an immune system. The method includes: supplying a recipient mammal, and introducing, preferably exogenously, into the recipient mammal, an immune system component from a donor mammal, which is Aiolos misexpressing, e.g., which carries at least one mutant allele at the Aiolos locus. The recipient mammal, can be, e.g., a human or a nonhuman mammal, e.g., a swine, a nonhuman primate, e.g., a monkey, a goat, or a rodent, e.g., a rat or a mouse. The donor mammal can be, e.g., a human or a nonhuman mammal, e.g., a swine, a monkey, a goat, or a rodent, e.g., a rat or a mouse. If the donor mammal is human, the manipulation that gives rise to Aiolos misexpression, e.g., the introduction of an Aiolos lesion, can be made in vitro. The donor mammal and the recipient mammal can be different individuals or the same individual.

In preferred embodiments, the component is or includes an Aiolos misexpressing cell, e.g., a hematopoietic cell, e.g., a pluripotent stem cell, or a descendent of a stem cell, e.g., a lymphocyte.

In preferred embodiments, the component is from a donor mammal, e.g., a human or a nonhuman mammal, e.g., a swine, a monkey, a goat, or a rodent, e.g., a rat or a mouse.

In a preferred embodiment, the method further includes: prior to introduction of a component into the subject, treating the lymphocyte to inhibit proliferation, e.g., by irradiating the component.

In a preferred embodiment, the donor mammal carries a mutation at the Aiolos gene, e.g., a deletion of all or part of the Aiolos gene.

In another preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue.

In a preferred embodiment: the immune system component is from the same species as the recipient mammal; the immune system component is from species different from the species of the recipient mammal.

In preferred embodiments: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In preferred embodiments: the immune system component is heterozygous at the Aiolos locus; the immune system component is carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the immune system component is heterozygous or homozygous for an Aiolos transgene; the immune system component carries a mutation in the control region of the Aiolos gene.

In preferred embodiments: the immune system component carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the immune system component carries deletion for all or part of exon 7.

In preferred embodiments: the method is performed in vivo, and the recipient mammal or the donor mammal or both are immunized with an antigen. The antigen can be: an alloantigen; a xenoantigen or an autoantigen; a protein; or an antigen which gives rise to an anti-idiotypic lymphocyte.

In a preferred embodiment, the method further includes: determining a value for a parameter related to immune system function. The parameter related to the immune system function can be any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In another aspect, the invention features, a method of evaluating the interaction of an Aiolos misexpressing cell, e.g., a hematopoietic cell, a B lymphocyte, with an immune system component. The method includes: supplying an animal, e.g., a swine, a nonhuman primate, e.g., a monkey, a goat, or a rodent, e.g., a rat or a mouse; introducing the cell and the immune component into the animal; and evaluating the interaction between the Aiolos misexpressing cell and the immune system component.

In a preferred embodiment, the method further includes: prior to introduction of a cell into the subject, treating the lymphocyte to inhibit proliferation, e.g., by irradiating the cell.

In a preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal; the immune system component is from the same species as the lymphocyte; the immune system component is from species different from the species from which the lymphocyte is obtained.

In another preferred embodiment: the cell is from the same species as the animal; the cell is from a species which is different from the species of the animal.

In another preferred embodiment: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In a preferred embodiment: the cell is heterozygous or homozygous for an Aiolos transgene.

In preferred embodiments evaluating can include evaluating any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments: the method is performed in vivo, and one or more of the animal, the donor of the Aiolos misexpressing cell, the donor of the immune system component, is immunized with an antigen. The antigen can be: an alloantigen; a xenoantigen or an autoantigen; a protein; or an antigen which gives rise to an anti-idiotypic lymphocyte.

In another aspect, the invention features, a mammal, e.g., a nonhuman mammal, e.g., e.g., a swine, a nonhuman primate, e.g., a monkey, a goat, or a rodent, e.g., a rat or a mouse, having an exogenously introduced immune system component, the component being from a human or nonhuman mammal, e.g., a swine, a nonhuman primate, e.g., a monkey, a goat, or a rodent, e.g., a rat or a mouse, or cell culture which is Aiolos misexpressing or which carries at least one mutant allele at the Aiolos locus. In preferred embodiments, e.g., if the immune system component is from a wild-type animal, e.g., a human, the manipulation that gives rise to Aiolos deregulation, e.g., an Aiolos lesion, can be made in vitro.

In preferred embodiments, the component is from a human or nonhuman mammal, e.g., a swine, a nonhuman primate, e.g., a monkey, a goat, or a rodent, e.g., a rat or a mouse, which is Aiolos misexpressing.

In preferred embodiments: the component is from a mammal which is Aiolos misexpressing; the component is from a mammal which is heterozygous at the Aiolos locus; the component is from a mammal which carries a mutation at the Aiolos gene, e.g., a point mutation in or a deletion for all or part of the Aiolos gene, e.g., a mutation in the DNA binding region, e.g., a point mutation in, or a deletion for all or part of one or more of the four N-terminal zinc finger regions which mediates DNA binding of the Aiolos protein or for one or more of the two C terminal zinc finger regions which mediate dimerization of the Aiolos protein; the component is from a mammal which is heterozygous or homozygous for an Aiolos transgene; the component is from a mammal which carries a mutation in the control region of the Aiolos gene.

In preferred embodiments: the component is from a mammal which carries a mutation at the Aiolos gene, e.g., a point mutation or a deletion, which, inactivates one or both of transcriptional activation or dimerization, which decreases the half life of the protein, or which inactivates one or both of the C terminal Zinc finger domains; the component is from a mammal which carries deletion for all or part of exon 7.

In preferred embodiments, the immune system component is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal.

In preferred embodiments: the mammal or the donor animal which produces the immune system component or both are immunized with an antigen. The antigen can be: an alloantigen; a xenoantigen or an autoantigen; a protein; or an antigen which gives rise to an anti-idiotypic lymphocyte.

In another aspect, the invention features, a reaction mixture, preferably an in vitro reaction mixture, including an immune system component, the component including cells which misexpress Aiolos or being from an animal or cell culture which is misexpresses Aiolos or which carries at least one mutant allele at the Aiolos locus, and a target tissue or cell, wherein preferably, the immune system component and the target differ in genotype at a locus other than the Aiolos or Ikaros locus; the component and the target are from different species, or the component and the target are from different animals.

In preferred embodiments, the component is from an animal or cell culture which misexpresses Aiolos.

In preferred embodiments: the immune system component is a lymphocyte heterozygous or homozygous for an Aiolos transgene, e.g., a transgene having a point mutation or a deletion, which, inactivates one or both of transcriptional activation or dimerization, which decreases the half life of the protein, or which inactivates one or both of the C terminal Zinc finger domains; the immune system component is a lymphocyte heterozygous or homozygous for a C terminal deletion.

In preferred embodiments, the immune system component is: a B cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the target cell; the immune system component is from species different from the species of the target cell.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, lymph node tissue, bone marrow tissue or thymic tissue, or is syngeneic, allogeneic, xenogeneic, or congenic tissue.

In preferred embodiments: the donor of the immune system component or the donor of the target or both are immunized with an antigen. The antigen can be: an alloantigen; a xenoantigen or an autoantigen; a protein; or an antigen which gives rise to an anti-idiotypic lymphocyte.

In preferred embodiments the donor of the components is: a human or nonhuman mammal, e.g., a swine, a nonhuman primate, e.g., a monkey, a goat, or a rodent, e.g., a rat or mouse. In preferred embodiments, e.g., in the case of a wild-type donor, e.g., a human, the manipulation that gives rise to Aiolos deregulation, e.g., an Aiolos lesion, can be introduced in vitro.

In preferred embodiments the donor of the target is: a human or nonhuman mammal, e.g., a swine, a nonhuman primate, e.g., a monkey, a goat, or a rodent, e.g., a rat or mouse.

In preferred embodiments the reaction mixture includes an exogenously add cytokine or antigen, e.g., a protein antigen.

In another aspect, the invention features, a method of promoting or inhibiting the proliferation of a cell, or of modulating the entry of a cell into the cell cycle. The method includes: administering to the cell a compound which inhibits the formation Aiolos-Aiolos or Aiolos-Ikaros dimers. The method can be performed in vivo or in vitro. The cell can be, e.g., a hematopoietic cell, e.g., a B lymphocyte.

In preferred embodiments, the compound is: a competitive or noncompetitive inhibitor of the association of Aiolos or Ikaros subunits, e.g., a mutant Aiolos peptide, e.g., a mutant Aiolos peptide which has a mutation which inhibits the ability of the Aiolos protein to bind DNA but which does not inhibit the ability of the protein to form a dimer, e.g., a mutation in one or more of the four N terminal Zinc fingers binding regions. Aiolos mutants which have mutations which inhibit dimerization, e.g., mutations in one of more of the two C terminal zinc finger regions, can also be used.

In preferred embodiments the compound is: a protein or peptide; a peptomimetic, a small molecule; a nucleic acid which encodes an inhibitor.

Methods for increasing cell division can be combined with procedures where it is desirable to increase cell division, e.g., the treatment, e.g., by chemotherapy or radiotherapy, of tumors or other cell-proliferative disorders.

Proliferation can be inhibited by administering wildtype Aiolos.

In another aspect, the invention features a cell, or purified preparation of cells, which include an Aiolos transgene, or which otherwise misexpress an Aiolos gene. The cell preparation can consist of human or non human cells, e.g., rodent cells, e.g., mouse or rat cells, rabbit cells, or pig cells. In preferred embodiments, the cell or cells include an Aiolos transgene, e.g., a heterologous form of an Aiolos gene, e.g., a gene derived from humans (in the case of a non-human cell). The Aiolos transgene can be misexpressed, e.g., overexpressed or underexpressed. In other preferred embodiments, the cell or cells include a gene which misexpress an endogenous Aiolos gene, e.g., a gene the expression of which is disrupted, e.g., a knockout. Such cells can serve as a model for studying disorders which are related to mutated or mis-expressed Aiolos alleles or for use in drug screening.

Cells, e.g., stem cells, treated by the method of the invention can be introduced into mammals, e.g., humans, non-human primates, or other mammals, e.g., rodents. In preferred embodiments the treatment is performed ex vivo and: the cell is autologous, e.g., it is returned to the same individual from which it was derived; the cell is allogeneic, i.e., it is from the same species as the mammal to which it is administered; the cell is xenogeneic, i.e., it is from a different species from the mammal to which it is administered.

An Aiolos-deregulated cell is a cell which has a mutant or misexpressed Aiolos gene, e.g., an inactivated Aiolos gene.

A hematopoietic cell, can be, e.g., stem cell, e.g., a totipotent or a pluripotent stem cell, or a descendent of a stem cell, e.g., a lymphocyte, e.g., a B lymphocyte or a T lymphocyte.

A proliferation-deregulated cell, as used herein, refers to a cell with other than wild.

An Aiolos misexpressing animal, as used herein, is an animal in which one or more, and preferably substantially all, of the cells misexpress Aiolos.

A mutation at the Aiolos locus, as used herein, includes any mutation which alters the expression, structure, or activity of the Aiolos gene or its gene product. These include point mutations in and in particular deletions of all or part of the Aiolos coding region or its control region.

An exogenously supplied cell, tissue, or cell product, e.g., a cytokine, as used herein, is a cell, tissue, or a cell product which is derived from an animal other than the one to which is supplied or administered. It can be from the same species or from different species than the animal to which it is supplied.

A clonal population of lymphocytes, as used herein, is a population of two or more lymphocytes which have one or more of the following properties: they share a common stem cell ancestor; they share a common pre-thymocyte or pre b cell ancestor; they share a common thymocyte ancestor; they share the same T cell receptor genomic rearrangement; they share a common CD4+CD8+ ancestor; they share a common CD4+ ancestor; they share a common CD8+ ancestor; they share a common CD4−CD8− ancestor; they recognize the same antigen.

A substantially homogenous population of two or more cells e.g., lymphocytes, as used herein, means a population of cells in which at least 50% of the cells, more preferably at least 70% of the cells, more preferably at least 80% of the cells, most preferably at least 90%, 95% or 99% of the subject cell type, e.g., lymphocytes. With respect to the Aiolos locus however, the cells can be all (+/−), all (−/−), or a mixture of (+/−) and (−/−) cells.

Culturing, as used herein, means contacting a cell or tissue with an environment which will support viability of the cell or tissue and which preferably supports proliferation of the cell or tissue.

A substantially purified preparation of cells, e.g., lymphocytes, as used herein, means a preparation of cells in which at least 50% of the cells, more preferably at least 70% of the cells, more preferably at least 80% of the cells, most preferably at least 90%, 95% or 99% of the cells of the subject cell, e.g., are lymphocytes. With respect to the Aiolos locus however, the cells can be all (+/−), all (−/−), or a mixture of (+/−) and (−/−) cells.

Immunocompromised, as used herein, refers to a mammal in which at least one aspect of the immune system functions below the levels observed in a wild-type mammal. The mammal can be immunocompromised by a chemical treatment, by irradiation, or by a genetic lesion resulting in, e.g., a nude, a beige, a nude-beige, or an Ikaros-phenotype. The mammal can also be immunocompromised by an acquired disorder, e.g., by a virus, e.g., HIV.

As used herein, an Aiolos transgene, is a transgene which includes all or part of an Aiolos coding sequence or regulatory sequence. The term also includes DNA sequences which when integrated into the genome disrupt or otherwise mutagenize the Aiolos locus. Aiolos transgenes sequences which when integrated result in a deletion of all or part of the Aiolos gene. Included are transgenes: which upon insertion result in the misexpression of an endogenous Aiolos gene; which upon insertion result in an additional copy of an Aiolos gene in the cell; which upon insertion place a non-Aiolos gene under the control of an Aiolos regulatory region. Also included are transgenes: which include a copy of the Aiolos gene having a mutation, e.g., a deletion or other mutation which results in misexpression of the transgene (as compared with wild type); which include a functional copy of an Aiolos gene (i.e., a sequence having at least 5% of a wild type activity, e.g., the ability to support the development of T, B, or NK cells); which include a functional (i.e., having at least 5% of a wild type activity, e.g., at least 5% of a wild type level of transcription) or nonfunctional (i.e., having less than 5% of a wild type activity, e.g., less than a 5% of a wild type level of transcription) Aiolos regulatory region which can (optionally) be operably linked to a nucleic acid sequence which encodes a wild type or mutant Aiolos gene product or, a gene product other than an Aiolos gene product, e.g., a reporter gene, a toxin gene, or a gene which is to be expressed in a tissue or at a developmental stage at which Aiolos is expressed. Preferably, the transgene includes at least 10, 20, 30, 40, 50, 100, 200, 500, 1,000, or 2,000 base pairs which have at least 50, 60, 70, 80, 90, 95, or 99% homology with a naturally occurring Aiolos sequence. Preferably, the transgene includes a deletion of all or some of exons 3 and 4, or a deletion for some or all of exon 7 of the Aiolos gene.

A "heterologous promoter", as used herein is a promoter which is not naturally associated with the Aiolos gene.

A "purified preparation" or a "substantially pure preparation" of an Aiolos polypeptide, or a fragment or analog thereof (or an Aiolos-Aiolos or Aiolos-Ikaros dimer), as used herein, means an Aiolos polypeptide, or a fragment or analog thereof (or an Aiolos-Aiolos or Aiolos-Ikaros dimer), which is free of one or more other proteins lipids, and nucleic acids with which the Aiolos polypeptide (or an Aiolos-Aiolos or Aiolos-Ikaros dimer) naturally occurs. Preferably, the polypeptide, or a fragment or analog thereof (or an Aiolos-Aiolos or Aiolos-Ikaros dimer), is also separated from substances which are used to purify it, e.g., antibodies or gel matrix, such as polyacrylamide. Preferably, the polypeptide, or a fragment or analog thereof (or an Aiolos-Aiolos or Aiolos-Ikaros dimer), constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

A "substantially pure nucleic acid", e.g., a substantially pure DNA encoding an Aiolos polypeptide, is a nucleic acid which is one or both of: not immediately contiguous with one or both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional Aiolos sequences.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The terms "peptides", "proteins", and "polypeptides" are used interchangeably herein.

As used herein, the term "transgene" means a nucleic acid sequence (encoding, e.g., one or more Aiolos polypeptides or Aiolos-Ikaros dimers), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence, such as the Aiolos and/or Ikaros gene, operably linked to the promoter, and which effects expression of the selected DNA sequence in specific cells of a tissue, such as lymphocytes. The term also covers so-called "leaky" promoters, which regulate expression of a selected DNA primarily in one tissue, but cause expression in other tissues as well.

A polypeptide has Aiolos biological activity if it has one or more of the following properties: (1) the ability to react with an antibody, or antibody fragment, specific for (a) a wild type Aiolos polypeptide, (b) a naturally-occurring mutant Aiolos polypeptide, or (c) a fragment of either (a) or (b); (2) the ability to form Aiolos dimers and/or Aiolos/Ikaros dimers; (3) the ability to modulate lymphocyte differentiation; (4) the ability to stimulate transcription from a sequence, e.g., a sequence described herein; or (5) the ability to act as an antagonist or agonist of the activities recited in (1), (2), (3) or (4).

"Misexpression", as used herein, refers to a non-wild type pattern of Aiolos gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-transitional modification, stability, or biological activity of the expressed Aiolos and/or Ikaros polypeptide; a pattern of expression that differs from wild type in terms of the effect of an environmental stimulus or extracellular stimulus on expression of the Aiolos and/or Ikaros gene, e.g., a pattern of increased or decreased expression (as compared with wild type) in the presence of an increase or decrease in the strength of the stimulus; a ratio of Ikaros-Ikaros dimer to Aiolos-Aiolos dimer which differs from wild type; a ratio of Aiolos to Aiolos-Aiolos dimer, Ikaros-Ikaros dimer, or Ikaros-Aiolos dimer that differs from wild type; a ratio of Ikaros-Aiolos dimer to Aiolos, Ikaros, Aiolos-Aiolos dimer, or Ikaros-Ikaros dimer that differs from wild type.

As described herein, one aspect of the invention features a pure (or recombinant) nucleic acid which includes a nucleotide sequence encoding an Aiolos, and/or equivalents of such nucleic acids. The term "nucleic acid", as used herein, can include fragments and equivalents. The term "equivalent" refers to nucleotide sequences encoding functionally equivalent polypeptides or functionally equivalent polypeptides which, for example, retain the ability to react with an antibody specific for an Aiolos polypeptide. Equivalent nucleotide sequences will include sequences that differ by one or more nucleotide substitutions, additions or deletions, such as allelic variants, and will, therefore, include sequences that differ from the nucleotide sequence of Aiolos shown in SEQ ID NO:1 or SEQ ID NO:7 due to the degeneracy of the genetic code.

An Aiolos-responsive control element, as used herein is a region of DNA which, when present upstream or downstream from a gene, results in regulation, e.g., increased transcription of the gene in the presence of an Aiolos protein.

A peptide has Ikaros activity if it has one or more of the following properties: the ability to stimulate transcription of a DNA sequence under the control any of a δA element, an NFKB element, or one of the Ikaros binding oligonucleotide consensus sequences disclosed herein; the ability to bind to any of a δA element, an NFKB element, or one of the Ikaros binding oligonucleotide consensus sequences disclosed herein; or the ability to competitively inhibit the binding of a naturally occurring Ikaros isoform to any of a δA element, an NFKB element, or one of the Ikaros binding oligonucleotide consensus sequences disclosed herein. An Ikaros peptide is a peptide with Ikaros activity.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1.984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

The Aiolos genes and polypeptides of the present invention are useful for studying, diagnosing and/or treating diseases associated with unwanted cell proliferation, e.g., leukemias or lymphomas. The gene (or fragment thereof) can be used to prepare antisense constructs capable of inhibiting expression of a mutant or wild type Aiolos gene encoding a polypeptide having an undesirable function. Alternatively, an Aiolos polypeptide can be used to raise antibodies capable of detecting proteins or protein levels associated with abnormal cell proliferation or lymphocyte differentiation, e.g., T cell maturation. Furthermore, Aiolos peptides, antibodies or nucleic acids, can be used to identify the stage of lymphocyte differentiation, e.g., the stage of T cell differentiation.

Other features and advantages of the invention will be apparent from the following detailed description, and from the claims.

Summary of Helios

In another general aspect, the invention features an Helios polypeptide, e.g., a polypeptide which includes all or part of the sequence shown in SEQ ID NO:24, SEQ ID NO:26, or SEQ ID NO:28. The invention also features fragments and analogs of Helios polypeptides, preferably having at least one biological activity of an Helios polypeptide.

In preferred embodiments, the polypeptide is a recombinant or a substantially pure preparation of an Helios polypeptide.

In preferred embodiments, the polypeptide is a vertebrate, e.g., a mammalian, e.g., a human polypeptide.

In preferred embodiments, the Helios polypeptide includes additional Helios coding sequences 5' to that of SEQ ID NO:24, SEQ ID NO:26, or SEQ ID NO:28.

In preferred embodiments: the polypeptide has at least one biological activity, e.g., it reacts with an antibody, or antibody fragment, specific for an Helios polypeptide; the polypeptide includes an amino acid sequence at least 60%, 74%, 80%, 90%, 95%, 98%, or 99% homologous to an amino acid sequence from SEQ ID NO:24, SEQ ID NO:26, or SEQ ID NO:28; the polypeptide includes an amino acid sequence essentially the same as an amino acid sequence in SEQ ID NO:24, SEQ ID NO:26, or SEQ ID NO:28; the polypeptide is at least 5, 10, 20, 50, 100, 150, 200, or 250 amino acids in length; the polypeptide includes at least 5, preferably at least 10, more preferably at least 20, most preferably at least 50, 100, 150, 200, or 250 contiguous amino acids from SEQ ID NO:24, SEQ ID NO:26, or SEQ ID NO:28; the polypeptide is preferably at least 10, but no more than 100, amino acids in length; the Helios polypeptide is either, an agonist or an antagonist, of a biological activity of a naturally occurring Helios polypeptide.

In preferred embodiments: the Helios polypeptide is encoded by the nucleic acid sequence of SEQ ID NO:23, SEQ ID NO:25, or SEQ ID NO:28, or by a nucleic acid having at least 60%, 70%, 80%, 90%, 95%, 98%, or 99% homology with the nucleic acid of SEQ ID NO:23, SEQ ID NO:25, or SEQ ID NO:28. For example, the Helios polypeptide can be encoded by a nucleic acid sequence which differs from a nucleic acid sequence of SEQ ID NO:23, SEQ ID NO:25, or SEQ ID NO:28 due to degeneracy in the genetic code.

In a preferred embodiment, the Helios polypeptide encodes amino acid residues 1–526 of SEQ ID NO:24, residues 1–500 of SEQ ID NO:26 or residues 1–526 of SEQ ID NO:28 or a functionally equivalent residue in the Helios sequence of another vertebrate or mammal, e.g., a monkey.

In a preferred embodiment the Helios polypeptide is an agonist of a naturally-occurring mutant or wild type Helios polypeptide (e.g., a polypeptide having an amino acid sequence shown in SEQ ID NO:24, SEQ ID NO:26, or SEQ ID NO:28). In another preferred embodiment, the polypeptide is an antagonist which, for example, inhibits an undesired activity of a naturally-occurring Helios polypeptide (e.g., a mutant polypeptide).

In a preferred embodiment, the Helios polypeptide differs in amino acid sequence at 1, 2, 3, 5, 10 or more residues, but preferably less than 15, from a sequence in SEQ ID NO:24, SEQ ID NO:26, or SEQ ID NO:28. The differences, however, are such that the Helios polypeptide exhibits at least one biological activity of an Helios polypeptide, e.g., the Helios polypeptide retains a biological activity of a naturally occurring Helios polypeptide. In other preferred embodiments, the Helios polypeptide differs at up to 1, 2, 3, 5, 10 amino acid residues from the sequence of SEQ ID NO:24, SEQ ID NO:26, or SEQ ID NO:28.

In preferred embodiments the Helios polypeptide includes an Helios polypeptide sequence, as described herein, as well as other N-terminal and/or C-terminal amino acid sequences.

In preferred embodiments, the polypeptide includes all or a fragment of an amino acid sequence from SEQ ID NO:24, SEQ ID NO:26, or SEQ ID NO:28, fused, in reading frame, to additional amino acid residues, preferably to residues encoded by genomic DNA 5' to the genomic DNA which encodes a sequence from SEQ ID NO:24, SEQ ID NO:26, or SEQ ID NO:28.

In another aspect, the invention features a fragment of an Helios polypeptide. In one embodiment, the fragment is a terminal fragment, e.g., an N- or C-terminal deletion, e.g., a zinc finger, or an internal deletion, e.g., a zinc finger or a transcriptional activation domain. In another embodiment, the fragment includes one or more of: a N-terminal zinc finger, e.g., N-zinc finger 1 (ZF1), N-zinc finger 2 (ZF2), N-zinc finger 3 (ZF3), N-zinc finger 4 (ZF4), a transcriptional activation domain, or a C-terminal zinc finger, e.g., C-zinc finger 1 (ZF5), C-zinc finger 2 (ZF6). In another embodiment, the Helios polypeptide includes a deletion of one or more of the following: a N-terminal zinc finger, e.g., N-zinc finger 1 (ZF1), N-zinc finger 2 (ZF2), N-zinc finger 3 (ZF3), N-zinc finger 4 (ZF4), a transcriptional activation domain, or a C-terminal zinc finger, e.g., a C-zinc finger 1 (ZF5) or a C-zinc finger 2 (ZF6). In another embodiment, the fragment is at least 20, 40, 60, or 80 amino acids in length.

In yet other preferred embodiments, the Helios polypeptide is a recombinant fusion protein having a first Helios polypeptide portion and a second polypeptide portion having an amino acid sequence unrelated to an Helios polypeptide. The second polypeptide portion can be, e.g., any of glutathione-S-transferase, a DNA binding domain, or a polymerase activating domain. In preferred embodiment the fusion protein can be used in a two-hybrid assay.

In a preferred embodiment, the Helios polypeptide is a fragment or analog of a naturally occurring Helios polypeptide which inhibits reactivity with antibodies, or F(ab')$_2$ fragments, specific for a naturally occurring Helios polypeptide.

In a preferred embodiment, the Helios polypeptide includes a sequence which is not present in the mature protein.

Polypeptides of the invention include those which arise as a result of the existence of multiple genes, alternative transcription events, alternative RNA splicing events, and alternative translational and postranslational events.

In preferred embodiments, the Helios polypeptide has one or more of the following properties:

(a) it can form a dimer with an Helios, Aiolos, or Ikaros polypeptide;

(b) it is expressed in hematopoietic stem cells;

(c) it has a molecular weight of approximately 64 kDa or 68 KDa;

(d) it has at least one zinc finger domain; or (e) it is a transcriptional activator of a lymphoid gene.

The invention includes an immunogen which includes an active or inactive Helios polypeptide, or an analog or a fragment thereof, in an immunogenic preparation, the immunogen being capable of eliciting an immune response specific for the Helios polypeptide, e.g., a humoral response, an antibody response, or a cellular response. In preferred embodiments, the immunogen comprising an antigenic determinant, e.g., a unique determinant, from a protein represented by SEQ ID NO:24, SEQ ID NO:26, or SEQ ID NO:28.

The invention also includes an antibody preparation, preferably a monoclonal antibody preparation, specifically reactive with an epitope of the Helios immunogen or generally of an Helios polypeptide.

In another aspect, the invention provides a substantially pure nucleic acid having, or comprising, a nucleotide sequence which encodes a polypeptide, the amino acid sequence of which includes, or is, the sequence of an Helios polypeptide, or analog or fragment thereof.

In preferred embodiments, the nucleic acid encodes a vertebrate, e.g., a mammalian, e.g., a human polypeptide.

In preferred embodiments, the nucleic acid encodes an Helios polypeptide which includes additional Helios coding sequences 5' to that SEQ ID NO:24, 26, or 28.

In preferred embodiments, the nucleic acid encodes a polypeptide having one or more of the following characteristics: at least one biological activity of an Helios, e.g., a polypeptide specifically reactive with an antibody, or antibody fragment, directed against an Helios polypeptide; an amino acid sequence at least 60%, 74%, 80%, 90%, 95%, 98%, or 99% homologous to an amino acid sequence from SEQ ID NO:24, SEQ ID NO:26, or SEQ ID NO:28; an amino acid sequence essentially the same as an amino acid sequence in SEQ ID NO:24, SEQ ID NO:26, or SEQ ID NO:28, the polypeptide is at least 5, 10, 20, 50, 100, 150, 200, or 250 amino acids in length; at least 5, preferably at least 10, more preferably at least 20, most preferably at least 50, 100, 150, 200, or 250 contiguous amino acids from SEQ ID NO:24, SEQ ID NO:26, or SEQ ID NO:28; an amino acid sequence which is preferably at least 10, but no more than 100, amino acids in length; the ability to act as an agonist or an antagonist of a biological activity of a naturally occurring Helios polypeptide.

In preferred embodiments: the nucleic acid is or includes the nucleotide sequence of SEQ ID NO:23, SEQ ID NO:25, or SEQ ID NO:28; the nucleic acid is at least 60%, 70%, 74%, 80%, 90%, 95%, 98%, or 99% homologous with a nucleic acid sequence of SEQ ID NO:23, SEQ ID NO:25, or SEQ ID NO:28; the nucleic acid includes a fragment of SEQ ID NO:23, SEQ ID NO:25, or SEQ ID NO:28 which is at least 25, 50, 100, 200, 300, 400, 500, or 1,000 bases in length; the nucleic acid differs from the nucleotide sequence of SEQ ID NO:23 due to degeneracy in the genetic code.

In a preferred embodiment, the Helios encoding nucleic acid sequence encodes amino acid residues 1–526 of SEQ ID NO:24, residues 1–500 of SEQ ID NO:26, residues 1–526 of SEQ ID NO:28 or a functionally equivalent residue in the Helios sequence of another vertebrate or mammal, e.g., a monkey.

In a preferred embodiment the polypeptide encoded by the nucleic acid is an agonist which, for example, is capable of enhancing an activity of a naturally-occurring mutant or wild type Helios polypeptide. In another preferred embodiment, the encoded polypeptide is an antagonist which, for example, inhibits an undesired activity of a naturally-occurring Helios polypeptide (e.g., a polypeptide having an amino acid sequence shown in SEQ ID NO:24, SEQ ID NO:26, or SEQ ID NO:28).

In a preferred embodiment, the encoded Helios polypeptide differs in amino acid sequence at 1, 2, 3, 5, 10 or more residues, but preferably less than 15, from a sequence in SEQ ID NO:24, SEQ ID NO:26, or SEQ ID NO:28. The differences, however, are such that the encoded Helios polypeptide exhibits at least one biological activity of a naturally occurring Helios polypeptide (e.g., the Helios polypeptide of SEQ ID NO:24, SEQ ID NO:26, or SEQ ID NO:28).

In preferred embodiments, the nucleic acid encodes an Helios polypeptide which includes an Helios polypeptide sequence, as described herein, as well as other N-terminal and/or C-terminal amino acid sequences.

In preferred embodiments, the nucleic acid encodes a polypeptide which includes all or a portion of an amino acid sequence shown in SEQ ID NO:24, SEQ ID NO:26, or SEQ ID NO:28, fused, in reading frame, to additional amino acid residues, preferably to residues encoded by genomic DNA 5' to the genomic DNA which encodes a sequence from SEQ ID NO:24, SEQ ID NO:26, or SEQ ID NO:28.

In preferred embodiments, the encoded polypeptide is a recombinant fusion protein having a first Helios polypeptide portion and a second polypeptide portion having an amino acid sequence unrelated to an Helios polypeptide. The second polypeptide portion can be, e.g., any of glutathione-S-transferase; a DNA binding domain; or a polymerase activating domain. In preferred embodiments the fusion protein can be used in a two-hybrid assay.

In preferred embodiments, the encoded polypeptide is a fragment or analog of a naturally occurring Helios polypeptide which inhibits reactivity with antibodies, or F(ab')₂ fragments, specific for a naturally occurring Helios polypeptide.

In preferred embodiments, the nucleic acid will include a transcriptional regulatory sequence, e.g., at least one of a transcriptional promoter or transcriptional enhancer sequence, operably linked to the Helios gene sequence, e.g., to render the Helios gene sequence suitable for use as an expression vector.

In yet another preferred embodiment, the nucleic acid of the invention hybridizes under stringent conditions to a nucleic acid probe corresponding to at least 12 consecutive nucleotides from SEQ ID NO:23, SEQ ID NO:25, or SEQ ID NO:28, or more preferably to at least 20 consecutive nucleotides from SEQ ID NO:23, SEQ ID NO:25, or SEQ ID NO:28, or more preferably to at least 40 consecutive nucleotides from SEQ ID NO:23, SEQ ID NO:25, or SEQ ID NO:28.

In a preferred embodiment, the nucleic acid encodes an Helios polypeptide which includes a sequence which is not present in the mature protein.

In preferred embodiments, the nucleic acid encodes an Helios polypeptide which has one or more of the following properties:

(a) it can form a dimer with an Helios, Aiolos, or Ikaros polypeptide;
(b) it is expressed in hematopoietic stem cells;
(c) it has a molecular weight of approximately 64 kDa or 68 KDa;
(d) it has at least one zinc finger domain; or
(e) it is a transcriptional activator of a lymphoid gene.

In another aspect, the invention includes: a vector including a nucleic acid which encodes an Helios polypeptide; a host cell transfected with the vector; and a method of producing a recombinant Helios polypeptide, including culturing the cell, e.g., in a cell culture medium, and isolating the Helios polypeptide, e.g., an Helios polypeptide from the cell or from the cell culture medium.

In another aspect, the invention features, a purified recombinant nucleic acid having at least 50%, 60%, 70%, 74%, 80%, 90%, 95%, 98%, or 99% homology with a nucleotide sequence shown in SEQ ID NO:23, SEQ ID NO:25, or SEQ ID NO:28.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:23, SEQ ID NO:25, or SEQ ID NO:28, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

The invention includes vertebrate, e.g., mammalian, e.g., rodent, e.g., mouse or rat, or human Helios polypeptides.

In another aspect, the invention features a method of evaluating a compound for the ability to interact with, e.g., bind, or modulate, e.g., inhibit or promote, the activity of an Helios polypeptide, e.g., an Helios monomer, or an Helios-Helios dimer, an Helios-Aiolos dimer, or an Helios-Ikaros dimer. The method includes contacting the compound with the Helios polypeptide, and evaluating the ability of the compound to interact with or form a complex with the Helios polypeptide. This method can be performed in vitro, e.g., in a cell free system, or in vivo, e.g., in a two-hybrid interaction trap assay. This method can be used to identify naturally occurring molecules which interact with the Helios polypeptide. It can also be used to find natural or synthetic inhibitors of mutant or wild type Helios polypeptide. The compound can be a peptide or a non peptide molecule, e.g., a small molecule preferably 500 to 5,000 molecular weight, more preferably 500 to 1,000 molecular weight, having an aromatic scaffold, e.g., a bis-amide phenol, decorated with various functional groups.

In brief, a two hybrid assay system (see e.g., Bartel et al. (1993) *Cellular Interaction in Development: A practical Approach*, D. A. Hartley, ed., Oxford University Press, Oxford, pp. 153–179) allows for detection of protein-protein interactions in yeast cells. The known protein, e.g., an Helios polypeptide, is often referred to as the "bait" protein. The proteins tested for binding to the bait protein are often referred to as "fish" proteins. The "bait" protein, e.g., an Helios polypeptide, is fused to the GAL4 DNA binding domain. Potential "fish" proteins are fused to the GAL4 activating domain. If the "bait" protein and a "fish" protein interact, the two GAL4 domains are brought into close proximity, thus rendering the host yeast cell capable of surviving a specific growth selection.

In another aspect, the invention features a method of identifying active fragments or analogs of an Helios polypeptide. The method includes first identifying a compound, e.g., an Ikaros peptide, which interacts with an Helios polypeptide and determining the ability of the compound to bind the candidate fragment or analog. The two hybrid assay described above can be used to obtain fragment-binding compounds. These compounds can then be used as "bait" to fish for and identify fragments of the Helios polypeptide which interact, bind, or form a complex with these compounds.

In another aspect, the invention features a method of making an Helios polypeptide, having a non-wild type activity, e.g., an antagonist, agonist, or super agonist of a naturally occurring Helios polypeptide. The method includes altering the sequence of an Helios polypeptide (e.g., SEQ ID NO:24, SEQ ID NO:26, or SEQ ID NO:28) by, for example, substitution or deletion of one or more residues of a non-conserved region, and testing the altered polypeptide for the desired activity.

In another aspect, the invention features a method of making a fragment or analog of an Helios polypeptide, e.g., an Helios polypeptide having at least one biological activity of a naturally occurring Helios polypeptide. The method includes altering the sequence, e.g., by substitution or deletion of one or more residues, preferably which are non-conserved residues, of an Helios polypeptide, and testing the altered polypeptide for the desired activity.

In another aspect, the invention features, a method of evaluating a compound for the ability to bind a nucleic acid encoding an Helios gene regulatory sequence. The method includes: contacting the compound with the nucleic acid; and evaluating ability of the compound to form a complex with the nucleic acid. In preferred embodiments the Helios gene regulatory sequence is functionally linked to a heterologous gene, e.g., a reporter gene.

In another aspect, the invention features a human cell, e.g., a hematopoietic stem cell or a lymphocyte e.g., a T or a B cell, transformed with a nucleic acid which encodes an Helios polypeptide.

In another aspect, the invention features a method for treating an animal, e.g., a human, a mouse, a transgenic animal, or an animal model for a disorder, e.g., an immune system disorder, e.g., a T or B cell related disorder, e.g., a nude mouse or a SCID mouse, including administering a therapeutically-effective amount of an Helios polypeptide to the animal. The Helios polypeptide can be monomeric or an Helios-Helios, an Helios-Aiolos dimer, or Helios-Ikaros dimer.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a cell selected, e.g., selected in vitro, for the expression of a product of the Helios gene, e.g., hematopoietic stem cells, e.g., cells transformed with Helios-peptide-encoding DNA, e.g., hematopoietic stem cells transformed with Helios-peptide-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse. The method includes administering to the animal a nucleic acid encoding an Helios peptide and expressing the nucleic acid.

In another aspect, the invention features a method of evaluating the effect of a treatment, e.g., a treatment designed to promote or inhibit hematopoiesis, including carrying out the treatment and evaluating the effect of the treatment on the expression of the Helios gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Helios gene or a disorder of the immune system, e.g., an immunodeficiency, or a T or B cell related disorder, e.g., a disorder characterized by a shortage of T or B cells. The method includes examining the subject for the expression of the Helios gene, non-wild type expression or mis-expression being indicative of risk.

In another aspect, the invention features a method for determining if a subject, e.g., a human, is at risk for a disorder related to mis-expression of the Helios gene or a disorder of the immune system, e.g., an immunodeficiency, or a T or B cell related disorder, e.g., a disorder characterized by a shortage of T or B cells. The method includes providing a nucleic acid sample from the subject and determining if the structure of an Helios gene allele of the subject differs from wild type.

In preferred embodiments: the determination includes determining if an Helios gene allele of the subject has a gross chromosomal rearrangement; the determination includes sequencing the subject's Helios gene.

In another aspect, the invention features, a method of evaluating an animal or cell model for a a proliferative disorder, e.g., a leukemic disorder, Hodgkin's lymphoma, a cutaneuous cell lymphoma, e.g., a cutaneous T cell lymphoma, or an immune disorder, e.g., a T cell related disorder, e.g., a disorder characterized by a shortage of T or B cells. The method includes determining if the Helios gene in the animal or cell model is expressed at a predetermined level or if the Helios gene is mis-expressed. In preferred embodiments: the predetermined level is lower than the level in a wild type or normal animal; the predetermined level is higher than the level in a wild type or normal animal; or the pattern of isoform expression is altered from wildtype.

In another aspect, the invention features, a transgenic animal, e.g., a mammal, e.g., a mouse or a nonhuman primate having an Helios transgene.

In preferred embodiments the animal is a transgenic mouse having a mutated Helios transgene, the mutation occurring in, or altering, e.g., a domain of the Helios gene described herein.

In preferred embodiments the transgenic animal, e.g., a transgenic mouse, is homozygous for null mutations, e.g., it is homozygous for a deletion of the C terminal end of the protein, at the Helios locus.

In preferred embodiments the transgenic animal, e.g., a transgenic mouse, is homozygous for null mutations, e.g., it is homozygous for a deletion of the C terminal end of the protein, at the Helios locus and includes a mutation at Ikaros or Aiolos, e.g., a dominant negative mutation at Ikaros or Aiolos. Preferably the Ikaros mutation is heterozygous.

In other preferred embodiments the transgenic animal or cell: is heterozygous for an Helios transgene; homozygous for an Helios transgene; includes a first Helios transgene and a second Helios transgene; includes an Helios transgene and a second transgene which is other than an Helios transgene, e.g., an Ikaros or Aiolos transgene.

In another aspect, the invention features a method for evaluating the effect of a treatment on a transgenic cell or animal having an Helios transgene, e.g., the effect of the treatment on the development of the immune system. The method includes administering the treatment to a cell or animal having an Helios transgene, and evaluating the effect of the treatment on the cell or animal. The effect can be, e.g., the effect of the treatment on: Helios or Ikaros expression or misexpression; the immune system or a component thereof; or the cell cycle. Immune system effects include e.g., T cell activation, T cell development, the ability to mount an immune response, the ability to give rise to a component of the immune system, B cell development, NK cell development, or the ratios $CD4^+/CD8^+$, $CD4^+/CD8^-$ and $CD4^-/CD8^+$.

In preferred embodiments the treatment can include: the administration of a drug, chemical, or other substance; the administration of ionizing radiation; the administration of an antibody, e.g., an antibody directed against a molecule or cell of the immune system; administration of a substance or other treatment which suppresses the immune system; or administration of a substance or other treatment which activates or boosts the function of the immune system; introduction of a nucleic acid, e.g., a nucleic acid which encodes or expresses a gene product, e.g., a component of the immune system; the introduction of a protein, e.g., a protein which is a component of the immune system.

In another aspect, the invention features a method for evaluating the effect of a treatment on an immune system component. The method includes: (1) supplying a transgenic cell or animal having an Helios transgene; (2) supplying the immune system component; (3) administering the treatment; and (4) evaluating the effect of the treatment on the immune system component.

In yet another aspect, the invention features a method for evaluating the interaction of a first immune system component with a second immune system component. The method includes: (1) supplying a transgenic cell or animal, e.g., a mammal, having an Helios transgene; (2) introducing the first and second immune system component into the transgenic cell or mammal; and (3) evaluating an interaction between the first and second immune system components.

In another aspect, the invention features a method for evaluating the effect of a treatment on an immune system disorder, e.g., a neoplastic disorder, a leukemia or a lymphoma, a T cell related lymphoma, including: administering the treatment to a cell or animal having an Helios transgene, and evaluating the effect of the treatment on the cell or animal. The effect can be, e.g., the effect of the treatment on: Helios or Ikaros expression or misexpression; the immune system or a component thereof; or the cell cycle. Immune system effects include e.g., T cell activation, T cell development, the ability to mount an immune response, the ability to give rise to a component of the immune system, B cell development, NK cell development, or the ratios $CD4^+/CD8^+$, $CD4^+/CD8^-$ and $CD4^-/CD8^+$.

The inventors have also discovered that Ikaros and Helios can form dimers (heterodimers) with other polypeptides. E.g., an Ikaros polypeptide can form dimers not only with Ikaros polypeptides, but with other polypeptides which bind to its C terminal region, e.g, other polypeptides having Zinc-finger regions, e.g., Helios polypeptides. Similarly, an Helios polypeptide can form dimers not only with Helios polypeptides, but with other polypeptides which bind to its C terminal region, e.g, other polypeptides having Zinc-finger regions, e.g., Ikaros polypeptides.

The invention also includes Ikaros-Helios or Aiolos/Helios dimers. The Ikaros member of the dimer can be any Ikaros polypeptide, e.g., any naturally occuring Ikaros or any Ikaros referred to in U.S. Ser. No. 08/238,212, filed May 2, 1994, hereby incorporated by reference. The Aiolos member of the dimer can be any Aiolos polypeptide, e.g., any naturally occurring Aiolos or any Aiolos referred to in U.S. Ser. No. 60/005,529 filed Oct. 18, 1995, hereby incorporated by reference.

The invention also includes: a cell, e.g., a cultured cell or a stem cell, containing purified Ikaros- or Aiolos-protein-encoding-DNA and purified Helios-protein-encoding-DNA; a cell capable of expressing an Ikaros and an Helios protein; a cell capable of giving rise to a transgenic animal or to a homogeneous population of hemopoietic cells, e.g., lymphoid cells, e.g., T cells; an essentially homogeneous population of cells, each of which includes purified Ikaros- or Aiolos-protein-encoding-DNA and purified Helios-protein-encoding-DNA; and a method for manufacture of a dimer of the invention including culturing a cell which includes a DNA, preferably a purified DNA, of the invention in a medium to express the peptides.

The invention also includes: a preparation of cells, e.g., cultured cells or a stem cells, including a cell a containing purified Ikaros- or Aiolos-protein-encoding-DNA and a cell encoding purified Helios-protein-encoding-DNA.

The invention also includes substantially pure preparation of an antibody, preferably a monoclonal antibody directed against an Ikaros-Helios dimer or an Aiolos-Helios dimer (which preferably does not bind to an Ikaros-Ikaros, Aiolos-Aiolos or Helios-Helios dimer); a therapeutic composition including an Ikaros-Helios dimer or an Aiolos-Helios dimer and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering a therapeutically-effective amount of an Ikaros-Helios or an Aiolos-Helios dimer to the animal.

In another aspect, the invention features a method for treating an animal, e.g., a human, a mouse, a transgenic animal, or an animal model for an immune system disorder, e.g., a T or B cell related disorder, e.g., a nude mouse or a SCID mouse including administering to the animal cells selected, e.g., selected in vitro, for the expression of a product of the Ikaros gene and of the Helios gene, e.g., hematopoietic stem cells, e.g., cells transformed with Ikaros- or Aiolos-peptide-encoding DNA and or Helios-peptide-encoding DNA, e.g., hematopoietic stem cells transformed with Ikaros or Aiolos and or Helios-peptide-encoding DNA. The Ikaros Aiolos and Helios DNA can be present in the same or in different cells.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for an immune system disorder, e.g., a T or B cell related disorder, e.g., a nude mouse or a SCID mouse, including administering to the animal a nucleic acid encoding an Ikaros peptide and a nucleic acid encoding an Helios peptide and expressing the nucleic acids.

In another aspect, the invention features a method of evaluating the effect of a treatment, e.g., a treatment designed to promote or inhibit hematopoiesis, including carrying out the treatment and evaluating the effect of the treatment on the expression of the Ikaros and the Helios gene.

In preferred embodiments the treatment is administered: to an animal, e.g., a human, a mouse, a transgenic animal, or an animal model for an immune system disorder, e.g., a T or B cell related disorder, e.g., a nude mouse or a SCID mouse, or a cell, e.g., a cultured stem cell.

In another aspect, the invention features a method for determining if a subject, e.g., a human, is at risk for a disorder related to mis-expression of the Ikaros gene, e.g., a leukemic disorder or other disorder of the immune system, e.g., an immunodeficiency, or a T or B cell related disorder, e.g., a disorder characterized by a shortage of T or B cells, including examining the subject for the expression of the Ikaros-Helios or Aiolos-Helios dimers, non-wild type expression or mis-expression being indicative of risk.

In another aspect, the invention features, a method of evaluating an animal or cell model for an immune disorder, e.g., a T cell related disorder, e.g., a disorder characterized by a shortage of T or B cells, including determining if Ikaros-Helios or Aiolos-Helios dimers in the animal or cell model are expressed at a predetermined level. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an Ikaros or Aiolos gene or Ikaros or Aiolos protein encoding DNA and an Helios gene or Helios protein encoding DNA. In preferred embodiments: the Ikaros, Aiolos and or Helios gene or DNA includes a deletion, e.g., a deletion of all or part of one or more exons.

In another aspect, the invention features, a method of culturing an Helios-misexpressing cell having at least one mutant allele at the Helios locus. The cell can be, e.g., a hematopoietic cell, e.g., a T lymphocyte. The method includes: introducing the cell into a mammal, wherein, preferably, the mammal is other than the one from which the cell has been isolated originally; and culturing the cell.

In a preferred embodiment, the method further includes: allowing the cell to proliferate in the mammal.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Helios-misexpressing cell cell to divide and give rise to a proliferation-deregulated cell, e.g., a transformed lymphocyte; providing a plurality of the proliferation-deregulated cells e.g., lymphocytes or transformed lymphocytes from the mammal.

In preferred embodiments: the mammal, the cell or both, are heterozygous at the Helios locus; the mammal, the cell or both, carry a mutation at the Helios gene, e.g., a point mutation in or a deletion for all or part of the Helios gene, e.g., a mutation in the DNA binding region, e.g., a point mutation in, or a deletion for all or part of one or more of the four N-terminal zinc finger regions which mediates DNA binding of the Helios protein or for one or more of the two C terminal zinc finger regions which mediate dimerization of the Helios protein; the mammal is heterozygous or homozygous for an Helios transgene; the mammal, the cell or both, carry a mutation in the control region of the Helios gene.

In preferred embodiments: the mammal, the cell or both, carry a mutation at the Helios gene, e.g., a point mutation or a deletion, which, inactivates one or both of transcriptional activation or dimerization, which decreases the half life of the protein, or which inactivates one or both of the C terminal Zinc finger domains.

In preferred embodiments the cell, e.g., a cell, is homozygous for null mutations, e.g., it is homozygous for a deletion of the C terminal end of the protein, at the Helios locus.

In preferred embodiments the cell, e.g., a mouse cell, is homozygous for null mutations, e.g., it is homozygous for a deletion of the C terminal end of the protein, at the Helios locus and includes a mutation at Ikaros, e.g., a dominant negative mutation at Ikaros. Preferably the Ikaros mutaion is heterozygous.

In preferred embodiments: the Helios-misexpressing cell is a homozygous mutant Helios cell e.g., a lymphocyte; the Helios-misexpressing cell is a B lymphocyte; the Helios-misexpressing cell is heterozygous or homozygous for an Helios transgene.

In preferred embodiments, the Helios-misexpressing cell is a lymphocyte and is: a cell which secretes one or more anti-inflammatory cytokines; a cell which is antigen or idiotype specific.

In preferred embodiments: the mammal is immunized with an antigen; the cell is exogenously supplied and one or both of the mammal or the mammal which donates the cell are immunized with an antigen. The antigen can be: an alloantigen; a xenoantigen; an autoantigen; a protein; or an antigen which gives rise to an anti-idiotypic lymphocyte.

In a preferred embodiment: the Helios-misexpressing cell, e.g., a lymphocyte, is supplied exogenously to the mammal, e.g., to a homozygous wild-type Helios mammal or a mammal carrying a mutation at the Helios gene, e.g., a point mutation or a deletion for all or part of the Helios gene. If exogenously supplied, the cell can be a human or a nonhuman, e.g., a swine, nonhuman primate, e.g., a monkey, a goat, or a rodent, e.g., a rat or a mouse, lymphocyte.

Helios wild type cells can be cultured in Helios misexpressing mammals.

In another aspect, the invention features, a method of modulating the activity of, or promoting the interaction of an Helios misexpressing cell with, a target tissue or cell. The method includes: supplying the target; and exposing the target to a Helios misexpressing cell, e.g., a hematopoietic cell, e.g., a T lymphocyte, preferably having at least one mutant allele at the Helios locus, preferably provided that: the target is not Helios-misexpressing; the target and the cell differ in genotype at a locus other than the Helios locus; the target and the cell are from different animals; the target and the cell are from different species; the target activity is modulated in a recipient mammal and either the target or the cell is from a donor mammal other than the recipient mammal; or the target is exposed to the cell in an in vitro system.

In a preferred embodiment: the donor of the Helios-misexpressing cell is heterozygous or homozygous for an Helios transgene; the donor of the Helios-misexpressing cell is heterozygous at the Helios locus; the donor of the Helios-misexpressing cell carries a point mutation in or a deletion for all or part of the Helios gene, e.g., mutation in the DNA binding region, e.g., a point mutation in, or a deletion for all or part of one or more of the four N-terminal zinc finger regions which mediate Helios binding to DNA or in one or both of the C-terminal zinc finger regions which mediates Helios dimerization; the donor of the Helios-misexpressing cell is human or a non-human mammal, e.g., a swine, a monkey, a goat, or a rodent, e.g., a rat or a mouse. In preferred embodiments, e.g., in the case of the human donor, the manipulation that gives rise to Helios deregulation, e.g., an Helios lesion, can be made in vitro.

In preferred embodiments: the mammal which provides the Helios misexpressing cell carries a mutation at the Helios gene, e.g., a point mutation or a deletion, which, inactivates one or both of transcriptional activation or dimerization, which decreases the half life of the protein, or which inactivates one or both of the C terminal Zinc finger domains.

In another preferred embodiment: the cell is heterozygous or homozygous for an Helios transgene; the cell is a heterozygous Helios cell; the cell is a homozygous mutant Helios cell; the lymphocyte is a T lymphocyte.

In preferred embodiments, the cell is a lymphocyte and is: a T cell; a cell which secretes one or more anti-inflammatory cytokines; a T cell which is antigen or idiotype specific.

In a preferred embodiment: the method is performed in an in vitro system; the method is performed in vivo, e.g., in a mammal, e.g., a rodent, e.g., a mouse or a rat, or a primate, e.g., a non-human primate or a human. If the method is performed in vitro, the donor of the target cell or tissue and the lymphocyte can be same or different. If the method is performed in vivo, there is a recipient animal and one or more donors.

In preferred embodiments: the method is performed in vivo and one or more of the recipient, the donor of the target cell or tissue, the donor of the cell, is immunized with an antigen; the method is performed in vitro and one or more of the donor of the target cell or tissue, the donor of the cell is immunized with an antigen. The antigen can be: an alloantigen; a xenoantigen or an autoantigen; a protein; or an antigen which gives rise to an anti-idiotypic lymphocyte.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, bone marrow tissue, lymph node tissue or thymic tissue, or the target is a syngeneic, allogeneic, or xenogeneic tissue.

In another preferred embodiment, the target is from a mammal, e.g., a human; the mammal is a non-human mammal, e.g., a swine, a monkey, a goat, or a rodent, e.g., a rat or a mouse.

In preferred embodiments, the activity of the target which is modulated is: the production of a cytokine; the proliferation or activation of a cell of the immune system; the production of an antibody; the lysis of an antigen presenting cell or the activation of a cytolytic T lymphocyte; the effect of target on resistance to infection; the effect of target on life span; the effect of target on body weight; the effect of target on the presence, function, or morphology of tissues or organs of the immune system; the effect of target on the ability of a component of the immune system to respond to a stimulus (e.g., a diffusable substance, e.g., cytokines, other cells of the immune system, or antigens); the effect of target on the ability to exhibit immunological tolerance to an alloantigen or a xenoantigen.

In preferred embodiments the interaction is the binding of an antibody produced by the Helios misexpressing cell with the target.

In preferred embodiments: the target and the cell differ in genotype at a locus other than the Helios locus; the target and the cell are from different animals; the target is not Helios-misexpressing.

In another aspect, the invention features, a method of reconstituting an immune system. The method includes: supplying a recipient mammal, and introducing, preferably exogenously, into the recipient mammal, an immune system component from a donor mammal, which is Helios misexpressing, e.g., which carries at least one mutant allele at the Helios locus. The recipient mammal, can be, e.g., a human or a nonhuman mammal, e.g., a swine, a nonhuman primate, e.g., a monkey, a goat, or a rodent, e.g., a rat or a mouse. The donor mammal can be, e.g., a human or a nonhuman mammal, e.g., a swine, a monkey, a goat, or a rodent, e.g., a rat or a mouse. If the donor mammal is human, the manipulation that gives rise to Helios misexpression e.g., an the introduction of an Helios lesion, can be made in vitro. The donor mammal and the recipient mammal can be different individuals or the same individual.

In preferred embodiments, the component is or includes an Helios misexpressing cell, e.g., a hematopoietic cell, e.g., a pluripotent stem cell, or a descendent of a stem cell, e.g., a lymphocyte.

In preferred embodiments, the component is from a donor mammal, e.g., a human or a nonhuman mammal, e.g., a swine, a monkey, a goat, or a rodent, e.g., a rat or a mouse.

In a preferred embodiment, the method further includes: prior to introduction of a component into the subject, treating the lymphocyte to inhibit proliferation, e.g., by irradiating the component.

In a preferred embodiment, the donor mammal carries a mutation at the Helios gene, e.g., a deletion of all or part of the Helios gene.

In another preferred embodiment: the immune system component is any of a T cell, a T cell progenitor, a totipotent hematopoietic stem cell, a pluripotent hematopoietic stem cell, a B cell progenitor, a natural killer cell, a natural killer cell progenitor, bone marrow tissue, spleen tissue, or thymic tissue.

In a preferred embodiment: the immune system component is from the same species as the recipient mammal; the immune system component is from species different from the species of the recipient mammal.

In preferred embodiments: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In preferred embodiments: the immune system component is heterozygous at the Helios locus; the immune system component is carries a mutation at the Helios gene, e.g., a point mutation in or a deletion for all or part of the Helios gene, e.g., a mutation in the DNA binding region, e.g., a point mutation in, or a deletion for all or part of one or more of the four N-terminal zinc finger regions which mediates DNA binding of the Helios protein or for one or more of the two C terminal zinc finger regions which mediate dimerization of the Helios protein; the immune system component is heterozygous or homozygous for an Helios transgene; the immune system component carries a mutation in the control region of the Helios gene.

In preferred embodiments: the immune system component carries a mutation at the Helios gene, e.g., a point mutation or a deletion, which, inactivates one or both of transcriptional activation or dimerization, which decreases the half life of the protein, or which inactivates one or both of the C terminal Zinc finger domains.

In preferred embodiments: the method is performed in vivo, and the recipient mammal or the donor mammal or both are immunized with an antigen. The antigen can be: an alloantigen; a xenoantigen or an autoantigen; a protein; or an antigen which gives rise to an anti-idiotypic lymphocyte.

In a preferred embodiment, the method further includes: determining a value for a parameter related to immune system function. The parameter related to the immune system function can be any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In another aspect, the invention features, a method of evaluating the interaction of an Helios misexpressing cell, e.g., a hematopoietic cell, a T lymphocyte, with an immune system component. The method includes: supplying an animal, e.g., a swine, a nonhuman primate, e.g., a monkey, a goat, or a rodent, e.g., a rat or a mouse; introducing the cell and the immune component into the animal; and evaluating the interaction between the Helios misexpressing cell and the immune system component.

In a preferred embodiment, the method further includes: prior to introduction of a cell into the subject, treating the lymphocyte to inhibit proliferation, e.g., by irradiating the cell.

In a preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal; the immune system component is from the same species as the lymphocyte; the immune system component is from species different from the species from which the lymphocyte is obtained.

In another preferred embodiment: the cell is from the same species as the animal; the cell is from a species which is different from the species of the animal.

In another preferred embodiment: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In a preferred embodiment: the cell is heterozygous or homozygous for an Helios transgene.

In preferred embodiments evaluating can include evaluating any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments: the method is performed in vivo, and one or more of the animal, the donor of the Helios misexpressing cell, the donor of the immune system component, is immunized with an antigen. The antigen can be: an alloantigen; a xenoantigen or an autoantigen; a protein; or an antigen which gives rise to an anti-idiotypic lymphocyte.

In another aspect, the invention features, a mammal, e.g., a nonhuman mammal, e.g., e.g., a swine, a nonhuman primate, e.g., a monkey, a goat, or a rodent, e.g., a rat or a mouse, having an exogenously introduced immune system component, the component being from a human or nonhuman mammal, e.g., a swine, a nonhuman primate, e.g., a monkey, a goat, or a rodent, e.g., a rat or a mouse, or cell culture which is Helios misexpressing or which carries at least one mutant allele at the Helios locus. In preferred embodiments, e.g., if the immune system component is from a wild-type animal, e.g., a human, the manipulation that gives rise to Helios deregulation, e.g., an Helios lesion, can be made in vitro.

In preferred embodiments, the component is from a human or nonhuman mammal, e.g., a swine, a nonhuman primate, e.g., a monkey, a goat, or a rodent, e.g., a rat or a mouse, which is Helios misexpressing.

In preferred embodiments: the component is from a mammal which is Helios misexpressing; the component is from a mammal which is heterozygous at the Helios locus; the component is from a mammal which carries a mutation at the Helios gene, e.g., a point mutation in or a deletion for all or part of the Helios gene, e.g., a mutation in the DNA binding region, e.g., a point mutation in, or a deletion for all or part of one or more of the four N-terminal zinc finger regions which mediates DNA binding of the Helios protein or for one or more of the two C terminal zinc finger regions which mediate dimerization of the Helios protein; the component is from a mammal which is heterozygous or homozygous for an Helios transgene; the component is from a mammal which carries a mutation in the control region of the Helios gene.

In preferred embodiments: the component is from a mammal which carries a mutation at the Helios gene, e.g., a point mutation or a deletion, which, inactivates one or both of transcriptional activation or dimerization, which decreases the half life of the protein, or which inactivates one or both of the C terminal Zinc finger domains.

In preferred embodiments, the immune system component is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal.

In preferred embodiments: the mammal or the donor animal which produces the immune system component or both are immunized with an antigen. The antigen can be: an alloantigen; a xenoantigen or an autoantigen; a protein; or an antigen which gives rise to an anti-idiotypic lymphocyte.

In another aspect, the invention features, a reaction mixture, preferably an in vitro reaction mixture, including an immune system component, the component including cells which misexpress Helios or being from an animal or cell culture which is misexpresses Helios or which carries at least one mutant allele at the Helios locus, and a target tissue or cell, wherein preferably, the immune system component and the target differ in genotype at a locus other than the Helios or Ikaros locus; the component and the target are from different species, or the component and the target are from different animals.

In preferred embodiments, the component is from an animal or cell culture which misexpresses Helios.

In preferred embodiments: the immune system component is a lymphocyte heterozygous or homozygous for an Helios transgene, e.g., a transgene having a point mutation or a deletion, which, inactivates one or both of transcriptional activation or dimerization, which decreases the half life of the protein, or which inactivates one or both of the C terminal Zinc finger domains; the immune system component is a lymphocyte heterozygous or homozygous for a C terminal deletion.

In preferred embodiments, the immune system component is: a B cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the target cell; the immune system component is from species different from the species of the target cell.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, lymph node tissue, bone marrow tissue or thymic tissue, or is syngeneic, allogeneic, xenogeneic, or congenic tissue.

In preferred embodiments: the donor of the immune system component or the donor of the target or both are immunized with an antigen. The antigen can be: an alloantigen; a xenoantigen or an autoantigen; a protein; or an antigen which gives rise to an anti-idiotypic lymphocyte.

In preferred embodiments the donor of the components is: a human or nonhuman mammal, e.g., a swine, a nonhuman primate, e.g., a monkey, a goat, or a rodent, e.g., a rat or mouse. In preferred embodiments, e.g., in the case of a wild-type donor, e.g., a human, the manipulation that gives rise to Helios deregulation, e.g., an Helios lesion, can be introduced in vitro.

In preferred embodiments the donor of the target is: a human or nonhuman mammal, e.g., a swine, a nonhuman primate, e.g., a monkey, a goat, or a rodent, e.g., a rat or mouse.

In preferred embodiments the reaction mixture includes an exogenously add cytokine or antigen, e.g., a protein antigen.

In another aspect, the invention features a cell, or purified preparation of cells, which include an Helios transgene, or which otherwise misexpress an Helios gene. The cell preparation can consist of human or non human cells, e.g., rodent cells, e.g., mouse or rat cells, rabbit cells, or pig cells. In preferred embodiments, the cell or cells include an Helios transgene, e.g., a heterologous form of an Helios gene, e.g., a gene derived from humans (in the case of a non-human cell). The Helios transgene can be misexpressed, e.g., overexpressed or underexpressed. In other preferred embodiments, the cell or cells include a gene which misexpress an endogenous Helios gene, e.g., a gene the expression of which is disrupted, e.g., a knockout. Such cells can serve as a model for studying disorders which are related to mutated or mis-expressed Helios alleles or for use in drug screening.

In another aspect, the invention features, a method of providing an antibody, e.g., a polyclonal or monoclonal antibody. The method includes: providing a mammal, e.g., a mouse, having a cell which is Helios deregulated, e.g., which misexpresses, preferably underexpresses, Helios, e.g., a hematopoietic cell; and isolating an antibody from the animal or from a cell derived from the animal, e.g., a hybridoma.

In preferred embodiments: the mammal is immunized with an antigen; the cell is exogenously supplied and one or both of the mammal, or the mammal which donates the cell, are immunized with an antigen. The antigen can be: an alloantigen; a xenoantigen; an autoantigen; a protein; or an antigen which gives rise to an anti-idiotypic lymphocyte. In preferred embodiments the antigen is an autoantigen and the animal is not immunized.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Helios-misexpressing cell to divide and give rise to a proliferation-deregulated or antibody producing cell, e.g., a lymphocyte.

In preferred embodiments: the proliferation-deregulated or antibody producing cell e.g., a lymphocyte, e.g., a transformed lymphocyte, is isolated from a lymphoma of the mammal.

In preferred embodiments: the mammal carries a mutation at the Helios gene, e.g., a point mutation in or a deletion for all or part of the Helios gene, e.g., a mutation in the DNA binding region, e.g., a point mutation in, or a deletion for all or part of one or more of the four N-terminal zinc finger regions which mediate DNA binding of the Helios protein or for one or more of the two C terminal zinc finger regions which mediate dimerization of the Helios protein; the mammal is heterozygous or homozygous for an Helios transgene; the mammal carries a mutation in the control region of the Helios gene.

In preferred embodiments the mammal, e.g., a mouse, is homozygous for null mutations, e.g., it is homozygous for a deletion of the C terminal end of the protein, at the Helios locus.

In preferred embodiments the mammal, e.g., a mouse, is homozygous for null mutations, e.g., it is homozygous for a deletion of the C terminal end of the protein, at the Helios locus and includes a mutation at Ikaros, e.g., a dominant negative mutation at Ikaros. Preferably the Ikaros mutation is heterozygous.

In preferred embodiments: the mammal carries homozygous mutations at the Helios gene, e.g., a point mutation or a deletion, which, inactivates one or both of transcriptional activation or dimerization, which decreases the half life of the protein, or which inactivates one or both of the C terminal Zinc finger domains.

In preferred embodiments: the proliferation-deregulated or antibody producing cell is a homozygous mutant Helios cell e.g., a lymphocyte; the proliferation-deregulated or antibody producing lymphocyte is a B lymphocyte; the proliferation-deregulated or antibody producing cell is heterozygous or homozygous for an Helios transgene.

In preferred embodiments, the cell is a lymphocyte and is: a cell which secretes one or more anti-inflammatory cytokines; a cell which is antigen or idiotype specific; a cell which produces, or over produces, antibodies, e.g., IgG, IgA, or IgE antibodies.

In a preferred embodiment: the Helios-misexpressing cell, e.g., a lymphocyte, is supplied exogenously to the mammal, e.g., to a homozygous wild-type Helios mammal or a mammal carrying a mutation at the Helios gene, e.g., a point mutation or a deletion for all or part of the Helios gene. If exogenously supplied, the cell can be a human or a nonhuman, e.g., a swine, nonhuman primate, e.g., a monkey, a goat, or a rodent, e.g., a rat or a mouse, lymphocyte. The exogenously supplied cell can be homozygous for null mutations, e.g., homozygous for a deletion of the C terminal end of the protein, at the Helios locus. The exogenously supplied cell can be homozygous for null mutations, e.g., homozygous for a deletion of the C terminal end of the protein, at the Helios locus and include a mutation at Ikaros, e.g., a dominant negative mutation at Ikaros. Preferably the Ikaros mutation is heterozygous.

In a preferred embodiment the method further comprises isolating one or more cells, e.g., lymphocytes, from the mammal, and allowing the cell or cells to proliferate into a clonal population of cells, e.g., lymphocytes.

In a preferred embodiment the method further comprises isolating one or more cells, e.g., lymphocytes, from the mammal, and allowing the cell or cells to proliferate into a clonal population of cells, e.g., lymphocytes, and isolating the antibody therefrom.

In preferred embodiments a cell from the animal is fused with a second cell to provide a hybridoma.

In preferred embodiments a cell from the animal is fused with a second cell to provide a hybridoma and the antibody is isolated from the hybridoma.

Cells, e.g., stem cells, treated by the method of the invention can be introduced into mammals, e.g., humans, non-human primates, or other mammals, e.g., rodents. In preferred embodiments the treatment is performed ex vivo and: the cell is autologous, e.g., it is returned to the same individual from which it was derived; the cell is allogeneic, i.e., it is from the same species as the mammal to which it is administered; the cell is xenogeneic, i.e., it is from a different species from the mammal to which it is administered.

An Helios-deregulated cell is a cell which has a mutant or misexpressed Helios gene, e.g., an inactiviated Helios gene.

A hematopoietic cell, can be, e.g., stem cell, e.g., a totipotent or a pluripotent stem cell, or a descendent of a stem cell, e.g., a lymphocyte, e.g., a B lymphocyte or a T lymphocyte.

An Helios misexpressing animal, as used herein, is an animal in which one or more, and preferably substantially all, of the cells misexpress Helios.

A mutation at the Helios locus, as used herein, includes any mutation which alters the expression, structure, or activity of the Helios gene or its gene product. These include point mutations in and in particular deletions of all or part of the Helios coding region or its control region.

An exogenously supplied cell, tissue, or cell product, e.g., a cytokine, as used herein, is a cell, tissue, or a cell product which is derived from an animal other than the one to which is supplied or administered. It can be from the same species or from different species than the animal to which it is supplied.

A substantially homogenous population of two or more cells e.g., lymphocytes, as used herein, means a population of cells in which at least 50% of the cells, more preferably at least 70% of the cells, more preferably at least 80% of the cells, most preferably at least 90%, 95% or 99% of the subject cell type, e.g., lymphocytes. With respect to the Helios locus however, the cells can be all (+/−), all (−/−), or a mixture of (+/−) and (−/−) cells.

Culturing, as used herein, means contacting a cell or tissue with an environment which will support viability of the cell or tissue and which preferably supports proliferation of the cell or tissue.

A substantially purified preparation of cells, e.g., lymphocytes, as used herein, means a preparation of cells in which at least 50% of the cells, more preferably at least 70% of the cells, more preferably at least 80% of the cells, most preferably at least 90%, 95% or 99% of the cells of the subject cell, e.g., are lymphocytes. With respect to the Helios locus however, the cells can be all (+/−), all (−/−), or a mixture of (+/−) and (−/−) cells.

Immunocompromised, as used herein, refers to a mammal in which at least one aspect of the immune system functions below the levels observed in a wild-type mammal. The mammal can be immunocompromised by a chemical treatment, by irradiation, or by a genetic lesion resulting in, e.g., a nude, a beige, a nude-beige, or an Ikaros-phenotype. The mammal can also be immunocompromised by an acquired disorder, e.g., by a virus, e.g., HIV.

As used herein, an Helios transgene, is a transgene which includes all or part of an Helios coding sequence or regulatory sequence. The term also includes DNA sequences which when integrated into the genome disrupt or otherwise mutagenize the Helios locus. Helios transgenes sequences which when integrated result in a deletion of all or part of the Helios gene. Included are transgenes: which upon insertion result in the misexpression of an endogenous Helios gene; which upon insertion result in an additional copy of an Helios gene in the cell; which upon insertion place a non-Helios gene under the control of an Helios regulatory region. Also included are transgenes: which include a copy of the Helios gene having a mutation, e.g., a deletion or other mutation which results in misexpression of the transgene (as compared with wild type); which include a functional copy of an Helios gene (i.e., a sequence having at least 5% of a wild type activity, e.g., the ability to support the development of T, B, or NK cells); which include a functional (i.e., having at least 5% of a wild type activity, e.g., at least 5% of a wild type level of transcription) or nonfunctional (i.e., having less than 5% of a wild type activity, e.g., less than a 5% of a wild type level of transcription) Helios regulatory region which can (optionally) be operably linked to a nucleic acid sequence which encodes a wild type or mutant Helios gene product or, a gene product other than an Helios gene product, e.g., a reporter gene, a toxin gene, or a gene which is to be expressed in a tissue or at a developmental stage at which Helios is expressed. Preferably, the transgene includes at least 10, 20, 30, 40, 50, 100, 200, 500, 1,000, or 2,000 base pairs which have at least 50, 60, 70, 80, 90, 95, or 99% homology with a naturally occurring Helios sequence. Preferably, the transgene includes a deletion of all or some of exons 3 and 4, or a deletion for some or all of exon 7 of the Helios gene.

A "heterologous promoter", as used herein is a promoter which is not naturally associated with the Helios gene.

A "purified preparation" or a "substantially pure preparation" of an Helios polypeptide, or a fragment or analog thereof (or an Helios-Helios or Helios-Ikaros dimer), as used herein, means an Helios polypeptide, or a fragment or analog thereof (or an Helios-Helios or Helios-Ikaros dimer), which is free of one or more other proteins lipids, and nucleic acids with which the Helios polypeptide (or an Helios-Helios or Helios-Ikaros dimer) naturally occurs. Preferably, the polypeptide, or a fragment or analog thereof (or an Helios-Helios or Helios-Ikaros dimer), is also separated from substances which are used to purify it, e.g., antibodies or gel matrix, such as polyacrylamide. Preferably, the polypeptide, or a fragment or analog thereof (or an Helios-Helios or Helios-Ikaros dimer), constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

A "substantially pure nucleic acid", e.g., a substantially pure DNA encoding an Helios polypeptide, is a nucleic acid which is one or both of: not immediately contiguous with one or both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional Helios sequences.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in one sequence (SEQ ID NO:24) is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100). For example, if 6 of 10, of the positions in two sequences are matched or homologous then the two sequences are 60% homologous or have 60% sequence identity. BY way of example, the DNA sequences ATTGCC and TATGGC share 50% homology or sequence identity. Generally, a comparison is made when two sequences are aligned to give e maximum homology or sequence identity.

The comparison of sequences and determination of percent homology between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. Blast nucleotide searches can be performed with the NBLAST program, score=100, wordlength=12 to obtain nucleotide sequences homologous to the nucleic acids of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Research 25(17): 3389–3402. When utilizing BLAST and Gapped BLAST programs, the default parameters of the respective programs (e.g., XBLAST and NBLAST) can be used. See http: \\www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Programs which are equivalent in terms of the results they produce can be used.

The terms "peptides", "proteins", and "polypeptides" are used interchangeably herein.

As used herein, the term "transgene" means a nucleic acid sequence (encoding, e.g., one or more Helios polypeptides or Helios-Ikaros dimers), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence, such as the Helios and/or Ikaros gene, operably linked to the promoter, and which effects expression of the selected DNA sequence in specific cells of a tissue, such as lymphocytes. The term also covers so-called "leaky" promoters, which regulate expression of a selected DNA primarily in one tissue, but cause expression in other tissues as well.

A polypeptide has Helios biological activity if it has one or more of the following properties: (1) the ability to react with an antibody, or antibody fragment, specific for (a) a wild type Helios polypeptide, (b) a naturally-occurring mutant Helios polypeptide, or (c) a fragment of either (a) or (b); (2) the ability to form Helios dimers, Helios/Aiolos, and/or Helios/Ikaros dimers; (3) the ability to modulate the development of hematopoietic stem cells; (4) the ability to stimulate transcription from a sequence; or (5) the ability to act as an antagonist or agonist of the activities recited in (1), (2), (3) or (4).

"Misexpression", as used herein, refers to a non-wild type pattern of Helios gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing, size, amino acid sequence, post-transitional modification, stability, or biological activity of the expressed Helios and/or Ikaros polypeptide; a pattern of expression that differs from wild type in terms of the effect of an environmental stimulus or extracellular stimulus on expression of the Helios and/or Ikaros gene, e.g., a pattern of increased or decreased expression (as compared with wild type) in the presence of an increase or decrease in the strength of the stimulus; a ratio of Ikaros-Ikaros dimer to Helios-Helios dimer which differs from wild type; a ratio of Helios to Helios-Helios dimer, Ikaros-Ikaros dimer, or Ikaros-Helios dimer that differs from wild type; a ratio of Ikaros-Helios dimer to Helios, Ikaros, Helios-Helios dimer, or Ikaros-Ikaros dimer that differs from wild type.

As described herein, one aspect of the invention features a pure (or recombinant) nucleic acid which includes a nucleotide sequence encoding an Helios, and/or equivalents of such nucleic acids. The term "nucleic acid", as used herein, can include fragments and equivalents. The term "equivalent" refers to nucleotide sequences encoding functionally equivalent polypeptides or functionally equivalent polypeptides which, for example, retain the ability to react with an antibody specific for an Helios polypeptide. Equivalent nucleotide sequences will include sequences that differ by one or more nucleotide substitutions, additions or deletions, such as allelic variants, and will, therefore, include sequences that differ from the nucleotide sequence of Helios shown in SEQ ID NO:23, SEQ ID NO:25, or SEQ ID NO:28 due to the degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The Helios genes and polypeptides of the present invention are useful for studying, diagnosing and/or treating diseases associated with unwanted cell proliferation, e.g., leukemias or lymphomas. The gene (or fragment thereof) can be used to prepare antisense constructs capable of inhibiting expression of a mutant or wild type Helios gene encoding a polypeptide having an undesirable function. Alternatively, an Helios polypeptide can be used to raise antibodies capable of detecting proteins or protein levels associated with abnormal cell proliferation or lymphocyte differentiation, e.g., T cell maturation. Furthermore, Helios peptides, antibodies or nucleic acids, can be used to identify the stage of lymphocyte differentiation, e.g., the stage of T cell differentiation.

Other features and advantages of the invention will be apparent from the following detailed description, and from the claims.

Summary of Dedalos

The invention is based, in part, on the discovery that Daedalos, a member of the Ikaros family of proteins, is differentially expressed at various stages of neural cell maturation. It was found that forced expression of Daedalos affected neural cell differentiation.

In general, the invention features a method of characterizing or detecting a cell, e.g., a neural cell, e.g., a neural progenitor cell, e.g., a neural progenitor cell in a cell sample. The method includes: providing a cell; and detecting the absence or presence of expression of Daedalos in the cell, wherein expression of Daedalos is indicative of a neural progenitor cell, to thereby characterize or detect a cell, e.g., a neural progenitor cell. The method can further include isolating or purifying the cell.

In one embodiment, the cell sample includes non-neural cells. The non-neural cells can be of any cell type. Non-neural cells can be included in the cell sample by extracting the cell sample from tissue of a subject, wherein the extraction results in a heterogeneous population of cells. Examples of non-neural cells that can be included in the cell sample are fibroblasts, epithelial cells, and hematopoietic cells. The method can be performed in vitro or in vivo.

In one embodiment, the absence or presence of a Daedalos mRNA is detected in the cell. Various techniques known to one of skill in the art can be used to detect a Daedalos mRNA. For example, a Daedalos mRNA can be detected by using a nucleic acid probe that hybridizes to a Daedalos mRNA. A detectable label, e.g., a radioactive or fluorescent label, can optionally be attached to the nucleic acid probe in this detection method. In another example, a Daedalos mRNA can be detected by PCR. Detection by PCR can include a further step of hybridization of a nucleic acid probe, e.g., a labeled nucleic acid probe, to the PCR product.

In one embodiment, the absence or presence of a Daedalos protein is detected. A Daedalos protein can be detected by various techniques known to one of skill in the art. For example, an antibody can be used that binds to a Daedalos protein. A detectable label, e.g., a radioactive or fluorescent label, can be attached to the antibody that binds to a Daedalos protein. Other known methods of protein detection include Western blot immunoassay, immunohistology, fluorescence activated cell sorting (FACS), radioimmunoassay (RIA), fluorescent immunoassay, enzyme linked immunosorbent assay (ELISA), or an immunoassay that uses a solid support, e.g., latex beads.

Expression of Daedalos can be used as a marker to characterize, detect, separate or purify cells.

In another embodiment, the method further includes separating the neural progenitor cell from at least one non-neural progenitor cell present in the cell sample. According to this method, the neural progenitor cell can be separated from other cells based upon expression of Daedalos detected in the neural progenitor cell.

In another embodiment, Daedalos expression is detected by providing a cell in which a Daedalos control region is functionally coupled to a nucleic acid which encodes a protein other than Daedalos, e.g., a reporter molecule, e.g., lacZ or a fluorescent product, e.g., green fluorescent protein. Expression can be used to follow development in a system, e.g., in a mouse, nematode, fish (e.g., a zebrafish), e.g., in a transgenic animal, e.g., a transgenic mouse, nematode or zebrafish.

In another aspect, the invention features a method of separating a neural progenitor cell from a cell population. The method includes: providing a cell population, e.g., two or more cells, containing a neural progenitor cell and a non-neural progenitor cell; evaluating expression of Daedalos in the neural progenitor cell and in the non-neural progenitor cell; and separating the neural progenitor cell from the non-neural progenitor cell based upon their expression of Daedalos. The cell population can be derived from neural tissue, e.g., glial cells. The cell population can contain neural and non-neural cells.

In one embodiment, the neural progenitor cell has a higher level of expression of Daedalos as compared to the non-neural progenitor cell.

In one embodiment, levels of Daedalos mRNA produced in the neural progenitor cell and in the non-neural progenitor cell are evaluated. Levels of Daedalos mRNA can be evaluated by various techniques known by one of skill in the art. In one example, levels of Daedalos mRNA are evaluated by a nucleic acid probe that hybridizes to the Daedalos mRNA. The nucleic acid probe can optionally include a detectable label attached to the nucleic acid probe. In another example, Daedalos mRNA is detected by PCR, as described herein. Additionally, Daedalos expression can be evaluated by detecting the level of Daedalos protein expression by the neural progenitor cell and the non-neural progenitor cell. In one example, the Daedalos protein is detected by an antibody that binds to the Daedalos protein. The antibody can optionally include a detectable label attached thereto. Other known methods of protein detection include Western blot immunoassay, immunohistology, fluorescence activated cell sorting (FACS), radioimmunoassay (RIA), fluorescent immunoassay, enzyme linked immunosorbent assay (ELISA), or an immunoassay that uses a solid support, e.g., latex beads.

In another aspect, the invention features a method of identifying the stage of neurogenesis of a cell. The method includes: providing a cell; evaluating the absence or presence of Daedalos expression in the cell; and identifying the stage of neurogenesis of the cell based upon the absence or presence of Daedalos expression in the cell.

In one embodiment, the cell is identified as a neural progenitor cell based upon the expression of Daedalos detected in the cell. For example, a high level of Daedalos expression detected in the cell can be used to identify the cell as a neural progenitor cell. In another example, the cell can be identified as a differentiated cell based upon the absence of Daedalos expression detected in the cell.

In one embodiment, the method further includes the step of isolating a first cell, based upon its stage of neurogenesis, from a second cell characterized by a different stage of neurogenesis.

The absence of presence of Daedalos expression in a cell can be evaluated by techniques known to those of skill in the art, as described herein. For example, the level of Daedalos mRNA produced in the cell can evaluated, e.g., using a nucleic acid probe and/or by PCR analysis. In another example, the level of Daedalos expression can be evaluated by detecting a Daedalos protein produced by the cell. A Daedalos protein can be detected by using an antibody, e.g., an antibody having a detectable label attached thereto or other known methods described herein. Expression can be evaluated by detecting the expression of a reporter product, e.g., a lacZ or a fluorescent product such as GFP, under the control of a Daedalos regulatory region.

In another aspect, the invention features a method of maintaining a cell, e.g., a neural progenitor cell or neural stem cell, in a non-differentiated state, or inhibiting differentiation of a cell, e.g., a neural progenitor cell or neural stem cell. The method includes: modulating, e.g., increasing Daedalos activity or expression, to thereby maintain a cell in a non-differentiated state. Expression of Daedalos can be increased by various techniques. A compound can optionally be provided to the cell that causes increased expression of Daedalos. Examples of compounds that can cause increased expression of Daedalos include: (1) a Daedalos polypeptide, fragment, or analog thereof; (2) a nucleic acid encoding a Daedalos polypeptide, fragment, or analog thereof; and (3) an agent that increases expression of the endogenous Daedalos gene of the cell. Nucleic acids according to example (2) can contain mRNA, cDNA, and/or genomic DNA. Nucleic acids can include all or a portion of the Daedalos coding region, regulatory sequences, such as a promoter, e.g., derived from the Daedalos gene or from another gene, and an enhancer, e.g., derived from the Daedalos gene or from another gene. Agents according to example (3) can cause an increase in expression of the endogenous Daedalos gene of the cell. Agents may increase expression of the endogenous Daedalos gene either directly or indirectly, e.g., by binding to the promoter of the Daedalos gene or another gene, or by altering the regulatory sequence the Daedalos gene or another gene.

Examples of agents that can increase expression of Daedalos include: a Daedalos polypeptide or a functional fragment or analog thereof; a peptide or protein agonist of Daedalos that increases the activity of Daedalos (e.g., by increasing or stabilizing Daedalos association with a Daedalos binding partner, e.g., DNA or another Ikaros family member, or by increasing nuclear translocation of Daedalos); a small molecule that increases expression of Daedalos, e.g., by binding to the promoter region of the Daedalos gene; an antibody, e.g., an antibody that binds to and stabilizes or assists the binding of Daedalos to a Daedalos binding partner (e.g., DNA or another DNA binding protein, e.g., homo or heterodimerization between Daedalos and Ikaros, Aiolos or Helios factor); or a nucleotide sequence encoding a Daedalos polypeptide or functional fragment or analog thereof. The nucleotide sequence can be a genomic sequence or a cDNA sequence. The nucleotide sequence can include: a Daedalos coding region; a promoter sequence, e.g., a promoter sequence from a Daedalos gene or from another gene; an enhancer sequence; untranslated regulatory sequences, e.g., a 5' untranslated region (UTR), e.g., a 5'UTR from a Daedalos gene or from another gene, a 3' UTR, e.g., a 3'UTR from a Daedalos gene or from another gene; a polyadenylation site; an insulator sequence. In another preferred embodiment, the level of Daedalos protein is increased by increasing the level of expression of an endogenous Daedalos gene, e.g., by increasing transcription of the Daedalos gene or increasing Daedalos mRNA stability. In a preferred embodiment, transcription of the Daedalos gene is increased by: altering the regulatory sequence of the endogenous Daedalos gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Daedalos gene to be transcribed more efficiently.

In a preferred embodiment, Daedalos expression or activity is increased in the presence of neural growth factor, e.g., exogenous or endogenous neural growth factor.

In another aspect, the invention features a method of determining if a subject is at risk for a neural cell related disorder. The method includes: evaluating expression of Daedalos in a cell of the subject; and determining the subject's risk for a neural cell related disorder based upon the absence or presence of expression of Daedalos in the cell. In this method, expression of Daedalos can be evaluated in a cell sample derived from neural tissue.

In one example, the neural cell related disorder is a proliferative disorder, e.g., cancer.

According to the method, a subject can be determined to be at risk for a neural cell related disorder based upon an increased expression of Daedalos in the cell of the subject, as compared to the level of expression of Daedalos in a cell of a subject not at risk. When evaluating expression of Daedalos in the cell of the subject, a comparison of expression levels can be made to a cell of the same type, e.g., a neural cell, derived from a healthy individual, e.g., an individual not believed to be at risk for or to have a neural cell related disorder. Expression of Daedalos in the cell of the subject can be evaluated by using techniques known to those of skill in the art, as described herein, e.g., detection of Daedalos mRNA and/or protein.

In another aspect, the invention features a method of controlling cell differentiation. The method includes: providing a cell; and modulating expression of Daedalos in the cell, to thereby control differentiation of the cell. Expression of Daedalos in a cell can be modulated either in vitro or in vivo.

In one embodiment, the cell is a neural progenitor cell.

In one embodiment, modulating expression of Daedalos can control the neural differentiation of the cell, e.g., a neural progenitor cell.

In one embodiment, expression of Daedalos is increased. Increasing Daedalos expression can affect the differentiation and/or proliferation of the cell, e.g., increased expression of Daedalos can inhibit neural cell differentiation. Expression of Daedalos can be increased by various techniques known to one of skill in the art. A compound can optionally be provided to the cell that causes increased expression of Daedalos. Examples of compounds that can cause increased expression of Daedalos include: (1) a Daedalos polypeptide, fragment, or analog thereof; (2) a nucleic acid encoding a Daedalos polypeptide, fragment, or analog thereof; and (3) an agent that increases expression of the endogenous Daedalos gene of the cell. Nucleic acids according to example (2) can contain mRNA, cDNA, and/or genomic DNA. Nucleic acids can include all or a portion of the Daedalos coding region, regulatory sequences, such as a promoter, e.g., derived from the Daedalos gene or from another gene, and an enhancer, e.g., derived from the Daedalos gene or from another gene. Agents according to example (3) can cause an increase in expression of the endogenous Daedalos gene of the cell. Agents may increase expression of the endogenous Daedalos gene either directly or indirectly, e.g., by binding to the promoter of the Daedalos gene or another gene, or by altering the regulatory sequence the Daedalos gene or another gene.

In another embodiment, a compound is provided to the cell that causes decreased expression of Daedalos. Decreasing Daedalos expression can affect the differentiation and/or proliferation of the cell, e.g., decreasing expression of Daedalos can promote neural cell differentiation. Expression of Daedalos can be decreased by various techniques known to one of skill in the art. A compound can optionally be provided to the cell that causes decreased expression of Daedalos. In one example, a compound causes a decrease in Daedalos expression by binding to a Daedalos nucleic acid sequence, e.g., a compound such as an antisense nucleic acid or a ribozyme that binds to a Daedalos mRNA. In another example, a compound causes a decrease in Daedalos expression by binding to a Daedalos polypeptide, e.g., a compound such as an antibody, small molecule, or a peptide. In another example, a compound causes a decrease in Daedalos expression by reducing expression of the endogenous Daedalos gene in the cell, e.g., a compound such as a small molecule, peptide, or nucleic acid that binds to the promoter or regulatory sequence of the Daedalos gene. In another embodiment, the compound can decrease Daedalos expression by, e.g., by binding to Daedalos and playing a dominant negative role. For example, the compound can be a Daedalos polypeptide or other polypeptide (e.g., an Ikaros, Helios or Aiolos polypeptide) which can form a dimer, e.g., a homo or heterodimer with Daedalos but that interferes with Daedalos DNA binding and/or transcriptional activity. Such polypeptide can include Ikaros, Helios, Aiolos or Daedalos polypeptides in which one or more of the N-terminal zinc fingers has been removed.

In another aspect the invention features a method of obtaining a population of neural progenitor cells. The method includes: providing a cell sample comprising at least one neural progenitor cell; and increasing the level of Daedalos in the cell sample. Increasing Daedalos expression can affect the differentiation and/or proliferation of the cell, e.g., increasing proliferation of the neural progenitor cell and/or inhibiting the differentiation of the neural progenitor cell. The level of Daedalos in the cell sample can be increased in vitro or in vivo. Additional compounds can be added to the neural progenitor cell that affect its proliferation, differentiation, and/or survival. For example, the level of growth factors, e.g., FGF-2 and/or EGF, provided to the neural progenitor cell can be increased.

In a preferred embodiment, the level of Daedalos can be increased by administering to the cell an agent that increases Daedalos expression (e.g., by increasing Daedalos transcription rate or mRNA half-life), protein levels, or activity. The agent can be, e.g., a Daedalos polypeptide or a functional fragment or analog thereof; a peptide or protein agonist of Daedalos that increases the activity of Daedalos (e.g., by increasing or stabilizing Daedalos association with a Daedalos binding partner, e.g., DNA or another Ikaros family member, or by increasing nuclear translocation of Daedalos); a small molecule that increases expression of Daedalos, e.g., by binding to the promoter region of the Daedalos gene; an antibody, e.g., an antibody that binds to and stabilizes or assists the binding of Daedalos to a Daedalos binding partner (e.g., DNA or another DNA binding protein, e.g., homo or heterodimerization between Daedalos and Ikaros, Aiolos or Helios factor); or a nucleotide sequence encoding a Daedalos polypeptide or functional fragment or analog thereof. The nucleotide sequence can be a genomic sequence or a cDNA sequence. The nucleotide sequence can include: a Daedalos coding region; a promoter sequence, e.g., a promoter sequence from a Daedalos gene or from another gene; an enhancer sequence; untranslated regulatory sequences, e.g., a 5' untranslated region (UTR), e.g., a 5'UTR from a Daedalos gene or from another gene, a 3' UTR, e.g., a 3'UTR from a Daedalos gene or from another gene; a polyadenylation site; an insulator sequence. In another preferred embodiment, the level of Daedalos protein is increased by increasing the level of expression of an endogenous Daedalos gene, e.g., by increasing transcription of the Daedalos gene or increasing Daedalos mRNA stability. In a preferred embodiment, transcription of the Daedalos gene is increased by: altering the regulatory sequence of the endogenous Daedalos gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Daedalos gene to be transcribed more efficiently.

In another aspect, the invention features a method of obtaining a population of neural cells. The method includes: providing a cell sample comprising a neural progenitor cell; and inhibiting the expression or activity of Daedalos in the neural progenitor cell, to thereby obtain neural cells. Inhibiting the expression or activity of Daedalos can affect the differentiation and/or proliferation of the cell, e.g., it can result in the differentiation of the neural progenitor cell.

In one embodiment, a compound is provided to the neural progenitor cell that causes decreased expression or activity of Daedalos. For example, the compound can cause a decrease in Daedalos expression by binding to a Daedalos nucleic acid sequence, e.g., a compound that binds to a Daedalos mRNA such as an antisense nucleic acid or a ribozyme. In another example, the compound causes a decrease in Daedalos expression or activity by binding to a Daedalos polypeptide, e.g., any such polypeptide described herein. In another example, the compound can cause a decrease in Daedalos expression by reducing expression of the endogenous Daedalos gene in the cell.

In a preferred embodiment, Daedalos expression, levels, or activity is decreased by administering to the cell an agent that decreases Daedalos expression, levels or activity. In a preferred embodiment, the agent that inhibits Daedalos levels and/or activity can be one or more of: a Daedalos binding protein, e.g., a soluble Daedalos binding protein that binds and inhibits a Daedalos activity, e.g., DNA binding activity, nuclear translocation activity, homo or heterodimerization activity, or transcriptional activation activity; an antibody that specifically binds to the Daedalos protein, e.g., an antibody that disrupts Daedalos's ability to bind DNA or another transcription factor, to translocate to the nucleus, or bind DNA; a mutated inactive Daedalos or fragment thereof which, e.g., binds to a Daedalos binding partner (e.g., DNA or another transcription factor, e.g., Ikaros, Aiolos or Helios factor) but disrupts a Daedalos activity, e.g., nuclear translocation activity or transcriptional activation activity; a Daedalos nucleic acid molecule that can bind to a cellular Daedalos nucleic acid sequence, e.g., mRNA, and inhibit expression of the protein, e.g., an antisense molecule or Daedalos ribozyme; an agent which decreases Daedalos gene expression, e.g., a small molecule which binds the promoter of Daedalos and decreases Daedalos gene expression. In another preferred embodiment, Daedalos is inhibited by decreasing the level of expression of an endogenous Daedalos gene, e.g., by decreasing transcription of the Daedalos gene. In a preferred embodiment, transcription of the Daedalos gene can be decreased by: altering the regulatory sequences of the endogenous Daedalos gene, e.g., by the addition of a negative regulatory sequence (such as a DNA-biding site for a transcriptional repressor), or by the removal of a positive regulatory sequence (such as an enhancer or a DNA-binding site for a transcriptional activator).

In another aspect, the invention features a method of treating a neural cell related disorder. The method includes: providing a subject having a neural cell related disorder; and modulating expression of Daedalos in a cell of the subject, to thereby treat the disorder. The neural cell related disorder can be a neurodegenerative disease, e.g., Parkinson's disease, Alzheimer's disease, ischemic damage such as stroke or spinal chord trauma, epilepsy, or multiple sclerosis.

In a preferred embodiment, Daedalos expression, protein level, or activity is increased to thereby treat the disorder, e.g., a disorder characterized by insufficient proliferation or aberrant differentiation of a Daedalos responsive cell. Daedalos expression, protein level, or activity can be increased by administering to the cell an agent that increases Daedalos expression (e.g., by increasing Daedalos transcription rate or mRNA half-life), protein levels, or activity. The agent can be, e.g., a Daedalos polypeptide or a functional fragment or analog thereof; a peptide or protein agonist of Daedalos that increases the activity of Daedalos (e.g., by increasing or stabilizing Daedalos association with a Daedalos binding partner, e.g., DNA or chromatin, or by increasing nuclear translocation of Daedalos); a small molecule that increases expression of Daedalos, e.g., by binding to the promoter region of the Daedalos gene; an antibody, e.g., an antibody that binds to and stabilizes or assists the binding of Daedalos to a Daedalos binding partner (e.g., another DNA binding protein or DNA); or a nucleotide sequence encoding a Daedalos polypeptide or functional fragment or analog thereof. The nucleotide sequence can be a genomic sequence or a cDNA sequence. The nucleotide sequence can include: a Daedalos coding region; a promoter sequence, e.g., a promoter sequence from a Daedalos gene or from another gene; an enhancer sequence; untranslated regulatory sequences, e.g., a 5' untranslated region (UTR), e.g., a 5' UTR from a Daedalos gene or from another gene, a 3' UTR, e.g., a 3' UTR from a Daedalos gene or from another gene; a polyadenylation site; an insulator sequence. In another preferred embodiment, the level of Daedalos protein is increased by increasing the level of expression of an endogenous Daedalos gene, e.g., by increasing transcription of the Daedalos gene or increasing Daedalos mRNA stability. In a preferred embodiment, transcription of the Daedalos gene is increased by: altering the regulatory sequence of the endogenous Daedalos gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Daedalos gene to be transcribed more efficiently.

In another embodiment, Daedalos expression, protein levels or activity is decreased to thereby treat the disorder, e.g., a proliferative disorder. In a preferred embodiment, Daedalos expression, levels, or activity is decreased by administering to the cell an agent that decreases Daedalos expression, levels or activity. In a preferred embodiment, the agent that inhibits Daedalos levels and/or activity can be one or more of: a Daedalos binding protein, e.g., a soluble Daedalos binding protein that binds and inhibits a Daedalos activity, e.g., chromatin binding activity, nuclear translocation activity, DNA binding activity, or transcriptional activation activity; an antibody that specifically binds to the Daedalos protein, e.g., an antibody that disrupts Daedalos's ability to bind a binding partner described herein, to translocate to the nucleus, or bind DNA; a mutated inactive Daedalos or fragment thereof which, e.g., binds to a Daedalos binding partner but disrupts a Daedalos activity, e.g., nuclear translocation activity or transcriptional activation activity; a Daedalos nucleic acid molecule that can bind to a cellular Daedalos nucleic acid sequence, e.g., mRNA, and inhibit expression of the protein, e.g., an antisense molecule or Daedalos ribozyme; an agent which decreases Daedalos gene expression, e.g., a small molecule which binds the promoter of Daedalos and decreases Daedalos gene expression. In another preferred embodiment, Daedalos is inhibited by decreasing the level of expression of an endogenous Daedalos gene, e.g., by decreasing transcription of the Daedalos gene. In a preferred embodiment, transcription of the Daedalos gene can be decreased by: altering the regulatory sequences of the endogenous Daedalos gene, e.g., by the addition of a negative regulatory sequence (such as a DNA-biding site for a transcriptional repressor), or by the removal of a positive regulatory sequence (such as an enhancer or a DNA-binding site for a transcriptional activator).

As used herein, "treatment" or "treating a subject" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, a symptoms of the disease or the predisposition toward disease. A therapeutic agent includes, but is not limited to, small molecules, peptides, antibodies, ribozymes and antisense oligonucleotides.

In one embodiment, the neural cell related disorder is characterized by insufficient neural cell differentiation.

In another embodiment, the neural cell related disorder is characterized by unwanted or excessive neural cell differentiation.

In one embodiment, the neural cell related disorder is a neural cell proliferative disorder, e.g., cancer, e.g., neuroma.

In one embodiment, the level of Daedalos in the cell of the subject is increased. Increasing the level of Daedalos in the cell of the subject can result in increased neural cell differentiation.

In one embodiment, the level of Daedalos in the cell of the subject is decreased. Decreasing the level of Daedalos in the cell of the subject can result in decreased neural cell differentiation.

In another aspect, the invention features a method of neural cell culture. The method includes: providing a neural cell in vitro; and modulating expression of Daedalos in the neural cell, to thereby provide a neural cell culture.

In one embodiment, the method includes increasing the expression of Daedalos in the neural cell.

In another embodiment, the method includes decreasing the expression of Daedalos in the neural cell.

A "progenitor cell", as used herein, is a cell that can divide to give rise to two cells, wherein the progenitor cell differs in its stage of maturation from at least one of the two cells.

A "neural cell" is a cell having one or more features of a cell of the neural lineage. The term "neural cell" includes all cells of the neural lineage, regardless of their stage of maturation.

A "neural progenitor cell" is a progenitor cell of the neural cell lineage, e.g., a cell that does not proliferate and/or differentiate to give rise to a non-neural cell under normal in vivo conditions.

A "cell sample" is a collection of two or more cells. A cell sample can be provided in any form, e.g., in a vessel, e.g., in a tube. The cell sample can contain cells derived from neural tissue of a subject. In one example, the cell sample also contains non-neural progenitor cells, e.g., differentiated neural cells.

A "differentiated neural cell" is a neural cell that cannot divide to give rise to a daughter cell that differs in its stage of maturation from the differentiated neural cell. A "differentiated neural cell" is also referred to as an end-stage cell.

A "control region" of a gene is a transcriptional regulatory element or combination of regulatory elements. For example, a control region of a Daedalos gene can be a promoter or functional fragment thereof, an enhancer sequence, an insulator sequence, or combinations thereof.

All publications and patents referred to herein are incorporated by reference.

Other features and advantages of the invention will be apparent from the following detailed description, and from the claims.

Summary of Ikaros

The Ikaros locus is a master regulatory locus which is intricately intertwined with the regulation of hematopoietic development. The Ikaros locus is also expressed in certain nervous tissue and is active in the regulation of the cell cycle. It is active at various times in development and exerts an extremely pleiotropic hematopoietic development phenotype. For example, the Ikaros gene is characterized by a complex and striking pattern of expression in terms of tissue-specificity, is temporally regulated, and is regulated in terms of the profile of isoform expression. All of these observations are consistent with a gene which provides critical developmental control at a number of points in development. The phenotypes of Ikaros transgenic animals of the invention confirm the fundamental and multifaceted role of the Ikaros gene. For example, mice which are heterozygotic for a deletion of portions of exons 3 and 4 (which encode a region involved in DNA binding), develop extremely aggressive lymphomas. Initial data suggest that human lymphoma tissue often exhibit chromosomal aberrations involving Ikaros. Homozygotes for the exon 3/4 deletion are poorly viable. Transgenic mice with a different deletion, a deletion of exon 7 (which is believed to be active in activation and dimerization of the Ikaros gene product) exhibits a very different phenotype. Mice which are heterozygous for an exon 7 deletion are healthy. Mice which are homozygous for an exon 7 deletion have no B cells, no NK cells, and no γδ T cells. While T cells are present, the populations of $CD4^+/CD8^+$, $CD4^+/CD8^-$, and $CD4^-/CD8^+$ are skewed (the proportion of $CD4^+/CD8^+$ cells is decreased relative to wild type, the proportion of $CD4^+/CD8^-$ cells is increased relative to wild type, and the proportion of $CD4^-/CD8^+$ cells is unchanged relative to wild type). It has also been found that Ikaros regulatory elements play an important role in directing hematopoietic development. Depending on which regulatory element, or combination of regulatory elements, is involved in transcription, progression along various differentiation pathways of the hematopoietic lineage can occur. For example, involvement of different Ikaros promoter elements can result in directed expression of B-cells, neutrophils or both. In addition, involvement of various Ikaros enhancer elements and/or insulator elements can result in, for example, directed expression of T-cells.

The central and multifaceted role of Ikaros in development, and the variety of phenotypes exhibited by Ikaros transgenic animals and cells, render Ikaros transgenic animals and cells useful, e.g., in a variety of assays, screens, and other methods. For example, animals, cells and methods of the invention can be used to elucidate and characterize the function of the immune system, mechanisms of development, ways in which components of the immune system interact, ways in which the cell cycle is regulated, mechanisms of immune tolerance, and mechanisms of the development of immune or nervous tissue disorders. The cells, animals, and methods of the invention are also useful, e.g., for evaluating or discovering treatments which can be used to treat immune or nervous tissue disorders, for discovering or for evaluating treatments or methods of inducing immunological tolerance, e.g., to transplanted tissues. By way of example, Ikaros mice which develop lymphomas are useful not only for investigating the molecular basis of these disorders but also for screening treatments for the ability to treat such disorders. Ikaros mice which lack one or more components of the immune system are useful in a variety of reconstitution experiments.

Accordingly, in one aspect, the invention features, a transgenic animal, e.g., a mammal, e.g., preferably a non-human primate or a rodent, e.g., a mouse, having an Ikaros transgene. In other preferred embodiments, the transgenic animal is a fish, e.g., a zebrafish; a nemaotde, e.g., *caenorhabditis elegans*; an amphibian, e.g., a frog or an axolotl.

In a preferred embodiment, the animal is a transgenic animal, e.g., a transgenic mouse, having a transgene which includes an Ikaros transcriptional control region and a sequence encoding a protein functionally unrelated to Ikaros, e.g., a sequence encoding a reporter molecule.

In preferred embodiments, the animal further includes a mutated Ikaros transgene, the mutation occurring in, or altering, e.g., a domain of the Ikaros gene described herein. The transgenic animal or cell can: be heterozygous for an Ikaros transgene, e.g., a mutated Ikaros transgene; be homozygous for an Ikaros transgene, e.g., a mutated Ikaros transgene; include a first Ikaros transgene, e.g., a transgene which includes an Ikaros transcriptional control region and a sequence encoding an unrelated protein, and a second Ikaros transgene, e.g., a mutated Ikaros transgene; include an Ikaros transgene, e.g., a transgene which includes an Ikaros transcriptional control region and a sequence encoding an unrelated protein, and a second transgene which is other than an Ikaros transgene, e.g., another protein involved in hematopoiesis, e.g., an Aiolos transgene and/or a Helios transgene, e.g., a mutated Aiolos and/or Helios transgene.

In another aspect, the invention features a method of evaluating a component or a cell lineage, e.g., for evaluating development of a component or cell lineage of the immune system, e.g., the development of a hematopoietic cell or cells of the immune system. The method includes providing a transgenic animal, or cell or tissue therefrom, having an Ikaros transgene which includes an Ikaros transcriptional control region and a sequence encoding a protein functionally unrelated to Ikaros, e.g., a sequence encoding a reporter molecule, and monitoring expression of the protein unrelated to Ikaros, e.g., monitoring expression of the reporter molecule. Preferably, the Ikaros transcriptional control region includes one or more regulatory element(s) of Ikaros which directs expression of the immune component of interest. Types of development which can be evaluated include, e.g., the ontogeny of a component or cell lineage of the immune system, activation of a component or cell lineage of the immune system, the migration of a component or cell lineage of the immune system, regions of action of a component or cell lineage of the immune system and ways in which components of the immune system interact. Examples of immune system components which can be evaluated include hematopoietic cells and cell lineages, e.g., hematopoietic stem cells, multipotent progenitors, oligopotent progenitors (e.g., lymphoid or myeloid progenitors), cells committed to the B-cell lineage, cells committed to the T-cell lineage, cells committed to a myeloid cell lineage (e.g., granulocyte monocyte CFU cells), T-lymphocytes, B-lymphocytes, NK cells, and neutrophils.

Development of a component or components of the immune system can be evaluated in a living animal, a dead animal, or a tissue taken from a live or dead animal. In a preferred embodiment, the protein unrelated to Ikaros is a reporter molecule, e.g., a colored or fluorescent molecule, and the immune system component is monitored on the live animal. Preferably, the method includes detecting a signal, e.g., a fluorescent signal, on the live animal, e.g., using a confocal microscope in order to monitor expression of the immune system component.

In another aspect, the invention features a method for evaluating the effect of a treatment on a transgenic cell or animal having an Ikaros transgene, e.g., the effect of the treatment on the development of the immune system. The method includes administering the treatment to a cell or animal having an Ikaros transgene, and evaluating the effect of the treatment on the cell or animal. Preferably, the Ikaros transgene includes an Ikaros transcriptional control region and a sequence functionally unrelated to Ikaros, e.g., a sequence encoding a reporter molecule. The effect can be, e.g., the effect of the treatment on: the immune system or a component thereof, the nervous system or a component thereof, or the cell cycle. Immune system effects include e.g., T cell activation, T cell development, the ability to mount an immune response, the ability to give rise to a component of the immune system, B cell development, NK cell development, myeloid cell development, or the ratios $CD4^+/CD8^+$, $CD4^+/CD8^-$ and $CD4^-/CD8^+$.

In preferred embodiments the treatment can include: the administration of a drug, chemical, or other substance; the administration of ionizing radiation; the administration of an antibody, e.g., an antibody directed against a molecule or cell of the immune system; administration of a substance or other treatment which suppresses the immune system; or administration of a substance or other treatment which activates or boosts the function of the immune system; introduction of a nucleic acid, e.g., a nucleic acid which encodes or expresses a gene product, e.g., a component of the immune system; the introduction of a protein, e.g., a protein which is a component of the immune system.

In another aspect, the invention features a method for evaluating the effect of a treatment on an immune system component. The method includes: (1) supplying a transgenic cell or animal having an Ikaros transgene; (2) supplying the immune system component; (3) administering the treatment; and (4) evaluating the effect of the treatment on the immune system component.

In yet another aspect, the invention features a method for evaluating the interaction of a first immune system component with a second immune system component. The method includes: (1) supplying a transgenic cell or animal, e.g., a mammal, having an Ikaros transgene; (2) introducing the first and second immune system component into the transgenic cell or mammal; and (3) evaluating an interaction between the first and second immune system components.

Mice with mutant Ikaros transgenes which eliminate many of the normal components of the immune system, e.g., mice homozygous for a transgene having a deletion for some or all of exon 7, are particularly useful for "reconstitution experiments."

Ikaros transgenic mice which exhibit a phenotype characteristic of an immune system disorder, e.g., mice which are homozygous for a transgene having a deletion of all or some of exons 3 and 4, can serve as model systems for human disorders, e.g., for lymphoma.

In another aspect, the invention features a method for evaluating the effect of a treatment on an immune system disorder, e.g., a neoplastic disorder, a lymphoma, a T cell related lymphoma, including: administering the treatment to a cell or animal having an Ikaros transgene, and evaluating the effect of the treatment on the cell or animal.

In another aspect, the invention features, a method for evaluating the effect of a treatment on the nervous system comprising administering the treatment to a transgenic cell or an animal having an Ikaros transgene, and evaluating the effect of the treatment on the cell or the animal.

In another aspect, the invention features, a method for evaluating the effect of a treatment on a disorder of the nervous system, e.g., neurodegenerative disorder, e.g., Alzheimer's disease, Huntington's disease, Parkinson's disease, e.g., a neuroactive substance, e.g., neurotransmitter, imbalance, including administering the treatment to a cell or animal having an Ikaros transgene, and evaluating the effect of the treatment on the cell or animal.

In another aspect, the invention features an Ikaros transcriptional control region which includes an Ikaros regulatory element or combinations of Ikaros regulatory elements. In a preferred embodiment, the regulatory element can be one or more of Ikaros promoter(s), enhancer(s) and/or insulator sequence(s). The regulatory elements can be 5' regulatory elements, intronic elements, and/or 3' regulatory elements of Ikaros. In a preferred embodiment, when there is a combination of Ikaros regulatory elements, the complement or placement of the regulatory elements can differ from where it is naturally found in the Ikaros gene. In a preferred embodiment, a DNase I HSS cluster of Ikaros includes the regulatory element and all or a portion of the DNase I HSS cluster is included in the transcriptional control region. In a preferred embodiment, the Ikaros transcriptional control region includes: at least a portion of the β cluster containing a promoter, e.g., an R19 promoter, and/or at least a portion of the γ cluster containing a promoter, e.g., an R10 promoter. In other embodiments, the Ikaros transcriptional control region can include one or more promoter(s), e.g., a promoter from the β cluster and/or the γ cluster, and one or more Ikaros regulatory element(s), e.g., one or more Ikaros regulatory element from the α cluster, the ε cluster, the η cluster and/or the θ cluster. For example, the Ikaros transcriptional control region can include the γ cluster or a promoter-containing portion thereof and the ε cluster or a portion thereof. In other embodiments, the Ikaros transgene can include all or a promoter-containing portion of the β cluster and/or all or a promoter-containing portion from the γ cluster and: all or a portion of the α cluster; all or a portion of the δ cluster; all or a portion of the ε cluster; all or a portion of the ζ cluster; all or a portion of the η cluster; all or a portion of the θ cluster; combinations of two, three, four, or five of the α cluster, the δ cluster, the ε cluster, the ζ cluster, the η cluster, the θ cluster, or portions thereof; all of the α cluster, the δ cluster, the ε cluster, the ζ cluster, the η cluster and the θ cluster, or portions thereof.

In another aspect, the invention features a DNA construct which includes an Ikaros transcriptional control region, as described herein, and a sequence encoding a protein or polypeptide. In a preferred embodiment, the sequence can encode an Ikaros protein or a variant thereof as described herein. In a preferred embodiment, when the sequence encodes Ikaros or a variant thereof, the Ikaros transcriptional control region preferably includes one or more Ikaros regulatory element(s) but not all of the Ikaros regulatory elements described herein. In another preferred embodiment, the sequence encodes a protein or polypeptide functionally unrelated to Ikaros, e.g., the sequence encodes a reporter molecule. When the sequence encodes a protein unrelated to Ikaros, e.g., a reporter molecule, the Ikaros transcriptional control region can include one, two, three, four, five, six, seven or all of the Ikaros regulatory elements described herein. Preferably, when there is a combination of Ikaros regulatory elements, the complement or placement of the regulatory elements can differ from where it is naturally found in the Ikaros gene. For example, an element: which is normally 5', can be 5', 3' or intronic with regard to the sequence encoding a protein or polypeptide, e.g., a reporter molecule; which is normally 3' can be 5', 3' or intronic with regard to the sequence encoding a protein or polypeptide, e.g., a reporter molecule; which is intronic can be 5', 3' or intronic with regard to the sequence encoding a protein or polypeptide, e.g., a reporter molecule.

The Ikaros gene is active in the early differentiation of lymphocytes, e.g., T cells and B cells. The gene encodes a family of unique zinc finger proteins, the Ikaros proteins. The proteins of the Ikaros family are isoforms which arise from differential splicing of Ikaros gene transcripts. The isoforms of the Ikaros family generally include a common 3' exon (Ikaros exon E7, which includes amino acid residues 283–518 of the mouse Ikaros protein represented by SEQ ID NO:56, and amino acid residues 229–461 of the human Ikaros protein represented by SEQ ID NO:54) but differ in the 5' region. The Ikaros family includes all naturally occurring splicing variants which arise from transcription and processing of the Ikaros gene. Five such isoforms are described in copending U.S. patent application Ser. No. 08/121,438, filed Sep. 14, 1993. The Ikaros family also includes other isoforms, including those generated by mutagenesis and/or by in vitro exon shuffling. The naturally occurring Ikaros proteins can bind and activate (to differing extents) the enhancer of the CD3δ gene, and are expressed primarily if not solely in T cells in the adult. The expression pattern of this transcription factor during embryonic development show that Ikaros proteins play a role as a genetic switch regulating entry into the T cell lineage. The Ikaros gene is also expressed in the proximal corpus striatum during early embryogenesis in mice.

As described above, the Ikaros gene is a master regulator for lymphocyte specification. The Ikaros gene was initially described for its ability to mediate the activity of an enhancer element in the CD3 3δ gene, an early and definitive marker of the T cell differentiation (Georgopoulos, K. et al. (1992) Science 258:808). During embryogenesis, Ikaros expression is restricted to sites of hemopoiesis where it precedes and overlaps with areas of lymphocyte differentiation. Ikaros is expressed in early B cells and in T cells and their progenitors in the adult organism. Consistent with its role as a master regulator of lymphocyte specific gene expression, the Ikaros gene encodes a family of zinc finger DNA binding proteins by means of differential splicing (Molnar et al., 1994). These protein isoforms display overlapping but distinct DNA binding specificities and range from strong activators to suppressors of transcription. Together, Ikaros proteins appear to control multiple layers of gene expression during lymphocyte ontogeny in the embryo and in the adult. Significantly, high affinity binding sites for the Ikaros proteins were identified in the regulatory domains of many lymphocyte specific genes among which are the members of the CD3/TCR complex, terminal deoxyribonucleotidyl transferase (TdT), the IL-2 receptor, immunoglobulin heavy and light chains and the signal transducing molecule Igα. These genes are all important components in T and B cell differentiation pathways and their expression is a prerequisite for lymphocyte development. In addition, the Ikaros proteins can bind and activate a subset of NF-κB sites implicated in stimulating gene expression in the activated T cell (Beg, A. A. and Baldwin, A. S. J. (1993) Genes Dev. 7:2064–2070; Lenardo, M. J. and Baltimore, D. (1989) Cell 58:227–229). The Ikaros gene and its splicing products are highly conserved between mice and man, in further support of a master switch function for the lymphopoietic system across species (Molnar, et al., 1994).

A small number of regulatory genes have been described which control cell fate decisions at specific stages of the hemo-lymphoid pathway (Sieweke et al. (1998) Curr. Opin. Genet. Dev. 8(5):545–551; Georgopoulos (1997) Curr. Opin. Immunology 9(2):222–227). Of these regulators, Ikaros encodes a family of zinc finger transcription factors which are critical for progression through a number of branch points of this developmental pathway. Georgopoulos (1997) Curr. Opin. Immunology 9(2):222–227. Mice with an inactivating mutation in the Ikaros gene, display a reduction in hematopoietic stem cell (HSC) activity in both the fetus and in the adult, indicating that either the production of HSC from a mesodermal precursor or its self-renewal properties are impaired. Nichogiannopoulou et al. (1999) J. Exp. Med. 190(9):1201–1214. Significantly, Ikaros null mice lack all B-lymphocytes from the earliest described precursors in the fetal liver and in the bone marrow to the mature populations present in peripheral lymphatic centers and in the peritoneum. Wang et al. (1996) Immunity 5(6):537–549. Cells of the fetal T-lineages are also absent and only a small number of T cell precursors is detected in the thymus after birth. Wang et al. (1996) Immunity 5(6):537–549. In sharp contrast to the severe impairment in the production of B and T cell precursors, there is an increase in myeloid and erythroid precursors in Ikaros null mice. CFU-Multi and CPU-GM are significantly elevated, especially relative to the decrease manifested in the HSC compartment and myelocytes are abundantly present in the bone marrow and spleen of the mutant mice. Nichogiannopoulou et al. (1999) J. Exp. Med. 190(9):1201–1214. Mac-1$^+$ cells of a Gr-1$^{h1}$ phenotype are absent although plenty of cells with a neutrophil morphology are detected in these sites indicating a potential deregulation of the Ly6G gene encoding Gr-1. Thus, Ikaros expression is not only important for production and possibly maintenance of the HSC, but also for its regulated differentiation along the lymphoid and myeloid pathways.

Ikaros plays also a critical role during T cell differentiation. The small number of postnatal T cell precursors detected in the thymus of Ikaros null mice CM progress to the double positive and positive CD4$^+$ single stage of differentiation in the absence of pre-TCR signaling. Winandy et al. (1999) J. Exp. Med. 190(8): 1039–1048. In the presence of TCR signaling, a relative increase in the number of CD4$^+$/TCR$^+$ thymocytes is detected which is accompanied by a decrease in double positives but not in CD8$^+$TCR$^+$ cells. Wang et al. (1996) Immunity 5(6):537–549. In their majority, these CD4$^+$/TCR$^+$ cells are not properly selected and do not exit to the periphery. In mice heterozygous for the Ikaros null or dominant negative mutations, T cell populations do not appear to be developmentally abnormal, however, when stimulated in vitro through the T cell receptor they display augmented proliferative responses and in vivo undergo transformation to a neoplastic stage. Avitahl et al. (1999) Immunity 10(3):333–343.

The phenotypes manifested in the Ikaros deficient mice are in accordance with its expression in the hemo-lymphoid system. In the developing embryo, Ikaros mRNA is seen at early sites of hemopoiesis; in ES blood islands of the yolk sac, in a small number of mesodermal cells within the embryo proper (T. Ikeda, unpublished results), and in the fetal liver from E9.5. Ikaros is expressed in the fetal thymus from E10.5 at the onset of its population with fetal lymphoid precursors. Georgopoulos, K. et al. (1992) *Science* 258:808). In the bone marrow, Ikaros is expressed in a population enriched for the pluripotent and self-renewing HSC (lin⁻/Scal⁻/ckit⁺), and continues to be expressed along a precursor population (lin−/Scal−/ckit+) enriched in myeloid potential. Morgan et al. (1997) *EMBO J.* 16(8):2004–2013; Kelley et al. (1998) *Curr. Biol.* 8(9):508–515. Upon differentiation to monocytes, macrophages and erythrocytes, Ikaros expression is down regulated, however, it is maintained at significant levels in neutrophils. Klug et al. (1998) *Proc. Natl. Acad. Sci. USA* 95(2):657–662. In contrast, Ikaros is upregulated from the early thymocyte precursors (DN) to differentiating (DP) thymocytes and is expressed in mature (SP) T cells in the fetus and in the adult. In a similar fashion, it is upregulated during differentiation from the pro-B to the pre-B cell stage. Georgopoulos (1997) *Curr. Opin. Immunology* 9(2):222–227. Among the hemo-lymphoid populations, Ikaros expression is highest in double positive thymocytes and mature T cells, populations that display strong haplo-insufficiency phenotypes in mice heterozygous for the Ikaros mutations.

Thus, proper regulation of Ikaros expression is critical for progression and homeostasis along multiple differentiation pathways in the hemo-lymphoid system. To identify the transcriptional regulatory elements involved, the mouse Ikaros locus was mapped over a region of approximately 120 kB and eight distinct clusters of lymphoid specific DNaseI HSS were identified. Two distinct 5'untranslated mRNA ends were identified by 5' RACE and primer extension and the encoding exons were mapped in the vicinity of two clusters of lymphoid-specific DNaseI HSS. Regions containing the two clusters and the associated promoters were tested for activity in transgenic mice. The two promoter regions, referred to herein as R10 and R19, directed expression in B cells and neutrophils or in neutrophils only. The R10 promoter region in conjunction with an intronic DNaseI HSS cluster gained high levels of activity in differentiating and mature T cells. Finally, the B cell specific elements that reside in the R10 promoter region appear to be amenable to negative auto regulation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. For example, incorporated herein by reference in their entirety (including sequence listings therein) are the following priority documents with U.S. Ser. No.: 09/019,348 filed on Feb. 5, 1998; Ser. No. 08/733,622, filed Oct. 17, 1996, (now issued U.S. Pat. No. 6,528,634); 60/005,529 filed Oct. 18, 1995; 60/017,646 filed May 14, 1996; Ser. No. 09/259,389 filed on Feb. 26, 1999; 60/076,325 filed on Feb. 27, 1998; Ser. No. 10/037,667 filed on Oct. 25, 2001 (now U.S. Pat. No. 6,759,201); 60/243,110, filed on Oct. 25, 2000; Ser. No. 09/755,830 filed on Oct. 25, 2001; U.S. Ser. No. 08/283,300, filed Jul. 29, 1994, (now U.S. Pat. No. 6,172,278); Ser. No. 08/238,212, filed May 2, 1994; Ser. No. 08/121,438, filed Sep. 14, 1993; and Ser. No. 07/946,233, filed Sep. 14, 1992. In case of conflict, the present specification, including definitions, will control. In addition, the materials, methods, and examples are illustrative only and not intended to be limiting.

BRIEF DESCRIPTION OF FIGURES

Brief Description of Aiolos Figures

FIG. 1 is a diagram depicting mouse Aiolos cDNA. 1A: is a mouse Aiolos cDNA nucleotide sequence (SEQ ID NO:1). 1B: is a corresponding amino acid sequence 507 amino acids in length (SEQ ID NO:2).

FIG. 2 is a diagram depicting homology at the amino acid level between the mouse (SEQ ID NO:99) and chicken (SEQ ID NO:98) Aiolos sequence and the mouse (SEQ ID NO:104) and chicken (SEQ ID NO:100) Ikaros exon 7 sequence.

FIG. 3 is a diagram depicting the homolgy between mouse Aiolos amino acid sequnce (SEQ ID NO:101) and mouse Ikaros amino acid sequnce (SEQ ID NO:102).

FIG. 4 is a diagram depicting Aiolos exons 3 (SEQ ID NO:103), 4 (SEQ ID NO:105), 5 (SEQ ID NO:106), 6 (SEQ ID NO:107), and 7 (SEQ ID NO:108). Based on homology to Ikaros, the exons encoding different segments of the Aiolos gene are deduced. The exon boundaries of exons 5/6 and 6/7 have been confirmed from genomic sequence (6/7) or from differential splice products (5/6). Three classes of cDNA were recovered. The first contains exons 3 though 7. A second class splices exon 5 directly to exon 7, skipping exon 6. The third contains exon 7 and contiguous genomic sequence extending upstream of this exon.

FIG. 5A: is a human Aiolos cDNA nucleotide sequence. Consensus sequence of human Aiolos cDNA from RTPCR using mouse AioF primer (ex3) in forward direction and human hAio2 primer (ex6) in reverse direction. This sequence does not include the AioF primer sequence but does include the hAio2 sequence. AioF=atg aaa gtg aaa gat gaa tac agc only human sequence is shown here. EcoRI sites flank directly 5' and 3'. The cDNA sequence in FIG. 5A is SEQ ID NO: 7. 5B: shows a corresponding human amino acid sequence 209 amino acids in length. 5B also shows the corresponding mouse sequence and shows regions of shared sequence. The human protein sequence in 5B is SEQ ID NO: 8. The mouse protein sequence in 5B is residues 66–273 of SEQ ID NO:2).

FIG. 6 is a diagram depicting comparison of the amino acid sequence of Aiolos (top sequence, SEQ ID NO:2) and Ikaros (bottom sequence, SEQ ID NO:43) proteins. The boxed methionines represent the three translation initiation codons. The boxed cysteines and histidines represent the paired cysteines and histidines of the zinc finger motifs. The conserved activation domain (amino acids 290–344 of Aiolos protein) is shaded. Identical residues are indicated by bars and conservative residues are indicated by dots.

Brief Description of Helios Figures

Figure 10:
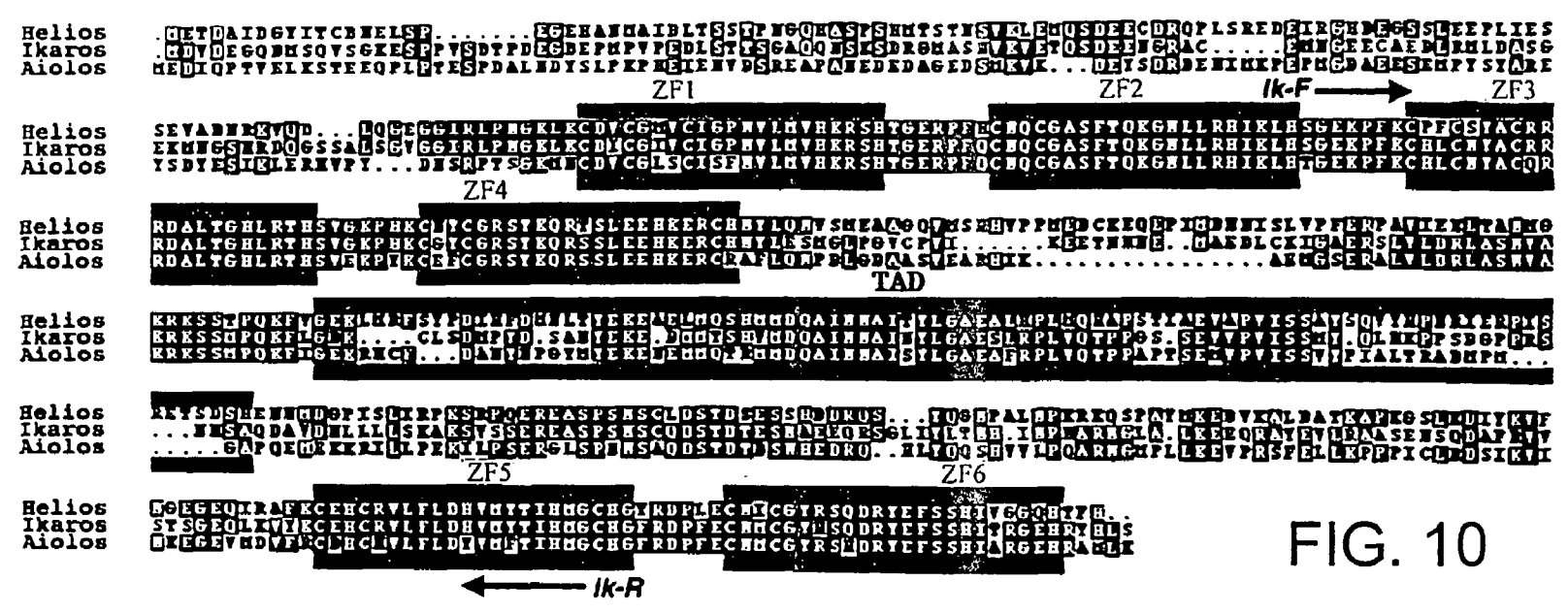

FIG. 10 depicts an alignment of the predicted amino acid sequence of Helios with that of Ikaros (SEQ ID NO:29) and Aiolos (SEQ ID NO:30). The four N-terminal zinc fingers (ZF1–4) comprising the DNA binding domain, the C-terminal zinc fingers (ZF5–6) that mediate protein dimerization and the conserved transcriptional activation domain (TAD) are outlined. Arrows indicate the conserved sequences to which the degenerate oligos Ik-1 (GEKPKF, Ik-F) and Ik-2 (YTIHMG, IK-R) were designed to clone the Helios gene.

FIG. 11 depicts a diagram of hemopoietic hierarchy of the progenitors and committed cells analyzed for Helios family gene expression.

FIG. 12A–12C depict the mouse Helios-1 nucleotide (SEQ ID NO:23) and amino acid (SEQ ID NO:24) sequences.

FIG. 13A–13C depict the mouse Helios-2 nucleotide (SEQ ID NO:25) and amino acid (SEQ ID NO:26) sequences.

FIG. 14A and 14B depict the human Helios-2 nucleotide (SEQ ID NO:27) and amino acid (SEQ ID NO: 28) sequences.

FIG. 15A and 15B depict an alignment of the nucleic acid sequence of mouse Helios (SEQ ID NO:23) with human Helios (SEQ ID NO:27).

FIG. 16 depicts an alignment of the amino acid sequence of mouse Helios with human Helios.

Brief Description of Daedalos Figures

Figure 17A:
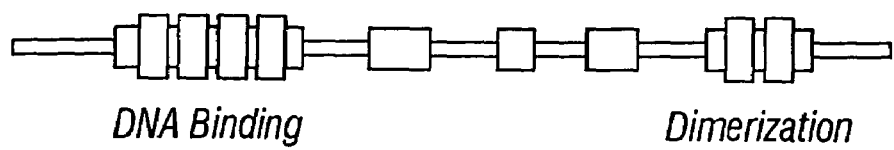

FIG. 17A is a schematic of the Ikaros family proteins, indicating the zinc finger domains (dark boxes) that confer sequence specific DNA binding properties or mediate dimerization, as well as additional regions of homology between all four proteins (gray boxes).

FIG. 17B depicts the predicted amino acid sequence of Daedalos (Daed; SEQ ID NO:40), aligned with the other Ikaros gene family members, Helios (Hel; SEQ ID NO:41), Aiolos (Aio; SEQ ID NO:42), and Ikaros (Ik; SEQ ID NO:43). Residues conserved in Ikaros family members are highlighted in gray and the zinc finger domains are boxed.

FIG. 17C depicts the amino acid sequence of the *Xenopus* Daedalos (xDaed; SEQ ID NO:44) protein, aligned with the amino acid sequence of the mouse Daedalos (mDaed) protein (SEQ ID NO:40).

Figure 18A:
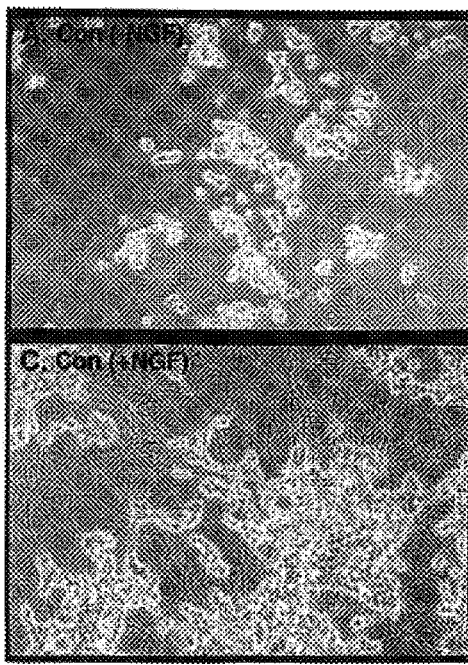

FIG. 18A depicts subcloned stable transfectants of PC12 cells harboring a control expression vector.

Figure 18B:
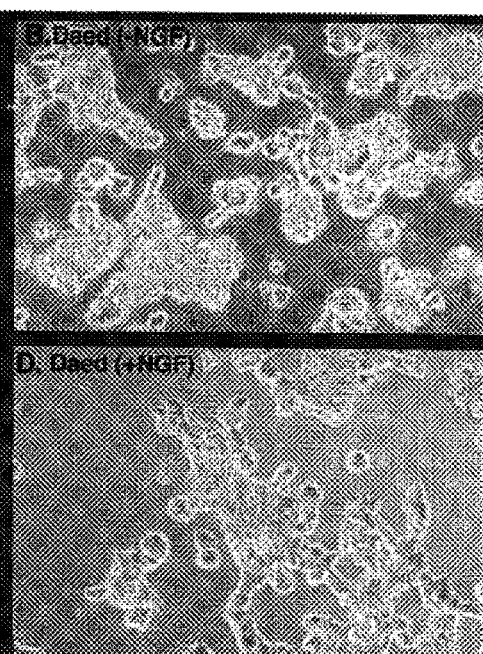

FIG. 18B depicts subcloned stable transfectants of PC12 cells harboring a Daedalos expression vector.

Figure 18C:
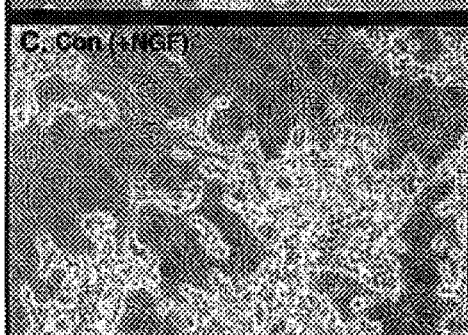

FIG. 18C depicts subcloned stable transfectants of PC12 cells harboring a control expression vector and cultured for two weeks in media supplemented with NGF.

Figure 18D:
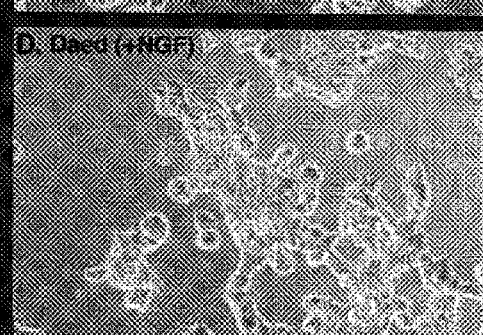

FIG. 18D depicts subcloned stable transfectants of PC12 cells harboring a Daedalos expression vector and cultured for two weeks in media supplemented with NGF.

Brief Description of Ikaros Figures

FIG. 19A–19C are the DNA sequence of a murine Ikaros cDNA (SEQ ID NO:53) and the desired amino acid sequence encoded thereby (SEQ ID NO:89).

FIG. 20A and 20B depict a partial sequence of a human Ikaros cDNA (SEQ ID NO:54) and the amino acid sequence (SEQ ID NO:90).

FIG. 21 is a depiction of the partial amino acid composition (SEQ ID NO:92) of the mouse IK-1 cDNA, including Ex3, Ex4, Ex5, Ex6, and Ex7 (SEQ ID NO:56).

Figure 22:
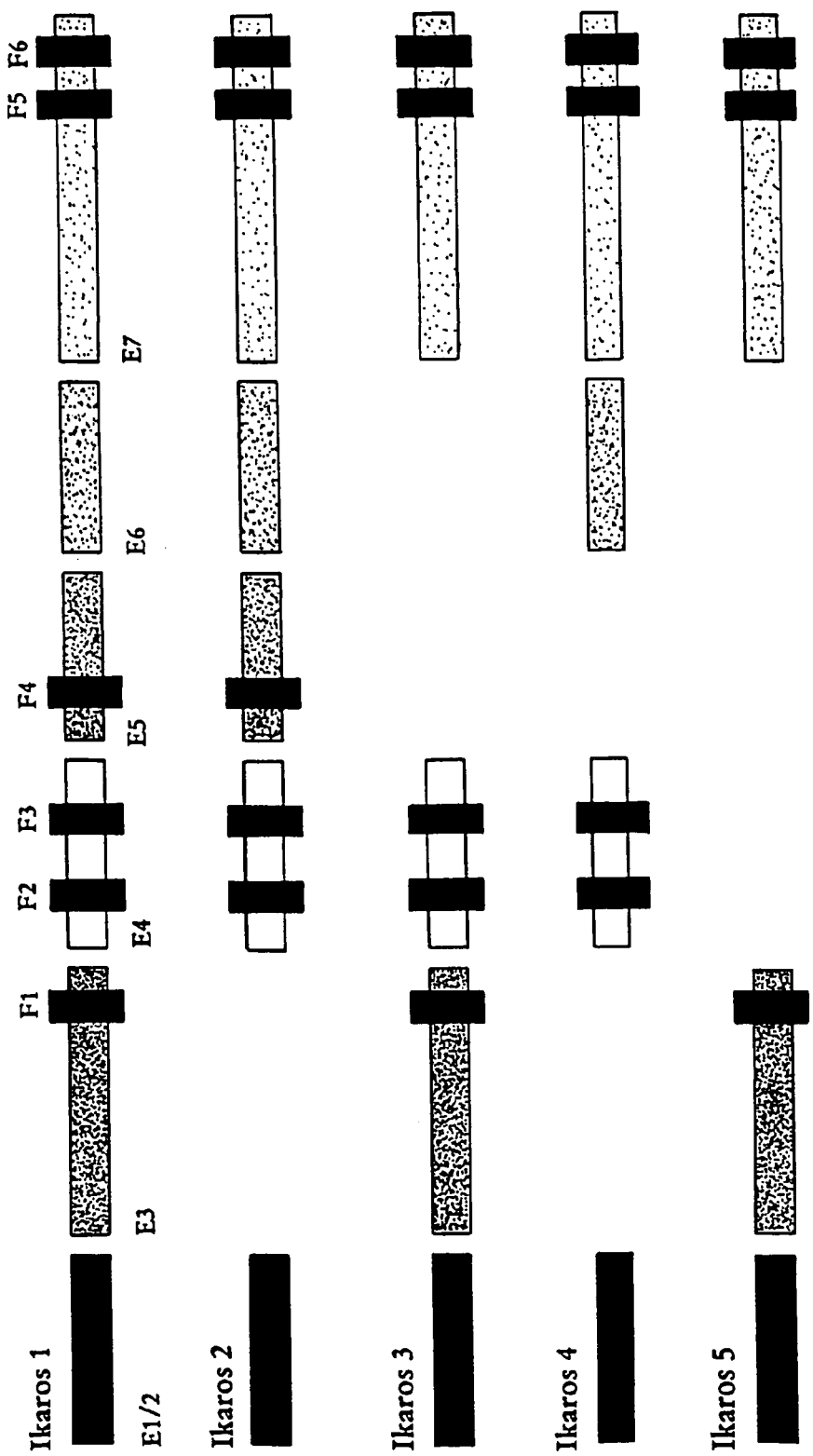

FIG. 22 is a diagram of exon usage in the Ikaros 1–5 cDNAs. Exon numbers are indicated at the bottom left hand corner of each box (Ex). Zinc finger modules are shown on top of the encoding exons (Fx).

Figure 23:
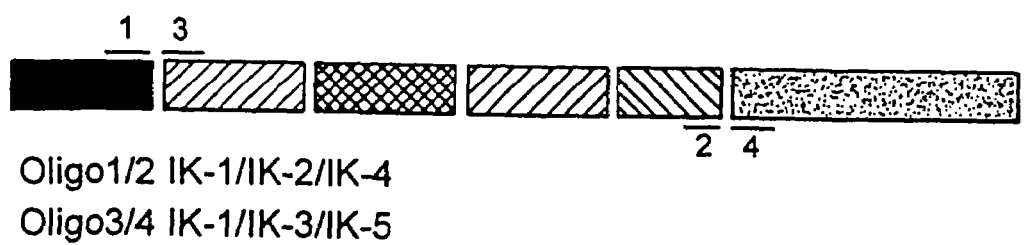

FIG. 23 is a depiction of the exon organization at the Ikaros locus indicating primer sets 1/2 and 3/4 used for amplification of the respective isoforms.

Figure 24:
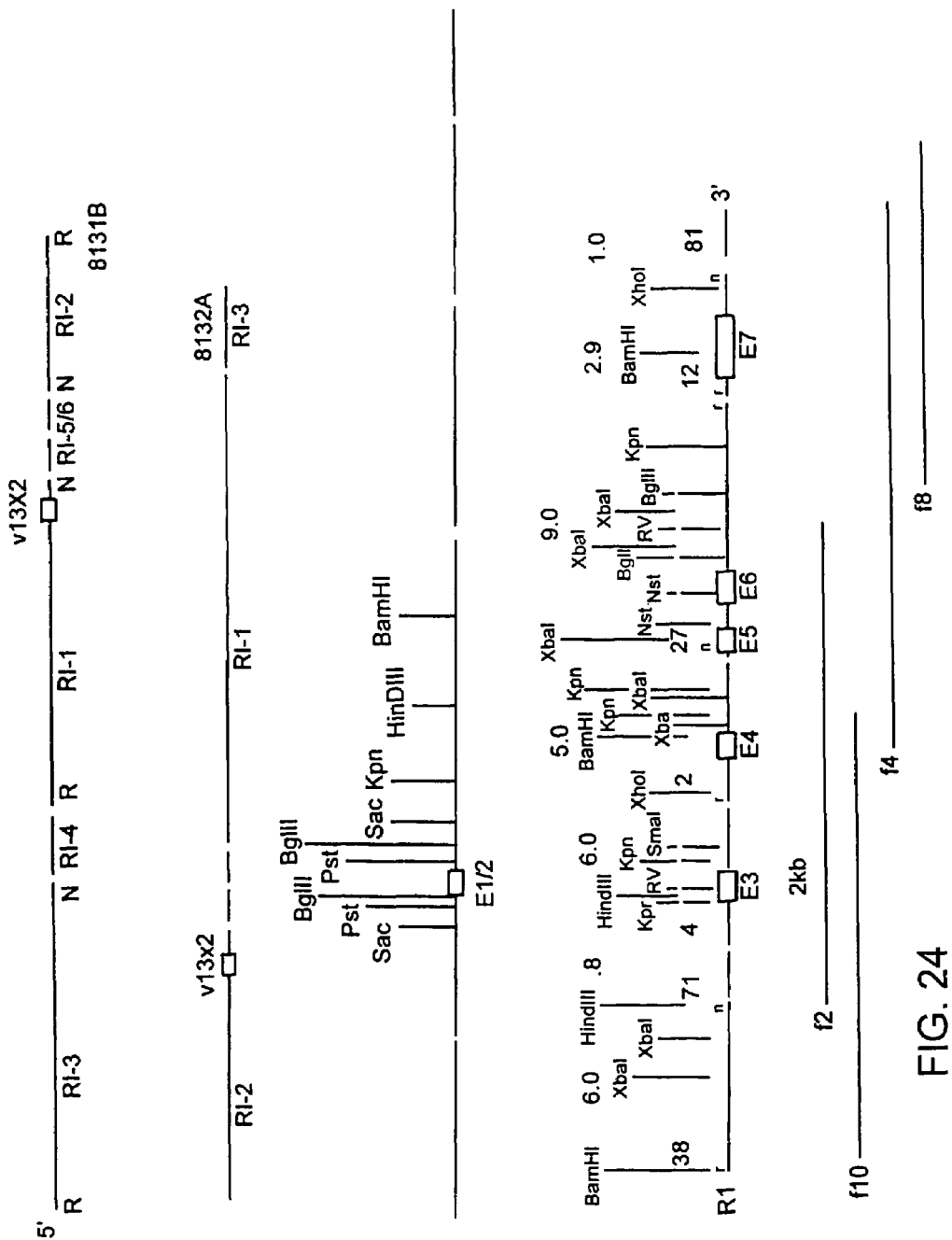

FIG. 24 is a map of the genomic organization of the mouse Ikaros gene. Intronic or uncharacterized DNA is indicated as a line between 5' and 3'. Exons are indicated as boxes. Lines numbered f2, f10, f4, and f8 indicate phage inserts corresponding to the sequence immediately above. Restriction sites are indicated by the usual abbreviations.

Figure 25:
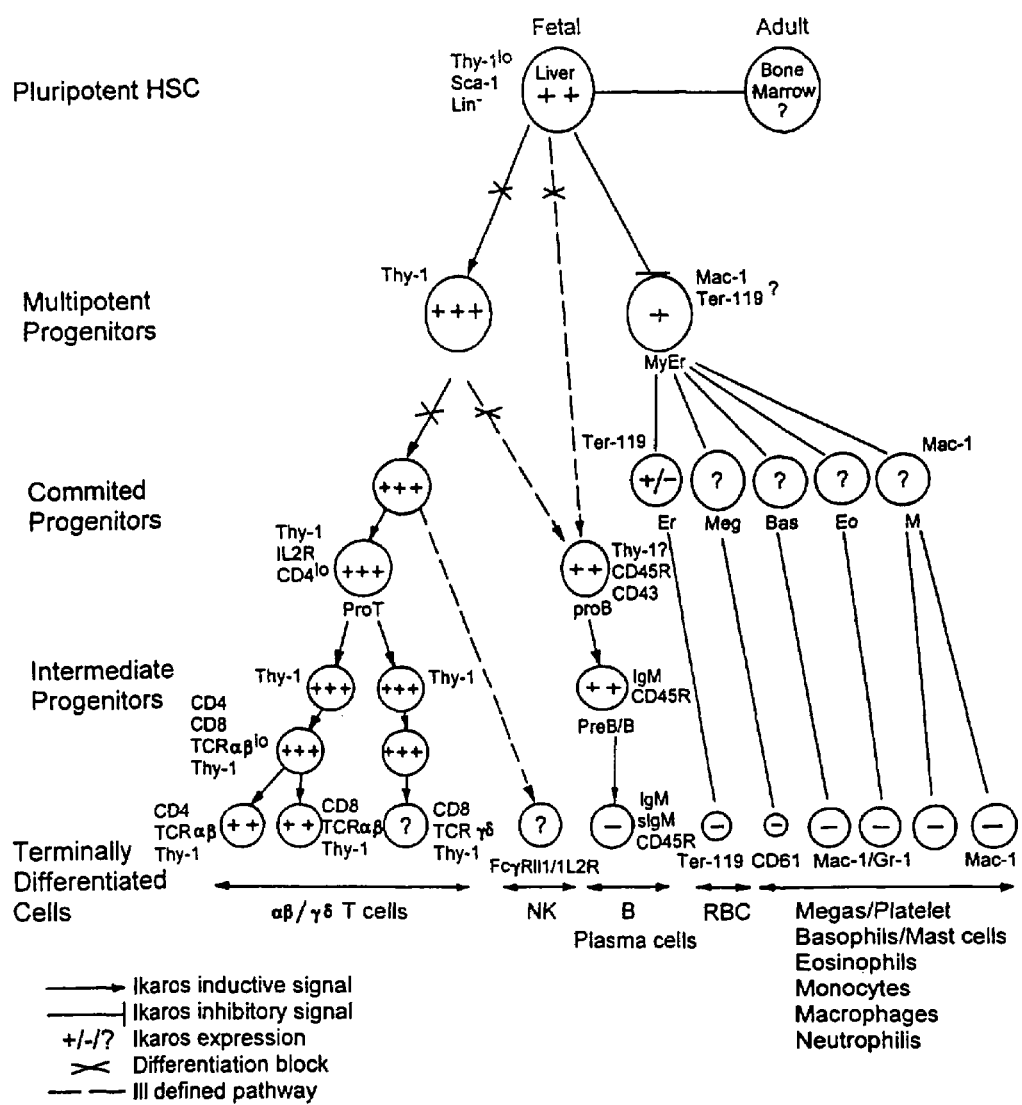

FIG. 25 is a schematic of an Ikaros view of the hemopoietic system which shows Ikaros expression and its putative roles in differentiation.

Figures 26A, 26B:
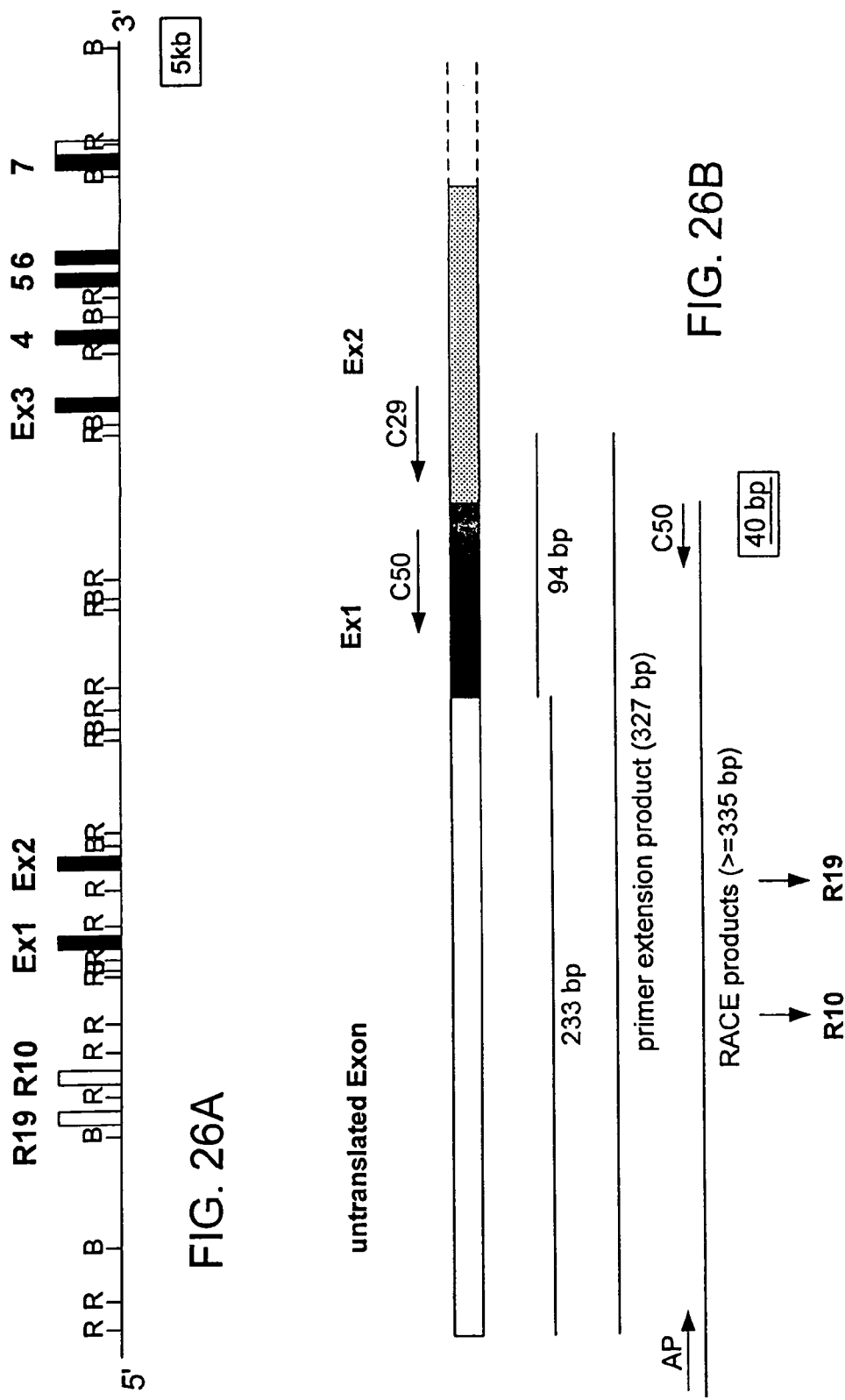

FIG. 26A is a map of the genomic organization of the mouse Ikaros gene. The entire gene is approximately 120 kb in length. Intronic or untranslated DNA is indicated as a line between 5' and 3'. Exons are indicated as solid boxes labeled Ex1, Ex2, Ex3, 4, 5, 6, and 7. The R19 and R10 promoters are indicated by open boxes labeled R19 and R10. FIG. 26B depicts the strategy for analysis of the 5' end of Ikaros mRNA by 5' rapid amplification of the cDNA ends and primer extension using primers from exons 1 and 2.

Figure 27A:
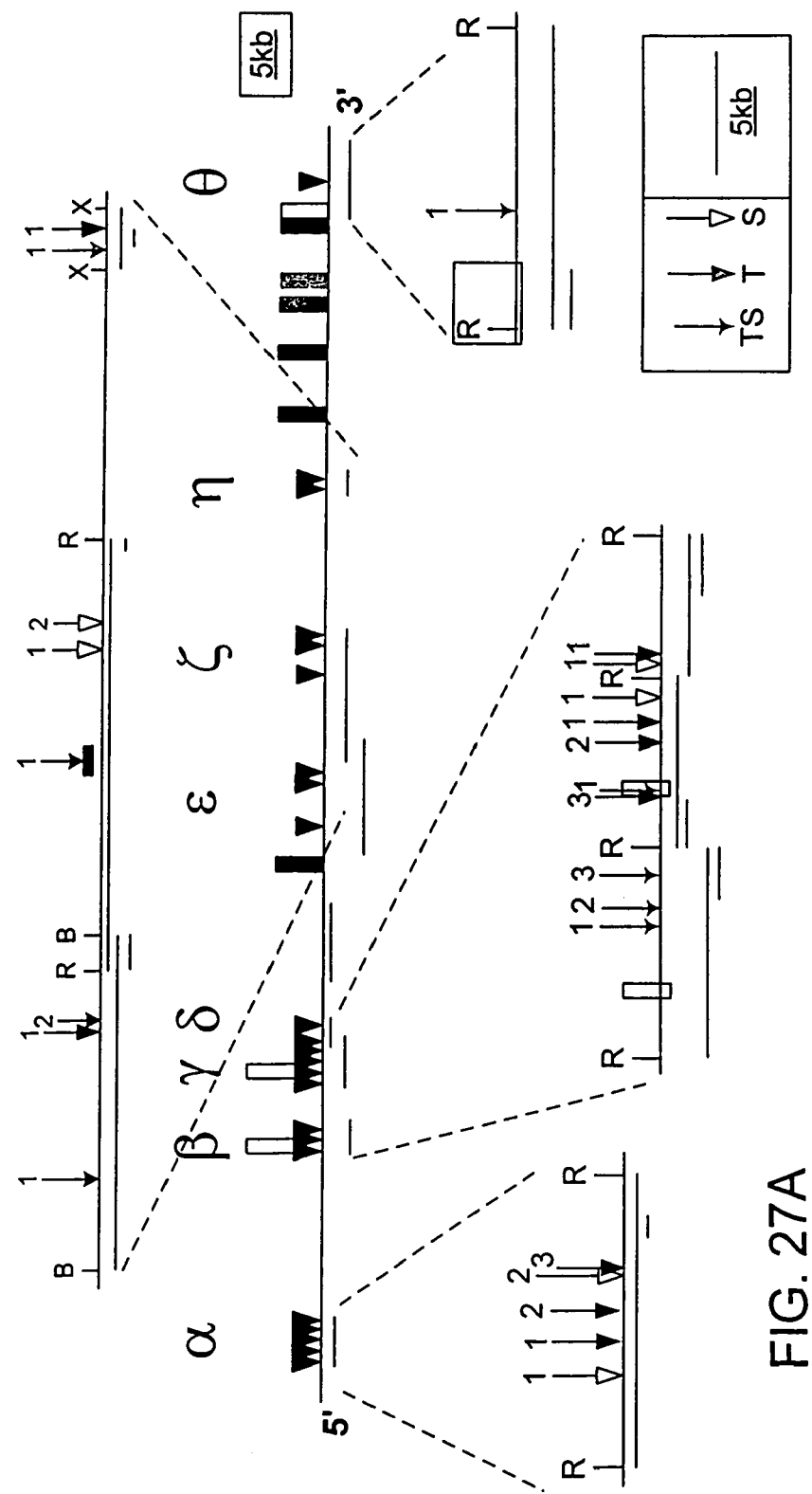
Figure 27B:
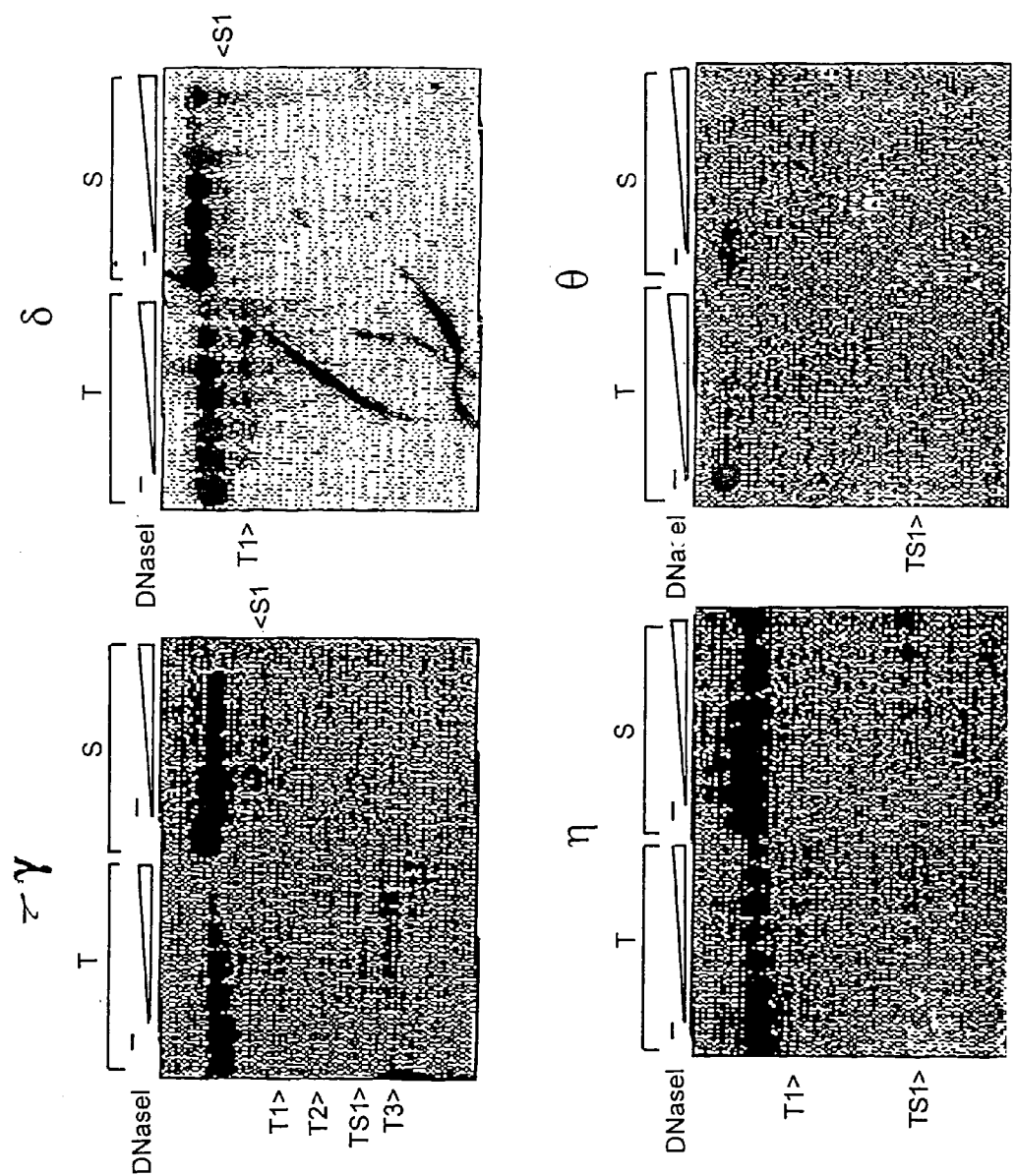
Figure 27C:
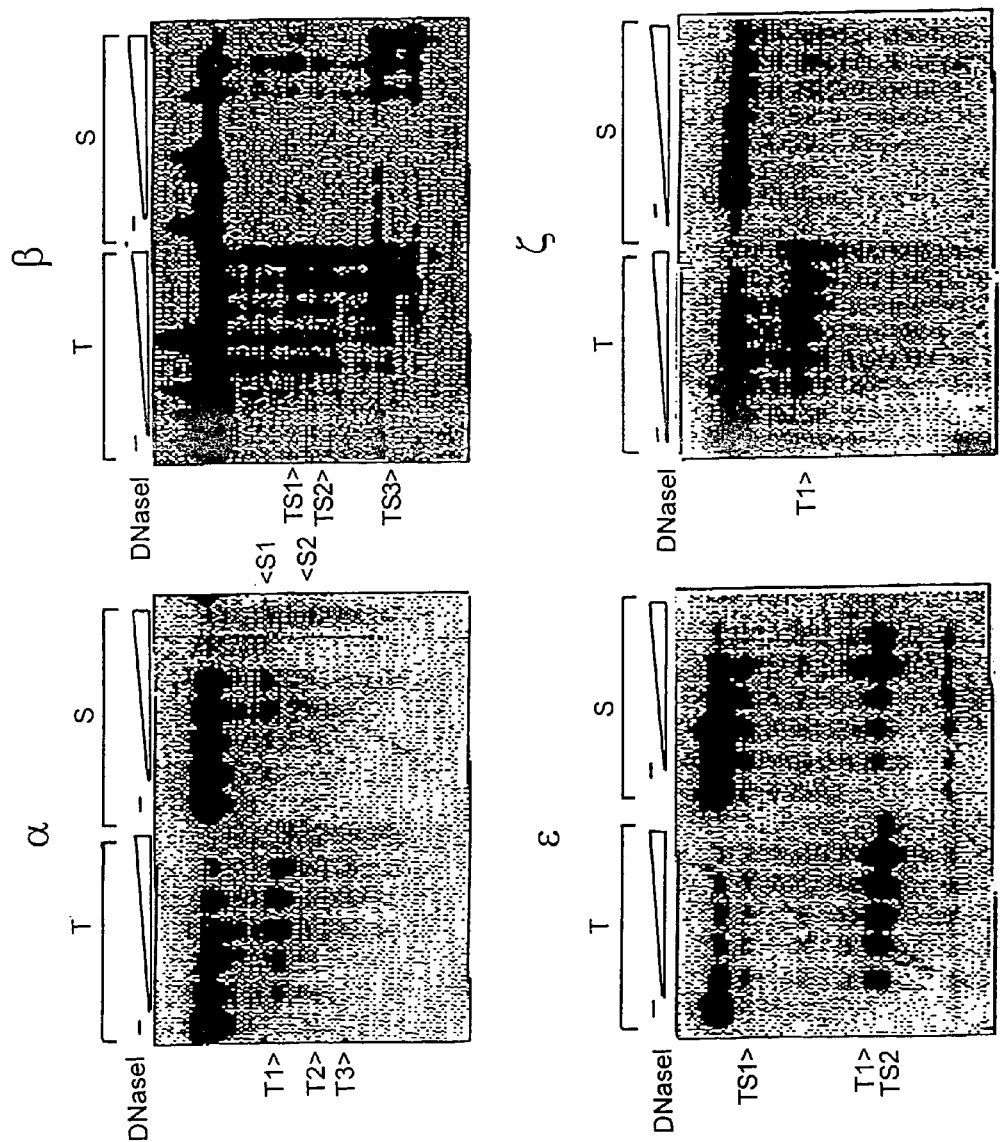

FIG. 27A is a map of the mouse Ikaros gene. Exons are indicated as solid boxes. The R19 and R10 promoters are indicated by open boxes. DNaseI HSS are indicated by arrows, solid black arrows ▲ designate the DNaseI HSS with specificity for the thymus, open arrows ▽ designate the DNaseI HSS with specificity for the spleen and partially solid arrows ▼ designate DNaseI HSS with specificity for both the thymus and spleen. The DNaseI HSS clusters are labeled α, γ, δ, ε, ζ, η and θ. FIGS. 27B and 27C show the results of Southern blot analysis of DNA which was obtained from nuclei of the thymus, spleen and liver that have been digested with increasing amounts of DNaseI, purified and digested with restriction enzymes.

FIG. 28A is a map of the regions of mouse Ikaros which includes the β DNase I HSS cluster (including the R19 promoter), the γ DNaseI HSS cluster (which includes the R10 promoter) and a portion of the ε DNaseI HSS cluster. Solid arrows indicate a DNaseI HSS, open boxes indicate the R19 and the R10 promoters. Exon 1 is indicated by a solid box (Ex1). FIG. 28B depicts various Ikaros regulatory elements which were used for expression of green fluorescent protein (GFP). The open boxes indicate either the R19 or the R10 promoter. The vertical black line indicates an Exon 1 splice acceptor (with a mutate ATG). The solid box indicates the sequence encoding EGFP (the open box at the end indicates a polyA site). The arrows indicate IαxP sites and the thicker line indicates a portion of the ε DNaseI HSS cluster which includes T1 (thymus) and TS2 (thymus and spleen) DNase HSS site.

Figure 29:
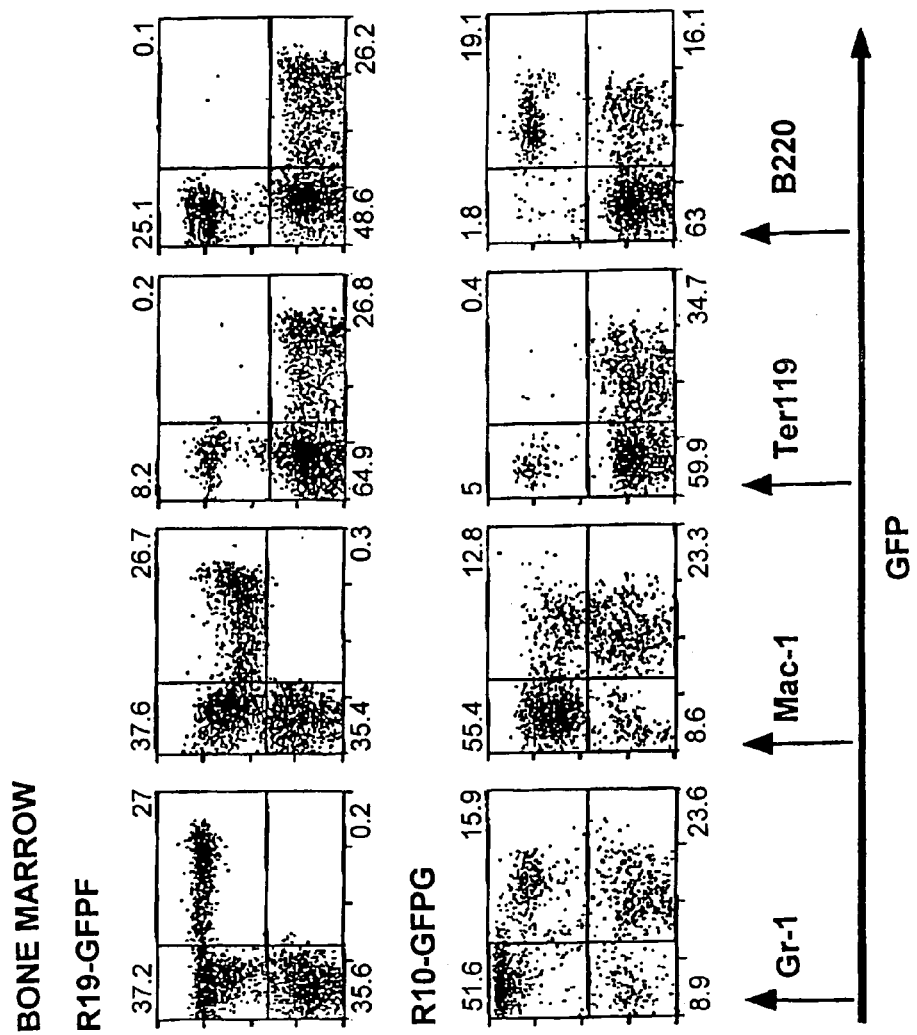

FIG. 29 depicts GFP expression in the bone marrow of transgenic mice in which the sequence encoding GFP is either under control of the R19 promoter (R19-GFP) or the R10 promoter (R10-GFP). The bone marrow was stained with lineage specific promoters (Mac-1+, and Gr-1+ are indicative of neutrophils; B220+ is indicative of B cells).

Figure 30:
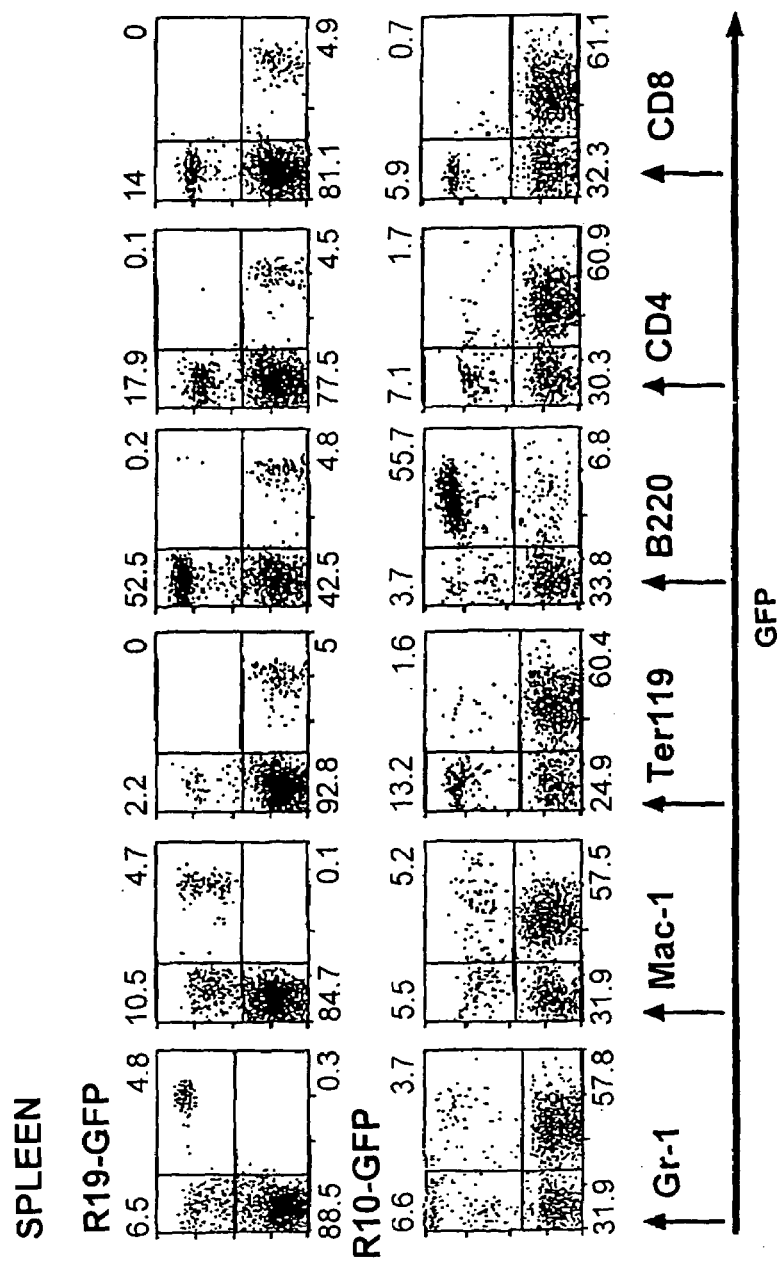
Figures 31A, 31B, 31C:
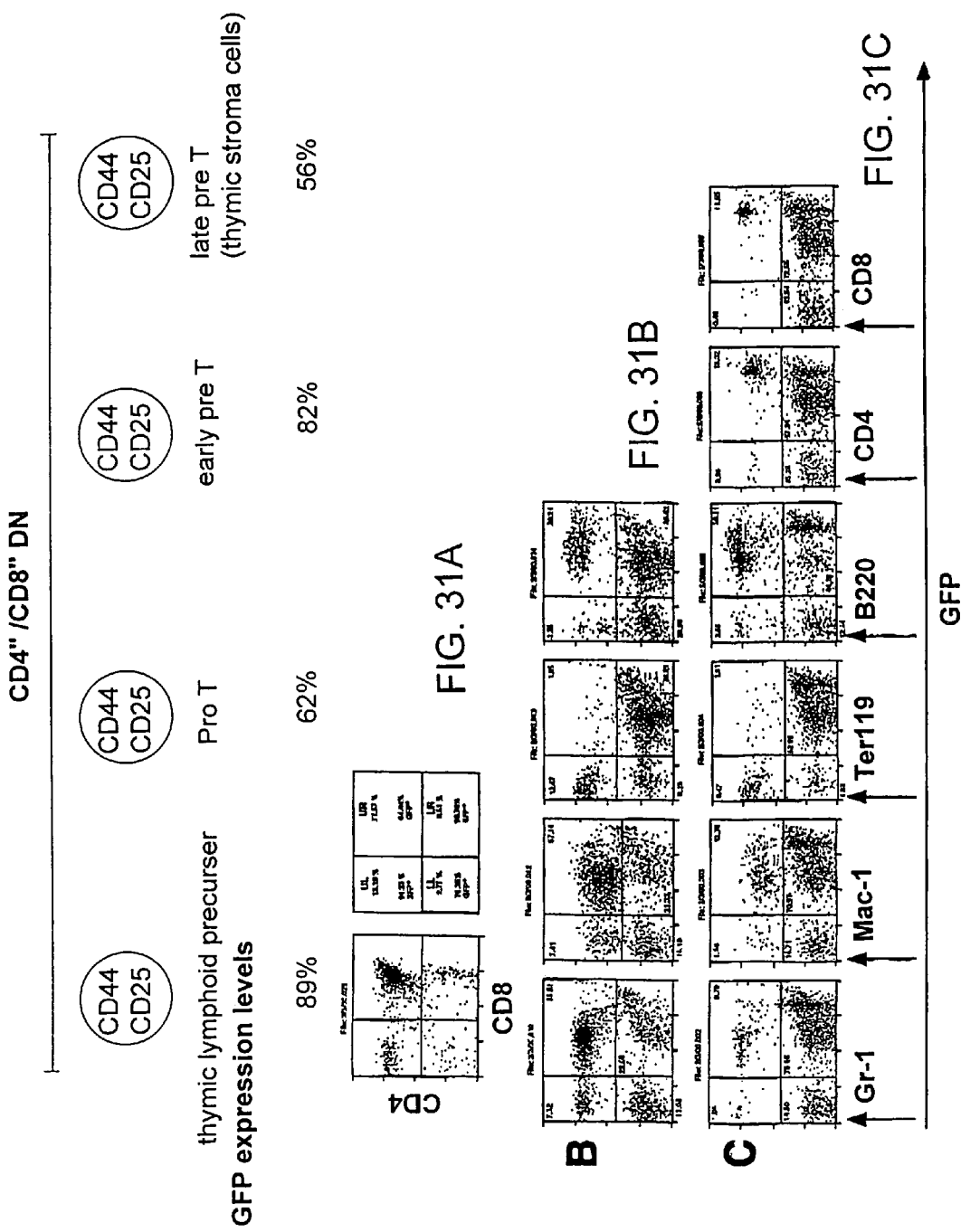

FIG. 30 depicts GFP expression in the spleen of transgenic mice in which the sequence encoding GFP is either under control of the R19 promoter (R19-GFP) or the R10 promoter (R10-GFP). The spleen was stained with lineage specific promoters (Mac-1+, and Gr-1+ are indicative of neutrophils; B220+ is indicative of B cells; CD4, CD8 can be indicative of T cells). FIG. 31A demonstrates the correlation of CD44 and/or CD25 expression and various stages of T cell development. The percentages provide the percentage of each cell type seen when the transgene includes the R10 promoter and a portion of the ε DNaseI HSS cluster. FIGS. 31B and 31C depict GFP expression in the spleen of transgenic mice in which the sequence encoding GFP is either under control of the R10 promoter (R10-GFP) and a portion of the ε DNaseI HSS cluster. The spleen was stained with lineage specific promoters (Mac-1+, and Gr-1+ are indicative of neutrophils; B220+ is indicative of B cells; CD4, CD8 can be indicative of T cells).

DETAILED DESCRIPTION

Detailed Description of Aiolos

Overview

The development of lymphocytes is dependent on the activity of the zinc finger transcription factor Ikaros (Georgopoulos et al. (1992) *Science* 258, 808; Georgopoulos et al. (1994) *Cell* 79, 143; Molnar et al. (1994) *Mol. Cell Biol.* 14, 8292; and Kaham et al. (1994) *Mol. Cell Biol.* 14, 7111). Ikaros mutant phenotypes suggest that this protein acts in concert with another protein with which it dimerizes. The Aiolos gene encodes a transcription factor which is homologous to Ikaros and can form dimers with it. In contrast to Ikaros which is expressed in pluripotent stem cells, Aiolos expression is first detected in committed lymphoid progenitors and increases as T and B cells mature. The expression patterns of Aiolos and Ikaros, the relative transcriptional activity of homo- and heterodimers of these proteins, and the dominant interfering effect of mutant Ikaros isoforms on the Aiolos activity suggest that Aiolos is an important regulator of lymphoid development. Thus, varying levels of Ikaros and Aiolos homodimers as well as heterodimers between these proteins modulate gene expression and regulate progression through the lymphoid lineages.

These examples are described in more detail herein.

Ikaros and Aiolos

The Ikaros gene encodes, by alternate splicing, a family of zinc finger transcription factors which are essential for development of the lymphopoietic system (Georgopoulos et al. (1992) *Science* 258, 808–812; Georgopoulos et al. (1994) *Cell* 79, 143–156; Molnar et al. (1994) *Mol. Cell. Biol.* 14 8292–8303; and Hahm et al. (1994) *Mol. Cell Biol* 14, 7111–7123). Ikaros expression is first detected in pluripotentient hemopoeitic stem cells and expression is maintained through all stages of lymphoid development. Mice homozygous for a deletion of the region encoding the Ikaros DNA binding domain lack committed progenitors as well as mature T and B lymphocytes and natural killer cells. (Georgopoulos et al. (1994) *Cell* 79, 143–156). In addition to this apparent role in the early development of lyphoid progenitors, Ikaros is also required for later events during T cell maturation (Winandy et al. (1995) *Cell* 83, 289–299). Mice heterozygous for this Ikaros mutation generate T cells which proliferate abnormally. They develop lymphoproliferative disorders and ultimately die of T cell leukemias and lymphomas.

The Ikaros protein isoforms all share a common C-terminal domain containing two zinc fingers to which different combinations of N-terminal zinc fingers are appended. The N-terminal zinc fingers are required for sequence specific DNA binding while the C-terminal zinc fingers mediate homo- and heterodimerization among the Ikaros isoforms (Molnar et al. (1994) *Mol. Cell. Biol.* 14 8292–8303. Homo- and heterodimerization or isoforms which contain a DNA-binding domain greatly increases their affinity for DNA and their transcriptional activity. Heterodimers containing one isoform which lacks a DNA binding domain are transcriptionally inert. Hence such isoforms can interfere with the activity of Ikaros isoforms which contain a DNA binding domain in a dominant negative fashion.

The C-terminal domain shared by all of the Ikaros isoforms was targeted by deletion in the mouse germ line. Mice homozygous for this mutation display a phenotype which is less severe than that caused by deletion of the DNA binding domain. The C-terminal Ikaros mutant mice lack most lymphocytes and NK cells but they do develop αβ T cells. The milder phenotype may be due to a low level of activity retained in the proteins generated by the C-terminal Ikaros mutant allele. Alternatively, the C-terminal mutation could be the equivalent of a null for Ikaros activity while the more severe phenotype of the N-terminal deletion mutant may be explained by a dominant interfering effect of the Ikaros isoforms produced by the mutant allele on the activity of some other protein which is also required for commitment to and differentiation of the αβ T lineage. The dominant negative influence of these proteins on other Ikaros isoforms with an intact DNA binding domain has been demonstrated by in vitro and in vivo assays Since the zinc fingers in the Ikaros C-terminal domain display strong homology to the C-terminal zinc fingers of the *Drosophila* suppressor protein Hunchback (Tautz et al. (1987) *Nature* 327, 383) it appears that this domain existed prior to the expansion of the vertebrate genome and may be included in other proteins as well. Such proteins would have the potential to interact with Ikaros proteins when co-expressed and would be candidate targets for the dominant negative activity of the truncated Ikaros isoforms.

Degenerate oligonucleotides were used to amplify the C-terminal zinc finger domain from the mouse genome. Among the genes identified was Aiolos, a homolog of Ikaros whose expression is restricted to lymphoyed lineage. The Aiolos protein showes extensive homology to the largest Ikaros isoform, Ik-1, throughout the DNA binding and C-terminal domains and can form homodimers and heterodimers with the Ikaros proteins. Aiolos homodimers are potent transcriptional activators while heterodimers between Aiolos and different Ikaros isoforms range in activity from slightly less potent to transcriptionally inert. Unlike Ikaros, Aiolos is not expressed in the hematopoietic stem cell compartment. Its expression is first detected at low levels in lymphoyed progenitors and is trongly upregulated at the stage when rearrangement of T and B antigen receptors occurs. Thus, heterodimers of Aiolos and Ikaros are essentisal for the normal maturation of lymphocytes. The profound effects of the Ikaros DNA binding mutation reflect interference with the normal activity of both Aiolos and Ikaros during lymphocyte development.

Cloning of the Aiolos cDNA

In order to identify Ikaros homologs, degenerate primers were constructed to the sequences conserved between mouse Ikaros and *Drosophila* hunchback proteins (PCR primers: Deg 3 TAC/TACCATC/TCACATGGGCTG/ACCA (SEQ ID NO:3) starting at residue 1278 of SEQ ID NO:1 and Deg 4 G/ACCA/GCACATGTTG/ACACTC/TG/AAA (SEQ ID NO:4) starting at residue 1339 of SEQ ID NO:1. PCR was performed on chicken genomic DNA and products of the expected size (61 bp) were purified on a low melt agarose gel and subcloned into PCR2 vector (Invitrogen). Nucleotide sequence demonstrated that these clones fell into three classes. Phage containing the genomic sequence encoding these fragments were isolated from a genomic DNA library and the regions flanking the amplified fragments were sequenced. Analysis of this sequence demonstrated that one class of the clones represented the chicken homologue of Ikaros, while a second class represented the corresponding exon from a highly homologous gene, designated Aiolos (FIG. 2). Aiolos cDNA was isolated from a mouse spleen cDNA library using a probe spanning residues 796–1156 of SEQ ID NO:1. Clones isolated from this library fall into three classes representing alternative RNAs derived from Aiolos gene (FIG. 4). The corresponding genomic region was isolated by hybridization to probes spanning residues 1–650 and 796–1156 of SEQ ID NO:1. The mouse Aiolos cDNA nucleotide and corresponding amino acid sequence is given in FIG. 1.

Isolation of Human Aiolos

Partial human Aiolos cDNAs were isolated by PCR amplification using mouse Aiolos primers Aio C (SEQ ID NO:5) and Aio A (SEQ ID NO:6), which are in mouse Aiolos exons 2 and 7, respectively. The nucleotide sequence of the longest of these cDNAs and the deduced amino acid sequence are presented in FIG. 5 and correspond to SEQ ID NO:7 and SEQ ID NO:8, respectively. The sequence does not include the primers used for the amplification.

Isolation of Aiolos cDNA from Other Species

One of ordinary skill in the art can apply routine methods to obtain Aiolos cDNA from yet other species. The experiments described above outline isolation of Aiolos cDNA from mouse, chicken, and human. The Aiolos cDNA can be isolated from other species, e.g., from bovine, by methods analogous to those described above. For example, the bovine Aiolos cDNA can be isolated by probing a bovine spleen or thymus cDNA or genomic library with a probe homologous to mouse or human Aiolos cDNA described above.

Alternative Splice Forms of Aiolos

PCR was used to determine whether alternative splice forms of Aiolos exist.

Primer combinations AioC/AioA, Aio4F/AioA, and Aio5F/AioA were used to examine the possibility of alternate splicing of the Aiolos mRNA. AioC anneals within exon 3, Aio4F within exon 4, Aio5F within exon 5, and AioA within exon 7. The primer sequences are the following:

```
AioC
GTG TGC GGG TTA TCC TGC ATT AGC    (SEQ ID NO:5)

AioF
GTA ACC TCC TCC GTC ATA TTA AAC    (SEQ ID NO:9)

Aio5F
CGA GCT TTT CTT CAG AAC CCT GAC    (SEQ ID NO:10)

AioA
ATC GAA GCA GTG CCG CTT CTC ACC    (SEQ ID NO:6)
```

Isoforms lacking exon 6 have been identified to date at a low abundance.

Functional Domains are Conserved Between Aiolos and Ikaros Proteins

Aiolos cDNA contains an open reading frame of 1521 nucleotides encoding a 58 KD protein with 70% similarity to Ikaros (FIG. 6).

The general structure of Aiolos and Ikaros proteins is very similar, and four blocks of sequence are particularly well conserved. The first block of conservation encodes the zinc finger modules contained in the Ik-1 isoform which mediate DNA binding of the Ikaros protein (Molnar et al. (1994) Mol. Cell. Biol. 14 8292–8303). The second block of conservation has not been characterized functionally. The third block of conservation is a domain required for transcriptional activation by Ikaros (this domain is boxed in FIG. 6). The fouth block of conservation corresponds to the zinc fingers which mediate dimerization.

Antibodies generated against two Aiolos peptides (amino acids 1–124 and amino acids 275–448) indicate that Aiolos polypeptide is approximately the same size as Ik-1 protein, i.e., approximately 57 kDa in size.

The structure and function of the Aiolos zinc finger domains are homologous with the zinc finger domains of Ikaros. Aiolos has four C terminal domains which mediate the binding of Aiolos to DNA and two C terminal regions which mediate the formation of Aiolos dimers.

Two Highly Conserved C-Terminal Zn Finger Motifs Mediate Interactions Between Aiolos and Ikaros Proteins The ability of the Aiolos zinc finger domain to engage in protein interactions was tested in a yeast two hybrid assay (Zervos et al. (1993) Cell 72, 223; and Gyuris et al. (1993) Cell 75, 1).

Segments of 500 nucleotides of the Aiolos or Ikaros cDNAs encoding the C-terminal 149 and 154 amino acids of these proteins, respectively, were inserted in the bait vector pLex202 to created in frame fusions with the LexA DNA binding domain (Ik-500 and Aio-500, repectively). The B42 transcriptional activation domain in the pGJ prey vector was fused in frame to the full length Ikaros and Aiolos proteins as well as the following fragments of the cDNAs: the first five coding exons of Ik-1(Ik-N); the 500 nucleotides segments used to construct the bait constructs (Aio-500 and Ik-500); the entire coding sequence of the C-terminal exon of Aiolos (Aio-800) encoding a 232 amino acid long sequence; the full length Ikaros protein with point mutations in either the penultimate (M1) or ultimate (M2) zinc fingers, or both (M1+M2). Combinations of Aiolos and Ikaros bait and prey vectors were transformed into the EGY48 yeast strain. EGY48 (MATa trp1 ura3 his3 LEU2:pLexAop6-LEU2) has a Leu2 gene as well as the pJK103 plasmid harboring the lacZ gene under the control of two high affinity ColE1 LexA operators maintained under Ura3 selection. Growth of yeast cells on Ura⁻His⁻Trp⁻Leu⁻-galactose plates and color development on Ura⁻His⁻Trp⁻-X-gal-galactose plates were used to score Aiolos and Ikaros protein interactions. Interactions between Aiolos and Ikaros baits and preys in the yeast two hybrid system result in the transcription of β-galactosidase and the production of blue colonies on X-gal indicator plates. Strong interactions between prey and bait recombinant proteins result in expression of both the Leu-2 and β-glactosidase genes.

The results are presented in Table 4. The rate at which transformed yeast colonies turn blue on indicator plates suggests that the affinities of Aiolos for itself and for Ikaros protein are similar (+++). White colonies indicate a lack of interaction (−). A domain in the Aiolos protein that contains the last two Krüppel-like zinc fingers (Aio-500) interacts with itself either as an isolated domain (Aio-500, Aio-800) or in the context of the full length protein (Aiolos). Similar interactions were observed with the analogous Ikaros domain (Ik-500), either alone or in the context of the full length protein (Ikaros). Mutations in the Ikaros zinc finger motifs (M1, M2 and M1+M2) which abrogate Ikaros dimerization also abrogated Aiolos-Ikaros protein interactions. In contrast to the C-terminal fingers, the N-terminal finger motifs (Ik-N) were not capable of mediating such protein interactions. PJG is the prey vector used as a negative control. In a similar fashion, the equivalent Ikaros bait (154 aminoacids in size), Ik-500, interacted with recombinant prey proteins that contained either the C-terminal domain of Aiolos or Ikaros or the full length proteins. Ik-500 was, similarly to Aio-500, unable to interact with the interaction incompetent Ikaros mutants. In this assay, the affinities of Aiolos for itself or Ikaros were similar and indistinguishable to that of Ikaros for itself.

TABLE 4

| PREY | BAIT | |
|---|---|---|
| | Aiolos-500 | Ikaros-500 |
| Aiolos | +++ | +++ |
| Aio-500 | +++ | +++ |
| Aio-800 | +++ | +++ |
| Ikaros | +++ | +++ |
| Ik-500 | +++ | +++ |
| Ik-N | − | − |
| Ikaros M1 | − | − |
| Ikaros M2 | − | − |
| Ikaros M1 + M2 | − | − |
| PJG | − | − |

Thus, this example shows that the C-terminal zinc fingers of Aiolos and Ikaros mediate protein dimerizations and that Aiolos and Ikaros can homodimerize and heterodimerize.

Aiolos and Ikaros Heterodimerize In Vivo

Heterodimers of Aiolos and Ikaros proteins were observed in transfected mammmalian cells. Heterodimerization was shown by coimmunoprecipitations of the two proteins and by showing that both proteins localize to the same region in a cell.

Interactions between Aiolos and Ikaros proteins were confirmed by coimmunoprecipitations. Aiolos-(Flag) protein (10) and Ikaros protein (Ik-1), or a mutant Ikaros protein having point mutations in the zinc finger domain which prevents Ikaros homodimerization (IkM) were expressed in the epithelial cell line 293T and immunoprecipitated using an antibody to the Flag epitope (6, Eastman Kodak). Immunoprecipitates were run on a 10% SDS gel and analyzed by Western blotting with an Ikaros antibody. No Ikaros was observed in immunoprecipitates from untransfected controls. To confirm the levels of Ikaros and Aiolos protein produced in the transfected cells, Westerns on total protein were performed with the Ikaros and Flag antibodies. Similar amounts of Ik-1 or IkM and Aiolos proteins were produced in the transfected cell populations.

The results indicate that Ikaros protein coprecipitates with Aiolos upon immunoprecipitation of Aiolos-(FLAG) with an antibody to the tagged Aiolos protein. However, the dimerization mutant IkM was not coprecipitated with Aiolos-(FLAG). Thus, these results indicate that Aiolos and Ikaros heterodimerize in vivo.

Aiolos and Ikaros also co-localize in the nucleus of cells. Subcellular localization of Aiolos protein was determined upon its expression in NIH-3T3 fibroblasts. NIH-3T3 fibroblasts were transfected with one or more of expression vectors encoding Aiolos-(FLAG), Ikaros Ik-1 or Ik-6. The Ik-6 isoform of Ikaros lacks a DNA binding domain and is normally found in the cytoplasm. The FLAG epitope was detected with a the same anti-FLAG monoclonal antibody described above and a secondary goat anti-mouse IgG antibody conjugated to rhodamine (Boehringer Mannheim). NIH-3T3 fibroblasts transfected with Aiolos and Ikaros expression vectors were stained with anti-FLAG and rhodamine conjugated goat anti-mouse and with anti-Ikaros and goat anti-rabbit IgG FITC sequentially. No crossreactivity between preadsorbed secondary antibodies was detected. Cells were counterstained with hoechst 33258 for one hour in PBS at 1 μg/ml.

The results show that the Aiolos protein, tagged with the FLAG epitope (Hopp et al. (1988) Biotech 6, 1204–1210) is found in the nucleus when expressed in fibroblast cells. Immunofluorescence staining for either Aiolos or Ikaros proteins revealed a punctuate pattern of staining similar to that observed with polycomb proteins, some splicing factors, and the GATA proteins (Messmer et al. (1992) Genes & Dev 6, 1241–1254; Colwill et al (1996) EMBO J 15, 65–275; and Elefanty et al. (1996) EMBO J 15, 319–333). When Aiolos is coexpressed with an Ikaros isoform that is localized in the nucleus, e.g., Ik-1, both proteins are detected within the same region of the nucleus. In fact, the red and green signals of the labels generate a yellow signal, confirming the co-localization of these proteins. Interestingly, when Aiolos is coexpressed with an Ikaros isoform that is localized in the cytoplasm, e.g., Ik-6, both proteins co-localize to the nucleus.

Conserved Function of the N-Terminal Zinc Finger DNA Binding Domain in Aiolos and Ikaros Proteins Contacts between DNA and the alpha helical region in the C-terminal half of Kruppel-like zinc fingers are important in determining the sequence specificity of these interactions (Lee et al. (1989) Science 245, 635 and Pavletich et al. (1993) Science 261: 1701). The regions that bind DNA are perfectly conserved between Aiolos and Ikaros (FIG. 6). This example demonstrates that both proteins are capable of binding the same DNA sequences.

DNA binding assays (EMSA) were performed essentially as described in Molnar et al. (1994) Mol. Cell. Biol. 14, 8292–8303. GST-Aiolos and Ikaros fusion proteins and their GST fusion partner (0.5 μg) were tested for binding to the IkBD1-TCAGCTTTTGGGAATACCCTGTCA (SEQ ID NO:11) oligonucleotide which contains a high affinity Ikaros binding site (100,000 cpm/reaction which equals 1 to 2 ngs of DNA). Competition assays were performed with Ik-BS 1 and with Ik-BS8 TCAGCTTTTGGGggTACCCTGTCA (SEQ ID NO:12) oligonucleotides used at 5–100× molar excess.

The results of these binding assys show that high affinity complexes are formed between an Aiolos-GST fusion protein and an oligonucleotide containing a binding site for the Ik-1 protein. Hence Aiolos and Ikaros can, in principle, compete for similar binding sites in the genome.

Aiolos is a More Potent Transcriptional Activator than Ikaros

Ikaros and Aiolos share a highly conserved 81 amino acid sequence which has been shown to mediate transcriptional activity of the Ikaros proteins. This activation domain of Ikaros is composed of a stretch of acidic amino acids followed by a stretch of hydrophobic residues, both of which are required for its full activation potential. This domain from Ikaros alone or the full length Ikaros protein confers transcriptional activity of a fusion protein with the LexA DNA binding domain. This example shows that the homologous domain in Aiolos is also a transcriptional activation domain in yeast and mammalian cells and that the Aiolos transcriptional activation domain provides stronger transcriptional activity than the homologous domain from Ikaros in mammalian cells.

The C-terminal domains of Aiolos and Ikaros were tested for their ability to activate transcription in yeast. For this example, expression constructs encoding the 232 and 149 C-terminal amino acids of Aiolos and fused to the LexA DNA binding domain were prepared, and termed Aio-800 and Aio-500, respectively. Expression constructs encoding the 232 and 154 most C-terminal residues of Ikaros fused to the LexA DNA binding domain were also prepared, and termed Ik-800 and Ik-500, respectively. These expression constructs were transformed into the EGY48 yeast strain. EGY48 (MATa trp1 ura3 his3 LEU2:pLexAop6-LEU2) has a Leu2 gene as well as the pJK103 plasmid harboring the lacZ gene under the control of two high affinity ColE1 LexA operators maintained under Ura3 selection. The recombinant proteins were tested for their ability to activate the Leu 2 gene and the lacZ genes using Ura⁻His⁻Leu⁻-glucose and Ura⁻His⁻Leu⁻-X-gal-glucose selections, respectively.

The results show that the 232 C-terminal amino acids of Aiolos fused to the LexA DNA binding domain activated strong expression of both the Leu-2 and β-galactosidase genes in the yeast one hybrid system. No activity was detected with the 149 most C-terminal amino acids of Aiolos, which do not contain the conserved domain, in either assay. Thus, the protein domain in Aiolos, which is closely related in amino acid sequence to the transcriptional activation domain of Ikaros, is also capable of conferring transcriptional activation in yeast cells.

Although Aiolos and Ikaros display similar activities in yeast, Aiolos is a stronger activator in mammalian cells. In this example, Aiolos and the Ikaros isoforms Ik-1 and Ik-6 were co-transfected at different ratios together with the Ikaros-tkCAT reporter gene in NIH-3T3 cells as follows.

The ability of Aiolos homo- and Aiolos-Ikaros heterodimers to stimulate CAT activity from the Ikaros reporter plasmid 4×IK-BS1-tkCAT was determined in transient expression assays in NIH-3T3 fibroblast cells. NIH-3T3 cells in 100 mm dish were co-transfected with the reporter plasmid 4×Ik-BS 1tkCAT, containing 4 copies of a single high affinity Ikaros binding site or tkCAT (4 μgs), with Aiolos and or Ikaros recombinant CDM8 expression vectors (5–15 μgs) and with the pxGH5 (4 μgs), a plasmid encoding the growth hormone which is used as an internal control of transfection. CDM8 was used to supplement amounts of expression vector DNA to 20 μgs. Each transfection point was performed in triplicate or quadriplicate. 48 hours after transfection CAT and growth hormone (GH) assays were performed on cell lysates and supernatants respectively. Transfection efficiencies were normalized by growth hormone levels. Part of the cell pellet was lysed in protein sample buffer and used for Western analysis to determine Aiolos and Ikaros protein expression in transfected fibroblasts. The amount of protein was determined using Ikaros and Flag antibodies. The activities of Aiolos with or without the Flag epitope were indistinguishable in this assay. Co-transfections of the reporter plasmids with CDM8 vector alone were performed to establish the base level for CAT activity. Up to 5% variability was detected between transfections performed in triplicate.

Figure 7:
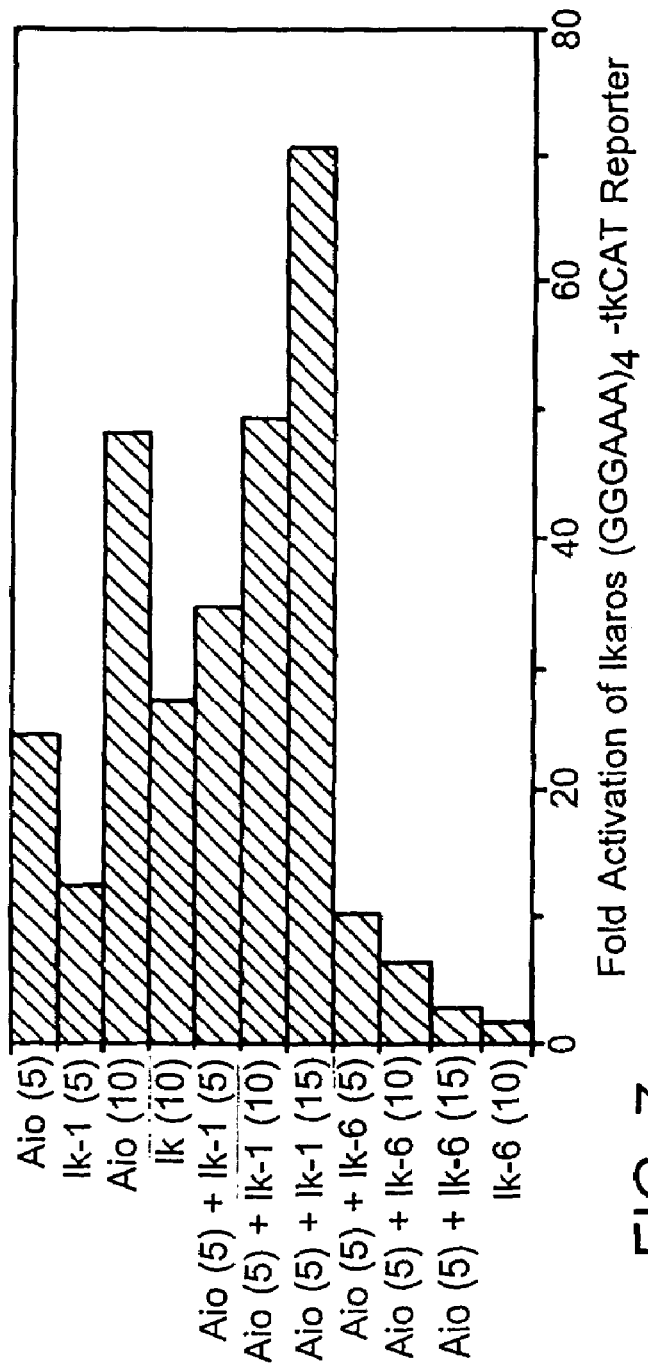
FIG. 7 is a bar graph depicting the effect of different isoforms on the transcriptional activation of Ikaros.

The results are presented in FIG. 7. Aiolos and Ikaros proteins were expressed at similar levels, but the levels of CAT activity elicited by Aiolos were higher than those observed with Ik-1, the most potent activator of the Ikaros isoforms. In fact, Aiolos stimulated CAT activity by 25–50 fold, whereas Ik-1 elicited a 12–25 fold increase in expression in this assay. Co-expression of Ika and Aiolos proteins stimulated expression of the reporter gene to levels intermediate between those seen with Aiolos or Ikaros homodimers (e.g., compare Aiolos [10] versus Aiolos[5]+ Ik-1[5] versus Ik-1 [10]).

Ikaros isoforms which lack a DNA binding domain interfere with the transcriptional activity of Aiolos proteins when both are expressed in the same cell (FIG. 7, Aio+Ik-6). Similar results were obtained when Ikaros isoforms with and without a DNA binding domain were co-expressed. Heterodimers of the interfering Ikaros isoforms with other Ikaros proteins do not bind DNA. The dramatic decrease in Aiolos activity is most probably due to the formation of Aiolos-Ikaros heterodimers that do not bind DNA and therefore cannot activate transcription. Transfection with equimolar amounts of Aiolos and the Ik-6 isoform leads to the 65% reduction in CAT activity expected if Aiolos/Ik-6 heterodimers are transcriptionally inert. Addition of higher levels of Ik-6 further reduces transcription of the reporter gene. This effect is specific for the interfering isoform since addition of similar amounts of activating isoforms leads to a linear increase in transcriptional activity (FIG. 7, Aio(5)+ Ik-1 (5)-(15)).

Therefore, Aiolos homodimers can compete with Ikaros homodimers for binding sites and can stimulate transcription to higher levels. The difference in activity of the two proteins can be accounted for by additional protein interactions that take place with a domain of the Ikaros proteins which is not conserved in Aiolos. Such protein interactions may specifically modulate the activity of Ikaros in mammalian cells during development without affecting Aiolos directly.

Aiolos Expression is Restricted to the Lymphoid System

This example shows that in the adult mouse, Aiolos transcripts are detected exclusively in lymphoid tissues.

Total RNAs (10–20 μgs) from thymus, spleen, bone marrow, brain, heart, kidney and liver of wild type mice and from bone marrow of mice homozygous for a mutation in the Ikaros DNA binding domain were used for Northern analysis. RNA purification and Northern analysis were performed as previously described (Georgopoulos et al. (1992) *Science* 258, 808–812). A 330 bp fragment derived from the last translated exon of Aiolos which does not cross-react with Ikaros sequences was used as a probe to detect Aiolos transcripts of 4.5 and 9 kb.

The results of the Northern blot hybridizations indicate that Aiolos expression levels are highest in the spleen, progressively lower in the thymus and bone marrow, and are undetectable in non-lymphoid tissues such as brain, heart, kidney or liver of a wild type mouse. The spleen is largely populated by mature B and T lymphocytes, while the majority of cells in the thymus are immature CD4+/CD8+ thymocytes which are in the process of rearranging their T antigen receptors. In the bone marrow, approximately 25% of the cells are pre-B cells at a stage of differentiation comparable to that of double positive thymocytes while the rest are predominantly erythroid and myeloid precursors (Hardy et al. (1991) *J. Exp. Med.* 173, 1213–1225). Aiolos mRNAs were not detected in the bone marrow of Ikaros mutant mice which is largely comprised of erythroid and myeloid cells and lacks detectable numbers of committed lymphoid precursors. These observations indicate that Aiolos is expressed in committed precursors of the B and T lineage and is upregulated upon their terminal differentiation.

Further information on Aiolos expression was obtained through in situ hybridization. Sections were prepared from E-12 to E-16 embryos as previously described (Georgopoulos et al. (1992) *Science* 258, 808–812). These were incubated with Ikaros or Aiolos specific $^{32}$P-UTP RNA sense and antisense probes at 51° C. for 12–16 hours. The Ikaros probe was 300 bp in size generated from the 3' untranslated region of its last exon. The Aiolos probe was generated from the first 330 bp of its last translated exon which show little homology to Ikaros sequences. Slides were washed with 0.5×SSC/0.1% SDS at 55° C. and at 65° C., dehydrated and dipped in diluted photographic emulsion (NBT2). Dipped slides were exposed for 4 weeks, developed, stained with hematoxylin and eosin and analyzed by bright and dark field illumination on an Olympus microscope.

In situ hybridization to embryo sections indicated that Ikaros is expressed at the earliest stages of hemopoiesis, prior to the development of committed lymphoid precursors (Georgopoulos et al. (1992) *Science* 258, 808). It is found in the hemopoietic fetal liver at day 9.5 of gestation and in the thymus from the onset of its development. In contrast, Aiolos is not detected in the nervous system, hemopoietic liver and appears in the thymus only during the later stages of its development. This indicates that Aiolos is not expressed in hemopoietic stem cells, erythroid precursors, or in the lymphoid progenitors of epidermal γδ T cells which predominate in the early thymus (Harvan et al. (1988) *Nature* 335, 443; Havran et al. (1990) *Nature* 344, 344; and Raulet et al. (1991) *Immunol Rev.* 120, 185). Expression in the late gestation thymus implies that Aiolos is found in double positive cells which are committed to the αβ T cell lineage and are in the process of rearranging their T antigen receptor genes.

To further characterize the relative expression of Ikaros and Aiolos during lymphocyte ontogeny, RNA from sorted lymphoid populations of wild type and mutant mice were analyzed by RT-PCR. cDNAs were prepared from FACS sorted populations isolated from the thymus, spleen, and bone marrow of wild type and mutant mice. cDNA yields wre normalized to GAPDH concentrations using GAPDH primers. Aiolos and Ikaros cDNAs were amplified with gene specific primers derived from exons 3 and 7 and from exons 2 and 7, respectively, for 28 cycles. The Aiolos primers generate a single band and the Ikaros primers generate multiple bands corresponding to the alternatively spliced products of the Ikaros transcript (Georgopoulos et al. (1994) *Cell* 79, 143; and Molnar et al. (1994) *Mol. Cell Biol* 14, 8292). Purification of the cells and RT PCR were performed essentially as set forth below.

Separation of purified cell populations were performed as follows. B220+ (pro-B, preB/B and B) and B220− (T) populations were obtained from bone marrow and spleen of wild type C57BL/6 or RAG-1 −/− mice by magnetic cells sorting (Hardy et al. (1991) *J. Exp. Med.* 173, 1213–1225). First, lymphocytes were enriched by centifugation of total bone marrow or spleen cells through a layer of Lymphocyte®-M (Cedarlane Laboratories, Hornby, Canada). The enriched lymphocytes were washed twice with cold PBS/BSA (PBS supplemented with 1% BSA, 5 mM EDTA and 0.01% sodium azide.), resuspended at a concentration of $10^7$ cells/ml in PBS/BSA, and incubated at 6°–12° C. for 15 minutes with anti-B220 MicroBeads (MACS). To monitor the purity of the the positively-selected cells and the flowthrough, fluorescein isothiocyanate (FITC) conjugated rat anti-B220 antibody was added and incubated for a further five minutes. B220+ cells were separated using a MACS magnetic separation column (Miltenyi Biotec GmbH). FACS analysis of the resulting B220+ and B220− populations determined that these were 85–95% pure. Double positive and single positive thymic-cell populations were obtained by flow cytometry of cells from thymuses of wild type C57BL/6 mice. Thymic cells were incubated 30 minutes on ice with phycoerythrin (PE)-conjugated anti-CD4 and FITC-conjugated anti-CD8 antibodies (Pharmingen), after which they were washed and separated, using a Coulter sorter, into a single positive population, which included both CD4+CD8− and CD4−CD8+ cells, and CD4+CD8+double positive population. The single positive population was then further sorted into CD4+CD8− and CD4−CD8+ populations.

Bone marrow cell suspensions were prepared from 8 to 12 week old C57BL/6J mice by gentle crushing of whole femurs and tibias in a ceramic mortar using PBS containing 2% heat inactivated fetal bovine serum (PBS/2% FBS). Cells were layered over Nycodenz with a density of 1.077 g/ml (Nycomed, Oslo, Norway) and centrifuged 30 minutes at 1000×g. The band of low density cells at the interface was removed, washed once in PBS/2% PBS, and resuspended in a cocktail of purified rat antibodies recgnizing the lineage-specific antigens CD11b/MAC-1, CD45R/B220, Ly6G/Gr-1, CD4, CD8, and Ter119 (Pharmingen, San Diego, Calif.). After a 30 minute incubation on ice, the antibody-coated cells were removed by two rounds of immunomagnetic bead depletion on a Vario MACS BS column (Miltenyi Biotec, Sunnyvale, Calif.) using a 23G needle to restrict flow. The lineage-negative cells were then stained with FITC-conjugated D7 (anti-Sca-1) and PE-conjugated anti-c-kit (Pharmingen) for 30 minutes on ice, followed by one wash in PBS/2% FBS containing 2 μg/ml propidium iodide (PI). Viable (PI-negative) cells were sorted on a FACStarPlus (Becton-Dickinson, San Jose, Calif.). Total RNA was prepared by homogenizing the samples (350 μl maximum) using QIAshredder columns and RNeasy spin columns (Qiagen). Samples of $5 \times 10^4$ cells were processed and the RNA was eluted in DEPC-treated water in a final volume of 30 μl. Two-color analysis of Sca-1 and c-kit revealed staining profiles identical to that reported by Okada et al., 1992. Based on these studies, Sca-1+c-kit (primitive repopulating stem cells) and Sca-1−c-kit+ (myeloid-committed progenitors) were sorted. Lineage negative cells were also stained with anti-Sca-1-FITC, anti-c-kit-PE and anti Sca-2-Red 613 and sorted into $Sca-1^+/Sca2^{-/lo}$, $Sca-1^+/Sca-2^{dull}$ and $Sca-1^+/Sca-2^{bright}$.

RT-PCR was peformed as follows. Up to 5 μg of RNA were reverse transcribed in a total volume of 25 μl, which included 1× first strand buffer (Gibeo-BRL), 4 mM DTT, 150 ng random hexamer primers, 0.4 mM of each deoxynucleotide triphosphate, 1U Prime RNase inhibitor (5'->3', Inc.) and 200 U Superscript II reverse transcriptase (Gibco-BRL). RNA and primers, in a total volume of 12 μl, were heated to 65° C. for 10 mins before adding buffer, deoxynucleotides, DTT, RNase inhibitor, and reverse transcriptase. The reactions were incubated at 37° C. for 45 minutes, follwed by an incubation at 42° C. for 45 minutes. Finally, 1 U RNase H (Gibco-BRL) was added, followed by an incubation at 37° C. for 30 minutes. cDNAs were prepared from CD4+/CD8+ and CD4+, CD8+ sorted thymocytes, Rag-1 −/− thymocytes, B220+ cells from wild type bone marrow, B220+ cells from Rag-1−/− bone marrow, B220+ and B220− cells isolated from wild type spleen, Rag-1 −/− spleen, Ikaros −/− bone marrow and spleen and from Sca1−/ckit+ and Sca1+/ckit+stem cells populations. cDNA from each reaction was used directly for radiolabeled PCR. Reactions included up to 4 μl of cDNA, 1×PCR reaction buffer (Boehringer-Mannheim), 0.1 μg BSA, 100 ng each of 5' and 3' primers, 0.2 mM of deach deoxynucleotide triphosphate, and 5 μCi each of $[\alpha\text{-}^{32}P]dATP$ and dCTP (3000 Ci/mmol) in a total volume of 50 μl. Primers specific for Ikaros, Ex2F and Ex7R have been previously described (Georgopoulos et al. (1994) *Cell* 79, 143–156). Primers specific for Aiolos were:

```
AioA:
ATCGAAGCAGTGCCGCTTCTCACC;      (SEQ ID NO:6)
and

AioC:
GTGTGCGGGTTATCCTGCATTAGC.      (SEQ ID NO:5)
```

Primers specific for GAPDH were:

```
GAPDHF:
ATGGTGAAGGTCGGTGTGAACGGATTTGGC;   (SEQ ID NO:13)
and

GAPDHR:
GCATCGAAGGTGGAAGAGTGGGAGTTGCTG.   (SEQ ID NO:14)
```

Amplification parameters consisted of 95° C. for 5 minutes, 60° C. for 5 minutes, at which point Taq polymerase (Boehringer-Mannheim) was added to each sample, followed by 27 cycles of 95° C. for 15 seconds, 60° C. for 20 seconds, and 72° C. for 30 seconds. PCR products were visualized by electrophoresis through an 8% polyacrylamide—1×TBE gel, followed by autoradiography of the dried gels.

The results indicate that Ikaros transcripts are readily detectable in the pluripotent stem cell population that can give rise to both lymphoid and myeloid/erythroid lineages (Sca-1$^+$/c-kit$^+$(Van de Rijn et al. (1989) *Proc. Natl. Acad. Sci. USA* 86, 4634; and Okada et al. (1992) *Blood* 80, 3044). Ikaros transcripts were also found to be expressed at high levels in the more committed hemopoietic precursors (Sca-1$^-$/c-kit$^+$, mainly myeloid and erythroid precursors (Van de Rijn et al. (1989) *Proc. Natl. Acad. Sci. USA* 86, 4634; and Okada et al. (1992) *Blood* 80, 3044). In contrast, Aiolos expression was not readily detected in either of these heterogeneous populations. Low amounts of Aiolos were detected by prolonged exposure of the RT-PCR reactions in the multipotent progenitor population which is enriched for cells whose potential is restricted to the lymphoid lineages (Sca-1$^+$/c-kit$^+$/Sca-2$^+$/lin$^{-/lo}$(15)). Similar exposures failed to detect Aiolos in the pluripotent stem cell population. Low levels of Aiolos were also detected in the bone marrow of Ikaros mutant mice. These mice lack definitive lymphocyte precursors as well as more mature lymphoid cells, but the bone marrow may contain the most primitive lymphoid progenitors arrested in their differentiation. No expression of Aiolos was detected in the spleen of these mice upon prolonged exposure. Thus, in contrast to Ikaros, which is present in significant amounts from the early pluripotent stem cell stage, Aiolos is expressed only in cells which are committed to the lymphoid lineage.

Committed T cell progenitors progress from a double negative precursor through a double positive stage to the single positive thymocytes (Pearse et al. (1989) *Proc. Natl. Acad. Sci. USA* 86, 1614; and Godfrey et al. (1993) *Immunol Today* 14, 547). The double negative precursor thymocytes are rare in wild type mice. In Rag-1 deficient mice, which lack a component of the recombinase complex required for lymphocyte maturation, early B and T cell precursors are arrested in development and accumulate in the bone marrow and thymus respectively (Mobaerts, et al. (1992) *Cell* 68, 869; and Shinkai et al. (1992) *Cell* 68 855). Aiolos was barely detected in double negative pre-thymocytes isolated from the Rag-1 mutant thymus but moderate levels of Ikaros were expressed. However, Aiolos mRNA was readily detectable in immature double positive thymocytes and in the CD4 and CD8 single positive thymocytes derived from them.

In the B lineage, a similar pattern of Aiolos expression was observed. The pro-B cells isolated from Rag-1 deficient mice expressed Ikaros but very low amounts of Aiolos. Pre-B and B cells from wild type bone marrow expressed high levels of both Ikaros and Aiolos. Among cells sorted from the spleen, Aiolos was expressed at higher levels in B cells than in T cells, while Ikaros displayed the opposite pattern. Therefore, although Ikaros predominates during the early stages of T and B cell maturation, expression of Aiolos increases significantly during the intermediate stages of the T and B lineage and and comes to exceed that of Ikaros in mature B cells.

It is believed that natural killer (NK) cells are of lymphoid origin and share a common precursor with T lymphocytes (Hackett et al. (1986) *J Immunol* 136, 3124; and Rodenwald et al. (1992) *Cell* 69, 139). Expression of Ikaros and Aiolos was examined in the spleen of Rag-1 deficient mice which is enriched for NK cells (Mobaerts, et al. (1992) *Cell* 68, 869; Shinkai et al. (1992) *Cell* 68, 855; Hackett et al. (1986) *J Immunol.* 136, 3124; and Rodenwald et al. (1992) *Cell* 69, 139). Although Ikaros was abundantly expressed in Rag mutant splenocytes, significantly lower amounts of Aiolos were detected. In Ikaros mutant mice the spleen is populated by the non-lymphoid branch of the hemopoietic lineage (Georgepoulos et al. (1994) *Cell* 79, 143). Aiolos expression was not detected among these myeloid and erythroid cells.

Figure 8:
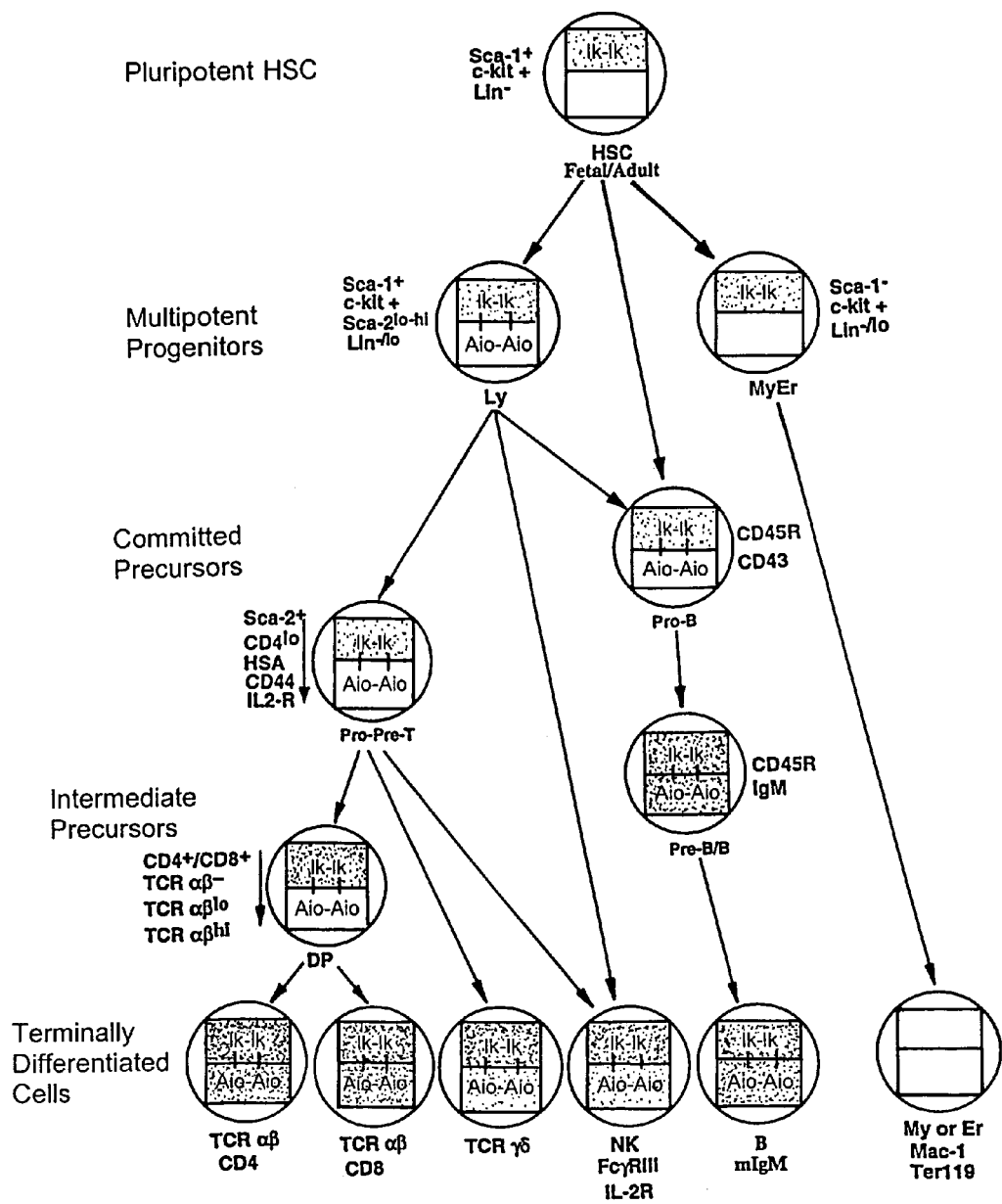
FIG. 8 is a schematic diagram depicting a model for the role of Aiolos and Ikaros in the progression of the lymphoyed lineage.
Figure 9:
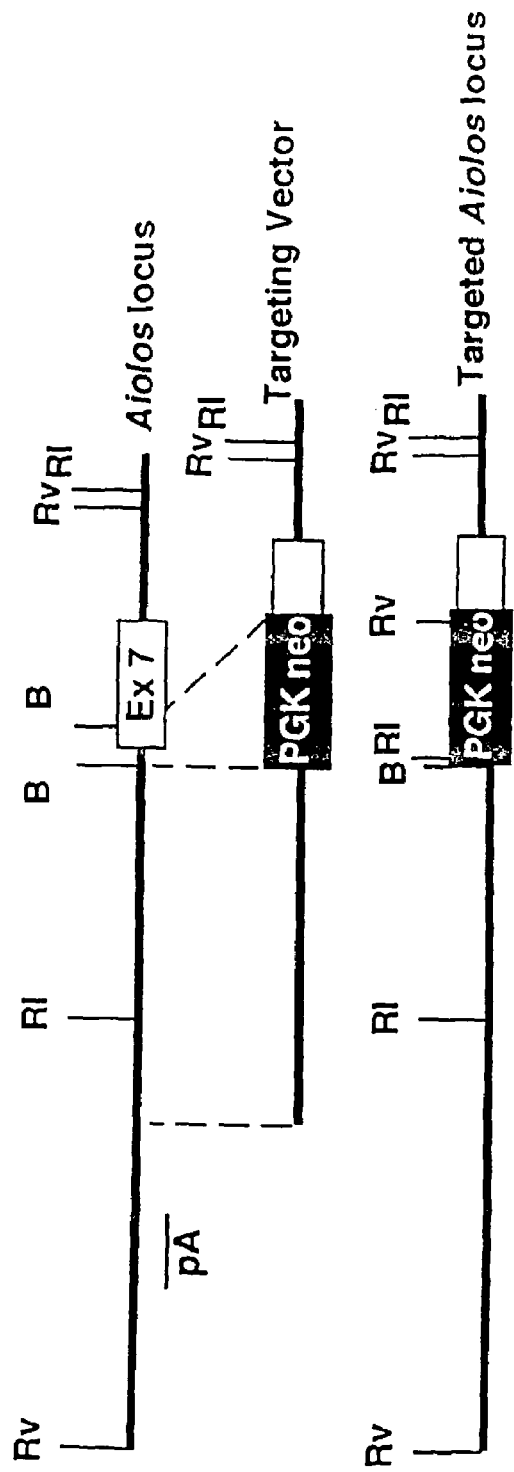
FIG. 9 is a depiction of the recombination strategy for targeting a replacement of a 0.35 kB genomic fragment encompassing the 5' coding region of exon-7 with the pgk-neo gene.

Role of Aiolos and Ikaros Homo- and Hetero-Dimers in Lineage Commitment and Differentiation in the Lymphoid Lineages The expression patterns of Ikaros and Aiolos indicates that variations in the relative levels of these proteins are important for the progression of a cell through the lymphoid lineage. A model of the role of these proteins in development of the lymphoid lineages is represented in FIG. 8. Early in hemopoiesis, only Ikaros is expressed and Ikaros dimeric complexes are required and perhaps are sufficient to regulate the expression of genes that set the lymphoid fate in the differentiation of a pluripotent hemopoietic stem cell. Alternatively, interactions of Ikaros with yet undescribed and distinct factors may be required for commitment to the lymphoid lineages. As a consequence of these Ikaros mediated commitment events, Aiolos becomes expressed in primitive lymphoid progenitors and can form heterodimers with the Ikaros proteins. These Ikaros-Aiolos heterodimers are transcriptionally more active than Ikaros homodimers and may regulate the expression of genes that control the transition to definitive T and B lymphocyte precursors. As Aiolos is upregulated in pre-T (CD4$^+$/CD8$^+$) and pre-B (B220/Igμ) cell precursors, the levels of Ikaros-Aiolos heterodimers increase and may allow for the later events in lymphocyte differentiation such as V to D–J and V–J rearrangement of immunoglobulin and TCR genes to take place (Hardy et al. (1993) *J. Exp. Med.* 178, 1213 and Li et al. *J. exp. Med.* 178, 951). Finally, in mature B cells where Aiolos expression predominates, transcriptionally potent Aiolos homodimers may control functions that are unique to these mature lymphocytes. Aiolos homodimers in mature T and B cells may be essential in regulating functions of these cells including gene expression events during their activation.

Therefore, normal progression through the T and B lineages may require the sequential expression of Ikaros-Ikaros, Ikaros-Aiolos and Aiolos-Aiolos dimeric complexes. Interference with Aiolos activity may affect lymphocyte maturation and function. In mice heterozygous for the DNA binding (dominant interfering) Ikaros mutation, defects in lymphocyte development are first observed in double positive thymocytes when Aiolos expression is normally upregulated. Since at this stage in differentiation Ikaros is expressed at higher levels than Aiolos, mutant Ikaros isoforms may readily sequester Aiolos proteins in inactive heterodimers which are unable to exert their function in T cell maturation. Although these dominant negative Ikaros isoforms are also expressed in B cells, defects in this mouse are limited to the T lineage. The different ratio of Aiolos to Ikaros mRNAs in B lymphocytes may result in insufficient mutant Ikaros proteins to titrate Aiolos and block its function in the B lineage.

Formation of transcriptionally potent Aiolos homodimers in developing thymocytes may also have adverse effects on their maturation. Although mice homozygous for a deletion of the Ikaros dimerization domain generate some a T cells, these cells differentiate abnormally. The Ikaros isoforms generated by this mutation cannot dimerize and do not prevent Aiolos from forming homodimers. The defects observed in the T lineage are consistent with the activation of transcriptional programs normally found in later stages, perhaps as a consequence of premature accumulation of Aiolos homodimers.

These studies on Aiolos and Ikaros expression and function indicate that both members of this gene family act in concert to regulate lymphocyte differentiation. At the earliest stage of lymphoid lineage determination, Ikaros is the predominant regulator of target gene activity while Aiolos is expressed at very low levels. As a cell progresses through the lymphoid lineage, Aiolos is upregulated and its heterodimers with Ikaros proteins become important regulators of the transcriptional changes required for lymphocyte maturation. Finally in mature B cells, Aiolos homodimers predominate, while in cells of the T lineage Ikaros remains expressed at relatively higher levels. Aiolos and Ikaros dimeric complexes may also regulate the function of mature B and T lymphocytes during an immune response.

Transgenic Animals

Aiolos knockouts with C terminal lesions (a deletions invoving exons 3–5) were made. Aiolos knockouts with N terminal lesions (a deletions invovling the 5' end of exon 7, whch contains the dimerization domain) were also made. The former knockout is a dominant negative and is thought to interfer with DNA binding. It resulted in hyperprolifertaion of B cells and shows increased serum levels of IgE but are otherwise normal at 2–3 weeks of age. Fifty percent of B cells were IgE secretors, thus Aiolos appears to be invovled in the Type I hyper acute response and in B cell regulation. The N terminal knockout homozygote produced no Aiolos protein, as determined by Western blotting.

Gene Therapy

The gene constructs of the invention can also be used as a part of a gene therapy protocol to deliver nucleic acids encoding either an agonistic or antagonistic form of an Aiolos polypeptide. The invention features expression vectors for in vivo transfection and expression of an Aiolos polypeptide in particular cell types (e.g., dermal cells) so as to reconstitute the function of, enhance the function of, or alternatively, antagonize the function of an Aiolos polypeptide in a cell in which the polypeptide is expressed or misexpressed.

Expression constructs of Aiolos polypeptide, may be administered in any biologically effective carrier, e.g., any formulation or composition capable of effectively delivering the Aiolos gene to cells in vivo. Approaches include insertion of the subject gene into viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA encoding an Aiolos polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76, 271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques*

6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject Aiolos gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an Aiolos polypeptide in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Aiolos gene by the targeted cell. Exemplary gene delivery systems of this type include liposomal derived systems, poly-lysine conjugates, and artificial viral envelopes.

In a representative embodiment, a gene encoding an Aiolos polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic Aiolos gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054–3057). In a preferred embodiment of the invention, the Aiolos gene is targeted to hematopoietic cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g., retroviral vectors, the pharmaceutical preparation can comprise one or more cells which produce the gene delivery system.

Antisense Therapy

Another aspect of the invention relates to the use of the isolated nucleic acid in "antisense" therapy. As used herein, "antisense" therapy refers to administration or in situ generation of oligonucleotides or their derivatives which specifically hybridize (e.g., bind) under cellular conditions, with the cellular mRNA and/or genomic DNA encoding an Aiolos polypeptide, or mutant thereof, so as to inhibit expression of the encoded protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

In one embodiment, the antisense construct binds to a naturally-occurring sequence of an Aiolos gene which, for example, is involved in expression of the gene. These sequences include, for example, start codons, stop codons, and RNA primer binding sites.

In another embodiment, the antisense construct binds to a nucleotide sequence which is not present in the wild type gene. For example, the antisense construct can bind to a region of an Aiolos gene which contains an insertion of an exogenous, non-wild type sequence. Alternatively, the antisense construct can bind to a region of an Aiolos gene which has undergone a deletion, thereby bringing two regions of the gene together which are not normally positioned together and which, together, create a non-wild type sequence.

When administered in vivo to a subject, antisense constructs which bind to non-wild type sequences provide the advantage of inhibiting the expression of mutant Aiolos gene, without inhibiting expression of any wild type Aiolos gene.

An antisense construct of the present invention can be delivered, for example, as an expression plasmid which, when transcribed in the cell, produces RNA which is complementary to at least a unique portion of the cellular mRNA which encodes a Aiolos polypeptide. Alternatively, the antisense construct is an oligonucleotide probe which is generated ex vivo and which, when introduced into the cell causes inhibition of expression by hybridizing with the mRNA and/or genomic sequences of an Aiolos gene. Such oligonucleotide probes are preferably modified oligonucleotide which are resistant to endogenous nucleases, e.g., exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally, or by transmucosal or transdermal means. For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind.

The antisense constructs of the present invention, by antagonizing the expression of an Aiolos gene, can be used in the manipulation of tissue, both in vivo and in ex vivo tissue cultures.

Transgenic Animals

The invention includes transgenic animals which include cells (of that animal) which contain an Aiolos transgene and which preferably (though optionally) express (or misexpress) an endogenous or exogenous Aiolos gene in one or more cells in the animal.

The Aiolos transgene can encode a mutant Aiolos polypeptide. Such animals can be used as disease models or can be used to screen for agents effective at correcting the misexpression of Aiolos. Alternatively, the Aiolos transgene can encode the wild-type forms of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" Aiolos gene, i.e., a deletion of all or a part of the Aiolos gene.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Aiolos gene. For example, excision of a target sequence which interferes with the expression of a recombinant Aiolos gene, such as one which encodes an agonistic homolog, can be designed to activate expression of that gene. This interference with expression of the protein can result from a variety of mechanisms, such as spatial separation of the Aiolos gene from the promoter element or an internal stop codon.

Moreover, the transgene can be made so that the coding sequence of the gene is flanked with recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. See e.g., descriptions of the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694). Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant Aiolos gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g., a recombinase or a prokaryotic protein, is delivered to the tissue and caused to be expressed, such as in a cell-type specific manner. By this method, the Aiolos transgene could remain silent into adulthood until "turned on" by the introduction of the trans-activator.

Production of Fragments and Analogs

The inventor has provided the primary amino acid structure of an Aiolos polypeptide. Once an example of this core structure has been provided, one skilled in the art can alter the disclosed structure by producing fragments or analogs, and testing the newly produced structures for activity. Examples of prior art methods which allow the production and testing of fragments and analogs are discussed below. These, or analogous methods can be used to make and screen fragments and analogs of an Aiolos polypeptide having at least one biological activity e.g., which react with an antibody (e.g., a monoclonal antibody) specific for an Aiolos polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765[1978]).

Cassette Mutagenesis

Another method for preparing variants, cassette mutagenesis, is based on the technique described by Wells et al. (*Gene,* 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants, e.g., a library of variants which is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to an antibody specific for a Aiolos polypeptide. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267: 16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the *Staphylococcus* protein A and the outer membrane protease IgA of *Neisseria* (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9): 1233–1251). These particular biases are not a factor in the LacI display system.

The number of small peptides available in recombinant random libraries is enormous. Libraries of $10^{7-10^9}$ independent clones are routinely prepared. Libraries as large as 1011 recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204, 357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of a protein of interest is identified, such as the primary amino acid sequence of Aiolos polypeptide as disclosed herein, it is routine to perform for one skilled in the art to obtain analogs and fragments.

Peptide Analogs of Aiolos

Peptide analogs of an Aiolos polypeptide are preferably less than 400, 300, 200, 150, 130, 110, 90, 70 amino acids in length, preferably less than 50 amino acids in length, most preferably less than 30, 20 or 10 amino acids in length. In preferred embodiments, the peptide analogs of an Aiolos polypeptide are at least about 10, 20, 30, 50, 100 or 130 amino acids in length.

Peptide analogs of an Aiolos polypeptide have preferably at least about 60%, 70%, 80%, 85%, 90%, 95% or 99% homology or sequence similarity with the naturally occurring Aiolos polypeptide.

Peptide analogs of an Aiolos polypeptide differ from the naturally occurring Aiolos polypeptide by at least 1, 2, 5, 10 or 20 amino acid residues; preferably, however, they differ in less than 15, 10 or 5 amino acid residues from the naturally occurring Aiolos polypeptide.

Useful analogs of an Aiolos polypeptide can be agonists or antagonists. Antagonists of an Aiolos polypeptide can be molecules which form the Aiolos-Ikaros dimers but which lack some additional biological activity such as transpriptional activation of genes that control lymphocyte development. Aiolos antagonists and agonists are derivatives which can modulate, e.g., inhibit or promote, lymphocyte maturation and function.

A number of important functional Aiolos domains have been identified by the inventors. This body of knowledge provides guidance for one skilled in the art to make Aiolos analogs. One would expect nonconservative amino acid changes made in a domain to disrupt activities in which that domain is involved. Conservative amino acid changes, especially those outside the important functional domains, are less likely to modulate a change in activity. A discussion of conservative amino acid substitutions is provided herein.

The general structure of Aiolos and Ikaros proteins is very similar, and four blocks of sequence are particularly well conserved. The first block of conservation encodes the zinc finger modules contained in the Ik-1 isoform which mediate DNA binding of the Ikaros protein (Molnar et al. (1994) *Mol. Cell. Biol.* 14 8292–8303). The second block of conservation has not been characterized functionally.

The third block of conservation a highly conserved 81 amino acid sequence which has been shown to mediate transcriptional activity of the Ikaros proteins (this domain is boxed in FIG. 6). This activation domain of Ikaros is composed of a stretch of acidic amino acids followed by a stretch of hydrophobic residues, both of which are required for its full activation potential. This domain from Ikaros alone or the full length Ikaros protein confers transcriptional activity of a fusion protein with the LexA DNA binding domain. This example shows that the homologous domain in Aiolos is also a transcriptional activation domain in yeast and mammalian cells and that the Aiolos transcriptional activation domain provides stronger transcriptional activity than the homologous domain from Ikaros in mammalian cells. The results show that the 232 C-terminal amino acids of Aiolos is capable of conferring transcriptional activation in yeast cells. No activity was detected with the 149 most C-terminal amino acids of Aiolos, which do not contain the conserved domain.

The fourth block of conservation corresponds to the zinc fingers which mediate dimerization. A C-terminal 149 amino acids of Aiolos which contain the two terminal zinc finger domains mediate protein dimerization.

Antibodies

The invention also includes antibodies specifically reactive with a subject Aiolos polypeptide or Aiolos-Ikarod dimers. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject Aiolos polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the Aiolos-Iakros dimers or Aiolos polypeptide of the invention, e.g., antigenic determinants of a polypeptide of SEQ ID NO:2 or SEQ ID NO:8.

The term "antibody", as used herein, intended to include fragments thereof which are also specifically reactive with an Aiolos polypeptide or Aiolos-Ikaros dimers. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Both monoclonal and polyclonal antibodies (Ab) directed against Aiolos-Ikaros dimers or Aiolos polypeptides, or fragments or analogs thereof, and antibody fragments such as Fab' and F(ab')$_2$, can be used to block the action of an Aiolos and/or Ikaros polypeptide and allow the study of the role of an Aiolos polypeptide of the present invention.

Antibodies which specifically bind Aiolos-Ikaros dimers or Aiolos polypeptide epitopes can also be used in immunohistochemical staining of tissue samples in order to evaluate the abundance and pattern of expression of Aiolos-Ikaros dimer or Aiolos polypeptide. Anti-Aiolos polypeptide antibodies can be used diagnostically in immuno-precipitation and immuno-blotting to detect and evaluate wild type or mutant Aiolos polypeptide levels in tissue or bodily fluid as part of a clinical testing procedure. Likewise, the ability to monitor Aiolos-Ikaros dimer or Aiolos polypeptide levels in an individual can allow determination of the efficacy of a given treatment regimen for an individual afflicted with disorders associated with modulation of lymphocyte differentiation and/or proliferation. The level of an Aiolos-Ikaros dimer or Aiolos polypeptide can be measured in tissue, such as produced by biopsy.

Another application of anti-Aiolos antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject Aiolos polypeptide can then be detected with antibodies, as, for example, reacting nitrocellulose filters lifted from infected plates with anti-Aiolos polypeptide antibodies. Phage, scored by this assay, can then be isolated from the infected plate. Thus, the presence of Aiolos homologs can be detected and cloned from other animals, and alternate isoforms (including splicing variants) can be detected and cloned from human sources.

Drug Screening Assays

By making available purified and recombinant-Aiolos polypeptides, the present invention provides assays which can be used to screen for drugs which are either agonists or antagonists of the normal cellular function, in this case, of the subject Aiolos polypeptide. In one embodiment, the assay evaluates the ability of a compound to modulate binding between an Aiolos polypeptide and a naturally occurring ligand, e.g., an antibody specific for a Aiolos polypeptide or an Ikaros polypeptide. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

Other Embodiments

Included in the invention are: allelic variations; natural mutants; induced mutants;

proteins encoded by DNA that hybridizes under high or low stringency conditions to a nucleic acids which encode polypeptides of SEQ ID NO:2 or SEQ ID NO:8 (for definitions of high and low stringency see Current Protocols in Molecular Biology, John Wiley & Sons, New York, 1989, 6.3.1–6.3.6, hereby incorporated by reference); and, polypeptides specifically bound by antisera to an Aiolos polypeptide.

Nucleic acids and polypeptides of the invention includes those that differ from the sequences discolosed herein by virtue of sequencing errors in the disclosed sequences.

Also included in the invention is a composition which includes an Aiolos polypeptide, e.g., an Aiolos/Aiolos dimer or an Aiolos/Ikaros peptide, and one or more additional components, e.g., a carrier, diluent, or solvent. The additional component can be one which renders the composition useful for in vitro, in vivo, pharmaceutical, or veterinary use. Examples of in vitro use are binding studies. Examples of in vivo use are the induction of antibodies.

The invention also includes fragments, preferably biologically active fragments, or analogs of an Aiolos polypeptide. A biologically active fragment or analog is one having any in vivo or in vitro activity which is characteristic of the Aiolos polypeptide shown in SEQ ID NO:2 or SEQ ID NO:8, or of other naturally occurring Aiolos polypeptides, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Because peptides, such as an Aiolos polypeptide, often exhibit a range of physiological properties and because such properties may be attributable to different portions of the molecule, a useful Aiolos polypeptide fragment or Aiolos polypeptide analog is one which exhibits a biological activity in any biological assay for Aiolos polypeptide activity. Most preferably the fragment or analog possesses 10%, preferably 40%, or at least 90% of the activity of an Aiolos polypeptide (SEQ ID NO:2 or SEQ ID NO:8), in any in vivo or in vitro Aiolos polypeptide activity assay.

Analogs can differ from a naturally occurring Aiolos polypeptide in amino acid sequence or in ways that do not involve sequence, or both. Non-sequence modifications include in vivo or in vitro chemical derivatization of an Aiolos polypeptide. Non-sequence modifications include changes in acetylation, methylation, phosphorylation, carboxylation, or glycosylation.

Preferred analogs include an Aiolos polypeptide (or biologically active fragments thereof) whose sequences differ from the wild-type sequence by one or more conservative amino acid substitutions or by one or more non-conservative amino acid substitutions, deletions, or insertions which do not abolish the Aiolos polypeptide biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from Table 1.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an Aiolos polypeptide analog, will ordinarily be at least about 20 residues, more typically at least about 40 residues, preferably at least about 60 residues in length. Fragments of an Aiolos polypeptide can be generated by methods known to those skilled in the art. The ability of a candidate fragment to exhibit a biological activity of an Aiolos polypeptide can be assessed by methods known to those skilled in the art, as described herein. Also included are Aiolos polypeptides containing residues that are not required for biological activity of the peptide or that result from alternative mRNA splicing or alternative protein processing events.

In order to obtain an Aiolos polypeptide, an Aiolos polypeptide-encoding DNA can be introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-Aiolos polypeptide antibodies by prior art methods.

Detailed Description of Helios

Gene Therapy

The gene constructs of the invention can also be used as a part of a gene therapy protocol to deliver nucleic acids encoding either an agonistic or antagonistic form of an Helios polypeptide. The invention features expression vectors for in vivo transfection and expression of an Helios polypeptide in particular cell types (e.g., dermal cells) so as to reconstitute the function of, enhance the function of, or alternatively, antagonize the function of an Helios polypeptide in a cell in which the polypeptide is expressed or misexpressed.

Expression constructs of Helios polypeptide, may be administered in any biologically effective carrier, e.g., any formulation or composition capable of effectively delivering the Helios gene to cells in vivo. Approaches include insertion of the subject gene into viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA encoding an Helios polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76, 271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject Helios gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of an Helios polypeptide in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject Helios gene by the targeted cell. Exemplary gene delivery systems of this type include liposomal derived systems, poly-lysine conjugates, and artificial viral envelopes.

In a representative embodiment, a gene encoding an Helios polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic Helios gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054–3057). In a preferred embodiment of the invention, the Helios gene is targeted to hematopoietic cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g., retroviral vectors, the pharmaceutical preparation can comprise one or more cells which produce the gene delivery system.

Antisense Therapy

Another aspect of the invention relates to the use of the isolated nucleic acid in "antisense" therapy. As used herein, "antisense" therapy refers to administration or in situ generation of oligonucleotides or their derivatives which specifically hybridize (e.g., bind) under cellular conditions, with the cellular mRNA and/or genomic DNA encoding an Helios polypeptide, or mutant thereof, so as to inhibit expression of the encoded protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

In one embodiment, the antisense construct binds to a naturally-occurring sequence of an Helios gene which, for example, is involved in expression of the gene. These sequences include, for example, start codons, stop codons, and RNA primer binding sites.

In another embodiment, the antisense construct binds to a nucleotide sequence which is not present in the wild type gene. For example, the antisense construct can bind to a region of an Helios gene which contains an insertion of an exogenous, non-wild type sequence. Alternatively, the antisense construct can bind to a region of an Helios gene which has undergone a deletion, thereby bringing two regions of the gene together which are not normally positioned together and which, together, create a non-wild type sequence.

When administered in vivo to a subject, antisense constructs which bind to non-wild type sequences provide the advantage of inhibiting the expression of mutant Helios gene, without inhibiting expression of any wild type Helios gene.

An antisense construct of the present invention can be delivered, for example, as an expression plasmid which, when transcribed in the cell, produces RNA which is complementary to at least a unique portion of the cellular mRNA which encodes a Helios polypeptide. Alternatively, the antisense construct is an oligonucleotide probe which is generated ex vivo and which, when introduced into the cell causes inhibition of expression by hybridizing with the mRNA and/or genomic sequences of an Helios gene. Such oligonucleotide probes are preferably modified oligonucleotide which are resistant to endogenous nucleases, e.g., exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally, or by transmucosal or transdermal means. For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind.

The antisense constructs of the present invention, by antagonizing the expression of an Helios gene, can be used in the manipulation of tissue, both in vivo and in ex vivo tissue cultures.

Transgenic Animals

The invention includes transgenic animals which include cells (of that animal) which contain an Helios transgene and which preferably (though optionally) express (or misexpress) an endogenous or exogenous Helios gene in one or more cells in the animal.

The Helios transgene can encode a mutant Helios polypeptide. Such animals can be used as disease models or can be used to screen for agents effective at correcting the misexpression of Helios. Alternatively, the Helios transgene can encode the wild-type forms of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" Helios gene, i.e., a deletion of all or a part of the Helios gene.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Helios gene. For example, excision of a target sequence which interferes with the expression of a recombinant Helios gene, such as one which encodes an agonistic homolog, can be designed to activate expression of that gene. This interference with expression of the protein can result from a variety of mechanisms, such as spatial separation of the Helios gene from the promoter element or an internal stop codon.

Moreover, the transgene can be made so that the coding sequence of the gene is flanked with recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. See e.g., descriptions of the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694). Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant Helios gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g., a recombinase or a prokaryotic protein, is delivered to the tissue and caused to be expressed, such as in a cell-type specific manner. By this method, the Helios transgene could remain silent into adulthood until "turned on" by the introduction of the trans-activator.

Production of Fragments and Analogs

The inventor has provided the primary amino acid structure of an Helios polypeptide. Once an example of this core structure has been provided, one skilled in the art can alter the disclosed structure by producing fragments or analogs, and testing the newly produced structures for activity. Examples of prior art methods which allow the production and testing of fragments and analogs are discussed below. These, or analogous methods can be used to make and screen fragments and analogs of an Helios polypeptide having at least one biological activity e.g., which react with an antibody (e.g., a monoclonal antibody) specific for an Helios polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249:404–406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (Proc. Natl. Acad. Sci. USA, 75: 5765[1978]).

Cassette Mutagenesis

Another method for preparing variants, cassette mutagenesis, is based on the technique described by Wells et al. (Gene, 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants, e.g., a library of variants which is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to an antibody specific for a Helios polypeptide. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267: 16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the *Staphylococcus* protein A and the outer membrane protease IgA of *Neisseria* (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as 1011 recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204, 357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of a protein of interest is identified, such as the primary amino acid sequence of Helios polypeptide as disclosed herein, it is routine to perform for one skilled in the art to obtain analogs and fragments.

Peptide Analogs of Helios

Peptide analogs of an Helios polypeptide are preferably less than 400, 300, 200, 150, 130, 110, 90, 70 amino acids in length, preferably less than 50 amino acids in length, most preferably less than 30, 20 or 10 amino acids in length. In preferred embodiments, the peptide analogs of an Helios polypeptide are at least about 10, 20, 30, 50, 100 or 130 amino acids in length.

Peptide analogs of an Helios polypeptide have preferably at least about 60%, 70%, 74%, 80%, 85%, 90%, 95% or 99% homology or sequence similarity with the naturally occurring Helios polypeptide.

Peptide analogs of an Helios polypeptide differ from the naturally occurring Helios polypeptide by at least 1, 2, 5, 10 or 20 amino acid residues; preferably, however, they differ in less than 15, 10 or 5 amino acid residues from the naturally occurring Helios polypeptide.

Useful analogs of an Helios polypeptide can be agonists or antagonists. Antagonists of an Helios polypeptide can be molecules which form the Helios-Ikaros dimers but which lack some additional biological activity such as transcriptional activation of genes that control lymphocyte development. Helios antagonists and agonists are derivatives which can modulate, e.g., inhibit or promote, lymphocyte maturation and function.

A number of important functional Helios domains have been identified by the inventors. This body of knowledge provides guidance for one skilled in the art to make Helios analogs. One would expect nonconservative amino acid changes made in a domain to disrupt activities in which that domain is involved. Conservative amino acid changes, especially those outside the important functional domains, are less likely to modulate a change in activity. A discussion of conservative amino acid substitutions is provided herein.

The general structure of Helios and Ikaros proteins is very similar, and four blocks of sequence are particularly well conserved. The first block of conservation encodes the zinc finger modules contained in the Ik-1 isoform which mediate DNA binding of the Ikaros protein (Molnar et al. (1994) *Mol. Cell. Biol.* 14 8292–8303). The second block of conservation has not been characterized functionally.

The third block of conservation a highly conserved 81 amino acid sequence which has been shown to mediate transcriptional activity of the Ikaros proteins. This activation domain of Ikaros is composed of a stretch of acidic amino acids followed by a stretch of hydrophobic residues, both of which are required for its full activation potential. This domain from Ikaros alone or the full length Ikaros protein confers transcriptional activity of a fusion protein with the LexA DNA binding domain. This example shows that the homologous domain in Helios is also a transcriptional activation domain in yeast and mammalian cells and that the Helios transcriptional activation domain provides stronger transcriptional activity than the homologous domain from Ikaros in mammalian cells. The results show that the 232 C-terminal amino acids of Helios is capable of conferring transcriptional activation in yeast cells. No activity was detected with the 149 most C-terminal amino acids of Helios, which do not contain the conserved domain.

The fourth block of conservation corresponds to the zinc fingers which mediate dimerization. A C-terminal 149 amino acids of Helios which contain the two terminal zinc finger domains mediate protein dimerization.

Antibodies

The invention also includes antibodies specifically reactive with a subject Helios polypeptide or Helios-Ikarod dimers. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject Helios polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the Helios-Iakros dimers or Helios polypeptide of the invention, e.g., antigenic determinants of a polypeptide of SEQ ID NO:24, SEQ ID NO:26, or SEQ ID NO:28.

The term "antibody", as used herein, intended to include fragments thereof which are also specifically reactive with an Helios polypeptide or Helios-Ikaros dimers. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Both monoclonal and polyclonal antibodies (Ab) directed against Helios-Ikaros dimers or Helios polypeptides, or fragments or analogs thereof, and antibody fragments such as Fab' and F(ab')$_2$, can be used to block the action of an Helios and/or Ikaros polypeptide and allow the study of the role of an Helios polypeptide of the present invention.

Antibodies which specifically bind Helios-Ikaros dimers or Helios polypeptide epitopes can also be used in immunohistochemical staining of tissue samples in order to evaluate the abundance and pattern of expression of Helios-Ikaros dimer or Helios polypeptide. Anti-Helios polypeptide antibodies can be used diagnostically in immuno-precipitation and immuno-blotting to detect and evaluate wild type or mutant Helios polypeptide levels in tissue or bodily fluid as part of a clinical testing procedure. Likewise, the ability to monitor Helios-Ikaros dimer or Helios polypeptide levels in an individual can allow determination of the efficacy of a given treatment regimen for an individual afflicted with disorders associated with modulation of lymphocyte differentiation and/or proliferation. The level of an Helios-Ikaros dimer or Helios polypeptide can be measured in tissue, such as produced by biopsy.

Another application of anti-Helios antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject Helios polypeptide can then be detected with antibodies, as, for example, reacting nitrocellulose filters lifted from infected plates with anti-Helios polypeptide antibodies. Phage, scored by this assay, can then be isolated from the infected plate. Thus, the presence of Helios homologs can be detected and cloned from other animals, and alternate isoforms (including splicing variants) can be detected and cloned from human sources.

Drug Screening Assays

By making available purified and recombinant-Helios polypeptides, the present invention provides assays which can be used to screen for drugs which are either agonists or antagonists of the normal cellular function, in this case, of the subject Helios polypeptide. In one embodiment, the assay evaluates the ability of a compound to modulate binding between an Helios polypeptide and a naturally occurring ligand, e.g., an antibody specific for a Helios polypeptide or an Ikaros polypeptide. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

Other Embodiments

Included in the invention are: allelic variations; natural mutants; induced mutants; proteins encoded by DNA that hybridizes under high or low stringency conditions to a nucleic acids which encode polypeptides of SEQ ID NO:24, SEQ ID NO:26, or SEQ ID NO:28 (for definitions of high and low stringency see Current Protocols in Molecular Biology, John Wiley & Sons, New York, 1989, 6.3.1–6.3.6, hereby incorporated by reference); and, polypeptides specifically bound by antisera to an Helios polypeptide.

Nucleic acids and polypeptides of the invention includes those that differ from the sequences discolosed herein by virtue of sequencing errors in the disclosed sequences.

Also included in the invention is a composition which includes an Helios polypeptide, e.g., an Helios/Helios dimer or an Helios/Ikaros peptide, and one or more additional components, e.g., a carrier, diluent, or solvent. The additional component can be one which renders the composition useful for in vitro, in vivo, pharmaceutical, or veterinary use. Examples of in vitro use are binding studies. Examples of in vivo use are the induction of antibodies.

The invention also includes fragments, preferably biologically active fragments, or analogs of an Helios polypeptide. A biologically active fragment or analog is one having any in vivo or in vitro activity which is characteristic of the Helios polypeptide shown in SEQ ID NO:24, SEQ ID NO:26, or SEQ ID NO:28, or of other naturally occurring Helios polypeptides, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Because peptides, such as an Helios polypeptide, often exhibit a range of physiological properties and because such properties may be attributable to different portions of the molecule, a useful Helios polypeptide fragment or Helios polypeptide analog is one which exhibits a biological activity in any biological assay for Helios polypeptide activity. Most preferably the fragment or analog possesses 10%, preferably 40%, or at least 90% of the activity of an Helios polypeptide (SEQ ID NO:24, SEQ ID NO:26, or SEQ ID NO:28), in any in vivo or in vitro Helios polypeptide activity assay.

Analogs can differ from a naturally occurring Helios polypeptide in amino acid sequence or in ways that do not involve sequence, or both. Non-sequence modifications include in vivo or in vitro chemical derivatization of an Helios polypeptide. Non-sequence modifications include changes in acetylation, methylation, phosphorylation, carboxylation, or glycosylation.

Preferred analogs include an Helios polypeptide (or biologically active fragments thereof) whose sequences differ from the wild-type sequence by one or more conservative amino acid substitutions or by one or more non-conservative amino acid substitutions, deletions, or insertions which do not abolish the Helios polypeptide biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from Table 1.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an Helios polypeptide analog, will ordinarily be at least about 20 residues, more typically at least about 40 residues, preferably at least about 60 residues in length. Fragments of an Helios polypeptide can be generated by methods known to those skilled in the art. The ability of a candidate fragment to exhibit a biological activity of an Helios polypeptide can be assessed by methods known to those skilled in the art, as described herein. Also included are Helios polypeptides containing residues that are not required for biological activity of the peptide or that result from alternative mRNA splicing or alternative protein processing events.

In order to obtain an Helios polypeptide, an Helios polypeptide-encoding DNA can be introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-Helios polypeptide antibodies by prior art methods.

HELIOS EXAMPLES

Example: Identification of Helios, a Novel Ikaros-Related Gene

To identify a novel Ikaros-related factor a PCR-based approach was used. Degenerate primers, GEKPFK and YTIHMG, encoding conserved sequences in the Ikaros N-terminal (Ik-F) and C-terminal zinc finger (Ik-R) domains (Turpen et al., Immunity, 7:325–334, 1997) were used to amplify cDNAs generated from the spleen of Aiolos mutant mice. A PCR product of the expected 980 base pair size was cloned and shown to have unique DNA sequence with homology to the Ikaros gene. Full length coding sequence was obtained by RACE PCR using nested specific internal primers. Nested gene specific primers were as follows:

```
5"-RACE R51:
GGGTGAAGGCCTCAGGT            (SEQ ID NO:31)
and

R52:
CCATCATATGAGACTGCATCAGCTCCAGCCTCC;  (SEQ ID NO:32)

3'-RACE R31:
GGAGGCTGAGCTGATGCACTCTCATATGATGG    (SEQ ID NO:33)
and

R32:
CACCTACCTTGGAGCTGAGGCCCTTCACCC.     (SEQ ID NO:34)
```

The RACE PCR was performed using the Marathon cDNA Amplification Kit (Clonetech, Palo Alto, Calif.) and TaKaRa LA Taq DNA polymerase (Takara Shuzo, Shiga, Japan). The amplification conditions were 1.5 min. at 95° C. for 1 cycle, 20 seconds at 98° C. and 2.5 minutes at 72° C. for 5 cycles, 20 seconds at 98° C. and 2.5 minutes at 70° C. for 5 cycles, 30 seconds at 98° C. and 2.5 minutes at 68° C. for 32 cycles, and 1 cycle of 10 minutes at 72° C. A second round of amplification using nested primers was performed using a portion of the first product as template. The second amplification was 1.5 minutes at 95° C. for 1 cycle, 20 seconds at 98° C. and 2.5 minutes at 68° C. for 20 cycles, followed by 72° C. for 10 minutes for 1 cycle. 5' and 3' products were cloned into the pGEM-T Easy vector (Promega, Madison, Wis.) and sequenced PCR analysis of Helios expression in hematopoietic cells using various combination of specific 5" and 3" primer pairs routinely yielded two bands. These two bands were cloned and sequenced to show that the two alternatively spliced transcripts differed in the presence of sequence encoding the first N-terminal zinc finger.

The encoded protein, designated Helios, shows a high degree of conservation to Ikaros and Aiolos (73% and 67% similarity overall, respectively) (FIG. 10). The three proteins are nearly identical throughout the N-terminal zinc finger DNA-binding domain. There is a 93% identity between Helios and Ikaros from the first through the fourth zinc fingers and 88% identity between the same regions of Helios and Aiolos. The protein dimerization domain, comprising the C-terminal zinc fingers is 86% identical between Helios and Ikaros and 75% identical between Helios and Aiolos. In a third region, that contains the transcriptional activation domain, Helios shares 68% similarity to Ikaros and 70% identity to Aiolos. As mentioned above, two alternatively spliced forms of Helios were identified by PCR from thymus cDNA. Sequence analysis of the two Helios isoforms revealed that they encode products that differ in the number of N-terminal zinc fingers. The full length isoform (Hel-1) is analogous to Ikaros isoform Ik-1 in that it contains all four DNA-binding zinc fingers. The second isoform (Hel-2) is similar to Ik-2 in that it is missing zinc finger 1, although the exon removed to generate Ik-2 includes additional sequence N-terminal to the zinc finger that is retained in the Hel-2 isoform. PCR analysis using various combinations of primer pairs revealed no other isoforms that migrate at approximately 64 and 66 kDa, as described below. No other proteins are detected by Western blot analysis of thymocyte nuclear extracts using an affinity purified polyclonal antibody against Helios. The strong conservation of the N-terminal zinc finger motifs of Hel-1 and Hel-2 with Ikaros isoforms Ik-1 and Ik-2 predicts that they will display similar affinities and DNA binding specificities.

5' and 3' RACE strategies were used to clone the ends of the human Helios cDNA after cloning of the internal section of this message using degenerate primers from the 5' and 3' zinc finger regions. The 3' untranslated sequence extends for an additional 3 kb. The human clone encodes a protein which is identical to mouse Helios. The nucleotide and inferred protein sequences of mouse and human Helios were compared using the GCG Bestfit program.

Example: Expression of Helios during embryogenesis

The expression of Helios during mouse embryogenesis was examined by in situ hybridization. Ikaros expression was analyzed in an adjacent section at each stage for comparison. In situ hybridization, including embryo preparation, probe synthesis and in situ hybridization, was carried out essentially as described [Ikeda, Dev. Dynamics, 20:318–329, 1996]. Four micrometer sections were prepared from embryonic days 8, 11, 13 and 16 and were hybridized with single stranded [33P]UTP labeled antisense RNA probes specific to each gene. Slides were exposed for 5 weeks, stained with hematoxylin and eosin and analyzed with both bright and dark field microscopy.

Helios was found to be expressed in all hematopoietic centers of the developing embryo. The blood islands of the yolk sac constituted the first site of embryonic hematopoiesis. Helios and Ikaros were expressed in this extraembryonic site at day 8 of gestation. However, by day 11, Helios expression was significantly decreased, while Ikaros expression was maintained through embryonic day 13 in this region. Both Helios and Ikaros were expressed in the liver at day 11; however, Helios mRNA was present in a subset of cells in this tissue. Throughout hematopoietic development, Helios expression in the liver was detected in a small number of scattered cells. In contrast, Ikaros was expressed at high levels in most of the cells present in this tissue during mid to late gestation. In the thymus, Helios was first detected at low levels at embryonic day 13, while Ikaros expression was readily detected in this site two days earlier. By day 16, Helios was expressed at high levels toward the center of the thymus, a region where early progenitors enter from the vasculature. In contrast, Ikaros was detected in most thymocytes. This pattern of Helios expression was maintained in the postnatal thymus. Helios was also detected in a small subset of cells within the spleen of the adult. Within the splenic germinal centers of an immunized animal, a small number of cells expressed moderate levels of Helios, while Ikaros was present at high levels throughout these centers. Their localization suggested that these may be $CD4^+TH_2$ cells.

Outside of the hematopoietic system, Helios expression was high in a number of epithelial tissues. These include the endoderm lining the gut, the tubules of the kidney, the lining of the respiratory tract and olfactory epithelium. During late gestation high levels of Helios expression were detected in the salivary glands and ducts.

The expression of Helios in adult tissues was examined by Northern blot analysis of polyA+ selected. RNAs using the region between the N- and C-terminal zinc fingers of Helios as a probe. Northern blot analysis and RT-PCR were carried out essentially as follows. A 980 bp cDNA was used as a probe for Northern analysis. This probe did not cross react with Ikaros or Aiolos, which yield transcripts of distinct sizes. The blot had previously been screen with a GAPDH probe to confirm equivalent loading of RNA samples. Northern results showed that a transcript of approximately 8 kb was detected in thymus. At various times during embryogenesis, Helios was expressed in the lung, liver, kidney and brain; however, Helios mRNA was not detected by Northern analysis in these tissues in the adult. The Helios probe did not cross react with either Ikaros or Aiolos that encode more abundant messages of distinct sizes in the thymus and spleen.

Example: Expression of Helios in Hematopoietic Subpopulations

The expression of Ikaros gene family members in sorted hematopoietic and lymphoid progenitors of the adult was examined by RT-PCR using specific primer pairs for Helios, Ikaros or Aiolos. RT-PCR conditions and Ikaros and Aiolos primers were carried out. HPRT primers (for.TGGCCCTCT-GTGGTGCTCAAG (SEQ ID NO:35); Rev:CACAGGAC-TAGAACACCTGC (SEQ ID NO:36) were used as a control for RNA recovery. For analysis of Helios expression in hematopoietic cells, the following primer pairs were used: Forward (2F): GAACACGCCAATATGGCC (SEQ ID NO:37) (nucleotides 60–78 of Helios cDNA) and Reverse (8R): GGCCTTGGTAGCATCCAAAGC (SEQ ID NO:38) (nucleotides 1327–47 of Helios cDNA). For PCRs, primers 125F: AGAATGTCAGCATGGAGGCT (SEQ ID NO:39) (nucleotides 707–726) and 8R were used for amplification. This forward primer is downstream of the region encoding the first zinc finger and therefore, only amplifies one Helios isoform. In all cases, the annealing temperature was 60° C. and amplification was determined to be in the linear range. For bone marrow derived progenitor populations where cells were limiting in number, cDNA from 50 cells equivalents was amplified for 32 cycles. For thymocyte precursors, amplification was done 1000 cell equivalents for 26 cycles for each primer pair, For other samples, e.g., Ikaros, 25 cycles were done and for Helios and Aiolos 28 cycles were done.

The subsets of hemo-lymphoid populations used for these studies and their ontogeny are diagrammed in FIG. 11. Stem cell population (ckit$^+$Sca-1$^+$, lineage$^-$), early progenitors (ckit$^+$Sca-1$^-$, lineage$^-$ and ckit$^+$SCA-1$^+$Sca2$^+$, lineage$^-$) were purified from the bone marrow of wild type mice. Lineage committed erythroid (ler119$^+$), pre B (B220$^+$), granulocyte (Mac]$^+$, GR$^+$) monocyte/macrophage (Mac1$^+$, GR$^-$ populations were purified form bone marrow of wild type mice using antibodies to cell surface markers, magnetic secondary antibodies and separated using a MACS magnetic separation column. Pro B cells were B220$^+$ sorted from the bone marrow of Rag−/− mice, mature B cells were B220$^+$ form the spleens of wild type mice. Splenocyte form −Rag−/− mice were depleted of red cells and used an enriched source of NK Thymic and splenic dendritic cells were purified. Double positive (CD4$^+$CD8$^+$) and single positive (CD4$^+$ or CD8$^+$) were sorted form wild type thymus and soluble negative (CD4 CD8) were obtained form thymocyte of Rag−/− mice that are arrested at this state of differentiation. Developmental stages of double thymocyte (CD4$^{lo}$, ckit$^+$CD25$^+$, ckit-CD25$^+$, ckit, CD25) were sorted to 98–99% purity.

Helios mRNA was detected in the bone marrow progenitor population that was highly enriched for stem cell activity (ckit$^+$/Sca-1+lineage−) and was also present in hematopoietic progenitors with more restricted lymphoid or erythromyeloid potential (ckit+/Sca-1+/Sca-2+ and ckit+/Sca-1−/Sca-2− respectively). Ikaros displays a similar pattern of expression in these hematopoietic progenitor populations whereas Aiolos was detected only in the progenitors that were more committed to lymphoid development (ckit+/Sca-1+/Sca-2+).

Helios was expressed in definitive erythroid precursors (ter119+) and very low levels of Helios mRNA are present within the monocyte (mac1+GR−) and granulocyte (Mac1+GR+) population sin the adult bone marrow. Ikaros, but not Aiolos, was detected at low levels in all three of these cell types. Helios was present at low levels in pro-B cells (CD45R+/CD43+), and decreases as they progress to pre-B cells (CD45R+/IgM+). In contrast, Aiolos expression was low in pro-B cells and dramatically increases in pre-B and mature B cells.

As HSCs differentiate along the myeloerythroid and B lymphoid lineages, Helios expression was diminished. However, Helios was present at varying levels in all T cell subsets analyzed. The earliest lymphoid progenitors entering the thymus are CD4$^{lo}$ (and ckit+) and are not necessarily committed to the T cell lineage. Helios and Ikaros are both detected in these earliest lymphoid progenitors. An increase in Helios was apparent during the progressive transition to the ckit+CD25+, and then ckit-CD25+, where Aiolos was first detected. A marked increase in Aiolos levels was observed at the next stage (ckit-CD25−), while Helios expression decreases. Ikaros levels remain constant during these early stages of T-cell differentiation. For comparison, the expression of these genes in RNA from total thymocyte populations of wild type and Rag−/− mice was done. In Rag−/− mice the majority of thymocytes are at the ckit+CD25+stage where T cell development was blocked, while in a wild type thymus, the majority of cells are at the later, double positive (CD4+CD8+) stage. Helios mRNA increases as T cells progress from the CD4−CD8− double negative to the CD4+CD8+ double positive stage and declines as these become single positive (CD4+ or CD8+) thymocytes. Peripheral T cells have lower expression of Helios than immature thymocytes with the highest levels detected among γδT cells of the skin (Vγδ) and the gut (IEL). Ikaros and Aiolos are present in these T cell populations but Aiolos was not detected in the fetally derived skin γδ T cells. All three genes are expressed in NK cells. The lymphoid derived thymic dendritic cells (DC) as well the splenic CD8+ and CD8− dendritic subsets express very low levels of Helios. Ikaros was present in all three populations, but was highest in the splenic CD8-DC subset. Among the DC subpopulations, Aiolos was also highest in the splenic DC8-DCs.

The expression of two Helios isoforms was routinely detected by PCR using a 5' primer preceding the first zinc finger. These isoforms correspond to the Hel-1 and Hel-2 cDNAs and are expressed at roughly equivalent levels in all cell types tested. As described previously, no significant difference in the ratio of Ikaros isoforms in different hematopoietic populations can be detected under our conditions, where amplification was determined to be within the linear range. In all hematopoietic cell types analyzed, Ik-1 an Ik-2 were expressed in highest abundance, while Ik-4 and 5 were expressed at low levels. A faint band corresponding to Ik-6 was also detected in all populations tested.

During hematopoietic development, Helios, Ikaros and Aiolos have overlapping but distinct patterns of expression. The differential patterns of expression of these three factors within the hematopoietic system may underscore their specific regulatory roles during differentiation.

The expression of Helios at the sites where HSCs arise suggest that this gene is an important regulators of the earlier stages of hematopoietic development. Hematopoietic progenitors accumulate in the yolk sac at day 8 and the fetal liver in day 11. Both Ikaros and Helios are expressed in similar numbers of cells in these regions at early states. As gestation continues these sites are increasingly populated by more committed erythroid progenitors as well. While Ikaros expression increases in both sites, Helios was only expressed in a limited number of cells. This may reflect its preferential expression in the less committed hematopoietic progenitors in the embryo. The expression of Helios in sorted hematopoietic cells in the adult supports this interpretation. Helios is expressed in adult HSC's but its expression decreases in the maturing erythroid, macrophage and B-lymphocyte lineages. Helios expression peaks in the early stages of T-cell development and decrease as T cells mature in the thymus and are exported to the periphery. Significant levels of Helios are maintained in only a small subset of mature T-cells. Upon immunization, Helios is detected in a very small number of cells in germinal centers of the spleen. When compared with that of Ikaros and Aiolos, this profile of Helios expression suggests that transcriptional complexes including Ikaros and Helios will predominate in the earlier stages of hematopoiesis. This combination may be important for the self-renewing capacity of early progenitors that is compromised in the Ikaros DN homozygous mice. The increasing expression of Aiolos and Ikaros as development proceeds may lead to complexes that promote lineage progression and differentiation.

While Ikaros and Aiolos are predominately expressed in the hematopoietic system, Helios is also expressed elsewhere in the embryo. Based on this observation, it likely that the Ikaros gene family regulates lineage progression on other tissues as will. The dynamic expression of Helios in the embryo is consistent with such a role. Mutational analysis of the Helios gene will help to dissect its role in regulating progenitor development in the hematopoietic system and elsewhere in the embryo.

Example: Helios Forms Homodimers and Heterdimerizes with Ikaros and Aiolos

The C-terminal zinc fingers of Ikaros and Aiolos, shown to mediate their homo- and heterodimerization, are highly conserved in Helios. Helios-specific polyclonal antibodies were generated to study the interactions between the Helios isoforms and the Ikaros and Aiolos proteins. Generation of Helios-specific polyclonal antibodies was carried out as follows. The region between the N- and C-terminal zinc fingers of Helios was amplified by PCR and cloned in frame into a pRSET vector (Invitrogen, Carlsbad, Calif.). The protein was expressed in BL21 *E. coli* and denatured protein was purified on a nickel affinity column as recommended by the manufacturer (Invitrogen, Carlsbad, Calif.). Rabbit polyclonal antibodies raised to this protein were affinity purified by pH elution. Specificity of this antibody for Helios and not other Ikaros homologs was confirmed by Western blot analysis of protein extracts from transfected 293T cells and by immunofluorescence of transfected cells. For Western analysis, protein lysates were taken up in 1× Laemmli sample buffer, heated at 95° C. for 15 minutes and resolved on a 10% SDS-PAGE gel. Resolved proteins were transferred to an Immobilon-P membrane that was probed with the affinity purified polyclonal Helios antibodies (1/500 dilution in PBS, 0.05% TWEEN-20). To detect Helios in primary cells, signal was amplified by incubation of the filter with a 1/5000 dilution of biotinylated Goat α-rabbit antibody followed by the same dilution of peroxidase coupled streptavidin (Jackson labs). The ECL kit (Amersham, Uppsala, Sweden) was used for detection.

The antibody generated against Helios recognized the two Helios isoforms in thymocyte nuclear extracts from wild type, Ikaros null, and Ikaros DN+/− mutant mice. The Helios isoforms detected in thymocytes were approximately 64 and 68 kDa, and co-migrated with the proteins produced by the Hel-1 and Hel-2 cDNAs when co-expressed in the epithelial cell line 293T.

To determine whether Helios physically interacts with Ikaros in primary cells, we used cell lysates from the thymuses of mice transgenic for an epitope-tagged (FLAG) tagged Ik-7 isoform expressed from the CD2 minigene. Ik-7 was the predominant isoform produced by the Ikaros DN mutant locus and lacks the DNA binding domain, but has intact C-terminal dimerization zinc finger motifs. Complexes were immunoprecipitated from thymic whole cell lysates using a mouse monoclonal antibody specific for the FLAG epitope. Western blot analysis using the Helios polyclonal antibody revealed the presence of both Helios isoforms in the immunoprecipitated complexes. Thus, the Ikaros DN protein formed a stable protein complex with Helios protein isoforms and may interfere with their normal activity in vivo.

To examine more closely the ability of Helios isoforms Hel-1 and Hel-2 to form dimers with self, as well as with Ikaros and Aiolos, these factors were transiently expressed in 293 T cells in pairwise combinations. Transient expression of Ikaros and Aiolos in 293T cells was carried out as follows. Full length Hel-1 or the Hel-2 isoforms were amplified by PCR from thymocyte cDNA using primers generated to the 5' or 3' ends (5' AATTGAATTCATGCACT-GCACTTTGACTATGG (SEQ ID NO:96) and 3'R: TTTTC-CTTTTGCGGCCGCATGTCGCCATCCGAGGGAAGG (SEQ ID NO:97) and cloned into the CDM8 mammalian expression vector between the EcoRI and Not1 sites (CDM8-Hel-1, CDM8-Hel-2). Additional constructs were generated having the FLAG or hemagglutanim (HA) tags (FLAG-Hel-1, FLAG-HEl-2, HA-HEl, HA-Hel-2). The clones were sequenced to confirm no mutations were introduced and that they were in frame with epitope tags. 293T cells were transfected with 10 μg of each cDNA. After two days, cells from each 10 cm plate were harvested in 0.5 ml lysis buffer, 10 μl of extract was used to confirm expression of each protein by Western blot analysis, and 100 μl of extract precleared with protein G-agarose followed by immunoprecipitation with anti-FLAG M5 affinity gel. After washing, beads were resuspended in 2× Laemmli sample buffer and incubated for 15 minutes at 95° C. The beads were spun down and one third of the supernatant was resolved on a 10% SDS-PAGE gel. Western blot analysis was carried out as described above except that for 293T extracts, incubation with affinity purified polyclonal antibodies specific for Ikaros or Helios was followed by incubation with peroxidase coupled Goat-α-rabbit secondary antibody. For immunoprecipitation from primary cells, thymocyte or splenocyte were obtained for transgenic mice expressing the FLAG-tagged dominant negative mutant Ikaros isoform Ik-7 from the CD2 minigene. Cells were harvested and washed in PBS/2% FCS. Protein extracts were prepared by lysis of $1\times10^7$ cells per 100 µl lysis buffer.

As mentioned above, to determine whether Helios isoforms Hel-1 and Hel-2 can form dimers with self, as well as with Ikaros and Aiolos, these factors were transiently expressed in 293 T cells in pairwise combinations. One protein in each expressed pair was epitope tagged (FLAG). After two days, cell lysates were prepared and Western blot analysis confirmed protein expression using antibodies specific for each of the Helios, Ikaros and Aiolos proteins. An antibody to the epitope tag (anti-FLAG) was used to immunoprecipitate complexes from 293T cell lysates, and precipitated complexes were analyzed for protein interactions using Ikaros or Helios specific antibodies. The anti FLAG antibody co-precipitates both FLAG-Hel-1 and Hel-2, demonstrating that the two isoforms can dimerize. A similar strategy was used to study Helios, Ikaros and Aiolos interactions. FLAG-Hel-1 or FLAG-Hel-2 were co-expressed with Ik-1. The anti-FLAG antibody brought down IK-1 in an immunoprecipitated complex in both cases. To control for the specificity of the Helios/Ikaros protein interactions, the IkM1 (Ik-1 mutant) was also used in these assays. IkM1 encodes two point mutations in the C-terminal zinc fingers of Ikaros that disrupt the ability to dimerize. In contrast to Ik-1, this dimerization deficient form of Ikaros was unable to interact with either Helios isoform. Finally, cells were co-transfected with FLAG-Aiolos and either Hel-1 or Hel-2 to show that each Helios isoform can form heterodimers with Aiolos. These studies show that the C-terminal zinc fingers in Helios, Ikaros and Aiolos are functionally conserved and mediate the stable interactions between these proteins which may be critical for hematopoiesis as well as lymphocyte differentiation and function.

Example: Helios is Part of a Higher Order Nuclear Structure that Contains Ikaros and Aiolos Our studies with Ikaros and Aiolos have shown that these proteins are part of a higher order structure in resting lymphocytes that undergoes dramatic changes upon activation. To determine whether Helios also participates in these nuclear macromolecular structures we examined its subcellular localization in primary lymphoid cells by confocal immunofluorescence microscopy. Primary thymocyte or splenocyte were obtained. Thymocyte were activated for 40 hours on plated precoated with 20 µg/ml CD3. Cells were harvested and washed in phosphate buffered saline (PBS). $1\times10^5$ cells were cytospun per slide and fixed 4% paraformaldehyde, 0.5% TWEEN in PBS at 4° C. and then washed in PBS. Prior to antibody incubation, cells were blocked for 1 hour in 3% BSA, 1% goat serum, 1% donkey serum in PBS. Slides were then incubated with 1/50 dilution of primary affinity purified a Helios antibody in blocking buffer overnight at 4° C., followed by a 60 min. incubation at room temperature with 5 ng/µl biotinylated goat α-rabbit 1 gG followed by a 60 min. incubation at room temperature with 5 ng/µl biotinylated goat a rabbit IgG (Jackson labs). Each antibody incubation step was followed by 3 washes in PBS. A 45 min. incubation with 5 ng/1 µl avidin-FITC (Southern Biotechnology Associates) in 1% dialyzed FCS/3% BSA in PBS was done for detection. For double staining, an overnight 4° C. incubation with affinity polyclonal Aiolos directly couple to the Alexa 568 flourophore (Molecular Probes) was done as the final step. For triple staining of Helios, Aiolos and the FLAG tagged IK-7 in cells from transgenic mice, were additionally incubated for 60 minutes at RT with 5 ng/1 µl of an anti-FLAG M5 monoclonal antibody (Kodak, washed and then incubated for 60 minutes with a 5 ng/µl Cy5 coupled goat anti-mouse antibody. Specific staining was visualized by confocal immunofluorescence microscopy.

Resting or activated thymocytes and splenocytes isolated from wild-type mice were prepared for these confocal studies. In contrast to Ikaros and Aiolos, bright staining for Helios was detected only in a small number of either resting or activated thymocytes (approximately 1 in 25 cells). In these few cells, Helios was detected in a punctate pattern within the nucleus, similar to that previously described for Ikaros and Aiolos. Upon thymocyte activation, Helios was redistributed into ring like structures in the nucleus, as are Ikaros and Aiolos. Helios was also detected in a very small number of splenocytes. The cells are likely to be T or NK cells, as RT-PCR analysis indicated that Helios was not expressed at significant levels in mature B cells, myeloid or erythroid cells.

To determine potential co-localization of these proteins in higher order structures, splenocytes were double stained for Aiolos and Helios. Although most cells in the spleen express Aiolos, a small subset of splenocytes express Helios as well. In most cases, there is complete overlap of these two proteins in a punctate pattern with the nucleus. However, there are a few small spots where either Helios or Aiolos is detected alone. In addition, a few cells were observed that showed bright staining for Helios, but only faint staining for Aiolos. Cells stained for Ikaros and Helios showed a similar co-localization of the proteins.

To further investigate the nuclear localization of Helios with Ikaros and Aiolos, T cells from the spleen of mice expressing the FLAG-Ik-7 transgene were used. The FLAG-epitope was utilized in triple staining studies to examine the localization of Ik-7 with the endogenous Helios and Aiolos proteins. In cells of young animals, these three proteins co-localize within nuclear structures, similar to that observed in wild type cells.

These studies establish the presence of all three family members in the same structures within the nucleus and demonstrate that Ikaros DN mutant proteins have the potential to interfere with the activity of the endogenous Helios and Aiolos proteins by co-localization within the same macromolecular nuclear structures. As inferred from the expression profiles of sorted cells, this immunofluorescence data also confirms the co-expression of different Ikaros family proteins in varying combinations within cells of distinct sub-populations in the thymus and spleen.

Example: Helios Can Function as Transcriptional Activator

Ikaros and Aiolos have been shown to function as positive transcriptional regulators upon ectopic expression in mammalian cells. The transcriptional activation domains of both proteins were identified using yeast one hybrid assays, and they were found to function similarly in mammalian cells. Helios protein exhibits conservation to the transcriptional activation domain of Ikaros and Aiolos. Given the near identity in the DNA binding domain between Helios and Ikaros, we tested the ability of Helios to activate transcription from Ikaros binding sties. The expression of a reporter gene under the control of four high affinity Ikaros binding sites (IkBS2) was tested in the presence of Helios or Ikaros in NIH3T3 cells. Both proteins were shown to increase expression of the reporter gene over background levels (FIG. 3). A five fold increase was detected in the presence of Helios while a 7.8 fold increase was detected in the presence of Ikaros. This transcriptional activation mediated by Helios requires the Ikaros consensus binding sites. These results confirm the functional conservation of both the DNA binding and transcriptional activation domains.

The present invention identifies and characterizes Helios, a new member of the Ikaros gene family. The proteins encoded by all three genes in the Ikaros family share grossly similar properties mediated by conserved functional domains. All three bind to the consensus DNA binding sites characterized for Ikaros and activate transcription form an adjacent promoter in co-transfection assays. Like Aliolos and Ikaros, Helios can dimerize with itself as well as other family members including a dominant negative isoform of Ikaros. Although the conservation of these domains emphasizes the similarity of these proteins, other regions differ between the proteins encoded by these genes and may confer functional specificity among them. The fact that the regions that diverge between family members are conserved in the orthologues of these genes in other species supports their functional significance.

The preferential expression of Helios in the earliest stages of the hemopoietic lineages suggests that gene may exert its predominant function in early progenitor cells. The facts that a dominant negative Ikaros protein causes defects in the HSC and that Helios is the only identified target of this protein expressed at this stage of the lineage imply a crucial role for Helios in HSC development. The expression of Helios outside the hemopoietic system may indicate a role for the Ikaros gene family in progenitor development in other tissues as well.

Detailed Description of Dedalos

Overview

Ikaros, and the related proteins Aiolos and Helios, regulate the development and differentiation of the hematopoietic stem cell (HSC) and its progeny in the lymphoid lineage. Daedalos, another member of the Ikaros gene family, is transiently expressed in the developing central nervous system (CNS) and is downregulated upon terminal differentiation. Expression of Daedalos was also observed in regions of the adult brain that harbor neural stem cells. Forced expression of Daedalos in the Xenopus embryo did not affect specification of the neurogenic region but prevented neuronal differentiation. The neuronal differentiation of PC12 cells in response to NGF was also blocked by forced expression of Daedalos. However, no effects on the behavior of PC12 cells were observed when they are maintained as cycling populations.

Cloning of the Daedalos cDNA

A fourth member of the Ikaros gene family, designated Daedalos, was cloned using PCR with degenerate primers (Morgan et al. (1997) EMBO J. 16:2004; Honma et al. (1999) FEBS Letters 447:76). PCR amplification was performed as follows. 40 cycles (95°, 30 seconds; 45°, 1.5 minutes; 72°, 2 minutes) were carried out in a Pfu buffer containing 3 mM MgSO$_4$, using degenerate primers designed from conserved regions of the murine Ikaros family of proteins:

```
DEG 10
(TG (T/C)AA(T/C)CA(A/G)TG(T/C)GGIGCI(T/A)CITT
(T/C)AC; SEQ ID NO:50)
``` and

```
DEG 12
(TG(G/A)CAICCCAT(G/A)TGIATIGT(G/A)(T/A)ACAT;

SEQ ID NO:51).
```

This resulted in the amplification of a 900 base pair product. 3'and 5' RACE (Marathon, Promega) were employed to clone the remaining coding sequences for each transcript as well as the 5'and 3'UTRs.

Daedalos cDNAs encode a protein highly homologous to the other Ikaros family members. The four N-terminal zinc fingers that mediate DNA binding and the two C-terminal fingers required for homo and heterodimerization between family members (Sun et al. (1996) EMBO J. 15:5358) are nearly identical in all four proteins (FIGS. 17A and 17B). Several other domains shared between Ikaros, Aiolos and Helios are conserved in Daedalos as well, although Daedalos is less similar to the other three than they are to each other (FIG. 17B).

Expression Patterns of Daedalos

In situ analysis performed during mouse embryogenesis revealed that Daedalos is the first member of the Ikaros family whose expression is detected in the neural plate at moderate levels by Day 7.5 of gestation. In contrast, Daedalos is not detected at similar levels until Day 11 of gestation, at which time it is expressed in the rostral neural tube and spreads caudally as the spinal chord develops. A cross-sectional view through the neural tube reveals that Daedalos expression is highest in cells that have migrated from the ventricular zone. In late gestation, Daedalos expression was detected in much of the developing CNS, but expression declined in most regions shortly after birth. In addition to expression in the CNS, Daedalos was also detected by in situ hybridization in some neural crest derivatives during embryogenesis, including a subset of cells in the developing dorsal root ganglia (DRGs) and adrenal medulla. Consistent with this pattern of expression in vivo, Daedalos mRNA was also detected in melanocyte cell lines and in PC12 and n-tera 2 cells which have neurogenic potential.

This pattern of expression during embryogenesis suggests a function for Daedalos in neurogenesis. Features of the Daedalos expression pattern in the adult CNS support this conclusion and suggest Daedalos expression identifies a persisting progenitor population. Expression is maintained in regions of the adult brain where neurogenesis continues throughout adult life (Luskin et al. (1993) Neuron 11:173; Palmer et al. (1997) Mol. Cell. Neurosci. 8:389), including the dentate gyrus of the hippocampus and the periventricular region of the forebrain which gives rise to interneurons that populate the olfactory bulb. Daedalos expression was detected in the ependymal layer lining the ventricles and in the adjacent subependymal zone, regions from which neural stem cells have been isolated in the adult (Chiasson et al. (1999) J. Neuroscience 19:4462; Corotto (1993) Neurosci Letter 149:111; Johansson et al. (1999) Cell 96:25). While it is uncertain whether neural stem cells reside in the ependymal region, the subependymal zone, or both, in vivo (Temple (1999) Curr. Biol. 9:R397), the expression of Daedalos in a subset of these cells could identify either neural stem cells or their recently generated progeny.

The expression patterns of the Ikaros family in the nervous system is formally analogous to that observed in the hematopoietic system, where differential expression of the family members occurs as cells proceed through the lineages, regulating expansion and differentiation of progressively committed progenitors (Kelley et al. (1998) Curr Biol. 8:508). In the nervous system, Daedalos expression was found to correlate with an intermediate step in neurogenesis, first appearing after neural plate formation, then predominating in cells that have migrated from the periventricular regions, and expression ultimately being extinguished in regions where terminal differentiation has occurred. This expression pattern suggests one or more of the following possibilities: (1) Daedalos expression is activated as a consequence of progression down the neural lineage; (2) Daedalos expression contributes to the maintenance of neural progenitors in an undifferentiated state; and (3) the subsequent suppression of Daedalos expression is required for terminal differentiation to occur.

Modulation of Daedalos Expression In Vitro

To test these possibilities described above directly, two types of experiments were performed, the effects of which were measured: (1) ectopically expressing Daedalos mRNA in a cell; and (2) maintaining the expression of Daedalos in a cell after the time when its expression would normally be extinguished.

Injection of RNA into *Xenopus* embryos was performed to alter Daedalos expression. Spatially restricted expression of transcription factors confers neurogenic potential on dorsal ectoderm, and a hierarchy of transcription factors, influenced by Notch-mediated lateral inhibition, dictates the neuronal differentiation of a subset of these cells. The expression of neurogenin-lb (Ma et al. (1996) Cell 87:43) and xDelta-1 (Chitnis et al. (1995) Nature 375:761) serve as markers of successive steps in neural commitment while expression of neuron specific tubulin 25 (n-tubulin) identifies differentiating neurons (Chitnis (1999) Curr. Opinion Neurobiol. 9:18).

Partial cDNAs derived from a *Xenopus* orthologue of Daedalos were cloned by PCR with degenerate primers. The cDNA ends were then identified by RACE, which provided the requisite information for subsequent recloning of the entire coding region from *Xenopus* embryo mRNA (FIG. 17C). 80% of the residues in the *Xenopus* Daedalos protein are identical to those in the mouse Daedalos protein, although some regions of the mouse protein are absent in the *Xenopus* protein (FIG. 17C). While the functional significance of these absent regions has not been explored, they correspond to segments of the mouse Daedalos that are not conserved among other murine paralogues.

PCR analysis of Daedalos transcripts confirmed that they are expressed from stage 11 while primary neurogenesis is occurring. Total RNA was prepared from 100 *Xenopus laevis* embryos at stage 11 or 12 and 2 micrograms were reverse transcribed. 165 nanograms of cDNA products (16.5 ng for histone H-4) were amplified in the presence of 1.5 µCi each of [P32] dATP and [P32] dCTP using the following primer pairs:

```
histone H-4 (20 cycles, using primers
5'-AGGGACAACATCCAGGGCATCACC      (SEQ ID NO:47)
and

3'-ATCCATGGCGGTAACGGTCTTCCT;     (SEQ ID NO:48))

XDaedalos (31 cycles, using primers
5'-ATTCTGTAACTACGCTTGTCGTCG      (SEQ ID NO:49)
and
3'-AACAATIGCCATAAGCAGTGTCCA;     (SEQ ID NO:50))
```

-continued
and

```
neurogenin-1b (28 cycles, using primers
5'-CATATTGGTACAGGACTCCTATCC      (SEQ ID NO:51)
and

3'-CTTGACCCTTATGGGAAGCAGGAA.     (SEQ ID NO:52))
```

The number of cycles employed were in the range for linear amplification of each target. The products were separated on a 5% polyacrylamide gel and quantitated on a phosphoimager (Molecular Dynamics). Input cDNA levels were corrected to achieve similar histone H-4 content.

For these experiments, capped mRNA was prepared using the mMessage mMachine (Ambion) and linearized templates for b-gal or full length *Xenopus* Daedalos coding sequence in the RN3 vector. Approximately 50 pg per embryo were injected in a volume of 6 nl.

Injection of RNA encoding *Xenopus* Daedalos into *Xenopus* embryos at the two cell stage did not result in any ectopic expression of either n-tubulin (n=100) or the earlier markers of the neurogenic lineage, neurogenin 1b (n=47) or Delta-1 (n=47), in cells normally fated to become lateral ectoderm. Thus, Daedalos was found to be insufficient to convert presumptive epidermis to a neurogenic fate.

The maintenance of Daedalos expression within the neurogenic region was found to lead to unilateral suppression of neuronal differentiation, which was revealed by suppression of n-tubulin expression. N-tubulin expression was repressed in cells containing injected RNA. These cells were identified by detection of the activity encoded by co-injected b-galactosidase (b-gal) mRNA. Reduced n-tubulin expression was not observed in embryos injected with b-gal tracer alone. Although Daedalos consistently repressed the expression of this terminal differentiation marker, both neurogenin-lb and Delta-1 transcripts could be found in cells harboring the exogenous Daedalos mRNA in both day 61 and day 73 embryos. While the expression of these markers was normal in the majority of the injected embryos, there were some alterations of their expression patterns in many of the injected embryos. 38% of the injected embryos showed some alteration of neurogenein expression, while 50% of the injected embryos showed some difference in expression of Delta-1 between the injected and uninjected sides. The normal expression patterns of these markers are quite dynamic and they are sensitive indicators of alterations in developmental rate. While forced expression of Daedalos does not prevent expression of these neurogenic markers, the variable effects on their expression in some cells may reflect interference with, or abnormal progression through, early steps in the neural lineage caused by heterochronic or overexpression of Daedalos in these cells.

These results suggest that Daedalos expression does not dictate a pro-neural fate but rather is activated as a consequence of the adoption of that fate. Furthermore, it suggests that the down regulation of Daedalos expression, normally observed during neuronal differentiation, is a required step in this process. To investigate this possibility further, the effects of forced Daedalos expression in a pheochromocytoma cell line, PC12, were examined. These cells can be maintained as an undifferentiated proliferating population, possessing characteristics of adrenal chromaffin cells. Alternatively, PC12 cells can be induced by the addition of NGF to the culture media to undergo differentiation to a cell type having neuronal characteristics (Greene et al. (1976) Proc. Natl. Acad. Sci. USA 73:2424). Thus PC12 may be used to assess the effects of maintained Daedalos expression on this specific step in neuronal differentiation. Similar to what was observed with both neural progenitors and adrenal chromaffin cells in vivo, PC12 cells express Daedalos mRNA when maintained in growth media. In these experiments, PC12 cells ($1\times10^5$ cells/well) were seeded on laminin-coated 12-well dishes (Sumitomo Bakelite Co., Akita, Japan) and cultured with DMEM (Gibco BRL, 23700-040) supplemented with 5% fetal bovine serum (Sanko Junyaku Co., Tokyo, Japan) and 5% horse serum (Gibco BRL). Neurite induction was induced by addition of 25 ng/ml of NGF (Sigma).

PC12 cells were subcloned to generate more homogeneous populations and were then transfected with either (1) a plasmid containing the coding sequences of Daedalos driven by a constitutively active promoter or (2) a vector alone. Four independent lines for each treatment were subcloned under growth conditions on selective media, and the increased expression of Daedalos mRNA in lines harboring the Daedalos expression construct was confirmed by Northern hybridization. No difference in the frequency of recovered clones or their rate of growth was observed between the experimental and control populations and the morphology of clones expressing the transfected Daedalos cDNA was indistinguishable from controls in growth media (FIGS. 18A and 18B). Thus, forced expression of Daedalos had no discernible effect on these cells while they are maintained as proliferating "progenitors". However, after 3 days in culture in media containing NGF, the control cell populations had extended an extensive arbor of neurites, while the Daedalos expressing subclones had few if any neurites after 3 days and failed to develop them over an additional 2 weeks in culture (FIGS. 18C and 18D). Thus, the repression of Daedalos expression that normally occurs during neuronal differentiation appears to be a necessary step for the conversion to a neuronal morphology in the PC12 cell line.

Methods of Detection

The invention provides methods for detecting a neural cell based upon the cell's expression of Daedalos. Daedalos has been shown to be expressed at significant levels in neural progenitor cells and to be absent or expressed at reduced levels in differentiated neural cells. By exploiting these expression patterns of Daedalos, methods can be devised for the detection of neural cells.

In one embodiment, Daedalos is detected in a cell sample, thereby permitting the identification of the cell sample as containing a neural progenitor cell and/or as containing committed neural cells. The cell sample can be analyzed in vitro or in vivo and the cell sample can be derived from any of the body's tissues, e.g., neural tissue. The cell sample can include neural and/or non-neural cells.

Daedalos expression can be detected by a variety of techniques known in the art. For example, Daedalos mRNA produced by a cell can be detected by, e.g., hybridization techniques or by PCR. Either of these techniques can use a detectable label attached to a nucleic acid probe. Additionally, Daedalos protein produced by a cell can be detected by, e.g., using an antibody, optionally including a detectable label, that binds to the Daedalos protein.

These methods of detection can be extended to include methods of separating one cell type from another based upon the presence or absence of Daedalos expression. For example, a neural progenitor cell can be identified based upon its expression of Daedalos and can then be separated from other cells in a cell sample having reduced Daedalos expression. This allows for the separation of a neural progenitor cell from other cell types such as differentiated or committed neural cells and non-neural cells.

In another embodiment, the invention provides methods of identifying the stage of neurogenesis of a cell based upon the cell's expression of Daedalos. For example, a cell can be identified as a neural progenitor cell based upon its expression of Daedalos. A cell can be identified as a neural progenitor by either the presence of Daedalos in the cell or by the presence of levels of Daedalos in the cell that are elevated as compared to non-neural progenitor cell populations. In another example, a cell can be identified as a non-neural progenitor cell, e.g., a differentiated or committed cell, based upon its expression of Daedalos. A cell can be identified as a non-neural progenitor cell by either the absence of Daedalos in the cell or by the presence of levels of Daedalos in the cell that are reduced as compared to neural progenitor cells. Expression of Daedalos can be evaluated by methods described herein, e.g., by analysis of Daedalos mRNA or protein. The methods can further include steps of isolating one cell from another based upon their differing stages of neurogenesis.

Methods of Separation

Another aspect of the invention relates to methods of separating cells based upon their expression of Daedalos. These methods can be used to separate neural cell populations, e.g., neural progenitor cells, from other cell populations. For example, in a cell population containing both neural progenitor cells and non-neural progenitor cells, expression of Daedalos can be evaluated and the cells can be divided based upon their expression of Daedalos. In this example, the neural progenitor cell has a higher level of Daedalos expression than does the non-neural progenitor cell. The cell population used for this separation method can be derived, for example, from neural tissue which can include neural cells, non-neural cells, or both. Expression of Daedalos can be evaluated according to this method by using any of the techniques described herein or known in the art, e.g., mRNA or protein analysis, e.g., Western blot immunoassay, immunohistology, fluorescence activated cell sorting (FACS), radioimmunoassay (RIA), fluorescent immunoassay, enzyme linked immunosorbent assay (ELISA), or an immunoassay that uses a solid support, e.g., latex beads.

Diagnostic Methods

Another aspect of the invention relates to diagnostic methods. These methods permit a determination of, based upon expression of Daedalos in a cell of the subject, whether a subject is at risk for (or has) a neural cell related disorder. These methods involve analyzing a cell of the subject, either in vitro or in vivo, to determine the subject's risk for a neural cell related disorder, e.g., a neural cell proliferative disorder.

In one embodiment, expression of Daedalos is evaluated in a cell of the subject, e.g., a cell derived from neural tissue. A subject can be determined to be at risk for a neural cell related disorder based upon an increased expression of Daedalos in a cell of the subject as compared to the level of expression of Daedalos in the same cell type of a subject not at risk for the disorder. Expression of Daedalos can be detected by methods known in the art as described herein, e.g., detection of Daedalos mRNA or of Daedalos protein.

In another embodiment, a subject is determined to be at risk for a neural cell related disorder by detecting an abnormality in a Daedalos gene. For example, a mutation in a Daedalos gene, e.g., a missense mutation, a nonsense mutation, or a mutation in a regulatory region of the gene, can result in a defective or inactive Daedalos protein product that is associated with a neural cell related disorder, e.g., a disorder related to inappropriate proliferation and/or differentiation of neural cells. An abnormality in a Daedalos gene can be detected in a variety of ways, e.g., PCR analysis of genomic DNA or cDNA, restriction fragment length polymorphism analysis, or analysis of a Daedalos protein by gel electrophoresis.

Methods of Treatment

Another aspect of the invention relates to methods of treating disorder, e.g., a neural cell related disorder. Such methods can include modulating the expression of Daedalos in a cell of a subject in vivo or in vitro. The subject can either be at risk for or have a disorder, e.g., a neural cell related disorder. Neural cell related disorders can include disorders associated with neurodegeneration or excessive or unwanted neural cells. For example, neurodegeneration can be the result of disease, injury and/or aging. Neurodegeneration refers to an abnormality of a neural cell including, but not limited to, physical degeneration and/or death of neural cells, abnormal growth patterns of neural cells, abnormal connections between neural cells, and/or under or over production of a substance or substances, e.g., a neurotransmitter, by neural cells. Neurodegenerative disorders can include Parkinson's disease, Alzheimer's disease, ischemic damage such as stroke or spinal chord trauma, epilepsy, or multiple sclerosis. Other neural cell related disorders associated with excessive or unwanted neural cells can include proliferative disorders such as cancer, e.g., neuroma. In one example, the neural cell related disorder is characterized by insufficient neural cell differentiation. In another example, the neural cell related disorder can be characterized by unwanted or excessive neural cell differentiation.

A disorder, e.g., a neural cell related disorder, can be treated by increasing or decreasing the level of Daedalos in a cell of the subject. For example, Daedalos levels can be increased in a cell (in vitro or in vivo) to reduce neural cell differentiation. In addition, agents which promote neural cell proliferation can be used to allow expansion of neural progenitor cells prior to differentiation. Such methods can be used to treat, e.g., neurodegenerative disorders. By increasing Daedalos expression, disorders can be treated that are characterized by excessive or unwanted neural cell differentiation. In other aspects, Daedalos expression levels can be decreased to reduce or inhibit unwanted or excessive neural cell proliferation and/or insufficient neural cell differentiation. Such methods can be used, e.g., to treat neural cell proliferative disorders such as neuroma.

The level of Daedalos in a cell can be increased by a variety of methods, e.g., by administering to a cell: (1) a Daedalos polypeptide, fragment, or analog thereof; (2) a nucleic acid encoding a Daedalos polypeptide, fragment, or analog thereof; or (3) an agent that increases expression of the endogenous Daedalos gene of a cell.

Nucleic acid constructs encoding a Daedalos polypeptide can be used as a part of a gene therapy protocol to deliver nucleic acids encoding either an agonistic or antagonistic form of a Daedalos polypeptide. The invention features expression vectors for in vivo transfection and expression of a Daedalos polypeptide in particular cell types (e.g., neural cells) so as to reconstitute the function of, enhance the function of, or alternatively, antagonize the function of a Daedalos polypeptide in a cell in which the polypeptide is expressed or misexpressed.

Expression constructs of Daedalos polypeptide or Daedalos agonist or antagonists, may be administered in any biologically effective carrier, e.g., any formulation or composition capable of effectively delivering the subject gene to cells in vivo. Approaches include insertion of the subject gene into viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA encoding an Daedalos polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid, as discussed further below.

In addition to viral transfer methods, such as those described herein, non-viral methods can also be employed to cause expression of a Daedalos polypeptide or agonist or antagonist of Daedalos in the tissue of a mammal, such as a human. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes.

In a representative embodiment, the subject can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075).

In clinical settings, the gene delivery systems for the therapeutic Daedalos gene or gene encoding a Daedalos antagonist can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). In a preferred embodiment of the invention, the subject gene is targeted to neural cells.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g., retroviral vectors, the pharmaceutical preparation can comprise one or more cells which produce the gene delivery system.

In addition, the levels of Daedalos expression in a cell can be decreased by various methods known in the art, e.g., antisense, ribozymes, antibodies, small molecule inhibitors, or compounds the suppress expression of the Daedalos gene, as described herein below.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

Administration

An agent which modulates the level of expression of Daedalos can be administered to a subject by standard methods. For example, the agent can be administered by any of a number of different routes including intravenous, intradermal, subcutaneous, oral (e.g., inhalation), transdermal (topical), and transmucosal. In one embodiment, the modulating agent can be administered orally. In another embodiment, the agent is administered by injection, e.g., intramuscularly, or intravenously.

The agent which modulates protein levels, e.g., nucleic acid molecules, polypeptides, fragments or analogs, modulators, and antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a small molecule, Daedalos nucleic acid, polypeptide, or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., PNAS 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Gene Therapy

The nucleic acids described herein, e.g., a nucleic acid encoding a Daedalos described herein, or an antisense nucleic acid, can be incorporated into gene constructs to be used as a part of a gene therapy protocol to deliver nucleic acids encoding either an agonistic or antagonistic form of a Daedalos described herein. The invention features expression vectors for in vivo transfection and expression of a Daedalos molecule described herein in particular cell types so as to reconstitute the function of, or alternatively, antagonize the function of the component in a cell in which that polypeptide is misexpressed. Expression constructs of such components may be administered in any biologically effective carrier, e.g., any formulation or composition capable of effectively delivering the component gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g., a cDNA, encoding a Daedalos described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol. 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

In addition to viral transfer methods, such as those illustrated above, non-viral methods can also be employed to cause expression of Daedalos in the tissue of a subject. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al. (2001) J Invest Dermatol. 116(1): 131–135; Cohen et al. (2000) Gene Ther 7(22):1896–905; or Tam et al. (2000) Gene Ther 7(21):1867–74.

In a representative embodiment, a gene encoding a Daedalos can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g., retroviral vectors, the pharmaceutical preparation can comprise one or more cells which produce the gene delivery system.

Cell Therapy

A Daedalos molecule described herein can also be increased in a subject by introducing into a cell, e.g., neural progenitor cell, neural cell, or non-neural cell, a nucleotide sequence that modulates the production of Daedalos, e.g., a nucleotide sequence encoding Daedalos, a polypeptide or functional fragment or analog thereof, a promoter sequence, e.g., a promoter sequence from a Daedalos gene or from another gene; an enhancer sequence, e.g., 5' untranslated region (UTR), e.g., a 5' UTR from a Daedalos gene or from another gene, a 3' UTR, e.g., a 3' UTR from a Daedalos gene or from another gene; a polyadenylation site; an insulator sequence; or another sequence that modulates the expression of the Daedalos molecule. The cell can then be introduced into the subject.

Primary and secondary cells to be genetically engineered can be obtained from a variety of tissues and include cell types which can be maintained propagated in culture. For example, primary and secondary cells include fibroblasts, glial cells, neural progenitor cells, neural cells, formed elements of the blood (e.g., lymphocytes, bone marrow cells), muscle cells (myoblasts) and precursors of these somatic cell types, keratinocytes, epithelial cells (e.g., mammary epithelial cells, intestinal epithelial cells), endothelial cells. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding a Daedalos, or an agonist or antagonist thereof, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration, all of which are routine in the art.

Transfected primary or secondary cells undergo a sufficient number of doublings to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from a neural disorder is a candidate for implantation of cells producing a Daedalos molecule described herein.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) N. Engl. J. Med. 327:1549; Spencer et al. (1992) N. Engl. J. Med. 327:1541' Widner et al. (1992) n. Engl. J. Med. 327:1556). Dosage values may vary according to factors such as the disease state, age, sex, and weight of the individual.

Methods of Controlling Cell Differentiation

Another aspect of the invention relates to methods of controlling cell differentiation by modulating expression of Daedalos in a cell. The cell can be either a neural cell, e.g., a neural progenitor cell or a committed neural cell, or a non-neural cell. Modulating the expression of Daedalos in a cell can be used to control the neural differentiation of the cell.

In one embodiment, Daedalos expression in a cell is increased, e.g., by treating the cell with a compound that causes increased expression of Daedalos. This increase in Daedalos expression can inhibit or antagonize neural differentiation in a cell. This is desirable, for example, in a cell characterized by excessive neural differentiation or as part of a technique to maintain a population of neural progenitor cells by blocking their differentiation.

Daedalos expression in a cell can be increased in a variety of ways. For example, a Daedalos polypeptide, fragment, or analog thereof can be added to a cell. A peptide can either be applied directly to a cell or a cell can be treated in a manner that allows for a more efficient uptake of the peptide by the cell.

In another example, a nucleic acid encoding a Daedalos polypeptide, fragment, or analog thereof can be added to a cell. Examples of nucleic acids are the nucleic acid vectors described herein for use in gene therapy methods. The nucleic acid can include all or a part of the Daedalos coding region, 5' regulatory sequences such as a promoter (from Daedalos or another gene) and/or an enhancer (from Daedalos or another gene); and/or 3' regulatory sequences such as a 3' untranslated region, e.g., a polyadenylation site.

In another example, a cell can be treated with an agent that increases the expression of the endogenous Daedalos gene of the cell. The agent can be, e.g., a compound that binds a Daedalos promoter or that alters the regulatory sequence of the Daedalos gene.

In another embodiment, Daedalos expression in a cell is decreased, e.g., by treating the cell with a compound that causes decreased expression of Daedalos. This decrease in Daedalos expression can result in enhanced neural differentiation in a cell. This is desirable, for example, in a cell characterized by insufficient neural differentiation and/or unwanted neural cell proliferation, e.g., neuroma or as part of a technique to create a population of differentiated neural cells by encouraging the differentiation of neural progenitor cells.

Daedalos expression can be decreased in a cell in a variety of ways. In one example, a compound can be administered to a cell that causes a decrease in Daedalos expression by binding to a Daedalos nucleic acid sequence. Examples of such compounds include antisense nucleic acid and ribozymes. In another example, a compound can cause a decrease in Daedalos expression by binding to a Daedalos polypeptide. Examples of such compounds include antibodies, small molecules, and peptides. Additionally, a compound can cause decreased expression of Daedalos by reducing expression of an endogenous Daedalos gene in the cell.

In one embodiment, the invention provides methods for obtaining a population of neural progenitor cells. According to these methods, a cell sample is provided, either in vitro or in vivo, containing a neural progenitor cell and the level of Daedalos is increased in the cell sample. Increasing the level of Daedalos expressed in a neural progenitor cell can have various effects, e.g., it may prevent differentiation or cause proliferation of the neural progenitor cell. These methods can also include steps of increasing the level of other compounds in the cell sample, e.g., FGF-2 or EGF. These compounds can cause the proliferation of a neural progenitor cell while Daedalos prevents its differentiation.

Also included in the invention is a method of obtaining a population of neural cells by inhibiting the expression or activity of Daedalos in a neural progenitor cell. Inhibition of the expression or activity of Daedalos in a neural progenitor cell can result in the differentiation of the neural progenitor cell. This method therefore allows for the expansion, in vitro or in vivo, of a population of differentiated, committed neural cells. Expression or activity of Daedalos can be inhibited by treating a cell with a compound described herein. The compound can, e.g., interfere with a Daedalos mRNA, a Daedalos protein, or a Daedalos gene in a cell.

Neural cells, e.g., differentiated neural cells, expanded in vivo or in vitro by the methods described above can be used to treat, for example, neurodegenerative disorders. In one aspect, the neural cells can be expanded in vitro and then introduced into an area of neurodegeneration in a subject. The neural cells can be introduced into a subject by any route of administration which results in delivery of the cells to the desired location in the subject, e.g., direct stereotaxic injection. In another aspect, the methods described above can be used to allow proliferation of neural progenitor cells and/or differentiation in vivo at a site of neurodegeneration.

Transgenic Animals

The invention includes transgenic animals which include cells (of that animal) which contain a Daedalos transgene and which preferably (though optionally) express (or misexpress) an endogenous or exogenous Daedalos gene in one or more cells in the animal.

The Daedalos transgene can encode a mutant Daedalos polypeptide. Such animals can be used as disease models or can be used to screen for agents effective at correcting the misexpression of Daedalos. Alternatively, the Daedalos transgene can encode the wild-type forms of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" Daedalos gene, i.e., a deletion of all or a part of the Daedalos gene.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject Daedalos gene. For example, excision of a target sequence which interferes with the expression of a recombinant Daedalos gene, such as one which encodes an agonistic homolog, can be designed to activate expression of that gene. This interference with expression of the protein can result from a variety of mechanisms, such as spatial separation of the Daedalos gene from the promoter element or an internal stop codon.

Moreover, the transgene can be made so that the coding sequence of the gene is flanked with recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation. See e.g., descriptions of the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694). Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant Daedalos gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g., a recombinase or a prokaryotic protein, is delivered to the tissue and caused to be expressed, such as in a cell-type specific manner. By this method, the Daedalos transgene could remain silent into adulthood until "turned on" by the introduction of the trans-activator.

Also included is a transgenic animal, or a cell or tissue therefrom, having a transgene including a Daedalos control region operably linked to a nucleic acid encoding a detectable marker, e.g., a fluorescent or luminescent marker, e.g., GFP. The detectable marker thus acts as a surrogate for evaluating Daedalos expression in the transgenic animal. For example, if the detectable marker is a fluorescent marker, e.g., GFP, expression of the marker can be detected by confocal microscopy of a tissue, e.g., skin or nerve tissue, of the animal.

Production of Fragments and Analogs

The invention provides the primary amino acid structure of a Daedalos polypeptide. Once an example of this core structure has been provided, one skilled in the art can alter the disclosed structure by producing fragments or analogs, and testing the newly produced structures for activity. Examples of prior art methods which allow the production and testing of fragments and analogs are discussed below. These, or analogous methods can be used to make and screen fragments and analogs of a Daedalos polypeptide having at least one biological activity e.g., which react with an antibody (e.g., a monoclonal antibody) specific for a Daedalos polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc* 3rd *Cleveland Sympos. Macromolecules*, ed. AG Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765[1978]).

Cassette Mutagenesis

Another method for preparing variants, cassette mutagenesis, is based on the technique described by Wells et al. (*Gene*, 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants, e.g., a library of variants which is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to an antibody specific for a Daedalos polypeptide. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370–1371; and Goward et al. (1992) TIBS 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267: 16007–16010; Griffiths et al. (1993) EMBO J 12:725–734; Clackson et al. (1991) Nature 352:624–628; and Barbas et al. (1992) PNAS 89:4457–4461).

A common approach uses the maltose receptor of E. coli (the outer membrane protein, LamB) as a peptide fusion partner (Charbit et al. (1986) EMBO 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387–392), PhoE (Agterberg, et al. (1990) Gene 88, 37–45), and PAL (Fuchs et al. (1991) Bio/Tech 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) Bio/Tech. 6, 1080–1083). Surface proteins of other bacterial species have also served as peptide fusion partners. Examples include the Staphylococcus protein A and the outer membrane protease IgA of Neisseria (Hansson et al. (1992) J. Bacteriol. 174, 4239–4245 and Klauser et al. (1990) EMBO J. 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) PNAS USA 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^{7-10^9}$ independent clones are routinely prepared. Libraries as large as 1011 recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204, 357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of a protein of interest is identified, such as the primary amino acid sequence of Daedalos polypeptide as disclosed herein, it is routine to perform for one skilled in the art to obtain analogs and fragments.

Peptide Analogs of Daedalos

Peptide analogs of a Daedalos polypeptide are preferably less than 400, 300, 200, 150, 130, 110, 90, 70 amino acids in length, preferably less than 50 amino acids in length, most preferably less than 30, 20 or 10 amino acids in length. In preferred embodiments, the peptide analogs of a Daedalos polypeptide are at least about 10, 20, 30, 50, 100 or 130 amino acids in length.

Peptide analogs of a Daedalos polypeptide have preferably at least about 60%, 70%, 80%, 85%, 90%, 95% or 99% homology or sequence similarity with the naturally occurring Daedalos polypeptide.

Peptide analogs of a Daedalos polypeptide differ from the naturally occurring Daedalos polypeptide by at least (but not more than) 1, 2, 5, 10 or 20 amino acid residues; preferably, however, they differ in less than 15, 10 or 5 amino acid residues from the naturally occurring Daedalos polypeptide.

Useful analogs of a Daedalos polypeptide can be agonists or antagonists. Antagonists of a Daedalos polypeptide can be molecules which form dimers with a member of the Ikaros family but which lack some additional biological activity such as transcriptional activation of genes that control neural development. Daedalos antagonists and agonists are derivatives which can modulate, e.g., inhibit or promote, neural maturation and function.

Antisense Nucleic Acid Sequences

Nucleic acid molecules which are antisense to a nucleotide encoding a Daedalos molecule described herein can be used as an agent which inhibits expression of Daedalos. An "antisense" nucleic acid includes a nucleotide sequence which is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequences encoding Daedalos are known. Given the coding strand sequences encoding these proteins, antisense nucleic acids can be designed according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Antibodies

The invention also includes antibodies specifically reactive with a subject Daedalos polypeptide. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject Daedalos polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the Daedalos polypeptide of the invention.

The term "antibody", as used herein, intended to include fragments thereof which are also specifically reactive with a Daedalos polypeptide. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Both monoclonal and polyclonal antibodies (Ab) directed against Daedalos polypeptides, or fragments or analogs thereof, and antibody fragments such as Fab' and F(ab')$_2$, can be used to block the action of a Daedalos polypeptide and allow the study of the role of a Daedalos polypeptide of the present invention.

Antibodies which specifically bind Daedalos polypeptide epitopes can also be used in immunohistochemical staining of tissue samples in order to evaluate the abundance and pattern of expression of Daedalos polypeptide. Anti-Daedalos polypeptide antibodies can be used diagnostically in immuno-precipitation and immuno-blotting to detect and evaluate wild type or mutant Daedalos polypeptide levels in tissue or bodily fluid as part of a clinical testing procedure. Likewise, the ability to monitor Daedalos polypeptide levels in an individual can allow determination of the efficacy of a given treatment regimen for an individual afflicted with disorders associated with modulation of lymphocyte differentiation and/or proliferation. The level of a Daedalos polypeptide can be measured in tissue, such as produced by biopsy.

Another application of anti-Daedalos antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject Daedalos polypeptide can then be detected with antibodies, as, for example, reacting nitrocellulose filters lifted from infected plates with anti-Daedalos polypeptide antibodies. Phage, scored by this assay, can then be isolated from the infected plate. Thus, the presence of Daedalos homologs can be detected and cloned from other animals, and alternate isoforms (including splicing variants) can be detected and cloned from human sources.

Drug Screening Assays

By making available purified and recombinant-Daedalos polypeptides, the present invention provides assays which can be used to screen for drugs which are either agonists or antagonists of the normal cellular function, in this case, of the subject Daedalos polypeptide. In one embodiment, the assay evaluates the ability of a compound to modulate binding between a Daedalos polypeptide and a naturally occurring ligand, e.g., an antibody specific for a Daedalos polypeptide. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

All publications and patents cited in this application are hereby incorporated by reference in their entirety.

Detailed Description of Ikaros

Ikaros Transgenic Animals and Uses Thereof

In one general aspect, the invention features, a transgenic animal, e.g., a mammal, having an Ikaros transgene.

In preferred embodiments, the mammal is a non-human mammal, e.g., a swine, a monkey, a goat, or a rodent, e.g., a rat, but preferably a mouse.

In preferred embodiments, the Ikaros transgene includes an Ikaros transcriptional control region operably linked to a sequence which is functionally unrelated to the Ikaros gene, or which is less than 60%, 50%, 40%, 30%, or 20% homologous with the Ikaros gene. In a preferred embodiment, the sequence functionally unrelated to Ikaros is a sequence encoding a reporter molecule, a nucleic acid encoding a toxin, or a nucleic acid encoding a gene to be placed under the control of an Ikaros regulatory region. Preferably, the sequence functionally unrelated to Ikaros encodes a reporter molecule which can be detected with relative ease, e.g., a protein, e.g., an enzyme, e.g., an enzyme which produces a colored or luminescent product or emission. In particularly preferred embodiments, the reporter gene can be a beta-galactosidase gene, a luciferase gene, a green fluorescent protein gene, an alkaline phosphatase gene, a horseradish peroxidase gene, or a chloramphenicol acetyl transferase gene. Preferably, the reporter product is capable of providing a signal which indicates the activity of the promoter to which it is linked. Preferred reporters are those which luminesce or fluoresce. Preferred reporters can luminesce or fluoresce, in vivo, without the addition of an exogenous substrate. A particularly suitable reporter is green fluorescent protein. Modified variants of green fluorescent protein, e.g., EGFP, EBFP, EYFP, d2EGFP, ECFP, GFPuv are included within the term green fluorescent protein. These variants of GFP are commercially available by Clontech, Laboratories, Inc. Palo Alto, Calif. Furthermore, GFP and variants thereof, are provided in the following references, all of which are incorporated by reference: Chalfie, M. et al. (1994) *Science* 263:802–805; Prasher, D. C., et al. (1992) *Gene* 111:229–233; Inouye, S. & Tsuji, F. I. (1994) *FEBS Letters* 341:277–280; Wang, S. & Hazelrigg, T. (1994) *Nature* 369:400–403; Cody, C. W., et al. (1993) *Biochemistry* 32:1212–1218; Inouye, S. & Tsuji, F. I. (1994) *FEBS Letters* 351:211–214; Heim, R., et al. (1994) *Proc. Natl. Acad. Sci., USA* 91:12501–12504; Yang, T. T., et al. (1996) *Nucleic Acids Res.* 24(22): 4592–4593; Cormack, B. P., et al. (1996) *Gene* 173:33–38; Crameri, A., et al. (1996) *Nature Biotechnol.* 12:315–319; Haas, J. et al, (1996) *Curr. Biol.* 6:315–324; Galbraith, D. W., et al. (1995) *Methods Cell Biol.* 50:1–12; Living Colors Destabilized EGFP Vectors (April 1998) CLONTECHniques XIII(2): 16–17, Living Colors pEBFP Vector (April 1997) CLONTECHniques XII (2):16–17; Heim, R. & Tsien, R. Y. (1996) *Curr. Biol.* 6:178–182; Ormö, et al. (1996) *Science* 273:1392–1395; Mitra, R. D. et al. (1996) *Gene* 173:13–17.

When the Ikaros transgene includes an Ikaros transcriptional control region operably linked to an unrelated sequence, e.g., a sequence encoding a reporter molecule, the transcriptional control region preferably includes one or more Ikaros regulatory elements. Such regulatory elements can include Ikaros promoters, enhancers and/or insulator sequences. The regulatory elements can be 5' regulatory elements, intronic elements and/or 3' regulatory elements of Ikaros. In a preferred embodiment, a DNase I HSS cluster of Ikaros includes the regulatory element and all or a portion of the DNase I HSS cluster is included in the transgene. A DNase I HSS cluster, as used herein, refers to a region of the Ikaros gene which includes more than one DNase I HSS. Preferably, the DNase I HSS cluster includes 2, 3, 4 or 5 DNase I HSS within about 0.001, 0.01, 0.1, 0.2, 0.4, 1, 2, 3, 4 kilobases from each other. Examples of such clusters include the α cluster, the β cluster, the γ cluster, the ε cluster, the η cluster and the θ cluster. These clusters in the murine Ikaros gene are shown in FIG. 27A. When the Ikaros transgene includes a portion of a DNase I HSS cluster, the portion can be, e.g., a region including one or more of the DNase I HSS sites in the cluster. For example, a portion of the ε cluster can include one or two of the three DNase I HSS sites of the ε cluster of the murine Ikaros gene.

In a particularly preferred embodiment, the Ikaros transcriptional control region includes: at least a portion of the β cluster containing a promoter, e.g., an R19 promoter, and/or at least a portion of the γ cluster containing a promoter, e.g., an R10 promoter. In other embodiments, the Ikaros transcriptional control region can include one or more promoter(s), e.g., a promoter from the β cluster and/or the γ cluster, and one or more Ikaros regulatory element(s), e.g., one or more Ikaros regulatory element from the α cluster, the ε cluster, the η cluster and/or the θ cluster. For example, the Ikaros transcriptional control region can include the γ cluster or a promoter-containing portion thereof and the ε cluster or a portion thereof. In other embodiments, the Ikaros transgene can include all or a promoter-containing portion of the β cluster and/or all or a promoter-containing portion from the γ cluster and: all or a portion of the α cluster; all or a portion of the δ cluster; all or a portion of the ε cluster; all or a portion of the ζ cluster; all or a portion of the η cluster; all or a portion of the θ cluster; combinations of two, three, four, or five of the α cluster, the δ cluster, the ε cluster, the ζ cluster, the η cluster, the θ cluster, or portions thereof; all of the α cluster, the δ cluster, the ε cluster, the ζ cluster, the η cluster and the θ cluster, or portions thereof.

In a preferred embodiment: the transgenic animal further includes a second Ikaros transgene having a mutation. In yet more preferred embodiments, the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments, the transgenic animal further includes a second Ikaros transgene having a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments, the transgenic animal further includes a second transgene and the second Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments, the transgenic animal: is heterozygous for an Ikaros transgene, e.g., a mutated Ikaros transgene; homozygous for an Ikaros transgene, e.g., a mutated Ikaros transgene; includes a first Ikaros transgene, e.g., a transgene which includes an Ikaros transcriptional control region and a sequence unrelated to the Ikaros gene, and a second Ikaros transgene, e.g., a mutated Ikaros transgene; includes an Ikaros transgene, e.g., a transgene which includes an Ikaros transcriptional control region and a sequence unrelated to the Ikaros gene, and a second transgene which is other than an Ikaros transgene, e.g., encoding another polypeptide involved in hematopoiesis, e.g., an Aiolos transgene and/or a Helios transgene, e.g., a mutated Aiolos transgene and/or a mutated Helios transgene.

In another aspect, the invention includes a transgenic mouse having a second transgene and the transgene is a mutated Ikaros transgene, the mutation occurring in, or altering, a domain of the Ikaros gene, e.g., a domain described herein, e.g., the mutation is in, or alters, the sequence of a DNA binding domain of the Ikaros transgene.

In preferred embodiments: the mutation is a deletion of one or more nucleotides from the Ikaros transgene; the mutation is a deletion which is in or which includes a portion of exon 3 and/or exon 4 of the Ikaros transgene.

In another aspect, the invention includes a transgenic mouse having a second transgene and the transgene is a mutated Ikaros transgene in which the mutation alters the expression, activation, or dimerization of an Ikaros gene product.

In preferred embodiments: the mutation is a deletion of one or more nucleotides from the Ikaros transgene; the mutation is a deletion which is in or which includes a portion of exon 7 of the Ikaros transgene.

In another preferred embodiment, the transgenic mouse includes an Ikaros transgene which includes an Ikaros transcriptional control region operably linked to a sequence which is functionally unrelated to the Ikaros gene, as described herein, and a second transgene other than Ikaros. For example, the second transgene can encode another polypeptide involved in hematopoiesis, e.g., an Aiolos and/or Helios transgene. Aiolos is described in PCT Publication Number WO 94/06814, published Mar. 31, 1994, Helios is described in PCT Publication Number WO 99/43288, published Sep. 2, 1999, the contents of which are incorporated herein by reference. In a preferred embodiment, the transgene encoding a polypeptide involved in hematopoiesis other than Ikaros is mutated, e.g., as described herein for mutated Ikaros transgenes. For example, when the second transgene encoding a polypeptide involved in hematopoiesis includes a mutation, the mutation can be, or can result from: a chromosomal alteration; any of an alteration resulting from homologous recombination, site-specific recombination, nonhomologous recombination; any of an inversion, deletion, insertion, translocation, or reciprocal translocation; any of a deletion of one or more nucleotides from the gene, an addition of one or more nucleotides to the gene, a change of identity of one or more nucleotides of the gene. In yet other preferred embodiments, when the second transgene encoding a polypeptide involved in hematopoiesis includes a mutation, the mutation can result in: mis-expression of the transgene or of another gene in the animal; mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene.

In another aspect, the invention features a method of evaluating a component or lineage of the immune system, e.g., evaluating development of a component or cell lineage of the immune system, e.g., development of a hematpoietic cell of the immune system. The method includes providing a transgenic animal, or cell or tissue therefrom, having an Ikaros transgene which includes an Ikaros transcriptional control region and a sequence encoding a protein functionally unrelated to the Ikaros gene, e.g., a sequence encoding a reporter molecule, and monitoring expression of the protein unrelated to Ikaros, e.g., monitoring expression of the reporter molecule. Preferably, the Ikaros transcriptional control region includes one or more regulatory element(s) of Ikaros which directs expression of the immune component of interest. Types of development which can be evaluated include, e.g., the ontogeny of a component or cell lineage of the immune system, activation of a component or cell lineage of the immune system, the migration of a component or cell lineage of the immune system, regions of action of a component or cell lineage of the immune system and ways in which components or cell lineages of the immune system interact. Examples of immune system components which can be evaluated include hematopoietic cells of the immune system, e.g., hematopoietic stem cells, multipotent progenitors, oligopotent progenitors (e.g., lymphoid or myeloid progenitors), cells committed to the B-cell lineage, cells committed to the T-cell lineage, cells committed to a myeloid cell lineage (e.g., granulocyte monocyte CFU cells), T-lymphocytes, B-lymphocytes, NK cells, and neutrophils.

Development can be evaluated in a living animal, a dead animal, or a cell or tissue taken from a live or dead animal.

In a preferred embodiment, the protein unrelated to Ikaros is a reporter molecule, e.g., a colored or fluorescent molecule, and the immune system component is monitored on the live animal. Preferably, the method includes detecting a signal, e.g., a fluorescent signal, on the live animal, e.g., using a confocal microscope in order to monitor expression of the immune system component. Methods of monitoring expression of a reporter molecule in a live animal are described in PCT Publication Number WO 99/30743, published Jun. 24, 1999, the contents of which is incorporated herein by reference.

In a preferred embodiment, the transgenic animal, or cell or tissue therefrom, includes a second transgene. Preferably, the second transgene is a sequence encoding a protein involved in hematopoiesis, e.g., the second transgene encodes an Ikaros polypeptide, an Aiolos polypeptide and/or a Helios polypeptide. The second transgene can encode a mutated transgene which results in altered expression of the transgene, e.g., misexpression of the transgene. Examples of such mutations are described herein.

In one embodiment, the transgenic animal, or cell or tissue therefrom, can include both a first transgene which includes an Ikaros transcriptional control region and a sequence encoding a polypeptide unrelated to Ikaros, e.g., a reporter molecule, and a second transgene which encodes a mutated polypeptide involved in hematopoiesis, e.g., a mutated Ikaros transgene, Aiolos transgene and/or Helios transgene. Preferably, the second transgene is altered such that the polypeptide involved in hematopoiesis is misexpressed, e.g., under-expressed or over-expressed as compared to animals which do not have the mutated second transgene. For example, the mutation in the second transgene can result in decreased expression of the polypeptide involved in hematopoiesis, and the effect of decreased expression, if any, on Ikaros expression can be evaluated by the presence or absence of the reporter expression, e.g., as compared to expression in a transgenic animal that does not have the second mutated transgene.

In another aspect, the invention features a method for evaluating the effect of a treatment on a transgenic cell or animal having an Ikaros transgene. The method includes administering the treatment to a cell or animal having an Ikaros transgene, and evaluating the effect of the treatment on the cell or animal. Preferably, the Ikaros transgene includes an Ikaros transcriptional control region and a sequence functionally unrelated to the Ikaros gene, e.g., a sequence encoding a reporter molecule. The effect can be, e.g., the effect of the treatment on the immune system or a component thereof, the nervous system or a component thereof, or the cell cycle. Immune system effects include e.g., T cell activation, T cell development, B cell development, NK cell development, myeloid cell development, and the ratios $CD4^+/CD8^+$, $CD4^+/CD8^-$ and $CD4^-/CD8^+$.

In preferred embodiments, when using a transgenic animal, the transgenic animal is a mammal, e.g., a non-human mammal, e.g., a nonhuman primate or a swine, a monkey, a goat, or a rodent, e.g., a rat, but preferably a mouse. In other preferred embodiments, the transgenic animal is a fish, e.g., a zebrafish; a nemaotde, e.g., *caenorhabditis elegans*; an amphibian, e.g., a frog or an axolotl.

In preferred embodiments, when using a transgenic cell, the transgenic cell is a mammalian cell, e.g., a non-human mammalian cell, e.g., a swine, a monkey, a goat, or a rodent, preferably a mouse, cell. In other preferred embodiments, the transgenic cell is from a fish, e.g., a zebrafish; a nemaotde, e.g., *caenorhabditis elegans*; an amphibian, e.g., a frog or an axolotl.

In other preferred embodiments: the transgenic animal or cell includes a second transgene, e.g., a mutated transgene. The mutated transgene can result, for example, in misexpression of a protein involved in hematopoiesis, e.g., misexpression of Ikaros, Helios and/or Aiolos. In yet more preferred embodiments the second transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments, the second transgene includes a mutation and: the mutation results in mis-expression of the transgene or of another gene in the animal or cell; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene. In a preferred embodiment, the second transgene includes a mutation and: the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments, the second transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments, the transgenic animal or cell: is heterozygous for an Ikaros transgene, e.g., a mutated Ikaros transgene; homozygous for an Ikaros transgene, e.g., a mutated Ikaros transgene; includes a first Ikaros transgene, e.g., a transgene which includes an Ikaros transcriptional control region and a sequence unrelated to the Ikaros gene, and a second Ikaros transgene, e.g., a mutated Ikaros transgene; includes an Ikaros transgene, e.g., a transgene which includes an Ikaros transcriptional control region and a sequence unrelated to the Ikaros gene, and a second transgene which is other than an Ikaros transgene, e.g., an Aiolos transgene and/or a Helios transgene, e.g., a mutated Aiolos transgene and/or a mutated Helios transgene.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; the presence function, or morphology of myeloid cells, e.g., neutrophils, or their progenitors; resistance to infection; life span; body weight; the presence, function, or morphology of tissues or organs of the immune system; the expression of the Ikaros transgene; the ability of a component of the immune system to respond to a stimulus (e.g., a diffusible substance, e.g., cytokines, other cells of the immune system, or antigens); the ability to exhibit immunological tolerance to an alloantigen or a xenoantigen.

In preferred embodiments, the evaluating step includes evaluating the expression of the sequence unrelated to the Ikaros gene, e.g., expression of the sequence encoding a reporter molecule.

In preferred embodiments, the treatment can include: the administration of a drug, chemical, or other substance; the administration of ionizing radiation; the administration of an antibody, e.g., an antibody directed against a molecule or cell of the immune system, e.g., an antibody directed against a T cell, B cell, NK cell, dendritic cell, or thymic cell, an antibody directed against a precursor of a T cell, B cell, NK cell, dendritic cell, or thymic cell, an antibody directed against a cell surface marker of a T cell, B cell, NK cell, dendritic cell, or thymic cell; introduction of a component of the immune system derived from an animal of the same species as the transgenic animal; the introduction of a component of the immune system derived from an animal of a different species from the transgenic animal; the introduction of an immune system component derived from an animal or cell other than the transgenic animal or cell; the introduction of an immune system component which is endogenous, (i.e., it is present in the transgenic animal or cell and does not have to be introduced into the transgenic animal or cell) to the transgenic animal or cell; the introduction of an immune system component derived from an animal or cell of the same species as the transgenic animal or cell; the introduction of an immune system component derived from an animal or cell (of the same species as the transgenic animal) which does not include the transgene; the introduction of an immune system component derived from an immunologically competent animal, or from a cell derived from an immunologically competent animal, of the same species as the transgenic animal or cell; the introduction of an immune system component derived from an animal or cell of a different species from the transgenic animal or cell; the introduction of an immune system component derived from an immunologically competent animal, or from a cell derived from an immunologically competent animal, of a different species than the transgenic animal or cell; administration of a substance or other treatment which suppresses the immune system; administration of a substance or other treatment which activates or boosts the function of the immune system; introduction of a nucleic acid, e.g., a nucleic acid which encodes or expresses a component of the immune system; or the introduction of a protein, e.g., a protein which is a component of the immune system.

In another aspect, the invention features a method for evaluating the effect of a treatment on an immune system component. The method includes: (1) supplying a transgenic cell or animal having an Ikaros transgene; (2) supplying the immune system component; (3) administering the treatment; and (4) evaluating the effect of the treatment on the immune system component.

In preferred embodiments using a transgenic animal the transgenic animal is a mammal, e.g., a non-human mammal, e.g., a nonhuman primate or a swine, a monkey, a goat, or a rodent, e.g., a rat, but preferably a mouse. In other preferred embodiments, the transgenic animal is a fish, e.g., a zebrafish; a nemaotde, e.g., *caenorhabditis elegans*; an amphibian, e.g., a frog or an axolotl.

In preferred embodiments using a transgenic cell the transgenic cell is a mammalian cell, e.g., a non-human mammalian cell, e.g., a swine, a monkey, a goat, or a rodent, preferably a mouse, cell. In other preferred embodiments, the transgenic cell is from a fish, e.g., a zebrafish; a nemaotde, e.g., *caenorhabditis elegans*; an amphibian, e.g., a frog or an axolotl.

In other preferred embodiments: the Ikaros transgene includes a mutation. In yet more preferred embodiments the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments: the immune system component is taken from an animal or cell other than the transgenic animal or cell and is introduced into the transgenic cell or animal; the component is endogenous, to the transgenic animal or cell; the immune system component is taken from an animal or cell of the same species as the transgenic animal or cell and is introduced into the transgenic cell or animal (i.e., it is present in the transgenic animal or cell and does not have to be introduced into the transgenic animal or cell); the immune system component is taken from an animal or cell (of the same species as the transgenic animal) which does not include the transgene and is introduced into the transgenic cell or animal; the immune system component is taken from an immunologically competent animal, or from a cell derived from an immunologically competent animal, of the same species as the transgenic animal or cell and is introduced into the transgenic cell or animal; the immune system component is taken from an animal or cell of a different species from the transgenic animal or cell and is introduced into the transgenic cell or animal; the immune system component is taken from an immunologically competent animal, or from a cell derived from an immunologically competent animal, of a different species than the transgenic animal or cell and is introduced into the transgenic cell or animal.

In preferred embodiments the immune system component is any of an antigen, a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue.

In other preferred embodiments the immune system component is: a nucleic acid which encodes an immune system component, e.g., a cell surface marker, a receptor, or a cytokine; a protein, e.g., a cell surface marker, a receptor, or a cytokine.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusible substance, e.g., cytokines, other cells of the immune system, or antigens); the ability to exhibit immunological tolerance to an alloantigen or a xenoantigen.

In preferred embodiments the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene or an Ikaros transgene.

In preferred embodiments the evaluating step includes evaluating the growth rate of a transgenic cell.

In preferred embodiments the treatment can include: the administration of a drug, chemical, or other substance; the administration of ionizing radiation; the administration of an antibody, e.g., an antibody directed against a molecule or cell of the immune system, e.g., an antibody directed against a T cell, B cell, NK cell, dendritic cell, or thymic cell, an antibody directed against a precursor of a T cell, B cell, NK cell, dendritic cell, or thymic cell, an antibody directed against a cell surface marker of a T cell, B cell, NK cell, dendritic cell, or thymic cell; introduction of a component of the immune system derived from an animal or cell of the same species as the transgenic animal or cell; the introduction of a component of the immune system derived from an animal or cell of a different species from the transgenic animal or cell; the introduction of an immune system component derived from an animal or cell other than the transgenic animal or cell; the introduction of an immune system component which is endogenous, (i.e., it is present in the transgenic animal or cell and does not have to be introduced into the transgenic animal or cell) to the transgenic animal or cell; the introduction of an immune system component derived from an animal or cell of the same species as the transgenic animal or cell; the introduction of an immune system component derived from an animal or cell (of the same species as the transgenic animal) which does not include the transgene; the introduction of an immune system component derived from an immunologically competent animal, or from a cell derived from an immunologically competent animal, of the same species as the transgenic animal or cell; the introduction of an immune system component derived from an animal or cell of a different species from the transgenic animal or cell; the introduction of an immune system component derived from an immunologically competent animal, or from a cell derived from an immunologically competent animal, of a different species than the transgenic animal or cell; administration of a substance or other treatment which suppresses the immune system; or administration of a substance or other treatment which activates or boosts the function of the immune system; introduction of a nucleic acid, e.g., a nucleic acid which encodes or expresses a component of the immune system; the introduction of a protein, e.g., a protein which is a component of the immune system.

In yet another aspect, the invention features a method for evaluating the interaction of a first immune system component with a second immune system component. The method includes: (1) supplying a transgenic cell or animal, e.g., a mammal, having an Ikaros transgene; (2) introducing the first and second immune system component into the transgenic cell or mammal; and (3) evaluating an interaction between the first and second immune system components.

In preferred embodiments, with respect to either the first and/or the second immune system component: the immune system component is taken from an animal or cell other than the transgenic cell or animal and is introduced into the transgenic cell or animal; the component is endogenous, (i.e., it is present in the transgenic animal or cell and does not have to be introduced into the transgenic animal or cell) to the transgenic animal or cell; the immune system component is taken from an animal or cell of the same species as the transgenic animal or cell and is introduced into the transgenic cell or animal; the immune system component is taken from an animal or cell (of the same species as the transgenic animal) which does not include the transgene and is introduced into the transgenic cell or animal; the immune system component is taken from an immunologically competent animal, or from a cell derived from an immunologically competent animal, of the same species as the transgenic animal or cell and is introduced into the transgenic cell or animal; the immune system component is taken from an animal or cell of a different species from the transgenic animal or cell and is introduced into the transgenic cell or animal; the immune system component is taken from an immunologically competent animal, or from a cell derived from an immunologically competent animal, of a different species than the transgenic animal or cell and is introduced into the transgenic cell or animal.

In preferred embodiments the immune system component is any of an antigen, a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, thymic tissue, or other lymphoid tissue and its stroma, e.g., encapsulated lymphoid tissue, e.g., lymph nodes, or unencapsulated lymphoid tissue, e.g., Peyer's patches in the ileum, lymphoid nodules found in the mucosa of the alimentary, respiratory, urinary, and reproductive tracts.

In other preferred embodiments the immune system component is: a nucleic acid which encodes an immune system component, e.g., a cell surface marker, a receptor, or a cytokine; a protein, e.g., a cell surface marker, a receptor, or a cytokine.

In preferred embodiments, the first component is the same as the second component; the first component is different from the second component; the first and the second components are from the same species as the transgenic mammal; the first and the second components are from species different from the species of the transgenic mammal; the first and second components are from different species.

In preferred embodiments, when using a transgenic animal, the transgenic animal is a mammal, e.g., a non-human mammal, e.g., a nonhuman primate or a swine, a monkey, a goat, or a rodent, e.g., a rat, but preferably a mouse. In other preferred embodiments, the transgenic animal is a fish, e.g., a zebrafish; a nemaotde, e.g., *caenorhabditis elegans*; an amphibian, e.g., a frog or an axolotl.

In preferred embodiments, when using a transgenic cell, the transgenic cell is a mammalian cell, e.g., a non-human mammalian cell, e.g., a swine, a monkey, a goat, or a rodent, preferably a mouse, cell. In other preferred embodiments, the transgenic cell is from a fish, e.g., a zebrafish; a nemaotde, e.g., *caenorhabditis elegans*; an amphibian, e.g., a frog or an axolotl.

In other preferred embodiments: the Ikaros transgene includes a mutation. In yet more preferred embodiments, the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments, the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments, the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments, the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments, the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusible substance, e.g., cytokines, other cells of the immune system, or antigens); the ability to exhibit immunological tolerance to an alloantigen or a xenoantigen.

In preferred embodiments, the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene or an Ikaros transgene.

In preferred embodiments, the evaluating step includes evaluating the growth rate of a transgenic cell.

In another aspect, the invention features a method for evaluating the effect of a treatment on an immune system disorder including: administering the treatment to a cell or animal having an Ikaros transgene, and evaluating the effect of the treatment on the cell or animal.

In preferred embodiments, the disorder is: a neoplastic disorder; a lymphoma; a T cell related lymphoma.

In preferred embodiments, when using a transgenic animal, the transgenic animal is a mammal, e.g., a non-human mammal, e.g., a swine, a monkey, a goat, or a rodent, e.g., a rat, but preferably a mouse.

In preferred embodiments, when using a transgenic cell, the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments, the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments, the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments, the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, or a nucleic acid encoding a gene to be placed under the control of an Ikaros regulatory region.

In yet other preferred embodiments, the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments, the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the immune system. The parameter related to the immune system can, e.g., be any of: the presence, function, or morphology of T cells or their progenitors: the presence, function, or morphology of B cells or their progenitors; the presence, function, or morphology of natural killer cells or their progenitors; resistance to infection; life span; body weight; the presence, function, or morphology of tissues or organs of the immune system; the expression of the Ikaros transgene; the ability of a component of the immune system to respond to a stimulus (e.g., a diffusible substance, e.g., cytokines, other cells of the immune system, or antigens); the ability to exhibit immunological tolerance to an alloantigen or a xenoantigen.

In preferred embodiments, the evaluating step includes evaluating the expression of a gene or transgene, e.g., a gene which encodes a component of the immune system, e.g., a cell surface marker, a receptor, or a cytokine; a gene which regulates the expression of a component of the immune system, a gene which modulates the ability of the immune system to function, the Ikaros gene or an Ikaros transgene.

In preferred embodiments, the evaluating step includes evaluating the growth rate of a transgenic cell.

In preferred embodiments, the treatment can include: the administration of a drug, chemical, or other substance; the administration of ionizing radiation; the administration of an antibody, e.g., an antibody directed against a molecule or cell of the immune system, e.g., an antibody directed against a T cell, B cell, NK cell, dendritic cell, or thymic cell, an antibody directed against a precursor of a T cell, B cell, NK cell, dendritic cell, or thymic cell, an antibody directed against a cell surface marker of a T cell, B cell, NK cell, dendritic cell, or thymic cell; introduction of a component of the immune system derived from an animal of the same species as the transgenic animal; the introduction of a component of the immune system derived from an animal of a different species from the transgenic animal; the introduction of an immune system component derived from an animal or cell other than the transgenic animal or cell; the introduction of an immune system component which is endogenous, (i.e., it is present in the transgenic animal or cell and does not have to be introduced into the transgenic animal or cell) to the transgenic animal or cell; the introduction of an immune system component derived from an animal or cell of the same species as the transgenic animal or cell; the introduction of an immune system component derived from an animal or cell (of the same species as the transgenic animal) which does not include the transgene; the introduction of an immune system component derived from an immunologically competent animal, or from a cell derived from an immunologically competent animal, of the same species as the transgenic animal or cell; the introduction of an immune system component derived from an animal or cell of a different species from the transgenic animal or cell; the introduction of an immune system component derived from an immunologically competent animal, or from a cell derived from an immunologically competent animal, of a different species than the transgenic animal or cell; administration of a substance or other treatment which suppresses the immune system; or administration of a substance or other treatment which activates or boosts the function of the immune system; introduction of a nucleic acid, e.g., a nucleic acid which encodes or expresses a component of the immune system; the introduction of a protein, e.g., a protein which is a component of the immune system.

In another aspect, the invention features a method for evaluating the effect of a treatment on the nervous system including administering the treatment to a transgenic cell or an animal having an Ikaros transgene, and evaluating the effect of the treatment on the cell or the animal.

In preferred embodiments, when using a transgenic animal, the transgenic animal is a mammal, e.g., a non-human mammal, e.g., a swine, a monkey, a goat, or a rodent, e.g., a rat, but preferably a mouse.

In preferred embodiments, when using a transgenic cell, the transgenic cell is a mammalian cell, e.g., a non-human mammalian cell, e.g., a swine, a monkey, a goat, or a rodent, preferably a mouse, cell.

In other preferred embodiments: the Ikaros transgene includes a mutation. In yet more preferred embodiments, the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments, the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments, the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments, the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments, the transgenic animal or cell: is heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the nervous system. The parameter related to the nervous system can, e.g., be any of: the presence, function, or morphology of cells (or their progenitors) of a nervous tissue, e.g., neurons, glial cells, brain cells, or cells of the basal ganglia, e.g., cells of the corpus striatum, cells of the substantia nigra; resistance to infection; life span; body weight; the presence, function, or morphology of tissues or organs of the nervous system; the expression of a gene, e.g., the Ikaros transgene.

In preferred embodiments, the evaluating step includes evaluating the expression of a gene or transgene, e.g., a gene which encodes a component of the nervous system, e.g., a cell surface marker, or a receptor, the Ikaros gene, or an Ikaros transgene.

In preferred embodiments, the evaluating step includes evaluating the growth rate of a transgenic cell.

In preferred embodiments, the treatment can include: the administration of a drug, chemical, or other substance; the administration of ionizing radiation; the administration of an antibody, e.g., an antibody directed against a molecule or cell of the nervous system; administration of a substance or other treatment which suppresses the immune system; or administration of a substance or other treatment which activates or boosts the function of the immune system; introduction of a nucleic acid, e.g., a nucleic acid which encodes or expresses a component of the nervous system; the introduction of a protein, e.g., a protein which is a component of the immune system.

In another aspect, the invention features, a method for evaluating the effect of a treatment on a disorder of the nervous system including administering the treatment to a cell or animal having an Ikaros transgene, and evaluating the effect of the treatment on the cell or animal.

In preferred embodiments, the disorder is: related to the presence, function, or morphology of cells (or their progenitors) of a nervous tissue, e.g., neurons, glial cells, brain cells, or cells of the basal ganglia, e.g., cells of the corpus striatum, cells of the substantia nigra; trauma; Alzheimer's disease; Parkinson's disease; or Huntington's disease.

In preferred embodiments, when using a transgenic animal, the transgenic animal is a mammal, e.g., a non-human mammal, e.g., a nonhuman primate or a swine, a monkey, a goat, or a rodent, e.g., a rat, but preferably a mouse. In other preferred embodiments, the transgenic animal is a fish, e.g., a zebrafish; a nemaotde, e.g., *caenorhabditis elegans*; an amphibian, e.g., a frog or an axolotl.

In preferred embodiments, when using a transgenic cell, the transgenic cell is a mammalian cell, e.g., a non-human mammalian cell, e.g., a swine, a monkey, a goat, or a rodent, preferably a mouse, cell. In other preferred embodiments, the transgenic cell is from a fish, e.g., a zebrafish; a nemaotde, e.g., *caenorhabditis elegans*; an amphibian, e.g., a frog or an axolotl.

In other preferred embodiments: the Ikaros transgene includes a mutation. In yet more preferred embodiments, the Ikaros transgene includes a mutation and: the mutation is, or results from, a chromosomal alteration; the mutation is, or results from, any of an alteration resulting from homologous recombination, site-specific recombination, nonhomologous recombination; the mutation is, or results from, any of an inversion, deletion, insertion, translocation, or reciprocal translocation; the mutation is, or results from, any of a deletion of one or more nucleotides from the gene, an addition of one or more nucleotides to the gene, a change of identity of one or more nucleotides of the gene.

In yet other preferred embodiments, the Ikaros transgene includes a mutation and: the mutation results in mis-expression of the transgene or of another gene in the animal; the mutation results in mis-expression of the transgene and the mis-expression is any of an alteration in the level of a messenger RNA transcript of the transgene, the presence of a non-wild type splicing pattern of a messenger RNA transcript of the transgene, or a non-wild type level of a protein encoded by the transgene; the mutation alters the relative abundance of a first Ikaros isoform with respect to a second Ikaros isoform, as compared, e.g., to a wild type animal or to an animal lacking the transgene; the mutation is in, or alters, the sequence, expression, or splicing of one or more of the following exons: exon 1/2, exon 3, exon 4, exon 5, exon 6, and exon 7; the mutation is in, or alters, the sequence, expression, or splicing of a DNA binding domain of, the Ikaros gene or DNA; the mutation is a deletion of portions of exon 3 and/or exon 4; the mutation is alters the expression, activation, or dimerization of an Ikaros gene product; the mutation is a deletion of a portion of exon 7.

In yet other preferred embodiments, the Ikaros transgene includes an Ikaros transcriptional control region operably linked to a sequence which is functionally unrelated to the Ikaros gene, or which is less than 50% homologous with the Ikaros gene, e.g., a nucleic acid encoding a reporter molecule, a nucleic acid encoding a toxin, or a nucleic acid encoding a gene to be placed under the control of an Ikaros regulatory region.

In yet other preferred embodiments, the Ikaros transgene encodes: an Ikaros protein which is a competitive inhibitor or an antagonist of a naturally occurring Ikaros protein; an Ikaros gene genetically engineered, e.g., by deletion of an exon, or by using a sequence which results in expression in a preselected tissue, to encode a specific isoform, or a specific subset of Ikaros isoforms, e.g., the transgene is genetically engineered to express one of mIK-1, mIK-2, mIK-3, mIK-4, mIK-5, hIK-1, hIK-2, hIK-3, hIK-4, or hIK-5.

In preferred embodiments the transgenic animal or cell is: heterozygous for an Ikaros transgene; homozygous for an Ikaros transgene; includes a first Ikaros transgene and a second Ikaros transgene; includes an Ikaros transgene and a second transgene which is other than an Ikaros transgene.

In preferred embodiments, the evaluating step includes determining the effect of the treatment on a parameter related to the nervous system. The parameter related to the nervous system can, e.g., be any of: the presence, function, or morphology of cells (or their progenitors) of a nervous tissue, e.g., neurons, glial cells, brain cells, or cells of the basal ganglia, e.g., cells of the corpus striatum, cells of the substantia nigra; resistance to infection; life span; body weight; the presence, function, or morphology of tissues or organs of the nervous system; the expression of a gene, e.g., the Ikaros transgene.

In preferred embodiments, the evaluating step includes evaluating the expression of a gene or transgene, e.g., a gene which encodes a component of the nervous system, e.g., a cell surface marker, or a receptor, the Ikaros gene, or an Ikaros transgene.

In preferred embodiments, the evaluating step includes evaluating the growth rate of a transgenic cell.

In preferred embodiments, the treatment can include: the administration of a drug, chemical, or other substance; the administration of ionizing radiation; the administration of an antibody, e.g., an antibody directed against a molecule or cell of the nervous system; administration of a substance or other treatment which suppresses the immune system; or administration of a substance or other treatment which activates or boosts the function of the immune system; introduction of a nucleic acid, e.g., a nucleic acid which encodes or expresses a component of the nervous system; the introduction of a protein, e.g., a protein which is a component of the immune system.

The term "Ikaros" as used herein to refer to a gene, a transgene, or a nucleic acid, refers to a nucleic acid sequence which is at least about 50%, preferably at least about 60%, more preferably at least about 70%, yet more preferably at least about 80%, most preferably at least about 90%-100% homologous with a naturally occurring Ikaros gene or portion thereof, e.g., with the nucleic acid sequence of human Ikaros as shown in SEQ ID NO:54 (FIGS. 20A–B) or of mouse Ikaros as shown in SEQ ID NO:53 (FIGS. 19A–C).

As used herein, the term "transgene" refers to a nucleic acid sequence (encoding, e.g., one or more Ikaros proteins), which is inserted by artifice into a cell. The transgene can become part of the genome of an animal which develops in whole or in part from that cell. If the transgene is integrated into the genome it results in a change in the nucleic acid sequence of the genome into which it is inserted. A transgene can be partly or entirely species-heterologous, i.e., the transgene, or a portion thereof, can be from a species which is different from the cell into which it is introduced. A transgene can be partly or entirely species-homologous, i.e., the transgene, or a portion thereof, can be from the same species as is the cell into which it is introduced. If a transgene is homologous (in the sequence sense or in the species-homologous sense) to an endogenous gene of the cell into which it is introduced, then the transgene, preferably, has one or more of the following characteristics: it is designed for insertion, or is inserted, into the cell's genome in such a way as to alter the sequence of the genome of the cell into which it is inserted (e.g., it is inserted at a location which differs from that of the endogenous gene or its insertion results in a change in the sequence of the endogenous endogenous gene); it includes a mutation, e.g., a mutation which results in misexpression of the transgene; by virtue of its insertion, it can result in misexpression of the gene into which it is inserted, e.g., the insertion can result in a knockout of the gene into which it is inserted. A transgene can include one or more transcriptional regulatory sequences and any other nucleic acid sequences, such as introns, that may be necessary for a desired level or pattern of expression of a selected nucleic acid, all operably linked to the selected nucleic acid. The transgene can include an enhancer sequence. The transgene is typically introduced into the animal, or an ancestor of the animal, at a prenatal, e.g., an embryonic stage.

As used herein, an Ikaros transgene, is a transgene which includes all or part of an Ikaros coding sequence or regulatory sequence. Included are transgenes: which upon insertion result in the misexpression of an endogenous Ikaros gene; which upon insertion results in an additional copy of an Ikaros gene in the cell; which upon insertion place a non-Ikaros gene under the control of an Ikaros regulatory region. Also included are transgenes: which include a copy of the Ikaros gene having a mutation, e.g., a deletion or other mutation which results in misexpression of the transgene (as compared with wild type); which include a functional copy of an Ikaros gene (i.e., a sequence having at least 5% of a wild type activity, e.g., the ability to support the development of T, B, or NK cells); which include a functional (i.e., having at least 5% of a wild type activity, e.g., at least 5% of a wild type level of transcription) or nonfunctional (i.e., having less than 5% of a wild type activity, e.g., less than a 5% of a wild type level of transcription) Ikaros regulatory region which can (optionally) be operably linked to a nucleic acid sequence which encodes a wild type or mutant Ikaros gene product or, a gene product other than an Ikaros gene product, e.g., a reporter gene, a toxin gene, or a gene which is to be expressed in a tissue or at a developmental stage at which Ikaros is expressed. Preferably, the transgene includes at least 10, 20, 30, 40, 50, 100, 200, 500, 1,000, or 2,000 base pairs which have at least 50, 60, 70, 80, 90, 95, or 99% homology with a naturally occurring Ikaros sequence.

As used herein, the term "transgenic cell" refers to a cell containing a transgene.

As used herein, a "transgenic animal" is any animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, by way of deliberate genetic manipulation, such as by microinjection or by infection with a recombinant virus. The term genetic manipulation is directed to the introduction of a recombinant DNA molecule. This molecule may be integrated within a chromosome, or it may be extrachromosomally replicating DNA.

The "transgenic animals" of the invention are preferably produced by introducing "transgenes" into the germline of an animal. Embryonal target cells at various developmental stages can be used to introduce transgenes. Different methods are used depending on the stage of development of the embryonal target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *Proc. Natl. Acad. Sci. USA* 82:4438–4442). As a consequence, all cells of the transgenic mammal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a mammal. The developing mammalian embryo can be cultured in vitro to the blastocyst stage. During this time, the blastomeres can be targets for retroviral infection (Jaenich, R. (1976) *Proc. Natl. Acad. Sci. USA* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *Proc. Natl. Acad. Sci. USA* 82:6927–6931; Van der Putten et al. (1985) *Proc. Natl. Acad. Sci. USA* 82:6148–6152). Transfection is easily and efficiently obtained by culturing the blastomeres on a monolayer of virus-producing cells (Van der Putten et al. (1985) *Proc. Natl. Acad. Sci. USA* 82:6148–6152; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1985) *Proc. Natl. Acad. Sci. USA* 82:6927–6931).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *Proc. Natl. Acad. Sci. USA* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a mammal. The ES cells thereafter colonize the embryo and contribute to the germ line of the resulting chimeric animal. For a review see Jaenisch, R. (1988) *Science* 240:1468–1474; Sedivy, J. M. and Joyner, A. L. (1992) "Gene Targeting" (W.H. Freeman and Company, N.Y.) 123–142.

For construction of transgenic mice, procedures for embryo manipulation and microinjection are described in, for example, *Manipulating the Mouse Embryo*, (Cold Spring Harbor Laboratory Press, Cold Spring Harbor, N.Y., 1986). Similar methods are used for production of other transgenic animals. In an exemplary embodiment, mouse zygotes are collected from six-week old females that have been superovulated with pregnant mares serum (PMS) followed 48 hours later with human chorionic gonadotropin. Primed females are placed with males and checked for vaginal plugs on the following morning. Pseudopregnant females are selected for estrus, placed with proven sterile vasectomized males and used as recipients. Zygotes are collected and cumulus cells removed. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of an Ikaros transgene encoding can be performed using standard micromanipulators attached to a microscope. For instance, embryos are typically held in 100 microliter drops of DPBS under oil while being microinjected. DNA solution is microinjected into the male pronucleus. Successful injection is monitored by swelling of the pronucleus. Immediately after injection embryos are transferred to recipient females, e.g., mature mice mated to vasectomized male mice. In a general protocol, recipient females are anesthetized, paralumbar incisions are made to expose the oviducts, and the embryos are transformed into the ampullary region of the oviducts. The body wall is sutured and the skin closed with wound clips.

Transgenic animals can be identified after birth by standard protocols. For instance, at three weeks of age, about 2–3 cm long tail samples are excised for DNA analysis. The tail samples are digested by incubating overnight at 55° C. in the presence of 0.7 ml 50 mM Tris, pH 8.0, 100 mM EDTA, 0.5% SDS and 350 mg of proteinase K. The digested material is extracted once with equal volume of phenol and once with equal volume of phenol:chloroform (1:1 mixture). The supernatants are mixed with 70 ml 3M sodium acetate (pH 6.0) and the nucleic acid precipitated by adding equal volume of 100% ethanol. The precipitate is collected by centrifugation, washed once with 70% ethanol, dried and dissolved in 100 ml TE buffer (10 mM Tris, pH 8.0 and 1 mM EDTA). The DNA is then cut with BamHI and BglII or EcoRI (or other frequent DNA cutter), electrophoresed on 1% agarose gels, blotted onto nitrocellulose paper and hybridized with labeled primers under very stringent conditions in order to discern between wild-type and mutant receptor genes. Alternatively, a ligation chain reaction (LCR) (see, e.g., Landegran et al. (1988) *Science* 241: 1077–1080; and Nakazawa et al. (1944) *Proc. Natl. Acad. Sci. USA* 91:360–364), which is useful for detecting point mutations, can be used to determine the presence of the transgene in the neonate.

The resulting transgenic mice or founders can be bred and the offspring analyzed to establish lines from the founders that express the transgene. In the transgenic animals, multiple tissues can be screened to observe for endothelial cell and parenchymal cell expression. RNA studies in the various transgenic mouse lines will allow evaluation of independence of the integration site to expression levels of the transgene.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of the tissue specificity of expression, e.g., increased or decreased expression (as compared with wild type) in a predetermined cell type or tissue type; a pattern of expression that differs from wild type in terms of the size, amino acid sequence, post-translational modification, or a biological activity of an Ikaros gene product; a pattern of expression that differs from wild type in terms of the effect of an environmental stimulus or extracellullar stimulus on expression of the gene, e.g., a pattern of increased or decreased expression (as compared with wild type) in the presence of an increase or decrease in the strength of the stimulus; or a pattern of isoform expression which differs from wild type.

An Ikaros-responsive control element, as used herein is a region of DNA which, when present upstream or downstream from a gene, results in regulation, e.g., increased transcription of the gene in the presence of an Ikaros protein.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

The terms peptide, protein, and polypeptide are used interchangeably herein.

A peptide has Ikaros activity if it has one or more of the following properties: the ability to stimulate transcription of a DNA sequence under the control any of a δA element, an NFKB element, or one of the Ikaros binding oligonucleotide consensus sequences disclosed herein; the ability to bind to any of a δA element, an NFKB element, or one of the Ikaros binding oligonucleotide consensus sequences disclosed herein; or the ability to competitively inhibit the binding of a naturally occurring Ikaros isoform to any of a δA element, an NFKB element, or one of the Ikaros binding oligonucleotide consensus sequences disclosed herein. An Ikaros peptide is a peptide with Ikaros activity.

"Ikaros antagonists", as used herein, refers to Ikaros isoforms arising naturally or by mutagenesis (including in vitro shuffling) which can inhibit at least one biological activity of a naturally occurring Ikaros protein. In preferred embodiments, the Ikaros antagonist is an inhibitor of: Ikaros-mediated transcriptional activation, e.g., it is a competitive inhibitor of Ikaros binding to Ikaros responsive elements, such as IK-BS1, IK-BS2, IK-BS4, IK-BS5, IK-BS6, IK-BS7, IK-BS8, or IK-BS9; or it is an inhibitor of protein-protein interactions of transcriptional complexes formed with naturally occurring Ikaros isoforms.

As used herein, the term "exon", refers to those gene (e.g., DNA) sequences which are transcribed and processed to form mature messenger RNA (mRNA) encoding an Ikaros protein, or portion thereof, e.g., Ikaros coding sequences, and which, at the chromosomal level, are interrupted by intron sequences. Exemplary exons of the subject Ikaros proteins and genes include: with reference to SEQ ID NO:56 (mIk-1), the nucleotide sequence encoding exon 1/2 (E1/2) corresponding to Met-1 through Met-53; the nucleotide sequence encoding exon 3 (E3) corresponding to Ala-54 through Thr-140; the nucleotide sequence encoding exon 4(E4) corresponding to Gly-141 through Ser-196; the nucleotide sequence encoding exon 5 (E5) corresponding to Val-197 through Pro-237; the nucleotide sequence encoding exon 6 (6) corresponding to Val-238 through Leu-282; the nucleotide sequence encoding exon 7 (E7) corresponding to Gly-283 through Ser-518; with reference to SEQ ID NO:54 (hIk-1), the nucleotide sequence encoding exon 3 (E3) corresponding to Asn-1 through Thr-85; the nucleotide sequence encoding exon 4 (E4) corresponding to Gly-86 through Ser-141; the nucleotide sequence encoding exon 5 (E5) corresponding to Val-142 through Pro-183; the nucleotide sequence encoding exon 6 (6) corresponding to Val-184 through Leu-228; the nucleotide sequence encoding exon 7 (E7) corresponding to Gly-229 through Ser-461. The term "intron" refers to a DNA sequence present in a given Ikaros gene which is not translated into protein and is generally found between exons. The term "gene" refers to a region of chromosomal DNA which contains DNA sequences encoding an Ikaros protein, including both exon and intron sequences. A "recombinant gene" refers to nucleic acid encoding an Ikaros protein and comprising Ikaros exon sequence, though it may optionally include intron sequences which are either derived from a chromosomal Ikaros gene or from an unrelated chromosomal gene. An exemplary recombinant gene is a nucleic acids having a sequence represented by any of SEQ ID NOS:53–59 or 65.

The term "Ikaros responsive element" or "IK-RE", refers to nucleic acid sequences which, when placed in proximity of a gene, act as transcriptional regulatory elements which control the level of transcription of the gene in an Ikaros protein-dependent manner. Exemplary IK-RE, as described below, includes IK-BS1, IK-BS2, IK-BS4, IK-BS5, IK-BS6, IK-BS7, IK-BS8, or IK-BS9.

Ikaros: A Master Regulator of Hemopoietic Differentiation

The Ikaros gene is described briefly here. A more detailed treatment can be found in the copending U.S. patent application referred to above. A hemopoietic stem cell in the appropriate microenvironment will commit and differentiate into one of many cell lineages. Signal transduction molecules and transcription factors operating at distinct check points in this developmental pathway will specify the cell fate of these early progenitors. Such molecules are viewed as master regulators in development but also serve as markers for the relatively poorly defined stages of early hemopoiesis.

In search of a lymphoid restricted transcriptional enhancer, in control of gene expression in early T cells, the Ikaros gene family was isolated, which encode zinc finger DNA binding proteins. In the early embryo, the Ikaros gene is expressed in the hemopoietic liver but from mid to late gestation becomes restricted to the thymus. The only other embryonic site with Ikaros mRNA is a small area in the corpus striatum. In the adult, the Ikaros mRNA is detected only in the thymus and in the spleen (Georgopoulos, K. et al. (1992) *Science* 258:808). The Ikaros gene functions as a transcriptional enhancer when ectopically expressed in non lymphoid cells.

The Ikaros gene plays an important role in early lymphocyte and T cell differentiation. The Ikaros gene is abundantly expressed at early embryonic hemopoietic sites is later on restricted in the developing thymus. The thymus together with the spleen is the prime sites of expression in the adult. This highly enriched expression of the Ikaros gene was also found in early and mature primary T cells and cell lines. This restricted pattern of expression of the Ikaros gene at sites where embryonic and adult T cell progenitors originate together with the ability of the encoded protein to activate transcription from the regulatory domain of an early T cell differentiation antigen supported a determining role in T cell specification.

Differential splicing at the Ikaros genomic locus generates at least five transcripts (Ik-1, Ik-2, Ik-3, Ik-4 and Ik-5) that encode proteins with distinct DNA binding domains. A high level of conservation was found between the human and mouse homologs of the Ikaros gene. The human and mouse Ikaros proteins exhibit nearly 100% identity at their N-terminal zinc finger domain (F1) which was shown to determine the DNA binding specificity of these proteins. In the mouse, differential splicing allows for the distinct combinations of zinc finger modules present in the Ik-1, Ik-2 Ik-3 and Ik-4 isoforms. This differential usage of zinc finger modules in the mouse isoforms establishes the basis of their distinct. DNA binding properties and abilities to activate transcription. Differential splicing of the exons encoding the zinc finger DNA binding modules is also manifested in the human Ikaros gene and generates at least two isoforms homologues of the mouse Ik-1 and Ik-4.

These Ikaros protein isoforms (IK-1, IK-2, IK-3, IK-4, IK-5) have overlapping but also distinct DNA binding specificity dictated by the differential usage of zinc finger modules at their N-terminus. In the mouse isoforms (hereinafter designated "mIk"), and presumably in the human isoforms (hereinafter designated "hIk"), the core binding site for four of the Ikaros proteins is the GGGA motif but outside this sequence their specificity differs dramatically. The mIK-3 protein shows strong preferences for bases at both the 5' and 3' flanking sequences which restricts the number of sites it can bind to. The mIk-1 protein also exhibits strong preference for some of these flanking bases and can bind to wider range of sequences. The mIk-2 protein, the most promiscuous of the three proteins, can bind to sites with just the GGGAa/t motif. Finally, the mIk-4 protein with similar sequences specificity to mIk-1 binds with high affinity only when a second site is in close proximity suggesting cooperative site occupancy by this protein. Given the identity between the human and mouse Ik-1 and Ik-4 DNA binding domains, the human isoforms are expected to bind similar sequences to their mouse homologues and regulate transcription in a similar fashion. This extreme species conservation between these two functionally diverse Ikaros isoforms supports an important role for these proteins in lymphocyte transcription. The C-terminal domain shared by all of the mouse and human Ikaros isoforms is also highly conserved. This portion of the Ikaros proteins contains conserved acidic motifs implicated as transcription activation domains.

The embryonic expression pattern and activation potential of the Ikaros isoforms are also markedly distinct. The stronger transcriptional activators, Ik-1 and Ik-2, are found in abundance in the early fetal liver, in the maturing thymus and in a small area in the developing brain, whereas the weak activators, e.g., Ik-3 and Ik-4, are present at significantly lower levels in these tissues during these times. Consequently, Ik-1 and Ik-2 are expected to play a primary role in transcription from sites that can bind all four of the Ikaros proteins. However, in the early embryonic thymus and in the late mid-gestation hemopoietic liver the weak activator Ik-4 is expressed at similar mRNA levels to the Ik-1 and Ik-2 isoforms. The Ik-4 weak activator can bind only to composite sites while Ik-1 and Ik-2 can bind to a range of single and composite sites. The Ik-1 and Ik-2 proteins recruited to composite sites (a fraction of the total protein), during early to mid gestation, will have to compete for binding with the Ik-4 isoform, solely recruited to these sites. Consequently the activity of these composite sites may be primarily controlled by the Ik-4 isoform, a weak transcription activator. Modulation of Ik-4 expression in the developing thymocyte, in combination with steady levels of the Ik-1 and Ik-2 expression may determine the temporal and stage specific expression of T cell differentiation antigens. Low affinity binding sites for these proteins may also become transcriptionally active in the late stages of T cell development when the most potent activators, Ik-1 and Ik-2, accumulate. In the fly embryo the NF-κB/rel homologue Dorsal, a maternal morphogen, engages in interactions with transcriptional factors binding to adjacent sites. These protein-protein interactions determine the activation level and threshold response from low and high affinity binding sites (Jiang et al. (1993) *Cell* 72:741–752). The transcriptional activity of the Ikaros proteins may be further regulated by such mechanisms in the developing lymphocyte. In addition, the activity of the Ikaros proteins may be under postranslational control operating during both lymphocyte differentiation and activation. It has been shown that concentrations of Ikaros isoforms at different developmental stages confer different reactivites on the various sites.

The transcriptional activity of the mIk-3 and mIk-4 proteins may be further regulated by T cell restricted signals mediating postranslational modifications or by protein-protein interactions. The mIk-4 protein binds NFkB motif in a cooperative fashion and may therefore interact in situ with other members of the Ikaros or of the NFkB family. These protein-protein-DNA complexes may dictate a differential transcriptional outcome.

The differential expression of the Ikaros isoforms during T cell ontogeny, their overlapping but also unique binding specificities and their diverse transcriptional potential may be responsible for the orderly activation of stage specific T cell differentiation markers. Multiple layers of gene expression in developing lymphocytes may be under the control of these Ikaros proteins. Synergistic interactions and/or competition between members of the Ikaros family and other transcription factors in these cells on qualitatively similar and distinct target sites could dictate the complex and ever changing gene expression in the differentiating and activated lymphocyte. This functional dissection of the Ikaros gene strongly suggest that it functions as a master gene in lymphocytes, and an important genetic switch for early hemopoiesis and both B and T cell development.

The Ikaros gene maps to the proximal arm of human chromosome 7 between p 11.2 and p13 next to Erbb In the mouse the Ikaros gene maps to the proximal arm of chromosome 11 tightly linked to Erbb. Other genes linked to the Ikaros locus in the mouse are the Leukemia inhibitory factor (Lif) and the oncogene Rel a member of the NFK-B family. All three of the genes linked to the Ikaros gene in the mouse appear to play an important role in the development of the hemopoietic system. The tight linkage between the Erbb and the Ikaros genes on syntenic loci in the mouse and human may be related to their genetic structure and regulation. Nevertheless, no known mutations were mapped to the Ikaros locus in the mouse. However, this does not preclude the importance of the Ikaros gene for the lymphopoietic system. Naturally occurring mutations that affect development of the immune system may not be readily obtained in mice since such mutant animals may only thrive under special care conditions.

That the Ikaros gene is a fundamentally important regulator of lymphocyte development is substantiated by analysis of its human homologue. The overall conservation of the Ikaros proteins between mice and man at the genetic level and protein level but also their restricted pattern of expression in the developing lymphocyte, e.g., in maturing T cells, e.g., in maturing B cell, strongly support their participation in the same regulatory pathway across species.

Cloning the Mouse Ikaros Gene

A T cell expression cDNA library from the mature T cell line E14 was constructed into the Λ ZAP phage vector.

A multimerized oligonucleotide encoding sequence (SEQ ID NO:66) from one of the protein binding sites of the CD38 enhancer was used as a radio labeled probe to screen this expression library for the T cell specific proteins that bind and mediate enhancer function by the southwestern protocol of Singh and McKnight. Four gene encoding DNA binding proteins were isolated. One, the Ikaros gene, encoded a T cell specific protein.

The Sequence of Mouse Ikaros

The sequence of the Ikaros gene was determined using the Sanger dideoxyl sequencing protocol. The derived amino acid sequence was determined using the MAP program of GCG (available from the University of Wisconsin) and Strider sequence analysis programs. FIG. 19 provides the sequence of a mouse Ikaros cDNA (mIk-2) and the derived amino acid sequence encoded thereby (SEQ ID NO:53). Sequence information for other isoforms of mouse Ikaros proteins (and cDNAs) are provided in SEQ ID NO:55 (mIk-3), SEQ ID NO:56 (mIk-1), SEQ ID NO:57 (mIk-4), and SEQ ID NO:58 (mIk-5).

A Mouse Ikaros Protein

The Ikaros protein shown in FIG. 19 (mIk-2) is comprised of 431 amino acids with five $CX_2CX_{12}HX_3H$ zinc finger motifs organized in two separate clusters. (See also FIG. 22.) The first cluster of three fingers is located 59 amino acids from the initiating methionine, while the second cluster is found at the C terminus of the protein 245 amino acids downstream from the first. Two of the finger modules of this protein deviate from the consensus amino acid composition of the Cys-His family of zinc fingers; finger 3 in the first cluster and finger 5 at the C terminus have four amino acids between the histidine residues. This arrangement of zinc fingers in two widely separated regions is reminiscent of that of the *Drosophila* segmentation gap gene Hunchback. Similarity searches in the protein database revealed a 43% identity between the second finger cluster of Ikaros and Hunchback at the C terminus of these molecules. This similarity at the C terminus of these proteins and the similar arrangement of their finger domains raises the possibility that these proteins are evolutionary related and belong to a subfamily of zinc finger proteins conserved across species.

Ikaros Isoforms

In addition to the cDNA corresponding to mIk-2, four other cDNAs produced by differential splicing at the Ikaros genomic locus were cloned. These isoform encoding cDNAs were identified using a 300 bp fragment from the 3' of the previously characterized Ikaros cDNA (mIk-2, FIGS. 19A–C). As shown in FIGS. 21 and 22, each isoform is derived from three or more of six exons, referred to as E1/2, E3, E4, E5, E6 and E7. All five cDNAs share exons E1/2 and E7 encoding respectively for the N-53 and C-terminal 236 amino acid domains. These five cDNAs consist of different combinations of exons E3–6 encoding the N-terminal zinc finger domain. The mIk-1 cDNA (SEQ ID NO:56) encodes a 57.5 kD protein with four zinc fingers at its N-terminus and two at its C-terminus and has the strongest similarity to the *Drosophila* segmentation protein Hunchback (Zinc fingers are indicated as F1, F2+F3, F4, and F5+F6 in FIG. 22). The mIk-2 (SEQ ID NO:53) and mIk-3 (SEQ ID NO:55) cDNAs encode 48 kd proteins with overlapping but different combinations of zinc fingers. The mIk-3 isoform contains fingers 1, 2, 3 while mIk-2 contains fingers 2, 3 and 4. The 43.5 kD mIk-4 protein (SEQ ID NO:57) has two fingers at its N-terminus also present in mIk-1 and mIk-2. The mIk-5 cDNA (SEQ ID NO:58) encodes a 42 kd protein with only one N-terminal finger shared by mIk-1 and mIk-3. This differential usage of the zinc finger modules by the Ikaros proteins support an overlapping but differential DNA binding specificity.

cDNA cloning of isoforms was performed as follows. A cDNA library made from the T cell line EL4 in λZAP was screened at high stringency with a 300 bp fragment from the 3' of the previously described Ikaros cDNA (isoform 2). Positive clones were characterized by sequencing using an antisense primer from the 5' of exon 7.

Cloning of the Human Ikaros Gene

A DNA fragment derived from the shared 3' coding region of the mouse Ikaros cDNAs was used as a probe to screen for human Ikaros homologs. This DNA fragment, which encodes the C-terminal part of the Ikaros proteins, is believed to be essential for their activity and does not exhibit significant sequence similarities with other DNA binding proteins. A cDNA library from the human T cell line Jurkat was screened at high stringency and 9 partial cDNAs were isolated. The most full length cDNA and its deduced amino acid sequence are shown in FIG. 20 (SEQ ID NO:54). This cDNA encodes a protein homologous to the mouse Ik-1 isoform, the largest of the mouse Ikaros proteins comprised of all the translated exons. A high degree of conservation was detected between the human and the mouse Ik-1 isoforms both at the DNA and the protein levels. The portion of the mouse Ik-1 that contains exons 3 through 7 display 89% and 91% identity to its human homologue at the DNA and protein levels respectively. However the N-terminal portion of the mouse Ik-1 isoform encoded by exons 1/2 was not found in any of the three human cDNAs. The cDNAs instead display distinct 5' ends. The lack of conservation in this part of the human and mouse Ikaros proteins suggest that each of their N-terminal portions are probably not functionally significant. The distinct 5' untranslated sequences present in these human cDNAs are reminiscent of the number of distinct 5' untranslated sequences present in mouse cDNA products of potential alternate promoter usage.

Of the human cDNAs isolated, only one contained the splicing junction between exons-4 and -6 found in the mouse Ik-4 isoform. The lower frequency of cloning of human Ik-4 relative to human Ik-1 cDNAs may reflect their relative concentrations in this T cell line. In the mouse, the Ik-1 isoform is found in excess relative to the Ik-4 isoform in the differentiating T cells (A. Molnar et al 1994).

Human Ikaros isoforms were cloned as follows: A human cDNA library made from the mature T cell line Jurkat (Stratagene) was screened with a 150 bp single stranded probe derived from the most 3' of the IK-1 mouse Ikaros cDNA. From the $8\times10^5$ recombinant phages screened, 9 positive clones were obtained. Filters with recombinant phage DNA were incubated overnight in hybridization buffer (7% SDS, 1% BSA, 0.25 Sodium-phosphate pH 6.5 and 0.5 mM EDTA) with $1\times10^6$ cpm/ml probe at 65° C. Washes were performed twice in 2×SSC/1% SDS, 0.2×SSC/1% SDS and 0.2×SSC/0 1% SDS at 65° prior to autoradiogarphy. Positive clones were purified and characterized by dideoxy sequencing.

Expression of the Ikaros gene in human tissues and cell lines.

Expression of the Ikaros gene was determined in human tissue and cell lines. Two major Ikaros RNA transcripts were detected only in polyA+ RNA from thymus, spleen, and peripheral leukocytes. Very low levels of Ikaros mRNA were also detected in the colon, and probably reflects the resident lymphocyte population in this tissue. The smaller (28S) of the two Ikaros mRNA forms correlates in size with the major Ikaros transcript detected in the mouse, while the larger form correlates in size with a low abundance transcript detected in the mouse upon overexposure of Northern blots. High levels of both of these mRNAs were expressed in the thymus, while the larger form predominated in the spleen. In peripheral leukocytes equal amounts of both transcripts were present, but at 2 fold lower level than in the thymus. These two mRNA species detected in the human may represent products of differential splicing with the larger species containing additional 5' and/or 3' non-coding exons. In addition, they may be transcribed from distinct promoters and may be comprised of different combinations of 5' untranslated exons.

Northern Analysis was carried out as follows: Two Northern blots each containing 2 μgs of poly A+RNA isolated from human heart, brain, placenta, lung, liver, skeletal muscle kidney, and pancreas (Clontech human blot) and from spleen, thymus, prostate, testis, ovary, small intestine, colon, and peripheral blood leukocytes (Clontech human blot II) were hybridized with a probe ($10^6$ cpm/ml in hybridization buffer) made from the 800 bp SacI-EcoRI fragment of hIk-1 cDNA. A northern blot containing 10 μgs of total RNA prepared from the T cell leukemic lines: CEM, Molt-4, from the acute myelogenous leukemia KG1, the acute monocytic leukemia THP-1, the U937 histiocytic lymphoma, 30 μgs of the T cell line HPB 1 and 2.5 μgs of human thymus.

The Ikaros protein isoforms are conserved between mouse and man.

The expression of the Ikaros protein isoforms was examined in human and mouse T cell nuclear extracts by Western blotting. Nuclear extracts from mouse and human fibroblast and epithelial cells were used to determine the specificity of the Ikaros antibody. A number of cross reacting proteins were detected in the nuclear extract from the mouse EL-4 T cell line. Since cDNAs that encode at least five size distinct Ikaros proteins were cloned from this cell line, the proteins detected with the Ikaros antibody are probably Ikaros isoforms expressed in this cell line. In the human T cell line Jurkat, the largest of these proteins was the most abundant form but other smaller proteins were detected at lower abundance. These human T cell nuclear proteins may represent the homologues of the mouse Ik-1, Ik-2, Ik-3 and Ik-4 isoforms in order of decreasing relative concentration. No cross reacting proteins were detected in the nuclear extracts from the CV1 and NIH-3T3 non expressing cell lines, thus confirming the specificity of the detecting antibody.

Western analysis of human and mouse nuclear extracts were carried out as follows: 20 μgs of protein, from nuclear extracts prepared from the Ikaros expressing mouse and human T cell lines EL4 and Jurkat, and from the Ikaros non-expressing mouse and monkey fibroblast and kidney epithelial lines NIH-3T3 and CV1, were run on 12% PAGE. Proteins were transferred to a nitrocellulose membrane and were analyzed with a 1:250 dilution of Ikaros antibody raised to the N-terminal portion of the mouse Ik-2 isoform containing exons 1, 3, 4, 5, and 6. The second step was performed using 1:3000 dilution of goat anti-rabbit antibody (BioRAD) conjugated to alkaline phosphatase. Antibody complexes were detected with BCIP and NBT substrates.

The Ikaros Mouse Genomic Locus

Based on sequence analysis of variant cDNAs, the genomic locus is thought to include about 9–11 exons. Genomic DNAs encompassing most or all of the Ikaros exons present in the genome were isolated by screening a mouse genomic SV129 library made into the λDASH II phage vector using the various Ikaros cDNAs as probes. The Ikaros gene includes at least 80–90 kb of genomic sequence which was isolated as distinct but also overlapping genomic clones. Some of the Ikaros genomic clones are indicated in FIG. 24. The exons are depicted as boxes while the introns as lines. The DNA sequence for: the 5' boundary (SEQ ID NO:60) and the 3' boundary (SEQ ID NO:61) of exon E5; the 5' boundary (SEQ ID NO:62) of exon E3; and the 5' boundary (SEQ ID NO:63) and the 3' boundary (SEQ ID NO:64) of exon E7, were determined.

The Mouse Ikaros Gene is Located at the Proximal Arm of Chromosome 11

The mouse chromosomal location of Ikaros was determined by interspecific backcross analysis using progeny derived from matings of [(C57BL/6J×F1×C57BL/6J] mice. This interspecific backcross mapping panel has been typed for over 1300 loci that are well distributed among all the autosomes as well as the X chromosome. C57B116J and M spretus DNAs were digested with several enzymes and analyzed by Southern blot hybridization for informative restriction fragment length polymorphisms (RFLPs) using a mouse cDNA fragment as a probe. The 6.5 kb M. Spretus PstI restriction-fragment-length polymorphism (RFLP) was used to follow the segregation of the Ikaros locus in backcross mice. The mapping results indicated that Ikaros is located in the proximal region of mouse chromosome 11 linked to Lif, Erbb and Rel. Although 129 mice were analyzed for every marker, up to 157 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere-Lif-6/167-Ikaros-3/146-Erbb-6/158-Rel. The recombination frequencies [expressed as genetic distances in centiMorgans (cM)+/−the standard error] are-Lif-3.6+/−1.4-Ikaros-2.1+/−1.2-Erbb-3.8+/−1.5-Rel.

The interspecific map of chromosome 11 was composed with a composite mouse linkage map that reports the map location of many uncloned mouse mutations (compiled by M. T. Davisson, T. H. Roderick, A. L. Hillyard, and D. P. Doolittle and provided from GBASE, a computerized database maintained at The Jackson Laboratory, Bar Harbor, Me.). Ikaros mapped in a region of the composite map that lacks mouse mutations with a phenotype that might be expected for an alteration in this locus.

The proximal region of mouse chromosome 11 shares a region of homology with human chromosomes 22, 7 and 2. In particular Erbb has been placed on human 7p 12. The tight linkage between Erbb and Ikaros in mouse suggests that Ikaros will reside on 7p as well.

Interspecific backcross progeny were generated by mating (C57BL/6J×M. spretus) F1 females and C57BL/6J males as described (Copeland and Jenkins, 1991). *Trends Genet* 7:113–118. A total of 205 F2 mice were used to map the Ikaros locus DNA isolation, restriction enzyme digestion, agarose gel electrophoresis, Southern blot transfer and hybridization were performed essentially as described (Jenkins et al. (1982) *J. Virol.* 43:26–36; and Jenkins et al (1982) *J. Virol.* 42:379–388). All blots were prepared with Zetabind nylon membrane (AMF-Cuno). The probe, a 350 bp mouse cDNA fragment was labeled with [α-$^{32}$P] dCTP using a random prime labeling kit (Amersham); washing was done to a final stringency of 1.0×SSCP, 0.1% SDS, 65° C. A fragment of 8.4 kb was detected in PstI digested C57BL/6J DNA and a fragment of 6.5 kb was detected in PstI digested M. spretus DNA. The presence or absence of the 6.5 kb M. spretus-specific PstI fragment was followed in backcross mice.

A description of the probes and RFLPs for the loci linked to Ikaros including leukemia inhibitory factor (Lif), avian erythroblastosis oncogene B (Erbb) and reticuloendotheliosis oncogene (Rel) has been reported previously (Karl et al. (1993) *Mol Cell Biol* 10:342–301; Karl et al. (1992) *Genetics* 131:103–173; and Karl et al. (1992) *Science* 256:100–102). Recombination distances were calculated using the computer program SPRETUS MADNESS. Gene order was determined by minimizing the number of recombination events required to explain the allele distribution patterns.

The Ikaros gene maps between p 11.2-p 13 on human chromosome 7.

The human chromosome assignment of the Ikaros gene was performed using DNAs prepared from a panel of somatic cell hybrids made between human and rodent. Primers designed after non-conserved sequences at the 3' end of the human cDNAs were used to distinguish between the human and rodent genes. A 375 bp fragment, as predicted from the human Ik-1 cDNA was amplified from human DNA used as a control and from DNA prepared from the cell hybrid 10791 which contains chromosome 7. The identity of the amplified band was confirmed using a probe derived from this region. To fine map the location of the Ikaros gene a panel of somatic cell hybrids which contained parts of chromosome 7 fused to the rodent genome were analyzed. A hybridizing 10 kb BglII genomic fragment was detected with human genomic DNA. A fragment of similar size was readily detected with DNA from the cell lines Ru Rag 4–13 and 1365 Rag12–9. The former cell line contained the proximal arm of chromosome 7 while the latter contained the distal and part of the proximal up to segment p13. DNA from Rag GN6, a cell line that contains the whole distal arm of chromosome 7 and the proximal arm up to segment p 11.2, did not hybridize. Another cell line which contained part of the proximal arm of chromosome 7 from p- to the telomere did not hybridize. This mapping restricts the location of the Ikaros gene between p 11.2 and p 13, placing it proximate to the Erbb gene locus, as predicted from the mouse.

PCR analysis of somatic cell hybrid DNA prepared from human-mouse-hamster and human-rodent somatic cell hybrids were used for the chromosome assignment of the human Ikaros gene DNAs from the following cell lines were used in PCR reactions h/h human-hamster hybrid h/m: human-mouse hybrid, 1 to 24 respectively 07299-h/h, 1082613-h/h, 10253-h/h, 10115-h/h 10114-h/h, 10629-h/h 10791-h/h, 10156B-h/h,10611-h/h, 10926B-h/h,10927A-h/h 10868-h/h, 10898-h/h 10479-h/m 11418-h/m 10567-h/m 10498-h/m 11010-h/h 10449-h/h 10478-h/m 10323-h/m 10888-h/h, 06318B-h/h 06317-h/h 25 human 26 mouse and 27: hamster DNAs were also used in control reactions 100 ngs of these DNAs were used in a PCR reaction together with 150 ngs of primers hIK-1 GGCTGCCACGGCTT-CCGTGATCCT (SEQ ID NO:67) and hIk-2: AGCG-GTCTGGGGAAACATCTAGGA (SEQ ID NO:68) designed after non-conserved sequences at the 3 min. of the human cDNA. Amplification parameters were: 95° C. for 5 min., 80° C. for 10 min. (with addition of 2.5 units of Taq polymerase), followed by 30 cycles at 93° C. for 1 min., 65° C. for 1 min. and 72° C. for 40", with an additional cycle at 93° C. for 5 min., 65° C. for 2 min. and 72° C. for 7 min. The amplified 375 bp product corresponds to the predicted size from the human cDNA. Fragment identity was confirmed by Southern hybridization with a probe derived from this region.

Fine mapping on human chromosome was further obtained by preparing 7 DNAs from a chromosome 7 hybrid panel which was used either in PCR amplification reactions with the primers described above, or in Southern analysis. The human chromosome 7 content of the hybrid cell lines used were 1365 Rag 12-9: 7qter-p13; Rag GN6:7qter-pl 1.2; Ru Rag 4-13: 7cen-pter (Vortkamp et. al. (1991) *Genomics* 11:737–743). For Southern blot analysis, 5 μg of human DNA and 10 μgs of hybrid and mouse DNA digested with BglII were hybridized with a 375 bp fragment contained within the hIk-1 and hIk-2 primers.

Generation of Transgenic Mice: Targeted Deletion of the DNA binding domain (exons 3 and 4) in the Ikaros gene (mutation 2) and the generation of Ikaros +/−and −/− mutant mice.

Cloning of the Ikaros gene, recombination constructs and targeting of embryonic stem (ES) cells.

A liver genomic library made from SV129 mouse liver DNA into the phage vector λ DASH II was screened with probes derived from the mouse Ikaros cDNA Ikaros-1 (Molnar, et al., 1994). Overlapping genomic clones were isolated that cover a region of 100 kb containing at least 6 translated exons. The recombination vector was constructed with Ikaros genomic fragments and the neomycin and thymidine kinase expression cassettes (Li, E. et al. (1992) *Cell* 69:915–926) using standard molecular biology protocols. 25 µgs of the recombination vector were electroporated into $1 \times 10^7$ J1 embryonic stem cells maintained on subconfluent embryonic fibroblasts. Transfected ES cells were originally plated on embryonic fibroblasts and grown without selection. 20 hrs later media containing G418(400 µgs/ml) and 48 hrs G418 and FIAU (0.2 µM Bristol Myers) were added. Cells were fed every two days, colonies were monitored for their undifferentiated morphology and picked between seven and nine days after plating. After DNA analysis, a number of ES cell clones with legitimate recombination events were placed back into culture and the ones which displayed undifferentiated properties were passaged once more before they were injected into a day 3.5 C57BL/6 or Balb/c blastocyst. Chimeric blastocysts were then injected in pseudo-pregnant foster mothers. Chimeric animals were born 18 days later and the ones that were more than 40% agouti were bred against background. Female and male F1 mice with germ line transmission of the Ikaros mutation were bred to homozygocity. The genotype of F1 and F2 mice was determined by Southern and by PCR analysis of tail DNA using either probe A as shown in FIG. 26A or appropriate primers designed from the neomycin (Neo1) and the Ikaros genes (Ex3F and Ex3R). Ex3F:AGT AAT GTT AAA GTA GAG ACT CAG (SEQ ID NO:69); Ex3R:GTA TGA CTT CTT TTG TGA ACC ATG (SEQ ID NO:70); Neo1: CCA GCC TCT GAG CCC AGA AAG CGA (SEQ ID NO:71).

Given the extensive differential splicing of Ikaros transcripts (Molnar, A. et al., (1994)), the multiple transcription initiation sites and the size and complexity of this genomic locus, a recombination vector was designed to replace an 8.5 kb genomic fragment containing part of exon 3 and exon 4 with the neomycin cassette. Probe A, which was derived from a region outside the recombination locus was used to screen for homologous recombination events. This mutation deletes zinc fingers –1, –2, and –3, responsible for mediating the sequence specific DNA binding of the Ikaros proteins. This mutation should prevent the Ikaros proteins from binding DNA and activating transcription (Molnar, et al., 1994).

This recombination vector was targeted in the embryonic stem (ES) cell line J1 (Li, E. et al. (1992) *Cell* 69:915–926). 300 neomycin and FIAU resistant ES cell colonies were picked and expanded. DNA was prepared and analyzed by Southern blotting using DNA probes from outside the homologous recombination area. Analysis of genomic DNA from 12 selected ES cell clones was performed. A 12.5 kB and a 10.5 kB BamHI genomic fragments from the wild type and the targeted Ikaros alleles respectively hybridized to probe A. Single integration events were scored using a probe derived from the neomycin gene. The homologous recombination frequency among the ES cell clones analyzed was 1:10. Two ES cell lines with legitimate homologous recombination events and with undifferentiated growth properties were passaged another time and were then injected into day 3.5 blastocysts ES cells whose DNA analysis is shown in lanes 4 and 9. Two distinct ES cell lines heterozygous for this mutation were used in separate blastocyst injections to rule out phenotypes that result from cell line mutations. To explore potential phenotype variability on different genetic backgrounds the mutant ES cells were injected in blastocysts from C57BL/6 and Balb/c mice. The chimeric blastocysts were reimplanted in pseudo-pregnant mice which gave birth to chimeric animals. Chimeras which were more than 40% agouti (SV129 positive) were bred against their host background. Male and female F1 progeny with germ line transmission were bred against each other. F2 litters were scored for wild type, heterozygous and homozygous pups. Southern analysis of tail DNAs from a 2-week old F2 litter which revealed the occurrence of homozygous offspring at the expected Mendelian frequency.

Characterization of Transgenic mice Heterozygous for the DNA-Binding Defective Transgene Ikaros –/+ transgenic animals develop lymphomas.

Animals heterozygous for the Ikaros mutations develop lymphoproliferations in the thymus, spleen, and lymph nodes. The lymphoid organs become significantly enlarged, the spleen reaches the size of 4.5×1.3×0.6 cm. The thymus can range from moderately enlarged to occupying the whole thoracic cavity and the cervical and auxiliary lymph nodes can reach the size of 1 cm. The penetrance of lymphoproliferation of 100%. Most animals develop this syndrome around 2–3 months and do not survive past the fifth month of age. Microscopic examination of blood smears from these animals revealed large nucleated blast like cells with azurophilic cytoplasm and prominent nucleoli. These large nucleated cells predominate leukocytes in the blood smear of all animals. The leukocyte count in the blood of these animals is often 6 times the number of that in the blood of their wild type littermates.

The cell populations of the spleen, the thymus, the lymph nodes and the bone marrow in the affected animals were analyzed with antibodies to T, B, myeloid and erythroid differentiation antigens by FACS. The majority of the cells analyzed were positive for Thy 1, CD5, TCR, CD25, CD18 antigens which demarcate mature but also activated T cells. This population was predominant in all four lymphoid tissues suggesting expansion of a T cell in all lymphomas. Cells obtained from these animals can be propagated in tissue culture in the presence of IL-2.

Preliminary cDNA and Northern analysis of these cells revealed three separate splicing events which join exon 2 to exon 5 and exon 7. These mutant mRNAs can generate proteins lacking the DNA binding domain (deleted exons 3 and 4) but containing their C-terminal part, similar or identical to the naturally occurring isoforms IL-5 and IK-6.

Characterization of Transgenic Animals Homozygous for the DNA-Binding Defective Transgene Ikaros –/– Mutant Mice are Born But Fail to Thrive Mice homozygous for the Ikaros mutation 2 were born with the expected Mendelian frequency indicating that the mutation does not affect their survival in utero. At birth homozygous, heterozygous and wild type littermates were indistinguishable. One week past birth, however, homozygous pups were identifiable by their smaller size. This size difference escalates during the third and fourth weeks of their lives. The size of homozygous animals varied from 1/3 to 2/3 of that of their wild type littermates and most of them displayed a matted coat appearance.

No morphological and hemopoietic cell differences were detected between wild type and heterozygous pups. A large majority of the Ikaros –/– mutant mice (approximately 95%) died between the first and third week of their life. A large proportion of these deaths were associated with cannibalism by the mothers. The mortality rate was higher on the C57BL/6 mixed background where mothers were less tolerant of defective pups. Mutant animals survived better in smaller litters suggesting that competition in a larger litter may escalate the death rate.

Analysis of homozygous mice derived from the two distinct ES cell clones verified that the phenotype observed was due to the mutation in the Ikaros gene. Ikaros −/− mutant mice derived from either ES cell clones were identical in terms of their growth, survival, hemopoietic populations and disease contraction. Animals were studied from several days to 12 weeks past birth on the SV129×Balbc, SV129×C57 and SV129 backgrounds. Normal looking and severely growth retarded mutant mice were examined. Their hemopoietic system was extensively studied. Finally their inability to thrive and cause of death was investigated. The overall hemopoietic phenotype and disease contraction in homozygous animals described in the following sections was the same on all three genetic backgrounds. The small number of mutant mice that survived for more than one month is exclusively on the Sv129×Balb/c background but its hemopoietic populations were not any different from the majority of homozygous animals analyzed.

Ikaros −/− Mutant Mice Have a Rudimentary Thymus with No Definitive T Cell Progenitors Gross anatomical examination of the thoracic cavity in Ikaros −/− mutant mice at 2–3 weeks of age failed to identify a thymic gland. However, upon careful microscopic inspection, a rudimentary organ was observed. The thymic rudiment was often found in adipose tissue and sometimes was located at a higher position in the thoracic cavity than the thymus in normal, age matched animals. The location and the often non-fused bilobed appearance of this thymus resemble those of the early embryonic organ. This mutant thymus contained approximately $1 \times 10^5$ cells in contrast to the $1–2 \times 10^8$ cells regularly obtained from wild type littermates. This thymic rudiment was difficult to identify in one week old mutant mice but it was easier to detect after the third postnatal week. The density of nucleated cells in the mutant thymus was low when compared to the cellularity of the normal thymus. Eosinophils detected in the wild type thymus were also seen in the mutant organ especially around the portal arteries.

Thymic rudiments from Ikaros −/− littermates (two to four mice depending on litter availability) were pooled and analyzed by fluorescent antibody staining and flow cytometry. Forward and side scatter analysis of the Ikaros −/− thymocytes revealed a smaller cell size population compared to wild type controls. The cell composition of the thymus in Ikaros mutant mice ($1 \times 10^5$ cells recovered per thymus) and wild type littermates ($2 \times 10^8$ cells recovered per thymus) was determined. Cells were double-stained with: anti-CD4$^{PE}$/anti-CD8$^{FITC}$, anti-CD3$^{PE}$/anti-TCRαβ$^{FITC}$, anti-Thy1.2$^{PE}$/anti-CD25$^{FITC}$, anti-CD4$^{PE}$/anti-HSA$^{FITC}$. Forward and side scatter analysis was performed on Ikaros −/− and wild type thymocytes to estimate the size and complexity of this population. Combinations of antibodies specific for Thy-1/CD25, CD4/CD8, CD3/TCRαβ, and CD4/HSA antigens were used to stain the Ikaros −/− and wild type thymocytes. These combinations of antigens demarcate the earliest and the later stages in T cell development (reviewed by Godfrey, D. I. and Zlotnik, A. (1993) *Immunology Today*; von Boehmer, 1993 #188; Weisman 1993). The wild type thymus contained the normal complement of mature and immature thymocytes. In sharp contrast, 95% of the mutant organs were devoid of single or double positive CD4 or CD8 cells and lacked cells that stained positively for CD3, TCRαβ, Thy-1 or CD25 (IL-2 receptor) (data is from two week old animals). The majority of these thymic cells stained positive with HSA known to be expressed on 95% of hemopoietic cells apart from early T and B cells. Interestingly, a small CD4$^{lo}$/HSA+ subpopulation was detected in some cases.

The HSA+ cells detected in the Ikaros −/− thymus may belong to other hemopoietic lineages. Alternatively these cells may represent the earliest T cell progenitors, closely related or perhaps identical to the HSC, which lack expression of any definitive T cell markers. These putative T cell precursors may be arrested at the entry point into the T lymphocyte pathway.

Ikaros −/− mutant mice lack peripheral lymphoid centers. Inguinal, cervical, axillary and mesenteric lymph nodes were absent by both visual and microscopic examination. Lymph nodes were absent in all of the Ikaros mutant mice examined but were readily detected in all of the wild type littermates. Peyer's patches and lymphocyte follicles were also absent from the gastrointestinal tract of the Ikaros −/− mutant mice but were present in the wild type intestines and colon.

Dendritic Epidermal T Cells are Absent in Ikaros −/− Mice

Epidermal sheets from ear skin from Ikaros −/− and wild type mice were examined for γδ T cells and for Langerhan cells. Ammonium thiocyanate-separated epidermal sheets were stained for immunofluorescence microscopy with fluorescein (FITC) conjugated monoclonal antibodies specific for γδ T cell receptors (mAb GL3) or unconjugated monoclonal antibodies specific for Class II molecules followed by FITC conjugated goat anti-mouse antibody as described in Bigby, M. et al. ((1987) *J. Invest. Dermatol.* 89:495–499), and Juhlin, L. and Shelly, W. B. ((1977) *Acta Dermatovener* (Stockholm) 57:289–296)). Isotype control antibodies were used as negative controls for GL3 and M5/114. Positively stained dendritic cells were identified by epifluorescence microscopy. Ears from three mice of each type were examined. γδ T cells were absent from epidermal sheets from Ikaros −/− mutant mice but were readily detectable in epidermal sheets from wild type mice. Staining with the Class II antibody revealed the presence of dendritic epidermal Langerhan cells in both mutant and wild type epidermis.

Hemopoietic Populations in the Bone Marrow of Ikaros −/− Mice

Hemopoietic populations in the bone marrow of the Ikaros −/− mice were analyzed by flow cytometry using antibodies to lineage specific differentiation antigens. Cells from the bone marrow of Ikaros mutant mice ($3–10 \times 10^7$ cells per animal) and, wild type littermates ($4–10 \times 10^7$ cells per animal) were analyzed with the following combinations of mAbs: CD3$^{PE}$/Thy1.2$^{FITC}$, Thy1.2$^{PE}$/Sca-1$^{FITC}$, CD3$^{PE}$/TCRαβ$^{ΦFITC}$, CD45R$^{PE}$/IgM$^{FITC}$, CD45R$^{PE}$/CD43$^{FITC}$, Mac-1$^{PE}$/Gr-1$^{FITC}$, Ter 119$^{PE}$/CD61$^{FITC}$.

Ikaros −/− mice were analyzed and compared to age matched wild type controls. At least six groups of animals were studied on each mixed background (SV129×C57BL/6 and on SV129×Balb/c) and one on Sv129. Each group consisted of pooled organs from one to four littermates at 2 to 3 weeks of age. Older animals (1 month+) were examined individually. Red blood cells in the spleen and bone marrow were lysed by ammonium chloride. Single cell suspensions of thymus, spleen or bone marrow cells were prepared and washed twice in staining wash (PBS with 0.1% BSA), incubated for 20 minutes on ice with a 1:20 dilution of normal rat serum and 1 μg mAb 2.4G2 (PharMingen, San Diego, Calif.) per $1 \times 10^6$ cells to block Fc receptors. Cells ($1 \times 10^6$) were incubated with PE conjugated mAb and FITC conjugated mAb for 40 minutes. $2 \times 10^4$ thymocytes were stained with appropriate combinations of PE and FITC conjugated mAbs since few cells were recovered from mutant thymus. Cells were then washed 3 times and one- and two-color flow cytometric analyses were performed on a FACScan (Becton-Dickinson, San Jose, Calif.). Gating for viable cells was performed using propidium iodide exclusion and SSC and FSC as described (Yokoyama, W. M. et al. (1993) "Flow Cytometry Analysis Using the Becton Dickinson FACScan. In Current Protocols in Immunology, Coligan, J. E. et al., eds. (Greene Publishing Associates, N.Y.) 5.4.1–5.4.14. Isotype matched control antibodies were used as negative controls. Ten-thousand cells were analyzed for each sample.

The first stages of B cell development take place in the late mid-gestation liver and spleen in the embryo, and in the bone marrow in the adult (Li, Y.-S. et al. (1993) *J. Exp. Med.* 178:951–960). These stages are demarcated by the sequential activation of cell surface antigens. Combinations and levels of expression of these stage specific markers are used to define the pro-B to pre-B stage (CD45R+/CD43+) and the pre-B to the B cell transitions (CD45R+/sIgM+) (Ehlich, A. et al. (1993) *Cell* 72:695–704; Hardy, R. R. et al. (1991) *J. Exp. Med.* 173:1213–1225; Li, Y.-S. et al. (1993) *J. Exp. Med.* 178:951–960; Rolink, A. and Melchers, R. (1991) *Cell* 66:1081–1094). In wild type bone marrow, the CD45R+ population contains B lymphocytes at various stages of their maturation. The small CD45R+/sIgM+ population consists of mature B cells while the even smaller population of CD45R$^{lo}$/CD43R$^{lo}$ cells contain immature lymphocytes at the pro-B cell stage (data shown is from a group of two week old animals).

The rest of the CD45R+ population consists of pre-B cells with rearranged heavy but not light chains as well as other hemopoietic cells. The CD45R+ population was greatly reduced and in many cases absent in the Ikaros mutant mice. The CD45R+ cells detected were low expressors and were negative for either CD43 or IgM. These cells may derive from an even earlier stage in B cell development than the one defined by the CD45R+/CD43+ combination. Alternatively they may belong to the CD5 lineage of B cells or to another hemopoietic lineage (Hardy, R. R. et al. (1986) *J. Exp. Med.* 173:1213–1225 and Herzenberg, et al., 1986).

T cell progenitors originate in the bone marrow in the adult and in the fetal liver in the embryo but the first definitive steps in T cell differentiation occur after their migration to the thymus. Given the lack of substantial numbers of defined T cell progenitors in the thymic rudiment of the Ikaros −/− mice, we examined their presence in the bone marrow. In most Ikaros −/− mice, a small population of Thy-1lo positive cells was present. These cells were not positive for CD3, Sca-1 or CD4 antigens which are expressed on early but definitive T cell precursors. This population of Thy-1 lo cells in the bone marrow of Ikaros −/− mice may contain the earliest lymphocyte progenitors including T and B cell precursors that are arrested in development and therefore unable to home to the thymus or proceed to the next stages differentiation.

The majority of nucleated cells in the bone marrow of Ikaros −/− mice were of the erythroid lineage. The proportion of erythrocyte precursors was larger in the Ikaros mutant mice than in wild type controls (53 vs. 31%). At two weeks of age, a similar number of bone marrow cells were positive for the myeloid lineage marker Mac-1 in the Ikaros −/− mice and in their wild type littermates (19 vs. 23% Mac-1+) which suggested that their myeloid compartment was also intact. However, in most cases the Mac-1+/Gr-1+ subpopulation that correlates with polymorphonuclear cells of a more mature granulocytic phenotype was not present among these Mac-1+ cells in most of the Ikaros mutant mice (Hestdal et al., 1991; Fleming et al., 1993, Lagasse and Weissman, 1993). Nevertheless, special stains and histological examination on blood smears and infected tissue has identified numerous circulating and infiltrating cells with mature polymorphonuclear and granulocytic morphology.

The Spleens of the Ikaros −/− Mutant Mice are Enlarged and Heavily Populated with Cells of Erythroid and Myeloid Origin Tissues harvested from euthanized wild type and Ikaros mutant mice were fixed in 4% buffered formalin for 1–2 days. They were then processed and embedded in paraffin. Sections were cut at 5 micron thickness, mounted and stained with hematoxylin and eosin or with modified gram stains. Light microscopy was performed at 20–600× magnification on an Olympus BMax-50 microscope. The spleens from the Ikaros −/− mice were enlarged compared to the wild type littermates. This size difference varied from one and a half to three times the size of the wild type spleen. The enlarged size of the Ikaros −/− spleens was in contrast to the absence of peripheral lymphatic centers and to the diminished size of the thymus detected in these mutant animals. The red and white pulp architecture of the wild type spleen was absent in the mutant organ. The white areas detected in mutant spleen were heavily populated with cells of myeloid morphology (m) and were surrounded by red areas populated by erythrocyte (e) precursors. A large number of megakaryocytes were also detected throughout these splenic sections.

The splenic populations in the Ikaros −/− mice were examined by flow cytometry to delineate the relative representation of the hemopoietic lineages. Single CD4+ and CD8+ cells which together comprise approximately 40% of spleen cells in normal mice were absent in all of the Ikaros −/− mice examined. $\alpha\beta$ and $\gamma\delta$ T cell receptor expressing cells were similarly absent from the Ikaros −/− spleens. However, a small but distinct population of Thy-1$^{lo}$ cells which were CD3− and Sca-1− was present as in the bone marrow.

The CD45R+/IgM+ population that represents the transition from the pre-B to the B cell stage in normal spleen was absent from this mutant organ. The CD45R+/CD43+ population that represent the pro-B to pre-B cell transition in the wild type bone marrow were not detected in either wild type or Ikaros −/− spleens.

The majority of the spleen cells in the Ikaros −/− mice were erythrocyte progenitors (TER119+). This population which ranged from 70% at 1–2 weeks of age to 25% in older mutant mice, never exceeded 20% in the spleen of wild type controls. Myeloid cells comprised the second predominant population in the spleen of Ikaros mutant mice and ranged from 9% in young animals to 60% in older mice. In the spleen of wild type mice, myeloid cells never exceeded 5%. In the Ikaros mutant spleen, the erythroid and myeloid lineages together accounted for the majority of the cells (80–100%). In contrast, in the wild type spleen these two lineages represent less than 20% of the total cell population which is accounted for by mature T and B cells.

The presence of myeloid progenitors in the spleen of Ikaros mutant mice was tested in a soft agar clonogenic assay. A large number of mixed macrophage and granulocyte (GM) colonies were established when spleen cells from two-week old mutant mice were grown on soft agar in the presence of GM-CSF (Table 1). Spleen cells from wild type littermates gave only a small number of mixed GM colonies. Similar numbers of mixed GM colonies were derived from cells from the spleen and bone marrow of mutant mice whereas in wild type animals' bone marrow and spleen derived GM colonies differed approximately by ten fold (Table 1).

TABLE 1

G/M progenitors in the spleen and bone marrow of Ikaros −/− mice

| Experiment 1 | | | | Experiment 2 | | | |
|---|---|---|---|---|---|---|---|
| Spleen | | Bone marrow | | Spleen | | Bone marrow | |
| +/+ | −/− | +/+ | −/− | +/+ | −/− | +/+ | −/− |
| 3 | 38 | 38 | 55 | 8 | 85 | 58 | 100 |

Natural Killer Cell Activity was Absent from the Spleens of Ikaros −/− Mice

NK cells do not appear to be present in the spleen of the Ikaros −/− mice (as detected by flow cytometry). A small population of these cells was present in wild type spleens (2–5% determined on the SV129×C57BL/6 background). Given the relatively small numbers of splenic NK cells, a functional assay was used to conclusively address their existence. Serial dilutions of spleen cells from Ikaros mutant and wild type animals were grown in the presence of 500 units/ml of IL-2 for 48 hours. These conditions are known to generate activated NK cells which can readily lyse their targets (Garni-Wagner, B. A. et al. (1990) *J. Immunol.* 144:796–803). After two days in culture, spleen cells from wild type control mice effectively lysed chromium labeled NK cell targets (Yac-1) over a wide range of effector to target cell ratios (Table 2). However, spleen cells from the Ikaros −/− mice were unable to lyse NK targets even at the highest effector to target cell ratio (60:1)(Table 2).

TABLE 2

NATURAL KILLER CELL ACTIVITY[a]

Percent Lysis[b]

| | Experiment 1 | | Experiment 2 | |
|---|---|---|---|---|
| Effector to Target Ratio | +/+ | −/− | +/+ | −/− |
| 60:1 | 59 | 1 | ND | ND |
| 30:1 | 48 | 2 | 75 | 4 |
| 15:1 | 43 | 4 | 57 | 10 |
| 7.5:1 | 16 | 4 | 29 | 2 |

[a]Spleen cells from wild type (+/+) or Ikaros deletion (−/−) mice were cultured in complete RPMI containing 500 units/ml recombinant IL-2 for 72 hours and were then cultured in triplicate with 3000 CR$^{51}$ labeled Yac-1 cells in indicated ratios in a standard 4 hour chromium release assay.

[b]Percent lysis = $\frac{[CPM - \text{Spontaneously released CPM}] \times 100}{[\text{Total lysis CPM} - \text{Spontaneously released CPM}]}$ Analysis of Ikaros mutant mRNAs and proteins.

The production of Ikaros mRNAs in the spleen of Ikaros mutant mice was investigated using a reverse transcription PCR amplification assay (RT-PCR). Georgopoulos, K. et al. (1992) *Science* 258:808. Primers derived from the Ikaros exons within and outside the targeted deletion were used to amplify cDNAs prepared from Ikaros −/− spleen. These primers, Ex2F/Ex7R, Ex2F/Ex6R, Ex3F/Ex7R, Ex4F/Ex7R, allow the determination of exon usage by the Ikaros transcripts. Ex2F: CAC TAC CTC TGG AGC ACA GCA GAA (SEQ ID NO:72); Ex3F: AGT AAT GTT AAA GTA GAG ACT CAG (SEQ ID NO:69); Ex4F: GGT GAA CGG CCT TTC CAG TGC (SEQ ID NO:73); Ex6R: TCT GAG GCA TAG AGC TCT TAC (SEQ ID NO:74); Ex7R: CAT AGG GCA TGT CTG ACA GGC ACT (SEQ ID NO:75). zinc finger modules −1, −2 and −3 of Ikaros encoded by the deleted exons 3 and 4 are responsible for the specific DNA contacts of the Ikaros proteins (Molnar et al., 1994a). cDNAs from wild type (+/+) thymus (T) or wild type and mutant (−/−) spleens (S) were PCR amplified with sets of primers that delineate their exon composition (primer sites are shown as filled boxes). These sets of primers amplified from wild type thymus and spleen predominantly products of the Ik-1 and Ik-2 transcripts as previously described (Molnar et al., 1994a). The major amplification product from the Ikaros mutant spleen cDNAs did not contain exon 3 and exon 4 but consisted of exons 1-2-5-6-7. The presence of Ikaros related DNA binding complexes were examined in nuclear extracts prepared from wild type thymus and from wild type and mutant spleen. Four sequence specific DNA binding complexes (arrows) were established by DNA competition assays. The presence of Ikaros proteins in these nuclear complexes was established by Ikaros specific and non-specific antibodies. These complexes are absent altogether from mutant spleen nuclear extracts which however support the formation of DNA binding complexes over an AP-1 site.

Analysis of these amplified products revealed the production of Ikaros mRNAs. These Ikaros mRNAs lack exons 3 and 4 and the major species corresponds in size to a transcript comprised of exons 1-2-5-6-7. Proteins encoded by these Ikaros mRNAs lack the DNA binding zinc fingers −1, −2 and −3 encoded by exons 3 and 4 (Molnar, et al., 1994).

The absence of Ikaros related DNA binding complexes in the hemopoietic populations of Ikaros mutant mice was confirmed in a gel retardation assay. Nuclear extracts were prepared and gel retardation assays were carried out as previously described. Georgopoulos, K. et al. (1992) *Science* 258:808. 2 μgs of nuclear extract were incubated with end labeled oligonucleotides containing either a high affinity Ikaros (IKBS4) or an AP-1 binding site. IK-BS4: TCAGCTTTTGGGAATGTATTCCCTGTCA (SEQ ID NO:76); IK-BS5: TCAGCTTTTGAGAATACCCTGTCA (SEQ ID NO:77); AP1: GGC ATG ACT CAG AGC GA (SEQ ID NO:78).

Nuclear extracts prepared from two week old wild type thymus and wild type and mutant spleens were tested for binding to a high affinity recognition sequence for the Ikaros proteins (Molnar, et al., 1994). Four DNA binding complexes with distinct mobilities were detected when nuclear proteins from wild type thymus and spleen were used. However, none of these four DNA binding complexes was formed when splenic nuclear extracts made from Ikaros mutant mice were used. Nevertheless, these nuclear extracts supported the formation of DNA binding complexes over an AP1 binding site. Competitor DNA with a high affinity recognition site for the Ikaros proteins abrogated binding of all four complexes while DNA with a mutation in the binding consensus for the Ikaros proteins had no effect (Molnar, et al., 1994). Pretreatment of the thymic nuclear extract with Ikaros antibodies also abrogated all four of these DNA binding complexes whereas an unrelated antibody showed no effect. These data indicate that nuclear complexes which contain Ikaros proteins are present in cell populations in the thymus and spleen of wild type animals but are absent in the spleen cells of the homozygous mutants.

Opportunistic Infections and Death in Ikaros −/− Mice

Deaths of Ikaros −/− mice occurred as early as the end of their first postnatal week. The mortality rate increased during the second and the third weeks of life. Approximately 95% of the mice died within 4 weeks. Gross and histopathological examination of the mouse gastrointestinal tract, liver, lung and blood was performed to evaluate the cause of their death.

Examination of the intestines did not reveal major histopathological abnormalities, however, Ikaros −/− mice consistently had numerous and diverse bacterial microorganisms in their intestinal tract. Large numbers of gram negative and positive rods and cocci were detected on tissue gram stains of intestinal sections from the mutant mice. Although a small number of bacteria were observed in wild type intestinal epithelia, their number and diversity did not compare to that detected in mutant mice. Cultures from gastrointestinal epithelia from Ikaros −/− mice identified a number of proliferating microorganisms. Interestingly, anaerobic endospore-forming bacteria of the Oscillospira caryophanon group were found at a highly prolific state in the intestines of the Ikaros mutant mice while they were not detected in wild type controls.

The liver in almost all animals examined contained focal infarcts that appeared as pale or white nodules. In extreme cases, half of the liver had undergone necrosis. Necrotic areas and accumulation of large numbers of monocytes, macrophages and eosinophils were present on hematoxylin and eosin stained liver sections. Hematoxylin and eosin staining of lung tissue from one-month old mutant animal revealed the destruction of normal tissue structure, bacterial abscessae and myeloid infiltration. This staining exhibited necrotic areas and bacterial growth mainly at the subcapsillary region and extensive infiltration with myelocytes and eosinophils. Cultures from the liver grew *pasturella pneumonotropica* and *enterobacteria* species, microorganisms which comprise part of the microbial flora in the oral and gastrointestinal cavities of normal mice. Cultures from wild type liver had no growth. In a Wright stain of blood smears from a one-month old Ikaros mutant mouse, basophils were the prevalent leukocyte population detected and were found concentrated over clusters of bacteria. The bacteria identified on Wright stained blood smears indicated high-grade septicemia (Fife, A. et al. (1994) *J. Clin. Pathol.* 47:82–84). Blood clots were cultured and frequently contained multiple strains of microorganisms.

Ikaros and Hematopoietic Development

The analysis of mice with a mutation in the Ikaros gene provides convincing evidence that the Ikaros gene plays a pivotal role in lymphocyte specification. An intact Ikaros gene is essential for the development of T and B lymphocytes and NK cells. The Ikaros gene is not essential for the production of totipotential hemopoietic stem cells, erythrocytes, myelocytes, monocytes, dendritic cells, megakaryocytes and platelets.

As shown above, a mutation in the Ikaros gene that abolishes the DNA binding domain in at least four of its protein products has profound effects on T lymphocyte development. T cell differentiation is arrested at a very early stage. Ikaros −/− mutant mice have a rudimentary thymus which contains $1 \times 10^5$ cells, 2000 times less than the wild type organ. These cells are HSA+ with a small subpopulation approximately 10% expressing low levels of HSA and CD4. No other definitive early T cell marker, e.g., Thy-1, Sca-1, CD25, CD3 was expressed on these cells. The majority of these HSA+ cells in the Ikaros −/− thymus may belong to other hemopoietic lineages. Alternatively, they may contain small non cycling T cell progenitors arrested at a very early stage of intrathymic differentiation. The Thy-1+CD3−SCA-1− cells detected in the bone marrow and spleen of the Ikaros mutant mice may also contain arrested T cell progenitors which may lack expression of the appropriate surface receptors that enable them to home to the thymus.

Lymphocyte progenitors that give rise mainly to the γδ T lineage populate the thymus from day 14 through day 17 of fetal development (Havran, W. L. and Allison, J. P. (1988) *Nature* 344:68–70; Ikuta, K. et al. (1992) *Annu. Rev. Immunol.* 10:759–783; Raulet, D. H. et al. (1991) *Immunol. Rev.* 120:185–204). Mature γδ T cells produced during this time populate the skin and vaginal epithelium and provide the life long supply of dendritic epidermal T cells (Asnarnow, D. M. et al. (1988) *Cell* need volume: 837–847; Havran and Allison, 1990; Havran, W. L. et al. (1989) *Proc. Natl. Acad. Sci. USA* 86:4185–4189). The absence of γδ T cells in Ikaros −/− mice implies that this stage in T cell ontogeny is never reached in these animals.

The Ikaros mutation has profound effects on the development of a third lineage of T cells, that of NK cells. Since these cytotoxic cells share differentiation antigens with T cells it has been proposed that they may be derived from a common progenitor (Rodewald, H. et al. (1992) *Cell* 139–150). Differentiation experiments with committed T cell progenitors have failed to generate the expected NK cell activity (Garni-Wagner, B. A. et al. (1990) *J. Immunol.* 144:796–803). Nevertheless, a common bipotential progenitor may exist which may not have a definitive T cell phenotype definable by early T cell differentiation antigens e.g., HSA, pgpl, CD4 and CD25. This progenitor pool may be part of the cell population detected in the Ikaros mutant thymus.

Many immunodeficient animals which do not produce mature lymphocytes appear to live well under relatively germ free conditions. This fact has been partly a attributed to the high numbers of circulating NK cells in these animals (Mombaerts, P. et al. (1992) *Cell* 68:869–877; Shinkai, Y. et al. (1992) *Cell* 68:855–867; Spanopoulou, E. et al. (1994) *Genes Dev.*). In contrast, Ikaros mutant mice fail to thrive even in relatively germ free conditions. A majority of these animals die soon after birth. Septicemia is the major cause of death in these animals. The rapid development of bacterial infections in Ikaros −/− animals may be due to the lack of NK cells in addition to lack of T and B lymphocytes.

No mature B cells or any of their well-defined progenitors were found in the bone marrow or the spleen of the Ikaros mutant mice. A small population of CD45R$^{lo}$ cells was detected which did not express CD43 or IgM, surface markers characteristic of the pro-B and pre-B cell transition. This total lack of T and B cell progenitors is unprecedented among naturally occurring and genetically engineered immunodeficient mice (Karasuyama, et al.; Mombaerts, P. et al. (1992) *Cell* 68:869–877; Shinkai, Y. et al. (1992) *Cell* 68:855–867) suggesting that Ikaros mutant mice may be arrested at the hemopoietic stem cell level before lymphocyte specification. The described functional disruption of the Ikaros gene may affect the development of a progenitor stem cell that gives rise to T, B and the NK cell lineages. However, the Ikaros gene products may control the development of three distinct progenitors each responsible for giving rise to a distinct lymphocyte lineage with each lineage arrested at the very first steps of its ontogeny.

Profound effects from this Ikaros mutation were also seen on the population dynamics of the erythroid and myeloid lineages. The relative proportion of erythroid and myeloid progenitors were increased in the bone marrow and especially in the spleen of Ikaros mutant mice compared to their wild type littermates. However, the absolute number of hemopoietic cells was lower in the bone marrow but higher in the spleen of mutant mice. These observations were in contrast to other immunodeficient mice where lack of mature T and B lymphocytes dramatically decreased the number of hemopoietic cells in the spleen but had smaller effects on bone marrow populations. These results may have several explanations.

One possibility is that one of the functions of the Ikaros gene products, potentially expressed in the pluripotential hemopoietic stem cell (HSC), is to signal its differentiation into the lymphocyte lineage. FIG. 25 shows an Ikaros view of the hemopoietic system; expression and putative roles in differentiation. Ikaros expression at the various stages of hemopoietic development is an approximation (Georgopoulos, K. et al. (1992) Science 258:808). Expression data was derived from Northern and PCR analysis of primary cells and cell lines and by in situ hybridization of fetal hemopoietic centers. Relative levels of expression (+) or lack of (−) are shown at various stages in development. Potential inductive signals for lymphocyte commitment and differentiation provided by the Ikaros gene are shown as arrows. Interrupted lines indicate putative Ikaros related negative signals for differentiation in the erythroid and myeloid lineages. Transitions in the lymphocyte pathway during which development is probably aborted in Ikaros −/− mice are drawn as Xs on the pathway. Dashed lines indicate unsettled transitions in lymphocyte differentiation, e.g., the existence of a common committed progenitor for the T and B lineages or their independent derivation from the pluripotent hemopoietic stem cell is a controversial issue (Ikuta, K. et al. (1992) Annu. Rev. Immunol. 10:759–783). In addition the origin of the T and NK lineages from a common committed T cell progenitor remains under debate (Hackett, J. J. et al. (1986) Proc. Natl. Acad. Sci. USA 83:3427–3431; Hackett, J. J. et al. (1986) J. Immunol. 136:3124–3131.; Rodewald, H. et al. (1992) Cell 139:150). Differentiation antigens representative of the various stages of hemopoietic and lymphocyte development (also used in the analysis of the Ikaros −/− mice) are shown. In the absence of these lymphocyte specific differentiation signals provided by the Ikaros gene products, the HSC is diverted by default into one of the other hemopoietic pathways.

The differentiation of HSC may be tightly regulated by Ikaros gene products which may provide both positive signals for lymphocyte differentiation and negative signals to prevent or attenuate entry into the other hemopoietic pathways (FIG. 25). Finally, the body may sense the lack of lymphocytes and may attempt to correct this defect by increasing hemopoiesis. However, since the lymphocyte pathway is blocked, stem cells produced will passively or actively generate more progenitors for the other non-lymphocyte hemopoietic lineages. This may explain in part the abundance of erythroid, myeloid and megakaryocyte progenitors encountered in Ikaros −/− mice. The increased levels of myelopoiesis relative to erythropoiesis detected in older mutant animals may be caused by infections and septicemia that develop in these animals.

Ikaros gene products expressed during the earliest stages of fetal hemopoiesis (before the development of the lymphopoietic system) may influence the hemopoietic system in other ways than directing HCSs toward lymphocyte lineage commitment. HCSs have distinct migration pathways in the embryo and in the adult (Ikuta, K. et al. (1992) Annu. Rev. Immunol. 10:759–783). The migration of HCSs from one organ to another during embryonic development and the switch from embryonic to adult hemopoiesis that takes place at the HSC level may be in part controlled by the Ikaros gene (FIG. 25). The hypocellular bone marrow in the Ikaros mutant mice may result from a failure of HCS to migrate to the bone marrow and the high degree of extramedullary erythropoiesis and myelopoiesis detected in the spleen of these animals may result from dysregulated transition from embryonic to adult hemopoiesis. Alternatively lack of thymocyte progenitors in the Ikaros mutant mice may hinder the homing of the HSC into bone marrow cavities. The spleen may become the primary site of extramedullary hemopoiesis in Ikaros mutant mice because the hemopoietic compartment in the bone marrow is severely deficient.

The Ikaros gene plays an essential role for lymphocyte specification in the mouse hemopoietic system. Absence of functional Ikaros proteins leads to a total blockade in the development of T cells, B cells and NK cells. Ikaros mutant mice will provide an experimental system for addressing the molecular components which exist downstream of the Ikaros gene and whose expression is detrimental for lymphocyte specification and development.

An Ikaros Transgenic Mouse with a Deletion at Exon 7 of the Ikaros Gene

The Ikaros gene is believed to be a necessary factor for the generation and maintenance of early hemopoietic progenitors since it is expressed during embryonic hemopoiesis prior to lymphocyte ontogeny (fetal liver day 10). A mutation at the Ikaros locus which brings about a total loss of function at the level of its transcription activators and suppressors can lead to an embryonic lethal due to an impairment in the production of embryonic blood.

A recombination vector targeting a deletion to the C-terminal part of the Ikaros proteins was made and used to generate transgenic animals heterozygous and homozygous for a deletion in exon 7. This mutation is expected to generate proteins that appear only partially active in transcription.

Transcripts from this mutated locus lack exon 7. The encoded proteins, are expected to bind homologous or heterologous nuclear factors during lymphocyte development. This mutation is expected to interfere with the role of the Ikaros proteins in gene regulation but is not expected to totally abrogate their function in lymphocyte transcription.

Truncated Ikaros isoforms lacking the C-terminal domain encoded by exon 7 and shared by all of these proteins can bind DNA with the same specificity as their full-length counterparts (as determined by gel retardation assays). However the ability of these truncated proteins to activate transcription appears to be significantly lower than that of their full-length counterparts as determined in transient expression assays and experiments using Ikaros-lex-A hybrid proteins. Acidic motifs present in this C-terminal portion may serve as potential transcription activation domains and may be responsible for this effect. Deletion of an activation domain located in the deleted C-terminal region may be responsible for the decrease on their ability to activate transcription. The deleted C-terminal region contains in addition to the activation a dimerization domain for the Ikaros proteins established in the yeast two-hybrid system.

Replacement of 700 bp of exon 7 by the neomycin gene gave rise to translation products which stop short of the shared C-terminal domain. These proteins are expected to bind DNA since they have a high affinity DNA binding domain at their N-terminus. However they should be compromised in their ability to activate transcription since part of their activation domain resides in their C-terminus. In lymphocytes heterozygous for this mutation, these mutant proteins may compete with their wild type counterparts for binding sites thus interfering with their function and with normal lymphocyte differentiation. Hematopoietic stem cells homozygous for this mutation may exhibit partial to total loss of Ikaros function depending on the ability of these truncated proteins to support transcription in vivo. The hematopoietic phenotype manifested by these cells can vary from an early to a late lymphocyte arrest or to aberrant events in T cell homeostasis.

The Hemopoietic Populations of Mice Homozygous for the C-Terminal Ikaros Mutation Two independent embryonic stem cell lines with legitimate homologous recombination events were used to generate mice with germ line transmission of this mutation. Mice homozygous for this Ikaros mutation are born with the expected Mendelian frequency and are indistinguishable from wild type littermates unless they are infected by opportunistic microorganisms. However the level of infections is not as extensive as with the N-terminal mutant homozygous mice and many animals survive for extended periods under sterile conditions. Male mutant homozygotes have successfully been bred with female heterozygous mutants.

Analysis of the hemopoietic system of a number of homozygous animals was performed. In contrast to the microscopically detectable thymic rudiment in the line of homozygous animals described above (the exon 3/4 deletion), this line of C-terminal homozygous mutants have a normal sized thymus. However, the ratio of $CD4^+$, $CD8^+$ and $CD4^+/CD8^+$ populations differed from those in wild type controls. The $CD4^+/CD8^+$ population was decreased in both healthy but mostly in the sick animals while the $CD4^+$ population was increased. Increased numbers of mature $CD4^+$ T cells were also detected in the spleen of healthy animals, while the $CD8^+$ population was similar in numbers to wild type littermates. However in many sick homozygous mice, these mature $CD4^+$ and $CD8^+$ populations but predominantly the $CD4^+/CD8^+$ cells were greatly diminished.

In contrast to the presence of T lymphocytes from the early to the late stages of their development, B cells and their earliest identifiable progenitors were absent from all the hemopoietic centers analyzed in the Ikaros C-terminal –/– mutant mice.

The myeloid and erythroid lineages in these hemopoietic organs were intact and in a few cases elevated as in the N-terminal Ikaros homozygous mice. No peripheral lymphatic centers, i.e. inguinal, cervical, axillary and mesenteric lymph nodes as well as Peyer's patches and lymphocyte follicles in the gastrointestinal tract were found in these Ikaros –/– mutant mice.

An Ikaros Transgenic Mouse with Two Ikaros Mutations (One Ikaros Allele with a Mutation that Deletes the C-Terminal Portion of the Protein, and the Other Ikaros Allele with a Deletion in its DNA Binding Domain)

Mice homozygous for a germ line deletion of exons encoding the DNA binding domain of the Ikaros proteins lack T, B and NK lymphocytes and their progenitors. Analysis of the hemolymphopoietic system of mice homozygous for a germ line deletion of the C-terminal part of the Ikaros proteins has begun. In addition, mice heterozygous for the C-terminal and DNA binding mutations have been bred with one another to determine whether the two mutations can functionally complement each other with intermediate effects or defects in the development of the lymphopoietic system.

Transgenic Mice which Overexpress Ikaros Isoforms

Overexpression of Ikaros isoforms (Ik-1, -2, -4, -5) can be obtained by using the pMu expression cassette (to drive expression in the B lineage, 4 transgenic lines) or by using the CD2 mini gene (to drive expression in the T lineage, 4 transgenic lines).

Ikaros overexpression vectors have been generated using the immunoglobulin promoter enhancer regulatory sequences driving Ikaros isoform expression in the hemopoietic/lymphopoietic system. These vectors were generated in order to determine whether expression of Ikaros at the wrong times during development affects the developmental outcome of the B or T cell pathways and to reconstitute the genetic background of the Ikaros mutant mice and functionally dissect the Ikaros proteins.

Overexpression of Ik-1 in the myeloid lineage can be obtained by using the Mac-1 (CD11b) expression cassette. The expression cassettes are excised from the pGEM backbone and introduced into mouse male pronuclei where they integrate into the pronuclei chromosomes. The male pronuclei are then used to generate transgenic mice as described above.

Analysis of the 5'ends of Ikaros mRNAs points to the existence of two promoters.

The Ikaros gene has been determined to span approximately 120 kb of DNA and is comprised of seven translated and two 5'untranslated exons (FIG. 26A). Ikaros was cloned and mapped as follows. Two phage clones with insert sizes of 15 and 19 kb respectively which cover exons 3 through 7 were obtained by screening a λ DASHII library. A PI phage clone was obtained (Genome Systems, Inc. St Louis, Mo.) through hybridization to a 350 bp PCR fragment from a region encompassing the 5'end Exon of 3. The genomic sequences contained within the PI clone spanned from about 35 kb upstream of exon 1 to about 5 kb downstream of exon 3. The two phage clones contained the 3'of the locus from exon 3 to 10 kb downstream of exon 7. PI DNA was recovered using standard plasmid isolation protocols and PI Manual by Genome Systems, Inc. St Louis, Mo. Fragments resulting from an EcoRI and/or BamHI digest were subcloned into either Bluescript II SK or Bluescript II KS (both Stratagene). The subcloned fragments were mapped using Southern Blots of EcoRI, BamHI, Kpnl, EcoRV single double digests of PI DNA from clone 2528. These blots were hybridized to regions of Ikaros cDNAs and cloned PI fragments. A map of the locus was drawn corresponding to the information compiled from these autoradiographs. The phage clones were mapped and subcloned in similar fashion. All restriction endonucleases were obtained from New England Biolabs.

Characteristic of the locus is a 41 kb intron located between the translated exons 2 and 3 which contains three out of the eight clusters of tissue specific DNaseI HSS described below. To map the transcriptional start sites in the Ikaros gene, the genomic sequence was analyzed directly upstream of the first translated exon. A splice-acceptor sequence was identified which suggested that the Ikaros promoter region lies further upstream possibly at the 5'end of an untranslated exon. To map the location of such a putative promoter, the 5'end of Ikaros mRNAs were analyzed by 5'RACE (Rapid amplification of cDNA ends) and by primer extension using primers from exons 1 and 2 (FIG. 26B).

The primer extension protocol used is according to Ausubel et al. (1999) *Cell Immunol.* 193(1):99–107 (Primer Extension) with a few modifications. Briefly, total RNA was prepared from Thymus, Spleen and Liver tissue using the guanidinium method (Ausubel et al. (1999)) (Single-Step RNA Isolation from Cultured Cells or Tissues). Subsequently poly $(A)^+$ RNA was isolated using the Oligotex procedure (Qiagen). The protocol is described in "Oligotex mRNA Handbook" Qiagen Inc. 1995. 1×10$^5$ cpm of a kinased and gel purified oligo was precipitated with 7.5 ug poly(A)$^+$, 20 µg glycogen, 0.3M NaAc, pH 5.5 in 100 µl final volume through the addition of 270 µl of 100% ethanol. The pellet was washed with 100% ethanol and then air-dried. Subsequently, the pellet was resuspended in 30 µl 1× hybridization (150 mM KCl; 10 mM Tris-Cl, pH 8.3; 1 mM EDTA), incubated at 85° C. for 10 minutes and then transferred to a 30° C. waterbath for 12 hours. The hybridization solution was brought to a final volume of 200 µl with H2O, then precipitated with 400 µl ethanol. The pellet was washed with 70% ethanol, air dried and resuspended in 18.4 µl 1× reverse transcription buffer (4 µl of 5× first strand buffer (GibcoBRL); 0.4 µl of 0.1 M DTT; 8 µl of 2.5 mM dNTPs (Boehringer); 6 µl of H$_2$O), 0.6 µl of PRIME RNase inhibitor (5'AΣ3', Inc.) and 1 µl of reverse transcriptase (Superscript II, Rnase H Reverse Transcriptase, GibcoBRL) was added. This was incubated in a 42° waterbath for 2 hours. Subsequently, 1 µl of Ribonuclease H (GibcoBRL) was added and incubated for 30 minutes at 37° C. The solution was then Phenol/Cloroform/isoamylalcohol (50/49/1) extracted after the addition of 150 µl STE. Then the DNA was precipitated with 500 µl ethanol. After a washing (70% ethanol) and air drying, the pellet was resuspended in 10 µl loading buffer (80%(vol/vol) formamide; 1 mM EDTA pH 8.0; 0.1% Bromophenol Blue; 0.1% Xylene Cyanol). Before loading on a 6% acrylamide/bisacrylamide (29:1), 7 M urea gel the samples were incubated at 80° C. for 5 minutes. As a size reference a sequencing reaction was run next to the sample. FIG. 27B shows the autoradiography of a characteristic primer extension analysis done with a P32 labeled primer that lies in exon 2 (C29). C29 primer sequence: cct tca tct gga gtg tca ctg act g (SEQ ID NO:79).

For RACE analysis, primer C29 was hybridized to 7.5 ug poly (A)+selected RNA and reverse transcribed as described in '5'RACE System for Rapid Amplification of cDNA Ends' kit from GibcoBRL (Cat. No. 18374–025). The resulting cDNA was 3'tailed with dCTP using the terminal deoxynucleotide transferase (GiccoBRL). The product was then PCR amplified with the nested primer C50 and a poly G/adaptor primer (GibcoBRL). As a negative control for the PCR reaction, the product of the PCR reaction was used with the exception that it lacked the 3'poly C tail (no TdT reaction). C50 primer sequence: ctg aaa ctt ggg aca tgt ctt g (SEQ ID NO:80). Primer extension with a primer deduced from exon 2 (C29) identified a major product of 327 bp which was highly enriched in mRNA from the thymus, was detectable in the spleen but not in the liver, thus recapitulating Ikaros expression or lack of it in these tissues. The size of the primer extension product shifted accordingly when a primer from exon 1 was used (C50-data not shown). Some larger and smaller but less abundant primer extension products (XX-319–280 bp) were also seen in the thymus and spleen but not in the liver. The 5'ends of Ikaros mRNAs were cloned from the thymus by 5'RACE. Sequencing of the RACE products revealed two types of untranslated sequence, designated as R10 and R19, that were independently spliced to exon 1. R10 was the longest and most abundant of the two RACE products and correlated with the largest and most abundant primer extension product. Two exons encoding the R10 and R19 sequences were located 10 and 15 kb, respectively, upstream of exon 1 (FIG. 26A). Sequence analysis of these regions revealed absence of a splice acceptor site and the presence of GC rich sequences frequently found in hemo-lymphoid-specific promoters. The non-canonical (non TATA box) nature of these promoters may account for a somewhat variable transcription start site that can give rise to the multiple primer extension products detected.

Taken together these studies show the possible utilization of two promoters in the Ikaros locus located upstream of two untranslated exons, R10 and R19, that splice independently to the first translated exon. These putative promoters are associated with two distinct clusters of lymphoid-specific DNaseI HSS (FIG. 27A, cluster β and γ) which are possibly active in distinct cell types.

The Ikaros Locus Contains Eight Distinct Regions of Accessible Chromatin in Lymphocytes To identify the regulatory regions responsible for Ikaros expression, lymphoid specific DNaseI HSS were searched for. These are indicative of altered chromatin structure that results from the action of tissue-specific regulatory factors. DNaseI hypersensitivity assays were performed as follows. Nuclei were isolated from splenic, thymic and liver single cell suspensions and were treated with 0–20 units of DNase I (Sigma), as previously described Wu, 1989. DNA was isolated and digested with the appropriate restriction enzyme indicated (EcoRI, BamHI; EcoRI-BamHI, all New England Biolabs), run on an 1% agarose gel, and transferred on Hybond % o N+membrane (Version 2.0, Amersham Life Science). The Southern transfers were probed with genomic fragments indicated in FIG. 26A. Probes were labeled by the oligonucleotide random priming method (NEBlot Kit, New England Biolabs). The restriction enzymes used to identify the various DNase I HS regions in the genomic locus were as follows. The length of the probe used and the restriction enzymes used to generate that probe are given in the parentheses: Region α: 9 kb BamHI Fragment (0.7 kb, HindIII/EcoRI fragment); region β: 5.9 kb BamHI/EcoRI fragment (0.7 kb EcoRI/EcoRV fragment); region γ: 5 kb EcoRI fragment (1.3 kb EcoRI/EcoR fragment); region δ: 4.2 kb EcoRI fragment (1.6 kb HindIII/EcoRI fragment); region ε: 11 kb BamHI fragment (1.2 kb EcoRI/BamHI fragment); region ζ: 13.5 kb EcoRI fragment (0.6 kb XbaI/EcoRI fragment); region η: 3.7 kb XbaI fragment (0.9 kb SpeI/XbaI fragment); region θ: 7.5 kb BamHI fragment (1.3 kb BamHI/EcoRI fragment).

Nuclei from the thymus, spleen and liver were digested with increasing amounts of DNase I. DNA was then purified, digested with appropriate restriction enzymes and analyzed by Southern blotting (FIG. 27B). Three groups of DNaseI HSS were identified (FIG. 27A). The first group contains clusters α, β, γ and δ which lie upstream of the first translated exon, two of which (β and γ) flank the untranslated exons and contain putative promoters. The second group lies in the largest intron between exons 2 and 3 and is comprised of clusters ε, ζ and η. The third group is comprised of only one weak HSS θ in the immediate vicinity of the Ikaros polyadenylation site in the last exon. The DNaseI HSS within each cluster are indicated by vertical arrows shown in FIG. 27A which also designate their specificity for the thymus, spleen or for both.

In summary, the chromatin structure of the Ikaros gene appears to be disrupted in a tissue-specific manner in thymocytes and splenocytes in eight distinct clusters of DNaseI HSS. Four of these DNaseI HSS clusters are located upstream of exon 1 and two of these lie in the vicinity of the Ikaros promoters. Another three clusters lie in the intron between exons 2 and 3. These tissue specific regions of accessible chromatin are potentially the sites of action of hemo-lymphoid nuclear proteins and remodeling complexes that potentate the complex pattern of Ikaros gene expression in a variety of cell types of the hemo-lymphoid system.

B cell and neutrophil-specific activities of the Ikaros promoter regions.

Regions that encompass sequences upstream and downstream of exons R10 and R19 and the associated β and γ DNaseI HSS clusters were tested for activity in transgenic mice (FIG. 28). The constructs including the β or γ clusters were made as follows. A genomic fragment encompassing 480 bp upstream exon I up to one base pair upstream of the start of translation was PCR amplified with primer 5'Ex1BHI and 3'Ex1AgeI. These primers had linkers at their 5'end to enable the cloning of the product into-pEGFP-1 (Clontech) after digestion with BamHI and AgeI. The resulting construct had 480 bp of exon 1 splice acceptor sequence upstream of the E-GFP-1 gene and is referred to as pEGFP-splice. At the 5'end of the construct was an endogenous EcoRI site and at the 3'of the SV40 poly adenylation signal was an AflII site.

```
5'Ex1BH1 primer sequence (non hybridizing sequence
underlined):
aaa gga tcc gaa cat aac tat gga tca  (SEQ ID NO:81)
gcc.

3'ExAgeI primer sequence (no hybridizing sequence
underlined):
ttt acc ggt gtc ttc agg tta tct cct  (SEQ ID NO:82)
gc.
```

DNase I HS region β was subcloned into Bluescript II SK (Stratagene) as a 5.9 kb BamHI/EcoRI fragment. pEGFP-splice was cloned at the 3'end utilizing the EcoRI and ClaI (Bluescript)/AflIII (pEGFP-splice) sites. The cohesive ends of ClaI and AflIII were blunted using the Klenow fragment of *E. coli* DNA Polymerase I. This resulted in the R19-GFP construct. The insert was released from the vector backbone in a BamHI/XhoI double digest and prepared for microinjection.

DNase I HS region γ was subcloned into Bluescript II KS (Stratagene) as a 5 kb EcoRI fragment. pEGFP-splice was cloned at the 3'utilizing the engineered BamHI and SpeI (Bluescript)/AflIII (pEGFP-splice) sites. The cohesive ends of SpeI and AflIII were blunted using the Klenow fragment of *E. coli* DNA Polymerase I. This resulted in the R10-GFP construct. The insert was released from the vector backbone in a XhoI/SacII double digest and prepared for microinjection.

The activity and tissue specificity of these promoter regions was examined by following their ability to drive expression of a GFP reporter in a variety of blood cells. The exon 1 splice acceptor site was included downstream of the R10 and R19 exons as shown in FIG. 28B. The ATG start codon of Ikaros present in Exon 1 was mutated, and the E-GFP-1 cDNA was cloned at its 3'. Two series of transgenic founders were generated using these promoter-reporter constructs which arc referred to as R19-GFP and R10-GFP (FIG. 28B and Table 3).

Transgenic mice were made through an oocyte injection protocol as described (find reference). The mice were bred and maintained under sterile conditions in a pathogen-free animal facility at Massachusetts General Hospital. Mice were 4–8 weeks of age at the time of analysis. The mice were genotyped for GFP by PCR analysis using the following primer combination: GFPup3: cgt aaa egg cca caa gtt ca GFPdown3: ctt gaqa gtt cac ctt gat gc. Cycling conditions were: 95° C. 5 min, 80° C. add Taq, (94° C. 45 sec., 58° C. 45 set, 72° C. 45 sec.)×28,72OC 10 min., 4° C. until taken out.

Four out of the eight R19-GFP founder lines express the reporter in a small subpopulation of the spleen and the bone marrow (Table 3, 0.8–4.8% of splenocytes and 0.8–27% of bone marrow cells) that displays a high FSC/SSC. Staining with lineage specific markers revealed that in both tissues these cells are neutrophils (Table 3 and FIGS. 29 and 30, R19-GFP, Mac-1$^+$, Gr-1$^+$. Indeed among myeloid cells, Ikaros is normally expressed in terminally differentiated neutrophils. Morgan et al. (1997) *EMBO J.* 16(8):2004–2013; Klug et al. (1998) *Proc. Natl. Acad. Sci. USA* 95(2):657–662. In the four R19-GFP founder lines, the expressing neutrophil population ranges from 1.7–41.58 (Table 3). This shows that the R19 promoter activity is specific for neutrophils and is subject to variegation effects, which are dependent on the site of its integration (FIG. 29, R19-GFP). Nonetheless, among different founder lines, the variegating neutrophil population expresses similar levels of GFP. In the analysis of the R19-GPP F37 line shown in FIGS. 29 and 30, approximately 41.5% of the neutrophils in the bone marrow and spleen express the reporter. The remaining four out of the eight R19-GFP founder lines did not express the reporter in any hemo-lymphoid or other cell type.

Cells from the thymus, spleen, and bone marrow were prepared and analyzed for expression of surface differentiation antigens as described previously (Georgopoulos (1994) *Cell* 79(1):143–56; Winandy et al. (1995) *Cell* 83(2):289–99). Flow cytometric analysis was performed using a Becton Dickinson FACScan flow cytometer and CellQuest software (Becton Dickinson, San Jose, Calif.) or the high speed MoFlo sorter (Cytomation, Inc.). All antibodies used for flow cytometric analysis were directly conjugated with fluorochromcs of choice (all from PharMingen, San Diego, Calif.). GFP expression was directly detected under FITC laser settings.

Expression was also seen in eight out of eleven R10-GFP founders, but here the majority of GFP+ cells fall within the lymphoid gate. Analysis with lineage specific markers revealed that these cells were B cells in both the bone marrow and spleen (Table 3,10-GFP). Among the different founders, the range of expressing cell population (GFP+) varied from 0.7–62% in the spleen and from <1–36.5% in the bone marrow. In all of the R10-GFP founder lines analyzed the great majority of GFP+ cells (89–98%) were cells of the B lineage (B220+) in the spleen (89–98%) and in the bone marrow (54%). A smaller fraction of GFP+ cells were neutrophils (4.6–35.5%) between spleen and bone marrow) (Table 3, 10-GFP). For the R10GFP line shown in FIGS. 29 and 30, 91–94% of bone marrow and splenic B cells (B220+) and 19–48% of neutrophils (Mac-1$^+$/Gr-1$^+$) were GFP+. Conversely, 89% of GFP+ splenocytes and 54% of GFP+ bone marrow cells were B cells and 8–35.5% neutrophils.

Thus, the R10 and R19 promoter regions appear to differ significantly in their cell type specificity. Whereas the activity of R19 is restricted to neutrophils, R10 is active in B cells and in a smaller fraction of neutrophils. Activity of both promoter regions in both populations is subject to position effect variegation indicating the lack of a locus control region (LCR).

An intronic DNAseI HSS cluster diversifies expression of the Ikaros B cell and neutrophil-specific promoter to the T cell lineage.

Although Ikaros is normally expressed in B cells and neutrophils, it is also expressed at its highest levels in differentiating thymocytes and mature T cells. Georgopoulos (1997) *Curr. Opin. Immunology* 9(2):222–227. Thus, additional regulatory elements must work in concert with the Ikaros promoter regions to direct expression in the T lineage. To determine the regulatory region(s) responsible for the Ikaros-T cell specific activity, the transcriptional potential of one of the most prominent DNaseI HSS present in the Ikaros locus in both the thymus and spleen was tested. A 4.7 kb EcoRI fragment containing two out of the three (T1/TS2) DNaseI HSS sites present in the ε cluster was introduced at the 3'end of the R10-GFP reporter (FIG. 28B, R10-GFP-11). Briefly, the construct for transgenic line R10-GFP-11 was generated as follows. The R10-GFP construct was modified so that it no longer contained a KpnI site at the 5'of the gene. Additionally, a KpnI site was introduced between the SacII and SacI sites at the 3'of the construct. This resulted in construct R10-GFP-11. A loxP site containing vector was generated by cloning a loxP site between SalI and HindIII and another loxP site between BamHI and XbaI of Bluescript II KS. For that, two annealed oligonucleotide were generated that contained a SaiI cohesive end and a HindIIX cohesive end flanking a loxP site (see sequences 5'top and 5' bottom). Similarly, two other oligonucleotides were generated and annealed that contained a BamHI and an XbaI site flanking the loxP sequence (see sequences 3'top and 3'bottom). This resulted in vector BS-loxP. DNase I HS ε T1/TS2 was subcloned as a 4.6 kb EcoRI fragment into BS-loxP in 3'to 5'orientation. This resulted in construct BS-loxP-11. Subsequently, BS-loxP-11 was digested with SacII and KpnI and cloned in an equally digested R10-GFP-mK. This resulted in construct R10-GFP-11. The insert was released from the vector backbone in a SalI digest and prepared for microinjection. 5'top sequence: tcg acg atc gat cga tcg atc ata act tcg tat aat gta tgc tat acg aag tta tta agc tt (SEQ ID NO:85). 5'bottom sequence: gat cca taa ctt cgt ata atg tat gct ata cga agt tat tt (SEQ ID NO:86). 3'top sequence: gat cca taa ctt cgt ata atg tat gct ata cga agt tat tt (SEQ ID NO:86). 3'bottom sequence: cta gaa ata act tcg tat agc ata cat tat acg aag tta tgg atc c (SEQ ID NO:87).

The transgenic mice were generated as described above.

Six out of the eight founder lines generated expressed GFP in the spleen, thymus and bone marrow (Table 3, 10-GFP-11, expression range in the spleen from 1.7–91%).

All mice used for this study were from the transgenic line R10-GFP-11, at 4–8 weeks of age. Thymic single cell suspensions were prepared as described previously [Winandy et al. (1999) *J. Exp. Med.* 190(8):1039–48. Thymocytes from 4–6 animals were pooled and depleted Mac-1, Terr119, B220, CD4 and CD8 cells using magnetic beads coated with anti rat Fc goat (Paesel and Lorei, Duisburg, Germany). The depleted population was restained with PE-lineage Antibodies and sorted for PE negative cells using a MoFlo high speed cell sorter. The resulting cells were stained with CD43(Cychrome) and CD25 (PE) and analyzed as described earlier (Winandy et al. (1999) *J. Exp. Med.* 190(8):1039–48.

Analysis of thymocyte populations in the R10-GFP-11 F225 line is shown in FIG. 31. GFP expression is seen in 76% of the CD4$^-$/CD8$^-$, in 64% of the CD4$^+$/CD8$^+$ and in 94% and 97% of the CD4$^+$ and CD8$^+$ cells, respectively. In sharp contrast to the R10-GFP-11 lines, no significant expression among the thymocyte populations of the R10-GFP lines was seen (data not shown). Reporter activity within the immature thymocyte compartment was analyzed further. Expression of GFP was detected in the majority of the T cell progenitor/precursor populations (FIG. 31A, 89% of CD44$^+$/CD25$^-$, 62% of CD44$^+$/CD25$^+$, 82% of CD44$^-$/CD25$^+$).

In the spleen of the R10-GFP-11 F225 line shown in FIG. 31C, 92% of B cells and 89% of neutrophils were also positive. In addition, 97% of the CD4$^+$/TCR$^+$ and 99% of the CD8$^+$/TCR$^+$ T cells were positive for GFP. Significantly, expression in the T cell populations was approximately eight fold higher than in B cells and neutrophils (FIG. 31C, compare GFP+: B220 vs. CD4 or CD8), thereby recapitulating the higher levels of Ikaros expression in the T lineage. Georgopoulos (1997) *Curr. Opin. Immunology* 9(2):222–227.

Another difference in the activity of the R 10-GFP and R10-GFP-11 reporter lines was noted within the neutrophil population. A greater percentage of neutrophils in the R10-GFP-11 (0.4–100%) vs. the R10-GFP (0.2–48%) lines expressed GFP. In the highest expressing R10-GFP vs. R10-GFP-11 founder lines, 48% vs. 100% of the Gr-1$^+$/Mac-1$^+$ populations was GFP+ (FIGS. 29–31).

In contrast to the T and neutrophil populations, GFP expression in the B lineage remained unchanged in the presence of the ε DNase I HSS cluster. Among the R10-GFP and R10-GFP-11 lines, the range of bone marrow and splenic B cells that were GFP+ was similar (Table 3, 1.4–94% vs. 1.5–94%). In both lines of transgenic founders, GFP expression in the B lineage was detected from the pro B (B220$^+$/CD43$^+$) cell stage on (data not shown).

In summary, transgenic mice that express the GFP reporter under the control of various transcriptional control elements associated with three DNAseI HSS clusters within the Ikaros locus have been generated. It was shown that B cell and neutrophil specificity for regions associated with two independently utilized promoters and an intronic enhancer region that diversifies one of the Ikaros promoters into T cells and gives it a higher level of activity was identified.

Differential labeling of T versus B cell zones by the Ikaros regulatory regions.

The ability of Ikaros-GFP reporters to demarcate lymphoid populations, the sites of their emergence and action is examined by fluorescence microscopy. At a macroscopic level no apparent staining has been detected with the neutrophil specific R19-GFP lines, possibly due to the small number of GFP+ cells present in lymphatic centers (Table 3, 0.8–4.8%). However, in both of the higher expressing R10-GFP and R10-GFP-11 lines, prominent staining of the lymphoid organs was seen. In the case of the R10-GFP lines, the B cell follicles of the spleen and peripheral lymphatics are prominently demarcated whereas the T cell zones remain negative.

In the R10GFP-11 lines, the T cell zones show the most prominent staining with B cell follicles also staining but at a lower level. This clearly reflects the expression pattern of these reporters in the T versus B cell populations. In addition to the spleen and lymph nodes, the thymus and bone marrow were also strongly positive in the R10-GFP-11 line.

Ikaros Auto Regulation of the R10 Promoter Region in B Cells

Sequence analysis of the Ikaros R10 promoter region revealed a number of Ikaros binding sites. The possibility of auto regulation for this region was examined by breeding the Ikaros R10-GFP reporter lines onto the Ikaros null and dominant negative mutations. In the absence of one Ikaros functional allele an increase in GFP levels per cell was detected with the R10-GFP founder line (F76) in which expression in 94% of the B cell population is detected. The increase in GFP levels was on average 3 fold in the pre-B and B cell population of the bone marrow and five fold in the mature B cell Population of the spleen. In contrast to the increase in GFP levels in B cells, no significant change was detected in the non-B cell GFP+ population of the bone marrow and spleen which in its majority consists of neutrophils. The same effect on R10-GFP levels was also seen upon breeding to the Ikaros DN+/−background. A second R10 founder line in which only 60% of B cells were GFP+ was also bred to the Ikaros mutations (Table 3, F30). Two effects were seen with this line of mice having the Ikaros DN+/−background: levels of GFP increased per cell and the expressing B cell population increased from 60% to 90%.

Thus Ikaros has two distinct effects on the B cell specific elements of the R10 promoter. On one hand the transcriptional activity of the R10 promoter region integrated in a permissive chromatin environment appears to be regulated in a negative fashion by Ikaros. When integrated at a site where chromatin is less permissive and is subject to variegation effects then Ikaros influences both variegation as well as levels of transcription. These effects are not seen with the transcriptional elements that confer neutrophil-specific activity to the Ikaros R10 promoter region.

most likely reflects the activity of developmentally regulated transcription factors which function by recruiting remodeling factors to potentate transcription of Ikaros in different cell types of the lymphoid and hematopoietic system. Significantly, one of these clusters (DNase I HSS $\epsilon$) is frequently found in the vicinity retroviral integrations associated with leukemias. This may underlie changes in its activity and cause the disease state.

Two putative promoters were mapped in the Ikaros locus in the vicinity of two of the tissue specific DNaseI HSS clusters. One of the promoter regions was only active in neutrophils (R19), whereas the second (R10) was active predominantly in B cells as well as in neutrophils. Activity of the R10 promoter region was noted in the early pro-pre-B cells in the bone marrow and was maintained in mature B cells in the periphery. Within both B and neutrophil populations, a variegation in the activity of promoter regions was seen, indicating that these were subject to position effects caused by the local chromatin. Thus, additional elements with insulator function that protect from restrictive effects of neighboring chromatin must be present in the Ikaros locus to allow for its consistent expression in the majority of B cells

TABLE 3

Expression of GFP Under Transcriptional Control of Various Ikaros Regulatory Elements in the Spleen and Bone Marrow

| | Spleen+ve | % Macl | % GFP+ve | % B | % GFP+ve | % T | % GFP+ve | Bom+ve | % Macl | % GFP+ve | % B | % GFP+ve | % T |
|---|---|---|---|---|---|---|---|---|---|---|---|---|---|
| 10-GFP | | | | | | | | | | | | | |
| F28 | 0.7 | 0.2 m | 4.6 m | 1.4 | 98.3 | 0 | 0.0 | nd | nd | nd | nd | nd | nd |
| F30 | 35 | 19.4 m | 7.8 m | 68 | 93.5 | 4.2 | 4.0 | nd | nd | nd | nd | nd | nd |
| F76 | 62.2 | 48.6 | 8.3 | 93.8 | 89.1 | 15 | 1.9 | 36.5 | 18.8 | 35.5 | 91.4 | 54.3 | nd |
| 19-GFP | | | | | | | | | | | | | |
| F45 | 0.8 | 9.2 | 93.4 | 0 | 0 | 0 | 0.0 | 2.2 | 6.7 | 98.5 | 0 | 0 | nd |
| F63 | 0.3 | 2.86 | 95 | 0 | 0 | 0 | 0.0 | 0.8 | 1.7 | 98.8 | 0 | 0 | nd |
| F35 | 0.3 | 5.8 | 81.4 | 0 | 0 | 0 | 0.0 | 2 | 5.36 | 96.8 | 0 | 0 | nd |
| F37 | 4.8 | 30.9 | 97.9 | 0.4 | 4 | 0 | 0.0 | 26.9 | 41.5 | 98.9 | 0.4 | 0.4 | nd |
| 10-GFP-11 | | | | | | | | | | | | | |
| F202 | 91 | 99.4 | 8.2 | 89.4 | 38.8 | 97.5 | 15.2 | nd | nd | nd | nd | nd | nd |
| F214 | 52 | 95.33 | 15.7 | 93.5 | Sk | >95 | Sk | nd | nd | nd | nd | nd | nd |
| F225 | 84 | 89.1 | 15.2 | 91.7 | 47.1 | 95.5 | 16.6 | 77.75 | 88.5 | 72.8 | 86.2 | 26.4 | nd |
| F226 | 1.7 | 0.4 | 3.3 | 1.5 | 53.1 | 1.7 | 39.7 | nd | nd | nd | nd | nd | nd |
| F215 | 60.26 | 50.3 | 15.2 | 63.5 | 63.1 | 75.6 | 10.5 | nd | nd | nd | nd | nd | nd |

Discussion

Ikaros has previously been shown to be essential for development and homeostasis in the hemo-lymphoid system. Mutations in the Ikaros gene that interfere with its normal levels of expression cause a range of hematological disorders including immunodeficiencies as well as leukemias and lymphomas. It was found that there is a number of key regulatory regions in the Ikaros genomic locus whose combinatorial action recapitulate the complex pattern of Ikaros expression during differentiation in the B- and T-lymphoid and myeloid lineages. Importantly, a subset of these elements that confer B cell specific expression are subject to auto regulation.

The Ikaros genomic locus spans approximately 120 kB and is comprised of two untranslated and seven translated exons. Eight putative regulatory regions were mapped within this locus using a DNaseI HSS approach. These tissue specific DNAseI HSS demarcate regions of chromatin that are uniquely accessible in differentiating thymocytes and/or in splenocytes. Accessibility in these chromatin regions and neutrophils. Festenstein et al. (1996) *Science* 271(5252): 1123–5; Kioussis et al. (1997) *Curr. Opin. Genet. Dev.* 7(5):614–9.

Neither of the two Ikaros promoter regions were active in T cells that normally express high level of Ikaros, which is critical for their regulated proliferation and homeostasis. However, the B cell/neutrophil-specific promoter region combined with the intronic $\epsilon$ DNaseI HSS cluster was highly active in T cells. Under the control of the $\epsilon$ enhancer region, expression was restored in the earliest double negative thymic precursors as well as in the double positive and single positive thymocytes and in peripheral T cells. Significantly, expression in cells of the T lineage was by approximately one order of magnitude greater than in B cells and neutrophils recapitulating expression of the endogenous Ikaros. Georgopoulos (1997) *Curr. Opin. Immunology* 9(2): 222–227. Furthermore, this combination of promoter and intronic DNaseI HSS cluster regions increased the number of expressing neutrophils, relative to that detected with either of the Ikaros promoter regions (R10 or R19) alone.

However, variegation of expression among the lymphoid and myeloid populations was still detected with this combination of promoter and enhancer elements, indicating that critical insulator elements were still missing. Insulators may be present in one or more of the four clusters of DNase I HSS that are under investigation. Nonetheless, the B cell/neutrophil specific promoter region when acting in concert with the $\epsilon$ intronic enhancer(s) is active in a pattern that closely resembles that of the endogenous Ikaros expression in the hemo-lymphoid system.

Many key transcriptional regulators are under positive and negative feed back control mechanisms that ensure their production at appropriate levels in support of normal differentiation. Regulation of Ikaros levels is of paramount importance for the proper development of the hematopoietic and immune systems and it appears to follow a negative feed back loop at least in cells of the B lineage. Ikaros negatively regulates the activity of its own B cell specific promoter elements integrated at sites of permissive chromatin. A greater expression (6–3 fold) is detected within pre-B and B cell populations when Ikaros levels are reduced. When these elements are integrated at sites where position effects are manifested, variegation is decreased upon Ikaros reduction. Both of these Ikaros effects on its own B cell specific regulatory elements can be explained by changes in the chromatin status. Recruitment of Ikaros at cognate binding sites present in this regulatory region may restrict the chromatin environment and reduce its overall transcriptional activity. A more severe reduction may be manifested at specific chromosome locations which are already in a more restricted conformation. This can lead to shut down in expression in a significant fraction of B cells. This Ikaros negative auto-regulation seems to be specific for the B cell restricted regulatory elements and is not detected with the neutrophil-restricted elements present in the same promoter region. These studies provide an insight into the function of Ikaros as a negative regulator of transcription in vivo and its ability to target its own locus.

Markers which can distinguish between stem cells, various multipotent and oligopotent progenitors, and lineage-restricted precursors are of paramount importance for stem cell biology. Given its early hematopoietic pattern of expression, Ikaros is an excellent candidate for dissecting the early hematopoietic hierarchy, in addition to probing its molecular regulation. The Ikaros expression cassettes described herein are comprised of subsets of its regulatory elements, which may allow for labeling and therefore distinguish between subsets of hemo-lymphoid cells. GFP reporters driven by these regulatory elements may also provide a way to address the ontogeny, migration properties of progenitors and precursors and the sites of action of their mature progeny in real time in the intact organism. They will also provide powerful tools to direct expression at stages of the hematopoietic system like the HSC and the early myeloid and lymphoid progenitors and precursors, that have been difficult to target so far and provide molecular intervention in these rare cell types.

Delineation of the Ikaros regulatory elements in normal and Ikaros deficient mouse models will provide a molecular understanding of the mechanisms that underlie the development of immune and hematological diseases in mice and men.

OTHER EMBODIMENTS

Nucleic acid encoding all or part of the Ikaros gene can be used to transform cells. For example, the Ikaros gene, e.g., a mis-expressing or mutant form of the Ikaros gene, e.g., a deletion, or DNA encoding an Ikaros protein can be used to transform a cell and to produce a cell in which the cell's genomic Ikaros gene has been replaced by the transformed gene, producing, e.g., a cell deleted for the Ikaros gene. As described above, this approach can be used with cells capable of being grown in culture, e.g., cultured stem cells, to investigate the function of the Ikaros gene.

Analogously, nucleic acid encoding all or part of the Ikaros gene, e.g., a mis-expressing or mutant form of the gene, e.g., a deletion, can be used to transform a cell which subsequently gives rise to a transgenic animal. This approach can be used to create, e.g., a transgenic animal in which the Ikaros gene is, e.g., inactivated, e.g., by a deletion. Homozygous transgenic animals can be made by crosses between the offspring of a founder transgenic animal. Cell or tissue cultures can be derived from a transgenic animal. A subject at risk for a disorder characterized by an abnormality in T cell development or function, e.g., leukemia, can be detected by comparing the structure of the subject's Ikaros gene with the structure of a wild type Ikaros gene. Departure from the wild type structure by, e.g., frameshifts, critical point mutations, deletions, insertions, or translocations, is indicative of risk. The DNA sequence of the coding region of several exons as well as several intron exon boundaries are included herein. Other regions can be obtained or sequenced by methods known to those skilled in the art.

Embodiments of the invention also include animals having an Ikaros transgene and a second transgene which allows control over the expression of the Ikaros gene.

In vivo site-specific genetic manipulation together with genetic crosses between transgenic animals can be used to make animals which express the subject Ikaros protein in a developmentally regulated or tissue-specific manner. It is often desirable to limit the expression of a transgene to a particular stage of development or to a specific tissue. For example, many transgenes have deleterious effects on the cells of the transgenic animal in which they are expressed; thus, it is difficult to construct transgenic animals expressing these genes. Also, many promoters are "leaky" resulting in minimal levels of transcription of their target gene in all cell types. In many instances, it is desirable for a gene to be tightly repressed in all cells except those of a specific tissue. It may also be useful to study the role of a particular gene in development by causing or preventing its expression in particular tissues or at particular stages of development. One approach to the regulation of transgenes involves control of gene expression in vivo in either a tissue-specific manner or at a specific stage of the animal's development via site-specific genetic recombination.

Genetic techniques which allow for the expression of transgenes can be regulated via site-specific genetic manipulation in vivo are known to those skilled in the art. Genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject protein. For example, excision of a target sequence which interferes with the expression of the subject protein can be designed to activate expression of that protein. This interference with expression of the subject protein can result from a variety of mechanisms, such as a spatial separation of the subject protein gene from the promoter element resulting in the inhibition of transcription of the Ikaros gene. In another instance, a target sequence containing an internal stop codon can be used to prevent translation of the subject protein. Alternatively, in situations where the target sequence comprises the subject gene coding sequence or the promoter element, recombinase catalyzed excision can be used to inhibit expression of the subject protein via excision of these sequences. Nucleic acid constructs can also be made wherein a target sequence containing a sequence encoding the subject protein is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The cre/loxP recombinase system of bacteriophage P1 (Lakso et al. *PNAS* 89:6232–6236; Orban et al. *PNAS* 89:6861–6865) and the FLP recombinase system of *Saccharomyces cerevisiae* (O'Gorman et al. *Science* 251:1351–1355; PCT publication WO 92/15694) are examples of in vivo site-specific genetic recombination systems known in the art. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. *J. Biol. Chem.* 259:1509–1514). The Cre recombinase catalyzes the excision of the target sequence when the loxP sequences are oriented as direct repeats and catalyzes inversion of the target sequence when loxP sequences are oriented as inverted repeats.

Use of the cre/loxP recombinase system to regulate expression of the Ikaros protein requires the construction of a transgenic animal containing transgenes encoding both the Cre recombinase and the subject protein. Mice containing both the Cre recombinase and the subject protein genes can be provided through the construction of double transgenic mice. A convenient method for providing such mice is to mate two transgenic animals each containing a transgene. Double transgenic progeny of this mating are identified by screening the resulting offspring for the presence of both transgenes. The progeny may be tested for the presence of the constructs by Southern blot analysis of a segment of tissue. Typically, a small part of the tail is used for this purpose.

Recombinant vectors can be constructed wherein the nucleic acid sequence encoding the Ikaros protein is separated from a promoter element, e.g., a constitutive promoter, by an target sequence flanked by loxP sequences. This excisable target sequence can be used to inhibit expression of the Ikaros protein by, for example, containing an internal stop codon. In such a case, expression of the subject protein will be activated in cells containing Cre recombinase activity by excision of the target sequence and ligation of the abutting sequences. In this instance, excision of the target sequence results in the activation of protein expression at the level of translational. Alternatively, the target sequence can be placed in such a position that Cre recombinase mediated excision results in the promoter element being brought into close enough proximity to the subject gene to confer transcriptional activation. In this instance, the target sequence inhibits transcription of the subject protein gene by spatially separating the promoter element from the coding sequence. In another construct, the target sequence can comprise the nucleic acid sequence encoding the Ikaros protein which is oriented in a 3' to 5' with respect to the promoter. In this orientation the promoter will not be capable of activating transcription of the subject nucleic acid sequence. In this instance, Cre recombinase will catalyze the inversion of the target sequence encoding the Ikaros protein and thereby bring the 5' region of the coding sequence into the proper orientation with respect to the promoter for transcriptional activation.

In each of the above instances, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation or inactivation expression of the Ikaros protein can be regulated via regulation of recombinase expression.

Suitable recombinant vectors can be produced, for example, wherein a gene encoding the Cre recombinase is operably linked to a tissue-specific promoter, e.g., the mouse lck promoter which activates transcription in thymocytes. Tissue-specific expression of the Cre recombinase in each of the instances given above will result in a corresponding tissue-specific excision of the target sequence and activation or inactivation of the expression of the subject protein in that particular tissue. Thus, expression of the Ikaros protein will be up- or down-regulated only in cells expressing Cre recombinase activity.

One advantage derived from initially constructing transgenic mice containing a nucleotide sequence encoding the subject protein in a Cre recombinase mediated expressible format is evident when expression of the subject protein is deleterious to the transgenic animal. In such an instance, a founder population, in which the subject transgene is silent in all tissues, can be maintained. Individuals of this founder population can be crossed with animals expressing the Cre recombinase in, for example, one or more tissues. Thus, the creation of a founder population in which the subject transgene is silent will allow the study of genes which when expressed confer, for example, a lethal phenotype.

In instances where expression of the subject protein is not highly deleterious to the transgenic animal, tissue-specific gene activation systems similar to those described above can be devised which employs transgenic mice transfected with a single nucleic acid molecule. In such instances, the Cre recombinase and the nucleotide sequence encoding the subject protein are carried by the same vector and are integrated at the same chromosomal locus. Since the Cre recombinase is a trans-acting factor, the recombinase and the gene for which tissue-specific transcriptional activation is desired may be integrated at the same or different locations in the host genome.

Moreover, a tissue-specific promoter can be operably linked to more than one nucleic acid sequence, each encoding a different protein. In addition, more than one nucleic acid sequence containing a target sequence which inhibits protein expression, for example, can be introduced into cells. Thus, if desired, the subject Ikaros protein can be co-expressed with other transgenes where the expression of each protein is regulated in a tissue-specific or developmental stage-specific manner.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A substantially pure polypeptide comprising the amino acid sequence of SEQ ID NO:24, 26, or 28.

2. A substantially pure polypeptide comprising an amino acid sequence which is at least 98% identical to SEQ ID NO:28.

3. The polypeptide of claim 2, wherein the polypeptide has the following properties:
   (a) it can form a dimer with an Helios, Aiolos, or Ikaros polypeptide;
   (b) it is expressed in hematopoietic stem cells;
   (c) it has a molecular weight of approximately 64 kDa or 68 KDa;
   (d) it has at least one zinc finger domain; and
   (e) it is a transcriptional activator of a lymphoid gene.

4. The polypeptide of claim 1 that comprises the amino acid sequence of SEQ ID NO:28.

* * * * *

SEQUENCE LISTING

<160> NUMBER OF SEQ ID NOS: 97

<210> SEQ ID NO 1
<211> LENGTH: 1984
<212> TYPE: DNA
<213> ORGANISM: Mus musculus
<220> FEATURE:
<221> NAME/KEY: CDS
<222> LOCATION: (374)...(1894)

<400> SEQUENCE: 1

```
cacgagcgca caccgctcgg ctctccttgc gacacgccct catcccggt gtttctcaag      60 tagacgtccc gagacggtcg ctgaggcact gtttccacgc gatcagggtt cctcaggctt     120
gacattcaaa agtgggtgcg gaacccgcgg cactcggagc gtgctttaaa gcggccgcca     180
gccagcgccg ctctaacctc gcgccccggc tgccggcggc tcccgccctg catctgcgcc     240
gacgcgaccg agcgatcccg gggcctccct gcgcccggaa tctcccgcca gccgcgcggg     300
tccccacggc agcagcacgt ggagcggccg cggagcctga gcgacagctg cagcccgcgc     360
ggcccgcggc gac atg gaa gat ata caa ccg act gtg gag ctg aaa agc       409
            Met Glu Asp Ile Gln Pro Thr Val Glu Leu Lys Ser
              1               5                  10 acg gag gag cag cct ctg ccc aca gag agc cca gac gct ctg aat gac       457
Thr Glu Glu Gln Pro Leu Pro Thr Glu Ser Pro Asp Ala Leu Asn Asp
         15                  20                  25 tac agc ttg ccc aaa cct cat gag ata gaa aac gtg gac agt aga gaa       505
Tyr Ser Leu Pro Lys Pro His Glu Ile Glu Asn Val Asp Ser Arg Glu
     30                  35                  40 gcc cca gcc aat gaa gac gaa gat gca gga gaa gat tcg atg aaa gtg       553
Ala Pro Ala Asn Glu Asp Glu Asp Ala Gly Glu Asp Ser Met Lys Val
 45                  50                  55                  60 aaa gat gaa tac agc gac aga gat gag aac att atg aag ccg gag ccc       601
Lys Asp Glu Tyr Ser Asp Arg Asp Glu Asn Ile Met Lys Pro Glu Pro
                 65                  70                  75 atg gga gat gca gaa gag agt gaa atg cct tac agc tat gca aga gaa       649
Met Gly Asp Ala Glu Glu Ser Glu Met Pro Tyr Ser Tyr Ala Arg Glu
             80                  85                  90 tac agc gac tat gaa agc att aag ctg gag aga cac gtg ccc tat gac       697
Tyr Ser Asp Tyr Glu Ser Ile Lys Leu Glu Arg His Val Pro Tyr Asp
         95                 100                 105 aac agc aga cca acc agt ggg aag atg aac tgc gac gtg tgc ggg tta       745
Asn Ser Arg Pro Thr Ser Gly Lys Met Asn Cys Asp Val Cys Gly Leu
    110                 115                 120 tcc tgc att agc ttc aac gtc ttg atg gtt cat aag cga agc cat acc       793
Ser Cys Ile Ser Phe Asn Val Leu Met Val His Lys Arg Ser His Thr
125                 130                 135                 140 ggc gaa cgc ccg ttc cag tgt aat cag tgc ggg gca tct ttt act cag       841
Gly Glu Arg Pro Phe Gln Cys Asn Gln Cys Gly Ala Ser Phe Thr Gln
                145                 150                 155 aaa ggt aac ctc ctc cgt cat att aaa ctg cac acg ggg gaa aaa cct       889
Lys Gly Asn Leu Leu Arg His Ile Lys Leu His Thr Gly Glu Lys Pro
            160                 165                 170 ttt aag tgt cac ctc tgc aac tac gca tgc caa agg aga gat gcg ctc       937
```

```
                Phe Lys Cys His Leu Cys Asn Tyr Ala Cys Gln Arg Arg Asp Ala Leu
                        175                 180                 185 acg gga cac ctt agg aca cat tct gtg gag aag ccg tac aag tgt gag        985
Thr Gly His Leu Arg Thr His Ser Val Glu Lys Pro Tyr Lys Cys Glu
    190                 195                 200 ttc tgc gga aga agc tac aag cag aga agc tcc ctg gag gag cac aag       1033
Phe Cys Gly Arg Ser Tyr Lys Gln Arg Ser Ser Leu Glu Glu His Lys
205                 210                 215                 220 gaa cgc tgc cga gct ttt ctt cag aac cct gac ctg ggg gac gct gca       1081
Glu Arg Cys Arg Ala Phe Leu Gln Asn Pro Asp Leu Gly Asp Ala Ala
                225                 230                 235 agt gtg gag gca aga cac atc aaa gcc gag atg gga agt gag aga gct       1129
Ser Val Glu Ala Arg His Ile Lys Ala Glu Met Gly Ser Glu Arg Ala
    240                 245                 250 ctc gtc ctg gac aga tta gca agc aat gtg gct aag cga aaa agc tcg       1177
Leu Val Leu Asp Arg Leu Ala Ser Asn Val Ala Lys Arg Lys Ser Ser
255                 260                 265 atg cct cag aaa ttc atc ggt gag aag cgg cac tgc ttc gat gcc aac       1225
Met Pro Gln Lys Phe Ile Gly Glu Lys Arg His Cys Phe Asp Ala Asn
        270                 275                 280 tac aat ccc ggc tac atg tac gag aag gag aac gag atg atg cag acc       1273
Tyr Asn Pro Gly Tyr Met Tyr Glu Lys Glu Asn Glu Met Met Gln Thr
285                 290                 295                 300 cgg atg atg gac caa gcc atc aat aac gcc atc agc tat cta ggg gct       1321
Arg Met Met Asp Gln Ala Ile Asn Asn Ala Ile Ser Tyr Leu Gly Ala
                305                 310                 315 gaa gcc ttc cgc ccc tta gtc cag act ccg cct gct ccc acc tct gag       1369
Glu Ala Phe Arg Pro Leu Val Gln Thr Pro Pro Ala Pro Thr Ser Glu
            320                 325                 330 atg gtc cca gtc atc agc agt gtg tac ccc ata gca ctt act cgg gcc       1417
Met Val Pro Val Ile Ser Ser Val Tyr Pro Ile Ala Leu Thr Arg Ala
        335                 340                 345 gat atg cca atg ggg gcc ccg cag gag atg gaa aag aaa cgg atc ctc       1465
Asp Met Pro Met Gly Ala Pro Gln Glu Met Glu Lys Lys Arg Ile Leu
    350                 355                 360 ctg cca gag aag atc ttg cct tct gaa cga ggt ctg tcc ccc aat aac       1513
Leu Pro Glu Lys Ile Leu Pro Ser Glu Arg Gly Leu Ser Pro Asn Asn
365                 370                 375                 380 agt gcc cag gac tcc aca gac acc gac agc aac cac gag gat cgc caa       1561
Ser Ala Gln Asp Ser Thr Asp Thr Asp Ser Asn His Glu Asp Arg Gln
                385                 390                 395 cat ctc tac cag caa agc cac gtg gtc ctc ccc cag gcc cgc aat ggg       1609
His Leu Tyr Gln Gln Ser His Val Val Leu Pro Gln Ala Arg Asn Gly
            400                 405                 410 atg cct ctt ctg aag gag gtc cct cgc tct ttt gaa ctc ctc aag ccc       1657
Met Pro Leu Leu Lys Glu Val Pro Arg Ser Phe Glu Leu Leu Lys Pro
        415                 420                 425 cct ccc atc tgc ctg agg gac tcc atc aaa gtg atc aac aaa gaa ggg       1705
Pro Pro Ile Cys Leu Arg Asp Ser Ile Lys Val Ile Asn Lys Glu Gly
    430                 435                 440 gag gtg atg gat gtg ttt cga tgt gac cac tgc cac gtc ctc ttc cta       1753
Glu Val Met Asp Val Phe Arg Cys Asp His Cys His Val Leu Phe Leu
445                 450                 455                 460 gat tat gtg atg ttc acc atc cac atg ggg tgc cat ggt ttc cgt gat       1801
Asp Tyr Val Met Phe Thr Ile His Met Gly Cys His Gly Phe Arg Asp
                465                 470                 475 ccc ttt gag tgt aac atg tgt ggc tat cga agc cac gat cgc tat gag       1849
Pro Phe Glu Cys Asn Met Cys Gly Tyr Arg Ser His Asp Arg Tyr Glu
            480                 485                 490
```

```
ttc tcc tct cac atc gcc aga gga gag cac aga gcc atg ttg aag        1894
Phe Ser Ser His Ile Ala Arg Gly Glu His Arg Ala Met Leu Lys
            495                 500                 505 tgagcatctg tcctcaatgc gagggtcaac attgtttttt aaagctgatg gtagccttat  1954
ccagtagact gaactcaaac ccacctcgag                                   1984

<210> SEQ ID NO 2
<211> LENGTH: 507
<212> TYPE: PRT
<213> ORGANISM: Mus musculus

<400> SEQUENCE: 2

Met Glu Asp Ile Gln Pro Thr Val Glu Leu Lys Ser Thr Glu Gln
 1               5                  10                  15

Pro Leu Pro Thr Glu Ser Pro Asp Ala Leu Asn Asp Tyr Ser Leu Pro
                20                  25                  30

Lys Pro His Glu Ile Glu Asn Val Asp Ser Arg Glu Ala Pro Ala Asn
            35                  40                  45

Glu Asp Glu Asp Ala Gly Glu Asp Ser Met Lys Val Lys Asp Glu Tyr
50                  55                  60

Ser Asp Arg Asp Glu Asn Ile Met Lys Pro Glu Pro Met Gly Asp Ala
65                  70                  75                  80

Glu Glu Ser Glu Met Pro Tyr Ser Tyr Ala Arg Glu Tyr Ser Asp Tyr
                85                  90                  95

Glu Ser Ile Lys Leu Glu Arg His Val Pro Tyr Asp Asn Ser Arg Pro
            100                 105                 110

Thr Ser Gly Lys Met Asn Cys Asp Val Cys Gly Leu Ser Cys Ile Ser
        115                 120                 125

Phe Asn Val Leu Met Val His Lys Arg Ser His Thr Gly Glu Arg Pro
130                 135                 140

Phe Gln Cys Asn Gln Cys Gly Ala Ser Phe Thr Gln Lys Gly Asn Leu
145                 150                 155                 160

Leu Arg His Ile Lys Leu His Thr Gly Glu Lys Pro Phe Lys Cys His
                165                 170                 175

Leu Cys Asn Tyr Ala Cys Gln Arg Arg Asp Ala Leu Thr Gly His Leu
            180                 185                 190

Arg Thr His Ser Val Glu Lys Pro Tyr Lys Cys Glu Phe Cys Gly Arg
        195                 200                 205

Ser Tyr Lys Gln Arg Ser Ser Leu Glu Glu His Lys Glu Arg Cys Arg
210                 215                 220

Ala Phe Leu Gln Asn Pro Asp Leu Gly Asp Ala Ala Ser Val Glu Ala
225                 230                 235                 240

Arg His Ile Lys Ala Glu Met Gly Ser Glu Arg Ala Leu Val Leu Asp
                245                 250                 255

Arg Leu Ala Ser Asn Val Ala Lys Arg Lys Ser Ser Met Pro Gln Lys
            260                 265                 270

Phe Ile Gly Glu Lys Arg His Cys Phe Asp Ala Asn Tyr Asn Pro Gly
        275                 280                 285

Tyr Met Tyr Glu Lys Glu Asn Glu Met Met Gln Thr Arg Met Met Asp
    290                 295                 300

Gln Ala Ile Asn Asn Ala Ile Ser Tyr Leu Gly Ala Glu Ala Phe Arg
305                 310                 315                 320

Pro Leu Val Gln Thr Pro Pro Ala Pro Thr Ser Glu Met Val Pro Val
                325                 330                 335
```

```
Ile Ser Ser Val Tyr Pro Ile Ala Leu Thr Arg Ala Asp Met Pro Met
            340                 345                 350

Gly Ala Pro Gln Glu Met Glu Lys Lys Arg Ile Leu Leu Pro Glu Lys
        355                 360                 365

Ile Leu Pro Ser Glu Arg Gly Leu Ser Pro Asn Asn Ser Ala Gln Asp
    370                 375                 380

Ser Thr Asp Thr Asp Ser Asn His Glu Asp Arg Gln His Leu Tyr Gln
385                 390                 395                 400

Gln Ser His Val Val Leu Pro Gln Ala Arg Asn Gly Met Pro Leu Leu
            405                 410                 415

Lys Glu Val Pro Arg Ser Phe Glu Leu Leu Lys Pro Pro Pro Ile Cys
            420                 425                 430

Leu Arg Asp Ser Ile Lys Val Ile Asn Lys Glu Gly Glu Val Met Asp
            435                 440                 445

Val Phe Arg Cys Asp His Cys His Val Leu Phe Leu Asp Tyr Val Met
450                 455                 460

Phe Thr Ile His Met Gly Cys His Gly Phe Arg Asp Pro Phe Glu Cys
465                 470                 475                 480

Asn Met Cys Gly Tyr Arg Ser His Asp Arg Tyr Glu Phe Ser Ser His
            485                 490                 495

Ile Ala Arg Gly Glu His Arg Ala Met Leu Lys
            500                 505

<210> SEQ ID NO 3
<211> LENGTH: 23
<212> TYPE: DNA
<213> ORGANISM: Artificial Sequence
<220> FEATURE:
<223> OTHER INFORMATION: primer for PCR

<400> SEQUENCE: 3
tayaccatyc acatgggctr cca                                         23

<210> SEQ ID NO 4
<211> LENGTH: 21
<212> TYPE: DNA
<213> ORGANISM: Artificial Sequence
<220> FEATURE:
<223> OTHER INFORMATION: primer for PCR

<400> SEQUENCE: 4
rccrcacatg ttrcactyra a                                           21

<210> SEQ ID NO 5
<211> LENGTH: 24
<212> TYPE: DNA
<213> ORGANISM: Artificial Sequence
<220> FEATURE:
<223> OTHER INFORMATION: primer for PCR

<400> SEQUENCE: 5
gtgtgcgggt tatcctgcat tagc                                        24

<210> SEQ ID NO 6
<211> LENGTH: 24
<212> TYPE: DNA
<213> ORGANISM: Artificial Sequence
<220> FEATURE:
<223> OTHER INFORMATION: primer for PCR

<400> SEQUENCE: 6
```

```
atcgaagcag tgccgcttct cacc                                              24
```

<210> SEQ ID NO 7
<211> LENGTH: 628
<212> TYPE: DNA
<213> ORGANISM: Homo sapiens
<220> FEATURE:
<221> NAME/KEY: CDS
<222> LOCATION: (1)...(627)

<400> SEQUENCE: 7

```
gaa aga gat gag aat gtt tta aag tca gaa ccc atg gga aat gca gaa        48
Glu Arg Asp Glu Asn Val Leu Lys Ser Glu Pro Met Gly Asn Ala Glu
  1               5                  10                  15 gag cct gaa atc cct tac agc tat tca aga gaa tat aat gaa tat gaa        96
Glu Pro Glu Ile Pro Tyr Ser Tyr Ser Arg Glu Tyr Asn Glu Tyr Glu
             20                  25                  30 aac att aag ttg gag aga cat gtt gtc tca ttc gat agt agc agg cca       144
Asn Ile Lys Leu Glu Arg His Val Val Ser Phe Asp Ser Ser Arg Pro
         35                  40                  45 acc agt gga aag atg aac tgc gat gtg tgt gga tta tcc tgc atc agc       192
Thr Ser Gly Lys Met Asn Cys Asp Val Cys Gly Leu Ser Cys Ile Ser
     50                  55                  60 ttc aat gtc tta atg gtt cat aag cga agc cat act ggt gaa cgc cca       240
Phe Asn Val Leu Met Val His Lys Arg Ser His Thr Gly Glu Arg Pro
 65                  70                  75                  80 ttc cag tgt aat cag tgt ggg gca tct ttt act cag aaa ggt aac ctc       288
Phe Gln Cys Asn Gln Cys Gly Ala Ser Phe Thr Gln Lys Gly Asn Leu
                 85                  90                  95 ctc cgc cac att aaa ctg cac aca ggg gaa aaa cct ttt aag tgt cac       336
Leu Arg His Ile Lys Leu His Thr Gly Glu Lys Pro Phe Lys Cys His
            100                 105                 110 ctc tgc aac tat gca tgc caa aga aga gat gcg ctc acg ggg cat ctt       384
Leu Cys Asn Tyr Ala Cys Gln Arg Arg Asp Ala Leu Thr Gly His Leu
        115                 120                 125 agg aca cat tct gtg gag aaa ccc tac aaa tgt gag ttt tgt gga agg       432
Arg Thr His Ser Val Glu Lys Pro Tyr Lys Cys Glu Phe Cys Gly Arg
    130                 135                 140 agt tac aag cag aga agt tcc ctt gag gag cac aag gag cgc tgc cgt       480
Ser Tyr Lys Gln Arg Ser Ser Leu Glu Glu His Lys Glu Arg Cys Arg
145                 150                 155                 160 aca ttt ctt cag agc act gac cca ggg gac act gca agt gcg gag gca       528
Thr Phe Leu Gln Ser Thr Asp Pro Gly Asp Thr Ala Ser Ala Glu Ala
                165                 170                 175 aga cac atc aaa gca gag atg gga agt gaa aga gct ctc gta ctg gac       576
Arg His Ile Lys Ala Glu Met Gly Ser Glu Arg Ala Leu Val Leu Asp
            180                 185                 190 aga tta gca agc aat gtg gca aaa cga aaa agc tca atg cct cag aaa       624
Arg Leu Ala Ser Asn Val Ala Lys Arg Lys Ser Ser Met Pro Gln Lys
        195                 200                 205 ttc a                                                                 628
Phe
```

<210> SEQ ID NO 8
<211> LENGTH: 209
<212> TYPE: PRT
<213> ORGANISM: Homo sapiens

<400> SEQUENCE: 8

```
Glu Arg Asp Glu Asn Val Leu Lys Ser Glu Pro Met Gly Asn Ala Glu
  1               5                  10                  15
```

```
Glu Pro Glu Ile Pro Tyr Ser Tyr Ser Arg Glu Tyr Asn Glu Tyr Glu
             20                  25                  30

Asn Ile Lys Leu Glu Arg His Val Val Ser Phe Asp Ser Ser Arg Pro
             35                  40                  45

Thr Ser Gly Lys Met Asn Cys Asp Val Cys Gly Leu Ser Cys Ile Ser
 50                  55                  60

Phe Asn Val Leu Met Val His Lys Arg Ser His Thr Gly Glu Arg Pro
 65                  70                  75                  80

Phe Gln Cys Asn Gln Cys Gly Ala Ser Phe Thr Gln Lys Gly Asn Leu
                 85                  90                  95

Leu Arg His Ile Lys Leu His Thr Gly Glu Lys Pro Phe Lys Cys His
                100                 105                 110

Leu Cys Asn Tyr Ala Cys Gln Arg Arg Asp Ala Leu Thr Gly His Leu
                115                 120                 125

Arg Thr His Ser Val Glu Lys Pro Tyr Lys Cys Glu Phe Cys Gly Arg
        130                 135                 140

Ser Tyr Lys Gln Arg Ser Ser Leu Glu Glu His Lys Glu Arg Cys Arg
145                 150                 155                 160

Thr Phe Leu Gln Ser Thr Asp Pro Gly Asp Thr Ala Ser Ala Glu Ala
                165                 170                 175

Arg His Ile Lys Ala Glu Met Gly Ser Glu Arg Ala Leu Val Leu Asp
                180                 185                 190

Arg Leu Ala Ser Asn Val Ala Lys Arg Lys Ser Ser Met Pro Gln Lys
        195                 200                 205

Phe

<210> SEQ ID NO 9
<211> LENGTH: 24
<212> TYPE: DNA
<213> ORGANISM: Artificial Sequence
<220> FEATURE:
<223> OTHER INFORMATION: primer for PCR

<400> SEQUENCE: 9
gtaacctcct ccgtcatatt aaac                                        24

<210> SEQ ID NO 10
<211> LENGTH: 24
<212> TYPE: DNA
<213> ORGANISM: Artificial Sequence
<220> FEATURE:
<223> OTHER INFORMATION: primer for PCR

<400> SEQUENCE: 10
cgagcttttc ttcagaaccc tgac                                        24

<210> SEQ ID NO 11
<211> LENGTH: 24
<212> TYPE: DNA
<213> ORGANISM: Artificial Sequence
<220> FEATURE:
<223> OTHER INFORMATION: probe for EMSA

<400> SEQUENCE: 11
tcagcttttg ggataccct gtca                                         24

<210> SEQ ID NO 12
<211> LENGTH: 24
<212> TYPE: DNA
<213> ORGANISM: Artificial Sequence
```

```
<220> FEATURE:
<223> OTHER INFORMATION: probe for EMSA

<400> SEQUENCE: 12
tcagcttttg ggggtaccct gtca                                           24

<210> SEQ ID NO 13
<211> LENGTH: 30
<212> TYPE: DNA
<213> ORGANISM: Artificial Sequence
<220> FEATURE:
<223> OTHER INFORMATION: primer for PCR

<400> SEQUENCE: 13
atggtgaagg tcggtgtgaa cggatttggc                                     30

<210> SEQ ID NO 14
<211> LENGTH: 30
<212> TYPE: DNA
<213> ORGANISM: Artificial Sequence
<220> FEATURE:
<223> OTHER INFORMATION: primer for PCR

<400> SEQUENCE: 14
gcatcgaagg tggaagagtg ggagttgctg                                     30

<210> SEQ ID NO 15
<211> LENGTH: 1788
<212> TYPE: DNA
<213> ORGANISM: Mus musculus
<220> FEATURE:
<221> NAME/KEY: CDS
<222> LOCATION: (223)...(1515)

<400> SEQUENCE: 15
```

| | |
|---|---|
| aattcgttct accttctctg aaccccagtg gtgtgtcaag gccggactgg gagcttgggg | 60 |
| gaagaggaag aggaagagga atctgcggct catccaggga tcagggtcct tcccaagtgg | 120 |
| ccactcagag gggactcaga gcaagtctag atttgtgtgg cagagagaga cagctctcgt | 180 |
| ttggccttgg ggaggcacaa gtctgttgat aacctgaaga ca atg gat gtc gat | 234 |
|                                                       Met Asp Val Asp<br>                                                         1 | |
| gag ggt caa gac atg tcc caa gtt tca gga aag gag agc ccc cca gtc<br>Glu Gly Gln Asp Met Ser Gln Val Ser Gly Lys Glu Ser Pro Pro Val<br> 5                       10                   15                   20 | 282 |
| agt gac act cca gat gaa ggg gat gag ccc atg cct gtc cct gag gac<br>Ser Asp Thr Pro Asp Glu Gly Asp Glu Pro Met Pro Val Pro Glu Asp<br>                    25                   30                   35 | 330 |
| ctg tcc act acc tct gga gca cag cag aac tcc aag agt gat cga ggc<br>Leu Ser Thr Thr Ser Gly Ala Gln Gln Asn Ser Lys Ser Asp Arg Gly<br>                 40                   45                   50 | 378 |
| atg ggt gaa cgg cct ttc cag tgc aac cag tct ggg gcc tcc ttt acc<br>Met Gly Glu Arg Pro Phe Gln Cys Asn Gln Ser Gly Ala Ser Phe Thr<br>55                   60                   65 | 426 |
| cag aaa ggc aac ctc ctg cgg cac atc aag ctg cac tcg ggt gag aag<br>Gln Lys Gly Asn Leu Leu Arg His Ile Lys Leu His Ser Gly Glu Lys<br> 70                       75                   80 | 474 |
| ccc ttc aaa tgc cat ctt tgc aac tat gcc tgc cgc cgg agg gac gcc<br>Pro Phe Lys Cys His Leu Cys Asn Tyr Ala Cys Arg Arg Arg Asp Ala<br>85                   90                   95                  100 | 522 |
| ctc acc ggc cac ctg agg acg cac tcc gtt ggt aag cct cac aaa tgt<br>Leu Thr Gly His Leu Arg Thr His Ser Val Gly Lys Pro His Lys Cys<br>                 105                 110                 115 | 570 |

-continued

| | | |
|---|---|---|
| gga tat tgt ggc cgg agc tat aaa cag cga agc tct tta gag gag cat<br>Gly Tyr Cys Gly Arg Ser Tyr Lys Gln Arg Ser Ser Leu Glu Glu His<br>120                                  125                            130 | 618 |
| aaa gag cga tgc cac aac tac ttg gaa agc atg ggc ctt ccg ggc gtg<br>Lys Glu Arg Cys His Asn Tyr Leu Glu Ser Met Gly Leu Pro Gly Val<br>135                                 140                           145 | 666 |
| tgc cca gtc att aag gaa gaa act aac cac aac gag atg gca gaa gac<br>Cys Pro Val Ile Lys Glu Glu Thr Asn His Asn Glu Met Ala Glu Asp<br>150                                 155                           160 | 714 |
| ctg tgc aag ata gga gca gag agg tcc ctt gtc ctg gac agg ctg gca<br>Leu Cys Lys Ile Gly Ala Glu Arg Ser Leu Val Leu Asp Arg Leu Ala<br>165                              170                       175                     180 | 762 |
| agc aat gtc gcc aaa cgt aag agc tct atg cct cag aaa ttt ctt gga<br>Ser Asn Val Ala Lys Arg Lys Ser Ser Met Pro Gln Lys Phe Leu Gly<br>                       185                            190                       195 | 810 |
| gac aag tgc ctg tca gac atg ccc tat gac agt gcc aac tat gag aag<br>Asp Lys Cys Leu Ser Asp Met Pro Tyr Asp Ser Ala Asn Tyr Glu Lys<br>                      200                           205                        210 | 858 |
| gag gat atg atg aca tcc cac gtg atg gac cag gcc atc aac aat gcc<br>Glu Asp Met Met Thr Ser His Val Met Asp Gln Ala Ile Asn Asn Ala<br>                 215                           220                       225 | 906 |
| atc aac tac ctg ggg gct gag tcc ctg cgc cca ttg gtg cag aca ccc<br>Ile Asn Tyr Leu Gly Ala Glu Ser Leu Arg Pro Leu Val Gln Thr Pro<br>230                                 235                           240 | 954 |
| ccc ggt agc tcc gag gtg gtg cca gtc atc agc tcc atg tac cag ctg<br>Pro Gly Ser Ser Glu Val Val Pro Val Ile Ser Ser Met Tyr Gln Leu<br>245                              250                       255                     260 | 1002 |
| cac aag ccc ccc tca gat ggc ccc cca cgg tcc aac cat tca gca cag<br>His Lys Pro Pro Ser Asp Gly Pro Pro Arg Ser Asn His Ser Ala Gln<br>                      265                           270                       275 | 1050 |
| gac gcc gtg gat aac ttg ctg ctg ctg tcc aag gcc aag tct gtg tca<br>Asp Ala Val Asp Asn Leu Leu Leu Leu Ser Lys Ala Lys Ser Val Ser<br>                 280                           285                       290 | 1098 |
| tcg gag cga gag gcc tcc ccg agc aac agc tgc caa gac tcc aca gat<br>Ser Glu Arg Glu Ala Ser Pro Ser Asn Ser Cys Gln Asp Ser Thr Asp<br>                      295                           300                     305 | 1146 |
| aca gag agc aac gcg gag gaa cag cgc agc ggc ctt atc tac cta acc<br>Thr Glu Ser Asn Ala Glu Glu Gln Arg Ser Gly Leu Ile Tyr Leu Thr<br>310                                 315                           320 | 1194 |
| aac cac atc aac ccg cat gca cgc aat ggg ctg gct ctc aag gag gag<br>Asn His Ile Asn Pro His Ala Arg Asn Gly Leu Ala Leu Lys Glu Glu<br>325                                 330                       335                     340 | 1242 |
| cag cgc gcc tac gag gtg ctg agg gcg gcc tca gag aac tcg cag gat<br>Gln Arg Ala Tyr Glu Val Leu Arg Ala Ala Ser Glu Asn Ser Gln Asp<br>                      345                           350                       355 | 1290 |
| gcc ttc cgt gtg gtc agc acg agt ggc gag cag ctg aag gtg tac aag<br>Ala Phe Arg Val Val Ser Thr Ser Gly Glu Gln Leu Lys Val Tyr Lys<br>                 360                           365                     370 | 1338 |
| tgc gaa cac tgc cgc gtg ctc ttc ctg gat cac gtc atg tat acc att<br>Cys Glu His Cys Arg Val Leu Phe Leu Asp His Val Met Tyr Thr Ile<br>375                                 380                       385 | 1386 |
| cac atg ggc tgc cat ggc tgc cat ggc ttt cgg gat ccc ttt gag tgt<br>His Met Gly Cys His Gly Cys His Gly Phe Arg Asp Pro Phe Glu Cys<br>390                                 395                       400 | 1434 |
| aac atg tgt ggt tat cac agc cag gac agg tac gag ttc tca tcc cat<br>Asn Met Cys Gly Tyr His Ser Gln Asp Arg Tyr Glu Phe Ser Ser His<br>405                                 410                       415                     420 | 1482 |
| atc acg cgg ggg gag cat cgt tac cac ctg agc taaacccagc caggccccac<br>Ile Thr Arg Gly Glu His Arg Tyr His Leu Ser | 1535 |

-continued

```
                   425                 430
tgaagcacaa agatagctgg ttatgcctcc ttcccggcag ctggacccac agcggacaat    1595
gtgggagtgg atttgcaggc agcatttgtt cttttatgtt ggttgtttgg cgtttcattt    1655
gcgttggaag ataagttttt aatgttagtg acaggattgc attgcatcag caacattcac    1715
aacatccatc cttctagcca gttttgttca ctggtagctg aggtttcccg gatatgtggc    1775 ttcctaaacac tct                                                      1788

<210> SEQ ID NO 16
<211> LENGTH: 1386
<212> TYPE: DNA
<213> ORGANISM: Homo sapiens
<220> FEATURE:
<221> NAME/KEY: CDS
<222> LOCATION: (1)...(1383)

<400> SEQUENCE: 16 aat gtt aaa gta gag act cag agt gat gaa gag aat ggg cgt gcc tgt     48
Asn Val Lys Val Glu Thr Gln Ser Asp Glu Glu Asn Gly Arg Ala Cys
 1               5                  10                  15 gaa atg aat ggg gaa gaa tgt gcg gag gat tta cga atg ctt gat gcc     96
Glu Met Asn Gly Glu Glu Cys Ala Glu Asp Leu Arg Met Leu Asp Ala
             20                  25                  30 tcg gga gag aaa atg aat ggc tcc cac agg gac caa ggc agc tcg gct    144
Ser Gly Glu Lys Met Asn Gly Ser His Arg Asp Gln Gly Ser Ser Ala
         35                  40                  45 ttg tcg gga gtt gga ggc att cga ctt cct aac gga aaa cta aag tgt    192
Leu Ser Gly Val Gly Gly Ile Arg Leu Pro Asn Gly Lys Leu Lys Cys
     50                  55                  60 gat atc tgt ggg atc att tgc atc ggg ccc aat gtg ctc atg gtt cac    240
Asp Ile Cys Gly Ile Ile Cys Ile Gly Pro Asn Val Leu Met Val His
 65                  70                  75                  80 aaa aga agc cac act gga gaa cgg ccc ttc cag tgc aat cag tgc ggg    288
Lys Arg Ser His Thr Gly Glu Arg Pro Phe Gln Cys Asn Gln Cys Gly
                 85                  90                  95 gcc tca ttc acc cag aag ggc aac ctg ctc cgg cac atc aag ctg cat    336
Ala Ser Phe Thr Gln Lys Gly Asn Leu Leu Arg His Ile Lys Leu His
            100                 105                 110 tcc ggg gag aag ccc ttc aaa tgc cac ctc tgc aac tac gcc tgc cgc    384
Ser Gly Glu Lys Pro Phe Lys Cys His Leu Cys Asn Tyr Ala Cys Arg
        115                 120                 125 cgg agg gac gcc ctc act ggc cac ctg agg acg cac tcc gtt ggt aaa    432
Arg Arg Asp Ala Leu Thr Gly His Leu Arg Thr His Ser Val Gly Lys
    130                 135                 140 cct cac aaa tgt gga tat tgt ggc cga agc tat aaa cag cga acg tct    480
Pro His Lys Cys Gly Tyr Cys Gly Arg Ser Tyr Lys Gln Arg Thr Ser
145                 150                 155                 160 tta gag gaa cat aaa gag cgc tgc cac aac tac ttg gaa agc atg ggc    528
Leu Glu Glu His Lys Glu Arg Cys His Asn Tyr Leu Glu Ser Met Gly
                165                 170                 175 ctt ccg ggc aca ctg tac cca gtc att aaa gaa gaa act aag cac agt    576
Leu Pro Gly Thr Leu Tyr Pro Val Ile Lys Glu Glu Thr Lys His Ser
            180                 185                 190 gaa atg gca gaa gac ctg tgc aag ata gga tca gag aga tct ctc gtg    624
Glu Met Ala Glu Asp Leu Cys Lys Ile Gly Ser Glu Arg Ser Leu Val
        195                 200                 205 ctg gac aga cta gca agt aat gtc gcc aaa cgt aag agc tct atg cct    672
Leu Asp Arg Leu Ala Ser Asn Val Ala Lys Arg Lys Ser Ser Met Pro
    210                 215                 220
```

| | | | | | | | | | | | | | | | | |
|---|---|---|---|---|---|---|---|---|---|---|---|---|---|---|---|---|
| cag | aaa | ttt | ctt | ggg | gac | aag | ggc | ctg | tcc | gac | acg | ccc | tac | gac | agt | 720 |
| Gln | Lys | Phe | Leu | Gly | Asp | Lys | Gly | Leu | Ser | Asp | Thr | Pro | Tyr | Asp | Ser | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| gcc | acg | tac | gag | aag | gag | aac | gaa | atg | atg | aag | tcc | cac | gtg | atg | gac | 768 |
| Ala | Thr | Tyr | Glu | Lys | Glu | Asn | Glu | Met | Met | Lys | Ser | His | Val | Met | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| caa | gcc | atc | aac | aac | gcc | atc | aac | tac | ctg | ggg | gcc | gag | tcc | ctg | cgc | 816 |
| Gln | Ala | Ile | Asn | Asn | Ala | Ile | Asn | Tyr | Leu | Gly | Ala | Glu | Ser | Leu | Arg | |
| | | | 260 | | | | | 265 | | | | | 270 | | | |

| | | | | | | | | | | | | | | | | |
|---|---|---|---|---|---|---|---|---|---|---|---|---|---|---|---|---|
| ccg | ctg | gtg | cag | acg | ccc | ccg | ggt | ggt | tcc | gag | gtg | gtc | ccg | gtc | atc | 864 |
| Pro | Leu | Val | Gln | Thr | Pro | Pro | Gly | Gly | Ser | Glu | Val | Val | Pro | Val | Ile | |
| | | | 275 | | | | | 280 | | | | | 285 | | | |

| | | | | | | | | | | | | | | | | |
|---|---|---|---|---|---|---|---|---|---|---|---|---|---|---|---|---|
| agc | ccg | atg | tac | cag | ctg | cac | agg | cgc | tcg | gag | ggc | acc | ccg | cgc | tcc | 912 |
| Ser | Pro | Met | Tyr | Gln | Leu | His | Arg | Arg | Ser | Glu | Gly | Thr | Pro | Arg | Ser | |
| | 290 | | | | | 295 | | | | | 300 | | | | | |

| | | | | | | | | | | | | | | | | |
|---|---|---|---|---|---|---|---|---|---|---|---|---|---|---|---|---|
| aac | cac | tcg | gcc | cag | gac | agc | gcc | gtg | gag | tac | ctg | ctg | ctc | tcc | | 960 |
| Asn | His | Ser | Ala | Gln | Asp | Ser | Ala | Val | Glu | Tyr | Leu | Leu | Leu | Ser | | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| aag | gcc | aag | ttg | gtg | ccc | tcg | gag | cgc | gag | gcg | tcc | ccg | agc | aac | agc | 1008 |
| Lys | Ala | Lys | Leu | Val | Pro | Ser | Glu | Arg | Glu | Ala | Ser | Pro | Ser | Asn | Ser | |
| | | | | 325 | | | | | 330 | | | | | 335 | | |

| | | | | | | | | | | | | | | | | |
|---|---|---|---|---|---|---|---|---|---|---|---|---|---|---|---|---|
| tgc | caa | gac | tcc | acg | gac | acc | gag | agc | aac | aac | gag | gag | cag | cgc | agc | 1056 |
| Cys | Gln | Asp | Ser | Thr | Asp | Thr | Glu | Ser | Asn | Asn | Glu | Glu | Gln | Arg | Ser | |
| | | | 340 | | | | | 345 | | | | | 350 | | | |

| | | | | | | | | | | | | | | | | |
|---|---|---|---|---|---|---|---|---|---|---|---|---|---|---|---|---|
| ggt | ctt | atc | tac | ctg | acc | aac | cac | atc | gcc | cga | cgc | gcg | caa | cgc | gtg | 1104 |
| Gly | Leu | Ile | Tyr | Leu | Thr | Asn | His | Ile | Ala | Arg | Arg | Ala | Gln | Arg | Val | |
| | | | 355 | | | | | 360 | | | | | 365 | | | |

| | | | | | | | | | | | | | | | | |
|---|---|---|---|---|---|---|---|---|---|---|---|---|---|---|---|---|
| tcg | ctc | aag | gag | gag | cac | cgc | gcc | tac | gac | ctg | ctg | cgc | gcc | gcc | tcc | 1152 |
| Ser | Leu | Lys | Glu | Glu | His | Arg | Ala | Tyr | Asp | Leu | Leu | Arg | Ala | Ala | Ser | |
| | 370 | | | | | 375 | | | | | 380 | | | | | |

| | | | | | | | | | | | | | | | | |
|---|---|---|---|---|---|---|---|---|---|---|---|---|---|---|---|---|
| gag | aac | tcg | cag | gac | gcg | ctc | cgc | gtg | gtc | agc | acc | agc | ggg | gag | cag | 1200 |
| Glu | Asn | Ser | Gln | Asp | Ala | Leu | Arg | Val | Val | Ser | Thr | Ser | Gly | Glu | Gln | |
| 385 | | | | 390 | | | | | 395 | | | | | 400 | | |

| | | | | | | | | | | | | | | | | |
|---|---|---|---|---|---|---|---|---|---|---|---|---|---|---|---|---|
| atg | aag | gtg | tac | aag | tgc | gaa | cac | tgc | cgg | gtg | ctc | ttc | ctg | gat | cac | 1248 |
| Met | Lys | Val | Tyr | Lys | Cys | Glu | His | Cys | Arg | Val | Leu | Phe | Leu | Asp | His | |
| | | | | 405 | | | | | 410 | | | | | 415 | | |

| | | | | | | | | | | | | | | | | |
|---|---|---|---|---|---|---|---|---|---|---|---|---|---|---|---|---|
| gtc | atg | tac | acc | atc | cac | atg | ggc | tgc | cac | ggc | ttc | cgt | gat | cct | ttt | 1296 |
| Val | Met | Tyr | Thr | Ile | His | Met | Gly | Cys | His | Gly | Phe | Arg | Asp | Pro | Phe | |
| | | | 420 | | | | | 425 | | | | | 430 | | | |

| | | | | | | | | | | | | | | | | |
|---|---|---|---|---|---|---|---|---|---|---|---|---|---|---|---|---|
| gag | tgc | aac | atg | tgc | ggc | tac | cac | agc | cag | gac | cgg | tac | gag | ttc | tcg | 1344 |
| Glu | Cys | Asn | Met | Cys | Gly | Tyr | His | Ser | Gln | Asp | Arg | Tyr | Glu | Phe | Ser | |
| | | | 435 | | | | | 440 | | | | | 445 | | | |

| | | | | | | | | | | | | |
|---|---|---|---|---|---|---|---|---|---|---|---|---|
| tcg | cac | ata | acg | cga | ggg | gag | cac | cgc | ttc | cac | atg | agc | taa | 1386 |
| Ser | His | Ile | Thr | Arg | Gly | Glu | His | Arg | Phe | His | Met | Ser | | |
| | 450 | | | | | 455 | | | | | 460 | | | |

<210> SEQ ID NO 17
<211> LENGTH: 1296
<212> TYPE: DNA
<213> ORGANISM: Mus musculus
<220> FEATURE:
<221> NAME/KEY: CDS
<222> LOCATION: (1)...(1296)

<400> SEQUENCE: 17

| | | | | | | | | | | | | | | | | |
|---|---|---|---|---|---|---|---|---|---|---|---|---|---|---|---|---|
| atg | gat | gtc | gat | gag | ggt | caa | gac | atg | tcc | caa | gtt | tca | gga | aag | gag | 48 |
| Met | Asp | Val | Asp | Glu | Gly | Gln | Asp | Met | Ser | Gln | Val | Ser | Gly | Lys | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | ccc | cca | gtc | agt | gac | act | cca | gat | gaa | ggg | gat | gag | ccc | atg | cct | 96 |
| Ser | Pro | Pro | Val | Ser | Asp | Thr | Pro | Asp | Glu | Gly | Asp | Glu | Pro | Met | Pro | |
| | | | 20 | | | | | 25 | | | | | 30 | | | |

-continued

```
gtc cct gag gac ctg tcc act acc tct gga gca cag cag aac tcc aag      144
Val Pro Glu Asp Leu Ser Thr Thr Ser Gly Ala Gln Gln Asn Ser Lys
         35                  40                  45 agt gat cga ggc atg gcc agt aat gtt aaa gta gag act cag agt gat      192
Ser Asp Arg Gly Met Ala Ser Asn Val Lys Val Glu Thr Gln Ser Asp
 50                  55                  60 gaa gag aat ggg cgt gcc tgt gaa atg aat ggg gaa gaa tgt gca gag      240
Glu Glu Asn Gly Arg Ala Cys Glu Met Asn Gly Glu Glu Cys Ala Glu
 65                  70                  75                  80 gat tta cga atg ctt gat gcc tcg gga gag aaa atg aat ggc tcc cac      288
Asp Leu Arg Met Leu Asp Ala Ser Gly Glu Lys Met Asn Gly Ser His
                 85                  90                  95 agg gac caa ggc agc tcg gct ttg tca gga gtt gga ggc att cga ctt      336
Arg Asp Gln Gly Ser Ser Ala Leu Ser Gly Val Gly Gly Ile Arg Leu
            100                 105                 110 cct aac gga aaa cta aag tgt gat atc tgt ggg atc gtt tgc atc ggg      384
Pro Asn Gly Lys Leu Lys Cys Asp Ile Cys Gly Ile Val Cys Ile Gly
        115                 120                 125 ccc aat gtg ctc atg gtt cac aaa aga agt cat act ggt gaa cgg cct      432
Pro Asn Val Leu Met Val His Lys Arg Ser His Thr Gly Glu Arg Pro
130                 135                 140 ttc cag tgc aac cag tct ggg gcc tcc ttt acc cag aaa ggc aac ctc      480
Phe Gln Cys Asn Gln Ser Gly Ala Ser Phe Thr Gln Lys Gly Asn Leu
145                 150                 155                 160 ctg cgg cac atc aag ctg cac tcg ggt gag aag ccc ttc aaa tgc cat      528
Leu Arg His Ile Lys Leu His Ser Gly Glu Lys Pro Phe Lys Cys His
                165                 170                 175 ctt tgc aac tat gcc tgc cgc cgg agg gac gcc ctc acc ggc cac ctg      576
Leu Cys Asn Tyr Ala Cys Arg Arg Arg Asp Ala Leu Thr Gly His Leu
            180                 185                 190 agg acg cac tcc gga gac aag tgc ctg tca gac atg ccc tat gac agt      624
Arg Thr His Ser Gly Asp Lys Cys Leu Ser Asp Met Pro Tyr Asp Ser
        195                 200                 205 gcc aac tat gag aag gag gat atg atg aca tcc cac gtg atg gac cag      672
Ala Asn Tyr Glu Lys Glu Asp Met Met Thr Ser His Val Met Asp Gln
210                 215                 220 gcc atc aac aat gcc atc aac tac ctg ggg gct gag tcc ctg cgc cca      720
Ala Ile Asn Asn Ala Ile Asn Tyr Leu Gly Ala Glu Ser Leu Arg Pro
225                 230                 235                 240 ttg gtg cag aca ccc ccc ggt agc tcc gag gtg gtg cca gtc atc agc      768
Leu Val Gln Thr Pro Pro Gly Ser Ser Glu Val Val Pro Val Ile Ser
                245                 250                 255 tcc atg tac cag ctg cac aag ccc ccc tca gat ggc ccc cca cgg tcc      816
Ser Met Tyr Gln Leu His Lys Pro Pro Ser Asp Gly Pro Pro Arg Ser
            260                 265                 270 aac cat tca gca cag gac gcc gtg gat aac ttg ctg ctg ctg tcc aag      864
Asn His Ser Ala Gln Asp Ala Val Asp Asn Leu Leu Leu Leu Ser Lys
        275                 280                 285 gcc aag tct gtg tca tcg gag cga gag gcc tcc ccg agc aac agc tgc      912
Ala Lys Ser Val Ser Ser Glu Arg Glu Ala Ser Pro Ser Asn Ser Cys
290                 295                 300 caa gac tcc aca gat aca gag agc aac gcg gag gaa cag cgc agc ggc      960
Gln Asp Ser Thr Asp Thr Glu Ser Asn Ala Glu Glu Gln Arg Ser Gly
305                 310                 315                 320 ctt atc tac cta acc aac cac atc aac ccg cat gca cgc aat ggg ctg     1008
Leu Ile Tyr Leu Thr Asn His Ile Asn Pro His Ala Arg Asn Gly Leu
                325                 330                 335 gct ctc aag gag gag cag cgc gcc tac gag gtg ctg agg gcg gcc tca     1056
Ala Leu Lys Glu Glu Gln Arg Ala Tyr Glu Val Leu Arg Ala Ala Ser
            340                 345                 350
```

| | |
|---|---|
| gag aac tcg cag gat gcc ttc cgt gtg gtc agc acg agt ggc gag cag<br>Glu Asn Ser Gln Asp Ala Phe Arg Val Val Ser Thr Ser Gly Glu Gln<br>355                    360                  365 | 1104 |
| ctg aag gtg tac aag tgc gaa cac tgc cgc gtg ctc ttc ctg gat cac<br>Leu Lys Val Tyr Lys Cys Glu His Cys Arg Val Leu Phe Leu Asp His<br>     370                   375                  380 | 1152 |
| gtc atg tat acc att cac atg ggc tgc cat ggc tgc cat ggc ttt cgg<br>Val Met Tyr Thr Ile His Met Gly Cys His Gly Cys His Gly Phe Arg<br>385                    390                  395                  400 | 1200 |
| gat ccc ttt gag tgt aac atg tgt ggt tat cac agc cag gac agg tac<br>Asp Pro Phe Glu Cys Asn Met Cys Gly Tyr His Ser Gln Asp Arg Tyr<br>                   405                  410                  415 | 1248 |
| gag ttc tca tcc cat atc acg cgg ggg gag cat cgt tac cac ctg agc<br>Glu Phe Ser Ser His Ile Thr Arg Gly Glu His Arg Tyr His Leu Ser<br>420                    425                  430 | 1296 |

<210> SEQ ID NO 18
<211> LENGTH: 2049
<212> TYPE: DNA
<213> ORGANISM: Mus musculus
<220> FEATURE:
<221> NAME/KEY: CDS
<222> LOCATION: (223)...(1776)

<400> SEQUENCE: 18

| | |
|---|---|
| aattcgttct accttctctg aacccagtg gtgtgtcaag gccggactgg gagcttgggg | 60 |
| gaagaggaag aggaagagga atctgcggct catccaggga tcagggtcct tcccaagtgg | 120 |
| ccactcagag gggactcaga gcaagtctag atttgtgtgg cagagagaga cagctctcgt | 180 |
| ttggccttgg ggaggcacaa gtctgttgat aacctgaaga ca atg gat gtc gat<br>                                                                      Met Asp Val Asp<br>                                                                       1 | 234 |
| gag ggt caa gac atg tcc caa gtt tca gga aag gag agc ccc cca gtc<br>Glu Gly Gln Asp Met Ser Gln Val Ser Gly Lys Glu Ser Pro Pro Val<br>5                     10                   15                       20 | 282 |
| agt gac act cca gat gaa ggg gat gag ccc atg cct gtc cct gag gac<br>Ser Asp Thr Pro Asp Glu Gly Asp Glu Pro Met Pro Val Pro Glu Asp<br>                 25                           30                           35 | 330 |
| ctg tcc act acc tct gga gca cag cag aac tcc aag agt gat cga ggc<br>Leu Ser Thr Thr Ser Gly Ala Gln Gln Asn Ser Lys Ser Asp Arg Gly<br>                     40                           45                         50 | 378 |
| atg gcc agt aat gtt aaa gta gag act cag agt gat gaa gag aat ggg<br>Met Ala Ser Asn Val Lys Val Glu Thr Gln Ser Asp Glu Glu Asn Gly<br>               55                           60                       65 | 426 |
| cgt gcc tgt gaa atg aat ggg gaa gaa tgt gca gag gat tta cga atg<br>Arg Ala Cys Glu Met Asn Gly Glu Glu Cys Ala Glu Asp Leu Arg Met<br>70                             75                           80 | 474 |
| ctt gat gcc tcg gga gag aaa atg aat ggc tcc cac agg gac caa ggc<br>Leu Asp Ala Ser Gly Glu Lys Met Asn Gly Ser His Arg Asp Gln Gly<br>85                     90                   95                       100 | 522 |
| agc tcg gct ttg tca gga gtt gga ggc att cga ctt cct aac gga aaa<br>Ser Ser Ala Leu Ser Gly Val Gly Gly Ile Arg Leu Pro Asn Gly Lys<br>                    105                       110                    115 | 570 |
| cta aag tgt gat atc tgt ggg atc gtt tgc atc ggg ccc aat gtg ctc<br>Leu Lys Cys Asp Ile Cys Gly Ile Val Cys Ile Gly Pro Asn Val Leu<br>               120                       125                    130 | 618 |
| atg gtt cac aaa aga agt cat act ggt gaa cgg cct ttc cag tgc aac<br>Met Val His Lys Arg Ser His Thr Gly Glu Arg Pro Phe Gln Cys Asn<br>               135                       140                    145 | 666 |
| cag tct ggg gcc tcc ttt acc cag aaa ggc aac ctc ctg cgg cac atc | 714 |

```
               Gln Ser Gly Ala Ser Phe Thr Gln Lys Gly Asn Leu Leu Arg His Ile
                   150                 155                 160 aag ctg cac tcg ggt gag aag ccc ttc aaa tgc cat ctt tgc aac tat        762
Lys Leu His Ser Gly Glu Lys Pro Phe Lys Cys His Leu Cys Asn Tyr
165                 170                 175                 180 gcc tgc cgc cgg agg gac gcc ctc acc ggc cac ctg agg acg cac tcc        810
Ala Cys Arg Arg Arg Asp Ala Leu Thr Gly His Leu Arg Thr His Ser
                185                 190                 195 gtt ggt aag cct cac aaa tgt gga tat tgt ggc cgg agc tat aaa cag        858
Val Gly Lys Pro His Lys Cys Gly Tyr Cys Gly Arg Ser Tyr Lys Gln
            200                 205                 210 cga agc tct tta gag gag cat aaa gag cga tgc cac aac tac ttg gaa        906
Arg Ser Ser Leu Glu Glu His Lys Glu Arg Cys His Asn Tyr Leu Glu
        215                 220                 225 agc atg ggc ctt ccg ggc gtg tgc cca gtc att aag gaa gaa act aac        954
Ser Met Gly Leu Pro Gly Val Cys Pro Val Ile Lys Glu Glu Thr Asn
    230                 235                 240 cac aac gag atg gca gaa gac ctg tgc aag ata gga gca gag agg tcc       1002
His Asn Glu Met Ala Glu Asp Leu Cys Lys Ile Gly Ala Glu Arg Ser
245                 250                 255                 260 ctt gtc ctg gac agg ctg gca agc aat gtc gcc aaa cgt aag agc tct       1050
Leu Val Leu Asp Arg Leu Ala Ser Asn Val Ala Lys Arg Lys Ser Ser
                265                 270                 275 atg cct cag aaa ttt ctt gga gac aag tgc ctg tca gac atg ccc tat       1098
Met Pro Gln Lys Phe Leu Gly Asp Lys Cys Leu Ser Asp Met Pro Tyr
            280                 285                 290 gac agt gcc aac tat gag aag gag gat atg atg aca tcc cac gtg atg       1146
Asp Ser Ala Asn Tyr Glu Lys Glu Asp Met Met Thr Ser His Val Met
        295                 300                 305 gac cag gcc atc aac aat gcc atc aac tac ctg ggg gct gag tcc ctg       1194
Asp Gln Ala Ile Asn Asn Ala Ile Asn Tyr Leu Gly Ala Glu Ser Leu
    310                 315                 320 cgc cca ttg gtg cag aca ccc ccc ggt agc tcc gag gtg gtg cca gtc       1242
Arg Pro Leu Val Gln Thr Pro Pro Gly Ser Ser Glu Val Val Pro Val
325                 330                 335                 340 atc agc tcc atg tac cag ctg cac aag ccc ccc tca gat ggc ccc cca       1290
Ile Ser Ser Met Tyr Gln Leu His Lys Pro Pro Ser Asp Gly Pro Pro
                345                 350                 355 cgg tcc aac cat tca gca cag gac gcc gtg gat aac ttg ctg ctg ctg       1338
Arg Ser Asn His Ser Ala Gln Asp Ala Val Asp Asn Leu Leu Leu Leu
            360                 365                 370 tcc aag gcc aag tct gtg tca tcg gag cga gag gcc tcc ccg agc aac       1386
Ser Lys Ala Lys Ser Val Ser Ser Glu Arg Glu Ala Ser Pro Ser Asn
        375                 380                 385 agc tgc caa gac tcc aca gat aca gag agc aac gcg gag gaa cag cgc       1434
Ser Cys Gln Asp Ser Thr Asp Thr Glu Ser Asn Ala Glu Glu Gln Arg
    390                 395                 400 agc ggc ctt atc tac cta acc aac cac atc aac ccg cat gca cgc aat       1482
Ser Gly Leu Ile Tyr Leu Thr Asn His Ile Asn Pro His Ala Arg Asn
405                 410                 415                 420 ggg ctg gct ctc aag gag gag cag cgc gcc tac gag gtg ctg agg gcg       1530
Gly Leu Ala Leu Lys Glu Glu Gln Arg Ala Tyr Glu Val Leu Arg Ala
                425                 430                 435 gcc tca gag aac tcg cag gat gcc ttc cgt gtg gtc agc acg agt ggc       1578
Ala Ser Glu Asn Ser Gln Asp Ala Phe Arg Val Val Ser Thr Ser Gly
            440                 445                 450 gag cag ctg aag gtg tac aag tgc gaa cac tgc cgc gtg ctc ttc ctg       1626
Glu Gln Leu Lys Val Tyr Lys Cys Glu His Cys Arg Val Leu Phe Leu
        455                 460                 465
```

-continued

```
gat cac gtc atg tat acc att cac atg ggc tgc cat ggc tgc cat ggc       1674
Asp His Val Met Tyr Thr Ile His Met Gly Cys His Gly Cys His Gly
        470                 475                 480 ttt cgg gat ccc ttt gag tgt aac atg tgt ggt tat cac agc cag gac       1722
Phe Arg Asp Pro Phe Glu Cys Asn Met Cys Gly Tyr His Ser Gln Asp
485                 490                 495                 500 agg tac gag ttc tca tcc cat atc acg cgg ggg gag cat cgt tac cac       1770
Arg Tyr Glu Phe Ser Ser His Ile Thr Arg Gly Glu His Arg Tyr His
                505                 510                 515 ctg agc taaacccagc caggccccac tgaagcacaa agatagctgg ttatgcctcc        1826
Leu Ser ttcccggcag ctggacccac agcggacaat gtgggagtgg atttgcaggc agcatttgtt    1886
cttttatgtt ggttgtttgg cgtttcattt gcgttggaag ataagttttt aatgttagtg    1946
acaggattgc attgcatcag caacattcac aacatccatc cttctagcca gttttgttca    2006
ctggtagctg aggtttcccg gatatgtggc ttcctaacac tct                      2049

<210> SEQ ID NO 19
<211> LENGTH: 1170
<212> TYPE: DNA
<213> ORGANISM: Mus musculus
<220> FEATURE:
<221> NAME/KEY: CDS
<222> LOCATION: (1)...(1170)

<400> SEQUENCE: 19 atg gat gtc gat gag ggt caa gac atg tcc caa gtt tca gga aag gag        48
Met Asp Val Asp Glu Gly Gln Asp Met Ser Gln Val Ser Gly Lys Glu
1               5                   10                  15 agc ccc cca gtc agt gac act cca gat gaa ggg gat gag ccc atg cct        96
Ser Pro Pro Val Ser Asp Thr Pro Asp Glu Gly Asp Glu Pro Met Pro
                20                  25                  30 gtc cct gag gac ctg tcc act acc tct gga gca cag cag aac tcc aag       144
Val Pro Glu Asp Leu Ser Thr Thr Ser Gly Ala Gln Gln Asn Ser Lys
            35                  40                  45 agt gat cga ggc atg ggt gaa cgg cct ttc cag tgc aac cag tct ggg       192
Ser Asp Arg Gly Met Gly Glu Arg Pro Phe Gln Cys Asn Gln Ser Gly
50                  55                  60 gcc tcc ttt acc cag aaa ggc aac ctc ctg cgg cac atc aag ctg cac       240
Ala Ser Phe Thr Gln Lys Gly Asn Leu Leu Arg His Ile Lys Leu His
65                  70                  75                  80 tcg ggt gag aag ccc ttc aaa tgc cat ctt tgc aac tat gcc tgc cgc       288
Ser Gly Glu Lys Pro Phe Lys Cys His Leu Cys Asn Tyr Ala Cys Arg
                85                  90                  95 cgg agg gac gcc ctc acc ggc cac ctg agg acg cac tcc gtc att aag       336
Arg Arg Asp Ala Leu Thr Gly His Leu Arg Thr His Ser Val Ile Lys
                100                 105                 110 gaa gaa act aac cac aac gag atg gca gaa gac ctg tgc aag ata gga       384
Glu Glu Thr Asn His Asn Glu Met Ala Glu Asp Leu Cys Lys Ile Gly
            115                 120                 125 gca gag agg tcc ctt gtc ctg gac agg ctg gca agc aat gtc gcc aaa       432
Ala Glu Arg Ser Leu Val Leu Asp Arg Leu Ala Ser Asn Val Ala Lys
130                 135                 140 cgt aag agc tct atg cct cag aaa ttt ctt gga gac aag tgc ctg tca       480
Arg Lys Ser Ser Met Pro Gln Lys Phe Leu Gly Asp Lys Cys Leu Ser
145                 150                 155                 160 gac atg ccc tat gac agt gcc aac tat gag aag gag gat atg atg aca       528
Asp Met Pro Tyr Asp Ser Ala Asn Tyr Glu Lys Glu Asp Met Met Thr
                165                 170                 175 tcc cac gtg atg gac cag gcc atc aac aat gcc atc aac tac ctg ggg       576
Ser His Val Met Asp Gln Ala Ile Asn Asn Ala Ile Asn Tyr Leu Gly
```

-continued

| | | |
|---|---|---|
| Ser His Val Met Asp Gln Ala Ile Asn Asn Ala Ile Asn Tyr Leu Gly<br>            180                  185                  190 | |
| gct gag tcc ctg cgc cca ttg gtg cag aca ccc ccc ggt agc tcc gag<br>Ala Glu Ser Leu Arg Pro Leu Val Gln Thr Pro Pro Gly Ser Ser Glu<br>        195                    200                    205 | 624 |
| gtg gtg cca gtc atc agc tcc atg tac cag ctg cac aag ccc ccc tca<br>Val Val Pro Val Ile Ser Ser Met Tyr Gln Leu His Lys Pro Pro Ser<br>    210                  215                    220 | 672 |
| gat ggc ccc cca cgg tcc aac cat tca gca cag gac gcc gtg gat aac<br>Asp Gly Pro Pro Arg Ser Asn His Ser Ala Gln Asp Ala Val Asp Asn<br>225                  230                  235                  240 | 720 |
| ttg ctg ctg ctg tcc aag gcc aag tct gtg tca tcg gag cga gag gcc<br>Leu Leu Leu Leu Ser Lys Ala Lys Ser Val Ser Ser Glu Arg Glu Ala<br>                245                  250                  255 | 768 |
| tcc ccg agc aac agc tgc caa gac tcc aca gat aca gag agc aac gcg<br>Ser Pro Ser Asn Ser Cys Gln Asp Ser Thr Asp Thr Glu Ser Asn Ala<br>                  260                  265                  270 | 816 |
| gag gaa cag cgc agc ggc ctt atc tac cta acc aac cac atc aac ccg<br>Glu Glu Gln Arg Ser Gly Leu Ile Tyr Leu Thr Asn His Ile Asn Pro<br>        275                    280                    285 | 864 |
| cat gca cgc aat ggg ctg gct ctc aag gag gag cag cgc gcc tac gag<br>His Ala Arg Asn Gly Leu Ala Leu Lys Glu Glu Gln Arg Ala Tyr Glu<br>    290                  295                    300 | 912 |
| gtg ctg agg gcg gcc tca gag aac tcg cag gat gcc ttc cgt gtg gtc<br>Val Leu Arg Ala Ala Ser Glu Asn Ser Gln Asp Ala Phe Arg Val Val<br>305                  310                  315                  320 | 960 |
| agc acg agt ggc gag cag ctg aag gtg tac aag tgc gaa cac tgc cgc<br>Ser Thr Ser Gly Glu Gln Leu Lys Val Tyr Lys Cys Glu His Cys Arg<br>                325                  330                  335 | 1008 |
| gtg ctc ttc ctg gat cac gtc atg tat acc att cac atg ggc tgc cat<br>Val Leu Phe Leu Asp His Val Met Tyr Thr Ile His Met Gly Cys His<br>            340                  345                  350 | 1056 |
| ggc tgc cat ggc ttt cgg gat ccc ttt gag tgt aac atg tgt ggt tat<br>Gly Cys His Gly Phe Arg Asp Pro Phe Glu Cys Asn Met Cys Gly Tyr<br>        355                    360                    365 | 1104 |
| cac agc cag gac agg tac gag ttc tca tcc cat atc acg cgg ggg gag<br>His Ser Gln Asp Arg Tyr Glu Phe Ser Ser His Ile Thr Arg Gly Glu<br>    370                  375                    380 | 1152 |
| cat cgt tac cac ctg agc<br>His Arg Tyr His Leu Ser<br>385                  390 | 1170 |

<210> SEQ ID NO 20
<211> LENGTH: 1128
<212> TYPE: DNA
<213> ORGANISM: Mus musculus
<220> FEATURE:
<221> NAME/KEY: CDS
<222> LOCATION: (1)...(1128)

<400> SEQUENCE: 20

| | |
|---|---|
| atg gat gtc gat gag ggt caa gac atg tcc caa gtt tca gga aag gag<br>Met Asp Val Asp Glu Gly Gln Asp Met Ser Gln Val Ser Gly Lys Glu<br>1                  5                    10                  15 | 48 |
| agc ccc cca gtc agt gac act cca gat gaa ggg gat gag ccc atg cct<br>Ser Pro Pro Val Ser Asp Thr Pro Asp Glu Gly Asp Glu Pro Met Pro<br>                20                  25                  30 | 96 |
| gtc cct gag gac ctg tcc act acc tct gga gca cag cag aac tcc aag<br>Val Pro Glu Asp Leu Ser Thr Thr Ser Gly Ala Gln Gln Asn Ser Lys<br>        35                    40                    45 | 144 |
| agt gat cga ggc atg gcc agt aat gtt aaa gta gag act cag agt gat | 192 |

```
                Ser Asp Arg Gly Met Ala Ser Asn Val Lys Val Glu Thr Gln Ser Asp
                     50                  55                  60 gaa gag aat ggg cgt gcc tgt gaa atg aat ggg gaa gaa tgt gca gag       240
Glu Glu Asn Gly Arg Ala Cys Glu Met Asn Gly Glu Glu Cys Ala Glu
 65                  70                  75                  80 gat tta cga atg ctt gat gcc tcg gga gag aaa atg aat ggc tcc cac       288
Asp Leu Arg Met Leu Asp Ala Ser Gly Glu Lys Met Asn Gly Ser His
                 85                  90                  95 agg gac caa ggc agc tcg gct ttg tca gga gtt gga ggc att cga ctt       336
Arg Asp Gln Gly Ser Ser Ala Leu Ser Gly Val Gly Gly Ile Arg Leu
            100                 105                 110 cct aac gga aaa cta aag tgt gat atc tgt ggg atc gtt tgc atc ggg       384
Pro Asn Gly Lys Leu Lys Cys Asp Ile Cys Gly Ile Val Cys Ile Gly
        115                 120                 125 ccc aat gtg ctc atg gtt cac aaa aga agt cat act gga gac aag tgc       432
Pro Asn Val Leu Met Val His Lys Arg Ser His Thr Gly Asp Lys Cys
    130                 135                 140 ctg tca gac atg ccc tat gac agt gcc aac tat gag aag gag gat atg       480
Leu Ser Asp Met Pro Tyr Asp Ser Ala Asn Tyr Glu Lys Glu Asp Met
145                 150                 155                 160 atg aca tcc cac gtg atg gac cag gcc atc aac aat gcc atc aac tac       528
Met Thr Ser His Val Met Asp Gln Ala Ile Asn Asn Ala Ile Asn Tyr
                165                 170                 175 ctg ggg gct gag tcc ctg cgc cca ttg gtg cag aca ccc ccc ggt agc       576
Leu Gly Ala Glu Ser Leu Arg Pro Leu Val Gln Thr Pro Pro Gly Ser
            180                 185                 190 tcc gag gtg gtg cca gtc atc agc tcc atg tac cag ctg cac aag ccc       624
Ser Glu Val Val Pro Val Ile Ser Ser Met Tyr Gln Leu His Lys Pro
        195                 200                 205 ccc tca gat ggc ccc cca cgg tcc aac cat tca gca cag gac gcc gtg       672
Pro Ser Asp Gly Pro Pro Arg Ser Asn His Ser Ala Gln Asp Ala Val
    210                 215                 220 gat aac ttg ctg ctg ctg tcc aag gcc aag tct gtg tca tcg gag cga       720
Asp Asn Leu Leu Leu Leu Ser Lys Ala Lys Ser Val Ser Ser Glu Arg
225                 230                 235                 240 gag gcc tcc ccg agc aac agc tgc caa gac tcc aca gat aca gag agc       768
Glu Ala Ser Pro Ser Asn Ser Cys Gln Asp Ser Thr Asp Thr Glu Ser
                245                 250                 255 aac gcg gag gaa cag cgc agc ggc ctt atc tac cta acc aac cac atc       816
Asn Ala Glu Glu Gln Arg Ser Gly Leu Ile Tyr Leu Thr Asn His Ile
            260                 265                 270 aac ccg cat gca cgc aat ggg ctg gct ctc aag gag gag cag cgc gcc       864
Asn Pro His Ala Arg Asn Gly Leu Ala Leu Lys Glu Glu Gln Arg Ala
        275                 280                 285 tac gag gtg ctg agg gcg gcc tca gag aac tcg cag gat gcc ttc cgt       912
Tyr Glu Val Leu Arg Ala Ala Ser Glu Asn Ser Gln Asp Ala Phe Arg
    290                 295                 300 gtg gtc agc acg agt ggc gag cag ctg aag gtg tac aag tgc gaa cac       960
Val Val Ser Thr Ser Gly Glu Gln Leu Lys Val Tyr Lys Cys Glu His
305                 310                 315                 320 tgc cgc gtg ctc ttc ctg gat cac gtc atg tat acc att cac atg ggc      1008
Cys Arg Val Leu Phe Leu Asp His Val Met Tyr Thr Ile His Met Gly
                325                 330                 335 tgc cat ggc tgc cat ggc ttt cgg gat ccc ttt gag tgt aac atg tgt      1056
Cys His Gly Cys His Gly Phe Arg Asp Pro Phe Glu Cys Asn Met Cys
            340                 345                 350 ggt tat cac agc cag gac agg tac gag ttc tca tcc cat atc acg cgg      1104
Gly Tyr His Ser Gln Asp Arg Tyr Glu Phe Ser Ser His Ile Thr Arg
        355                 360                 365
```

```
ggg gag cat cgt tac cac ctg agc                                          1128
Gly Glu His Arg Tyr His Leu Ser
    370             375

<210> SEQ ID NO 21
<211> LENGTH: 1004
<212> TYPE: DNA
<213> ORGANISM: Homo sapiens
<220> FEATURE:
<221> NAME/KEY: CDS
<222> LOCATION: (1)...(1002)

<400> SEQUENCE: 21 gga gaa cgg ccc ttc cag tgc aat cag tgc ggg gcc tca ttc acc cag           48
Gly Glu Arg Pro Phe Gln Cys Asn Gln Cys Gly Ala Ser Phe Thr Gln
  1               5                  10                  15 aag ggc aac ctg ctc cgg cac atc aag ctg cat tcc ggg gag aag ccc           96
Lys Gly Asn Leu Leu Arg His Ile Lys Leu His Ser Gly Glu Lys Pro
             20                  25                  30 ttc aaa tgc cac ctc tgc aac tac gcc tgc cgc cgg agg gac gcc ctc          144
Phe Lys Cys His Leu Cys Asn Tyr Ala Cys Arg Arg Arg Asp Ala Leu
         35                  40                  45 act ggc cac ctg agg acg cac tcc gtc att aaa gaa gaa act aag cac          192
Thr Gly His Leu Arg Thr His Ser Val Ile Lys Glu Glu Thr Lys His
     50                  55                  60 agt gaa atg gca gaa gac ctg tgc aag ata gga tca gag aga tct ctc          240
Ser Glu Met Ala Glu Asp Leu Cys Lys Ile Gly Ser Glu Arg Ser Leu
 65                  70                  75                  80 gtg ctg gac aga cta gca agt aat gtc gcc aaa cgt aag agc tct atg          288
Val Leu Asp Arg Leu Ala Ser Asn Val Ala Lys Arg Lys Ser Ser Met
                 85                  90                  95 cct cag aaa ttt ctt ggg gac aag ggc ctg tcc gac acg ccc tac gac          336
Pro Gln Lys Phe Leu Gly Asp Lys Gly Leu Ser Asp Thr Pro Tyr Asp
            100                 105                 110 agt gcc acg tac gag aag gag aac gaa atg atg aag tcc cac gtg atg          384
Ser Ala Thr Tyr Glu Lys Glu Asn Glu Met Met Lys Ser His Val Met
        115                 120                 125 gac caa gcc atc aac aac gcc atc aac tac ctg ggg gcc gag tcc ctg          432
Asp Gln Ala Ile Asn Asn Ala Ile Asn Tyr Leu Gly Ala Glu Ser Leu
    130                 135                 140 cgc ccg ctg gtg cag acg ccc ccg ggt ggt tcc gag gtg gtc ccg gtc          480
Arg Pro Leu Val Gln Thr Pro Pro Gly Gly Ser Glu Val Val Pro Val
145                 150                 155                 160 atc agc ccg atg tac cag ctg cac agg cgc tcg gag ggc acc ccg cgc          528
Ile Ser Pro Met Tyr Gln Leu His Arg Arg Ser Glu Gly Thr Pro Arg
                165                 170                 175 tcc aac cac tcg gcc cag gac agc gcc gtg gag tac ctg ctg ctc             576
Ser Asn His Ser Ala Gln Asp Ser Ala Val Glu Tyr Leu Leu Leu Leu
            180                 185                 190 tcc aag gcc aag ttg gtg ccc tcg gag cgc gag gcg tcc ccg agc aac          624
Ser Lys Ala Lys Leu Val Pro Ser Glu Arg Glu Ala Ser Pro Ser Asn
        195                 200                 205 agc tgc caa gac tcc acg gac acc gag agc aac aac gag gag cag cgc          672
Ser Cys Gln Asp Ser Thr Asp Thr Glu Ser Asn Asn Glu Glu Gln Arg
    210                 215                 220 agc ggt ctt atc tac ctg acc aac cac atc gcc cga cgc gcg caa cgc          720
Ser Gly Leu Ile Tyr Leu Thr Asn His Ile Ala Arg Arg Ala Gln Arg
225                 230                 235                 240 gtg tcg ctc aag gag gag cac cgc gcc tac gac ctg ctg cgc gcc gcc          768
Val Ser Leu Lys Glu Glu His Arg Ala Tyr Asp Leu Leu Arg Ala Ala
                245                 250                 255
```

```
tcc gag aac tcg cag gac gcg ctc cgc gtg gtc agc acc agc ggg gag      816
Ser Glu Asn Ser Gln Asp Ala Leu Arg Val Val Ser Thr Ser Gly Glu
        260                 265                 270 cag atg aag gtg tac aag tgc gaa cac tgc cgg gtg ctc ttc ctg gat      864
Gln Met Lys Val Tyr Lys Cys Glu His Cys Arg Val Leu Phe Leu Asp
    275                 280                 285 cac gtc atg tac acc atc cac atg ggc tgc cac ggc ttc cgt gat cct      912
His Val Met Tyr Thr Ile His Met Gly Cys His Gly Phe Arg Asp Pro
290                 295                 300 ttt gag tgc aac atg tgc ggc tac cac agc cag gac cgg tac gag ttc      960
Phe Glu Cys Asn Met Cys Gly Tyr His Ser Gln Asp Arg Tyr Glu Phe
305                 310                 315                 320 tcg tcg cac ata acg cga ggg gag cac cgc ttc cac atg agc             1002
Ser Ser His Ile Thr Arg Gly Glu His Arg Phe His Met Ser
                325                 330 ta                                                                  1004
```

<210> SEQ ID NO 22
<211> LENGTH: 470
<212> TYPE: PRT
<213> ORGANISM: Artificial Sequence
<220> FEATURE:
<223> OTHER INFORMATION: majority sequence
<220> FEATURE:
<221> NAME/KEY: VARIANT
<222> LOCATION: (1)...(470)
<223> OTHER INFORMATION: Xaa = Any Amino Acid

<400> SEQUENCE: 22

```
Xaa Xaa Ala Ser Asn Val Lys Val Glu Thr Gln Ser Asp Glu Glu Asn
1               5                   10                  15

Gly Arg Ala Cys Glu Met Asn Gly Glu Glu Cys Ala Glu Asp Leu Arg
            20                  25                  30

Met Leu Asp Ala Ser Gly Glu Lys Met Asn Gly Ser His Arg Asp Gln
        35                  40                  45

Gly Ser Ser Ala Leu Ser Gly Val Gly Gly Ile Arg Leu Pro Asn Gly
    50                  55                  60

Lys Leu Lys Cys Asp Ile Cys Gly Ile Xaa Cys Ile Gly Pro Asn Val
65                  70                  75                  80

Leu Met Val His Lys Arg Ser His Thr Gly Glu Arg Pro Phe Gln Cys
                85                  90                  95

Asn Gln Cys Gly Ala Ser Phe Thr Gln Lys Gly Asn Leu Leu Arg His
            100                 105                 110

Ile Lys Leu His Ser Gly Glu Lys Pro Phe Lys Cys His Leu Cys Asn
        115                 120                 125

Tyr Ala Cys Arg Arg Arg Asp Ala Leu Thr Gly His Leu Arg Thr His
    130                 135                 140

Ser Val Gly Lys Pro His Lys Cys Gly Tyr Cys Gly Arg Ser Tyr Lys
145                 150                 155                 160

Gln Arg Xaa Ser Leu Glu Glu His Lys Glu Arg Cys His Asn Tyr Leu
                165                 170                 175

Glu Ser Met Gly Leu Pro Gly Xaa Xaa Xaa Pro Val Ile Lys Glu Glu
            180                 185                 190

Thr Xaa His Xaa Glu Met Ala Glu Asp Leu Cys Lys Ile Gly Xaa Glu
        195                 200                 205

Arg Ser Leu Val Leu Asp Arg Leu Ala Ser Asn Val Ala Lys Arg Lys
    210                 215                 220

Ser Ser Met Pro Gln Lys Phe Leu Gly Asp Lys Xaa Leu Ser Asp Xaa
```

```
                225                 230                 235                 240
Pro Tyr Asp Ser Ala Xaa Tyr Glu Lys Glu Xaa Xaa Met Met Xaa Ser
                245                 250                 255

His Val Met Asp Xaa Ala Ile Asn Asn Ala Ile Asn Tyr Leu Gly Ala
            260                 265                 270

Glu Ser Leu Arg Pro Leu Val Gln Thr Pro Pro Gly Xaa Ser Glu Val
        275                 280                 285

Val Pro Val Ile Ser Pro Met Tyr Gln Leu His Xaa Xaa Xaa Ser Xaa
    290                 295                 300

Gly Xaa Pro Arg Ser Asn His Ser Ala Gln Asp Xaa Ala Val Xaa Xaa
305                 310                 315                 320

Leu Leu Leu Leu Ser Lys Ala Lys Xaa Val Xaa Ser Glu Arg Glu Ala
                325                 330                 335

Ser Pro Ser Asn Ser Cys Gln Asp Ser Thr Asp Thr Glu Ser Asn Xaa
            340                 345                 350

Glu Glu Gln Arg Ser Gly Leu Ile Tyr Leu Thr Asn His Ile Xaa Xaa
        355                 360                 365

Xaa Ala Xaa Xaa Xaa Xaa Xaa Leu Lys Glu Glu Xaa Arg Ala Tyr Xaa
    370                 375                 380

Xaa Leu Arg Ala Ala Ser Glu Asn Ser Gln Asp Ala Xaa Arg Val Val
385                 390                 395                 400

Ser Thr Ser Gly Glu Gln Xaa Lys Val Tyr Lys Cys Glu His Cys Arg
                405                 410                 415

Val Leu Phe Leu Asp His Val Met Tyr Thr Ile His Met Xaa Xaa Xaa
            420                 425                 430

Gly Cys His Gly Phe Arg Asp Pro Phe Glu Cys Asn Met Cys Gly Tyr
        435                 440                 445

His Ser Gln Asp Arg Tyr Glu Phe Ser Ser His Ile Thr Arg Gly Glu
    450                 455                 460

His Arg Xaa His Xaa Ser
465                 470

<210> SEQ ID NO 23
<211> LENGTH: 1598
<212> TYPE: DNA
<213> ORGANISM: Mus musculus
<220> FEATURE:
<221> NAME/KEY: CDS
<222> LOCATION: (1)...(1578)

<400> SEQUENCE: 23 atg gaa aca gac gct att gat ggc tat ata aca tgt gac aat gag ctt    48
Met Glu Thr Asp Ala Ile Asp Gly Tyr Ile Thr Cys Asp Asn Glu Leu
  1               5                  10                  15 tca ccc gaa ggg gaa cac gcc aat atg gcc att gac ctc acc tca agc    96
Ser Pro Glu Gly Glu His Ala Asn Met Ala Ile Asp Leu Thr Ser Ser
             20                  25                  30 acg ccc aat gga cag cac gcc tcg cca agt cac atg aca agc aca aat   144
Thr Pro Asn Gly Gln His Ala Ser Pro Ser His Met Thr Ser Thr Asn
         35                  40                  45 tct gta aag ctg gaa atg cag agt gat gaa gag tgt gac agg cag ccc   192
Ser Val Lys Leu Glu Met Gln Ser Asp Glu Glu Cys Asp Arg Gln Pro
     50                  55                  60 ctg agc cgt gag gat gag atc agg ggc cac gat gag ggg agc agc cta   240
Leu Ser Arg Glu Asp Glu Ile Arg Gly His Asp Glu Gly Ser Ser Leu
 65                  70                  75                  80 gaa gaa ccc cta att gag agc agc gag gtg gcc gac aac agg aaa gtc   288
```

-continued

```
Glu Glu Pro Leu Ile Glu Ser Ser Glu Val Ala Asp Asn Arg Lys Val
            85                  90                  95 cag gac ctt caa ggc gag gga gga atc cgg ctt ccg aat ggt aaa ctg       336
Gln Asp Leu Gln Gly Glu Gly Gly Ile Arg Leu Pro Asn Gly Lys Leu
                100                 105                 110 aaa tgt gac gtc tgt ggc atg gtt tgc att ggg ccc aat gtg ctt atg       384
Lys Cys Asp Val Cys Gly Met Val Cys Ile Gly Pro Asn Val Leu Met
                115                 120                 125 gta cat aaa agg agt cac act ggt gag cgg ccc ttc cac tgt aac cag       432
Val His Lys Arg Ser His Thr Gly Glu Arg Pro Phe His Cys Asn Gln
    130                 135                 140 tgc gga gct tct ttt acc cag aag ggc aac ctt ctg aga cac ata aag       480
Cys Gly Ala Ser Phe Thr Gln Lys Gly Asn Leu Leu Arg His Ile Lys
145                 150                 155                 160 tta cac tct gga gag aag ccc ttc aaa tgt cct ttc tgt agc tat gct       528
Leu His Ser Gly Glu Lys Pro Phe Lys Cys Pro Phe Cys Ser Tyr Ala
                165                 170                 175 tgt aga aga agg gac gct ctc aca gga cac ctc agg acc cat tct gtg       576
Cys Arg Arg Arg Asp Ala Leu Thr Gly His Leu Arg Thr His Ser Val
                180                 185                 190 ggt aaa cct cac aag tgt aac tac tgt ggc cga agc tac aag cag cgc       624
Gly Lys Pro His Lys Cys Asn Tyr Cys Gly Arg Ser Tyr Lys Gln Arg
            195                 200                 205 acg tca ctg gag gaa cac aag gaa cgc tgt cac aac tat ctc cag aat       672
Thr Ser Leu Glu Glu His Lys Glu Arg Cys His Asn Tyr Leu Gln Asn
        210                 215                 220 gtc agc atg gag gct gcc ggg cag gtc atg agt cac cat gta ccg cct       720
Val Ser Met Glu Ala Ala Gly Gln Val Met Ser His His Val Pro Pro
225                 230                 235                 240 atg gaa gat tgt aag gaa caa gag cct atc atg gac aac aat att tct       768
Met Glu Asp Cys Lys Glu Gln Glu Pro Ile Met Asp Asn Asn Ile Ser
                245                 250                 255 ctg gtg cct ttt gag aga cct gct gtc ata gag aag ctc acg gca aat       816
Leu Val Pro Phe Glu Arg Pro Ala Val Ile Glu Lys Leu Thr Ala Asn
                260                 265                 270 atg gga aag cgc aaa agc tcc act cct cag aag ttt gtg ggg gaa aag       864
Met Gly Lys Arg Lys Ser Ser Thr Pro Gln Lys Phe Val Gly Glu Lys
            275                 280                 285 ctt atg cga ttc agc tac cca gat att cat ttt gat atg aac tta aca       912
Leu Met Arg Phe Ser Tyr Pro Asp Ile His Phe Asp Met Asn Leu Thr
        290                 295                 300 tat gag aag gag gct gag ctg atg cag tct cat atg atg gac caa gcc       960
Tyr Glu Lys Glu Ala Glu Leu Met Gln Ser His Met Met Asp Gln Ala
305                 310                 315                 320 atc aac aat gca atc acc tac ctt gga gct gag gcc ctt cac cct ctg      1008
Ile Asn Asn Ala Ile Thr Tyr Leu Gly Ala Glu Ala Leu His Pro Leu
                325                 330                 335 atg cag cat gca cca agc aca atc gct gag gtg gcc cca gtt ata agc      1056
Met Gln His Ala Pro Ser Thr Ile Ala Glu Val Ala Pro Val Ile Ser
                340                 345                 350 tca gct tat tct cag gtc tat cat cca aac agg ata gaa aga ccc att      1104
Ser Ala Tyr Ser Gln Val Tyr His Pro Asn Arg Ile Glu Arg Pro Ile
            355                 360                 365 agc agg gaa aca tct gat agt cac gaa aac aac atg gat ggc ccc atc      1152
Ser Arg Glu Thr Ser Asp Ser His Glu Asn Asn Met Asp Gly Pro Ile
        370                 375                 380 tct ctc atc aga cca aag agt cga ccc cag gaa aga gag gcc tcg ccc      1200
Ser Leu Ile Arg Pro Lys Ser Arg Pro Gln Glu Arg Glu Ala Ser Pro
385                 390                 395                 400
```

|  |  |
|---|---|
| agc aat agc tgc ctc gat tct act gac tca gaa agt agc cat gat gac<br>Ser Asn Ser Cys Leu Asp Ser Thr Asp Ser Glu Ser Ser His Asp Asp<br>                 405                       410                      415 | 1248 |
| cgc cag tcc tac caa gga aac cct gcc tta aat ccc aag agg aaa caa<br>Arg Gln Ser Tyr Gln Gly Asn Pro Ala Leu Asn Pro Lys Arg Lys Gln<br>                 420                       425                       430 | 1296 |
| agc cca gct tac atg aag gag gat gtc aag gct ttg gat gct acc aag<br>Ser Pro Ala Tyr Met Lys Glu Asp Val Lys Ala Leu Asp Ala Thr Lys<br>                 435                       440                       445 | 1344 |
| gcc ccc aag ggc tct ctg aag gac atc tat aag gtt ttc aat gga gaa<br>Ala Pro Lys Gly Ser Leu Lys Asp Ile Tyr Lys Val Phe Asn Gly Glu<br>450                       455                       460 | 1392 |
| gga gaa cag ata agg gcc ttc aag tgt gag cac tgc cga gtc ctt ttt<br>Gly Glu Gln Ile Arg Ala Phe Lys Cys Glu His Cys Arg Val Leu Phe<br>465                       470                       475                       480 | 1440 |
| cta gac cat gtc atg tac acc att cac atg ggt tgc cat ggc tac cgg<br>Leu Asp His Val Met Tyr Thr Ile His Met Gly Cys His Gly Tyr Arg<br>                 485                       490                       495 | 1488 |
| gac cca ctg gaa tgc aac atc tgt ggc tac aga agc cag gac cgc tac<br>Asp Pro Leu Glu Cys Asn Ile Cys Gly Tyr Arg Ser Gln Asp Arg Tyr<br>                 500                       505                       510 | 1536 |
| gaa ttt tca tca cac att gtt ggg ggg cag cac aca ttc cac<br>Glu Phe Ser Ser His Ile Val Gly Gly Gln His Thr Phe His<br>                 515                       520                       525 | 1578 |
| taggcgtttg cattccaagg | 1598 |

<210> SEQ ID NO 24
<211> LENGTH: 526
<212> TYPE: PRT
<213> ORGANISM: Mus musculus

<400> SEQUENCE: 24

Met Glu Thr Asp Ala Ile Asp Gly Tyr Ile Thr Cys Asp Asn Glu Leu
1               5                   10                  15

Ser Pro Glu Gly Glu His Ala Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Gln Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Asp Leu Gln Gly Glu Gly Ile Arg Leu Pro Asn Gly Lys Leu
            100                 105                 110

Lys Cys Asp Val Cys Gly Met Val Cys Ile Gly Pro Asn Val Leu Met
        115                 120                 125

Val His Lys Arg Ser His Thr Gly Glu Arg Pro Phe His Cys Asn Gln
    130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
                165                 170                 175

Cys Arg Arg Arg Asp Ala Leu Thr Gly His Leu Arg Thr His Ser Val
            180                 185                 190

Gly Lys Pro His Lys Cys Asn Tyr Cys Gly Arg Ser Tyr Lys Gln Arg

```
                    195                 200                 205
Thr Ser Leu Glu Glu His Lys Glu Arg Cys His Asn Tyr Leu Gln Asn
            210                 215                 220
Val Ser Met Glu Ala Ala Gly Gln Val Met Ser His His Val Pro Pro
225                 230                 235                 240
Met Glu Asp Cys Lys Glu Gln Glu Pro Ile Met Asp Asn Asn Ile Ser
                    245                 250                 255
Leu Val Pro Phe Glu Arg Pro Ala Val Ile Glu Lys Leu Thr Ala Asn
                260                 265                 270
Met Gly Lys Arg Lys Ser Ser Thr Pro Gln Lys Phe Val Gly Glu Lys
            275                 280                 285
Leu Met Arg Phe Ser Tyr Pro Asp Ile His Phe Asp Met Asn Leu Thr
        290                 295                 300
Tyr Glu Lys Glu Ala Glu Leu Met Gln Ser His Met Met Asp Gln Ala
305                 310                 315                 320
Ile Asn Asn Ala Ile Thr Tyr Leu Gly Ala Glu Ala Leu His Pro Leu
                    325                 330                 335
Met Gln His Ala Pro Ser Thr Ile Ala Glu Val Ala Pro Val Ile Ser
                340                 345                 350
Ser Ala Tyr Ser Gln Val Tyr His Pro Asn Arg Ile Glu Arg Pro Ile
            355                 360                 365
Ser Arg Glu Thr Ser Asp Ser His Glu Asn Asn Met Asp Gly Pro Ile
        370                 375                 380
Ser Leu Ile Arg Pro Lys Ser Arg Pro Gln Glu Arg Glu Ala Ser Pro
385                 390                 395                 400
Ser Asn Ser Cys Leu Asp Ser Thr Asp Ser Glu Ser Ser His Asp Asp
                    405                 410                 415
Arg Gln Ser Tyr Gln Gly Asn Pro Ala Leu Asn Pro Lys Arg Lys Gln
                420                 425                 430
Ser Pro Ala Tyr Met Lys Glu Asp Val Lys Ala Leu Asp Ala Thr Lys
            435                 440                 445
Ala Pro Lys Gly Ser Leu Lys Asp Ile Tyr Lys Val Phe Asn Gly Glu
450                 455                 460
Gly Glu Gln Ile Arg Ala Phe Lys Cys Glu His Cys Arg Val Leu Phe
465                 470                 475                 480
Leu Asp His Val Met Tyr Thr Ile His Met Gly Cys His Gly Tyr Arg
                    485                 490                 495
Asp Pro Leu Glu Cys Asn Ile Cys Gly Tyr Arg Ser Gln Asp Arg Tyr
                500                 505                 510
Glu Phe Ser Ser His Ile Val Gly Gly Gln His Thr Phe His
            515                 520                 525

<210> SEQ ID NO 25
<211> LENGTH: 1520
<212> TYPE: DNA
<213> ORGANISM: Mus musculus
<220> FEATURE:
<221> NAME/KEY: CDS
<222> LOCATION: (1)...(1500)

<400> SEQUENCE: 25 atg gaa aca gac gct att gat ggc tat ata aca tgt gac aat gag ctt    48
Met Glu Thr Asp Ala Ile Asp Gly Tyr Ile Thr Cys Asp Asn Glu Leu
  1               5                  10                  15 tca ccc gaa ggg gaa cac gcc aat atg gcc att gac ctc acc tca agc    96
Ser Pro Glu Gly Glu His Ala Asn Met Ala Ile Asp Leu Thr Ser Ser
```

-continued

|  |  |  |  |  |  |  |  |  |  |  |  |  |  |  |  |
|---|---|---|---|---|---|---|---|---|---|---|---|---|---|---|---|
|  |  | 20 |  |  |  | 25 |  |  |  | 30 |  |  |  |  |  |
| acg | ccc | aat | gga | cag | cac | gcc | tcg | cca | agt | cac | atg | aca | agc | aca | aat | 144 |
| Thr | Pro | Asn | Gly | Gln | His | Ala | Ser | Pro | Ser | His | Met | Thr | Ser | Thr | Asn |  |
|  |  | 35 |  |  |  | 40 |  |  |  | 45 |  |  |  |  |  |
| tct | gta | aag | ctg | gaa | atg | cag | agt | gat | gaa | gag | tgt | gac | agg | cag | ccc | 192 |
| Ser | Val | Lys | Leu | Glu | Met | Gln | Ser | Asp | Glu | Glu | Cys | Asp | Arg | Gln | Pro |  |
| 50 |  |  |  |  | 55 |  |  |  |  | 60 |  |  |  |  |  |  |
| ctg | agc | cgt | gag | gat | gag | atc | agg | ggc | cac | gat | gag | ggg | agc | agc | cta | 240 |
| Leu | Ser | Arg | Glu | Asp | Glu | Ile | Arg | Gly | His | Asp | Glu | Gly | Ser | Ser | Leu |  |
| 65 |  |  |  |  | 70 |  |  |  |  | 75 |  |  |  |  | 80 |  |
| gaa | gaa | ccc | cta | att | gag | agc | agc | gag | gtg | gcc | gac | aac | agg | aaa | gtc | 288 |
| Glu | Glu | Pro | Leu | Ile | Glu | Ser | Ser | Glu | Val | Ala | Asp | Asn | Arg | Lys | Val |  |
|  |  |  |  | 85 |  |  |  |  | 90 |  |  |  |  | 95 |  |  |
| cag | gac | ctt | caa | ggc | gag | gga | gga | atc | cgg | ctt | ccg | aat | ggt | gag | cgg | 336 |
| Gln | Asp | Leu | Gln | Gly | Glu | Gly | Gly | Ile | Arg | Leu | Pro | Asn | Gly | Glu | Arg |  |
|  |  |  | 100 |  |  |  |  | 105 |  |  |  |  | 110 |  |  |  |
| ccc | ttc | cac | tgt | aac | cag | tgc | gga | gct | tct | ttt | acc | cag | aag | ggc | aac | 384 |
| Pro | Phe | His | Cys | Asn | Gln | Cys | Gly | Ala | Ser | Phe | Thr | Gln | Lys | Gly | Asn |  |
|  |  | 115 |  |  |  |  | 120 |  |  |  |  | 125 |  |  |  |  |
| ctt | ctg | aga | cac | ata | aag | tta | cac | tct | gga | gag | aag | ccc | ttc | aaa | tgt | 432 |
| Leu | Leu | Arg | His | Ile | Lys | Leu | His | Ser | Gly | Glu | Lys | Pro | Phe | Lys | Cys |  |
|  | 130 |  |  |  |  | 135 |  |  |  |  | 140 |  |  |  |  |  |
| cct | ttc | tgt | agc | tat | gct | tgt | aga | aga | agg | gac | gct | ctc | aca | gga | cac | 480 |
| Pro | Phe | Cys | Ser | Tyr | Ala | Cys | Arg | Arg | Arg | Asp | Ala | Leu | Thr | Gly | His |  |
| 145 |  |  |  |  | 150 |  |  |  |  | 155 |  |  |  |  | 160 |  |
| ctc | agg | acc | cat | tct | gtg | ggt | aaa | cct | cac | aag | tgt | aac | tac | tgt | ggc | 528 |
| Leu | Arg | Thr | His | Ser | Val | Gly | Lys | Pro | His | Lys | Cys | Asn | Tyr | Cys | Gly |  |
|  |  |  |  | 165 |  |  |  |  | 170 |  |  |  |  | 175 |  |  |
| cga | agc | tac | aag | cag | cgc | acg | tca | ctg | gag | gaa | cac | aag | gaa | cgc | tgt | 576 |
| Arg | Ser | Tyr | Lys | Gln | Arg | Thr | Ser | Leu | Glu | Glu | His | Lys | Glu | Arg | Cys |  |
|  |  |  | 180 |  |  |  |  | 185 |  |  |  |  | 190 |  |  |  |
| cac | aac | tat | ctc | cag | aat | gtc | agc | atg | gag | gct | gcc | ggg | cag | gtc | atg | 624 |
| His | Asn | Tyr | Leu | Gln | Asn | Val | Ser | Met | Glu | Ala | Ala | Gly | Gln | Val | Met |  |
|  |  | 195 |  |  |  |  | 200 |  |  |  |  | 205 |  |  |  |  |
| agt | cac | cat | gta | ccg | cct | atg | gaa | gat | tgt | aag | gaa | caa | gag | cct | atc | 672 |
| Ser | His | His | Val | Pro | Pro | Met | Glu | Asp | Cys | Lys | Glu | Gln | Glu | Pro | Ile |  |
| 210 |  |  |  |  | 215 |  |  |  |  | 220 |  |  |  |  |  |  |
| atg | gac | aac | aat | att | tct | ctg | gtg | cct | ttt | gag | aga | cct | gct | gtc | ata | 720 |
| Met | Asp | Asn | Asn | Ile | Ser | Leu | Val | Pro | Phe | Glu | Arg | Pro | Ala | Val | Ile |  |
| 225 |  |  |  |  | 230 |  |  |  |  | 235 |  |  |  |  | 240 |  |
| gag | aag | ctc | acg | gca | aat | atg | gga | aag | cgc | aaa | agc | tcc | act | cct | cag | 768 |
| Glu | Lys | Leu | Thr | Ala | Asn | Met | Gly | Lys | Arg | Lys | Ser | Ser | Thr | Pro | Gln |  |
|  |  |  |  | 245 |  |  |  |  | 250 |  |  |  |  | 255 |  |  |
| aag | ttt | gtg | ggg | gaa | aag | ctt | atg | cga | ttc | agc | tac | cca | gat | att | cat | 816 |
| Lys | Phe | Val | Gly | Glu | Lys | Leu | Met | Arg | Phe | Ser | Tyr | Pro | Asp | Ile | His |  |
|  |  |  | 260 |  |  |  |  | 265 |  |  |  |  | 270 |  |  |  |
| ttt | gat | atg | aac | tta | aca | tat | gag | aag | gag | gct | gag | ctg | atg | cag | tct | 864 |
| Phe | Asp | Met | Asn | Leu | Thr | Tyr | Glu | Lys | Glu | Ala | Glu | Leu | Met | Gln | Ser |  |
|  | 275 |  |  |  |  | 280 |  |  |  |  | 285 |  |  |  |  |  |
| cat | atg | atg | gac | caa | gcc | atc | aac | aat | gca | atc | acc | tac | ctt | gga | gct | 912 |
| His | Met | Met | Asp | Gln | Ala | Ile | Asn | Asn | Ala | Ile | Thr | Tyr | Leu | Gly | Ala |  |
|  | 290 |  |  |  |  | 295 |  |  |  |  | 300 |  |  |  |  |  |
| gag | gcc | ctt | cac | cct | ctg | atg | cag | cat | gca | cca | agc | aca | atc | gct | gag | 960 |
| Glu | Ala | Leu | His | Pro | Leu | Met | Gln | His | Ala | Pro | Ser | Thr | Ile | Ala | Glu |  |
| 305 |  |  |  |  | 310 |  |  |  |  | 315 |  |  |  |  | 320 |  |
| gtg | gcc | cca | gtt | ata | agc | tca | gct | tat | tct | cag | gtc | tat | cat | cca | aac | 1008 |
| Val | Ala | Pro | Val | Ile | Ser | Ser | Ala | Tyr | Ser | Gln | Val | Tyr | His | Pro | Asn |  |
|  |  |  |  | 325 |  |  |  |  | 330 |  |  |  |  | 335 |  |  |
| agg | ata | gaa | aga | ccc | att | agc | agg | gaa | aca | tct | gat | agt | cac | gaa | aac | 1056 |

```
                                              -continued

Arg Ile Glu Arg Pro Ile Ser Arg Glu Thr Ser Asp Ser His Glu Asn
            340                 345                 350 aac atg gat ggc ccc atc tct ctc atc aga cca aag agt cga ccc cag        1104
Asn Met Asp Gly Pro Ile Ser Leu Ile Arg Pro Lys Ser Arg Pro Gln
        355                 360                 365 gaa aga gag gcc tcg ccc agc aat agc tgc ctc gat tct act gac tca        1152
Glu Arg Glu Ala Ser Pro Ser Asn Ser Cys Leu Asp Ser Thr Asp Ser
    370                 375                 380 gaa agt agc cat gat gac cgc cag tcc tac caa gga aac cct gcc tta        1200
Glu Ser Ser His Asp Asp Arg Gln Ser Tyr Gln Gly Asn Pro Ala Leu
385                 390                 395                 400 aat ccc aag agg aaa caa agc cca gct tac atg aag gag gat gtc aag        1248
Asn Pro Lys Arg Lys Gln Ser Pro Ala Tyr Met Lys Glu Asp Val Lys
                405                 410                 415 gct ttg gat gct acc aag gcc ccc aag ggc tct ctg aag gac atc tat        1296
Ala Leu Asp Ala Thr Lys Ala Pro Lys Gly Ser Leu Lys Asp Ile Tyr
            420                 425                 430 aag gtt ttc aat gga gaa gga gaa cag ata agg gcc ttc aag tgt gag        1344
Lys Val Phe Asn Gly Glu Gly Glu Gln Ile Arg Ala Phe Lys Cys Glu
        435                 440                 445 cac tgc cga gtc ctt ttt cta gac cat gtc atg tac acc att cac atg        1392
His Cys Arg Val Leu Phe Leu Asp His Val Met Tyr Thr Ile His Met
    450                 455                 460 ggt tgc cat ggc tac cgg gac cca ctg gaa tgc aac atc tgt ggc tac        1440
Gly Cys His Gly Tyr Arg Asp Pro Leu Glu Cys Asn Ile Cys Gly Tyr
465                 470                 475                 480 aga agc cag gac cgc tac gaa ttt tca tca cac att gtt ggg ggg cag        1488
Arg Ser Gln Asp Arg Tyr Glu Phe Ser Ser His Ile Val Gly Gly Gln
                485                 490                 495 cac aca ttc cac taggcgtttg cattccaagg                                   1520
His Thr Phe His
            500

<210> SEQ ID NO 26
<211> LENGTH: 500
<212> TYPE: PRT
<213> ORGANISM: Mus musculus

<400> SEQUENCE: 26

Met Glu Thr Asp Ala Ile Asp Gly Tyr Ile Thr Cys Asp Asn Glu Leu
1               5                   10                  15

Ser Pro Glu Gly Glu His Ala Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Gln Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Asp Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
        115                 120                 125

Leu Leu Arg His Ile Lys Leu His Ser Gly Glu Lys Pro Phe Lys Cys
    130                 135                 140

Pro Phe Cys Ser Tyr Ala Cys Arg Arg Arg Asp Ala Leu Thr Gly His
```

```
              145                 150                 155                 160
Leu Arg Thr His Ser Val Gly Lys Pro His Lys Cys Asn Tyr Cys Gly
                165                 170                 175
Arg Ser Tyr Lys Gln Arg Thr Ser Leu Glu Glu His Lys Glu Arg Cys
            180                 185                 190
His Asn Tyr Leu Gln Asn Val Ser Met Glu Ala Ala Gly Gln Val Met
            195                 200                 205
Ser His His Val Pro Pro Met Glu Asp Cys Lys Glu Gln Glu Pro Ile
        210                 215                 220
Met Asp Asn Asn Ile Ser Leu Val Pro Phe Glu Arg Pro Ala Val Ile
225                 230                 235                 240
Glu Lys Leu Thr Ala Asn Met Gly Lys Arg Lys Ser Ser Thr Pro Gln
                245                 250                 255
Lys Phe Val Gly Glu Lys Leu Met Arg Phe Ser Tyr Pro Asp Ile His
                260                 265                 270
Phe Asp Met Asn Leu Thr Tyr Glu Lys Glu Ala Glu Leu Met Gln Ser
            275                 280                 285
His Met Met Asp Gln Ala Ile Asn Asn Ala Ile Thr Tyr Leu Gly Ala
        290                 295                 300
Glu Ala Leu His Pro Leu Met Gln His Ala Pro Ser Thr Ile Ala Glu
305                 310                 315                 320
Val Ala Pro Val Ile Ser Ser Ala Tyr Ser Gln Val Tyr His Pro Asn
                325                 330                 335
Arg Ile Glu Arg Pro Ile Ser Arg Glu Thr Ser Asp Ser His Glu Asn
            340                 345                 350
Asn Met Asp Gly Pro Ile Ser Leu Ile Arg Pro Lys Ser Arg Pro Gln
            355                 360                 365
Glu Arg Glu Ala Ser Pro Ser Asn Ser Cys Leu Asp Ser Thr Asp Ser
        370                 375                 380
Glu Ser Ser His Asp Asp Arg Gln Ser Tyr Gln Gly Asn Pro Ala Leu
385                 390                 395                 400
Asn Pro Lys Arg Lys Gln Ser Pro Ala Tyr Met Lys Glu Asp Val Lys
                405                 410                 415
Ala Leu Asp Ala Thr Lys Ala Pro Lys Gly Ser Leu Lys Asp Ile Tyr
            420                 425                 430
Lys Val Phe Asn Gly Glu Gly Glu Gln Ile Arg Ala Phe Lys Cys Glu
        435                 440                 445
His Cys Arg Val Leu Phe Leu Asp His Val Met Tyr Thr Ile His Met
    450                 455                 460
Gly Cys His Gly Tyr Arg Asp Pro Leu Glu Cys Asn Ile Cys Gly Tyr
465                 470                 475                 480
Arg Ser Gln Asp Arg Tyr Glu Phe Ser Ser His Ile Val Gly Gly Gln
                485                 490                 495
His Thr Phe His
            500

<210> SEQ ID NO 27
<211> LENGTH: 1927
<212> TYPE: DNA
<213> ORGANISM: Homo sapiens
<220> FEATURE:
<221> NAME/KEY: CDS
<222> LOCATION: (190)...(1767)

<400> SEQUENCE: 27
```

```
gcccgggcag gtcgcattgc tatagcactg actgacctct ctctctctct tttttttcct      60
ctttcctgaa acccgacatt gtcacctcct ctttgagggt tagaagaagc tgagatctcc     120
cgacagagct ggaaatggtg atgaatcttt tttaatcaaa ggacaatttc ttttcattgc     180 actttgact atg gaa aca gag gct att gat ggc tat ata acg tgt gac aat     231
          Met Glu Thr Glu Ala Ile Asp Gly Tyr Ile Thr Cys Asp Asn
          1               5                  10 gag ctt tca ccc gaa agg gag cac tcc aat atg gca att gac ctc acc       279
Glu Leu Ser Pro Glu Arg Glu His Ser Asn Met Ala Ile Asp Leu Thr
15              20                  25                  30 tca agc aca ccc aat gga cag cat gcc tca cca agt cac atg aca agc       327
Ser Ser Thr Pro Asn Gly Gln His Ala Ser Pro Ser His Met Thr Ser
                35                  40                  45 aca gat tca gta aag cta gaa atg cag agt gat gaa gag tgt gac agg       375
Thr Asp Ser Val Lys Leu Glu Met Gln Ser Asp Glu Glu Cys Asp Arg
            50                  55                  60 aaa ccc ctg agc cgt gaa gat gag atc agg ggc cat gat gag ggt agc       423
Lys Pro Leu Ser Arg Glu Asp Glu Ile Arg Gly His Asp Glu Gly Ser
            65                  70                  75 agc cta gaa gaa ccc cta att gag agc agc gag gtg gct gac aac agg       471
Ser Leu Glu Glu Pro Leu Ile Glu Ser Ser Glu Val Ala Asp Asn Arg
        80                  85                  90 gaa gtc cag gag ctt caa ggc gag gga gga atc cgg ctt ccg aat ggt       519
Glu Val Gln Glu Leu Gln Gly Glu Gly Gly Ile Arg Leu Pro Asn Gly
95                  100                 105                 110 aaa ctg aaa tgt gac gtc tgt ggc atg gtt tgc att ggg ccc aat gtg       567
Lys Leu Lys Cys Asp Val Cys Gly Met Val Cys Ile Gly Pro Asn Val
                115                 120                 125 ctt atg gta cat aaa agg agt cac act ggt gaa cgc ccc ttc cac tgt       615
Leu Met Val His Lys Arg Ser His Thr Gly Glu Arg Pro Phe His Cys
                130                 135                 140 aac cag tgt gga gct tct ttt act cag aag ggc aac ctt ctg aga cac       663
Asn Gln Cys Gly Ala Ser Phe Thr Gln Lys Gly Asn Leu Leu Arg His
            145                 150                 155 ata aag tta cac tct gga gag aag ccg ttc aaa tgt cct ttc tgt agt       711
Ile Lys Leu His Ser Gly Glu Lys Pro Phe Lys Cys Pro Phe Cys Ser
160                 165                 170 cac gcc tgt aga aga agg gac gcc ctc aca gga tac ctc agg acc cat       759
His Ala Cys Arg Arg Arg Asp Ala Leu Thr Gly Tyr Leu Arg Thr His
175             180                 185                 190 tct gtg ggt aaa cct cac aag tgc aac tac tgt gga cga agc tac aag       807
Ser Val Gly Lys Pro His Lys Cys Asn Tyr Cys Gly Arg Ser Tyr Lys
                195                 200                 205 cag cgc agt tca ctg gag gag cac aag gaa cgc tgc cac aac tat ctc       855
Gln Arg Ser Ser Leu Glu Glu His Lys Glu Arg Cys His Asn Tyr Leu
            210                 215                 220 cag aat gtc agc atg gag gct gct ggg cag gtc atg agt cac cat gta       903
Gln Asn Val Ser Met Glu Ala Ala Gly Gln Val Met Ser His His Val
        225                 230                 235 cct cct atg gaa gat tgt aag gaa caa gag cct att atg gac aac aat       951
Pro Pro Met Glu Asp Cys Lys Glu Gln Glu Pro Ile Met Asp Asn Asn
240                 245                 250 att tct ctg gtg cct ttt gag aga cct gct gtc ata gag aag ctc acg       999
Ile Ser Leu Val Pro Phe Glu Arg Pro Ala Val Ile Glu Lys Leu Thr
255                 260                 265                 270 ggg aat atg gga aaa cgt aaa agc tcc act cca caa aag ttt gtg ggg      1047
Gly Asn Met Gly Lys Arg Lys Ser Ser Thr Pro Gln Lys Phe Val Gly
                275                 280                 285 gaa aag ctc atg cga ttc agc tac cca gat att cac ttt gat atg aac      1095
```

-continued

```
Glu Lys Leu Met Arg Phe Ser Tyr Pro Asp Ile His Phe Asp Met Asn
            290                 295                 300 tta aca tat gag aag gag gct gag ctg atg cag tct cat atg atg gac      1143
Leu Thr Tyr Glu Lys Glu Ala Glu Leu Met Gln Ser His Met Met Asp
        305                 310                 315 caa gcc atc aac aat gca atc acc tac ctt gga gct gag gcc ctt cac      1191
Gln Ala Ile Asn Asn Ala Ile Thr Tyr Leu Gly Ala Glu Ala Leu His
    320                 325                 330 cct ctg atg cag cac ccg cca agc aca atc gct gaa gtg gcc cca gtt      1239
Pro Leu Met Gln His Pro Pro Ser Thr Ile Ala Glu Val Ala Pro Val
335                 340                 345                 350 ata agc tca gct tat tct cag gtc tat cat cca aat agg ata gaa aga      1287
Ile Ser Ser Ala Tyr Ser Gln Val Tyr His Pro Asn Arg Ile Glu Arg
                355                 360                 365 ccc att agc agg gaa act gct gat agt cat gaa aac aac atg gat ggc      1335
Pro Ile Ser Arg Glu Thr Ala Asp Ser His Glu Asn Asn Met Asp Gly
            370                 375                 380 ccc atc tct ctc atc aga cca aag agt cga ccc cag gaa aga gag gcc      1383
Pro Ile Ser Leu Ile Arg Pro Lys Ser Arg Pro Gln Glu Arg Glu Ala
        385                 390                 395 tct ccc agc aat agc tgc ctg gat tcc act gac tca gaa agc agc cat      1431
Ser Pro Ser Asn Ser Cys Leu Asp Ser Thr Asp Ser Glu Ser Ser His
    400                 405                 410 gat gac cac cag tcc tac caa gga cac cct gcc tta aat ccc aag agg      1479
Asp Asp His Gln Ser Tyr Gln Gly His Pro Ala Leu Asn Pro Lys Arg
415                 420                 425                 430 aaa caa agc cca gct tac atg aag gag gat gtc aaa gct ttg gat act      1527
Lys Gln Ser Pro Ala Tyr Met Lys Glu Asp Val Lys Ala Leu Asp Thr
                435                 440                 445 acc aag gct cct aag ggc tct ctg aag gac atc tac aag gtc ttc aat      1575
Thr Lys Ala Pro Lys Gly Ser Leu Lys Asp Ile Tyr Lys Val Phe Asn
            450                 455                 460 ggg gaa gga gaa cag att agg gcc ttc aag tgt gag cac tgc cga gtc      1623
Gly Glu Gly Glu Gln Ile Arg Ala Phe Lys Cys Glu His Cys Arg Val
        465                 470                 475 ctt ttc cta gac cat gtc atg tac acc att cac atg ggt tgc cat ggc      1671
Leu Phe Leu Asp His Val Met Tyr Thr Ile His Met Gly Cys His Gly
    480                 485                 490 tac cgg gac cca ctg gaa tgt aac atc tgt ggc tac aga agc cag gac      1719
Tyr Arg Asp Pro Leu Glu Cys Asn Ile Cys Gly Tyr Arg Ser Gln Asp
495                 500                 505                 510 cgt tat gag ttt tca tca cac att gtt cga ggg gag cac aca ttc cac      1767
Arg Tyr Glu Phe Ser Ser His Ile Val Arg Gly Glu His Thr Phe His
                515                 520                 525 taggccttt  cattccaaag  gggaccctat  gaagtaaaga  ctgcacatga  agaaatactg   1827
cacttacaat  cccacctttc  ctcaaatgtt  gtaccttta  tttttttaat  ataatactgg   1887
tgataatctt  attttgtgga  gcagtgtcat  ttgctctgct                          1927

<210> SEQ ID NO 28
<211> LENGTH: 526
<212> TYPE: PRT
<213> ORGANISM: Homo sapiens

<400> SEQUENCE: 28

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30
```

```
Thr Pro Asn Gly Gln His Ala Ser Pro Ser His Met Thr Ser Thr Asp
         35                  40                  45

Ser Val Lys Leu Glu Met Gln Ser Asp Glu Glu Cys Asp Arg Lys Pro
     50                  55                  60

Leu Ser Arg Glu Asp Glu Ile Arg Gly His Asp Glu Gly Ser Ser Leu
 65                  70                  75                  80

Glu Glu Pro Leu Ile Glu Ser Ser Glu Val Ala Asp Asn Arg Glu Val
                 85                  90                  95

Gln Glu Leu Gln Gly Glu Gly Gly Ile Arg Leu Pro Asn Gly Lys Leu
                100                 105                 110

Lys Cys Asp Val Cys Gly Met Val Cys Ile Gly Pro Asn Val Leu Met
             115                 120                 125

Val His Lys Arg Ser His Thr Gly Glu Arg Pro Phe His Cys Asn Gln
130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser His Ala
                165                 170                 175

Cys Arg Arg Arg Asp Ala Leu Thr Gly Tyr Leu Arg Thr His Ser Val
             180                 185                 190

Gly Lys Pro His Lys Cys Asn Tyr Cys Gly Arg Ser Tyr Lys Gln Arg
            195                 200                 205

Ser Ser Leu Glu Glu His Lys Glu Arg Cys His Asn Tyr Leu Gln Asn
        210                 215                 220

Val Ser Met Glu Ala Ala Gly Gln Val Met Ser His His Val Pro Pro
225                 230                 235                 240

Met Glu Asp Cys Lys Glu Gln Glu Pro Ile Met Asp Asn Asn Ile Ser
                245                 250                 255

Leu Val Pro Phe Glu Arg Pro Ala Val Ile Glu Lys Leu Thr Gly Asn
                260                 265                 270

Met Gly Lys Arg Lys Ser Ser Thr Pro Gln Lys Phe Val Gly Glu Lys
            275                 280                 285

Leu Met Arg Phe Ser Tyr Pro Asp Ile His Phe Asp Met Asn Leu Thr
        290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
                325                 330                 335

Met Gln His Pro Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
        355                 360                 365

Ser Arg Glu Thr Ala Asp Ser His Glu Asn Asn Met Asp Gly Pro Ile
 370                 375                 380

Ser Leu Ile Arg Pro Lys Ser Arg Pro Gln Glu Arg Glu Ala Ser Pro
385                 390                 395                 400

Ser Asn Ser Cys Leu Asp Ser Thr Asp Ser Glu Ser Ser His Asp Asp
                405                 410                 415

His Gln Ser Tyr Gln Gly His Pro Ala Leu Asn Pro Lys Arg Lys Gln
            420                 425                 430

Ser Pro Ala Tyr Met Lys Glu Asp Val Lys Ala Leu Asp Thr Thr Lys
            435                 440                 445

Ala Pro Lys Gly Ser Leu Lys Asp Ile Tyr Lys Val Phe Asn Gly Glu
```

```
                450             455             460
Gly Glu Gln Ile Arg Ala Phe Lys Cys Glu His Cys Arg Val Leu Phe
465                 470                 475                 480

Leu Asp His Val Met Tyr Thr Ile His Met Gly Cys His Gly Tyr Arg
                485                 490                 495

Asp Pro Leu Glu Cys Asn Ile Cys Gly Tyr Arg Ser Gln Asp Arg Tyr
            500                 505                 510

Glu Phe Ser Ser His Ile Val Arg Gly Glu His Thr Phe His
            515                 520                 525

<210> SEQ ID NO 29
<211> LENGTH: 517
<212> TYPE: PRT
<213> ORGANISM: Mus musculus

<400> SEQUENCE: 29

Met Asp Val Asp Glu Gly Gln Asp Met Ser Gln Val Ser Gly Lys Glu
 1               5                  10                  15

Ser Pro Pro Val Ser Asp Thr Pro Asp Glu Gly Asp Glu Pro Met Pro
                20                  25                  30

Val Pro Glu Asp Leu Ser Thr Ser Gly Ala Gln Gln Asn Ser Lys
            35                  40                  45

Ser Asp Arg Gly Met Gly Ser Asn Val Lys Val Glu Thr Gln Ser Asp
 50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Val Cys Ile Gly
        115                 120                 125

Pro Asn Val Leu Met Val His Lys Arg Ser His Thr Glu Arg Pro Phe
130                 135                 140

Gln Cys Asn Gln Cys Gly Ala Ser Phe Thr Gln Lys Gly Asn Leu Leu
145                 150                 155                 160

Arg His Ile Lys Leu His Ser Gly Glu Lys Pro Phe Lys Cys His Leu
                165                 170                 175

Cys Asn Tyr Ala Cys Arg Arg Arg Asp Ala Leu Thr Gly His Leu Arg
            180                 185                 190

Thr His Ser Val Gly Lys Pro His Lys Cys Gly Tyr Cys Gly Arg Ser
        195                 200                 205

Tyr Lys Gln Arg Ser Ser Leu Glu Glu His Lys Glu Arg Cys His Asn
210                 215                 220

Tyr Leu Glu Ser Met Gly Leu Pro Gly Val Cys Pro Val Ile Lys Glu
225                 230                 235                 240

Glu Thr Asn His Asn Glu Met Ala Glu Asp Leu Cys Lys Ile Gly Ala
                245                 250                 255

Glu Arg Ser Leu Val Leu Asp Arg Leu Ala Ser Asn Val Ala Lys Arg
            260                 265                 270

Lys Ser Ser Met Pro Gln Lys Phe Leu Gly Asp Lys Cys Leu Ser Asp
        275                 280                 285

Met Pro Tyr Asp Ser Ala Asn Tyr Glu Lys Glu Asp Met Met Thr Ser
290                 295                 300
```

His Val Met Asp Gln Ala Ile Asn Asn Ala Ile Asn Tyr Leu Gly Ala
305                 310                 315                 320

Glu Ser Leu Arg Pro Leu Val Gln Thr Pro Gly Ser Ser Glu Val
            325                 330                 335

Val Pro Val Ile Ser Ser Met Tyr Gln Leu His Lys Pro Pro Ser Asp
            340                 345                 350

Gly Pro Pro Arg Ser Asn His Ser Ala Gln Asp Ala Val Asp Asn Leu
            355                 360                 365

Leu Leu Leu Ser Lys Ala Lys Ser Val Ser Ser Glu Arg Glu Ala Ser
    370                 375                 380

Pro Ser Asn Ser Cys Gln Asp Ser Thr Asp Thr Glu Ser Asn Ala Glu
385                 390                 395                 400

Glu Gln Arg Ser Gly Leu Ile Tyr Leu Thr Asn His Ile Asn Pro His
                405                 410                 415

Ala Arg Asn Gly Leu Ala Leu Lys Glu Glu Gln Arg Ala Tyr Glu Val
                420                 425                 430

Leu Arg Ala Ala Ser Glu Asn Ser Gln Asp Ala Phe Arg Val Val Ser
        435                 440                 445

Thr Ser Gly Glu Gln Leu Lys Val Tyr Lys Cys Glu His Cys Arg Val
    450                 455                 460

Leu Phe Leu Asp His Val Met Tyr Thr Ile His Met Gly Cys His Gly
465                 470                 475                 480

Cys His Gly Phe Arg Asp Pro Phe Glu Cys Asn Met Cys Gly Tyr His
                485                 490                 495

Ser Gln Asp Arg Tyr Glu Phe Ser Ser His Ile Thr Arg Gly Glu His
                500                 505                 510

Arg Tyr His Leu Ser
        515

<210> SEQ ID NO 30
<211> LENGTH: 507
<212> TYPE: PRT
<213> ORGANISM: Mus musculus

<400> SEQUENCE: 30

Met Glu Asp Ile Gln Pro Thr Val Glu Leu Lys Ser Thr Glu Gln
1               5                   10                  15

Pro Leu Pro Thr Glu Ser Pro Asp Ala Leu Asn Asp Tyr Ser Leu Pro
            20                  25                  30

Lys Pro His Glu Ile Glu Asn Val Asp Ser Arg Glu Ala Pro Ala Asn
        35                  40                  45

Glu Asp Glu Asp Ala Gly Glu Asp Ser Met Lys Val Lys Asp Glu Tyr
    50                  55                  60

Ser Asp Arg Asp Glu Asn Ile Met Lys Pro Glu Pro Met Gly Asp Ala
65                  70                  75                  80

Glu Glu Ser Glu Met Pro Tyr Ser Tyr Ala Arg Glu Tyr Ser Asp Tyr
                85                  90                  95

Glu Ser Ile Lys Leu Glu Arg His Val Pro Tyr Asp Asn Ser Arg Pro
                100                 105                 110

Thr Ser Gly Lys Met Asn Cys Asp Val Cys Gly Leu Ser Cys Ile Ser
            115                 120                 125

Phe Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

```
Leu Arg His Ile Lys Leu His Thr Gly Glu Lys Pro Phe Lys Cys His
                165                 170                 175
Leu Cys Asn Tyr Ala Cys Gln Arg Arg Asp Ala Leu Thr Gly His Leu
            180                 185                 190
Arg Thr His Ser Val Glu Lys Pro Tyr Lys Cys Glu Phe Cys Gly Arg
        195                 200                 205
Ser Tyr Lys Gln Arg Ser Ser Leu Glu Glu His Lys Glu Arg Cys Arg
    210                 215                 220
Ala Phe Leu Gln Asn Pro Asp Leu Gly Asp Ala Ala Ser Val Glu Ala
225                 230                 235                 240
Arg His Ile Lys Ala Glu Met Gly Ser Glu Arg Ala Leu Val Leu Asp
                245                 250                 255
Arg Leu Ala Ser Asn Val Ala Lys Arg Lys Ser Ser Met Pro Gln Lys
            260                 265                 270
Phe Ile Gly Glu Lys Arg His Cys Phe Asp Ala Asn Tyr Asn Pro Gly
        275                 280                 285
Tyr Met Tyr Glu Lys Glu Asn Glu Met Met Gln Thr Arg Met Met Asp
    290                 295                 300
Gln Ala Ile Asn Asn Ala Ile Ser Tyr Leu Gly Ala Glu Ala Phe Arg
305                 310                 315                 320
Pro Leu Val Gln Thr Pro Pro Ala Pro Thr Ser Glu Met Val Pro Val
                325                 330                 335
Ile Ser Ser Val Tyr Pro Ile Ala Leu Thr Arg Ala Asp Met Pro Met
            340                 345                 350
Gly Ala Pro Gln Glu Met Glu Lys Lys Arg Ile Leu Leu Pro Glu Lys
        355                 360                 365
Ile Leu Pro Ser Glu Arg Gly Leu Ser Pro Asn Asn Ser Ala Gln Asp
    370                 375                 380
Ser Thr Asp Thr Asp Ser Asn His Glu Asp Arg Gln His Leu Tyr Gln
385                 390                 395                 400
Gln Ser His Val Val Leu Pro Gln Ala Arg Asn Gly Met Pro Leu Leu
                405                 410                 415
Lys Glu Val Pro Arg Ser Phe Glu Leu Leu Lys Pro Pro Pro Ile Cys
            420                 425                 430
Leu Arg Asp Ser Ile Lys Val Ile Asn Lys Glu Gly Glu Val Met Asp
        435                 440                 445
Val Phe Arg Cys Asp His Cys His Val Leu Phe Leu Asp Tyr Val Met
    450                 455                 460
Phe Thr Ile His Met Gly Cys His Gly Phe Arg Asp Pro Phe Glu Cys
465                 470                 475                 480
Asn Met Cys Gly Tyr Arg Ser His Asp Arg Tyr Glu Phe Ser Ser His
                485                 490                 495
Ile Ala Arg Gly Glu His Arg Ala Met Leu Lys
            500                 505

<210> SEQ ID NO 31
<211> LENGTH: 17
<212> TYPE: DNA
<213> ORGANISM: Mus musculus

<400> SEQUENCE: 31
gggtgaaggc ctcaggt                                                  17

<210> SEQ ID NO 32
```

<211> LENGTH: 33
<212> TYPE: DNA
<213> ORGANISM: Mus musculus

<400> SEQUENCE: 32
ccatcatatg agactgcatc agctccagcc tcc        33

<210> SEQ ID NO 33
<211> LENGTH: 32
<212> TYPE: DNA
<213> ORGANISM: Mus musculus

<400> SEQUENCE: 33
ggaggctgag ctgatgcact ctcatatgat gg         32

<210> SEQ ID NO 34
<211> LENGTH: 30
<212> TYPE: DNA
<213> ORGANISM: Mus musculus

<400> SEQUENCE: 34
cacctacctt ggagctgagg cccttcaccc            30

<210> SEQ ID NO 35
<211> LENGTH: 21
<212> TYPE: DNA
<213> ORGANISM: Mus musculus

<400> SEQUENCE: 35
tggccctctg tggtgctcaa g                     21

<210> SEQ ID NO 36
<211> LENGTH: 20
<212> TYPE: DNA
<213> ORGANISM: Mus musculus

<400> SEQUENCE: 36
cacaggacta gaacacctgc                       20

<210> SEQ ID NO 37
<211> LENGTH: 18
<212> TYPE: DNA
<213> ORGANISM: Mus musculus

<400> SEQUENCE: 37
gaacacgcca atatggcc                         18

<210> SEQ ID NO 38
<211> LENGTH: 21
<212> TYPE: DNA
<213> ORGANISM: Mus musculus

<400> SEQUENCE: 38
ggccttggta gcatccaaag c                     21

<210> SEQ ID NO 39
<211> LENGTH: 20
<212> TYPE: DNA
<213> ORGANISM: Mus musculus

<400> SEQUENCE: 39
agaatgtcag catggaggct                       20

-continued

<210> SEQ ID NO 40
<211> LENGTH: 537
<212> TYPE: PRT
<213> ORGANISM: Mus musculus

<400> SEQUENCE: 40

```
Met Glu Ser Leu Phe Cys Glu Ser Ser Gly Asp Ser Ser Leu Glu Lys
  1               5                  10                  15

Glu Phe Leu Gly Ala Pro Val Gly Pro Ser Val Ser Thr Pro Asn Ser
             20                  25                  30

Gln His Ser Ser Pro Ser Arg Ser Leu Ser Ala Asn Ser Ile Lys Val
         35                  40                  45

Glu Met Tyr Ser Asp Glu Ser Ser Arg Leu Leu Gly Pro Asp Glu
     50                  55                  60

Arg Leu Leu Asp Lys Asp Ser Val Ile Val Glu Asp Ser Leu Ser
 65                  70                  75                  80

Glu Pro Leu Gly Tyr Cys Asp Gly Ser Gly Pro Glu Pro His Ser Pro
                 85                  90                  95

Gly Gly Ile Arg Leu Pro Asn Gly Lys Leu Lys Cys Asp Val Cys Gly
            100                 105                 110

Met Val Cys Ile Gly Pro Asn Val Leu Met Val His Lys Arg Ser His
        115                 120                 125

Thr Gly Glu Arg Pro Phe His Cys Asn Gln Cys Gly Ala Ser Phe Thr
    130                 135                 140

Gln Lys Gly Asn Leu Leu Arg His Ile Lys Leu His Ser Gly Glu Lys
145                 150                 155                 160

Pro Phe Lys Cys Pro Phe Cys Asn Tyr Ala Cys Arg Arg Arg Asp Ala
                165                 170                 175

Leu Thr Gly His Leu Arg Thr His Ser Val Ser Ser Pro Thr Val Gly
            180                 185                 190

Lys Pro Tyr Lys Cys Asn Tyr Cys Gly Arg Ser Tyr Lys Gln Gln Ser
        195                 200                 205

Thr Leu Glu Glu His Lys Glu Arg Cys His Asn Tyr Leu Gln Ser Leu
    210                 215                 220

Ser Thr Asp Ala Gln Ala Leu Thr Gly Gln Pro Gly Asp Glu Ile Arg
225                 230                 235                 240

Asp Leu Glu Met Val Pro Asp Ser Met Leu His Pro Ser Thr Glu Arg
                245                 250                 255

Pro Thr Phe Ile Asp Arg Leu Ala Asn Ser Leu Thr Lys Arg Lys Arg
            260                 265                 270

Ser Thr Pro Gln Lys Phe Val Gly Glu Lys Gln Met Arg Phe Ser Leu
        275                 280                 285

Ser Asp Leu Pro Tyr Asp Val Asn Ala Ser Gly Tyr Glu Lys Asp
    290                 295                 300

Val Glu Leu Val Ala His His Gly Leu Glu Pro Gly Phe Gly Gly Ser
305                 310                 315                 320

Leu Ala Phe Val Gly Thr Glu His Leu Arg Pro Leu Arg Leu Pro Pro
                325                 330                 335

Thr Asn Cys Ile Ser Glu Leu Thr Pro Val Ile Ser Ser Val Tyr Thr
            340                 345                 350

Gln Met Gln Pro Ile Pro Ser Arg Leu Glu Leu Pro Gly Ser Arg Glu
        355                 360                 365

Ala Gly Glu Gly Pro Glu Asp Leu Gly Asp Gly Pro Leu Leu Tyr
    370                 375                 380
```

```
Arg Ala Arg Gly Ser Leu Thr Asp Pro Gly Ala Ser Pro Ser Asn Gly
385                 390                 395                 400

Cys Gln Asp Ser Thr Asp Thr Glu Ser Asn His Glu Asp Arg Ile Gly
                405                 410                 415

Gly Val Val Ser Leu Pro Gln Gly Pro Pro Gln Pro Pro Thr
                420                 425                 430

Ile Val Val Gly Arg His Ser Pro Ala Tyr Ala Lys Glu Asp Pro Lys
                435                 440                 445

Pro Gln Glu Gly Leu Leu Arg Gly Thr Pro Gly Pro Ser Lys Glu Val
        450                 455                 460

Leu Arg Val Val Gly Glu Ser Gly Glu Pro Val Lys Ala Phe Lys Cys
465                 470                 475                 480

Glu His Cys Arg Ile Leu Phe Leu Asp His Val Met Phe Thr Ile His
                485                 490                 495

Met Gly Cys His Gly Phe Arg Asp Pro Phe Glu Cys Asn Ile Cys Gly
                500                 505                 510

Tyr His Ser Gln Asp Arg Tyr Glu Phe Ser Ser His Ile Val Arg Gly
                515                 520                 525

Glu His Lys Val Gly Ser Cys Arg Ile
530                 535

<210> SEQ ID NO 41
<211> LENGTH: 532
<212> TYPE: PRT
<213> ORGANISM: Mus musculus

<400> SEQUENCE: 41

Met His Cys Thr Leu Thr Met Glu Thr Asp Ala Ile Asp Gly Tyr Ile
1               5                   10                  15

Thr Cys Asp Asn Glu Leu Ser Pro Glu Gly Glu His Ala Asn Met Ala
                20                  25                  30

Ile Asp Leu Thr Ser Ser Thr Pro Asn Gly Gln Gln Ala Ser Pro Ser
            35                  40                  45

His Met Thr Ser Thr Asn Ser Val Lys Leu Glu Met Gln Ser Asp Glu
        50                  55                  60

Glu Cys Asp Arg Gln Pro Leu Ser Arg Glu Asp Glu Ile Arg Gly His
65                  70                  75                  80

Asp Glu Gly Ser Ser Leu Glu Ala Leu Ile Glu Ser Ser Glu Val
                85                  90                  95

Ala Asp Asn Arg Lys Val Gln Asp Leu Gln Gly Glu Arg Gly Ile Arg
                100                 105                 110

Leu Pro Asn Gly Lys Leu Lys Cys Asp Val Cys Gly Met Val Cys Ile
                115                 120                 125

Gly Pro Asn Val Leu Met Val His Lys Arg Ser His Thr Gly Glu Arg
        130                 135                 140

Pro Phe His Cys Asn Gln Cys Gly Arg Ser Phe Thr Gln Lys Gly Asn
145                 150                 155                 160

Leu Leu Arg His Ile Lys Leu His Ser Gly Glu Lys Pro Phe Lys Cys
                165                 170                 175

Pro Phe Cys Ser Tyr Ala Cys Arg Arg Arg Asp Ala Leu Thr Gly His
                180                 185                 190

Leu Arg Thr His Ser Val Gly Lys Pro His Lys Cys Asn Tyr Cys Gly
        195                 200                 205

Arg Ser Tyr Lys Gln Arg Thr Ser Leu Glu Glu His Lys Glu Arg Cys
        210                 215                 220
```

His Asn Tyr Leu Gln Asn Val Ser Met Glu Ala Ala Gly Gln Val Met
225                 230                 235                 240

Ser His His Val Pro Pro Met Glu Asp Cys Lys Glu Gln Pro Ile
        245                 250                 255

Met Asp Asn Asn Ile Ser Leu Val Ala Phe Glu Arg Pro Ala Val Ile
            260                 265                 270

Glu Lys Leu Thr Ala Asn Met Gly Lys Arg Lys Ser Ser Thr Pro Gln
        275                 280                 285

Lys Phe Val Gly Glu Lys Leu Met Arg Phe Ser Tyr Pro Asp Ile His
        290                 295                 300

Phe His Met Asn Leu Thr Tyr Glu Lys Glu Ala Glu Leu Met Gln Ser
305                 310                 315                 320

His Met Met Asp Gln Ala Ile Asn Asn Ala Ile Thr Tyr Leu Gly Ala
            325                 330                 335

Glu Ala Leu His Pro Leu Met Gln His Ala Pro Ser Thr Ile Ala Glu
        340                 345                 350

Val Ala Pro Val Ile Ser Ser Ala Tyr Ser Gln Val Tyr His Pro Asn
        355                 360                 365

Arg Ile Glu Arg Pro Ile Ser Arg Glu Thr Ser Asp Ser His Glu Asn
        370                 375                 380

Asn Met Asp Gly Pro Ile Ser Leu Ile Arg Pro Lys Ser Arg Pro Gln
385                 390                 395                 400

Glu Arg Glu Ala Ser Pro Ser Asn Ser Cys Leu Asp Ser Thr Asp Ser
            405                 410                 415

Glu Ser Ser His Asp Asp Arg Gln Ser Tyr Gln Gly Asn Pro Ala Leu
        420                 425                 430

Asn Pro Lys Arg Lys Gln Ser Pro Ala Tyr Met Lys Glu Asp Val Lys
        435                 440                 445

Ala Leu Asp Ala Thr Lys Ala Pro Lys Gly Ser Leu Lys Asp Ile Tyr
450                 455                 460

Lys Val Phe Asn Gly Glu Gly Glu Gln Ile Arg Ala Phe Lys Cys Glu
465                 470                 475                 480

His Cys Arg Val Leu Phe Leu Asp His Val Met Tyr Thr Ile His Met
            485                 490                 495

Gly Cys His Gly Tyr Arg Asp Pro Leu Glu Cys Asn Ile Cys Gly Tyr
        500                 505                 510

Arg Ser Gln Asp Arg Tyr Glu Phe Ser Ser His Ile Val Gly Gly Gln
        515                 520                 525

His Thr Phe His
    530

<210> SEQ ID NO 42
<211> LENGTH: 507
<212> TYPE: PRT
<213> ORGANISM: Mus musculus

<400> SEQUENCE: 42

Met Glu Asp Ile Gln Pro Thr Val Glu Leu Lys Ser Thr Glu Glu Gln
 1               5                  10                  15

Pro Leu Pro Thr Glu Ser Pro Asp Ala Leu Asn Asp Tyr Ser Leu Pro
            20                  25                  30

Lys Pro His Glu Ile Glu Asn Val Asp Ser Arg Glu Ala Pro Ala Asn
        35                  40                  45

Glu Asp Glu Asp Ala Gly Glu Asp Ser Met Lys Val Lys Asp Glu Tyr

```
                50                  55                  60
Ser Asp Arg Asp Glu Asn Ile Met Lys Pro Glu Pro Met Gly Asp Ala
 65                  70                  75                  80

Glu Glu Ser Glu Met Pro Tyr Ser Tyr Ala Arg Glu Tyr Ser Asp Tyr
                 85                  90                  95

Glu Ser Ile Lys Leu Glu Arg His Val Pro Tyr Asp Asn Ser Arg Pro
                100                 105                 110

Thr Ser Gly Lys Met Met Cys Asp Val Cys Gly Leu Ser Cys Ile Ser
                115                 120                 125

Phe Asn Val Leu Met Val His Lys Arg Ser His Thr Gly Glu Arg Pro
130                 135                 140

Phe Gln Cys Asn Gln Cys Gly Ala Ser Phe Thr Gln Lys Gly Asn Leu
145                 150                 155                 160

Leu Arg His Ile Lys Leu His Thr Gly Glu Lys Pro Phe Lys Cys His
                165                 170                 175

Leu Cys Asn Tyr Ala Cys Gln Arg Arg Asp Ala Leu Thr Gly His Leu
                180                 185                 190

Arg Thr His Ser Val Glu Lys Pro Tyr Lys Cys Glu Phe Cys Gly Arg
                195                 200                 205

Ser Tyr Lys Gln Arg Ser Ser Leu Glu Glu His Lys Glu Arg Cys Arg
                210                 215                 220

Ala Phe Leu Gln Asn Pro Asp Leu Gly Asp Ala Ala Ser Val Glu Ala
225                 230                 235                 240

Arg His Ile Lys Ala Glu Met Gly Ser Glu Arg Ala Leu Val Leu Asp
                245                 250                 255

Arg Leu Ala Ser Asn Val Ala Lys Arg Lys Ser Ser Met Pro Gln Lys
                260                 265                 270

Phe Ile Gly Glu Lys Arg His Cys Phe Asp Ala Asn Tyr Asn Pro Gly
                275                 280                 285

Tyr Met Tyr Glu Lys Glu Asn Glu Met Met Gln Thr Arg Met Met Asp
                290                 295                 300

Gln Ala Ile Asn Asn Ala Ile Ser Tyr Leu Gly Ala Glu Ala Phe Arg
305                 310                 315                 320

Pro Leu Val Gln Thr Pro Pro Ala Pro Thr Ser Glu Met Val Pro Val
                325                 330                 335

Ile Ser Ser Val Tyr Pro Ile Ala Leu Thr Arg Ala Asp Met Pro Met
                340                 345                 350

Gly Ala Pro Gln Glu Met Glu Lys Lys Arg Ile Leu Leu Pro Glu Lys
                355                 360                 365

Ile Leu Pro Ser Glu Arg Gly Leu Ser Pro Asn Asn Ser Ala Gln Asp
                370                 375                 380

Ser Thr Asp Thr Asp Ser Asn His Glu Asp Arg Gln His Leu Tyr Gln
385                 390                 395                 400

Gln Ser His Val Val Leu Pro Gln Ala Arg Asn Gly Met Pro Leu Leu
                405                 410                 415

Lys Glu Val Pro Arg Ser Phe Glu Leu Leu Lys Pro Pro Pro Ile Cys
                420                 425                 430

Leu Arg Asp Ser Ile Lys Val Ile Asn Lys Glu Gly Glu Val Met Asp
                435                 440                 445

Val Phe Arg Cys Asp His Cys His Val Leu Phe Leu Asp Tyr Val Met
                450                 455                 460

Phe Thr Ile His Met Gly Cys His Gly Phe Arg Asp Pro Phe Glu Cys
465                 470                 475                 480
```

-continued

```
Asn Met Cys Gly Tyr Arg Ser His Asp Arg Tyr Glu Phe Ser Ser His
                485                 490                 495
Ile Ala Arg Gly Glu His Arg Ala Met Leu Lys
            500                 505

<210> SEQ ID NO 43
<211> LENGTH: 515
<212> TYPE: PRT
<213> ORGANISM: Mus musculus

<400> SEQUENCE: 43

Met Asp Val Asp Glu Gly Gln Asp Met Ser Gln Val Ser Gly Lys Glu
 1               5                  10                  15
Ser Pro Pro Val Ser Asp Thr Pro Asp Glu Gly Asp Glu Pro Met Pro
            20                  25                  30
Val Pro Glu Asp Leu Ser Thr Thr Ser Gly Ala Gln Gln Asn Ser Lys
        35                  40                  45
Ser Asp Arg Gly Met Ala Ser Asn Val Lys Val Glu Thr Gln Ser Asp
    50                  55                  60
Glu Glu Asn Gly Arg Ala Cys Glu Met Asn Gly Glu Glu Cys Ala Glu
65                  70                  75                  80
Asp Leu Arg Met Leu Asp Ala Ser Gly Glu Lys Met Asn Gly Ser His
                85                  90                  95
Arg Asp Gln Gly Ser Ser Ala Leu Ser Gly Val Gly Gly Ile Arg Leu
            100                 105                 110
Pro Asn Gly Lys Leu Lys Cys Asp Ile Cys Gly Ile Val Cys Ile Gly
        115                 120                 125
Pro Asn Val Leu Met Val His Lys Arg Ser His Thr Gly Glu Arg Pro
    130                 135                 140
Phe Gln Cys Asn Gln Cys Gly Ala Ser Phe Thr Gln Lys Gly Asn Leu
145                 150                 155                 160
Leu Arg His Ile Lys Leu His Ser Gly Glu Lys Pro Phe Lys Cys His
                165                 170                 175
Leu Cys Asn Tyr Ala Cys Arg Arg Arg Asp Ala Leu Thr Gly His Leu
            180                 185                 190
Arg Thr His Ser Val Gly Lys Pro His Lys Cys Gly Tyr Cys Gly Arg
        195                 200                 205
Ser Tyr Lys Gln Arg Ser Ser Leu Glu Glu His Lys Glu Arg Cys His
    210                 215                 220
Asn Tyr Leu Glu Ser Met Gly Leu Pro Gly Val Cys Pro Val Ile Lys
225                 230                 235                 240
Glu Glu Thr Asn His Asn Glu Met Ala Glu Asp Leu Cys Lys Ile Gly
                245                 250                 255
Ala Glu Arg Ser Leu Val Leu Asp Arg Leu Ala Ser Asn Val Ala Lys
            260                 265                 270
Arg Lys Ser Ser Met Pro Gln Lys Phe Leu Gly Asp Lys Cys Leu Ser
        275                 280                 285
Asp Met Pro Tyr Asp Ser Ala Asn Tyr Glu Lys Glu Asp Met Met Thr
    290                 295                 300
Ser His Val Met Asp Gln Ala Ile Asn Asn Ala Ile Asn Tyr Leu Gly
305                 310                 315                 320
Ala Glu Ser Leu Arg Pro Leu Val Gln Thr Pro Pro Gly Ser Ser Glu
                325                 330                 335
Val Val Pro Val Ile Ser Ser Met Tyr Gln Leu His Lys Pro Pro Ser
```

```
                    340                 345                 350
Asp Gly Pro Pro Arg Ser Asn His Ser Ala Gln Asp Ala Val Asp Asn
            355                 360                 365

Leu Leu Leu Leu Ser Lys Ala Lys Ser Val Ser Ser Glu Arg Glu Ala
        370                 375                 380

Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
                405                 410                 415

His Ala Arg Asn Gly Leu Ala Leu Lys Glu Glu Gln Arg Ala Tyr Glu
            420                 425                 430

Val Leu Arg Ala Ala Ser Glu Asn Ser Gln Asp Ala Phe Arg Val Val
        435                 440                 445

Ser Thr Ser Gly Glu Gln Leu Lys Val Tyr Lys Cys Glu His Cys Arg
    450                 455                 460

Val Leu Phe Leu Asp His Val Met Tyr Thr Ile His Met Gly Cys His
465                 470                 475                 480

Gly Phe Arg Asp Pro Phe Glu Cys Asn Met Cys Gly Tyr His Ser Gln
                485                 490                 495

Asp Arg Tyr Glu Phe Ser Ser His Ile Thr Arg Gly Glu His Arg Tyr
            500                 505                 510

His Leu Ser
        515

<210> SEQ ID NO 44
<211> LENGTH: 498
<212> TYPE: PRT
<213> ORGANISM: Mus musculus

<400> SEQUENCE: 44

Met Ser Gly Ser Thr Phe Pro Thr Val Val Gly His Lys Leu Glu Ser
1               5                   10                  15

Ile Phe Tyr Ser Ser Thr Val Ala Ala Leu Asp Arg Pro Lys Ala Gly
            20                  25                  30

Asp Ser Ser Leu Glu Lys Asp Phe Ser Asp Ala Leu Ile Gly Pro Thr
        35                  40                  45

Val Ser Thr Pro Asn Ser Arg His Ser Ser Pro Ser Arg Ser Arg Ser
    50                  55                  60

Ala Asn Ser Ile Lys Val Glu Met Tyr Gly Asp Asp Glu Ser Gly Arg
65                  70                  75                  80

Leu Leu Ser His Glu Asp Arg Leu Ser Glu Lys Glu Asp Glu Ile Met
                85                  90                  95

Gly Asp Asp Ser Leu Val Glu Pro Leu Gly Tyr Cys Asp Gly Pro Gly
            100                 105                 110

Gln Asp Pro His Ser Pro Gly Ile Leu Leu Pro Asn Gly Lys Leu Lys
        115                 120                 125

Cys Asp Ile Cys Gly Met Val Cys Ile Gly Pro Asn Val Leu Met Val
    130                 135                 140

His Lys Arg Ser His Thr Gly Glu Arg Pro Phe His Cys Asn Gln Cys
145                 150                 155                 160

Gly Ala Pro Phe Thr Gln Lys Gly Asn Leu Leu Arg His Ile Lys Leu
                165                 170                 175

His Ser Gly Glu Lys Pro Phe Lys Cys Pro Phe Cys Asn Tyr Ala Cys
            180                 185                 190
```

-continued

```
Arg Arg Arg Asp Ala Leu Ser Gly His Leu Arg Thr His Ala Val Gly
        195                 200                 205
Lys Pro Tyr Lys Cys Asn Tyr Cys Gly Arg Ser Tyr Lys Gln Gln Asn
    210                 215                 220
Thr Leu Glu Glu His Lys Glu Arg Cys His Asn Tyr Leu Gln Ser Leu
225                 230                 235                 240
Ser Asn Glu Ala Gln His Leu Pro Ala His Pro Gly Glu Trp Gly Pro
                245                 250                 255
Gln Gly Gly Asn Cys Ile Cys Thr Arg Glu Lys Gln Met Arg Leu Ser
            260                 265                 270
Leu Ala Asp Leu Pro Tyr Glu Met Asn Ser Ser Phe Glu Lys Asp Val
        275                 280                 285
Glu Ile Val Ser His His Pro Leu Asp Thr Ala Tyr Gly Asn Ser Leu
    290                 295                 300
Ala Phe Val Gly Gly Pro Met Arg Leu Pro Pro Thr Asn Cys Ile Ser
305                 310                 315                 320
Glu Ile Thr Pro Val Ile Ser Ser Val Tyr Thr Gln Leu Gln Pro Met
                325                 330                 335
Gln Gly Arg Pro Asp Met Pro Gly Asn Arg Glu Ala Ala Glu Gly His
            340                 345                 350
Glu Asp Ile Pro Asp Gly Thr Gln Ile His Tyr Arg Gly Arg Ser Glu
        355                 360                 365
His Gly Ala Ser Pro Thr Asn Gly Cys Gln Asp Ser Asn Thr Asp Thr
    370                 375                 380
Glu Ser Asn His Glu Glu Arg Gly Ser Gln Ala Thr Ser Ser Arg Gln
385                 390                 395                 400
Ser Ser Ala Tyr Ala Lys Glu Asp Gln Arg Pro Ser Asp Gly Gly Leu
                405                 410                 415
Leu Leu Pro Ser Arg Ser Met Pro Gly Thr Ala Lys Glu Ser Leu Arg
            420                 425                 430
Val Leu Gly Glu Asp Gly Val Gln Val Lys Val Phe Lys Cys Glu His
        435                 440                 445
Cys Arg Val Leu Phe Leu Asp His Val Met Phe Thr Ile His Met Gly
    450                 455                 460
Cys His Gly Glu Arg Asp Pro Phe Glu Cys Asn Ile Cys Gly Tyr His
465                 470                 475                 480
Cys Gln Asp Arg Tyr Glu Phe Ser Ser His Ile Val Arg Gly Glu His
                485                 490                 495
Lys Val
```

```
<210> SEQ ID NO 45
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 15, 18, 21
<223> OTHER INFORMATION: n = inosine

<400> SEQUENCE: 45
tgyaaycart gyggngcnwc nttyac                                    26

<210> SEQ ID NO 46
<211> LENGTH: 26
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: 6, 15, 18
<223> OTHER INFORMATION: n = inosine

<400> SEQUENCE: 46
tgrcanccca trtgnatngt rwacat                                    26

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
agggacaaca tccagggcat cacc                                      24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
atccatggcg gtaacggtct tcct                                      24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
attctgtaac tacgcttgtc gtcg                                      24

<210> SEQ ID NO 50
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 7
<223> OTHER INFORMATION: n = inosine

<400> SEQUENCE: 50
aacaatngcc ataagcagtg tcca                                      24

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
catattggta caggactcct atcc                                      24

<210> SEQ ID NO 52
<211> LENGTH: 24
```

```
<212> TYPE: DNA
<213> ORGANISM: Artificial Sequence
<220> FEATURE:
<223> OTHER INFORMATION: Primer

<400> SEQUENCE: 52
cttgaccctt atgggaagca ggaa                                              24

<210> SEQ ID NO 53
<211> LENGTH: 1788
<212> TYPE: DNA
<213> ORGANISM: Mus musculus
<220> FEATURE:
<221> NAME/KEY: CDS
<222> LOCATION: (223)...(1515)
<223> OTHER INFORMATION: mIk-2

<400> SEQUENCE: 53
aattcgttct accttctctg aaccccagtg gtgtgtcaag gccggactgg gagcttgggg        60
gaagaggaag aggaagagga atctgcggct catccaggga tcagggtcct tcccaagtgg       120
ccactcagag gggactcaga gcaagtctag atttgtgtgg cagagagaga cagctctcgt       180
ttggccttgg ggaggcacaa gtctgttgat aacctgaaga ca atg gat gtc gat          234
                                                Met Asp Val Asp
                                                  1 gag ggt caa gac atg tcc caa gtt tca gga aag gag agc ccc cca gtc         282
Glu Gly Gln Asp Met Ser Gln Val Ser Gly Lys Glu Ser Pro Pro Val
 5                  10                  15                  20 agt gac act cca gat gaa ggg gat gag ccc atg cct gtc cct gag gac         330
Ser Asp Thr Pro Asp Glu Gly Asp Glu Pro Met Pro Val Pro Glu Asp
                25                  30                  35 ctg tcc act acc tct gga gca cag cag aac tcc aag agt gat cga ggc         378
Leu Ser Thr Thr Ser Gly Ala Gln Gln Asn Ser Lys Ser Asp Arg Gly
            40                  45                  50 atg ggt gaa cgg cct ttc cag tgc aac cag tct ggg gcc tcc ttt acc         426
Met Gly Glu Arg Pro Phe Gln Cys Asn Gln Ser Gly Ala Ser Phe Thr
        55                  60                  65 cag aaa ggc aac ctc ctg cgg cac atc aag ctg cac tcg ggt gag aag         474
Gln Lys Gly Asn Leu Leu Arg His Ile Lys Leu His Ser Gly Glu Lys
    70                  75                  80 ccc ttc aaa tgc cat ctt tgc aac tat gcc tgc cgc cgg agg gac gcc         522
Pro Phe Lys Cys His Leu Cys Asn Tyr Ala Cys Arg Arg Arg Asp Ala
 85                  90                  95                 100 ctc acc ggc cac ctg agg acg cac tcc gtt ggt aag cct cac aaa tgt         570
Leu Thr Gly His Leu Arg Thr His Ser Val Gly Lys Pro His Lys Cys
                105                 110                 115 gga tat tgt ggc cgg agc tat aaa cag cga agc tct tta gag gag cat         618
Gly Tyr Cys Gly Arg Ser Tyr Lys Gln Arg Ser Ser Leu Glu Glu His
            120                 125                 130 aaa gag cga tgc cac aac tac ttg gaa agc atg ggc ctt ccg ggc gtg         666
Lys Glu Arg Cys His Asn Tyr Leu Glu Ser Met Gly Leu Pro Gly Val
        135                 140                 145 tgc cca gtc att aag gaa gaa act aac cac aac gag atg gca gaa gac         714
Cys Pro Val Ile Lys Glu Glu Thr Asn His Asn Glu Met Ala Glu Asp
    150                 155                 160 ctg tgc aag ata gga gca gag agg tcc ctt gtc ctg gac agg ctg gca         762
Leu Cys Lys Ile Gly Ala Glu Arg Ser Leu Val Leu Asp Arg Leu Ala
165                 170                 175                 180 agc aat gtc gcc aaa cgt aag agc tct atg cct cag aaa ttt ctt gga         810
Ser Asn Val Ala Lys Arg Lys Ser Ser Met Pro Gln Lys Phe Leu Gly
                185                 190                 195
```

-continued

| | | |
|---|---|---|
| gac aag tgc ctg tca gac atg ccc tat gac agt gcc aac tat gag aag<br>Asp Lys Cys Leu Ser Asp Met Pro Tyr Asp Ser Ala Asn Tyr Glu Lys<br>            200                     205                     210 | 858 |
| gag gat atg atg aca tcc cac gtg atg gac cag gcc atc aac aat gcc<br>Glu Asp Met Met Thr Ser His Val Met Asp Gln Ala Ile Asn Asn Ala<br>            215                     220                     225 | 906 |
| atc aac tac ctg ggg gct gag tcc ctg cgc cca ttg gtg cag aca ccc<br>Ile Asn Tyr Leu Gly Ala Glu Ser Leu Arg Pro Leu Val Gln Thr Pro<br>230                     235                     240 | 954 |
| ccc ggt agc tcc gag gtg gtg cca gtc atc agc tcc atg tac cag ctg<br>Pro Gly Ser Ser Glu Val Val Pro Val Ile Ser Ser Met Tyr Gln Leu<br>245                     250                     255                     260 | 1002 |
| cac aag ccc ccc tca gat ggc ccc cca cgg tcc aac cat tca gca cag<br>His Lys Pro Pro Ser Asp Gly Pro Pro Arg Ser Asn His Ser Ala Gln<br>            265                     270                     275 | 1050 |
| gac gcc gtg gat aac ttg ctg ctg ctg tcc aag gcc aag tct gtg tca<br>Asp Ala Val Asp Asn Leu Leu Leu Leu Ser Lys Ala Lys Ser Val Ser<br>            280                     285                     290 | 1098 |
| tcg gag cga gag gcc tcc ccg agc aac agc tgc caa gac tcc aca gat<br>Ser Glu Arg Glu Ala Ser Pro Ser Asn Ser Cys Gln Asp Ser Thr Asp<br>295                     300                     305 | 1146 |
| aca gag agc aac gcg gag gaa cag cgc agc ggc ctt atc tac cta acc<br>Thr Glu Ser Asn Ala Glu Glu Gln Arg Ser Gly Leu Ile Tyr Leu Thr<br>310                     315                     320 | 1194 |
| aac cac atc aac ccg cat gca cgc aat ggg ctg gct ctc aag gag gag<br>Asn His Ile Asn Pro His Ala Arg Asn Gly Leu Ala Leu Lys Glu Glu<br>325                     330                     335                     340 | 1242 |
| cag cgc gcc tac gag gtg ctg agg gcg gcc tca gag aac tcg cag gat<br>Gln Arg Ala Tyr Glu Val Leu Arg Ala Ala Ser Glu Asn Ser Gln Asp<br>                     345                     350                     355 | 1290 |
| gcc ttc cgt gtg gtc agc acg agt ggc gag cag ctg aag gtg tac aag<br>Ala Phe Arg Val Val Ser Thr Ser Gly Glu Gln Leu Lys Val Tyr Lys<br>                     360                     365                     370 | 1338 |
| tgc gaa cac tgc cgc gtg ctc ttc ctg gat cac gtc atg tat acc att<br>Cys Glu His Cys Arg Val Leu Phe Leu Asp His Val Met Tyr Thr Ile<br>375                     380                     385 | 1386 |
| cac atg ggc tgc cat ggc tgc cat ggc ttt cgg gat ccc ttt gag tgt<br>His Met Gly Cys His Gly Cys His Gly Phe Arg Asp Pro Phe Glu Cys<br>390                     395                     400 | 1434 |
| aac atg tgt ggt tat cac agc cag gac agg tac gag ttc tca tcc cat<br>Asn Met Cys Gly Tyr His Ser Gln Asp Arg Tyr Glu Phe Ser Ser His<br>405                     410                     415                     420 | 1482 |
| atc acg cgg ggg gag cat cgt tac cac ctg agc taaacccagc caggccccac<br>Ile Thr Arg Gly Glu His Arg Tyr His Leu Ser<br>                     425                     430 | 1535 |
| tgaagcacaa agatagctgg ttatgcctcc ttcccggcag ctggacccac agcggacaat | 1595 |
| gtgggagtgg atttgcaggc agcatttgtt cttttatgtt ggttgtttgg cgtttcattt | 1655 |
| gcgttggaag ataagttttt aatgttagtg acaggattgc attgcatcag caacattcac | 1715 |
| aacatccatc cttctagcca gttttgttca ctggtagctg aggtttcccg gatatgtggc | 1775 |
| ttcctaaacac tct | 1788 |

<210> SEQ ID NO 54
<211> LENGTH: 1386
<212> TYPE: DNA
<213> ORGANISM: Homo sapiens
<220> FEATURE:
<221> NAME/KEY: CDS
<222> LOCATION: (1)...(1383)
<223> OTHER INFORMATION: hIk-1

<400> SEQUENCE: 54

```
aat gtt aaa gta gag act cag agt gat gaa gag aat ggg cgt gcc tgt      48
Asn Val Lys Val Glu Thr Gln Ser Asp Glu Glu Asn Gly Arg Ala Cys
  1               5                  10                  15 gaa atg aat ggg gaa gaa tgt gcg gag gat tta cga atg ctt gat gcc      96
Glu Met Asn Gly Glu Glu Cys Ala Glu Asp Leu Arg Met Leu Asp Ala
             20                  25                  30 tcg gga gag aaa atg aat ggc tcc cac agg gac caa ggc agc tcg gct     144
Ser Gly Glu Lys Met Asn Gly Ser His Arg Asp Gln Gly Ser Ser Ala
         35                  40                  45 ttg tcg gga gtt gga ggc att cga ctt cct aac gga aaa cta aag tgt     192
Leu Ser Gly Val Gly Gly Ile Arg Leu Pro Asn Gly Lys Leu Lys Cys
     50                  55                  60 gat atc tgt ggg atc att tgc atc ggg ccc aat gtg ctc atg gtt cac     240
Asp Ile Cys Gly Ile Ile Cys Ile Gly Pro Asn Val Leu Met Val His
 65                  70                  75                  80 aaa aga agc cac act gga gaa cgg ccc ttc cag tgc aat cag tgc ggg     288
Lys Arg Ser His Thr Gly Glu Arg Pro Phe Gln Cys Asn Gln Cys Gly
                 85                  90                  95 gcc tca ttc acc cag aag ggc aac ctg ctc cgg cac atc aag ctg cat     336
Ala Ser Phe Thr Gln Lys Gly Asn Leu Leu Arg His Ile Lys Leu His
            100                 105                 110 tcc ggg gag aag ccc ttc aaa tgc cac ctc tgc aac tac gcc tgc cgc     384
Ser Gly Glu Lys Pro Phe Lys Cys His Leu Cys Asn Tyr Ala Cys Arg
        115                 120                 125 cgg agg gac gcc ctc act ggc cac ctg agg acg cac tcc gtt ggt aaa     432
Arg Arg Asp Ala Leu Thr Gly His Leu Arg Thr His Ser Val Gly Lys
    130                 135                 140 cct cac aaa tgt gga tat tgt ggc cga agc tat aaa cag cga acg tct     480
Pro His Lys Cys Gly Tyr Cys Gly Arg Ser Tyr Lys Gln Arg Thr Ser
145                 150                 155                 160 tta gag gaa cat aaa gag cgc tgc cac aac tac ttg gaa agc atg ggc     528
Leu Glu Glu His Lys Glu Arg Cys His Asn Tyr Leu Glu Ser Met Gly
                165                 170                 175 ctt ccg ggc aca ctg tac cca gtc att aaa gaa gaa act aag cac agt     576
Leu Pro Gly Thr Leu Tyr Pro Val Ile Lys Glu Glu Thr Lys His Ser
            180                 185                 190 gaa atg gca gaa gac ctg tgc aag ata gga tca gag aga tct ctc gtg     624
Glu Met Ala Glu Asp Leu Cys Lys Ile Gly Ser Glu Arg Ser Leu Val
        195                 200                 205 ctg gac aga cta gca agt aat gtc gcc aaa cgt aag agc tct atg cct     672
Leu Asp Arg Leu Ala Ser Asn Val Ala Lys Arg Lys Ser Ser Met Pro
    210                 215                 220 cag aaa ttt ctt ggg gac aag ggc ctg tcc gac acg ccc tac gac agt     720
Gln Lys Phe Leu Gly Asp Lys Gly Leu Ser Asp Thr Pro Tyr Asp Ser
225                 230                 235                 240 gcc acg tac gag aag gag aac gaa atg atg aag tcc cac gtg atg gac     768
Ala Thr Tyr Glu Lys Glu Asn Glu Met Met Lys Ser His Val Met Asp
                245                 250                 255 caa gcc atc aac aac gcc atc aac tac ctg ggg gcc gag tcc ctg cgc     816
Gln Ala Ile Asn Asn Ala Ile Asn Tyr Leu Gly Ala Glu Ser Leu Arg
            260                 265                 270 ccg ctg gtg cag acg ccc ccg ggc ggt tcc gag gtg gtc ccg gtc atc     864
Pro Leu Val Gln Thr Pro Pro Gly Gly Ser Glu Val Val Pro Val Ile
        275                 280                 285 agc ccg atg tac cag ctg cac agg cgc tcg gag ggc acc ccg cgc tcc     912
Ser Pro Met Tyr Gln Leu His Arg Arg Ser Glu Gly Thr Pro Arg Ser
    290                 295                 300
```

```
aac cac tcg gcc cag gac agc gcc gtg gag tac ctg ctg ctc tcc        960
Asn His Ser Ala Gln Asp Ser Ala Val Glu Tyr Leu Leu Leu Ser
305                 310                 315                 320 aag gcc aag ttg gtg ccc tcg gag cgc gag gcg tcc ccg agc aac agc   1008
Lys Ala Lys Leu Val Pro Ser Glu Arg Glu Ala Ser Pro Ser Asn Ser
                325                 330                 335 tgc caa gac tcc acg gac acc gag agc aac aac gag gag cag cgc agc   1056
Cys Gln Asp Ser Thr Asp Thr Glu Ser Asn Asn Glu Glu Gln Arg Ser
                340                 345                 350 ggt ctt atc tac ctg acc aac cac atc gcc cga cgc gcg caa cgc gtg   1104
Gly Leu Ile Tyr Leu Thr Asn His Ile Ala Arg Arg Ala Gln Arg Val
            355                 360                 365 tcg ctc aag gag gag cac cgc gcc tac gac ctg ctg cgc gcc gcc tcc   1152
Ser Leu Lys Glu Glu His Arg Ala Tyr Asp Leu Leu Arg Ala Ala Ser
370                 375                 380 gag aac tcg cag gac gcg ctc cgc gtg gtc agc acc agc ggg gag cag   1200
Glu Asn Ser Gln Asp Ala Leu Arg Val Val Ser Thr Ser Gly Glu Gln
385                 390                 395                 400 atg aag gtg tac aag tgc gaa cac tgc cgg gtg ctc ttc ctg gat cac   1248
Met Lys Val Tyr Lys Cys Glu His Cys Arg Val Leu Phe Leu Asp His
                405                 410                 415 gtc atg tac acc atc cac atg ggc tgc cac ggc ttc cgt gat cct ttt   1296
Val Met Tyr Thr Ile His Met Gly Cys His Gly Phe Arg Asp Pro Phe
            420                 425                 430 gag tgc aac atg tgc ggc tac cac agc cag gac cgg tac gag ttc tcg   1344
Glu Cys Asn Met Cys Gly Tyr His Ser Gln Asp Arg Tyr Glu Phe Ser
435                 440                 445 tcg cac ata acg cga ggg gag cac cgc ttc cac atg agc taa           1386
Ser His Ile Thr Arg Gly Glu His Arg Phe His Met Ser
450                 455                 460

<210> SEQ ID NO 55
<211> LENGTH: 1296
<212> TYPE: DNA
<213> ORGANISM: Mus musculus
<220> FEATURE:
<221> NAME/KEY: CDS
<222> LOCATION: (1)...(1296)
<223> OTHER INFORMATION: mIk-3

<400> SEQUENCE: 55 atg gat gtc gat gag ggt caa gac atg tcc caa gtt tca gga aag gag     48
Met Asp Val Asp Glu Gly Gln Asp Met Ser Gln Val Ser Gly Lys Glu
1               5                   10                  15 agc ccc cca gtc agt gac act cca gat gaa ggg gat gag ccc atg cct    96
Ser Pro Pro Val Ser Asp Thr Pro Asp Glu Gly Asp Glu Pro Met Pro
                20                  25                  30 gtc cct gag gac ctg tcc act acc tct gga gca cag cag aac tcc aag   144
Val Pro Glu Asp Leu Ser Thr Thr Ser Gly Ala Gln Gln Asn Ser Lys
            35                  40                  45 agt gat cga ggc atg gcc agt aat gtt aaa gta gag act cag agt gat   192
Ser Asp Arg Gly Met Ala Ser Asn Val Lys Val Glu Thr Gln Ser Asp
50                  55                  60 gaa gag aat ggg cgt gcc tgt gaa atg aat ggg gaa gaa tgt gca gag   240
Glu Glu Asn Gly Arg Ala Cys Glu Met Asn Gly Glu Glu Cys Ala Glu
65                  70                  75                  80 gat tta cga atg ctt gat gcc tcg gga gag aaa atg aat ggc tcc cac   288
Asp Leu Arg Met Leu Asp Ala Ser Gly Glu Lys Met Asn Gly Ser His
                85                  90                  95 agg gac caa ggc agc tcg gct ttg tca gga gtt gga ggc att cga ctt   336
Arg Asp Gln Gly Ser Ser Ala Leu Ser Gly Val Gly Gly Ile Arg Leu
                100                 105                 110
```

-continued

| | |
|---|---|
| cct aac gga aaa cta aag tgt gat atc tgt ggg atc gtt tgc atc ggg<br>Pro Asn Gly Lys Leu Lys Cys Asp Ile Cys Gly Ile Val Cys Ile Gly<br>          115                    120                    125 | 384 |
| ccc aat gtg ctc atg gtt cac aaa aga agt cat act ggt gaa cgg cct<br>Pro Asn Val Leu Met Val His Lys Arg Ser His Thr Gly Glu Arg Pro<br>130                    135                    140 | 432 |
| ttc cag tgc aac cag tct ggg gcc tcc ttt acc cag aaa ggc aac ctc<br>Phe Gln Cys Asn Gln Ser Gly Ala Ser Phe Thr Gln Lys Gly Asn Leu<br>145                    150                    155                    160 | 480 |
| ctg cgg cac atc aag ctg cac tcg ggt gag aag ccc ttc aaa tgc cat<br>Leu Arg His Ile Lys Leu His Ser Gly Glu Lys Pro Phe Lys Cys His<br>                    165                    170                    175 | 528 |
| ctt tgc aac tat gcc tgc cgc cgg agg gac gcc ctc acc ggc cac ctg<br>Leu Cys Asn Tyr Ala Cys Arg Arg Arg Asp Ala Leu Thr Gly His Leu<br>              180                    185                    190 | 576 |
| agg acg cac tcc gga gac aag tgc ctg tca gac atg ccc tat gac agt<br>Arg Thr His Ser Gly Asp Lys Cys Leu Ser Asp Met Pro Tyr Asp Ser<br>                    195                    200                    205 | 624 |
| gcc aac tat gag aag gag gat atg atg aca tcc cac gtg atg gac cag<br>Ala Asn Tyr Glu Lys Glu Asp Met Met Thr Ser His Val Met Asp Gln<br>210                    215                    220 | 672 |
| gcc atc aac aat gcc atc aac tac ctg ggg gct gag tcc ctg cgc cca<br>Ala Ile Asn Asn Ala Ile Asn Tyr Leu Gly Ala Glu Ser Leu Arg Pro<br>225                    230                    235                    240 | 720 |
| ttg gtg cag aca ccc ccc ggt agc tcc gag gtg gtg cca gtc atc agc<br>Leu Val Gln Thr Pro Pro Gly Ser Ser Glu Val Val Pro Val Ile Ser<br>                    245                    250                    255 | 768 |
| tcc atg tac cag ctg cac aag ccc ccc tca gat ggc ccc cca cgg tcc<br>Ser Met Tyr Gln Leu His Lys Pro Pro Ser Asp Gly Pro Pro Arg Ser<br>              260                    265                    270 | 816 |
| aac cat tca gca cag gac gcc gtg gat aac ttg ctg ctg ctg tcc aag<br>Asn His Ser Ala Gln Asp Ala Val Asp Asn Leu Leu Leu Leu Ser Lys<br>                    275                    280                    285 | 864 |
| gcc aag tct gtg tca tcg gag cga gag gcc tcc ccg agc aac agc tgc<br>Ala Lys Ser Val Ser Ser Glu Arg Glu Ala Ser Pro Ser Asn Ser Cys<br>290                    295                    300 | 912 |
| caa gac tcc aca gat aca gag agc aac gcg gag gaa cag cgc agc ggc<br>Gln Asp Ser Thr Asp Thr Glu Ser Asn Ala Glu Glu Gln Arg Ser Gly<br>305                    310                    315                    320 | 960 |
| ctt atc tac cta acc aac cac atc aac ccg cat gca cgc aat ggg ctg<br>Leu Ile Tyr Leu Thr Asn His Ile Asn Pro His Ala Arg Asn Gly Leu<br>                    325                    330                    335 | 1008 |
| gct ctc aag gag gag cag cgc gcc tac gag gtg ctg agg gcg gcc tca<br>Ala Leu Lys Glu Glu Gln Arg Ala Tyr Glu Val Leu Arg Ala Ala Ser<br>              340                    345                    350 | 1056 |
| gag aac tcg cag gat gcc ttc cgt gtg gtc agc acg agt ggc gag cag<br>Glu Asn Ser Gln Asp Ala Phe Arg Val Val Ser Thr Ser Gly Glu Gln<br>                    355                    360                    365 | 1104 |
| ctg aag gtg tac aag tgc gaa cac tgc cgc gtg ctc ttc ctg gat cac<br>Leu Lys Val Tyr Lys Cys Glu His Cys Arg Val Leu Phe Leu Asp His<br>370                    375                    380 | 1152 |
| gtc atg tat acc att cac atg ggc tgc cat ggc tgc cat ggc ttt cgg<br>Val Met Tyr Thr Ile His Met Gly Cys His Gly Cys His Gly Phe Arg<br>385                    390                    395                    400 | 1200 |
| gat ccc ttt gag tgt aac atg tgt ggt tat cac agc cag gac agg tac<br>Asp Pro Phe Glu Cys Asn Met Cys Gly Tyr His Ser Gln Asp Arg Tyr<br>                    405                    410                    415 | 1248 |
| gag ttc tca tcc cat atc acg cgg ggg gag cat cgt tac cac ctg agc<br>Glu Phe Ser Ser His Ile Thr Arg Gly Glu His Arg Tyr His Leu Ser | 1296 |

-continued

```
                     420           425           430
```

<210> SEQ ID NO 56
<211> LENGTH: 2049
<212> TYPE: DNA
<213> ORGANISM: Mus musculus
<220> FEATURE:
<221> NAME/KEY: CDS
<222> LOCATION: (223)...(1776)
<223> OTHER INFORMATION: mIk-1

<400> SEQUENCE: 56

```
aattcgttct accttctctg aaccccagtg gtgtgtcaag gccggactgg gagcttgggg      60
gaagaggaag aggaagagga atctgcggct catccaggga tcagggtcct tcccaagtgg    120
ccactcagag gggactcaga gcaagtctag atttgtgtgg cagagagaga cagctctcgt    180
ttggccttgg ggaggcacaa gtctgttgat aacctgaaga ca atg gat gtc gat       234
                                                Met Asp Val Asp
                                                 1 gag ggt caa gac atg tcc caa gtt tca gga aag gag agc ccc cca gtc      282
Glu Gly Gln Asp Met Ser Gln Val Ser Gly Lys Glu Ser Pro Pro Val
 5                  10                  15                  20 agt gac act cca gat gaa ggg gat gag ccc atg cct gtc cct gag gac      330
Ser Asp Thr Pro Asp Glu Gly Asp Glu Pro Met Pro Val Pro Glu Asp
             25                  30                  35 ctg tcc act acc tct gga gca cag cag aac tcc aag agt gat cga ggc      378
Leu Ser Thr Thr Ser Gly Ala Gln Gln Asn Ser Lys Ser Asp Arg Gly
         40                  45                  50 atg gcc agt aat gtt aaa gta gag act cag agt gat gaa gag aat ggg      426
Met Ala Ser Asn Val Lys Val Glu Thr Gln Ser Asp Glu Glu Asn Gly
     55                  60                  65 cgt gcc tgt gaa atg aat ggg gaa gaa tgt gca gag gat tta cga atg      474
Arg Ala Cys Glu Met Asn Gly Glu Glu Cys Ala Glu Asp Leu Arg Met
 70                  75                  80 ctt gat gcc tcg gga gag aaa atg aat ggc tcc cac agg gac caa ggc      522
Leu Asp Ala Ser Gly Glu Lys Met Asn Gly Ser His Arg Asp Gln Gly
 85                  90                  95                 100 agc tcg gct ttg tca gga gtt gga ggc att cga ctt cct aac gga aaa      570
Ser Ser Ala Leu Ser Gly Val Gly Gly Ile Arg Leu Pro Asn Gly Lys
                105                 110                 115 cta aag tgt gat atc tgt ggg atc gtt tgc atc ggg ccc aat gtg ctc      618
Leu Lys Cys Asp Ile Cys Gly Ile Val Cys Ile Gly Pro Asn Val Leu
            120                 125                 130 atg gtt cac aaa aga agt cat act ggt gaa cgg cct ttc cag tgc aac      666
Met Val His Lys Arg Ser His Thr Gly Glu Arg Pro Phe Gln Cys Asn
        135                 140                 145 cag tct ggg gcc tcc ttt acc cag aaa ggc aac ctc ctg cgg cac atc      714
Gln Ser Gly Ala Ser Phe Thr Gln Lys Gly Asn Leu Leu Arg His Ile
    150                 155                 160 aag ctg cac tcg ggt gag aag ccc ttc aaa tgc cat ctt tgc aac tat      762
Lys Leu His Ser Gly Glu Lys Pro Phe Lys Cys His Leu Cys Asn Tyr
165                 170                 175                 180 gcc tgc cgc cgg agg gac gcc ctc acc ggc cac ctg agg acg cac tcc      810
Ala Cys Arg Arg Arg Asp Ala Leu Thr Gly His Leu Arg Thr His Ser
                185                 190                 195 gtt ggt aag cct cac aaa tgt gga tat tgt ggc cgg agc tat aaa cag      858
Val Gly Lys Pro His Lys Cys Gly Tyr Cys Gly Arg Ser Tyr Lys Gln
            200                 205                 210 cga agc tct tta gag gag cat aaa gag cga tgc cac aac tac ttg gaa      906
Arg Ser Ser Leu Glu Glu His Lys Glu Arg Cys His Asn Tyr Leu Glu
        215                 220                 225
```

-continued

```
agc atg ggc ctt ccg ggc gtg tgc cca gtc att aag gaa gaa act aac      954
Ser Met Gly Leu Pro Gly Val Cys Pro Val Ile Lys Glu Glu Thr Asn
    230                 235                 240 cac aac gag atg gca gaa gac ctg tgc aag ata gga gca gag agg tcc     1002
His Asn Glu Met Ala Glu Asp Leu Cys Lys Ile Gly Ala Glu Arg Ser
245                 250                 255                 260 ctt gtc ctg gac agg ctg gca agc aat gtc gcc aaa cgt aag agc tct    1050
Leu Val Leu Asp Arg Leu Ala Ser Asn Val Ala Lys Arg Lys Ser Ser
                265                 270                 275 atg cct cag aaa ttt ctt gga gac aag tgc ctg tca gac atg ccc tat    1098
Met Pro Gln Lys Phe Leu Gly Asp Lys Cys Leu Ser Asp Met Pro Tyr
            280                 285                 290 gac agt gcc aac tat gag aag gag gat atg atg aca tcc cac gtg atg    1146
Asp Ser Ala Asn Tyr Glu Lys Glu Asp Met Met Thr Ser His Val Met
        295                 300                 305 gac cag gcc atc aac aat gcc atc aac tac ctg ggg gct gag tcc ctg    1194
Asp Gln Ala Ile Asn Asn Ala Ile Asn Tyr Leu Gly Ala Glu Ser Leu
    310                 315                 320 cgc cca ttg gtg cag aca ccc ccc ggt agc tcc gag gtg gtg cca gtc    1242
Arg Pro Leu Val Gln Thr Pro Pro Gly Ser Ser Glu Val Val Pro Val
325                 330                 335                 340 atc agc tcc atg tac cag ctg cac aag ccc ccc tca gat ggc ccc cca    1290
Ile Ser Ser Met Tyr Gln Leu His Lys Pro Pro Ser Asp Gly Pro Pro
                345                 350                 355 cgg tcc aac cat tca gca cag gac gcc gtg gat aac ttg ctg ctg ctg    1338
Arg Ser Asn His Ser Ala Gln Asp Ala Val Asp Asn Leu Leu Leu Leu
            360                 365                 370 tcc aag gcc aag tct gtg tca tcg gag cga gag gcc tcc ccg agc aac    1386
Ser Lys Ala Lys Ser Val Ser Ser Glu Arg Glu Ala Ser Pro Ser Asn
        375                 380                 385 agc tgc caa gac tcc aca gat aca gag agc aac gcg gag gaa cag cgc    1434
Ser Cys Gln Asp Ser Thr Asp Thr Glu Ser Asn Ala Glu Glu Gln Arg
    390                 395                 400 agc ggc ctt atc tac cta acc aac cac atc aac ccg cat gca cgc aat    1482
Ser Gly Leu Ile Tyr Leu Thr Asn His Ile Asn Pro His Ala Arg Asn
405                 410                 415                 420 ggg ctg gct ctc aag gag gag cag cgc gcc tac gag gtg ctg agg gcg    1530
Gly Leu Ala Leu Lys Glu Glu Gln Arg Ala Tyr Glu Val Leu Arg Ala
                425                 430                 435 gcc tca gag aac tcg cag gat gcc ttc cgt gtg gtc agc acg agt ggc    1578
Ala Ser Glu Asn Ser Gln Asp Ala Phe Arg Val Val Ser Thr Ser Gly
            440                 445                 450 gag cag ctg aag gtg tac aag tgc gaa cac tgc cgc gtg ctc ttc ctg    1626
Glu Gln Leu Lys Val Tyr Lys Cys Glu His Cys Arg Val Leu Phe Leu
        455                 460                 465 gat cac gtc atg tat acc att cac atg ggc tgc cat ggc tgc cat ggc    1674
Asp His Val Met Tyr Thr Ile His Met Gly Cys His Gly Cys His Gly
    470                 475                 480 ttt cgg gat ccc ttt gag tgt aac atg tgt ggt tat cac agc cag gac    1722
Phe Arg Asp Pro Phe Glu Cys Asn Met Cys Gly Tyr His Ser Gln Asp
485                 490                 495                 500 agg tac gag ttc tca tcc cat atc acg cgg ggg gag cat cgt tac cac    1770
Arg Tyr Glu Phe Ser Ser His Ile Thr Arg Gly Glu His Arg Tyr His
                505                 510                 515 ctg agc taaacccagc caggccccac tgaagcacaa agatagctgg ttatgcctcc    1826
Leu Ser ttcccggcag ctggacccac agcggacaat gtgggagtgg atttgcaggc agcatttgtt    1886
cttttatgtt ggttgtttgg cgtttcattt gcgttggaag ataagttttt aatgttagtg    1946
```

```
acaggattgc attgcatcag caacattcac aacatccatc cttctagcca gttttgttca      2006
ctggtagctg aggtttcccg gatatgtggc ttcctaacac tct                        2049

<210> SEQ ID NO 57
<211> LENGTH: 1170
<212> TYPE: DNA
<213> ORGANISM: Mus musculus
<220> FEATURE:
<221> NAME/KEY: CDS
<222> LOCATION: (1)...(1170)
<223> OTHER INFORMATION: mIk-4

<400> SEQUENCE: 57 atg gat gtc gat gag ggt caa gac atg tcc caa gtt tca gga aag gag        48
Met Asp Val Asp Glu Gly Gln Asp Met Ser Gln Val Ser Gly Lys Glu
 1               5                  10                  15 agc ccc cca gtc agt gac act cca gat gaa ggg gat gag ccc atg cct        96
Ser Pro Pro Val Ser Asp Thr Pro Asp Glu Gly Asp Glu Pro Met Pro
             20                  25                  30 gtc cct gag gac ctg tcc act acc tct gga gca cag cag aac tcc aag       144
Val Pro Glu Asp Leu Ser Thr Thr Ser Gly Ala Gln Gln Asn Ser Lys
         35                  40                  45 agt gat cga ggc atg ggt gaa cgg cct ttc cag tgc aac cag tct ggg       192
Ser Asp Arg Gly Met Gly Glu Arg Pro Phe Gln Cys Asn Gln Ser Gly
     50                  55                  60 gcc tcc ttt acc cag aaa ggc aac ctc ctg cgg cac atc aag ctg cac       240
Ala Ser Phe Thr Gln Lys Gly Asn Leu Leu Arg His Ile Lys Leu His
 65                  70                  75                  80 tcg ggt gag aag ccc ttc aaa tgc cat ctt tgc aac tat gcc tgc cgc       288
Ser Gly Glu Lys Pro Phe Lys Cys His Leu Cys Asn Tyr Ala Cys Arg
                 85                  90                  95 cgg agg gac gcc ctc acc ggc cac ctg agg acg cac tcc gtc att aag       336
Arg Arg Asp Ala Leu Thr Gly His Leu Arg Thr His Ser Val Ile Lys
            100                 105                 110 gaa gaa act aac cac aac gag atg gca gaa gac ctg tgc aag ata gga       384
Glu Glu Thr Asn His Asn Glu Met Ala Glu Asp Leu Cys Lys Ile Gly
        115                 120                 125 gca gag agg tcc ctt gtc ctg gac agg ctg gca agc aat gtc gcc aaa       432
Ala Glu Arg Ser Leu Val Leu Asp Arg Leu Ala Ser Asn Val Ala Lys
    130                 135                 140 cgt aag agc tct atg cct cag aaa ttt ctt gga gac aag tgc ctg tca       480
Arg Lys Ser Ser Met Pro Gln Lys Phe Leu Gly Asp Lys Cys Leu Ser
145                 150                 155                 160 gac atg ccc tat gac agt gcc aac tat gag aag gag gat atg atg aca       528
Asp Met Pro Tyr Asp Ser Ala Asn Tyr Glu Lys Glu Asp Met Met Thr
                165                 170                 175 tcc cac gtg atg gac cag gcc atc aac aat gcc atc aac tac ctg ggg       576
Ser His Val Met Asp Gln Ala Ile Asn Asn Ala Ile Asn Tyr Leu Gly
            180                 185                 190 gct gag tcc ctg cgc cca ttg gtg cag aca ccc ccg ggt agc tcc gag       624
Ala Glu Ser Leu Arg Pro Leu Val Gln Thr Pro Pro Gly Ser Ser Glu
        195                 200                 205 gtg gtg cca gtc atc agc tcc atg tac cag ctg cac aag ccc ccc tca       672
Val Val Pro Val Ile Ser Ser Met Tyr Gln Leu His Lys Pro Pro Ser
    210                 215                 220 gat ggc ccc cca cgg tcc aac cat tca gca cag gac gcc gtg gat aac       720
Asp Gly Pro Pro Arg Ser Asn His Ser Ala Gln Asp Ala Val Asp Asn
225                 230                 235                 240 ttg ctg ctg ctg tcc aag gcc aag tct gtg tca tcg gag cga gag gcc       768
Leu Leu Leu Leu Ser Lys Ala Lys Ser Val Ser Ser Glu Arg Glu Ala
```

-continued

|  |  |
|---|---|
| tcc ccg agc aac agc tgc caa gac tcc aca gat aca gag agc aac gcg<br>Ser Pro Ser Asn Ser Cys Gln Asp Ser Thr Asp Thr Glu Ser Asn Ala<br>260      265      270 | 816 |
| gag gaa cag cgc agc ggc ctt atc tac cta acc aac cac atc aac ccg<br>Glu Glu Gln Arg Ser Gly Leu Ile Tyr Leu Thr Asn His Ile Asn Pro<br>275      280      285 | 864 |
| cat gca cgc aat ggg ctg gct ctc aag gag gag cag cgc gcc tac gag<br>His Ala Arg Asn Gly Leu Ala Leu Lys Glu Glu Gln Arg Ala Tyr Glu<br>290    295      300 | 912 |
| gtg ctg agg gcg gcc tca gag aac tcg cag gat gcc ttc cgt gtg gtc<br>Val Leu Arg Ala Ala Ser Glu Asn Ser Gln Asp Ala Phe Arg Val Val<br>305      310      315      320 | 960 |
| agc acg agt ggc gag cag ctg aag gtg tac aag tgc gaa cac tgc cgc<br>Ser Thr Ser Gly Glu Gln Leu Lys Val Tyr Lys Cys Glu His Cys Arg<br>      325      330      335 | 1008 |
| gtg ctc ttc ctg gat cac gtc atg tat acc att cac atg ggc tgc cat<br>Val Leu Phe Leu Asp His Val Met Tyr Thr Ile His Met Gly Cys His<br>    340      345      350 | 1056 |
| ggc tgc cat ggc ttt cgg gat ccc ttt gag tgt aac atg tgt ggt tat<br>Gly Cys His Gly Phe Arg Asp Pro Phe Glu Cys Asn Met Cys Gly Tyr<br>      355      360      365 | 1104 |
| cac agc cag gac agg tac gag ttc tca tcc cat atc acg cgg ggg gag<br>His Ser Gln Asp Arg Tyr Glu Phe Ser Ser His Ile Thr Arg Gly Glu<br>370      375      380 | 1152 |
| cat cgt tac cac ctg agc<br>His Arg Tyr His Leu Ser<br>385    390 | 1170 |

<210> SEQ ID NO 58
<211> LENGTH: 1128
<212> TYPE: DNA
<213> ORGANISM: Mus musculus
<220> FEATURE:
<221> NAME/KEY: CDS
<222> LOCATION: (1)...(1128)
<223> OTHER INFORMATION: mIk-5

<400> SEQUENCE: 58

|  |  |
|---|---|
| atg gat gtc gat gag ggt caa gac atg tcc caa gtt tca gga aag gag<br>Met Asp Val Asp Glu Gly Gln Asp Met Ser Gln Val Ser Gly Lys Glu<br>1      5      10      15 | 48 |
| agc ccc cca gtc agt gac act cca gat gaa ggg gat gag ccc atg cct<br>Ser Pro Pro Val Ser Asp Thr Pro Asp Glu Gly Asp Glu Pro Met Pro<br>      20      25      30 | 96 |
| gtc cct gag gac ctg tcc act acc tct gga gca cag cag aac tcc aag<br>Val Pro Glu Asp Leu Ser Thr Thr Ser Gly Ala Gln Gln Asn Ser Lys<br>    35      40      45 | 144 |
| agt gat cga ggc atg gcc agt aat gtt aaa gta gag act cag agt gat<br>Ser Asp Arg Gly Met Ala Ser Asn Val Lys Val Glu Thr Gln Ser Asp<br>50      55      60 | 192 |
| gaa gag aat ggg cgt gcc tgt gaa atg aat ggg gaa gaa tgt gca gag<br>Glu Glu Asn Gly Arg Ala Cys Glu Met Asn Gly Glu Glu Cys Ala Glu<br>65      70      75      80 | 240 |
| gat tta cga atg ctt gat gcc tcg gga gag aaa atg aat ggc tcc cac<br>Asp Leu Arg Met Leu Asp Ala Ser Gly Glu Lys Met Asn Gly Ser His<br>      85      90      95 | 288 |
| agg gac caa ggc agc tcg gct ttg tca gga gtt gga ggc att cga ctt<br>Arg Asp Gln Gly Ser Ser Ala Leu Ser Gly Val Gly Gly Ile Arg Leu<br>    100      105      110 | 336 |
| cct aac gga aaa cta aag tgt gat atc tgt ggg atc gtt tgc atc ggg<br> | 384 |

```
                                                                              -continued
Pro Asn Gly Lys Leu Lys Cys Asp Ile Cys Gly Ile Val Cys Ile Gly
        115                 120                 125 ccc aat gtg ctc atg gtt cac aaa aga agt cat act gga gac aag tgc              432
Pro Asn Val Leu Met Val His Lys Arg Ser His Thr Gly Asp Lys Cys
        130                 135                 140 ctg tca gac atg ccc tat gac agt gcc aac tat gag aag gag gat atg              480
Leu Ser Asp Met Pro Tyr Asp Ser Ala Asn Tyr Glu Lys Glu Asp Met
145                 150                 155                 160 atg aca tcc cac gtg atg gac cag gcc atc aac aat gcc atc aac tac              528
Met Thr Ser His Val Met Asp Gln Ala Ile Asn Asn Ala Ile Asn Tyr
                165                 170                 175 ctg ggg gct gag tcc ctg cgc cca ttg gtg cag aca ccc ccc ggt agc              576
Leu Gly Ala Glu Ser Leu Arg Pro Leu Val Gln Thr Pro Pro Gly Ser
        180                 185                 190 tcc gag gtg gtg cca gtc atc agc tcc atg tac cag ctg cac aag ccc              624
Ser Glu Val Val Pro Val Ile Ser Ser Met Tyr Gln Leu His Lys Pro
        195                 200                 205 ccc tca gat ggc ccc cca cgg tcc aac cat tca gca cag gac gcc gtg              672
Pro Ser Asp Gly Pro Pro Arg Ser Asn His Ser Ala Gln Asp Ala Val
        210                 215                 220 gat aac ttg ctg ctg ctg tcc aag gcc aag tct gtg tca tcg gag cga              720
Asp Asn Leu Leu Leu Leu Ser Lys Ala Lys Ser Val Ser Ser Glu Arg
225                 230                 235                 240 gag gcc tcc ccg agc aac agc tgc caa gac tcc aca gat aca gag agc              768
Glu Ala Ser Pro Ser Asn Ser Cys Gln Asp Ser Thr Asp Thr Glu Ser
                245                 250                 255 aac gcg gag gaa cag cgc agc ggc ctt atc tac cta acc aac cac atc              816
Asn Ala Glu Glu Gln Arg Ser Gly Leu Ile Tyr Leu Thr Asn His Ile
                260                 265                 270 aac ccg cat gca cgc aat ggg ctg gct ctc aag gag gag cag cgc gcc              864
Asn Pro His Ala Arg Asn Gly Leu Ala Leu Lys Glu Glu Gln Arg Ala
        275                 280                 285 tac gag gtg ctg agg gcg gcc tca gag aac tcg cag gat gcc ttc cgt              912
Tyr Glu Val Leu Arg Ala Ala Ser Glu Asn Ser Gln Asp Ala Phe Arg
        290                 295                 300 gtg gtc agc acg agt ggc gag cag ctg aag gtg tac aag tgc gaa cac              960
Val Val Ser Thr Ser Gly Glu Gln Leu Lys Val Tyr Lys Cys Glu His
305                 310                 315                 320 tgc cgc gtg ctc ttc ctg gat cac gtc atg tat acc att cac atg ggc             1008
Cys Arg Val Leu Phe Leu Asp His Val Met Tyr Thr Ile His Met Gly
                325                 330                 335 tgc cat ggc tgc cat ggc ttt cgg gat ccc ttt gag tgt aac atg tgt             1056
Cys His Gly Cys His Gly Phe Arg Asp Pro Phe Glu Cys Asn Met Cys
                340                 345                 350 ggt tat cac agc cag gac agg tac gag ttc tca tcc cat atc acg cgg             1104
Gly Tyr His Ser Gln Asp Arg Tyr Glu Phe Ser Ser His Ile Thr Arg
        355                 360                 365 ggg gag cat cgt tac cac ctg agc                                             1128
Gly Glu His Arg Tyr His Leu Ser
        370                 375

<210> SEQ ID NO 59
<211> LENGTH: 1004
<212> TYPE: DNA
<213> ORGANISM: Mus musculus
<220> FEATURE:
<221> NAME/KEY: CDS
<222> LOCATION: (1)...(1002)

<400> SEQUENCE: 59 gga gaa cgg ccc ttc cag tgc aat cag tgc ggg gcc tca ttc acc cag               48
```

-continued

| | | | | | | | | | | | | | | | | |
|---|---|---|---|---|---|---|---|---|---|---|---|---|---|---|---|---|
| | Gly | Glu | Arg | Pro | Phe | Gln | Cys | Asn | Gln | Cys | Gly | Ala | Ser | Phe | Thr | Gln |
| | 1 | | | | 5 | | | | | 10 | | | | | 15 | |

```
aag ggc aac ctg ctc cgg cac atc aag ctg cat tcc ggg gag aag ccc        96
Lys Gly Asn Leu Leu Arg His Ile Lys Leu His Ser Gly Glu Lys Pro
             20                  25                  30 ttc aaa tgc cac ctc tgc aac tac gcc tgc cgc cgg agg gac gcc ctc       144
Phe Lys Cys His Leu Cys Asn Tyr Ala Cys Arg Arg Arg Asp Ala Leu
         35                  40                  45 act ggc cac ctg agg acg cac tcc gtc att aaa gaa gaa act aag cac       192
Thr Gly His Leu Arg Thr His Ser Val Ile Lys Glu Glu Thr Lys His
     50                  55                  60 agt gaa atg gca gaa gac ctg tgc aag ata gga tca gag aga tct ctc       240
Ser Glu Met Ala Glu Asp Leu Cys Lys Ile Gly Ser Glu Arg Ser Leu
 65                  70                  75                  80 gtg ctg gac aga cta gca agt aat gtc gcc aaa cgt aag agc tct atg       288
Val Leu Asp Arg Leu Ala Ser Asn Val Ala Lys Arg Lys Ser Ser Met
                 85                  90                  95 cct cag aaa ttt ctt ggg gac aag ggc ctg tcc gac acg ccc tac gac       336
Pro Gln Lys Phe Leu Gly Asp Lys Gly Leu Ser Asp Thr Pro Tyr Asp
             100                 105                 110 agt gcc acg tac gag aag gag aac gaa atg atg aag tcc cac gtg atg       384
Ser Ala Thr Tyr Glu Lys Glu Asn Glu Met Met Lys Ser His Val Met
         115                 120                 125 gac caa gcc atc aac aac gcc atc aac tac ctg ggg gcc gag tcc ctg       432
Asp Gln Ala Ile Asn Asn Ala Ile Asn Tyr Leu Gly Ala Glu Ser Leu
     130                 135                 140 cgc ccg ctg gtg cag acg ccc ccg ggc ggt tcc gag gtg gtc ccg gtc       480
Arg Pro Leu Val Gln Thr Pro Pro Gly Gly Ser Glu Val Val Pro Val
145                 150                 155                 160 atc agc ccg atg tac cag ctg cac agg cgc tcg gag ggc acc ccg cgc       528
Ile Ser Pro Met Tyr Gln Leu His Arg Arg Ser Glu Gly Thr Pro Arg
                 165                 170                 175 tcc aac cac tcg gcc cag gac agc gcc gtg gag tac ctg ctg ctg ctc       576
Ser Asn His Ser Ala Gln Asp Ser Ala Val Glu Tyr Leu Leu Leu Leu
             180                 185                 190 tcc aag gcc aag ttg gtg ccc tcg gag cgc gag gcg tcc ccg agc aac       624
Ser Lys Ala Lys Leu Val Pro Ser Glu Arg Glu Ala Ser Pro Ser Asn
         195                 200                 205 agc tgc caa gac tcc acg gac acc gag agc aac aac gag gag cag cgc       672
Ser Cys Gln Asp Ser Thr Asp Thr Glu Ser Asn Asn Glu Glu Gln Arg
     210                 215                 220 agc ggt ctt atc tac ctg acc aac cac atc gcc cga cgc gcg caa cgc       720
Ser Gly Leu Ile Tyr Leu Thr Asn His Ile Ala Arg Arg Ala Gln Arg
225                 230                 235                 240 gtg tcg ctc aag gag gag cac cgc gcc tac gac ctg ctg cgc gcc gcc       768
Val Ser Leu Lys Glu Glu His Arg Ala Tyr Asp Leu Leu Arg Ala Ala
                 245                 250                 255 tcc gag aac tcg cag gac gcg ctc cgc gtg gtc agc acc agc ggg gag       816
Ser Glu Asn Ser Gln Asp Ala Leu Arg Val Val Ser Thr Ser Gly Glu
             260                 265                 270 cag atg aag gtg tac aag tgc gaa cac tgc cgg gtg ctc ttc ctg gat       864
Gln Met Lys Val Tyr Lys Cys Glu His Cys Arg Val Leu Phe Leu Asp
         275                 280                 285 cac gtc atg tac acc atc cac atg ggc tgc cac ggc ttc cgt gat cct       912
His Val Met Tyr Thr Ile His Met Gly Cys His Gly Phe Arg Asp Pro
     290                 295                 300 ttt gag tgc aac atg tgc ggc tac cac agc cag gac cgg tac gag ttc       960
Phe Glu Cys Asn Met Cys Gly Tyr His Ser Gln Asp Arg Tyr Glu Phe
305                 310                 315                 320
```

```
tcg tcg cac ata acg cga ggg gag cac cgc ttc cac atg agc       1002
Ser Ser His Ile Thr Arg Gly Glu His Arg Phe His Met Ser
            325                 330 ta                                                            1004

<210> SEQ ID NO 60
<211> LENGTH: 103
<212> TYPE: DNA
<213> ORGANISM: Mus musculus

<400> SEQUENCE: 60
tttggttata aatgtattga ttgcatcccc attacccaga aggccaatat ttaattggag    60
tcttaactca attgtgtttt cgtcagttgg taagcctcac aaa                    103

<210> SEQ ID NO 61
<211> LENGTH: 116
<212> TYPE: DNA
<213> ORGANISM: Mus musculus

<400> SEQUENCE: 61
atgggccttc cgggcatgta cccaggtaag cactgaggcc ctgctgagct gcacccctcc    60
ccctcccagc gcctgggcca ggatggggct ctgtggcctg tttcagccac aggagg      116

<210> SEQ ID NO 62
<211> LENGTH: 94
<212> TYPE: DNA
<213> ORGANISM: Mus musculus

<400> SEQUENCE: 62
ccttgttgct gctgtgttgc tatcttgtga cttattttg cagtgacact gagtggcctc     60
ctgtgttgtc tctttcagcc agtaatgtta aagt                                94

<210> SEQ ID NO 63
<211> LENGTH: 120
<212> TYPE: DNA
<213> ORGANISM: Mus musculus

<400> SEQUENCE: 63
gagccctggc agatgtgtcc tgtctgctgt gacactagaa caccattcaa cccctgggtg    60
tagatttcac ttatgaccat ctacttcccg caggagacaa gtgcctgtca gacatgccct   120

<210> SEQ ID NO 64
<211> LENGTH: 120
<212> TYPE: DNA
<213> ORGANISM: Mus musculus

<400> SEQUENCE: 64
acatgtgtgg ttatcacagc caggacaggt acgagttctc atcccatatc acgcgggggg    60
agcatcgtta ccacctgagc taaacccagc caggccccac tgaagcacaa agatagctgg   120

<210> SEQ ID NO 65
<211> LENGTH: 470
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(470)
<223> OTHER INFORMATION: Xaa = Any Amino Acid

<400> SEQUENCE: 65
```

```
Xaa Xaa Ala Ser Asn Val Lys Val Glu Thr Gln Ser Asp Glu Glu Asn
 1           5                  10                  15

Gly Arg Ala Cys Glu Met Asn Gly Glu Glu Cys Ala Glu Asp Leu Arg
            20                  25                  30

Met Leu Asp Ala Ser Gly Glu Lys Met Asn Gly Ser His Arg Asp Gln
            35                  40                  45

Gly Ser Ser Ala Leu Ser Gly Val Gly Gly Ile Arg Leu Pro Asn Gly
    50                  55                  60

Lys Leu Lys Cys Asp Ile Cys Gly Ile Xaa Cys Ile Gly Pro Asn Val
65                  70                  75                  80

Leu Met Val His Lys Arg Ser His Thr Gly Glu Arg Pro Phe Gln Cys
                85                  90                  95

Asn Gln Cys Gly Ala Ser Phe Thr Gln Lys Gly Asn Leu Leu Arg His
            100                 105                 110

Ile Lys Leu His Ser Gly Glu Lys Pro Phe Lys Cys His Leu Cys Asn
            115                 120                 125

Tyr Ala Cys Arg Arg Arg Asp Ala Leu Thr Gly His Leu Arg Thr His
    130                 135                 140

Ser Val Gly Lys Pro His Lys Cys Gly Tyr Cys Gly Arg Ser Tyr Lys
145                 150                 155                 160

Gln Arg Xaa Ser Leu Glu Glu His Lys Glu Arg Cys His Asn Tyr Leu
            165                 170                 175

Glu Ser Met Gly Leu Pro Gly Xaa Xaa Xaa Pro Val Ile Lys Glu Glu
            180                 185                 190

Thr Xaa His Xaa Glu Met Ala Glu Asp Leu Cys Lys Ile Gly Xaa Glu
    195                 200                 205

Arg Ser Leu Val Leu Asp Arg Leu Ala Ser Asn Val Ala Lys Arg Lys
    210                 215                 220

Ser Ser Met Pro Gln Lys Phe Leu Gly Asp Lys Xaa Leu Ser Asp Xaa
225                 230                 235                 240

Pro Tyr Asp Ser Ala Xaa Tyr Glu Lys Glu Xaa Xaa Met Met Xaa Ser
            245                 250                 255

His Val Met Asp Xaa Ala Ile Asn Asn Ala Ile Asn Tyr Leu Gly Ala
            260                 265                 270

Glu Ser Leu Arg Pro Leu Val Gln Thr Pro Pro Gly Xaa Ser Glu Val
    275                 280                 285

Val Pro Val Ile Ser Pro Met Tyr Gln Leu His Xaa Xaa Xaa Ser Xaa
    290                 295                 300

Gly Xaa Pro Arg Ser Asn His Ser Ala Gln Asp Xaa Ala Val Xaa Xaa
305                 310                 315                 320

Leu Leu Leu Leu Ser Lys Ala Lys Xaa Val Xaa Ser Glu Arg Glu Ala
                325                 330                 335

Ser Pro Ser Asn Ser Cys Gln Asp Ser Thr Asp Thr Glu Ser Asn Xaa
            340                 345                 350

Glu Glu Gln Arg Ser Gly Leu Ile Tyr Leu Thr Asn His Ile Xaa Xaa
            355                 360                 365

Xaa Ala Xaa Xaa Xaa Xaa Xaa Leu Lys Glu Glu Xaa Arg Ala Tyr Xaa
    370                 375                 380

Xaa Leu Arg Ala Ala Ser Glu Asn Ser Gln Asp Ala Xaa Arg Val Val
385                 390                 395                 400

Ser Thr Ser Gly Glu Gln Xaa Lys Val Tyr Lys Cys Glu His Cys Arg
            405                 410                 415
```

```
Val Leu Phe Leu Asp His Val Met Tyr Thr Ile His Met Xaa Xaa Xaa
            420                 425                 430

Gly Cys His Gly Phe Arg Asp Pro Phe Glu Cys Asn Met Cys Gly Tyr
            435                 440                 445

His Ser Gln Asp Arg Tyr Glu Phe Ser Ser His Ile Thr Arg Gly Glu
        450                 455                 460

His Arg Xaa His Xaa Ser
465             470

<210> SEQ ID NO 66
<211> LENGTH: 38
<212> TYPE: DNA
<213> ORGANISM: Artificial Sequence
<220> FEATURE:
<223> OTHER INFORMATION: probe

<400> SEQUENCE: 66
agaagtttcc ataagatgat gaatgggggt ggcagaga                          38

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
ggctgccacg gcttccgtga tcct                                         24

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
agcggtctgg ggaaacatct agga                                         24

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
agtaatgtta aagtagagac tcag                                         24

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
gtatgacttc ttttgtgaac catg                                         24

<210> SEQ ID NO 71
<211> LENGTH: 24
<212> TYPE: DNA
<213> ORGANISM: Artificial Sequence
<220> FEATURE:
<223> OTHER INFORMATION: Primer
```

<400> SEQUENCE: 71
ccagcctctg agcccagaaa gcga                                    24

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
cactacctct ggagcacagc agaa                                    24

<210> SEQ ID NO 73
<211> LENGTH: 21
<212> TYPE: DNA
<213> ORGANISM: Artificial Sequence
<220> FEATURE:
<223> OTHER INFORMATION: Primer

<400> SEQUENCE: 73
ggtgaacggc ctttccagtg c                                       21

<210> SEQ ID NO 74
<211> LENGTH: 21
<212> TYPE: DNA
<213> ORGANISM: Artificial Sequence
<220> FEATURE:
<223> OTHER INFORMATION: Primer

<400> SEQUENCE: 74
tctgaggcat agagctctta c                                       21

<210> SEQ ID NO 75
<211> LENGTH: 24
<212> TYPE: DNA
<213> ORGANISM: Artificial Sequence
<220> FEATURE:
<223> OTHER INFORMATION: Primer

<400> SEQUENCE: 75
catagggcat gtctgacagg cact                                    24

<210> SEQ ID NO 76
<211> LENGTH: 28
<212> TYPE: DNA
<213> ORGANISM: Artificial Sequence
<220> FEATURE:
<223> OTHER INFORMATION: Primer

<400> SEQUENCE: 76
tcagcttttg ggaatgtatt ccctgtca                                28

<210> SEQ ID NO 77
<211> LENGTH: 24
<212> TYPE: DNA
<213> ORGANISM: Artificial Sequence
<220> FEATURE:
<223> OTHER INFORMATION: Primer

<400> SEQUENCE: 77
tcagcttttg agaataccct gtca                                    24

<210> SEQ ID NO 78

```
<211> LENGTH: 17
<212> TYPE: DNA
<213> ORGANISM: Artificial Sequence
<220> FEATURE:
<223> OTHER INFORMATION: Primer

<400> SEQUENCE: 78
ggcatgactc agagcga                                                    17

<210> SEQ ID NO 79
<211> LENGTH: 25
<212> TYPE: DNA
<213> ORGANISM: Artificial Sequence
<220> FEATURE:
<223> OTHER INFORMATION: Primer

<400> SEQUENCE: 79
ccttcatctg gagtgtcact gactg                                           25

<210> SEQ ID NO 80
<211> LENGTH: 22
<212> TYPE: DNA
<213> ORGANISM: Artificial Sequence
<220> FEATURE:
<223> OTHER INFORMATION: Primer

<400> SEQUENCE: 80
ctgaaacttg ggacatgtct tg                                              22

<210> SEQ ID NO 81
<211> LENGTH: 30
<212> TYPE: DNA
<213> ORGANISM: Artificial Sequence
<220> FEATURE:
<223> OTHER INFORMATION: Primer

<400> SEQUENCE: 81
aaaggatccg aacataacta tggatcagcc                                      30

<210> SEQ ID NO 82
<211> LENGTH: 29
<212> TYPE: DNA
<213> ORGANISM: Artificial Sequence
<220> FEATURE:
<223> OTHER INFORMATION: Primer

<400> SEQUENCE: 82
tttaccggtg tcttcaggtt atctcctgc                                       29

<210> SEQ ID NO 83
<211> LENGTH: 19
<212> TYPE: DNA
<213> ORGANISM: Artificial Sequence
<220> FEATURE:
<223> OTHER INFORMATION: Primer

<400> SEQUENCE: 83
cgtaaaggcc acaagttca                                                  19

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
```

```
cttgaagttc accttgatgc                                              20

<210> SEQ ID NO 85
<211> LENGTH: 62
<212> TYPE: DNA
<213> ORGANISM: Artificial Sequence
<220> FEATURE:
<223> OTHER INFORMATION: Primer

<400> SEQUENCE: 85
tcgacgatcg atcgatcgat cataacttcg tataatgtat gctatacgaa gttattaagc   60
tt                                                                 62

<210> SEQ ID NO 86
<211> LENGTH: 41
<212> TYPE: DNA
<213> ORGANISM: Artificial Sequence
<220> FEATURE:
<223> OTHER INFORMATION: Primer

<400> SEQUENCE: 86
gatccataac ttcgtataat gtatgctata cgaagttatt t                       41

<210> SEQ ID NO 87
<211> LENGTH: 46
<212> TYPE: DNA
<213> ORGANISM: Artificial Sequence
<220> FEATURE:
<223> OTHER INFORMATION: Primer

<400> SEQUENCE: 87
ctagaaataa cttcgtatag catacattat acgaagttat ggatcc                  46

<210> SEQ ID NO 88
<211> LENGTH: 21
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: (1)...(21)
<223> OTHER INFORMATION: Xaa = Any Amino Acid

<400> SEQUENCE: 88

Cys Xaa Xaa Cys Xaa Xaa Xaa Xaa Xaa Xaa Xaa Xaa Xaa Xaa Xaa
 1               5                  10                  15

His Xaa Xaa Xaa His
            20

<210> SEQ ID NO 89
<211> LENGTH: 431
<212> TYPE: PRT
<213> ORGANISM: Mus musculus

<400> SEQUENCE: 89

Met Asp Val Asp Glu Gly Gln Asp Met Ser Gln Val Ser Gly Lys Glu
 1               5                  10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Gln Arg Pro Phe Gln Cys Asn Gln Ser Gly
```

```
            50                  55                  60
Ala Ser Phe Thr Gln Lys Gly Asn Leu Leu Arg His Ile Lys Leu His
 65                  70                  75                  80

Ser Gly Glu Lys Pro Phe Lys Cys His Leu Cys Asn Tyr Ala Cys Arg
                 85                  90                  95

Arg Arg Asp Ala Leu Thr Gly His Leu Arg Thr His Ser Val Gly Lys
            100                 105                 110

Pro His Lys Cys Gly Tyr Cys Gly Arg Ser Tyr Lys Gln Arg Ser Ser
        115                 120                 125

Leu Glu Glu His Lys Glu Arg Cys His Asn Tyr Leu Glu Ser Met Gly
    130                 135                 140

Leu Pro Gly Val Cys Pro Val Ile Lys Glu Glu Thr Asn His Asn Glu
145                 150                 155                 160

Met Ala Glu Asp Leu Cys Lys Ile Gly Ala Glu Arg Ser Leu Val Leu
                165                 170                 175

Asp Arg Leu Ala Ser Asn Val Ala Lys Arg Lys Ser Ser Met Pro Gln
            180                 185                 190

Lys Phe Leu Gly Asp Lys Cys Leu Ser Asp Met Pro Tyr Asp Ser Ala
        195                 200                 205

Asn Tyr Glu Lys Glu Asp Met Met Thr Ser His Val Met Asp Gln Ala
    210                 215                 220

Ile Asn Asn Ala Ile Asn Tyr Leu Gly Ala Glu Ser Leu Arg Pro Leu
225                 230                 235                 240

Val Gln Thr Pro Pro Gly Ser Ser Glu Val Pro Val Ile Ser Ser
                245                 250                 255

Met Tyr Gln Leu His Lys Pro Pro Ser Asp Gly Pro Pro Arg Ser Asn
            260                 265                 270

His Ser Ala Gln Asp Ala Val Asp Asn Leu Leu Leu Ser Lys Ala
        275                 280                 285

Lys Ser Val Ser Ser Glu Arg Glu Ala Ser Pro Ser Asn Ser Cys Gln
    290                 295                 300

Asp Ser Thr Asp Thr Glu Ser Asn Ala Glu Glu Gln Arg Ser Gly Leu
305                 310                 315                 320

Ile Tyr Leu Thr Asn His Ile Asn Pro His Ala Arg Asn Gly Leu Ala
                325                 330                 335

Leu Lys Glu Glu Gln Arg Ala Tyr Glu Val Leu Arg Ala Ala Ser Glu
            340                 345                 350

Asn Ser Gln Asp Ala Phe Arg Val Val Ser Thr Ser Gly Glu Gln Leu
        355                 360                 365

Lys Val Tyr Lys Cys Glu His Cys Arg Val Leu Phe Leu Asp His Val
    370                 375                 380

Met Tyr Thr Ile His Met Gly Cys His Gly Cys His Gly Phe Arg Asp
385                 390                 395                 400

Pro Phe Glu Cys Asn Met Cys Gly Tyr His Ser Gln Asp Arg Tyr Glu
                405                 410                 415

Phe Ser Ser His Ile Thr Arg Gly Glu His Arg Tyr His Leu Ser
            420                 425                 430

<210> SEQ ID NO 90
<211> LENGTH: 461
<212> TYPE: PRT
<213> ORGANISM: Homo sapiens

<400> SEQUENCE: 90
```

-continued

```
Asn Val Lys Val Glu Thr Gln Ser Asp Glu Asn Gly Arg Ala Cys
 1               5                  10                  15

Glu Met Asn Gly Glu Cys Ala Glu Asp Leu Arg Met Leu Asp Ala
            20                  25                  30

Ser Gly Glu Lys Met Asn Gly Ser His Arg Asp Gln Gly Ser Ser Ala
            35                  40                  45

Leu Ser Gly Val Gly Gly Ile Arg Leu Pro Asn Gly Lys Leu Lys Cys
     50                  55                  60

Asp Ile Cys Gly Ile Ile Cys Ile Gly Pro Asn Val Leu Met Val His
 65              70                  75                  80

Lys Arg Ser His Thr Gly Glu Arg Pro Phe Gln Cys Asn Gln Cys Gly
                85                  90                  95

Ala Ser Phe Thr Gln Lys Gly Asn Leu Leu Arg His Ile Lys Leu His
            100                 105                 110

Ser Gly Glu Lys Pro Phe Lys Cys His Leu Cys Asn Tyr Ala Cys Arg
            115                 120                 125

Arg Arg Asp Ala Leu Thr Gly His Leu Arg Thr His Ser Val Gly Lys
 130                 135                 140

Pro His Lys Cys Gly Tyr Cys Gly Arg Ser Tyr Lys Gln Arg Thr Ser
145                 150                 155                 160

Leu Glu Glu His Lys Glu Arg Cys His Asn Tyr Leu Glu Ser Met Gly
                165                 170                 175

Leu Pro Gly Thr Leu Tyr Pro Val Ile Lys Glu Glu Thr Lys His Ser
            180                 185                 190

Glu Met Ala Glu Asp Leu Cys Lys Ile Gly Ser Glu Arg Ser Leu Val
            195                 200                 205

Leu Asp Arg Leu Ala Ser Asn Val Ala Lys Arg Lys Ser Ser Met Pro
 210                 215                 220

Gln Lys Phe Leu Gly Asp Lys Gly Leu Ser Asp Thr Pro Tyr Asp Ser
225                 230                 235                 240

Ala Thr Tyr Glu Lys Glu Asn Glu Met Met Lys Ser His Val Met Asp
                245                 250                 255

Gln Ala Ile Asn Asn Ala Ile Asn Tyr Leu Gly Ala Glu Ser Leu Arg
            260                 265                 270

Pro Leu Val Gln Thr Pro Pro Gly Gly Ser Glu Val Pro Val Ile
            275                 280                 285

Ser Pro Met Tyr Gln Leu His Arg Arg Ser Glu Gly Thr Pro Arg Ser
 290                 295                 300

Asn His Ser Ala Gln Asp Ser Ala Val Glu Tyr Leu Leu Leu Ser
305                 310                 315                 320

Lys Ala Lys Leu Val Pro Ser Glu Arg Glu Ala Ser Pro Ser Asn Ser
                325                 330                 335

Cys Gln Asp Ser Thr Asp Thr Glu Ser Asn Asn Glu Glu Gln Arg Ser
            340                 345                 350

Gly Leu Ile Tyr Leu Thr Asn His Ile Ala Arg Arg Ala Gln Arg Val
            355                 360                 365

Ser Leu Lys Glu Glu His Arg Ala Tyr Asp Leu Leu Arg Ala Ala Ser
     370                 375                 380

Glu Asn Ser Gln Asp Ala Leu Arg Val Val Ser Thr Ser Gly Glu Gln
385                 390                 395                 400

Met Lys Val Tyr Lys Cys Glu His Cys Arg Val Leu Phe Leu Asp His
                405                 410                 415

Val Met Tyr Thr Ile His Met Gly Cys His Gly Phe Arg Asp Pro Phe
```

```
                420             425             430
Glu Cys Asn Met Cys Gly Tyr His Ser Gln Asp Arg Tyr Glu Phe Ser
            435                 440                 445
Ser His Ile Thr Arg Gly Glu His Arg Phe His Met Ser
    450                 455                 460

<210> SEQ ID NO 91
<211> LENGTH: 432
<212> TYPE: PRT
<213> ORGANISM: Mus musculus

<400> SEQUENCE: 91

Met Asp Val Asp Glu Gly Gln Asp Met Ser Gln Val Ser Gly Lys Glu
 1               5                  10                  15
Ser Pro Pro Val Ser Asp Thr Pro Asp Glu Gly Asp Glu Pro Met Pro
            20                  25                  30
Val Pro Glu Asp Leu Ser Thr Thr Ser Gly Ala Gln Gln Asn Ser Lys
        35                  40                  45
Ser Asp Arg Gly Met Ala Ser Asn Val Lys Val Glu Thr Gln Ser Asp
    50                  55                  60
Glu Glu Asn Gly Arg Ala Cys Glu Met Asn Gly Glu Glu Cys Ala Glu
65                  70                  75                  80
Asp Leu Arg Met Leu Asp Ala Ser Gly Glu Lys Met Asn Gly Ser His
                85                  90                  95
Arg Asp Gln Gly Ser Ser Ala Leu Ser Gly Val Gly Gly Ile Arg Leu
            100                 105                 110
Pro Asn Gly Lys Leu Lys Cys Asp Ile Cys Gly Ile Val Cys Ile Gly
        115                 120                 125
Pro Asn Val Leu Met Val His Lys Arg Ser His Thr Gly Glu Arg Pro
    130                 135                 140
Phe Gln Cys Asn Gln Ser Gly Ala Ser Phe Thr Gln Lys Gly Asn Leu
145                 150                 155                 160
Leu Arg His Ile Lys Leu His Ser Gly Glu Lys Pro Phe Lys Cys His
                165                 170                 175
Leu Cys Asn Tyr Ala Cys Arg Arg Arg Asp Ala Leu Thr Gly His Leu
            180                 185                 190
Arg Thr His Ser Gly Asp Lys Cys Leu Ser Asp Met Pro Tyr Asp Ser
        195                 200                 205
Ala Asn Tyr Glu Lys Glu Asp Met Met Thr Ser His Val Met Asp Gln
    210                 215                 220
Ala Ile Asn Asn Ala Ile Asn Tyr Leu Gly Ala Glu Ser Leu Arg Pro
225                 230                 235                 240
Leu Val Gln Thr Pro Pro Gly Ser Ser Glu Val Val Pro Val Ile Ser
                245                 250                 255
Ser Met Tyr Gln Leu His Lys Pro Pro Ser Asp Gly Pro Pro Arg Ser
            260                 265                 270
Asn His Ser Ala Gln Asp Ala Val Asp Asn Leu Leu Leu Leu Ser Lys
        275                 280                 285
Ala Lys Ser Val Ser Ser Glu Arg Glu Ala Ser Pro Ser Asn Ser Cys
    290                 295                 300
Gln Asp Ser Thr Asp Thr Glu Ser Asn Ala Glu Gln Arg Ser Gly
305                 310                 315                 320
Leu Ile Tyr Leu Thr Asn His Ile Asn Pro His Ala Arg Asn Gly Leu
                325                 330                 335
```

```
Ala Leu Lys Glu Glu Gln Arg Ala Tyr Glu Val Leu Arg Ala Ala Ser
            340                 345                 350

Glu Asn Ser Gln Asp Ala Phe Arg Val Val Ser Thr Ser Gly Glu Gln
            355                 360                 365

Leu Lys Val Tyr Lys Cys Glu His Cys Arg Val Leu Phe Leu Asp His
        370                 375                 380

Val Met Tyr Thr Ile His Met Gly Cys His Gly Cys His Gly Phe Arg
385                 390                 395                 400

Asp Pro Phe Glu Cys Asn Met Cys Gly Tyr His Ser Gln Asp Arg Tyr
                405                 410                 415

Glu Phe Ser Ser His Ile Thr Arg Gly Glu His Arg Tyr His Leu Ser
            420                 425                 430
```

<210> SEQ ID NO 92
<211> LENGTH: 518
<212> TYPE: PRT
<213> ORGANISM: Mus musculus

<400> SEQUENCE: 92

```
Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Ile Arg Leu
            100                 105                 110

Pro Asn Gly Lys Leu Lys Cys Asp Ile Cys Gly Ile Val Cys Ile Gly
        115                 120                 125

Pro Asn Val Leu Met Val His Lys Arg Ser His Thr Gly Glu Arg Pro
    130                 135                 140

Phe Gln Cys Asn Gln Ser Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Val Cys Pro Val Ile Lys
225                 230                 235                 240

Glu Glu Thr Asn His Asn Glu Met Ala Glu Asp Leu Cys Lys Ile Gly
                245                 250                 255

Ala Glu Arg Ser Leu Val Leu Asp Arg Leu Ala Ser Asn Val Ala Lys
            260                 265                 270

Arg Lys Ser Ser Met Pro Gln Lys Phe Leu Gly Asp Lys Cys Leu Ser
        275                 280                 285
```

-continued

```
Asp Met Pro Tyr Asp Ser Ala Asn Tyr Glu Lys Glu Asp Met Met Thr
    290                 295                 300

Ser His Val Met Asp Gln Ala Ile Asn Asn Ala Ile Asn Tyr Leu Gly
305                 310                 315                 320

Ala Glu Ser Leu Arg Pro Leu Val Gln Thr Pro Pro Gly Ser Ser Glu
                325                 330                 335

Val Val Pro Val Ile Ser Ser Met Tyr Gln Leu His Lys Pro Pro Ser
            340                 345                 350

Asp Gly Pro Pro Arg Ser Asn His Ser Ala Gln Asp Ala Val Asp Asn
        355                 360                 365

Leu Leu Leu Leu Ser Lys Ala Lys Ser Val Ser Glu Arg Glu Ala
    370                 375                 380

Ser Pro Ser Asn Ser Cys Gln Asp Ser Thr Asp Thr Glu Ser Asn Ala
385                 390                 395                 400

Glu Glu Gln Arg Ser Gly Leu Ile Tyr Leu Thr Asn His Ile Asn Pro
                405                 410                 415

His Ala Arg Asn Gly Leu Ala Leu Lys Glu Gln Arg Ala Tyr Glu
            420                 425                 430

Val Leu Arg Ala Ala Ser Glu Asn Ser Gln Asp Ala Phe Arg Val Val
        435                 440                 445

Ser Thr Ser Gly Glu Gln Leu Lys Val Tyr Lys Cys Glu His Cys Arg
    450                 455                 460

Val Leu Phe Leu Asp His Val Met Tyr Thr Ile His Met Gly Cys His
465                 470                 475                 480

Gly Cys His Gly Phe Arg Asp Pro Phe Glu Cys Asn Met Cys Gly Tyr
                485                 490                 495

His Ser Gln Asp Arg Tyr Glu Phe Ser Ser His Ile Thr Arg Gly Glu
            500                 505                 510

His Arg Tyr His Leu Ser
        515

<210> SEQ ID NO 93
<211> LENGTH: 390
<212> TYPE: PRT
<213> ORGANISM: Mus musculus

<400> SEQUENCE: 93

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Val Pro Glu Asp Leu Ser Thr Thr Ser Gly Ala Gln Gln Asn Ser Lys
        35                  40                  45

Ser Asp Arg Gly Met Gly Glu Arg Pro Phe Gln Cys Asn Gln Ser Gly
    50                  55                  60

Ala Ser Phe Thr Gln Lys Gly Asn Leu Leu Arg His Ile Lys Leu His
65                  70                  75                  80

Ser Gly Glu Lys Pro Phe Lys Cys His Leu Cys Asn Tyr Ala Cys Arg
                85                  90                  95

Arg Arg Asp Ala Leu Thr Gly His Leu Arg Thr His Ser Val Ile Lys
            100                 105                 110

Glu Glu Thr Asn His Asn Glu Met Ala Glu Asp Leu Cys Lys Ile Gly
        115                 120                 125

Ala Glu Arg Ser Leu Val Leu Asp Arg Leu Ala Ser Asn Val Ala Lys
```

```
            130                 135                 140
Arg Lys Ser Ser Met Pro Gln Lys Phe Leu Gly Asp Lys Cys Leu Ser
145                 150                 155                 160

Asp Met Pro Tyr Asp Ser Ala Asn Tyr Glu Lys Glu Asp Met Met Thr
                165                 170                 175

Ser His Val Met Asp Gln Ala Ile Asn Asn Ala Ile Asn Tyr Leu Gly
            180                 185                 190

Ala Glu Ser Leu Arg Pro Leu Val Gln Thr Pro Pro Gly Ser Ser Glu
        195                 200                 205

Val Val Pro Val Ile Ser Ser Met Tyr Gln Leu His Lys Pro Pro Ser
    210                 215                 220

Asp Gly Pro Pro Arg Ser Asn His Ser Ala Gln Asp Ala Val Asp Asn
225                 230                 235                 240

Leu Leu Leu Leu Ser Lys Ala Lys Ser Val Ser Ser Glu Arg Glu Ala
                245                 250                 255

Ser Pro Ser Asn Ser Cys Gln Asp Ser Thr Asp Thr Glu Ser Asn Ala
                260                 265                 270

Glu Glu Gln Arg Ser Gly Leu Ile Tyr Leu Thr Asn His Ile Asn Pro
            275                 280                 285

His Ala Arg Asn Gly Leu Ala Leu Lys Glu Glu Gln Arg Ala Tyr Glu
        290                 295                 300

Val Leu Arg Ala Ala Ser Glu Asn Ser Gln Asp Ala Phe Arg Val Val
305                 310                 315                 320

Ser Thr Ser Gly Glu Gln Leu Lys Val Tyr Lys Cys Glu His Cys Arg
                325                 330                 335

Val Leu Phe Leu Asp His Val Met Tyr Thr Ile His Met Gly Cys His
            340                 345                 350

Gly Cys His Gly Phe Arg Asp Pro Phe Glu Cys Asn Met Cys Gly Tyr
        355                 360                 365

His Ser Gln Asp Arg Tyr Glu Phe Ser Ser His Ile Thr Arg Gly Glu
    370                 375                 380

His Arg Tyr His Leu Ser
385                 390

<210> SEQ ID NO 94
<211> LENGTH: 376
<212> TYPE: PRT
<213> ORGANISM: Mus musculus

<400> SEQUENCE: 94

Met Asp Val Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
                20                  25                  30

Val Pro Glu Asp Leu Ser Thr Thr Ser Gly Ala Gln Gln Asn Ser Lys
            35                  40                  45

Ser Asp Arg Gly Met Ala Ser Asn Val Lys Val Glu Thr Gln Ser Asp
        50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110
```

```
Pro Asn Gly Lys Leu Lys Cys Asp Ile Cys Gly Ile Val Cys Ile Gly
            115                 120                 125

Pro Asn Val Leu Met Val His Lys Arg Ser His Thr Gly Asp Lys Cys
        130                 135                 140

Leu Ser Asp Met Pro Tyr Asp Ser Ala Asn Tyr Glu Lys Glu Asp Met
145                 150                 155                 160

Met Thr Ser His Val Met Asp Gln Ala Ile Asn Asn Ala Ile Asn Tyr
                165                 170                 175

Leu Gly Ala Glu Ser Leu Arg Pro Leu Val Gln Thr Pro Pro Gly Ser
            180                 185                 190

Ser Glu Val Val Pro Val Ile Ser Ser Met Tyr Gln Leu His Lys Pro
        195                 200                 205

Pro Ser Asp Gly Pro Pro Arg Ser Asn His Ser Ala Gln Asp Ala Val
    210                 215                 220

Asp Asn Leu Leu Leu Leu Ser Lys Ala Lys Ser Val Ser Ser Glu Arg
225                 230                 235                 240

Glu Ala Ser Pro Ser Asn Ser Cys Gln Asp Ser Thr Asp Thr Glu Ser
                245                 250                 255

Asn Ala Glu Glu Gln Arg Ser Gly Leu Ile Tyr Leu Thr Asn His Ile
            260                 265                 270

Asn Pro His Ala Arg Asn Gly Leu Ala Leu Lys Glu Glu Gln Arg Ala
        275                 280                 285

Tyr Glu Val Leu Arg Ala Ala Ser Glu Asn Ser Gln Asp Ala Phe Arg
    290                 295                 300

Val Val Ser Thr Ser Gly Glu Gln Leu Lys Val Tyr Lys Cys Glu His
305                 310                 315                 320

Cys Arg Val Leu Phe Leu Asp His Val Met Tyr Thr Ile His Met Gly
                325                 330                 335

Cys His Gly Cys His Gly Phe Arg Asp Pro Phe Glu Cys Asn Met Cys
            340                 345                 350

Gly Tyr His Ser Gln Asp Arg Tyr Glu Phe Ser Ser His Ile Thr Arg
        355                 360                 365

Gly Glu His Arg Tyr His Leu Ser
    370                 375

<210> SEQ ID NO 95
<211> LENGTH: 334
<212> TYPE: PRT
<213> ORGANISM: Mus musculus

<400> SEQUENCE: 95

Gly Glu Arg Pro Phe Gln Cys Asn Gln Cys Gly Ala Ser Phe Thr Gln
1               5                   10                  15

Lys Gly Asn Leu Leu Arg His Ile Lys Leu His Ser Gly Glu Lys Pro
            20                  25                  30

Phe Lys Cys His Leu Cys Asn Tyr Ala Cys Arg Arg Arg Asp Ala Leu
        35                  40                  45

Thr Gly His Leu Arg Thr His Ser Val Ile Lys Glu Glu Thr Lys His
    50                  55                  60

Ser Glu Met Ala Glu Asp Leu Cys Lys Ile Gly Ser Glu Arg Ser Leu
65                  70                  75                  80

Val Leu Asp Arg Leu Ala Ser Asn Val Ala Lys Arg Lys Ser Ser Met
                85                  90                  95

Pro Gln Lys Phe Leu Gly Asp Lys Gly Leu Ser Asp Thr Pro Tyr Asp
            100                 105                 110
```

```
Ser Ala Thr Tyr Glu Lys Glu Asn Glu Met Met Lys Ser His Val Met
        115                 120                 125

Asp Gln Ala Ile Asn Asn Ala Ile Asn Tyr Leu Gly Ala Glu Ser Leu
        130                 135                 140

Arg Pro Leu Val Gln Thr Pro Pro Gly Gly Ser Glu Val Val Pro Val
145                 150                 155                 160

Ile Ser Pro Met Tyr Gln Leu His Arg Arg Ser Glu Gly Thr Pro Arg
                165                 170                 175

Ser Asn His Ser Ala Gln Asp Ser Ala Val Glu Tyr Leu Leu Leu Leu
                180                 185                 190

Ser Lys Ala Lys Leu Val Pro Ser Glu Arg Glu Ala Ser Pro Ser Asn
        195                 200                 205

Ser Cys Gln Asp Ser Thr Asp Thr Glu Ser Asn Asn Glu Glu Gln Arg
        210                 215                 220

Ser Gly Leu Ile Tyr Leu Thr Asn His Ile Ala Arg Arg Ala Gln Arg
225                 230                 235                 240

Val Ser Leu Lys Glu Glu His Arg Ala Tyr Asp Leu Leu Arg Ala Ala
                245                 250                 255

Ser Glu Asn Ser Gln Asp Ala Leu Arg Val Val Ser Thr Ser Gly Glu
                260                 265                 270

Gln Met Lys Val Tyr Lys Cys Glu His Cys Arg Val Leu Phe Leu Asp
        275                 280                 285

His Val Met Tyr Thr Ile His Met Gly Cys His Gly Phe Arg Asp Pro
        290                 295                 300

Phe Glu Cys Asn Met Cys Gly Tyr His Ser Gln Asp Arg Tyr Glu Phe
305                 310                 315                 320

Ser Ser His Ile Thr Arg Gly Glu His Arg Phe His Met Ser
                325                 330

<210> SEQ ID NO 96
<211> LENGTH: 32
<212> TYPE: DNA
<213> ORGANISM: Artificial Sequence
<220> FEATURE:
<223> OTHER INFORMATION: Primer

<400> SEQUENCE: 96
aattgaattc atgcactgca ctttgactat gg                                32

<210> SEQ ID NO 97
<211> LENGTH: 39
<212> TYPE: DNA
<213> ORGANISM: Artificial Sequence
<220> FEATURE:
<223> OTHER INFORMATION: Primer

<400> SEQUENCE: 97
ttttcctttt gcggccgcat gtcgccatcc gagggaagg                         39
```